(12) United States Patent
Okuno et al.

(10) Patent No.: US 8,227,618 B2
(45) Date of Patent: Jul. 24, 2012

(54) AMINE-DERIVATIVES HAVING NPY Y5 RECEPTOR ANTAGONISTIC ACTIVITY AND THE USES THEREOF

(75) Inventors: Takayuki Okuno, Osaka (JP); Masahiro Sakagami, Sapporo (JP)

(73) Assignee: Shionogi & Co., Ltd., Osaka-shi (JP)

( * ) Notice: Subject to any disclaimer, the term of this patent is extended or adjusted under 35 U.S.C. 154(b) by 0 days.

(21) Appl. No.: 12/766,458

(22) Filed: Apr. 23, 2010

(65) Prior Publication Data
US 2010/0273841 A1 Oct. 28, 2010

Related U.S. Application Data

(60) Provisional application No. 61/171,967, filed on Apr. 23, 2009.

(51) Int. Cl.
*C07D 263/58* (2006.01)
*A61K 31/423* (2006.01)

(52) U.S. Cl. ........................... 548/222; 514/375

(58) Field of Classification Search ................ None
See application file for complete search history.

(56) References Cited

U.S. PATENT DOCUMENTS

| | | | |
|---|---|---|---|
| 6,699,891 B1 | 3/2004 | Kawanishi et al. | |
| 7,265,130 B2 | 9/2007 | Kawanishi et al. | |
| 7,534,892 B2 | 5/2009 | Nakatani | |
| 2004/0176462 A1 | 9/2004 | Kawanishi et al. | |
| 2006/0258728 A1 | 11/2006 | Tani et al. | |
| 2006/0293341 A1 | 12/2006 | Jubian et al. | |
| 2007/0015762 A1 | 1/2007 | Kawanishi et al. | |
| 2007/0060598 A1 | 3/2007 | Albers et al. | |
| 2007/0099938 A1 | 5/2007 | Ohmoto et al. | |
| 2008/0221082 A1 | 9/2008 | Geneste et al. | |
| 2009/0203712 A1 | 8/2009 | Yano | |
| 2010/0004295 A1 | 1/2010 | Kouyama | |
| 2010/0063027 A1 | 3/2010 | Okuno et al. | |
| 2010/0267945 A1* | 10/2010 | Okuno et al. | 540/490 |

FOREIGN PATENT DOCUMENTS

| | | |
|---|---|---|
| EP | 1 249 233 | 10/2002 |
| EP | 1 719 765 | 11/2006 |
| EP | 1 736 467 | 12/2006 |
| EP | 1 760 073 | 3/2007 |
| EP | 1 787 657 | 5/2007 |
| EP | 2 017 261 | 1/2009 |
| JP | 2006-124387 | 5/2006 |
| WO | 94/22835 | 10/1994 |
| WO | 96/16542 | 6/1996 |
| WO | 97/20823 | 6/1997 |
| WO | 99/55667 | 11/1999 |
| WO | 99/67203 | 12/1999 |
| WO | 00/61562 | 10/2000 |
| WO | 00/64880 | 11/2000 |
| WO | 00/68197 | 11/2000 |
| WO | 01/02379 | 1/2001 |
| WO | 2005/121107 | 12/2005 |
| WO | 2006/014482 | 2/2006 |
| WO | 2007/002126 | 1/2007 |
| WO | 2007/103295 | 9/2007 |
| WO | WO 2007125952 A1 * | 11/2007 |
| WO | 2008/134228 | 11/2008 |
| WO | 2009/054434 | 4/2009 |

OTHER PUBLICATIONS

Ambikaipakan Balasubramaniam, "Neuropeptide Y Family of Hormones: Receptor Subtypes and Antagonists", Peptides, vol. 18 No. 3, pp. 445-457, 1997.
Yutaka Takeba, et al., "SRα Promoter: an Efficient and Versatile Mammalian cDNA Expression System Composed of the Simian Virus 40 Early Promoter and the R-U5 Segment of Human T-Cell Leukemia Virus Type 1 Long Terminal Repeat", Molecular and Cellular Biology, Jan. 1988, pp. 466-472.
Akio Inui, et al., "Evidence for Further Heterogeneity of the Receptors for Neuropeptide-Y and Peptide-YY in Tumor Cell Lines Derived from Neural Crest", Endocrinology, vol. 131, No. 5, pp. 2090-2096, 1992.
Sumit Deswal, et al. "A novel range based QSAR study of human neuropeptide Y (NPY) Y5 receptor inhibitors", European Journal of Medicinal Chemistry, 2006, 42(4), pp. 463-470.
Lars Grundemar, et al., "Neuropeptide Y effector systems: perspectives for drug development", Trends in Pharmacological Sciences, vol. 15, May 1994, pp. 153-159.
Catalina Batancur, et al., "Nonpeptide antagonists of neuropeptide receptors: tools for research and therapy", Trends in Pharmacological Sciences, vol. 18, Oct. 1997, pp. 372-386.
Motonao Nakamura, et al., "Molecular cloning, organization and localization of the gene for the mouse neuropeptide Y-Y5 receptor", Biochimica et Biophysica Acta 1328, pp. 83-89, 1997.
U.S. Appl. No. 12/767,641, filed Apr. 26, 2010, Okuno, et al.
U.S. Appl. No. 12/823,568, filed Jun. 25, 2010, Okuno, et al.
U.S. Appl. No. 12/936,693, filed Oct. 7, 2010, Sakagami, et al.

* cited by examiner

*Primary Examiner* — Kamal Saeed
*Assistant Examiner* — Nyeemah A Grazier
(74) *Attorney, Agent, or Firm* — Oblon, Spivak, McClelland, Maier & Neustadt, L.L.P.

(57) ABSTRACT

This invention provides an anorectic or anti-obesity composition comprising a compound of the formula (I):
formula (I):

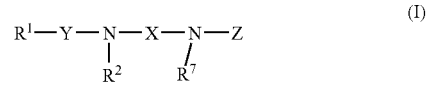

a pharmaceutically acceptable salt or solvate thereof,
wherein
$R^1$ is optionally substituted lower alkyl,
Y is —S(O)n- wherein n is 1 or 2, or —CO—,
$R^2$ is hydrogen or lower alkyl,
$R^7$ is hydrogen or lower alkyl,
X is lower alkylene, lower alkenylene, arylene, cycloalkylene or the like, and
Z is lower alkyl, optionally substituted carbocyclyl, optionally substituted heterocyclyl or the like.

12 Claims, 1 Drawing Sheet

[Figure 1]
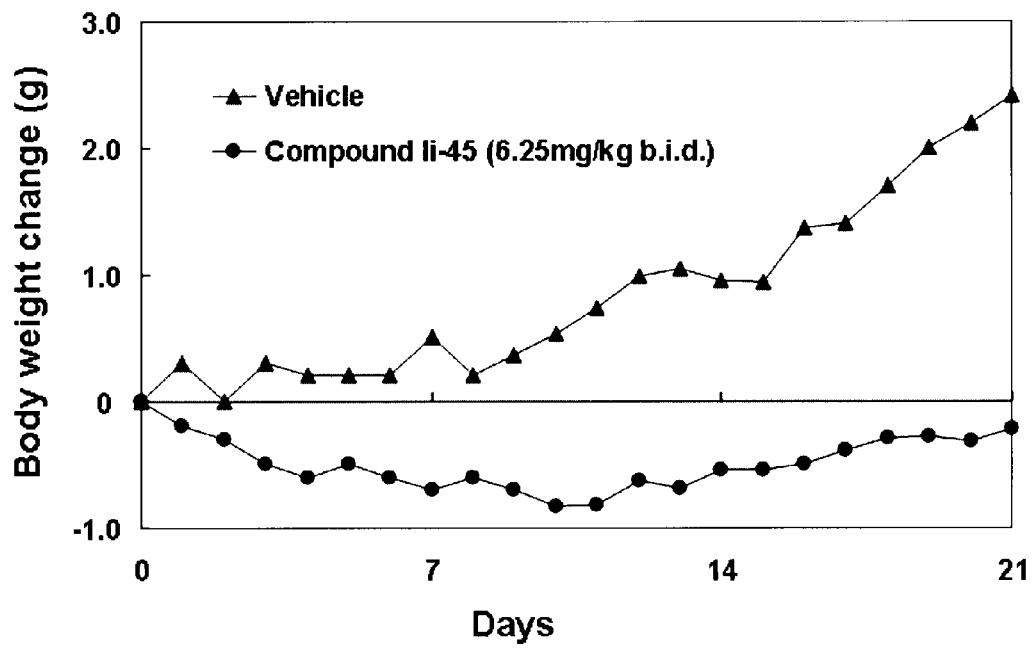
[Figure 2]
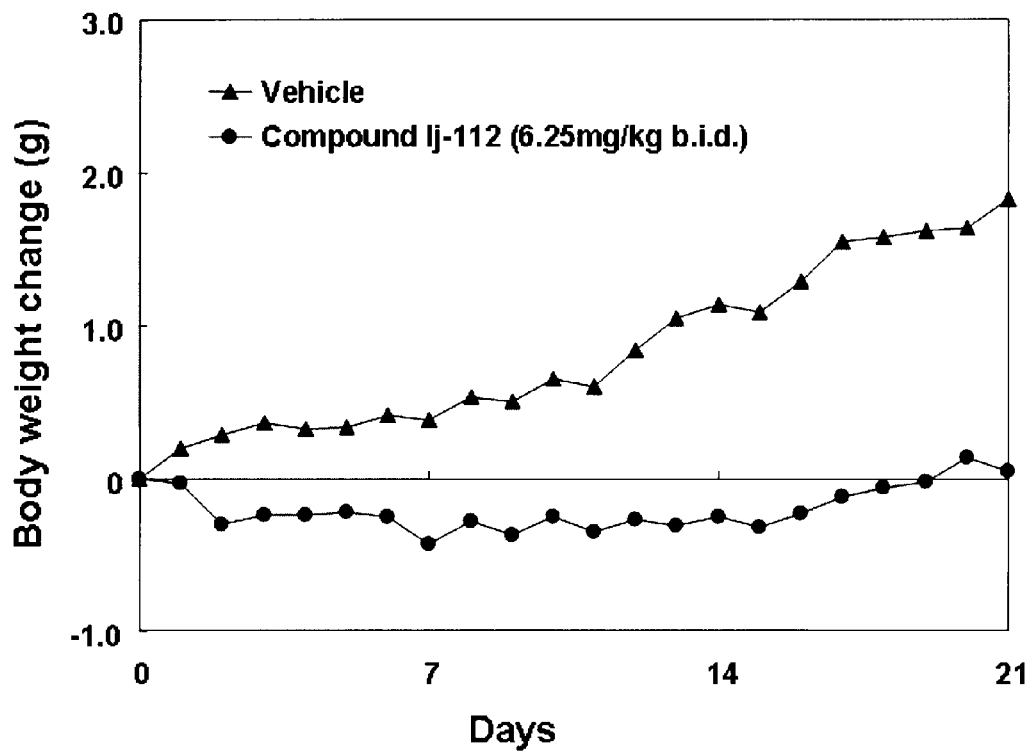

AMINE-DERIVATIVES HAVING NPY Y5 RECEPTOR ANTAGONISTIC ACTIVITY AND THE USES THEREOF

CROSS-REFERENCE TO RELATED APPLICATIONS

The present application claims the benefits of priority to U.S. Application No. 61/171,967, filed Apr. 23, 2009. The contents of that application are incorporated herein by reference in their entirety.

FIELD OF THE INVENTION

A compound for this invention has NPY Y5 receptor antagonistic activity and useful as an anorectic or anti-obesity composition.

BACKGROUND ART

Obesity is classified as primary obesity (simple obesity) and secondary obesity (symptomatic obesity) according to its cause. The cause of primary obesity is thought to include the excess energy intake (e.g., overeating), energy under consumption (e.g., lack of exercise) and lower heat production. Currently, over 90% of obesity is primary obesity. When this primary obesity is developed and the condition is kept, it causes various health problems. On the other hand, secondary obesity results from some underlying disease. The Examples of the secondary obesity include endocrine obesity, hypothalamic obesity, hereditary obesity, obesity caused by a medicament and the like. Obesity triggers lifestyle-related diseases and obese people is susceptible to complications such as diabetes, hypertension, hyperlipemia, coronary atherosclerosis (angina or myocardial infarction), gout, cholelithiasis, fatty liver, infertility, osteoarthritis and the like.

The basic treatment for obesity is a combination of diet therapy and exercise therapy. However, this has a limitation and drug therapy is expected to be effective especially for morbid obesity.

Y5 receptor, which is a subtype of Neuropeptide Y (hereinafter referred to as NPY) receptor, at least involves in the feeding behavior and its antagonist is expected as an anti-obesity agent (Non-patent Document 1).

Amine derivatives having sulfonyl group and similar structures to compounds for this invention and exhibiting NPY Y5 receptor antagonistic activity are disclosed in Patent Document 1, 2, 3, 4 and the like. Amide derivatives having sulfonyl group and exhibiting NPY Y5 receptor antagonistic activity are disclosed in Patent Document 5, 8, 9, 10 and 11. Derivatives having sulfonyl group and exhibiting NPY Y5 receptor antagonistic activity are disclosed in Patent Document 12. The structures of these compounds are different from those of the compounds for this invention.

Furthermore, although compounds having similar structures to compounds for this invention are disclosed in Patent Document 6, 7, 13, 14 and the like, the activities of their compounds are quite different from those of the compounds for this invention. These documents do not disclose that their compounds are useful as an anorectic or anti-obesity composition and do not suggest this invention.

[Non-patent Document 1] Peptides, Vol. 18, 445 (1997)
[Non-patent Document 2] European Journal of Medicinal Chemistry, 2006, 42(4), pp. 463-470
[Patent Document 1] WO01/002379
[Patent Document 2] WO00/064880
[Patent Document 3] WO99/055667
[Patent Document 4] WO00/068197
[Patent Document 5] WO01/037826
[Patent Document 6] WO2006/014482
[Patent Document 7] WO2005/097738
[Patent Document 8] WO97/20823
[Patent Document 9] US2006/293341
[Patent Document 10] WO2007/002126
[Patent Document 11] WO2006/001318
[Patent Document 12] WO2005/080348
[Patent Document 13] US2007/060598
[Patent Document 14] WO2005/121107
[Patent Document 15] WO2007/125952
[Patent Document 16] WO2008/134228

DISCLOSURE OF INVENTION

Problems to be Solved by the Invention

The object of this invention is to provide excellent anorectic or anti-obesity compositions.

Means for Solving the Problem

The present inventors have intensively studied to synthesize the following excellent novel compounds having NPY Y5 receptor antagonistic activity. Patent Document 5 disclosed amide derivatives having sulfonyl group and exhibiting NPY Y5 receptor antagonistic activity. However, the present inventors found that transportability through the blood-brain barrier of compounds which the amide is substituted with the amine is much higher than those of the unsubstituted compounds. Furthermore, the inventors found that compounds for this invention have less the induction of a drug-metabolizing enzyme compared to compounds disclosed in Patent Document 1 or 2. It was confirmed that these novel compounds suppress food intake or body weight gain by verification tests for suppression of food intake, body weight gain and the like to achieve this invention. The inventors found that a compound for this invention has high metabolic stability and water solubility. Furthermore, compounds for this invention are less toxic and thought to be safe enough as a medicament.

This invention includes the followings.

(1) An anorectic or anti-obesity composition comprising a compound of the formula (I):

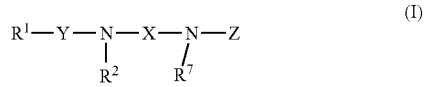

a pharmaceutically acceptable salt or solvate thereof,
wherein
$R^1$ is optionally substituted lower alkyl,
Y is —S(O)n- wherein n is 1 or 2, or —CO—,
$R^2$ is hydrogen or optionally substituted lower alkyl,
$R^1$ and $R^2$ taken together may form lower alkylene,
$R^7$ is hydrogen or optionally substituted lower alkyl,
X is optionally substituted lower alkylene,
optionally substituted lower alkenylene,
optionally substituted —CO-lower alkylene,
optionally substituted —CO-lower alkenylene or
a group of the formula:

wherein
$R^3$, $R^4$, $R^5$ and $R^6$ are each independently hydrogen or optionally substituted lower alkyl,
a group of the formula:

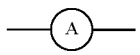

is optionally substituted cycloalkylene, optionally substituted cycloalkenylene, optionally substituted bicycloalkylene, optionally substituted arylene or optionally substituted heterocyclediyl,
p and q are each independently an integer between 0 and 2, and
either p or q is not 0,
—$NR^2$—X— may be a group of the formula:

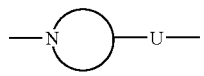

wherein a group of the formula:

is piperidinediyl, piperazinediyl, pyridinediyl, pyrazinediyl, pyrrolidinediyl or pyrroldiyl, and U is lower alkylene or lower alkenylene,
Z is optionally substituted lower alkyl, optionally substituted lower alkenyl, optionally substituted amino, optionally substituted lower alkoxy, optionally substituted carbocyclyl, optionally substituted heterocyclyl, and
provided that Z is not fused heterocyclyl consisting of three rings or optionally substituted thiazolyl or optionally substituted quinazolinyl.
(2) The anorectic or anti-obesity composition of (1) comprising a compound, pharmaceutically acceptable salt or solvate thereof, wherein $R^1$ is lower alkyl.
(3) The anorectic or anti-obesity composition of (1) comprising a compound, pharmaceutically acceptable salt or solvate thereof, wherein Y is —$S(O)_2$—.
(4) The anorectic or anti-obesity composition of (1) comprising a compound, pharmaceutically acceptable salt or solvate thereof, wherein Z is optionally substituted carbocyclyl or optionally substituted heterocyclyl.
(5) The anorectic or anti-obesity composition of (1) comprising a compound, pharmaceutically acceptable salt or solvate thereof, wherein
X is a group of the formula:

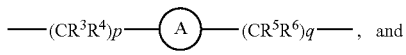

$R^1$ is optionally substituted C2 to C10 alkyl.
(6) The anorectic or anti-obesity composition of (5) comprising a compound, pharmaceutically acceptable salt or solvate thereof, wherein Z is optionally substituted heterocyclyl.
(7) The anorectic or anti-obesity composition of (5) comprising a compound, pharmaceutically acceptable salt or solvate thereof, wherein a group of the formula:

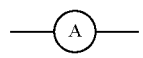

is optionally substituted cycloalkylene, optionally substituted cycloalkenylene, optionally substituted bicycloalkylene or optionally substituted piperidinylene.
(8) The anorectic or anti-obesity composition of (5) comprising a compound, pharmaceutically acceptable salt or solvate thereof,
wherein
a group of the formula:

is optionally substituted cyclohexylene or optionally substituted piperidinylene,
p and q are each independently 0 or 1, and either p or q is not 0.
(9) The anorectic or anti-obesity composition of (7) or (8) comprising the compound, pharmaceutically acceptable salt or solvate thereof, wherein Z is optionally substituted lower alkyl, optionally substituted phenyl, optionally substituted pyridyl, optionally substituted pyrazolyl, optionally substituted isoxazolyl, optionally substituted oxadiazolyl, optionally substituted pyridazinyl, optionally substituted pyrazinyl, optionally substituted pyrimidinyl or optionally substituted fused heterocycle consisting of two rings.
(10) The anorectic or anti-obesity composition of (1) comprising a compound, pharmaceutically acceptable salt or solvate thereof, wherein
X is a group of the formula:

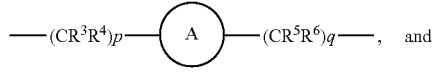

p+q is 1 or 2.
(11) The anorectic or anti-obesity composition of (10) comprising a compound, pharmaceutically acceptable salt or solvate thereof, wherein p+q is 1.
(12) An anorectic or anti-obesity composition comprising a compound of the formula (I):

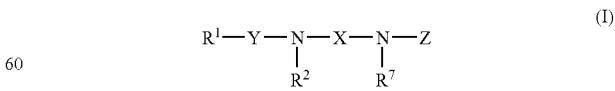

a pharmaceutically acceptable salt or solvate thereof,
wherein
$R^1$ is optionally substituted lower alkyl,
Y is —$S(O)_2$—,
$R^2$ is hydrogen or optionally substituted lower alkyl, R⁷ is hydrogen or optionally substituted lower alkyl,
X is a group of the formula:

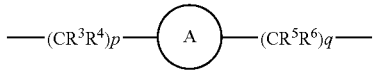

wherein
R⁵ and R⁶ are each independently hydrogen,
a group of the formula:

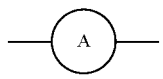

is optionally substituted cycloalkylene, p is 0, and
q is 1 or 2,
Z is optionally substituted carbocyclyl or optionally substituted heterocyclyl, and
provided that a compound wherein Z is fused heterocyclyl consisting of three rings is excluded.
(13) The anorectic or anti-obesity composition of (12) comprising a compound, pharmaceutically acceptable salt or solvate thereof, wherein Z is optionally substituted phenyl, optionally substituted indanyl, optionally substituted pyridyl, optionally substituted pyridazinyl, optionally substituted pyrimidinyl, optionally substituted pyrazolyl, optionally substituted isoxazolyl, optionally substituted oxadiazolyl or optionally substituted fused heterocycle consisting of two rings.
(14) The anorectic or anti-obesity composition of (12) comprising a compound, pharmaceutically acceptable salt or solvate thereof, wherein Z is optionally substituted isoquinolyl, optionally substituted benzothiazolyl, optionally substituted benzoxazolyl, optionally substituted benzopyridyl, optionally substituted benzopyridazinyl, optionally substituted benzimidazolyl, optionally substituted thiazolopyridyl, optionally substituted isoxazolinonyl, optionally substituted oxazolinonyl, optionally substituted benzoxadinonyl or optionally substituted benzoxyazepinonyl.
(15) An anorectic or anti-obesity composition comprising a compound of the formula (I):

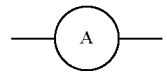 (I)

a pharmaceutically acceptable salt or solvate thereof,
wherein
R¹ is optionally substituted lower alkyl,
Y is —S(O)₂—,
R² is hydrogen or optionally substituted lower alkyl,
R⁷ is hydrogen or optionally substituted lower alkyl,
X is a group of the formula:

wherein R³ and R⁴ are each independently hydrogen, a group of the formula:

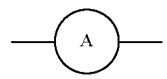

is optionally substituted cycloalkylene,
p is 1 or 2, and
q is 0,
Z is optionally substituted carbocyclyl or optionally substituted heterocyclyl, and
provided that a compound wherein Z is fused heterocyclyl consisting of three rings, optionally substituted thiazolyl or optionally substituted quinazolinyl is excluded.
(16) The anorectic or anti-obesity composition of (15) comprising a compound, pharmaceutically acceptable salt or solvate thereof, wherein Z is optionally substituted phenyl, optionally substituted pyridyl, optionally substituted pyridazinyl, optionally substituted pyrazinyl, optionally substituted pyrimidinyl, optionally substituted quinolyl, optionally substituted isoquinolyl, optionally substituted benzothiazolyl, optionally substituted benzimidazolyl, optionally substituted benzoxazolyl, optionally substituted thiazolopyridyl or optionally substituted oxazolopyridyl.
(17) An anorectic or anti-obesity composition comprising a compound of the formula (I):

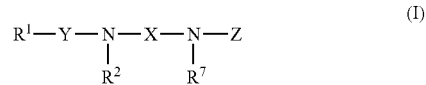 (I)

a pharmaceutically acceptable salt or solvate thereof, wherein
R¹ is optionally substituted lower alkyl,
Y is —S(O)₂—,
R² is hydrogen or optionally substituted lower alkyl,
R⁷ is hydrogen or optionally substituted lower alkyl,
X is a group of the formula:

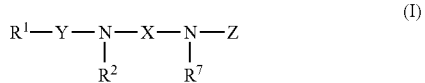

wherein R³ and R⁴ are each independently hydrogen, a group of the formula:

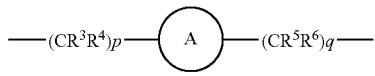

is optionally substituted cycloalkylene,
p is 1 or 2, and
q is 0, and
Z is optionally substituted phenyl, optionally substituted pyridyl, optionally substituted pyridazinyl, optionally substituted pyrazinyl, optionally substituted pyrimidinyl, optionally substituted quinolyl, optionally substituted isoquinolyl, optionally substituted benzothiazolyl, optionally substituted benzimidazolyl, optionally substituted benzoxazolyl, optionally substituted thiazolopyridyl or optionally substituted oxazolopyridyl.

(18) A compound of the formula:

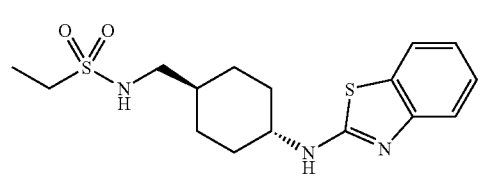
Ij-149

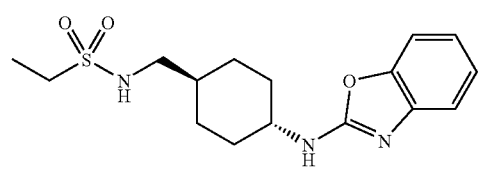
Ij-150

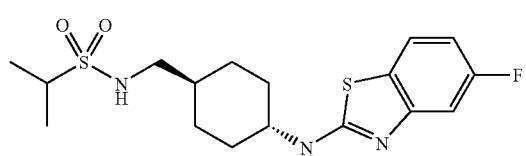
Ij-151

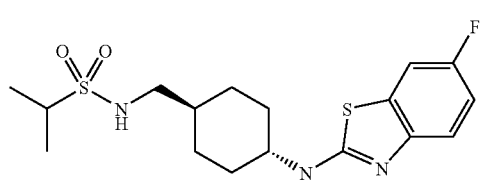
Ij-152

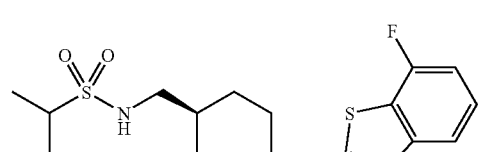
Ij-153

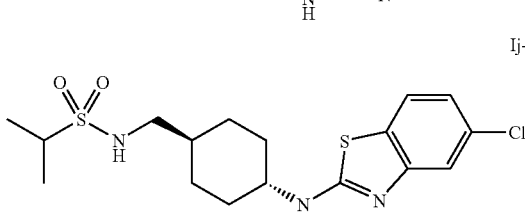
Ij-154

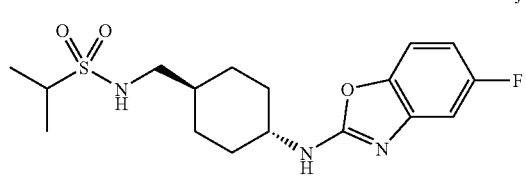
Ij-155

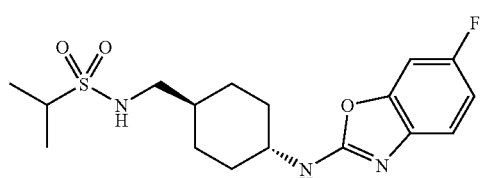
Ij-156

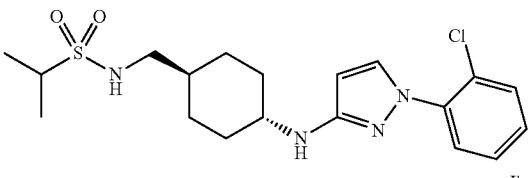
Ij-157

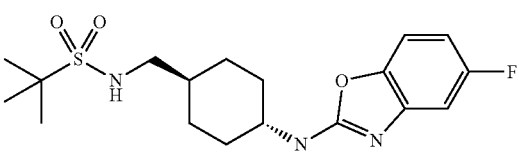
Ij-158

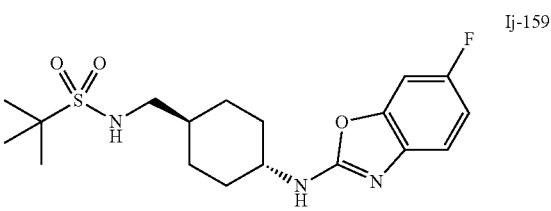
Ij-159

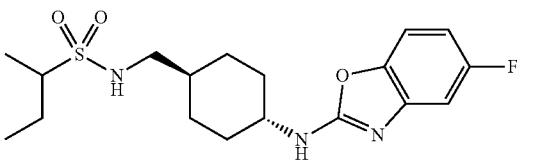
Ij-160 or

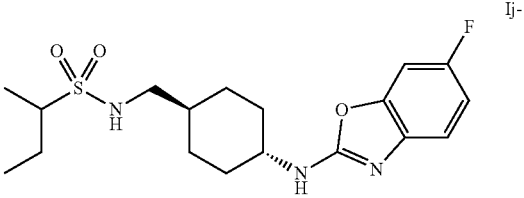
Ij-161 a pharmaceutically acceptable salt or solvate thereof.

(19) A pharmaceutical composition comprising the compound, pharmaceutically acceptable salt or solvate thereof of (18).

(20) A pharmaceutical composition comprising the compound, pharmaceutically acceptable salt or solvate thereof of (18) and exhibiting NPY Y5 receptor antagonistic activity.

(21) An anorectic or anti-obesity composition comprising the compound, pharmaceutically acceptable salt or solvate thereof of (18).

(22) A method for suppression of appetite by administering the compound, pharmaceutically acceptable salt or solvate thereof of (18).

(23) A method for treatment or prevention of obesity by administering the compound, pharmaceutically acceptable salt or solvate thereof of (18).

(24) Use of the compound, pharmaceutically acceptable salt or solvate thereof of (18) for manufacture of an anorectic or anti-obesity composition.

(25) A compound of the formula:
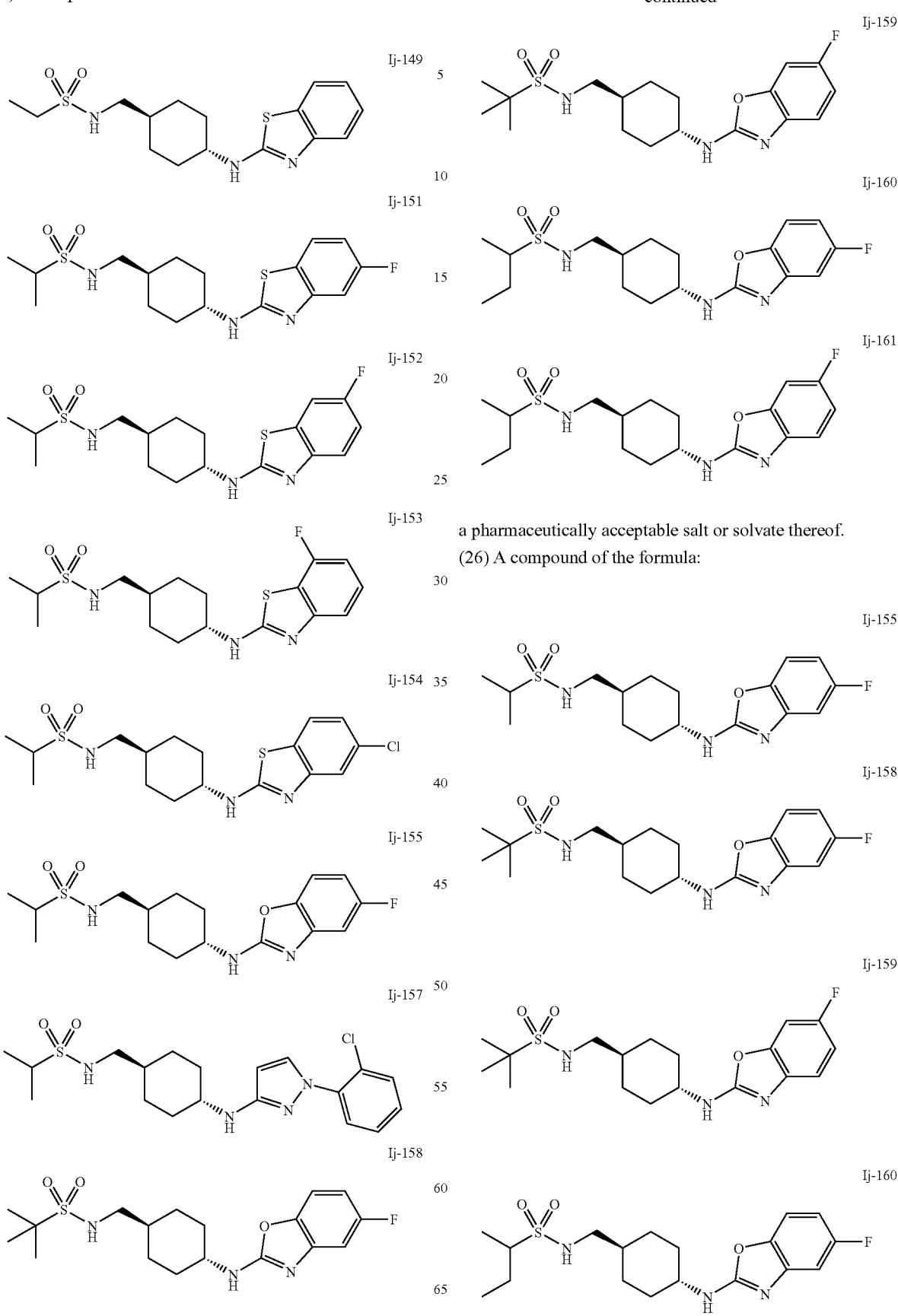
a pharmaceutically acceptable salt or solvate thereof.
(26) A compound of the formula:

-continued

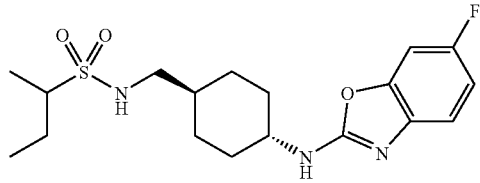
Ij-161 a pharmaceutically acceptable salt or solvate thereof.

(27) A compound of the formula:

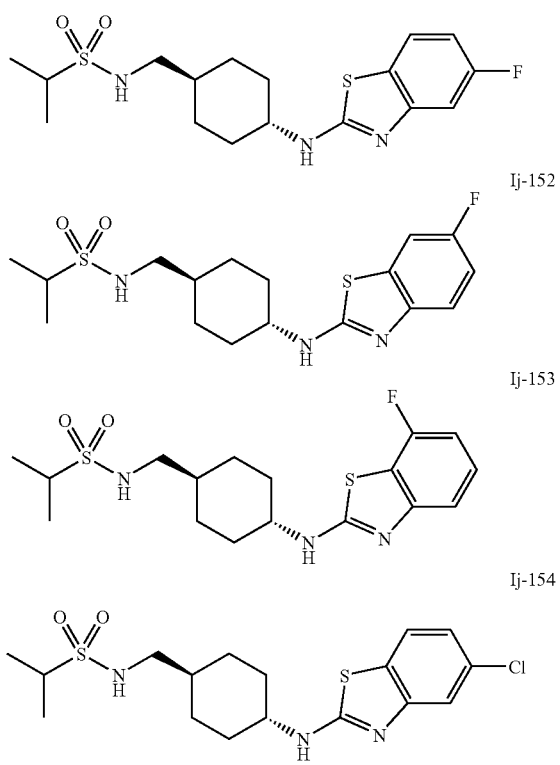

a pharmaceutically acceptable salt or solvate thereof.

(28) A pharmaceutical composition comprising the compound, pharmaceutically acceptable salt or solvate thereof of (25).

(29) The pharmaceutical composition of (28), exhibiting NPY Y5 receptor antagonistic activity.

(30) The pharmaceutical composition of (28) for the prevention or treatment of obesity or an obesity-related disorder, or the weight management for obesity.

(31) An anorectic or anti-obesity composition comprising the compound, pharmaceutically acceptable salt or solvate thereof of (25).

(32) A method for suppression of appetite by administering the compound, pharmaceutically acceptable salt or solvate thereof of (25).

(33) A method for treatment or prevention of obesity or an obesity-related disorder, or the weight management for obesity by administering the compound, pharmaceutically acceptable salt or solvate thereof of (25).

(34) A method for inducing or accelerating weight loss, or maintaining or managing body weight, by administering the compound, pharmaceutically acceptable salt or solvate thereof of (25).

Effect of the Invention

Compounds for this invention exhibit NPY Y5 receptor antagonistic activity and are very useful as a medicine, especially as an anorectic or anti-obesity composition for preventing and/or treating feeding disorder, obesity or hyperorexia. The compounds are also very useful as a medicine for prevention or treatment of obesity-related disorders. Furthermore, the compounds are very useful for the weight management for obesity.

BRIEF DESCRIPTION OF DRAWINGS

FIG. 1 Compound Ii-45 suppresses Body Weight Gain
FIG. 2 Compound Ij-112 suppresses Body Weight Gain

BEST MODE FOR CARRYING OUT THE INVENTION

Terms used in the present description are explained below. Each term has the same meaning alone or together with other terms in this description.

"Halogen" includes fluorine, chlorine, bromine and iodine. Especially preferred is fluorine or chlorine.

The protective group in "optionally protected hydroxyl" or "optionally protected hydroxyl (lower alkyl)" includes all of hydroxy protecting groups usually used. Examples are acyl such as acetyl, trichloroacetyl, benzoyl and the like, lower alkoxycarbonyl such as t-butoxycarbonyl and the like, lower alkylsulfonyl such as methane sulfonyl and the like, lower alkoxy(lower alkyl) such as methoxymethyl and the like, and trialkylsilyl such as t-butyldimethylsilyl and the like.

"Lower alkyl" includes C1 to C10 straight or branched alkyl. Examples are methyl, ethyl, n-propyl, isopropyl, n-butyl, isobutyl, sec-buthyl, tert-butyl, n-pentyl, isopentyl, neopentyl, hexyl, isohexyl, n-heptyl, isoheptyl, n-octyl, isooctyl, n-nonyl, n-decyl and the like.

"Lower alkyl" of $R^1$ is preferably C2 to C10, more preferably C2 to C6 alkyl and most preferably ethyl, isopropyl or t-butyl.

"Lower alkyl" in other cases is preferably C1 to C6 and more preferably C1 to C4 alkyl.

The examples of substituents of "optionally substituted lower alkyl" of Z are, (1) halogen; (2) cyano;
(3) the following groups (i) to (xvi), which are optionally substituted with one or more substituents selected from "Substituent group 6" defined below,
(i) hydroxy, (ii) lower alkoxy, (iii) mercapto, (iv) lower alkylthio, (v) acyl, (vi) acyloxy, (vii) carboxy, (viii) lower alkoxycarbonyl, (ix) imino, (x) carbamoyl, (xi) thiocarbamoyl, (xii) lower alkylcarbamoyl, (xiii) lower alkylthiocarbamoyl, (xiv) amino, (xv) lower alkylamino or (xvi) heterocyclylcarbonyl; or
(4) a group of the formula:

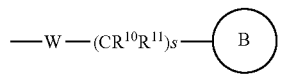

wherein $R^{10}$ and $R^{11}$ are each independently hydrogen or lower alkyl and when this group has two or more of $R^{10}$ and/or $R^{11}$, each $R^{10}$ and/or $R^{11}$ may be different,
W is single bond, O, S or $NR^{12}$,
$R^{12}$ is hydrogen, lower alkyl or phenyl, a group of the formula:

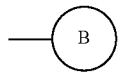

is cycloalkyl, bicycloalkyl, cycloalkenyl, aryl or heterocyclyl, each of which is optionally substituted with one or more of substituent(s) selected from "Substituent group α" defined below and
s is an integer of 0 to 4.

"Substituent group α" is a group consisting of (1) halogen; (2) oxo; (3) cyano; (4) nitro; (5) imino optionally substituted with lower alkyl or hydroxy;
(6) the following groups (i) to (xxi), which are optionally substituted with one or more of group(s) selected from Substituent group β, (i) hydroxy, (ii) lower alkyl, (iii) lower alkenyl, (iv) lower alkoxy, (v) carboxy, (vi) lower alkoxycarbonyl, (vii) acyl, (viii) acyloxy, (ix) imino, (x) mercapto, (xi) lower alkylthio, (xii) carbamoyl, (xiii) lower alkylcarbamoyl, (xiv) cycloalkylcarbamoyl, (xv) thiocarbamoyl, (xvi) lower alkylthiocarbamoyl, (xvii) lower alkylsulfinyl, (xviii) lower alkylsulfonyl, (xix) sulfamoyl, (xx) lower alkylsulfamoyl and (xxi) cycloalkylsulfamoyl; (7) the following groups (i) to (v), which are optionally substituted with Substituent group β, lower alkyl, lower alkoxy(lower alkyl), optionally protected hydroxy(lower alkyl), halogeno (lower alkyl), lower alkylsulfonyl and/or arylsulfonyl,
(i) cycloalkyl, (ii) cycloalkenyl, (iii) cycloalkyloxy, (iv) amino and (v) alkylenedioxy; and
(8) the following groups (i) to (xii), which are optionally substituted with Substituent group β, lower alkyl, halogeno (lower alkyl) and/or oxo, (i) phenyl, (ii) naphthyl, (iii) phenoxy, (iv) phenyl(lower alkoxy), (v) phenylthio, (vi) phenyl (lower alkylthio), (vii) phenylazo, (viii) heterocyclyl, (ix) heterocyclyloxy, (x) heterocyclylthio, (xi) heterocyclylcarbonyl and (xii) heterocyclylsulfonyl.

The preferable examples of Substituent group a as substituents for Ring B are halogen; nitro; hydroxy;
optionally substituted lower alkyl wherein the substituent(s) is halogen, cyano, phenyl, carboxy and/or lower alkoxycarbonyl;
lower alkenyl; lower alkoxycarbonyl(lower alkenyl);
optionally substituted lower alkoxy wherein the substituent(s) is halogen, hydroxy, lower alkoxy, carboxy, lower alkoxycarbonyl, lower alkylamino and/or cyano;
acyl; hydroxyimino; lower alkylthio; lower alkylsulfinyl; sulfamoyl; optionally substituted amino wherein the substituent (s) is lower alkyl, optionally protected hydroxy(lower alkyl), phenyl and/or acyl; alkylenedioxy; cyanophenyl; phenyl substituted heterocycle; biphenylyl; phenoxy; phenylazo optionally substituted with lower alkyl; or optionally substituted heterocyclyl wherein the substituent(s) is optionally protected hydroxy, mercapto, halogen, lower alkyl, cycloalkyl, lower alkoxycarbonyl, amino, lower alkoxycarbonyl amino, carbamoyl, oxo, phenyl, lower alkoxyphenyl or heterocyclyl. More preferable examples are halogen; lower alkyl optionally substituted with halogen; or lower alkoxy optionally substituted with halogen.

"Substituent group β" is a group consisting of halogen, optionally protected hydroxy, mercapto, lower alkoxy, lower alkenyl, amino, lower alkylamino, lower alkoxycarbonylamino, lower alkylthio, acyl, carboxy, lower alkoxycarbonyl, carbamoyl, cyano, cycloalkyl, phenyl, phenoxy, lower alkylphenyl, lower alkoxyphenyl, halogenophenyl, naphthyl and heterocyclyl.

Examples of the substituent(s) for "optionally substituted lower alkyl" of any other than Z (e.g., $R^1$) are one or more substituent(s) selected from Substituent group β. The lower alkyl may be substituted with these substituents at any possible position(s).

The lower alkyl part in "lower alkoxy", "lower alkoxycarbonyl", "lower alkoxycarbonyl(lower alkyl)", "lower alkylphenyl", "lower alkoxyphenyl", "lower alkylcarbamoyl", "lower alkylthiocarbamoyl", "lower alkylamino", "halogeno (lower alkyl)", "hydroxy(lower alkyl)", "phenyl(lower alkoxy)", "lower alkylthio", "phenyl(lower alkylthio)", "lower alkoxycarbonylamino", "lower alkoxycarbonyl (lower alkenyl)", "lower alkylsulfinyl", "lower alkylsulfonyl", "aryl(lower alkoxycarbonyl)", "lower alkylbenzoyl" or "lower alkoxybenzoyl" is the same as defined in the above "lower alkyl".

Examples of the substituent(s) for "optionally substituted lower alkoxy" are one or more substituent(s) selected from Substituent group β. Preferable examples are phenyl, lower alkylphenyl, lower alkoxyphenyl, naphthyl and heterocyclyl.

"Cycloalkyl" includes C3 to C8 and preferably C5 to C6 cyclic alkyl. Examples are cyclopropyl, cyclobutyl, cyclopentyl, cyclohexyl, cycloheptyl, cyclooctyl and the like.

Examples of the substituent(s) for "optionally substituted cycloalkyl" are one or more substituent(s) selected from Substituent group α and the cycloalkyl may be substituted with these substituents at any possible position(s).

"Bicycloalkyl" includes a group which is formed by excluding one hydrogen atom from C5 to C8 aliphatic cycle containing two rings which possess two or more of atoms in common. Examples are bicyclo[2.1.0]pentyl, bicyclo[2.2.1] heptyl, bicyclo[2.2.2]octyl, bicyclo[3.2.1]octyl and the like.

"Lower alkenyl" includes C2 to C10, preferably C2 to C8 and more preferably C3 to C6 straight or branched alkenyl having one or more double bond(s) at any possible position(s). Examples are vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl and the like.

The "lower alkenyl" part in "lower alkoxycarbonyl(lower alkenyl)" is the same as the above "lower alkenyl".

Examples of the substituent(s) for "optionally substituted lower alkenyl" are halogen, lower alkoxy, lower alkenyl, amino, lower alkylamino, lower alkoxycarbonylamino, lower alkylthio, acyl, carboxy, lower alkoxycarbonyl, carbamoyl, cyano, cycloalkyl, phenyl, lower alkylphenyl, lower alkoxyphenyl, naphthyl and/or heterocyclyl.

"Acyl" includes (1) C1 to C10, preferably C1 to C6 and more preferably C1 to C4 straight or branched alkylcarbonyl or alkenylcarbonyl, (2) C4 to C9 and preferably C4 to C7 cycloalkylcarbonyl and (3) C7 to C11 arylcarbonyl. Examples are formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl, benzoyl and the like.

The "acyl" part in "acyloxy" is same as above.

"Cycloalkenyl" includes a group having one or more double bond(s) at any possible position(s) in the above cycloalkyl. Examples are cyclopropenyl, cyclobutenyl, cyclopentenyl, cyclohexenyl, cyclohexadienyl and the like.

Examples of substituent(s) for "optionally substituted cycloalkenyl" are one or more substituent(s) selected from Substituent group β.

Examples of the substituent(s) for "optionally substituted amino" are Substituent(s) group β, optionally substituted benzoyl and/or optionally substituted heterocyclylcarbonyl wherein the substituent(s) is hydroxy, lower alkyl, lower alkoxy and/or lower alkylthio.

"Aryl" includes a monocyclic or polycyclic aromatic carbocyclyl. Examples are phenyl, naphthyl, anthryl, phenanthryl and the like. It also includes aryl fused with other non-aromatic carbocyclyl. Examples are indanyl, indenyl, biphenylyl, acenaphthyl, tetrahydronaphthyl, fluorenyl and the like. Phenyl is preferable.

The aryl part in "aryl lower alkoxycarbonyl" is same as above.

"Optionally substituted aryl" or "optionally substituted phenyl" of Z includes the above "aryl" or "phenyl" respectively, which is optionally substituted with Substituent group α or lower alkyl optionally substituted with one or more group(s) selected from Substituent group α.

Examples of the substituent(s) for "optionally substituted aryl" and "optionally substituted phenyl" of any other than Z are one or more group(s) selected from Substituent group β.

"Carbocyclyl" includes the above "cycloalkyl", "cycloalkenyl", "bicycloalkyl" and "aryl".

"Non-aromatic carbocyclyl" includes the above "cycloalkyl", "cycloalkenyl" and "bicycloalkyl".

"Optionally substituted carbocyclyl" includes the above "optionally substituted cycloalkyl", "optionally substituted cycloalkenyl", "optionally substituted bicycloalkyl" and "optionally substituted aryl".

"Heterocyclyl" includes a heterocyclic group containing one or more heteroatom(s) arbitrarily selected from O, S and N. Examples are 5- or 6-membered heteroaryl such as pyrrolyl, imidazolyl, pyrazolyl, pyridyl, pyridazinyl, pyrimidinyl, pyrazinyl, triazolyl, triazinyl, tetrazolyl, isooxazolyl, oxazolyl, oxadiazolyl, isothiazolyl, thiazolyl, thiadiazolyl, furyl, thienyl and the like; fused heterocyclyl consisting of two rings such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazoropyridyl, imidazothiazolyl, pyrazinopyridazinyl, tetrahydroquinolyl, tetrahydrobenzothienyl, oxazolopyridyl, thiazolopyridyl (e.g., thiazolo[5,4-b]pyridine-2-yl, thiazolo[5,4-c]pyridine-2-yl, thiazolo[4,5-b]pyridine-2-yl, thiazolo[4,5-c]pyridine-2-yl and the like), benzoxazolinonyl, benzisoxazolinonyl, benzoxazinonyl, benzoxyazepinonyl, oxazolopyridinonyl, benzodioxolyl and the like; fused heterocyclyl consisting of three rings such as carbazolyl, acridinyl, xanthenyl, phenothiazinyl, phenoxathiinyl, phenoxazinyl, dibenzofuryl and the like; and non-aromatic heterocyclyl such as dioxanyl, thiiranyl, oxiranyl, oxathiolanyl, azetidinyl, thianyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydrofuryl, tetrahydropyranyl, tetrahydrothiazolyl, tetrahydroisothiazolyl and the like.

"Fused heterocyclyl" fused with a ring other than a heterocycle (e.g., benzothiazolyl and the like) may attach with the other group(s) at any possible position.

The substituent(s) for "optionally substituted heterocyclyl" or "optionally substituted fused heterocyclyl consisting of two rings" are the same as those for the above "optionally substituted aryl".

The heterocyclyl part in "heterocyclylcarbonyl", "heterocyclyloxy", "heterocyclylthio" or "heterocyclyl substituted phenyl" is the same as the above "heterocyclyl".

"Lower alkylene" includes a bivalent group comprising 1 to 6 of methylene, preferably 2 to 6 of methylene and more preferably 3 to 6 of methylene. Examples are methylene, ethylene, trimethylene, tetramethylene, pentamethylene, hexamethylene and the like. Tetramethylene is especially preferable.

"$R^1$ and $R^2$ taken together may form lower alkylene" includes the case

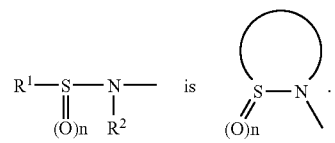

Preferable examples are

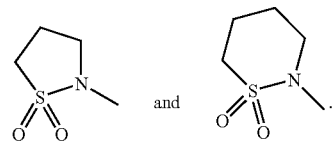

The lower alkylene part in "lower alkylenedioxy" is the same as the above "lower alkylene". Methylenedioxy or ethylenedioxy is preferable.

"Lower alkenylene" includes a bivalent group comprising 2 to 6 of methylene, preferably 3 to 6 of methylene and more preferably 4 to 5 of methylene and including at least one double bond.

"Cycloalkylene" includes a bivalent group which is formed by excluding one hydrogen atom from the above "cycloalkyl". As cycloalkylene of X is 1,4-cyclohexanediyl is preferable.

The term "cycloalkenylene" includes a group containing at least one double bond in the above cycloalkylene.

"Bicycloalkylene" includes a group which is formed by excluding one hydrogen atom from the above "bicycloalkyl". Examples are bicyclo[2.1.0]pentylene, bicyclo[2.2.1]heptylene, bicyclo[2.2.2]octylene, bicyclo[3.2.1]octylene and the like.

"Heterocyclediyl" includes a bivalent group which is formed by excluding one hydrogen atom from the above "heterocyclyl". Piperidinediyl, piperazinediyl, pyridinediyl, pyrimidinediyl, pyrazinediyl, pyrrolidinediyl or pyrrolediyl is preferable. Piperidinediyl is more preferable.

"Arylene" includes a bivalent group which is formed by excluding one hydrogen atom from the above "aryl". Phenylene is preferable.

"Heteroarylene" includes aromatic groups in the above "heterocyclediyl". Examples are pyrrolediyl, imidazolediyl, pyrazolediyl, pyridinediyl, pyridazinediyl, pyrimidinediyl, pyrazinediyl, triazolediyl, triazinediyl, isoxazolediyl, oxazolediyl, oxadiazolediyl, isothiazolediyl, thiazolediyl, thiadiazolediyl, furandiyl, thiophenediyl and the like.

Examples of substituent(s) for "optionally substituted lower alkylene", "optionally substituted lower alkenylene", "optionally substituted cycloalkylene", "optionally substituted cyclohexylene", "optionally substituted bicycloalkylene", "optionally substituted cycloalkenylene", "optionally substituted phenylene", "optionally substituted heterocyclyldiyl" and "optionally substituted piperidinylene" are one or more group(s) selected from Substituents group β. Preferred is Halogen, hydroxy, lower alkyl, halogeno (lower) alkyl, lower alkoxy, amino, lower alkylamino, acyl, carboxy, lower alkoxycarbonyl or the like. These substituent(s) may attach to any possible position(s).

When —NR$^2$—X— is a group of the formula:

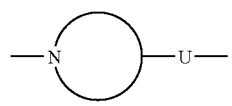

U is preferably methylene or ethylene. More preferred is a group of the formula:

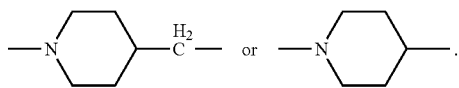

The following compounds are preferable as a compound for this invention.

A compound of the formula (I):

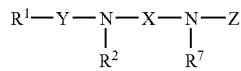
(I)

wherein
R$^1$ is lower alkyl,
Y is —S(O)$_2$—,
R$^2$ is hydrogen,
R$^7$ is hydrogen,
X is a group of the formula:

wherein
R$^3$ and R$^4$ are each independently hydrogen,
a group of the formula:

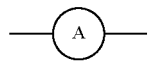

is cycloalkylene, p is 1, and
q is 0, and
Z is optionally substituted pyrazolyl, optionally substituted benzothiazolyl or optionally substituted benzoxazolyl.

The following compounds are more preferable.

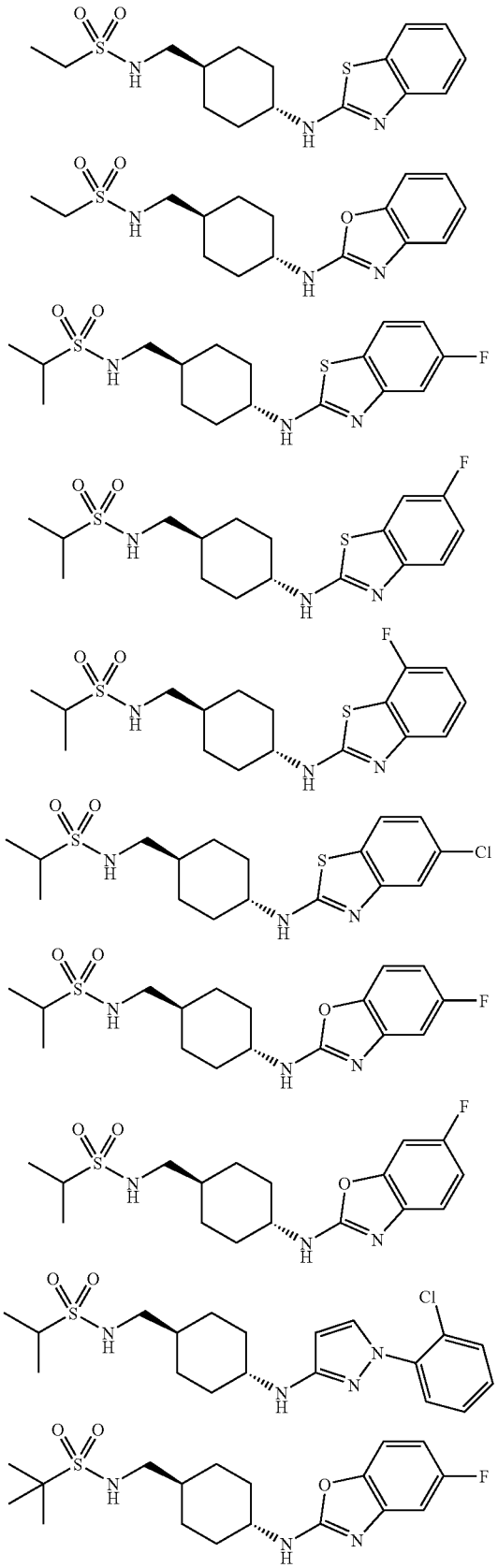

-continued

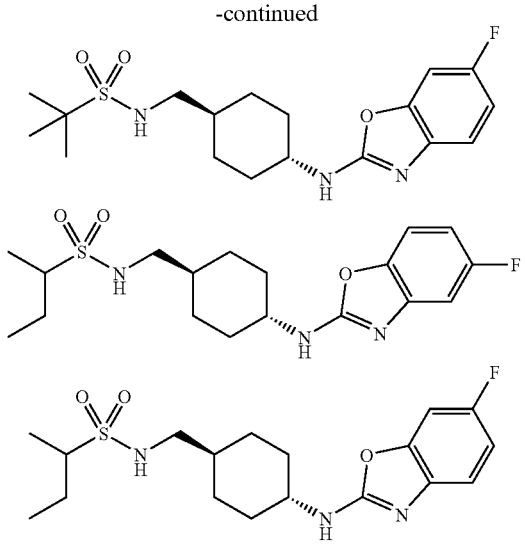

The above compounds have a good character especially that they show effect of suppressing body weight gain at low doses.

The compounds for this invention include any formable and pharmaceutically acceptable salts thereof. Examples of "the pharmaceutically acceptable salt" are salts with mineral acids such as hydrochloric acid, sulfuric acid, nitric acid, phosphoric acid and the like; salts with organic acids such as para-toluenesulfonic acid (tosic acid), methanesulfonic acid, oxalic acid, citric acid, besylic acid, ethanedisulfonic acid, ethane sulfonic acid, maleic acid, tartaric acid, succinic acid, lactic acid and the like; salts with organic bases such as ammonium, trimethylammonium, triethylammonium and the like; salts with alkaline metals such as sodium, potassium and the like; and salts with alkaline earth metals such as calcium, magnesium and the like.

The compounds for this invention include solvates thereof. Hydrate is preferable and arbitrary numbers of water molecules may coordinate to the compound for this invention.

When Compound (I) for this invention has an asymmetric carbon atom, it includes racemates, all of enantiomers and all of stereoisomers such as diastereomer, epimer, enantiomer thereof and the like. When Compound (I) for this invention having one or more double bond(s) forms an E isomer or Z isomer, Compound (I) includes both isomers. When X is cycloalkylene, Compound (I) includes both of cis isomer and trans isomer.

This invention includes within its scope prodrugs of the compounds in pharmaceutical compositions of this invention. In general, such prodrugs will be functional derivatives of the compounds which are readily convertible in vivo into the required compound. Thus, "a compound" of this invention shall encompass compounds specifically disclosed as elements of the composition or compounds which may not be specifically disclosed, but which convert to the specified compounds in vivo after administration to the patient. Conventional procedures for the selection and preparation of suitable prodrug derivatives are described, for example, in Design of Prodrugs (ed. H. Bundgaard, Elsevier, 1985).

For example, Compound (I) for this invention can be synthesized by the following methods. Hereinafter, X will be described as —$CH_2$-G- or -G-$CH_2$—.

[Compounds wherein Y is S(O)n]

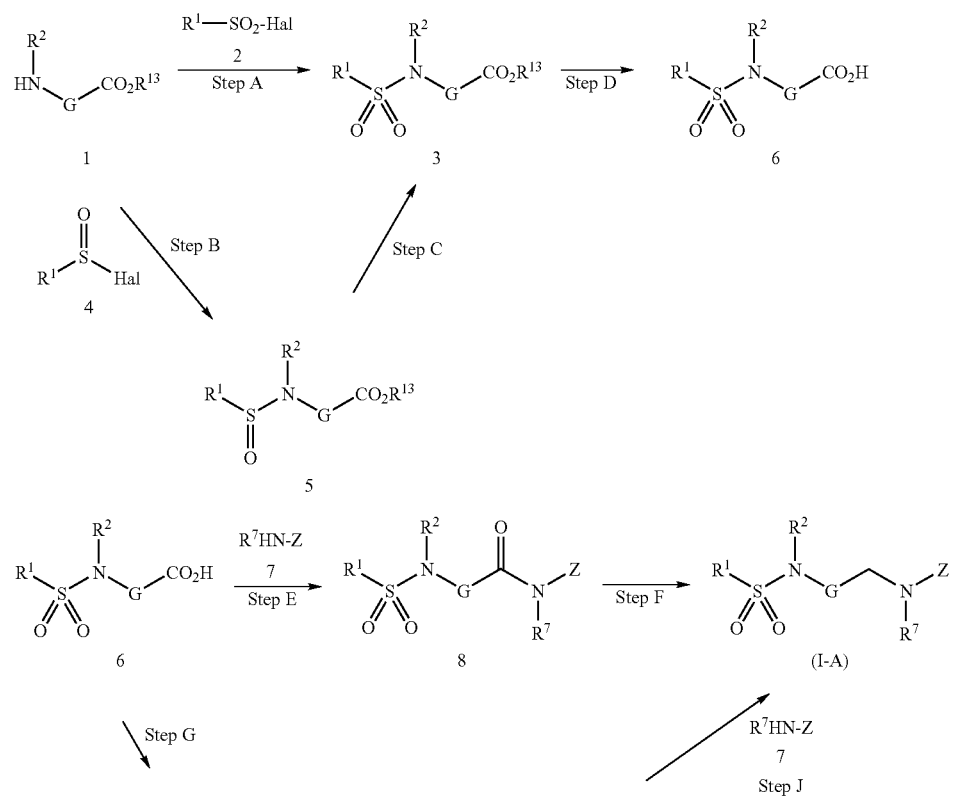

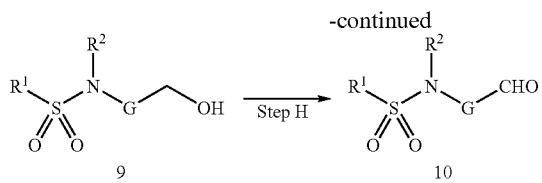

In the above scheme, Hal is halogen, -G-CH$_2$— is the same as —X— in the formula (I), R$^{13}$ is lower alkyl and the other symbols have the same meanings as above.

Step A

Compound 1 is reacted with Sulfonyl Halide 2 having the desired substituent R$^1$ in a suitable solvent within the range of 0° C. to 50° C. for several minutes to several hours to give Compound 3 wherein n is 2. Examples of the solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, mixtures thereof and the like.

Step B

Compound 5 wherein n is 1 can be synthesized by reacting Compound 1 and Sulfinyl Halide 4 having substituent R$^1$. The conditions for the reaction are the same as those of the above Step A.

Step C

Compound 5 obtained in Step B is oxidized by the usual method to give Compound 3 wherein n is 2. Examples of an oxidizer are m-chloroperbenzoic acid, peracetic acid, hydrogen peroxide, trifluoroperacetic acid, sodium periodate, sodium hypochlorite, potassium permanganate and the like. The reaction may be carried out within the range of 0° C. to 50° C. Examples of solvents are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water, methanol, ethanol, isopropanol, mixtures thereof and the like.

Step D

Compound 3 obtained from Step A or C is treated with base in a suitable solvent to give Compound 6. Examples of the base are barium hydroxide, sodium hydroxide, potassium hydroxide, hydrazine, lithium salt of propanethiol and the like. Examples of the solvent are tetrahydrofuran, dimethylformamide, dioxane, acetone, acetonitrile, methanol, ethanol, propanol, water, mixed solvents thereof and the like. The reaction may be carried out within the range of 0° C. to 100° C. for several minutes to tens of hours.

Step E

Compound 6 obtained form Step D is reacted with Amino Compound 7 having the desired substituent Z and R$^7$ in a suitable solvent within the range of 0° C. to 50° C. for several minutes to several hours to give Compound 8. Examples of the solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, mixed solvents thereof and the like. An activator such as thionyl chloride, acid halide, acid anhydride, activated ester and the like can be used, if necessary.

Step F

The obtained Compound 8 is treated with a suitable reducing agent in a suitable solvent to give Compound (I-A). Examples of the reducing agent are sodium borohydride, lithium boron hydride, lithium aluminum hydride and the like. Examples of the solvent are tetrahydrofuran, dimethylformamide, dioxane, acetonitrile, methanol, ethanol, propanol, acetic acid, mixed solvents thereof and the like. The reaction may be carried out within the range of 0° C. to 100° C. for several minutes to tens of hours.

Step G

Compound 6 obtained from Step D is treated with a reducing agent in a suitable solvent to give Compound 9. Examples of the reducing agent are sodium borohydride, lithium boron hydride, lithium aluminum hydride, diborane and the like. Examples of the solvent are tetrahydrofuran, dimethylformamide, dioxane, acetonitrile, methanol, ethanol, propanol, mixed solvents thereof and the like. The reaction may be carried out within the range of 0° C. to 100° C. for several minutes to tens of hours. Compound 9 can be obtained through the intermediate such as acid halide, acid anhydride, activated ester and the like, if necessary.

Step H

Compound 9 obtained from Step G is oxidized by the usual method to give Compound 10. Examples of an oxidizer are m-chloroperbenzoic acid, peracetic acid, hydrogen peroxide, pertrifluoroacetic acid, sodium periodate, sodium hypochlorite, potassium permanganate, Dess-Martin periodinane, dimethylsulfoxide/oxalyl chloride (Swern oxidation), ruthenium-catalyst and the like. The reaction may be carried out within the range of –80° C. to 50° C. Examples of the solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water, methanol, ethanol, isopropanol, mixed solvents thereof and the like.

Step J

The obtained Compound 10 and Amino Compound 7 having the desired substituent Z and R$^7$ are subjected to reductive amination reaction by a ordinary method to give Compound (I-A). Examples of the reducing agent are sodium borohydride, triacetoxy sodium borohydride, cyano sodium borohydride and the like. The reaction may be carried out within the range of 0° C. to 50° C. Examples of the solvent are tetrahydrofuran, dimethylformamide, dioxane, acetonitrile, methanol, ethanol, propanol, acetic acid, hydrochloric acid, mixed solvents thereof and the like.

[Compounds wherein Y is CO]

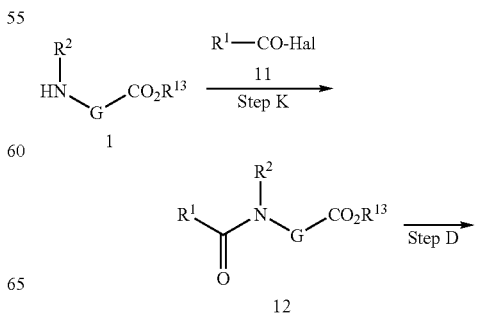

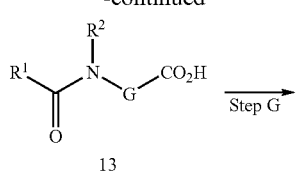

13

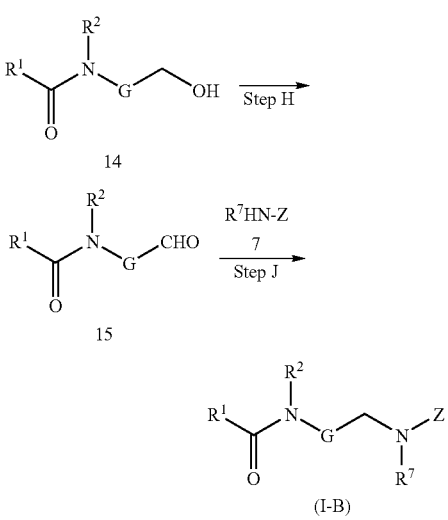

14

15

(I-B)

In the above scheme, each symbol has the same meaning as above and -G-CH$_2$— is the same as —X— in the formula (I).

Step K

Compound 1 is reacted with Acyl Halide 11 having the desired substituent R$^1$ in a suitable solvent within the range of −20° C. to 50° C. for several minutes to several hours to give Compound 12. Examples of the solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, mixed solvents thereof and the like.

Step D, G, H and J

The obtained Compound 12 is subjected to the similar method to the above Step D, G, H and J to give Compound (I-B) for this invention.

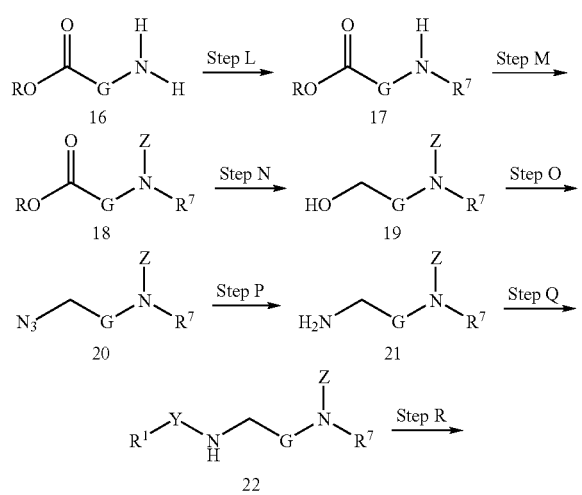

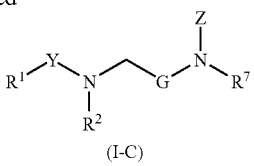

(I-C)

In the above scheme, each symbol has the same meaning as above, —CH$_2$-G- is the same as —X— in the formula (I) and R is alkyl.

Step L

This is the step to introduce substituent R$^7$ into Compound 16. For example, Compound 16 is reacted with R$^7$X$^1$ wherein X$^1$ is halogen under the presence of a base to give Compound 17. Examples of the solvent are tetrahydrofuran and dimethylformamide. The reaction may be carried out at room temperature. Examples of the base are triethylamine, pyridine, dimethylamino pyridine and the like. This step is not necessary for the compounds wherein R$^7$ is hydrogen in the formula (I-C).

Step M

This is the step to introduce substituent Z into Compound 17. For example, Compound 17 is reacted with ZX$^1$ wherein X$^1$ is halogen under the presence of a base to give Compound 18. Examples of the solvent are methanol, ethanol, isopropanol, dimethylformamide and the like. The reaction may be carried out at room temperature or under heating. For example, it can be carried out in a sealed tube by a microwave reactor. Examples of the base are N,N-diisopropyl ethyl amine and the like.

Step N

This is the step to reduce Compound 18 to give Compound 19. An example of reducing agent is lithium aluminum hydride. Examples of the solvent are tetrahydrofuran and the like. The reaction may be carried out at room temperature.

Step O

This is the step to give Compound 20 by azidation of Compound 19. For example, methanesulfonyl chloride is reacted with Compound 19 by using triethylamine as a base to give mesylate. Chloroform can be used as the solvent for the mesylation. Sodium azide is reacted with the obtained compound and azidation is carried out in dimethylformamide or the like at room temperature or under heating to give Compound 20.

Step P

This is the step to reduce Compound 20 to give Compound 21. It can be carried out by catalytic reduction. Examples of the catalyst are 10% palladium carbon and the like. Examples of the solvent are ethanol and the like.

Step Q

This is the step to a compound of the formula: R$^1$—Y—X$^1$ wherein X$^1$ is halogen or the like, and Y is S, SO, SO$_2$ or CO is reacted with Compound 21 to give Compound 22. Examples of a compound of the formula: R$^1$—Y—X$^1$ are various sulfonyl chloride, sulfinyl chloride, acyl chloride and the like. Examples of the solvent are tetrahydrofuran, dimethylformamide and the like. The reaction may be carried out at room temperature or under heating. The reaction is preferably carried out under a base. Examples of the base are pyridine, triethylamine and the like. A compound wherein R$^2$ is hydrogen in the formula (I-C) do not need the subsequent Step R and Compound 22 is a final target compound. This reaction can be carried out with a compound of the formula: R$^1$—Y—X$^1$ wherein Y is S or SO to give Compound 22, and then the oxidation can be carried out to transform to a compound wherein Y is SO₂ used for the next step.

Step R

This is the step to introduce substituent R² into Compound 22. R²X¹ wherein X¹ is halogen or the like is reacted with Compound 22 under the presence of a base to give Compound (I-C). Examples of base are sodium hydride and the like. Examples of the solvent are dimethylformamide and the like.

The following intermediates are useful in the above steps.

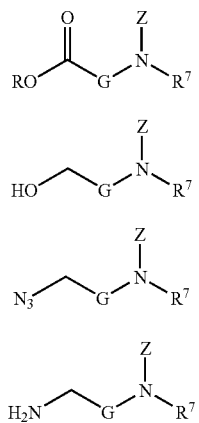

wherein

R is optionally substituted lower alkyl,

R⁷ is hydrogen or optionally substituted lower alkyl,

G is 1,4-cycloalkylene, and

Z is optionally substituted carbocyclyl or optionally substituted heterocyclyl.

R is preferably lower alkyl and more preferably methyl and ethyl. Ethyl is especially preferable.

Preferable R⁷ is hydrogen.

Preferable Z is optionally substituted heterocyclyl.

The following compounds are especially preferable.

A compound of the formula:

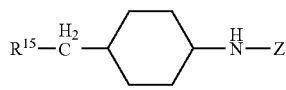

wherein

R¹⁵ is NH₂ or OH, and

Z is optionally substituted pyridyl, optionally substituted pyridazinyl, optionally substituted pyrazinyl, optionally substituted pyrimidinyl, optionally substituted quinolyl, optionally substituted isoquinolyl, optionally substituted benzothiazolyl, optionally substituted benzoxazolyl, optionally substituted benzopyridyl, optionally substituted benzopyridazinyl, optionally substituted benzimidazolyl, optionally substituted benzoxazolyl, optionally substituted thiazolopyridyl optionally substituted isoxazolinonyl, optionally substituted oxazolinonyl, optionally substituted benzoxazinonyl or optionally substituted benzoxyazepinonyl.

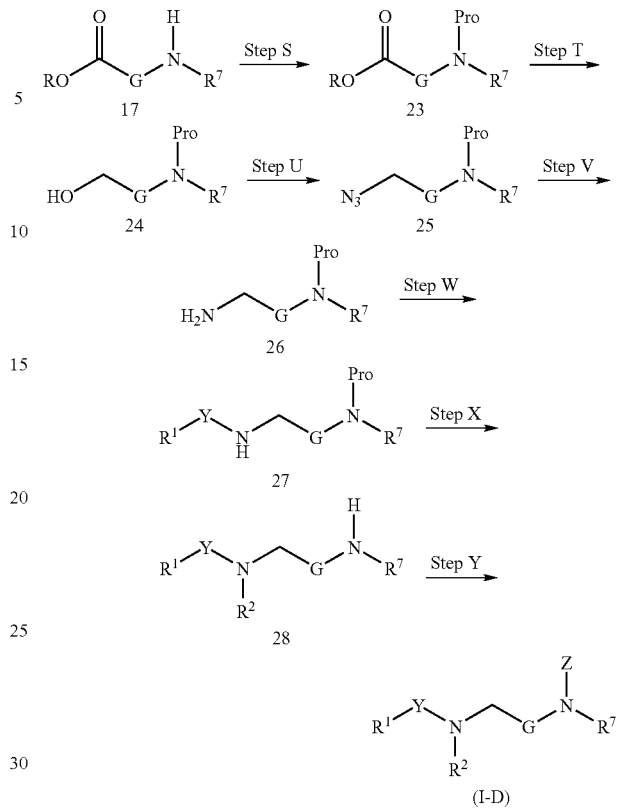

In the above scheme, each symbol has the same meaning as above, —CH₂-G- is the same as —X— in the formula (I), R is alkyl and Pro is an amino protecting group.

Step S

This is the step to introduce a protecting group into Compound 17. As a protecting group, the protecting group described in Protective Groups in Organic Synthesis (Theodra W. Greene) or the like can be used. The amino protecting groups which can be removed under the acid condition are preferable. Examples are benzyloxycarbonyl, tert-butyloxycarbonyl and the like. For example, ProX¹ wherein X¹ is halogen or the like and Pro is benzyloxycarbonyl, tert-butyloxycarbonyl or the like and Pro-O-Pro wherein Pro is benzyloxycarbonyl, tert-butyloxycarbonyl or the like are reacted under the presence of the base to give Compound 23. Examples of the solvent are tetrahydrofuran and dimethylformamide. The reaction may be carried out at room temperature. Examples of the base are triethylamine, pyridine, dimethyl amino pyridine and the like. The reaction also can be carried out with a compound wherein R⁷ is hydrogen.

Step T

This is the step to reduce Compound 23 to give Compound 24. Lithium aluminum hydride can be used as the reducing agent. Examples of the solvent are tetrahydrofuran and the like. The reaction may be carried out at room temperature.

Step U

This is the step to give Compound 25 by azidation of Compound 24. For example, methanesulfonyl chloride is reacted with Compound 24 by using triethylamine as a base to give mesylate. Chloroform can be used as the solvent for the mesylation. Sodium azide is reacted with the obtained compound and azidation is carried out in dimethylformamide or the like at room temperature or under heating to give Compound 25.

Step V

This is the step to reduce Compound 25 to give Compound 26. Compound 25 is reduced with triphenylphosphine and water to give Compound 26. The reaction may be carried out under heating. An example of the solvent is tetrahydrofuran. Except for the reduction method with triphenylphosphine, the catalytic reduction can be used. For the catalytic reduction, 10% palladium carbon or the like can be used as catalyst. Examples of the solvent are ethanol and the like. The reduction method can be suitably selected depending on the used protecting group.

Step W

This is the step to react a compound of the formula: $R^1$—Y—$X^1$ wherein $X^1$ is halogen or the like, Y is S, SO, $SO_2$ or CO with Compound 26 to give Compound 27. Examples of the compound of the formula: $R^1$—Y—$X^1$ wherein $X^1$ is halogen or the like are various sulfonyl chloride, sulfinyl chloride and acyl chloride. Examples of the solvent are tetrahydrofuran, dimethylamide and the like. The reaction may carry out at room temperature or under heating. The reaction is preferably carried out under a base. Examples of the base are pyridine, triethylamine and the like. This reaction can be carried out with a compound of the formula: $R^1$—Y—$X^1$ wherein Y is S or SO to give Compound 27, and then the oxidation can be carried out to transform to a compound wherein Y is $SO_2$ used for the next step.

Step X

This is the step to remove the protecting group of Compound 27. The method for removing the protecting group can be used by selecting various conditions depending on the protecting group. For example, tert-butyloxycarbonyl can be removed with acid. Benzyloxycarbonyl can be removed by catalytic reduction or the like.

Step Y

This is the step to introduce substituent Z into Compound 28. For example, $ZX^1$ wherein $X^1$ is halogen is reacted under the presence of the base to give Compound (I-D). Examples of the solvent are methanol, ethanol, isopropanol, dimethylformamide and the like. The reaction may carry out at room temperature or under heating. For example, it can be carried out in a sealed tube by a microwave reactor. Examples of the base are N,N-diisopropyl ethyl amine and the like.

In the above steps, the following intermediates are useful.

A compound of the formula:

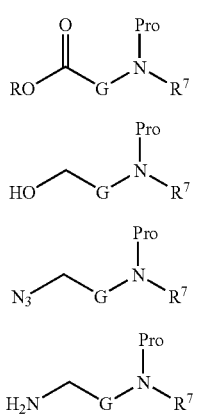

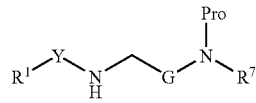

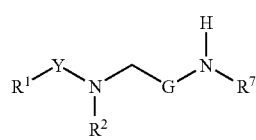

wherein

R is optionally substituted lower alkyl,

Pro is a protecting group, $R^7$ is hydrogen or optionally substituted lower alkyl, G is 1,4-cycloalkylene, Y is $SO_2$ or SO, $R^1$ is optionally substituted lower alkyl, and $R^2$ is hydrogen or optionally substituted lower alkyl.

R is preferably lower alkyl and more preferably methyl and ethyl. Ethyl is especially preferable.

Preferable Pro is amino protecting group which can be removed under the acid condition. Examples of Pro are the formula: —(C=O)—O—R, wherein R is optionally substituted lower alkyl or optionally substituted lower alkenyl. Tert-butyloxycarbonyl is especially preferable.

Preferable $R^7$ is hydrogen.

Preferable Y is $SO_2$.

$R^1$ is preferably lower alkyl and more preferably isopropyl, ethyl and tert-butyl. Tert-butyl is especially preferable.

Preferable $R^2$ is hydrogen.

The following compounds are especially preferable.

A compound of the formula:

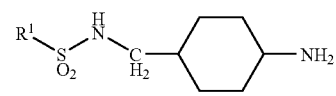

wherein $R^1$ is ethyl or tert-butyl.

A compound of the formula:

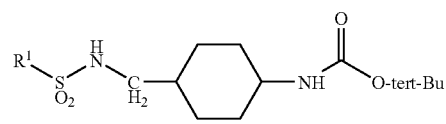

wherein $R^1$ is ethyl, isopropyl or tert-butyl.

A compound of the formula

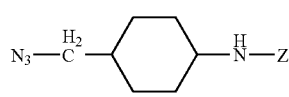

wherein Z is optionally substituted carbocyclyl or optionally substituted heterocyclyl.

All of the compounds for this invention have an NPY Y5 antagonistic activity and the following compounds are especially preferable.

In the formula (I),
a compound wherein $R^1$ is optionally substituted lower alkyl (hereinafter referred to as "$R^1$ is $R^1$-1"),
a compound wherein $R^1$ is C1 to C10 alkyl optionally substituted with halogen (hereinafter referred to as "$R^1$ is R1-2"),
a compound wherein $R^1$ is isopropyl or t-butyl (hereinafter referred to as "$R^1$ is $R^1$-3"),
a compound wherein $R^2$ is hydrogen or C1 to C3 alkyl (hereinafter referred to as "$R^2$ is $R^2$-1"),
a compound wherein $R^2$ is hydrogen (hereinafter referred to as "$R^2$ is $R^2$-2"),
a compound wherein X is optionally substituted lower alkylene, optionally substituted lower alkenylene or a group of the formula:

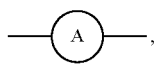

wherein a group of the formula:

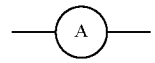

is optionally substituted cycloalkylene, optionally substituted cycloalkenylene, optionally substituted bicycloalkylene, optionally substituted phenylene or optionally substituted heterocyclediyl (hereinafter referred to as "X is X-1"),
a compound wherein X is C2 to C6 alkylene, C3 to C6 alkenylene or a group of the formula:

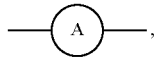

wherein a group of the formula:

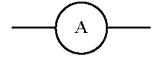

is optionally substituted cycloalkylene, optionally substituted cycloalkenylene, optionally substituted bicycloalkylene, optionally substituted phenylene, optionally substituted piperidinylene, optionally substituted thiophenediyl or optionally substituted furandiyl (hereinafter referred to as "X is X-2"),
a compound wherein X is C2 to C6 alkylene or a group of the formula:

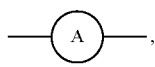

wherein a group of the formula:

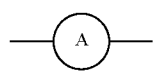

wherein is optionally substituted cycloalkylene, optionally substituted phenylene, optionally substituted piperidinylene, optionally substituted thiophenediyl or optionally substituted furandiyl (hereinafter referred to as "X is X-3"),
a compound wherein X is (i) C2 to C6 alkylene or (ii) cycloalkylene or phenylene, each of which is optionally substituted with halogen, hydroxy, lower alkyl or halogeno (lower alkyl) (hereinafter referred to as "X is X-4"), a compound wherein X is C2 to C6 alkylene or to C5 to C6 cycloalkylene (hereinafter referred to as "X is X-5"),
a compound wherein X is C3 to C6 alkylene or 1,4-cyclohexylene (hereinafter referred to as "X is X-6"),
a compound wherein Y is —SO— (hereinafter referred to as "Y is Y-1"),
a compound wherein Y is —SO$_2$— (hereinafter referred to as "Y is Y-2"),
a compound wherein Y is —CO— (hereinafter referred to as "Y is Y-3"),
a compound wherein Z is optionally substituted lower alkyl, optionally substituted carbocyclyl or optionally substituted heterocyclyl (hereinafter referred to as "Z is Z-1"),
a compound wherein Z is —(CR$^8$, R$^9$)r-W—(CR$^{19}$R$^{11}$)s-V wherein R$^8$, R$^9$, R$^{19}$ and R$^{11}$ are each independently hydrogen or lower alkyl and when Z has two or more of R$^8$, R$^9$, R$^{10}$ and/or R$^{11}$, each of R$^8$, R$^9$, R$^{19}$ and R$^{11}$ may be different,
W is single bond, O, S or NR$^{12}$,
R$^{12}$ is hydrogen, lower alkyl or phenyl,
V is hydrogen, optionally substituted cycloalkyl, optionally substituted bicycloalkyl, optionally substituted aryl or optionally substituted heterocyclyl,
r is an integer of 1 to 4 and
s is an integer of 0 to 4
(hereinafter referred to as "Z is Z-2"),
a compound wherein Z is —(CH$_2$)r-W—(CH$_2$)s-V
wherein W is single bond, O, S or NR$^{12}$,
R$^{12}$ is hydrogen or lower alkyl,
V is optionally substituted aryl or optionally substituted heterocyclyl wherein the substituent(s) is halogen, hydroxy, lower alkyl, halogeno (lower alkyl), lower alkoxy, lower alkenyl, amino, lower alkylamino, acyl, carboxy, lower alkoxycarbonyl, phenyl or monocyclic heteroaryl,
r is an integer of 1 to 4 and
s is an integer of 0 to 4
(hereinafter referred to as "Z is Z-3"),
a compound wherein Z is —(CH$_2$)r-W—(CH$_2$)s-V
wherein W is single bond, O, S, NH or NMe,
V is optionally substituted phenyl or optionally substituted heteroaryl wherein the substituent(s) is halogen, lower alkyl, halogeno (lower alkyl), lower alkoxy, amino or lower alkylamino,
r is an integer of 1 to 3 and
s is an integer of 0 or 1
(hereinafter referred to as "Z is Z-4"),
a compound wherein Z is optionally substituted carbocyclyl, wherein the substituent(s) is halogen; hydroxy; optionally substituted lower alkyl wherein the substituents is halogen, hydroxy, carboxy, lower alkoxycarbonyl, cyano and/or phenyl;
lower alkenyl optionally substituted with lower alkoxycarbonyl;
optionally substituted lower alkoxy wherein the substituents is halogen, hydroxy, lower alkoxy, carboxy, lower alkoxycarbonyl, lower alkylamino, cycloalkyl, cyano and/or heterocyclyl;
cycloalkyl; cycloalkyloxy; acyl; lower alkylthio; carbamoyl; lower alkylcarbamoyl; cycloalkylcarbamoyl; hydroxy imino;

optionally substituted amino wherein the substituents is lower alkyl, optionally protected hydroxy(lower alkyl), lower alkoxy(lower alkyl), acyl, lower alkylsulfonyl, arylsulfonyl and/or phenyl;
phenyl optionally substituted with halogen, cyano, phenyl and/or heterocyclyl;
lower alkylsulfinyl; lower alkylsulfamoyl; cycloalkylsulfamoyl; nitro; cyano; alkylenedioxy; phenylazo optionally substituted with lower alkyl; phenoxy; oxo;
optionally substituted heterocyclyl wherein the substituents is optionally protected hydroxy, mercapto, halogen, lower alkyl, cycloalkyl, lower alkoxycarbonyl, acyl, amino, lower alkoxycarbonylamino, carbamoyl, oxo, phenyl, lower alkoxyphenyl, halogenophenyl, heterocyclyl and/or oxo; heterocyclylsulfonyl optionally substituted with lower alkyl; heterocyclyloxy; heterocyclylcarbonyl optionally substituted with lower alkyl
(hereinafter referred to as "Z is Z-5"),
a compound wherein Z is optionally substituted phenyl wherein the substituent(s) is halogen; hydroxy; lower alkyl optionally substituted with halogen, hydroxy, lower alkoxycarbonyl, cyano and/or phenyl; lower alkoxycarbonyl(lower alkenyl); lower alkoxy optionally substituted with halogen, lower alkoxy, lower alkoxycarbonyl, cycloalkyl and/or heterocyclyl; cycloalkyl; cycloalkyloxy; acyl; lower alkylthio; carbamoyl; lower alkycarbamoyl; amino optionally substituted with lower alkyl, hydroxy(lower alkyl), acyl, lower alkylsulfonyl and/or phenyl; phenyl optionally substituted with halogen, cyano, phenyl and/or heterocyclyl;
lower alkyl sulfamoyl; cycloalkylsulfamoyl; nitro; alkylenedioxy; phenylazo optionally substituted with lower alkyl; phenoxy; oxo; heterocyclyl optionally substituted with hydroxy, halogen, lower alkyl, lower alkoxycarbonyl, amino, carbamoyl, phenyl, halogenophenyl, heterocyclyl and/or oxo; heterocyclyloxy; and/or heterocyclylsulfonyl optionally substituted with lower alkyl
(hereinafter referred to as "Z is Z-6"),
a compound wherein Z is optionally substituted phenyl wherein the substituent(s) is halogen; lower alkyl optionally substituted with halogen, hydroxy, lower alkoxycarbonyl and/or phenyl; lower alkoxy optionally substituted with halogen and/or cycloalkyl; cycloalkyl; cycloalkyloxy; acyl; lower alkylthio; lower alkylcarbamoyl; amino optionally substituted with lower alkyl, hydroxy(lower alkyl), acyl and/or phenyl; phenyl optionally substituted with piperidyl; cycloalkylsulfamoyl; alkylenedioxy; phenoxy;
morpholinyl or morpholino, each of which is optionally substituted with lower alkyl; piperidyl optionally substituted with hydroxy, lower alkyl, lower alkoxycarbonyl, phenyl, halogenophenyl and/or oxo; pyrrolidinyl optionally substituted with hydroxy, carbamoyl and/or oxo; piperazinyl optionally substituted with phenyl or pyrimidinyl; dihydropyridyl; pyrrolyl; pyrrolinyl; imidazolyl optionally substituted with halogen and/or lower alkyl; pyrazolyl; thienyl; thiadiazolyl; furyl; oxazolyl; isoxazolyl; tetrazolyl optionally substituted with lower alkyl and/or phenyl; indolinyl; indolyl; tetrahydroquinolyl; benzothiazolyl optionally substituted with lower alkyl; tetrahydroisothiazolyl optionally substituted with oxo; benzopyranyl optionally substituted with oxo; tetrahydropyranyloxy; tetrahydrofuryloxy; morpholinosulfonyl optionally substituted with lower alkyl; and/or piperidylsulfonyl optionally substituted with lower alkyl
(hereinafter referred to as "Z is Z-7"),
a compound wherein Z is optionally substituted phenyl wherein the substituent(s) is halogen, lower alkyl, halogeno (lower alkyl), lower alkoxy, cycloalkyloxy, lower alkylcarbamoyl, phenyl, lower alkyl morpholino and/or tetrahydropyranyloxy
(hereinafter referred to as "Z is Z-8"),
a compound wherein Z is optionally substituted heterocyclyl wherein the substituent(s) is halogen, hydroxy, lower alkyl, halogeno (lower alkyl), lower alkoxy, mercapto, lower alkylthio, acyl, carboxy, lower alkoxycarbonyl, amino, lower alkylamino, phenyl, naphthyl, phenylthio optionally substituted with halogen, phenoxy optionally substituted with halogen, oxo and/or heterocyclyl optionally substituted with lower alkyl
(hereinafter referred to as "Z is Z-9"),
a compound wherein Z is thienyl, pyrazolyl, thiazolyl, thiadiazolyl, pyridyl, pyrimidinyl, pyrazinyl, pyridazinyl, triazinyl, indolyl, isoindolyl, indolinyl, isoindolinyl, indazolyl, benzopyranyl, benzoxazolyl, benzothienyl, benzothiazolyl, benzothiazolinyl, benzothiadiazolyl, benzimidazolyl, quinolyl, isoquinolyl, dihydrobenzofuryl, carbazolyl, acridinyl, dibenzofuryl or thiazolopyridyl, each of which is optionally substituted with the substituent(s) selected from the group of lower alkyl; halogeno (lower alkyl); lower alkoxy; lower alkoxycarbonyl; acyl; lower alkoxycarbonyl(lower alkyl); mercapto; phenyl, naphthyl, phenylthio or phenoxy, each of which is optionally substituted with halogen; furyl; nitro; oxo; and morpholino optionally substituted with lower alkyl
(hereinafter referred to as "Z is Z-10"),
a compound wherein Z is thienyl, thiazolyl, thiadiazolyl, pyridyl, pyrazinyl, indolyl, isoindolinyl, benzopyranyl, quinolyl, carbazolyl, dibenzofuryl, benzopyranyl, benzothienyl or benzothiazolyl, each of which is optionally substituted with one or more substituent(s) selected from the group of lower alkyl, halogeno (lower alkyl), lower alkoxy, lower alkoxycarbonyl, acyl, phenyl, naphthyl, phenylthio, lower alkyl morpholino and oxo
(hereinafter referred to as "Z is Z-11"), a compound wherein R1 is $R^1$-2, R2 is R2-2, n is 2 and a combination of X, Y and Z, i.e., (X, Y, Z), is any one of the followings.
(X,Y,Z)=(X-3,Y-2,Z-1), (X-3,Y-2,Z-2), (X-3,Y-2,Z-3), (X-3,Y-2,Z-4), (X-3,Y-2,Z-5), (X-3,Y-2,Z-6), (X-3,Y-2,Z-7), (X-3,Y-2,Z-8), (X-3,Y-2,Z-9), (X-3,Y-2,Z-10), (X-3,Y-2,Z-11),
(X-3,Y-3,Z-1), (X-3,Y-3,Z-2), (X-3,Y-3,Z-3), (X-3,Y-3,Z-4), (X-3,Y-3,Z-5), (X-3,Y-3,Z-6), (X-3,Y-3,Z-7), (X-3,Y-3,Z-8), (X-3,Y-3,Z-9), (X-3,Y-3,Z-10), (X-3,Y-3,Z-11)
(X-4,Y-2,Z-1), (X-4,Y-2,Z-2), (X-4,Y-2,Z-3), (X-4,Y-2,Z-4), (X-4,Y-2,Z-5), (X-4,Y-2,Z-6), (X-4,Y-2,Z-7), (X-4,Y-2,Z-8), (X-4,Y-2,Z-9), (X-4,Y-2,Z-10), (X-4,Y-2,Z-11)
(X-4,Y-3,Z-1), (X-4,Y-3,Z-2), (X-4,Y-3,Z-3), (X-4,Y-3,Z-4), (X-4,Y-3,Z-5), (X-4,Y-3,Z-6), (X-4,Y-3,Z-7), (X-4,Y-3,Z-8), (X-4,Y-3,Z-9), (X-4,Y-3,Z-10), (X-4,Y-3,Z-11),
(X-5,Y-2,Z-1), (X-5,Y-2,Z-2), (X-5,Y-2,Z-3), (X-5,Y-2,Z-4), (X-5,Y-2,Z-5), (X-5,Y-2,Z-6), (X-5,Y-2,Z-7), (X-5,Y-2,Z-8), (X-5,Y-2,Z-9), (X-5,Y-2,Z-10), (X-5,Y-2,Z-11),
(X-5,Y-3,Z-1), (X-5,Y-3,Z-2), (X-5,Y-3,Z-3), (X-5,Y-3,Z-4), (X-5,Y-3,Z-5), (X-5,Y-3,Z-6), (X-5,Y-3,Z-7), (X-5,Y-3,Z-8), (X-5,Y-3,Z-9), (X-5,Y-3,Z-10), or (X-5,Y-3,Z-11)
the pharmaceutically acceptable salt or solvate thereof.

The compounds for this invention are useful for the prevention or treatment of obesity, obesity-related disorders or the like, and for the weight management for obesity.

The "obesity-related disorders" are associated with, caused by, or result from obesity. Examples of obesity-related disorder are overeating, hypertension, impaired glucose tolerance, diabetes, metabolic syndrome, abnormal lipid metabolism, dislipidemia, arteriosclerosis, hyperuricemia, gout, fatty liver, endometrial, breast, prostate and colon cancer, osteoarthritis, lumbago, obstructive sleep apnea syndrome, coronary artery disease (coronary heart disease), cerebral infarction, menstrual disorder, the Prader-Willi Syndrome, Frohlich's syndrome, pickwickian syndrome and the like. The pharmaceutical compositions of the present invention are also useful for reducing the risk of secondary outcomes of obesity, such as reducing the risk of left ventricular hypertrophy or the like. They are also useful to treat Alzheimer's disease.

The anorectic or anti-obesity composition of this invention is especially useful for preventing and/or treating obesity and suppressing food intake. Moreover, the composition is effective for preventing and/or treating the diseases in which obesity acts as a risk factor, for example, diabetes, hypertension, hyperlipemia, atherosclerosis, acute coronary syndrome and the like.

Furthermore, a compound for this invention has not only NPY Y5 receptor antagonistic activity but also any or all good characters as a medicine selected from the followings.
a) weak CYP enzyme (e.g., CYP1A2, CYP2C9, CYP3A4 or the like) inhibition.
b) less induction of a drug-metabolizing enzyme.
c) good drug disposition such as high bioavailability.
d) low toxicity of anemia-inducing activity or the like.
e) high metabolic stability.
f) high selectivity for Y5 receptor.
g) high water solubility.
h) high transportability through the blood-brain barrier.
i) no reproductive toxicity (e.g., teratogenicity or the like).
j) no gastrointestinal tract disturbance (e.g., hemorrhagic enteritis, gastrointestinal ulceration, gastrointestinal hemorrhage or the like).

In addition, a compound for this invention has a low affinity for NPY Y1 and Y2 receptors, and has a high selectivity for NPY Y5 receptor. NPY causes a sustained vasoconstrictive action in the periphery and this action is mainly via Y1 receptor. Since Y5 receptor is not involved in this action at all, the compound has a low risk of inducing side effects based on the peripheral vasoconstriction, and is expected to be suitably used as a safe medicine.

The compound for this invention shows an anti-obesity effect by suppressing food intake. Therefore, it is one of the features of the present antagonist not to induce side effects such as dyspepsia caused by an anti-obesity agent which inhibits digestion and absorption, or central nervous system side-effects such as an antidepressant effect due to a serotonin transporter inhibitor that shows an anti-obesity effect.

An anorectic or anti-obesity composition of this invention can be administered orally or parenterally. In the case of oral administration, it may be in any usual form such as tablets, granules, powders, capsules, pills, solutions, syrups, buccal tablets, sublingual tablets and the like. When the composition is parenterally administered, any usual form is preferable, for example, injections (e.g., intravenous, intramuscular and the like), suppositories, endermic agents, inhalations and the like. Oral administration is especially preferable because the compounds for this invention show a high oral absorbability.

A pharmaceutical composition may be manufactured by mixing an effective amount of a compound for this invention with various pharmaceutical additives suitable for the administration form, such as excipients, binders, moistening agents, disintegrants, lubricants and diluents. When the composition is of an injection, an active ingredient together with a suitable carrier can be sterilized to give a pharmaceutical composition.

Examples of the excipients include lactose, saccharose, glucose, starch, calcium carbonate, crystalline cellulose and the like. Examples of the binders include methylcellulose, carboxymethylcellulose, hydroxypropylcellulose, gelatin, polyvinylpyrrolidone and the like. Examples of the disintegrants include carboxymethylcellulose, sodium carboxymethylcellulose, starch, sodium alginate, agar, sodium lauryl sulfate and the like. Examples of the lubricants include talc, magnesium stearate and macrogol, and the like. Cacao oil, macrogol, methylcellulose or the like may be used as base materials of suppositories. When the composition is manufactured as solutions, emulsified injections or suspended injections, solubilizing agents, suspending agents, emulsifiers, stabilizers, preservatives, isotonic agents and the like which are usually used may be added. For oral administration, sweetening agents, flavors and the like which are usually used may be added.

Although the dosage of a compound of this invention as an anorectic or anti-obesity composition should be determined in consideration of the patient's age and body weight, the type and degree of diseases, the administration route and the like, a usual oral dosage for an adult is 0.05 to 100 mg/kg/day and preferable is 0.1 to 10 mg/kg/day. For parenteral administration, although the dosage highly varies with administration routes, a usual dosage is 0.005 to 10 mg/kg/day and preferably 0.01 to 1 mg/kg/day. The dosage may be administered in one to several divisions per day.

A pharmaceutical composition of this invention can be used in combination of the other known anti-obesity agent(s). Furthermore, a method of treatment by administering a pharmaceutical composition of this invention can be used in combination of the known dietary therapy, drug therapy, exercise and the like.

This invention is further explained by the following Examples, which are not intended to limit the scope of this invention.

The abbreviations used in the present description stand for the following meanings.

| | |
|---|---|
| Me: | methyl |
| Et: | ethyl |
| i-Pr: | isopropyl |
| DMSO: | dimethylsulfoxide |
| Pd—C: | palladium carbon |
| THF: | tetrahydrofuran |
| DMF: | N,N-dimethylformamide |
| mCPBA: | meta-Chloroperoxybenzoic acid |

EXAMPLE

Example 1

Synthesis of Compound (Ii-1)

Step 1

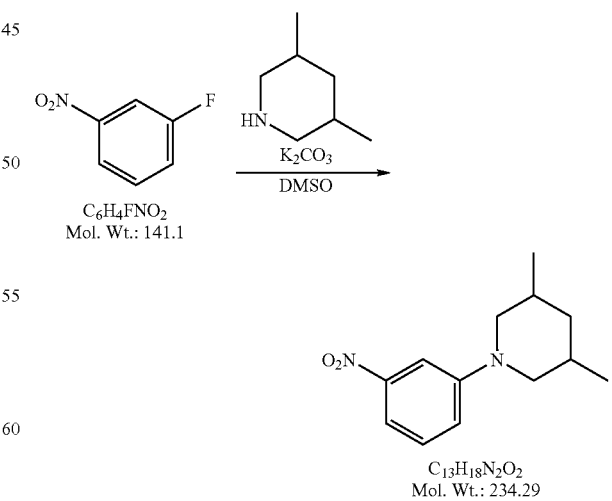

3-Fluoronitrobenzene (2.00 g, 14.2 mmol) was dissolved in dimethylsulfoxide (15 ml). 3,5-Dimethylpiperidine (3.21 g, 28.4 mmol) and potassium carbonate (3.92 g, 28.4 mmol)

were added thereto and the mixture was stirred for 3 hours at 150° C. The reactant was poured into water and extracted with ethyl acetate. The organic layer was washed with water and dried over sodium sulphate anhydrous. The solvent was removed under reduced pressure. Ethyl acetate and hexane were added to the residue. The precipitated crystals were collected with filtration to give the desired substituted nitrobenzene (2.05 g, 62% yield).

$^1$H-NMR (CDCl$_3$) δ ppm: 0.76 (q, 1H, J=12.0 Hz), 0.96 (d, 6H, J=6.3 Hz), 1.70-1.91 (m, 3H), 2.32 (t, 2H, J=12.0 Hz), 3.62-3.72 (m, 2H), 7.17-7.25 (m, 1H), 7.34 (t, 1H, J=8.1 Hz), 7.59 (d, 1H, J=8.1 Hz), 7.71 (s, 1H).

Step 2

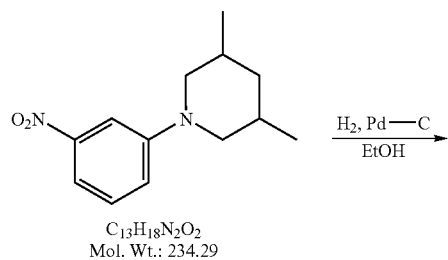

The compound obtained in Step 1 (2.05 g, 8.75 mmol) was dissolved in ethanol (25 ml) and 10% Pd—C (0.20 g) was added thereto to carry out the hydrogenation reaction for 12 hours. Pd—C was removed by celite filtration and the filtrate was condensed under reduced pressure. The residue was purified by silica gel chromatography to give the desired Aniline (1.62 g, 90% yield).

$^1$H-NMR (CDCl$_3$) δ ppm: 0.69 (q, 1H, J=12.0 Hz), 0.92 (d, 6H, J=6.3 Hz), 1.75-1.98 (m, 3H), 2.22 (t, 2H, J=12.0 Hz), 3.53-3.62 (m, 2H), 6.21 (d, 1H, J=7.5 Hz), 6.38 (s, 1H), 6.42 (d, 1H, J=8.1 Hz), 7.04 (t, 1H, J=8.1 Hz).

Step 3

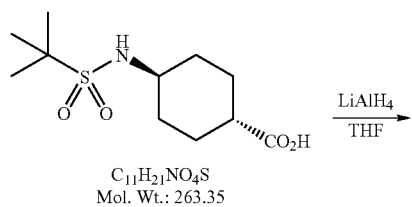

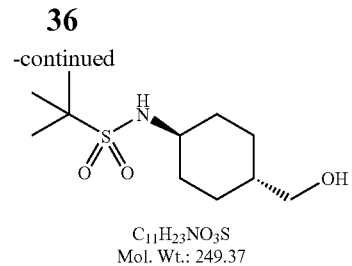

Carboxylic acid (the synthesis method was described in WO01/037826) (5.04 g, 19.1 mmol) was suspended in tetrahydrofuran (50 ml). Lithium aluminum hydride (0.726 g, 19.1 mmol) was added thereto under ice-cooling and the mixture was stirred at room temperature for 1 hour. The reactant was stirred under ice-cooling and water (1.5 mL) was carefully added dropwise. After that, the mixture was stirred at room temperature for 5 minutes and the generated deposit was removed by filtration. The filtrate was condensed under reduced pressure. Ethyl acetate and hexane were added to the residue. The precipitated crystals were collected with filtration to give the desired Alcohol (3.15 g, 66% yield).

$^1$H-NMR (DMSO-d6) δ ppm: 0.88 (q, 2H, J=11.6 Hz), 1.25 (s, 9H), 1.15-1.30 (m, 3H), 1.67-1.76 (m, 2H), 1.83-1.92 (m, 2H), 2.97 (m, 1H), 3.13-3.20 (m, 2H), 4.35 (t, 1H, J=5.2 Hz), 6.71 (d, 1H, J=8.8 Hz).

Step 4

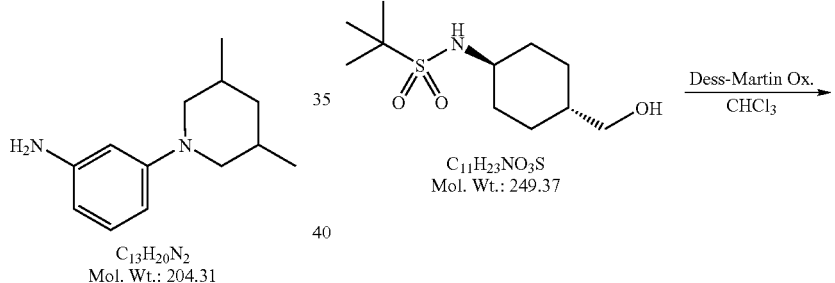

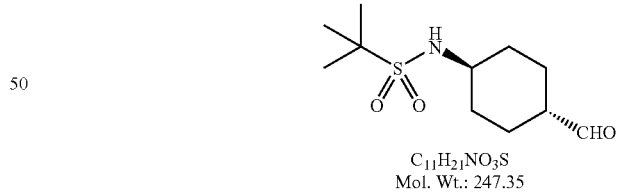

The compound obtained in Step 3 (500 mg, 2.01 mmol) was dissolved in chloroform (5 ml) and Dess-Martin periodinane (893 mg, 2.11 mmol) was added thereto. The mixture was stirred at room temperature for 1 hour. The deposit was removed by filtration and the filtrate was condensed under reduced pressure. The residue was purified by silica gel chromatography to give the desired Aldehyde (385 mg, 77% yield).

$^1$H-NMR (DMSO-d6) δ ppm: 1.26 (s, 9H), 1.13-1.38 (m, 4H), 1.85-1.98 (m, 4H), 2.16 (m, 1H), 3.01 (m, 1H), 6.80 (d, 1H, J=8.0 Hz), 9.54 (s, 1H).

Step 5

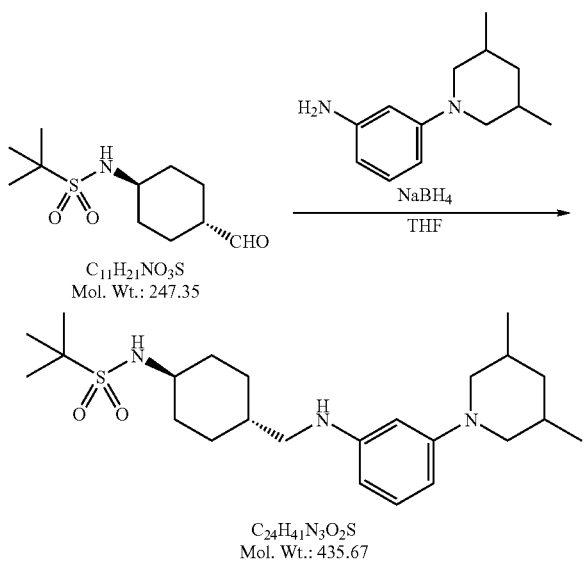

Aniline obtained in Step 2 (107 mg, 0.523 mmol) was dissolved in tetrahydrofuran (3 ml). Aldehyde obtained in Step 4 (130 mg, 0.523 mmol) was added thereto and the mixture was stirred at room temperature for 1 hour. To the reactant was added sodium borohydride (23.7 mg, 0.628 mmol) and the mixture was stirred at room temperature for 3 hours. The reactant was poured into water and extracted with ethyl acetate. The organic layer was washed with water and dried over sodium sulphate anhydrous. The solvent was removed under reduced pressure and the residue was purified by silica gel chromatography to give the desired compound (99.3 mg, yield 43%).

$^1$H-NMR (DMSO-d6) δ ppm: 0.64 (q, 1H, J=11.6 Hz), 0.87 (d, 6H, J=6.0 Hz), 0.92-1.08 (m, 2H), 1.25 (s, 9H), 1.15-1.32 (m, 2H), 1.41 (m, 1H), 1.58-1.95 (m, 7H), 2.08 (t, 2H, J=11.6 Hz), 2.75-2.82 (m, 2H), 3.00 (m, 1H), 3.48-3.55 (m, 2H), 5.31 (m, 1H), 5.94 (d, 1H, J=8.5 Hz), 6.08-6.13 (m, 2H), 6.71 (d, 1H, J=8.5 Hz), 6.85 (t, 1H, J=8.5 Hz). Melting point: 161 to 162° C.

Example 2

Synthesis of Compound (Ij-1)

Step 1

Amine (1.20 g, 3.64 mmol) and 2-chloro-5-trifluoromethylpyridine (727 mg, 4.01 mmol) was suspended in isopropanol (4 ml) and N,N-diisopropyl ethyl amine (1.87 ml, 10.9 mmol) was added thereto. After the mixture was in sealed tubes, the reaction was carried out by a microwave reactor for 1 hour at 160° C. The reactant was poured into water and extracted with ethyl acetate. The organic layer was washed with water and dried over sodium sulphate anhydrous. The solvent was removed under reduced pressure and the residue was purified by silica gel chromatography to give the desired Ester (222 mg, 20% yield).

Step 2

Ester obtained in Step 1 (207 mg, 0.685 mmol) was dissolved in tetrahydrofuran (3 ml). Lithium aluminum hydride (31.1 mg, 0.822 mmol) was added thereto under ice-cooling and the mixture was stirred at room temperature for 0.5 hour. The reactant was poured into iced water and extracted with ethyl acetate. The organic layer was washed with water and dried over sodium sulphate anhydrous. The solvent was removed under reduced pressure to give alcohol. The obtained alcohol was dissolved in chloroform (3 ml). Triethylamine (0.28 ml, 2.04 mmol) was added thereto and methanesulfonyl chloride (0.12 ml, 1.64 mmol) was added dropwise under ice-cooling. The mixture was stirred at room temperature for 1 hour. The reactant was poured into water and extracted with ethyl acetate. The organic layer was washed with water and dried over sodium sulphate anhydrous. The solvent was removed under reduced pressure to give mesylate. The obtained mesylate was dissolved in dimethylformamide (3 ml) and sodium azide (221 mg, 3.40 mmol) was added thereto. The mixture was stirred for 3 hours at 100° C. The reactant was poured into water and extracted with ethyl acetate. The organic layer was washed with water and dried over sodium sulphate anhydrous. The solvent was removed under reduced pressure. The residue was purified by silica gel chromatography to give the desired Azide (178 mg, 87% yield).

Step 3

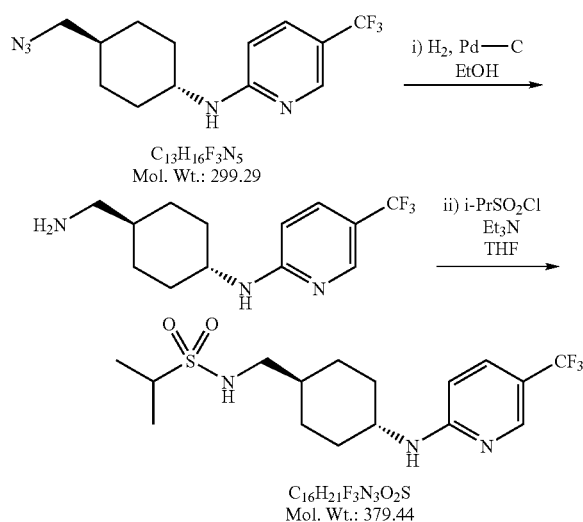

Azide (178 mg, 0.595 mmol) obtained in Step 2 was dissolved in ethanol (3 ml) and 10% Pd—C (30 mg) was added thereto to carry out the hydrogenation reaction for 4 hours. Pd—C was removed by celite filtration and the filtrate was condensed under reduced pressure to give amine.

The obtained amine was dissolved in tetrahydrofuran (3 ml) and triethylamine (0.28 ml, 0.714 mmol) was added thereto. Isopropyl sulfonyl chloride (0.10 ml, 1.64 mmol) was added dropwise under ice-cooling and the mixture was stirred for 1 hour. The reactant was poured into water and extracted with ethyl acetate. The organic layer was washed with water and dried over sodium sulphate anhydrous. The solvent was removed under reduced pressure. The residue was purified by silica gel chromatography to give the desired compound (64.8 mg, 29% yield).

$^1$H-NMR (DMSO-d$_6$) δ: 0.92-1.06 (m, 2H), 1.10-1.25 (m, 2H,), 1.22 (d, 6H, J=6.4 Hz), 1.38 (m, 1H), 1.76-1.84 (m, 2H), 1.93-2.02 (m, 2H), 2.81 (t, 2H, J=6.0 Hz), 3.08-3.19 (m, 1H), 3.69 (m, 1H), 6.53 (d, 1H, J=8.8 Hz), 6.95 (t, 1H, J=5.6 Hz), 7.16 (d, 1H, J=7.6 Hz), 7.58 (d, 1H, J=8.8 Hz), 8.26 (s, 1H) Melting point: 155-156° C.

Example 3

Synthesis of Compound (Ij-62)

Step 1

MeO$_2$C⋯⋯NH$_2$
C$_{15}$H$_{23}$NO$_5$S
Mol. Wt.: 329.41

$\xrightarrow{\text{(Boc)}_2\text{O}, \text{Et}_3\text{N}, \text{CH}_2\text{Cl}_2}$ -continued MeO$_2$C⋯⋯N(H)Boc
C$_{13}$H$_{23}$NO$_4$
Mol. Wt.: 257.33

Amine (132 g, 401 mmol) was suspended in dichloromethane (1000 ml) under ice-cooling. Triethylamine (123 ml, 882 mmol) and (Boc)$_2$O (101 ml, 440 mmol) were sequentially added thereto and stirred for 10 minutes. After that, the mixture was stirred at room temperature for 2 hours and the solvent was removed. The residue was poured into aqueous citric acid (citric acid monohydrate 50 g in water 400 ml) to become pH4 and extracted with ethyl acetate. The organic layer was washed with water and dried over magnesium sulfate anhydrous. The solvent was removed under reduced pressure to quantitatively give the target compound.

$^1$H-NMR (DMSO-d6) δ ppm: 1.06-1.25 (m, 2H), 1.25-1.43 (m, 2H), 1.37 (s, 9H), 1.75-1.94 (m, 4H), 2.19 (tt, 1H, J=11.7, 3.9 Hz), 3.07-3.24 (m, 1H), 3.58 (s, 3H), 6.74 (d, 1H, J=6.6 Hz).

Step 2

MeO$_2$C⋯⋯N(H)Boc
C$_{13}$H$_{23}$NO$_4$
Mol. Wt.: 257.33

$\xrightarrow{\text{LiAlH}_4, \text{THF}}$

HO⋯⋯N(H)Boc
C$_{12}$H$_{23}$NO$_3$
Mol. Wt.: 229.32

Lithium aluminum hydride (18.3 g, 483 mmol) was suspended in tetrahydrofuran (800 ml) and ester in tetrahydrofuran (300 ml) obtained in Step 1 was slowly added thereto under ice-cooling with stirring over 1 hour. The mixture was reacted under ice-cooling for 10 minutes and at room temperature for 2.5 hours. The reactant was ice-cooled and the mixture of water and tetrahydrofuran (1:1, 36 ml), 2 N aqueous sodium hydroxide (18 ml) and water (18 ml) were sequentially added thereto. The mixture was stirred for 20 minutes and at room temperature for 1.5 hours. The deposit was removed by filtration and the filtrate was condensed under reduced pressure. Ethyl acetate and hexane were added to the residue. The precipitated crystals were collected with filtration to give the desired Alcohol (79.5 g, 87% yield) (through Step 1 to 2). $^1$H-NMR (DMSO-d6) δ ppm: 0.78-1.00 (m, 2H), 1.00-1.32 (m, 3H), 1.37 (s, 9H), 1.65-1.84 (m, 4H), 3.04-3.24 (m, 3H), 4.32-4.42 (m, 1H), 6.66 (d, 1H, J=7.8 Hz).

Step 3

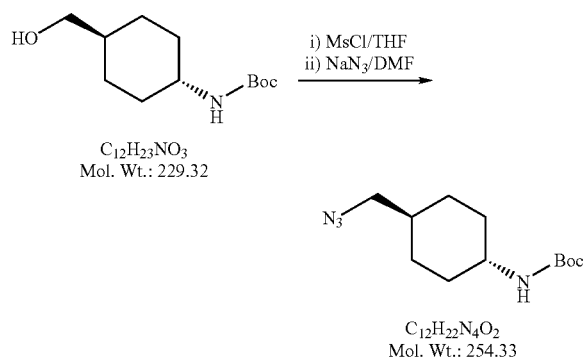

Alcohol (79.5 g, 347 mmol) was dissolved in tetrahydrofuran (800 ml). Triethylamine (72.5 ml, 520 mmol) and methanesulfonyl chloride (32.2 ml, 416 mmol) were sequentially added thereto under ice-cooling with stirring and the mixture was reacted for 1.5 hour. The reactant was poured into aqueous citric acid (citric acid monohydrate 30 g in water 500 ml) to become pH 4 and extracted with ethyl acetate. The organic layer was washed with water and dried over magnesium sulfate anhydrous. The solvent was removed under reduced pressure. The crystal deposited in the removal process was collected by filtration and washed with hexane to give mesylate (100 g). The obtained mesylate was dissolved in dimethylformamide (100 ml) and sodium azide (63.7 g, 980 mmol) was added thereto and reacted at 80° C. for 2 hours. The reactant was poured into water and extracted with ethyl acetate. The organic layer was washed with water and dried over magnesium sulfate anhydrous. The solvent was removed under reduced pressure to quantitatively give the desired Azide (the crude weight is 85.4 g).

$^1$H-NMR (DMSO-d6) δ ppm: 0.90-1.21 (m, 4H), 1.32-1.50 (m, 1H), 1.37 (s, 9H), 1.65-1.84 (m, 4H), 3.06-3.24 (m, 3H), 6.71 (d, 1H, J=8.1 Hz).

Step 4

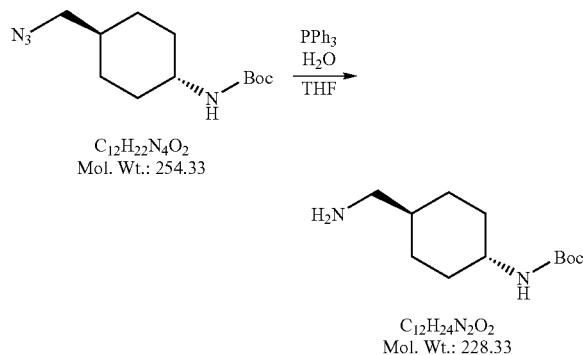

Azide obtained in Step 3 was dissolved in tetrahydrofuran (900 ml) at room temperature. Triphenylphosphine (103 g, 392 mmol) and water (90 ml) were sequentially added thereto and reacted at 80° C. for 1.5 hours. The solvent (770 ml) was removed and water (300 ml), ethyl acetate (400 ml) and 2 N hydrochloric acid (150 ml) were sequentially added thereto to become pH 2.5 and liquid-liquid extraction was carried out. The organic layer was backextracted with 2 N hydrochloric acid. After washing with ethyl acetate, the aqueous layer was alkalinized and extracted repeatedly with ethyl acetate and chloroform. The organic layers were combined and dried over magnesium sulfate anhydrous. The solvent was removed under reduced pressure and hexane was added to the residue. The precipitated crystals were collected with filtration and washed with hexane to give the desired Amine (41.7 g, 53% yield) (through Step 3 to 4).

$^1$H-NMR (DMSO-d6) δ ppm: 0.77-0.96 (m, 2H), 1.00-1.18 (m, 3H), 1.37 (s, 9H), 1.67-1.82 (m, 4H), 2.30-2.38 (m, 2H), 2.90-3.60 (m, 2H), 3.05-3.22 (m, 1H), 6.66 (d, 1H, J=7.2 Hz).

Step 5

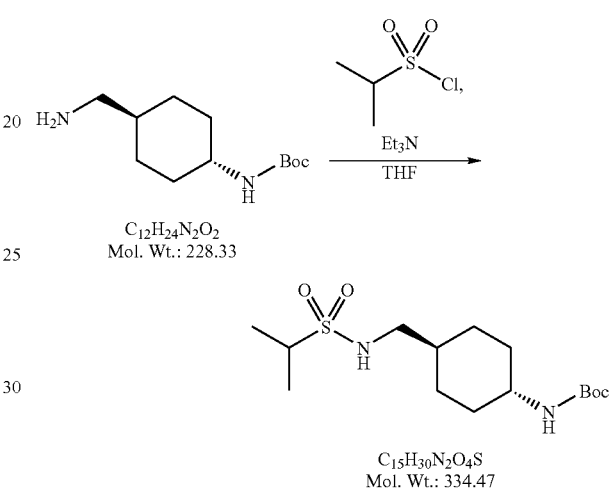

Amine (37.5 g, 164 mmol) was suspended in tetrahydrofuran (400 ml). Triethylamine (91.7 ml, 656 mmol) and isopropyl sulfonyl chloride (32.2 ml, 416 mmol) were slowly and sequentially added thereto within the range of −55° C. to −40° C. with stirring. The mixture was stirred for 6 hours with gradually warming to 0° C. The reactant was poured into the ice-cooled dilute aqueous acid and extracted with ethyl acetate. The organic layer was washed with water and dried over magnesium sulfate anhydrous. The solvent was removed under reduced pressure and isopropyl ether was added to the residue. The precipitated crystals were collected with filtration and washed with isopropyl ether to give the desired Sulfonamide (43.1 g, 79% yield).

$^1$H-NMR (DMSO-d6) δ ppm: 0.79-0.98 (m, 2H), 1.00-1.36 (m, 3H), 1.20 (d, 6H, J=6.6 Hz), 1.37 (s, 9H), 1.70-1.84 (m, 4H), 2.72-2.80 (m, 2H), 3.04-3.22 (m, 2H), 6.68 (d, 1H, J=8.1 Hz), 6.94 (t, 1H, J=6.0 Hz).

Step 6

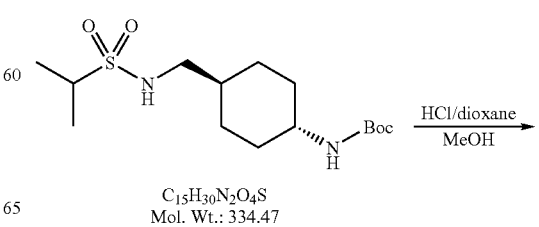

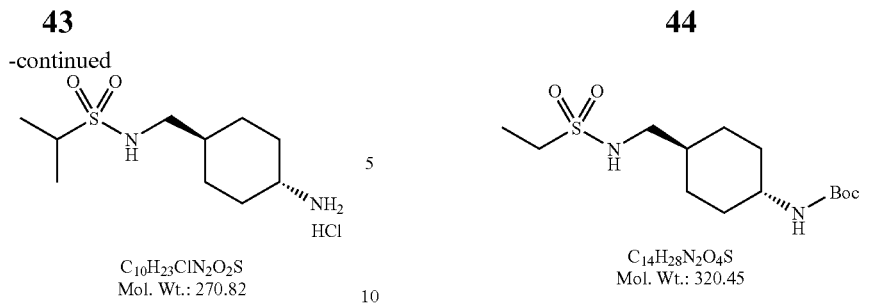

Boc-protected amine (43.0 g, 128 mmol) was suspended in methanol (200 ml) and 4 N hydrochloric acid in dioxane (96 ml, 384 mmol) was added thereto under ice-cooling with stirring for 20 minutes and at room temperature for 3 hours. The reactant was ice-cooled and isopropyl ether (220 ml) was added thereto. After stirring for 30 minutes, the precipitated crystals were collected with filtration and washed with isopropyl ether to give the desired Amine hydrochloride (30.8 g, 89% yield).

$^1$H-NMR (DMSO-d6) δ ppm: 0.85-1.02 (m, 2H), 1.20 (d, 6H, J=6.6 Hz), 1.20-1.40 (m, 3H), 1.75-1.84 (m, 2H), 1.90-2.00 (m, 2H), 2.73-2.82 (m, 2H), 2.83-2.97 (m, 1H), 3.08-3.20 (m, 1H), 7.01 (t, 1H, J=5.7 Hz), 8.01 (s, 3H).

Step 7

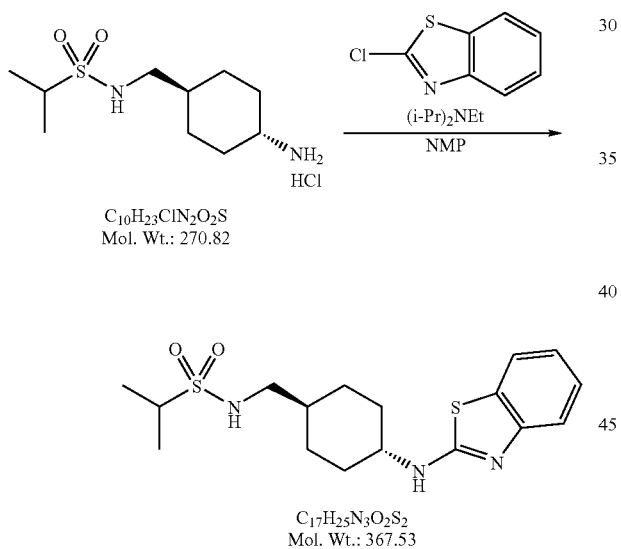

Amine hydrochloride (1.4 g, 5.16 mmol) and 2-chlorobenzothiazole (2.63 g, 15.5 mmol) were suspended in N-methylpyrrolidone (15 ml) and N,N-diisopropylethyl amine (4.50 ml, 25.8 mmol) was added thereto. After the mixture was divided into two reaction vials, the reaction were carried out by a microwave reactor for 30 minutes at 220° C. The reactants from the two vials were poured into water and extracted with ethyl acetate. The organic layer was washed with water and dried over sodium sulphate anhydrous. The solvent was removed under reduced pressure and the residue was purified by silica gel chromatography to give the desired Compound (Ij-62) (1.5 g, 79% yield).

In Step 5, ethanesulfonyl chloride instead of isopropyl sulfonyl chloride was reacted to give the following compound wherein $R^1$ is ethyl.

$^1$H-NMR (DMSO-d6) δ ppm: 0.80-0.98 (m, 2H), 1.02-1.18 (m, 2H), 1.17 (t, 3H, J=7.2 Hz), 1.22-1.34 (m, 1H), 1.37 (s, 9H), 1.68-1.82 (m, 4H), 2.68-2.78 (m, 2H), 2.96 (q, 2H, J=7.2 Hz), 3.04-3.22 (m, 1H), 6.68 (d, 1H, J=8.1 Hz), 6.94 (t, 1H, J=6.0 Hz).

In Step 5, tert-butyl sulfinylchloride instead of isopropyl sulfonyl chloride was reacted and the oxidation with mCPBA was carried out to give the following compound wherein $R^1$ is tert-butyl (WO2001037826, Example 3).

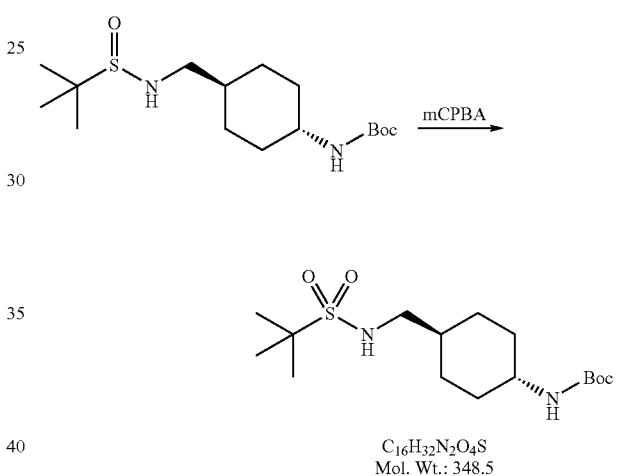

$^1$H-NMR (DMSO-d6) δ ppm: 0.79-1.00 (m, 2H), 1.01-1.20 (m, 2H), 1.22-1.34 (m, 1H), 1.25 (s, 9H), 1.37 (s, 9H), 1.70-1.86 (m, 4H), 2.81-2.90 (m, 2H), 3.04-3.22 (m, 1H), 6.68 (d, 1H, J=8.1 Hz), 6.83 (t, 1H, J=6.0 Hz).

The following compounds wherein $R^1$ is ethyl or tert-butyl were obtained in Step 6 by using the above compound.

A compound wherein $R^1$ is ethyl.

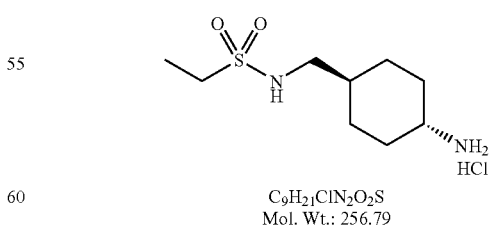

H-NMR (DMSO-d6) δ ppm: 0.84-1.02 (m, 2H), 1.18 (t, 3H, J=7.5 Hz), 1.20-1.40 (m, 3H), 1.74-1.82 (m, 2H), 1.90-2.00 (m, 2H), 2.72-2.80 (m, 2H), 2.83-2.96 (m, 1H), 2.97 (q, 2H, J=7.5 Hz), 7.04 (t, 1H, J=6.0 Hz), 8.03 (s, 3H).

A compound wherein R¹ is tert-butyl.

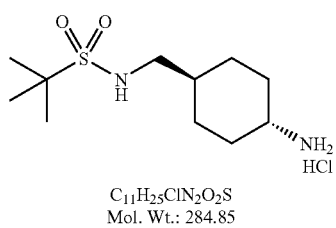

C₁₁H₂₅ClN₂O₂S
Mol. Wt.: 284.85

H-NMR (DMSO-d6) δ ppm: 0.84-1.04 (m, 2H), 1.16-1.38 (m, 3H), 1.26 (s, 9H), 1.74-1.84 (m, 2H), 1.92-2.02 (m, 2H), 2.82-2.98 (m, 3H), 6.90 (d, 1H, J=6.0 Hz), 8.01 (s, 3H).

Example 4

Synthesis of Compound (Ij-162)

Step 1

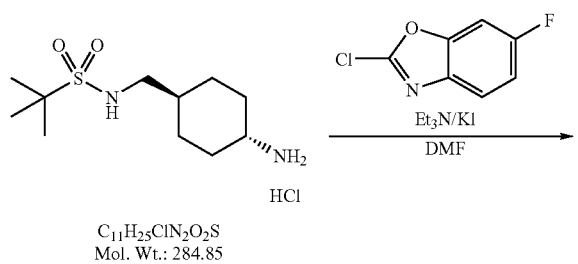

C₁₁H₂₅ClN₂O₂S
Mol. Wt.: 284.85

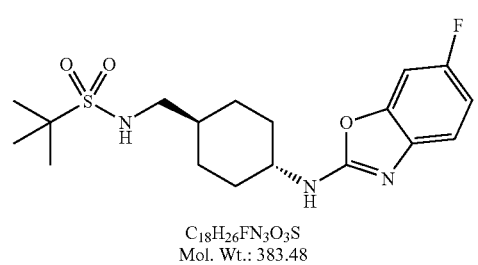

C₁₈H₂₆FN₃O₃S
Mol. Wt.: 383.48

Amine hydrochloride (737.4 g, 2.59 mol) and 2-chloro-5-fluorobenzoxazole (457.4 g, 2.67 mol) were suspended in N,N-dimethylformamide (3.69 L). Triethylamine (2.17 L, 15.54 mol) and potassium iodide (128.9 g, 0.78 mol) were added thereto. To the mixture, 2-chloro-5-fluorobenzoxazole (457.4 g, 2.67 mol) dissolved in N,N-dimethylformamide (1.48 L) was added dropwise under ice-cooling and stirring. After finishing the drop-wise addition, the mixture was stirred under ice-cooling for 1 hour, at room temperature for 1 hour and then at 40° C. for 2 hours. The mixture was cooled to room temperature under ice-cooling. Water (5.16 L) was added dropwise and the mixture was suspended. After stirring at room temperature for 3 hours, the precipitated crystals were filtrated and washed with water (5.16 L) to give the desired crude product (903.4 g).

Step 2

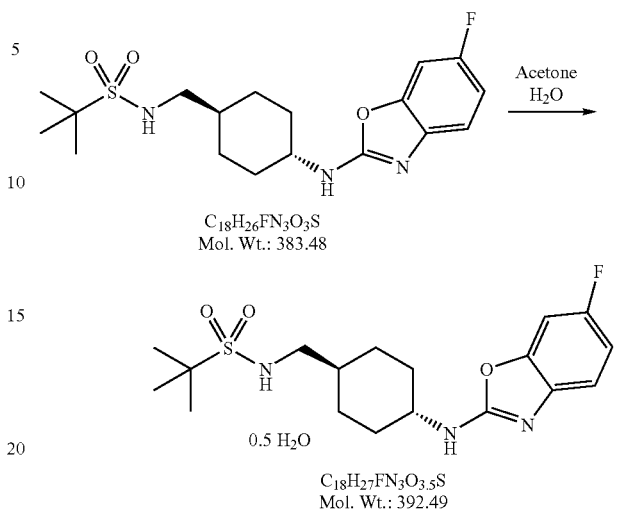

C₁₈H₂₆FN₃O₃S
Mol. Wt.: 383.48

0.5 H₂O

C₁₈H₂₇FN₃O₃.₅S
Mol. Wt.: 392.49

The obtained crude product in Step 1 (10.0 g) was dissolved in acetone (160 ml) at 70° C. and insoluble matter was removed by the filtration with filter paper. After washing with acetone (20 ml), pure water (60 ml) was added dropwise under stirring at room temperature. After finishing the drop-wise addition, the mixture was stirred at room temperature for 150 minutes, and then under ice-cooling for 120 minutes. After the suspension was filtrated and washed with cold 50% aqueous acetone solution (30 ml) and pure water (30 ml). The filtrated crystals were dried at 50° C. under reduced pressure to give the desired compound (Ij-162) (8.49 g).

¹H-NMR (DMSO-d₆) δ: 0.93-1.06 (m, 2H), 1.21-1.49 (m, 3H), 1.27 (s, 9H), 1.77-1.87 (m, 2H), 1.98-2.10 (m, 2H), 2.89 (t, 2H, J=6.3 Hz), 3.38-3.54 (m, 1H), 6.87 (t, 1H, J=5.7 Hz), 6.90-6.98 (m, 1H), 7.20 (dd, 1H, J=8.7, 5.1 Hz), 7.33 (dd, 1H, J=8.4, 2.4 Hz), 7.88 (d, 1H, J=7.8 Hz). Anal. Calcd for C₁₈H₂₆FN₃O₃S.0.5H₂O: C, 55.08; H, 6.93; F, 4.84; N, 10.71; S, 8.17. Found: C, 55.22; H, 7.05; F, 4.68; N, 10.79; S, 7.78.

The following compounds synthesized in similar methods also include this invention.

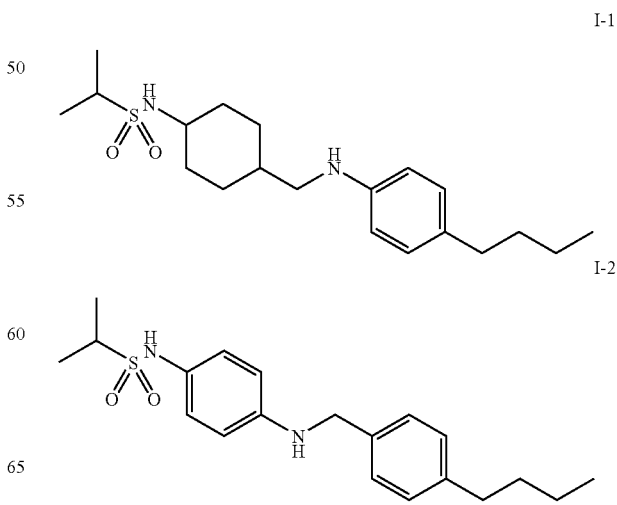

I-1

I-2

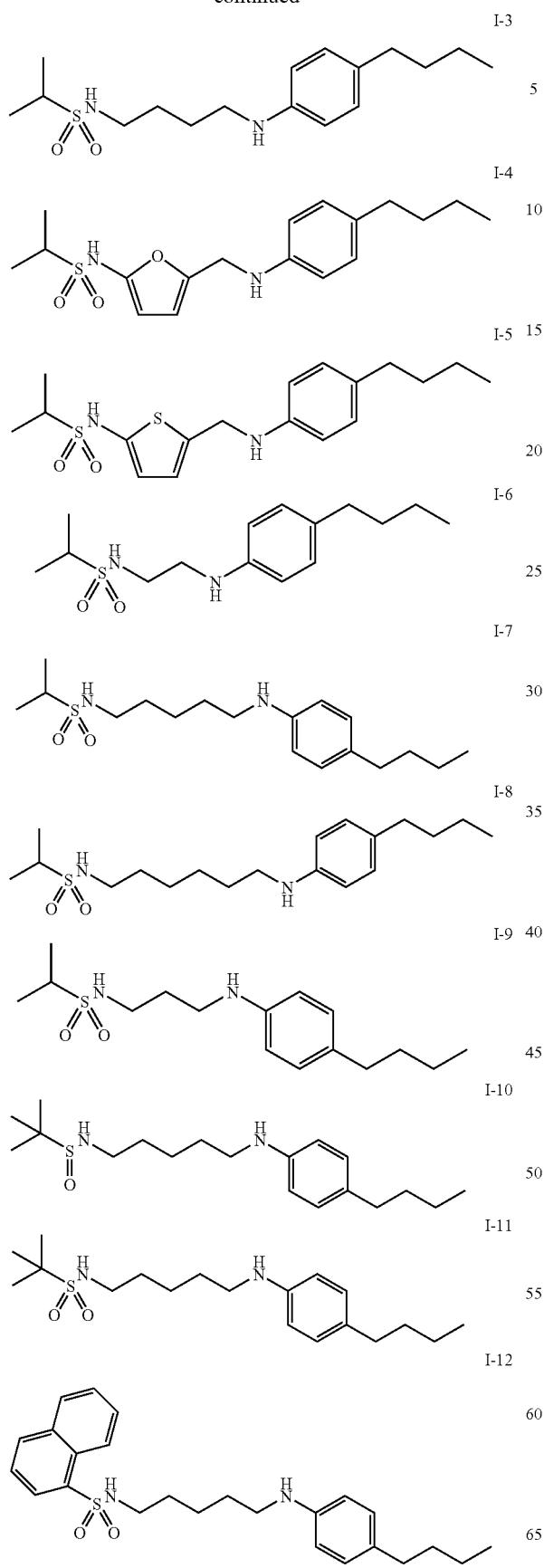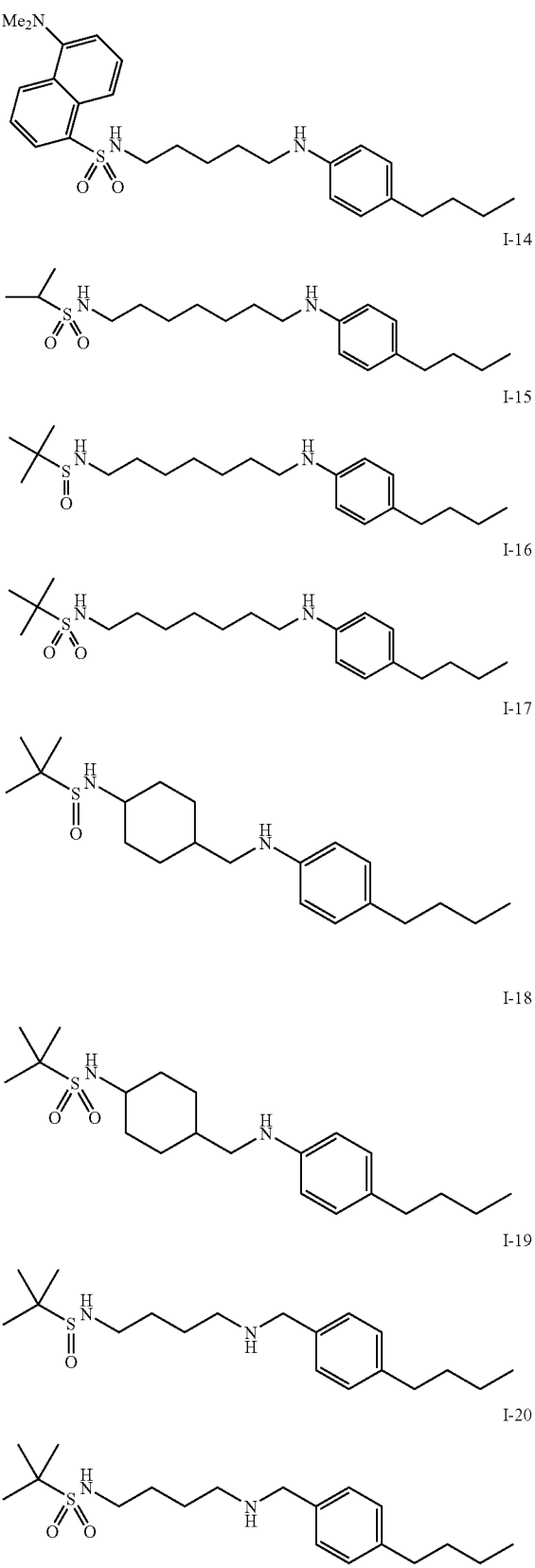

-continued
I-21
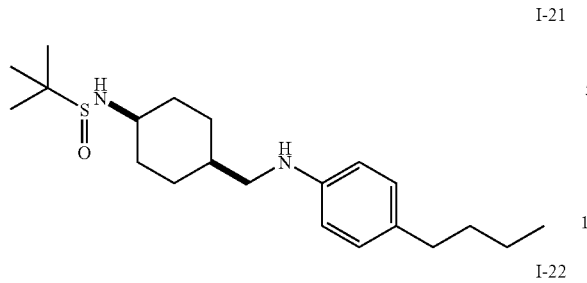
I-22

I-23

I-24
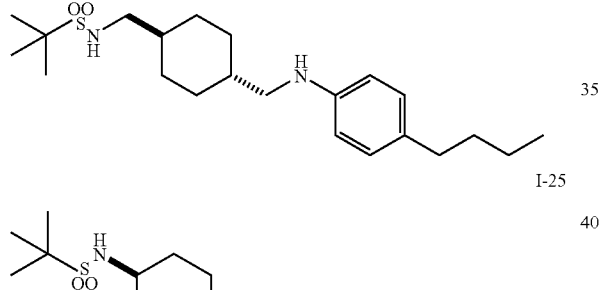
I-25
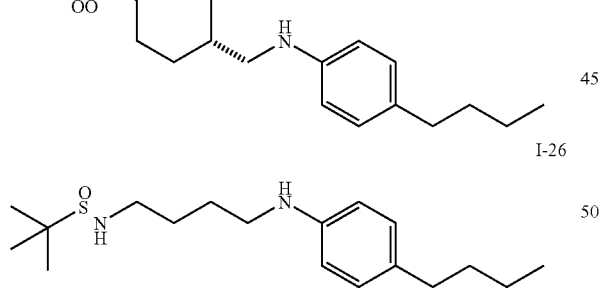
I-26
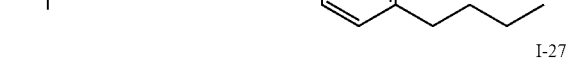
I-27
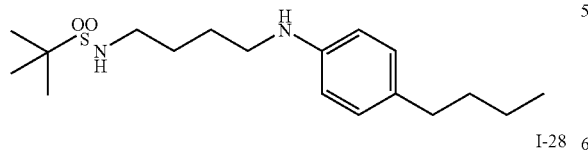
I-28
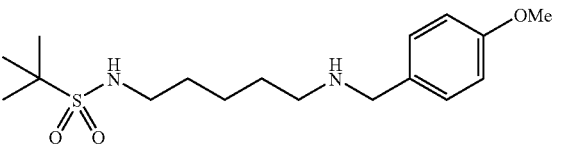
-continued
I-29
I-30
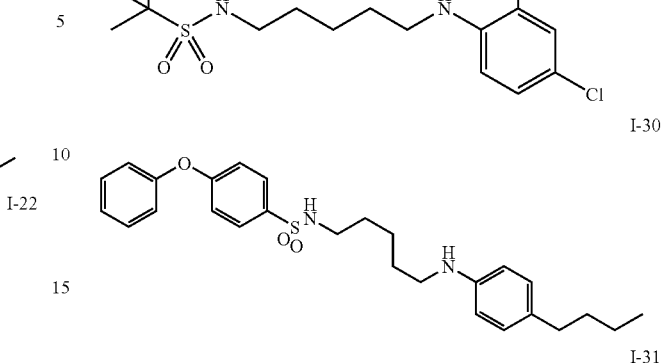
I-31
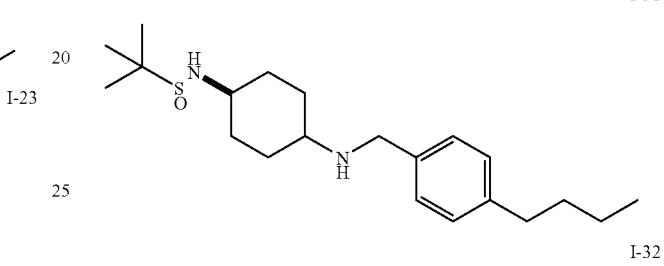
I-32

I-33
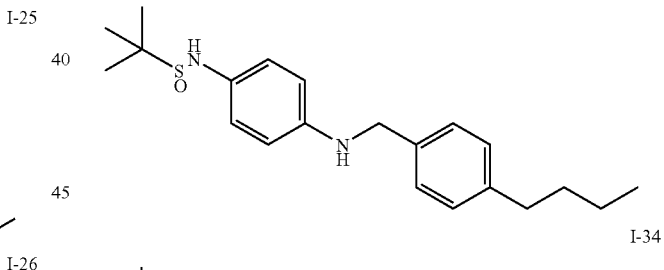
I-34

I-35
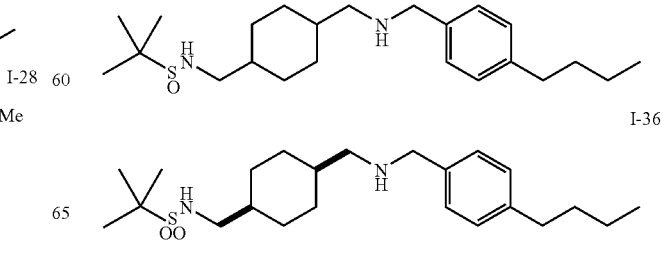
I-36

I-37
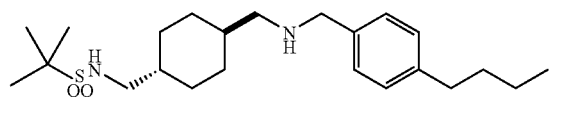
I-38
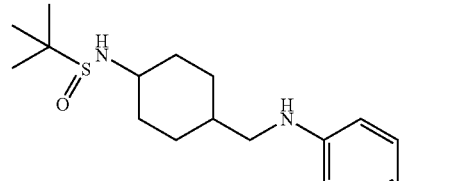
I-39
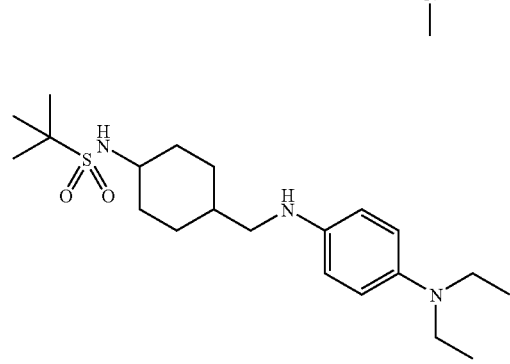
I-40
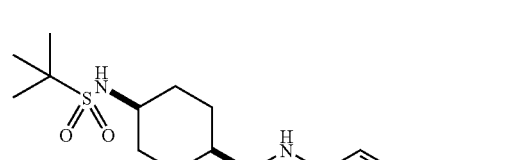
I-41
I-42
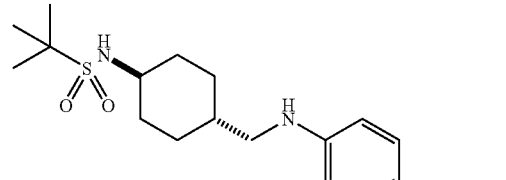
I-43
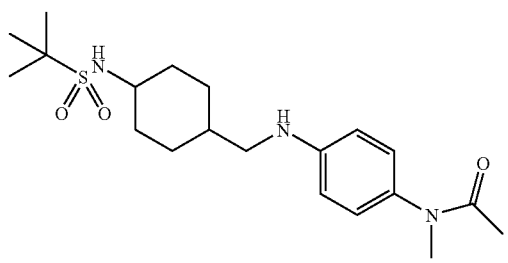
I-44
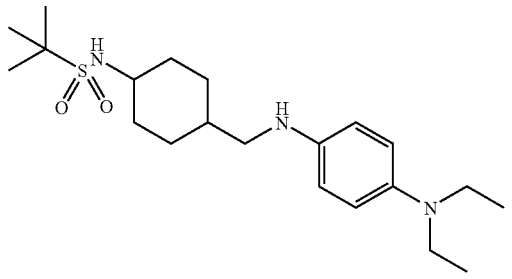
I-45
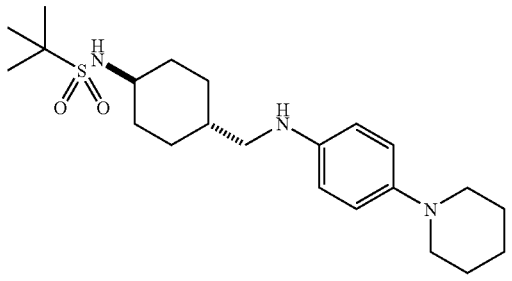
I-46
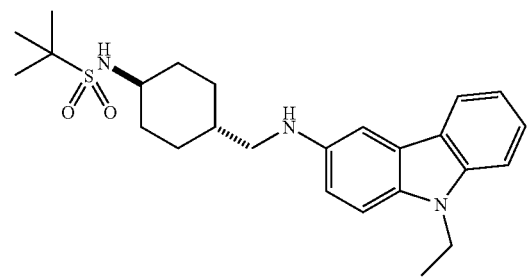
I-47
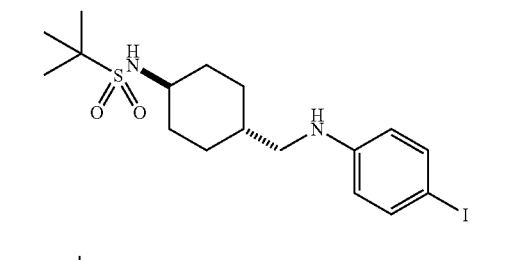
I-48
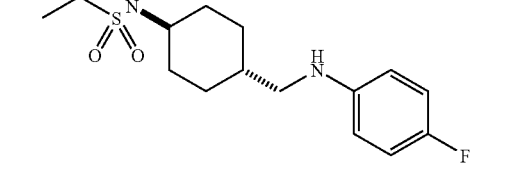

I-49
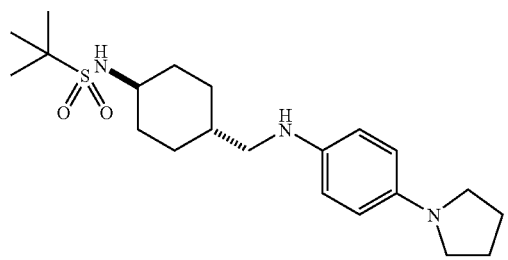
I-50
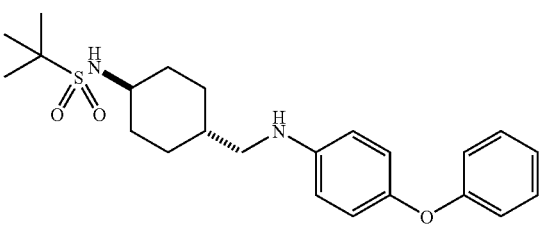
I-51
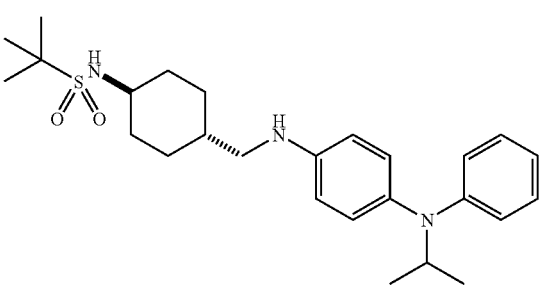
I-52
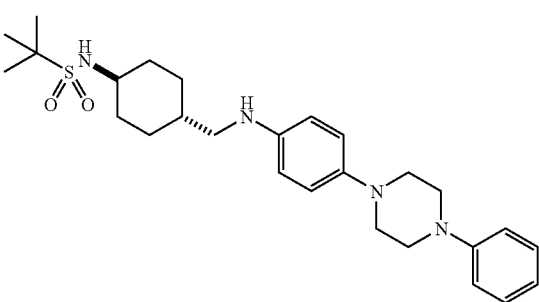
I-53
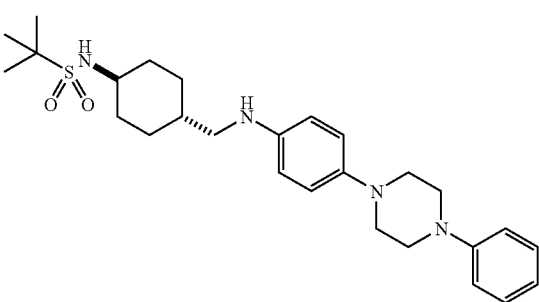
I-54
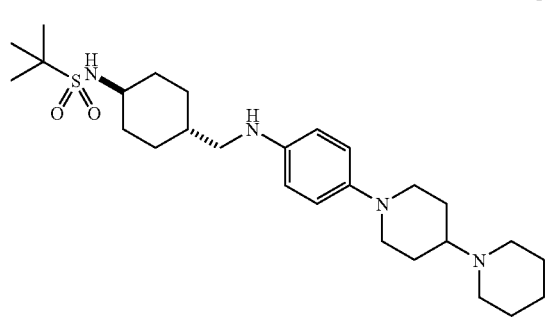
I-55
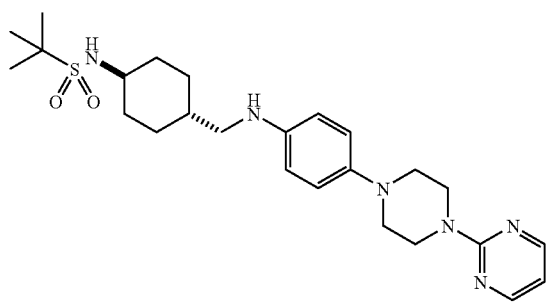
I-56
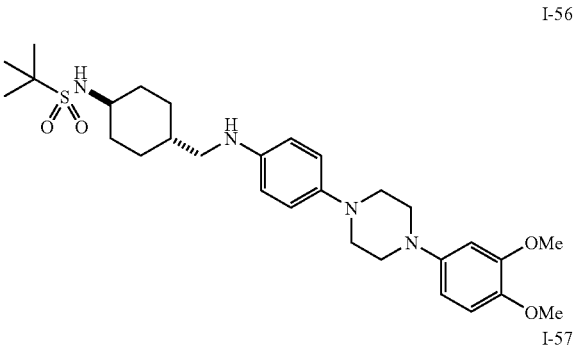
I-57
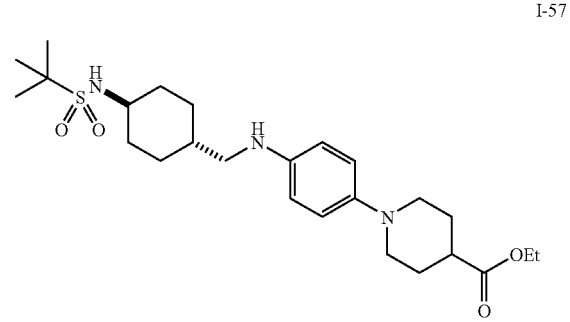
I-58
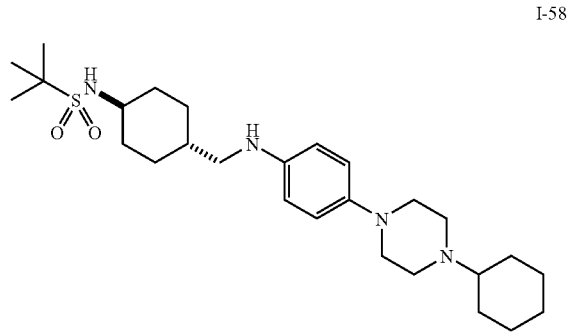

I-59
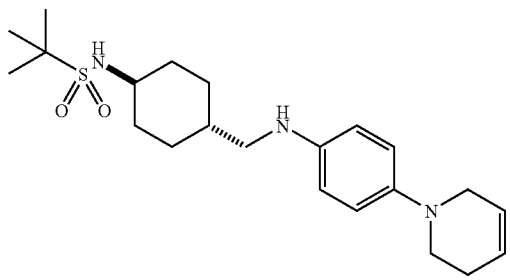
I-60
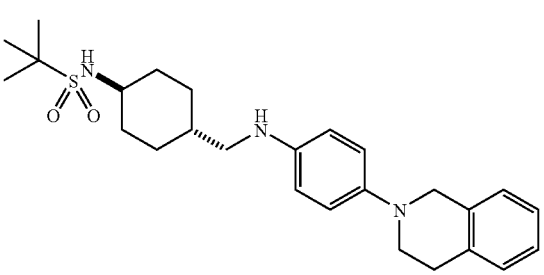
I-61
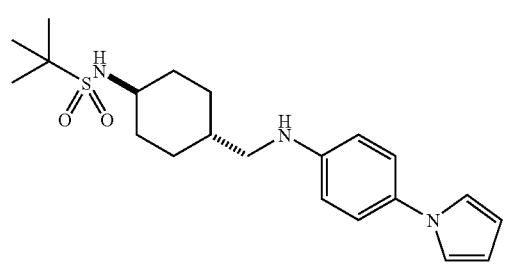
I-62
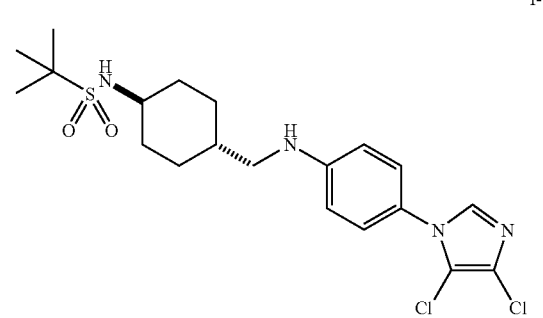
I-63
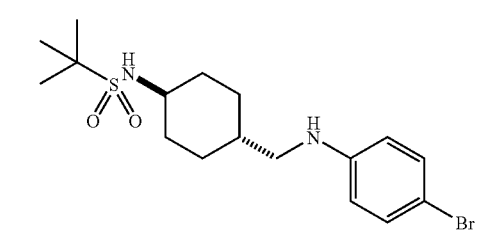
I-64
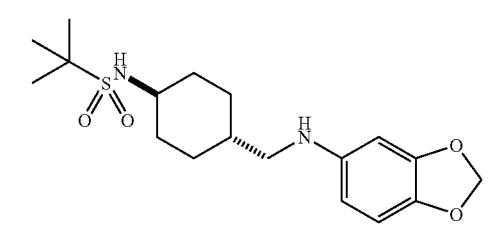
I-65
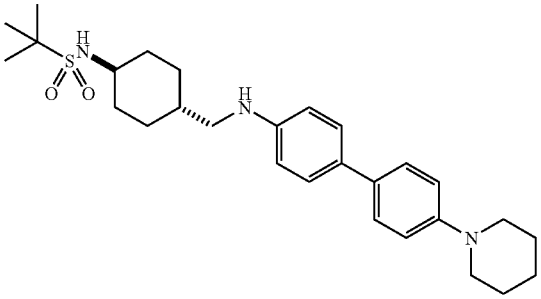
I-66
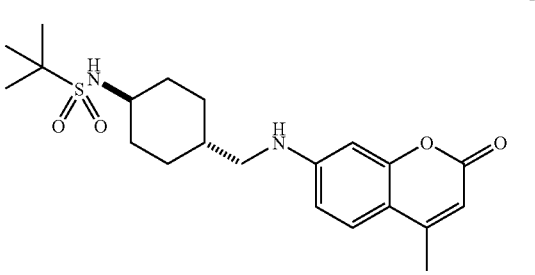
I-67
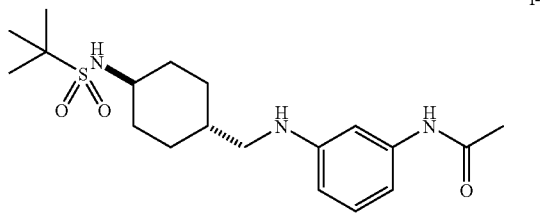
I-68
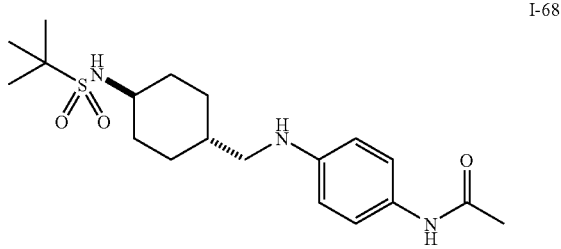
I-69
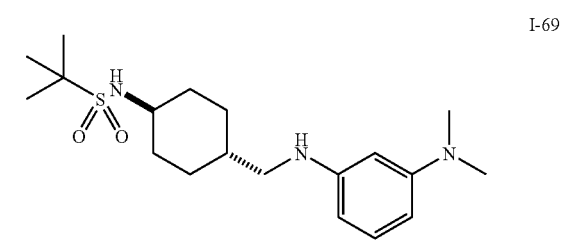
I-70
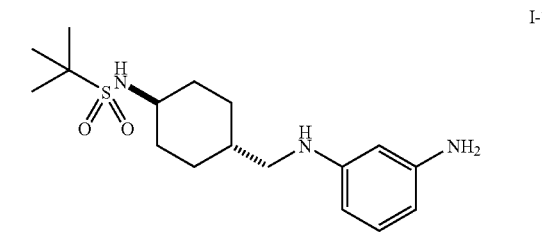

I-71 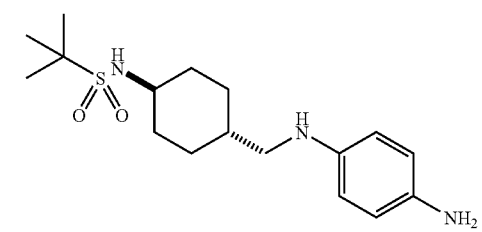
I-72 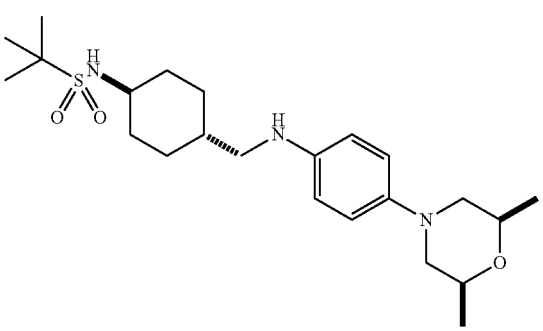
I-73 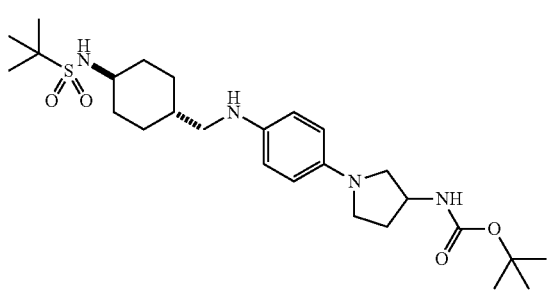
I-74 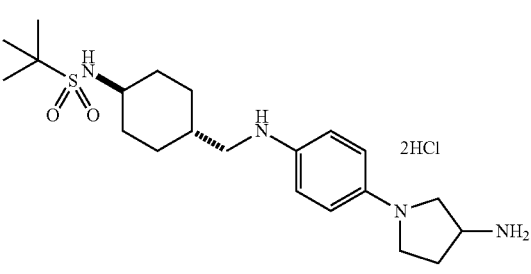
I-75 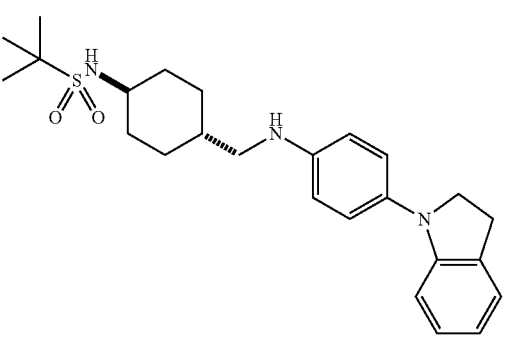
I-76 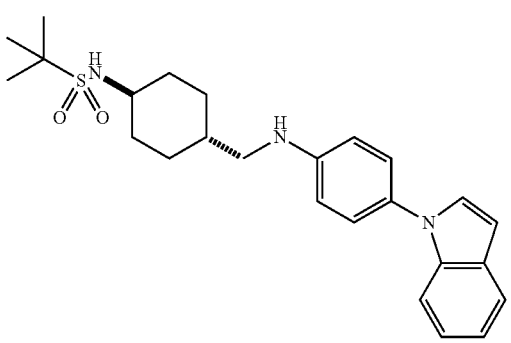
I-77 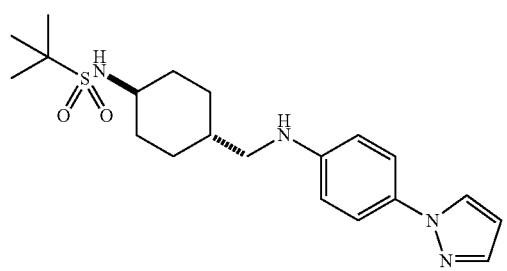
I-78 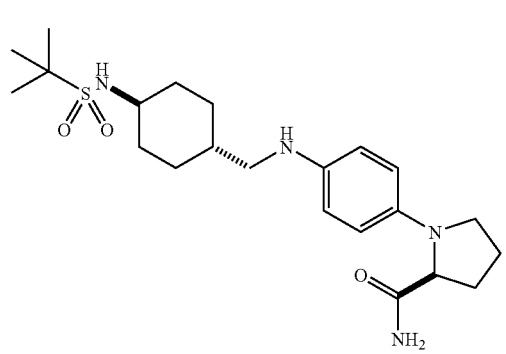
I-79 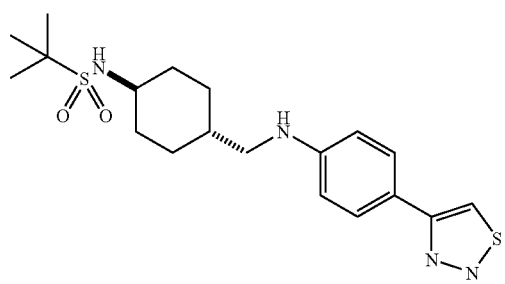
I-80

I-81
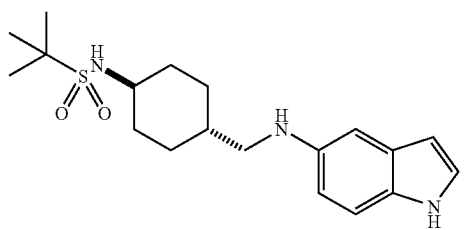
I-82
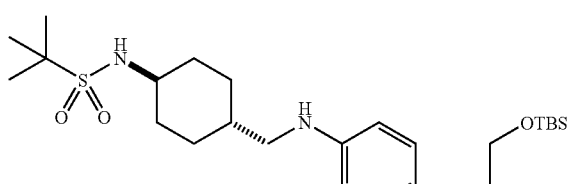
I-83
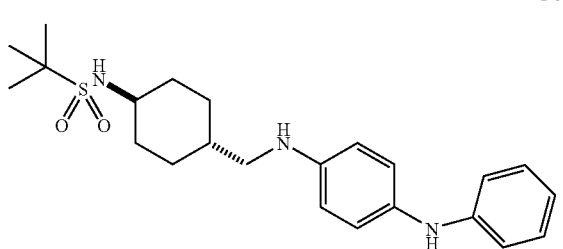
I-84
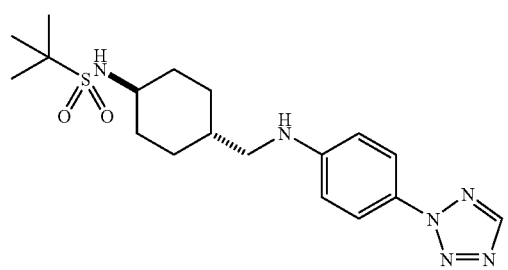
I-85
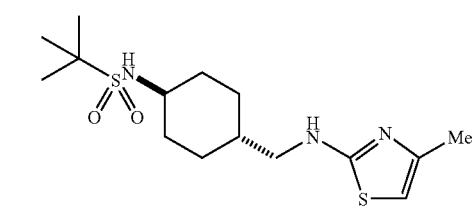
I-86
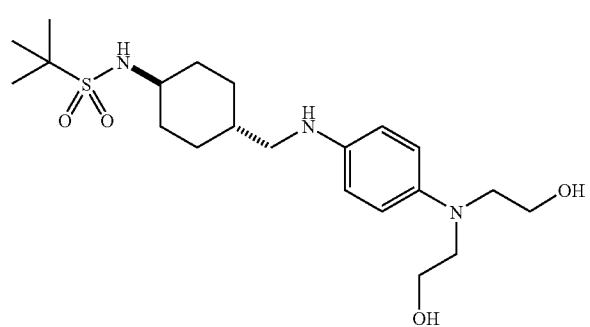
I-87
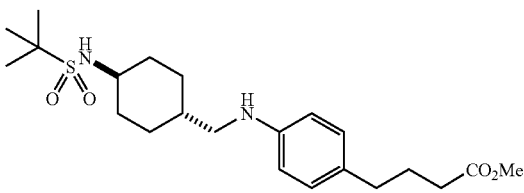
I-88
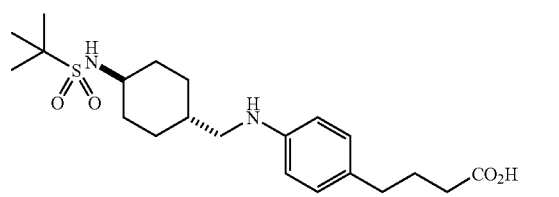
I-89
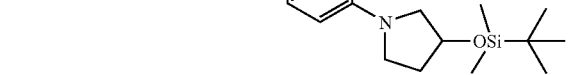
I-90
I-91
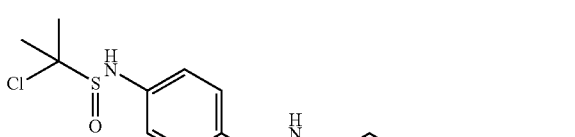
I-92
I-93

-continued

I-108
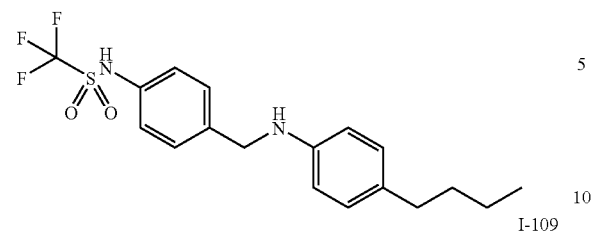
I-109

I-110
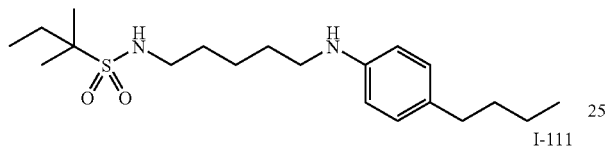
I-111
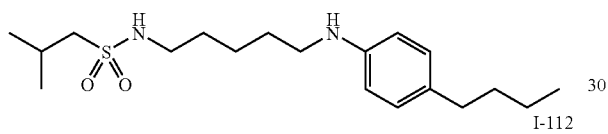
I-112
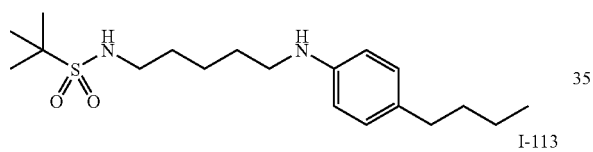
I-113
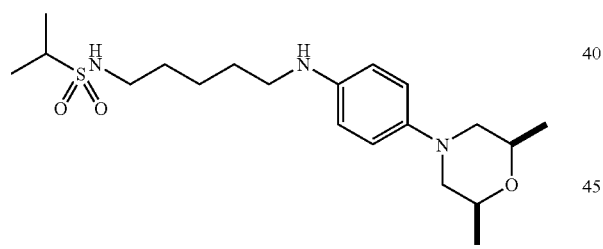
I-115
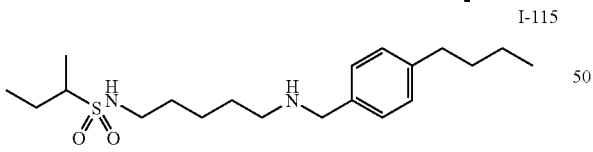
I-116

I-117
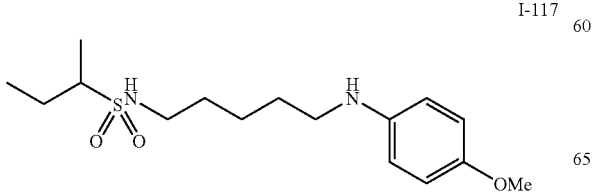
I-118
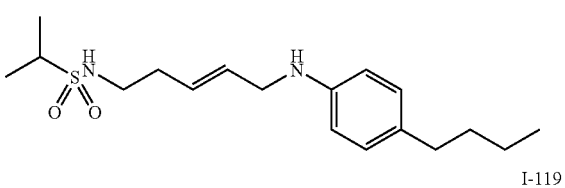
I-119
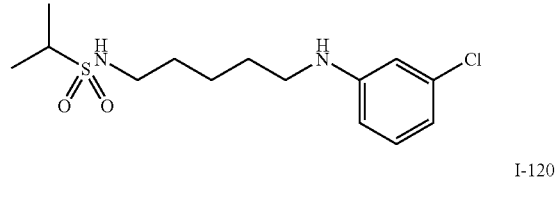
I-120
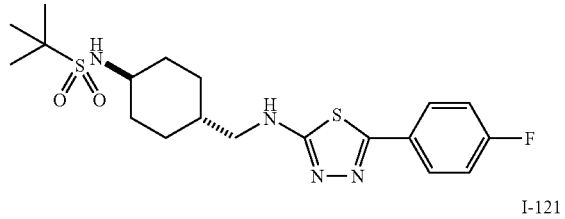
I-121
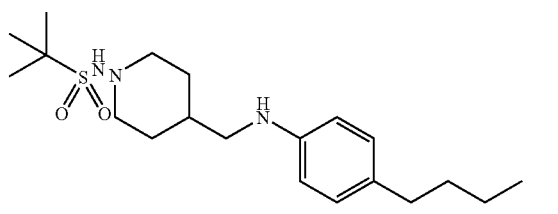
I-122
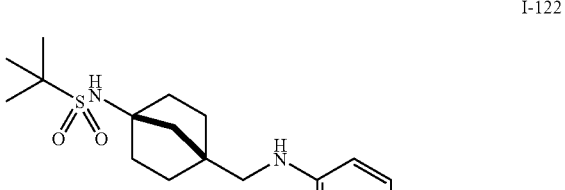
I-123
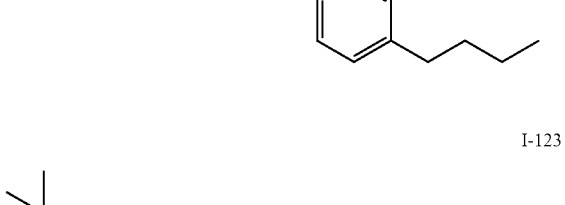
I-124
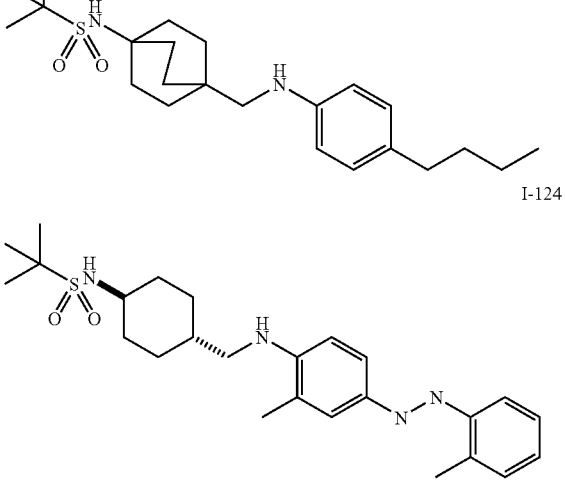

-continued
I-125
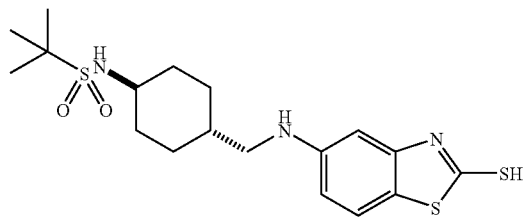
I-126
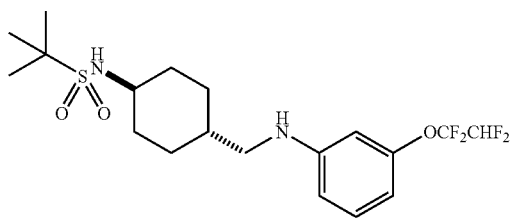
I-127
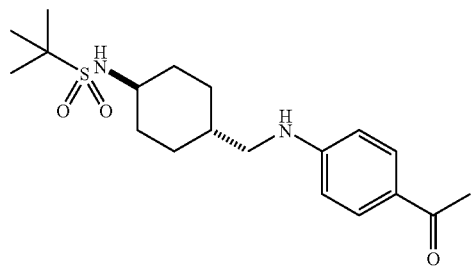
I-128
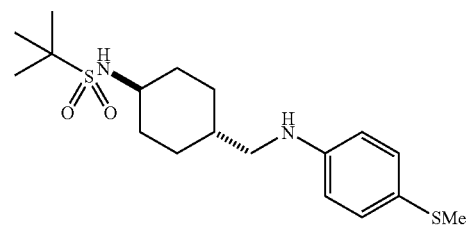
I-129
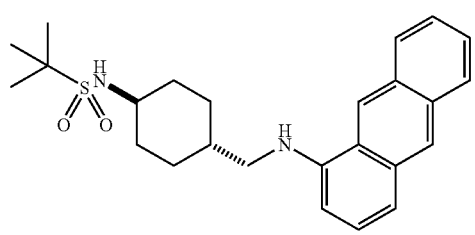
I-130
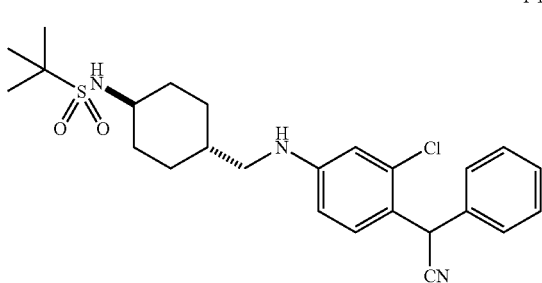
-continued
I-131
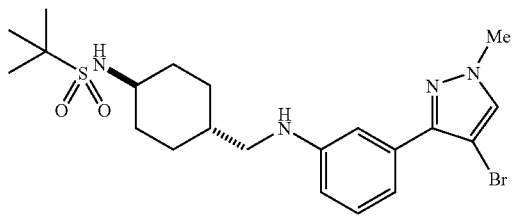
I-132
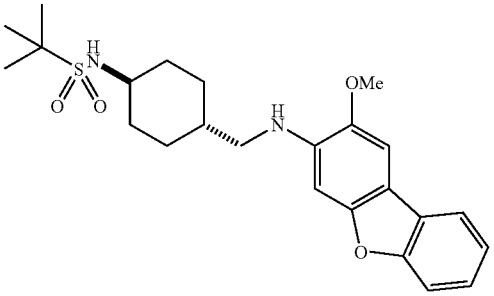
I-133
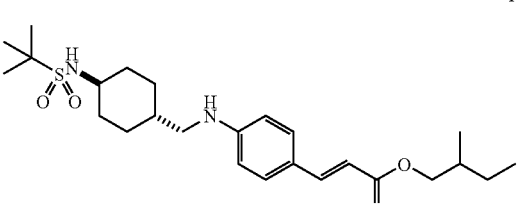
I-134
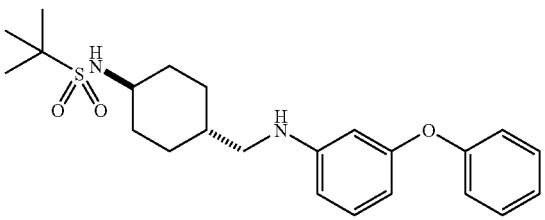
I-135
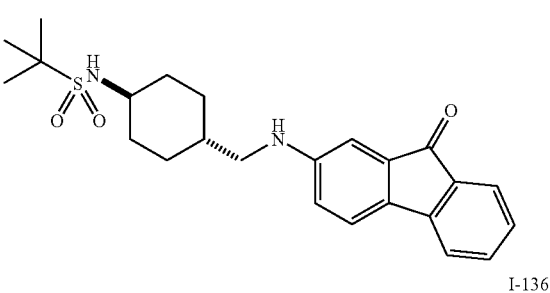
I-136

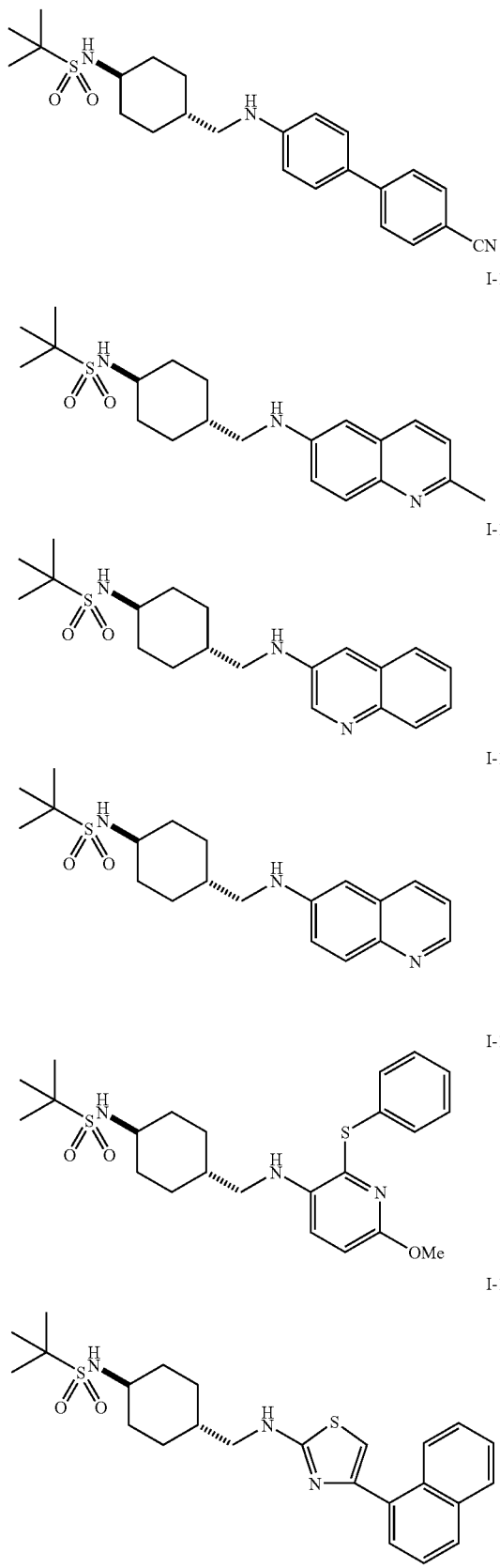
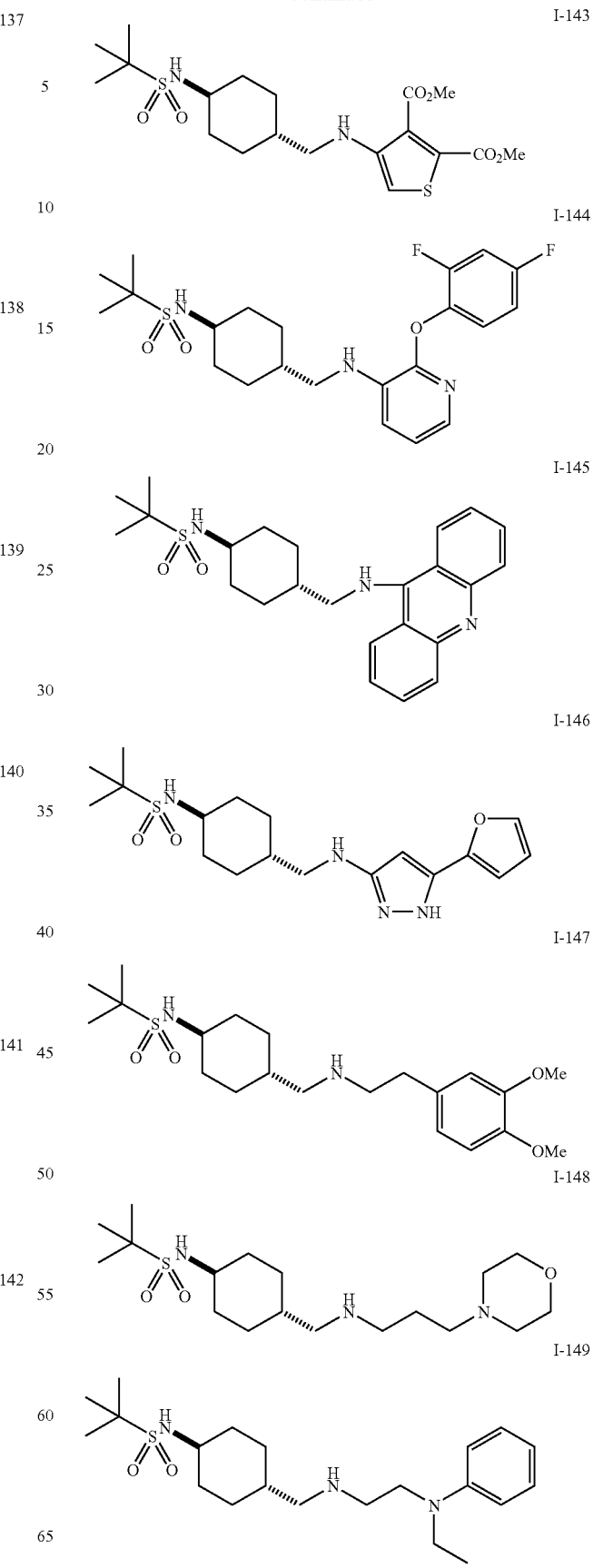

I-150
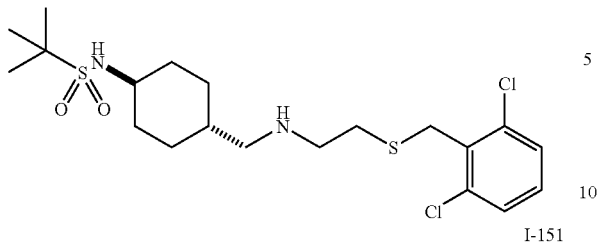
I-151
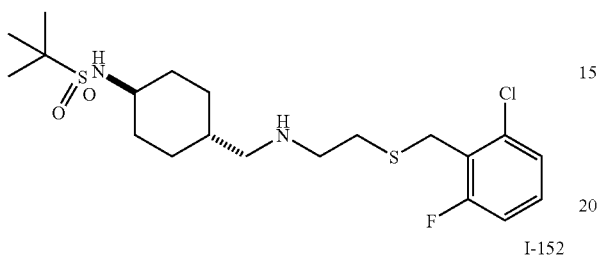
I-152
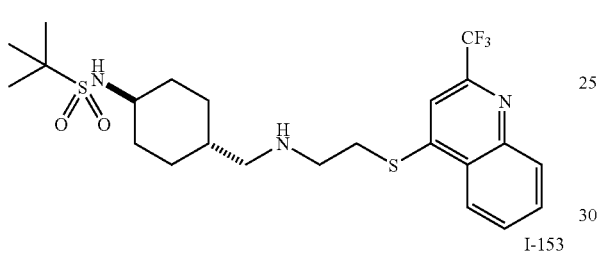
I-153
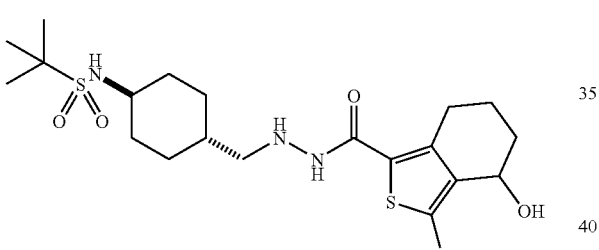
I-154
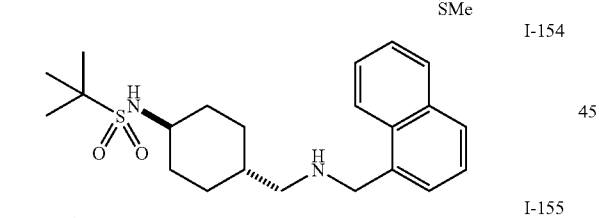
I-155
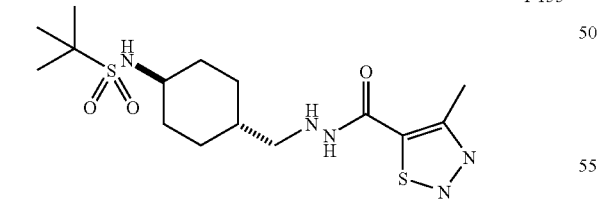
I-156
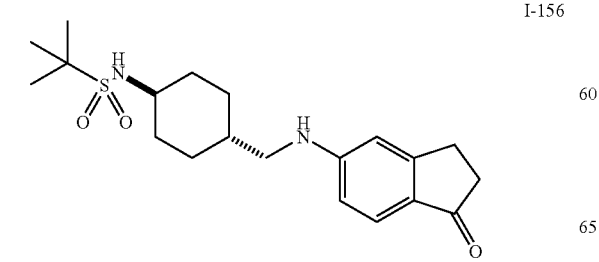
I-157
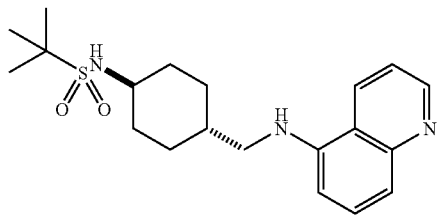
I-158
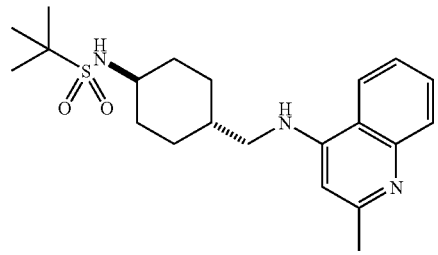
I-159
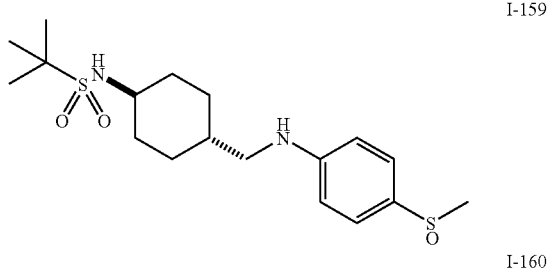
I-160
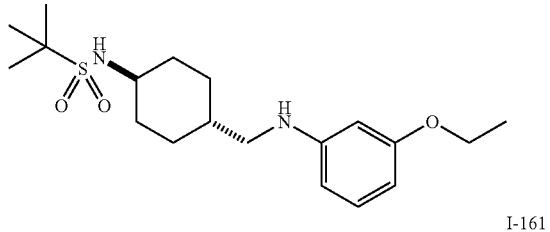
I-161
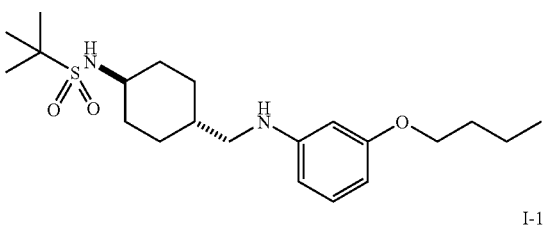
I-162
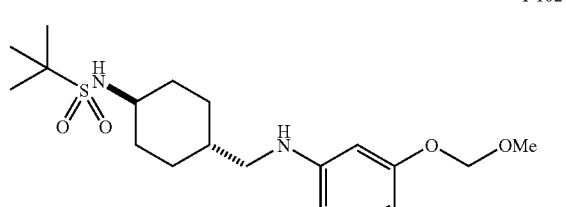
I-163
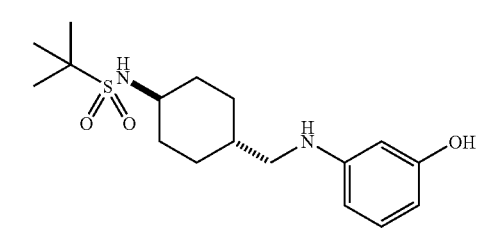

I-164
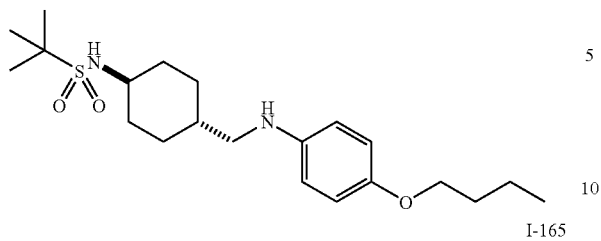
I-165
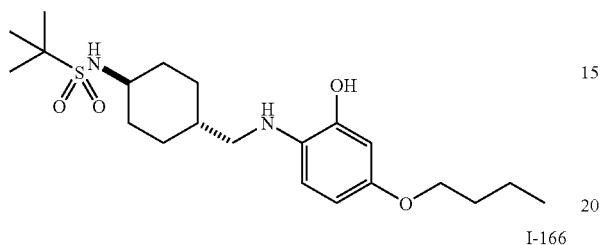
I-166
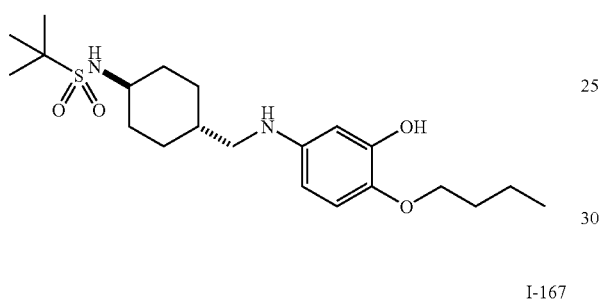
I-167
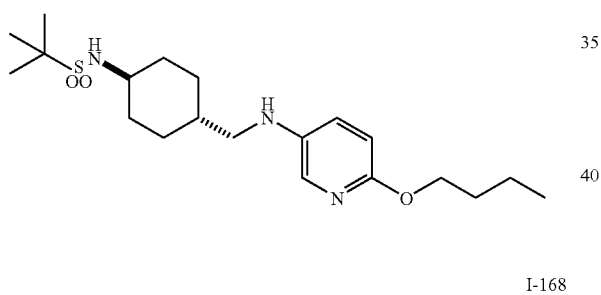
I-168
I-169
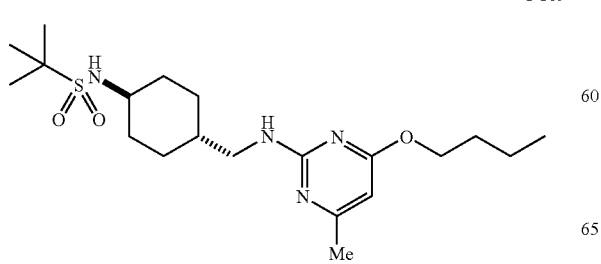
I-170
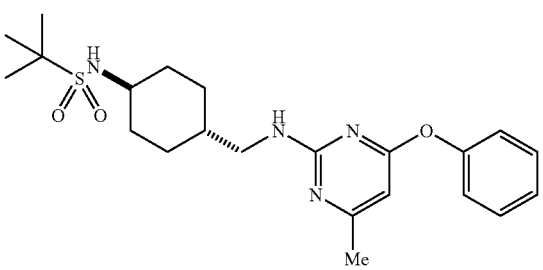
I-171
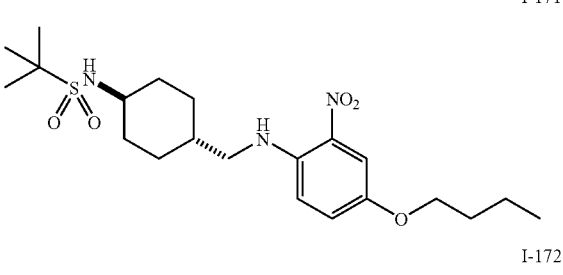
I-172
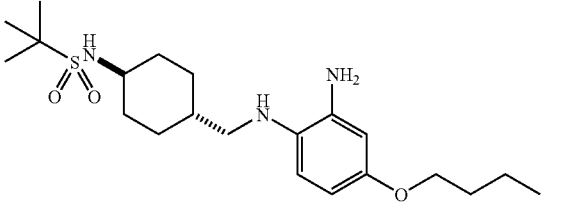
I-173
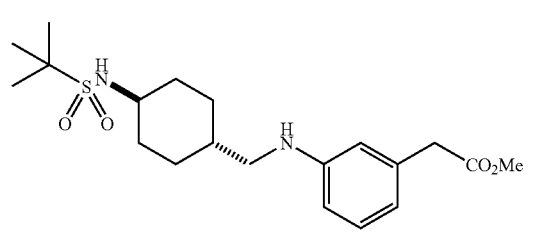
I-174
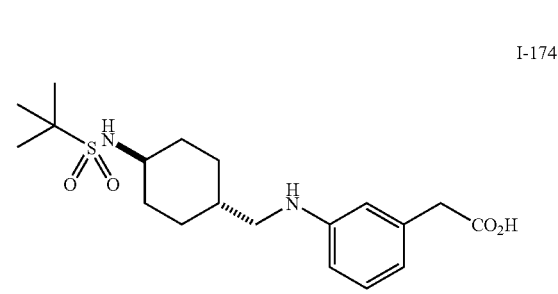
I-175
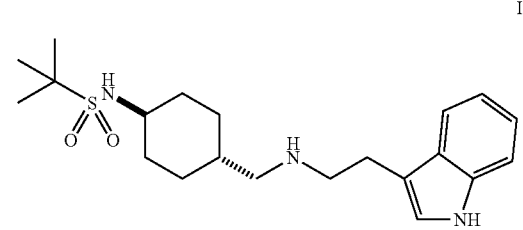

I-176
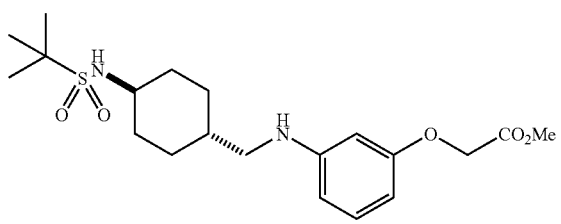
I-177
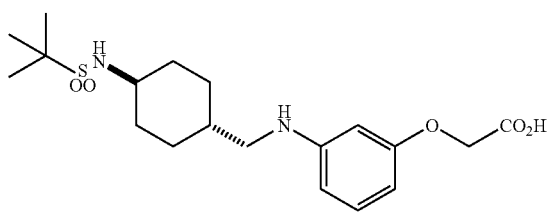
I-178
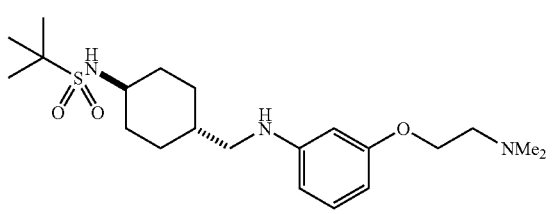
I-179
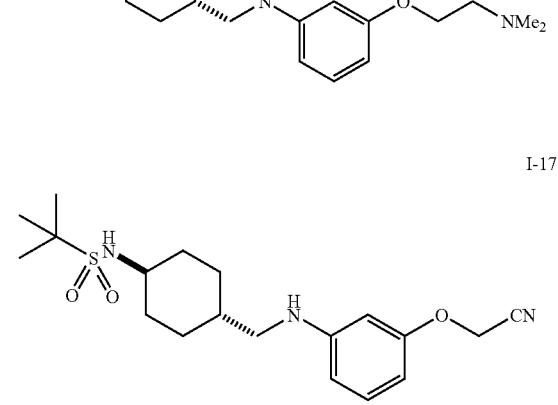
I-180
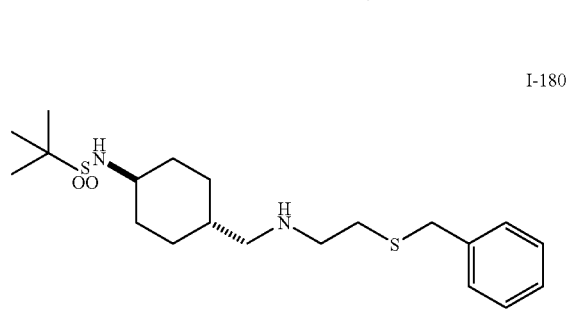
I-181
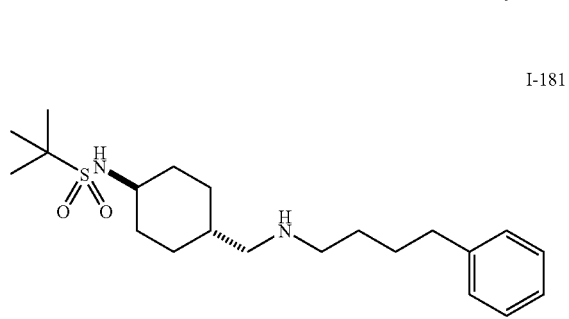
I-182
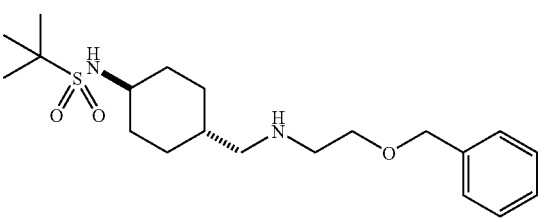
I-183
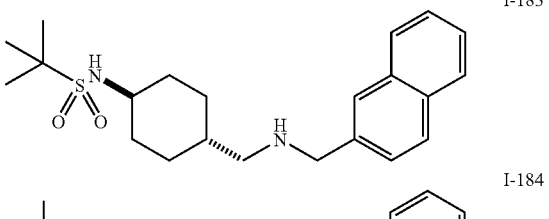
I-184

I-185
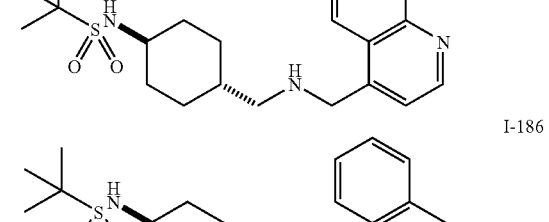
I-186
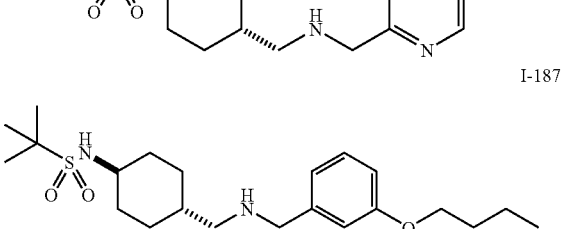
I-187
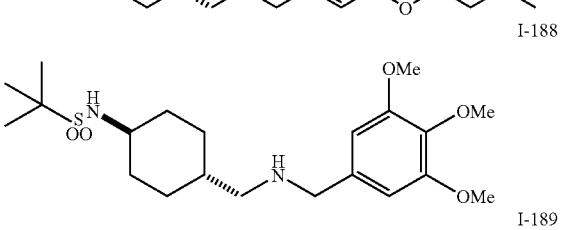
I-188
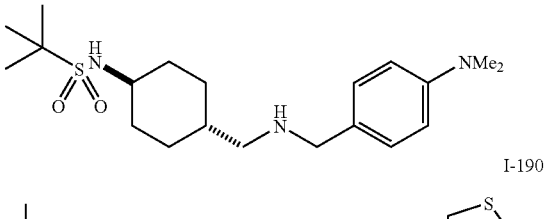
I-189
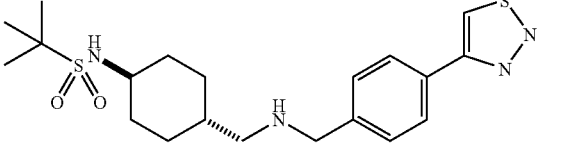
I-190
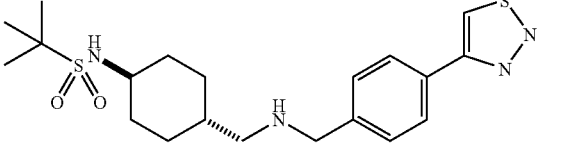

I-191
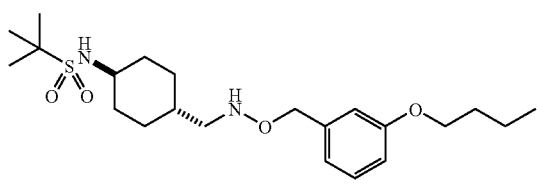
I-192
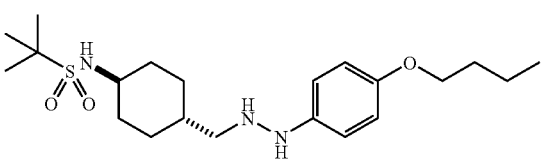
I-193
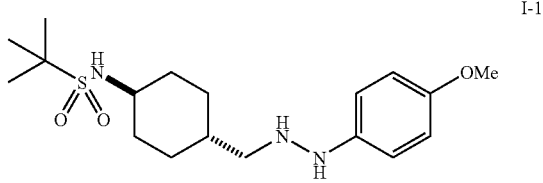
I-194
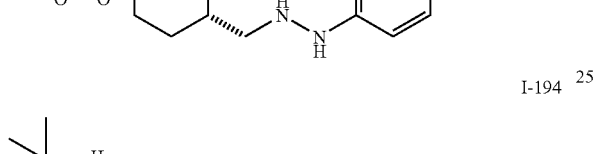
I-195

I-196

I-197

I-198
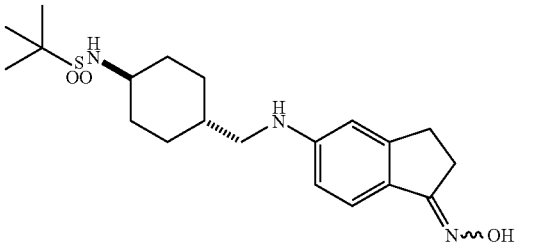
I-199
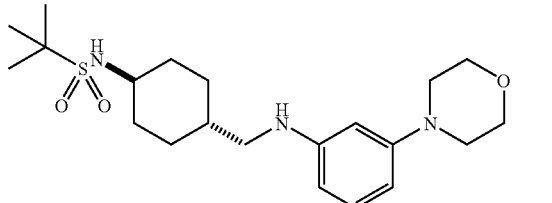
I-200
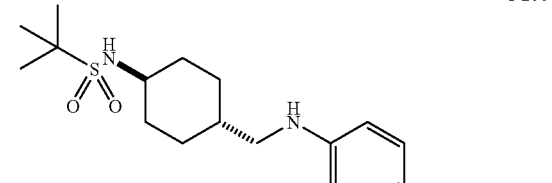
I-201
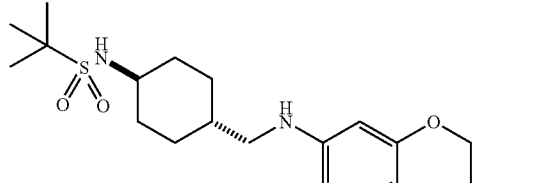
I-202
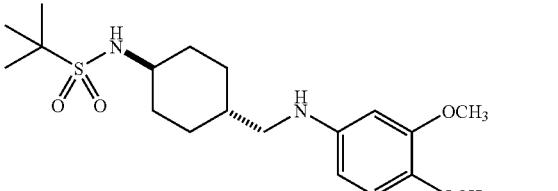
I-203
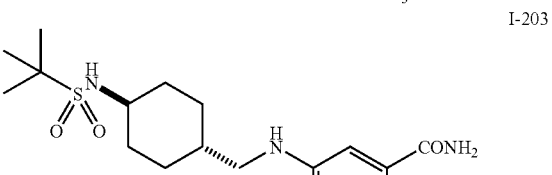
I-204
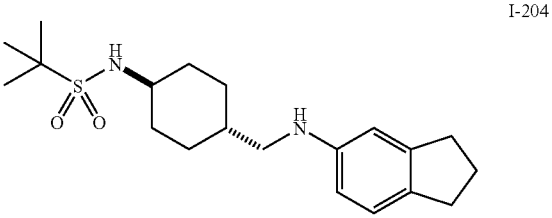

I-205
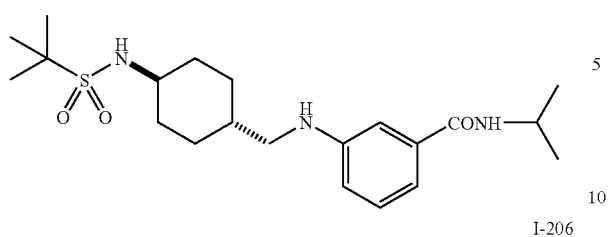
I-206
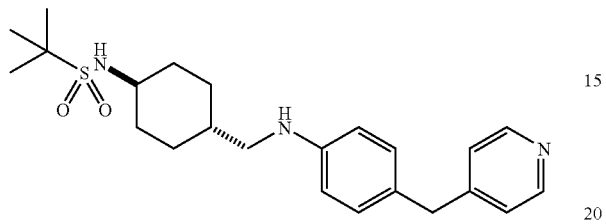
I-207
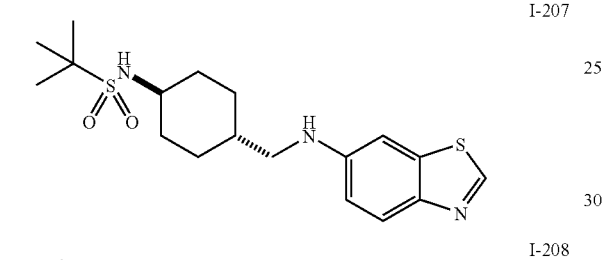
I-208
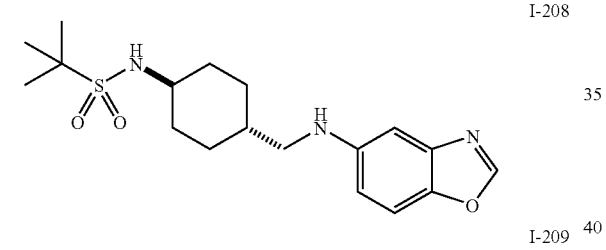
I-209

I-210
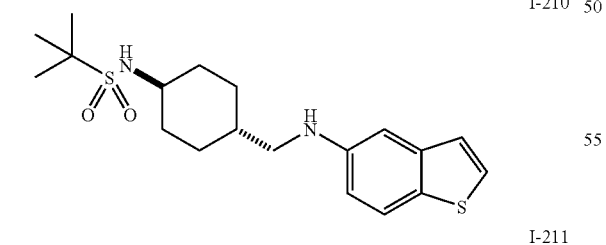
I-211
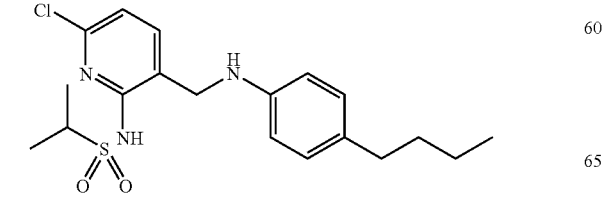
I-212
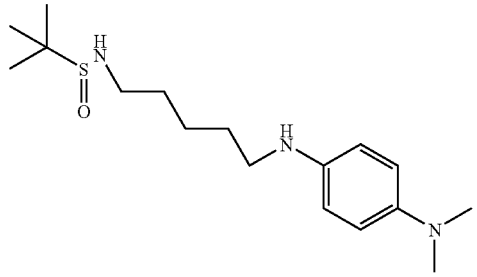
I-213
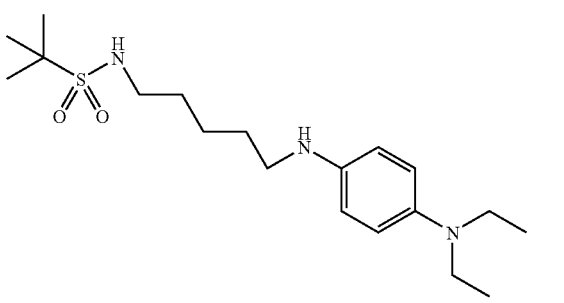
I-214
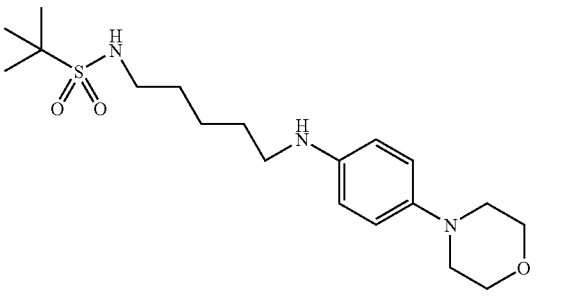
I-215
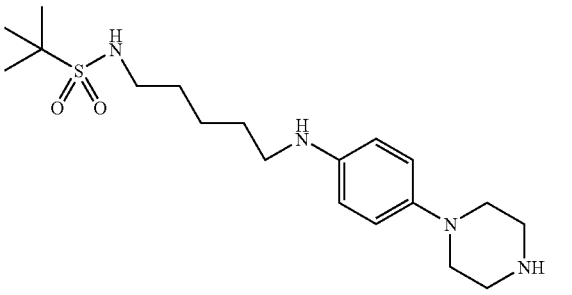
I-216
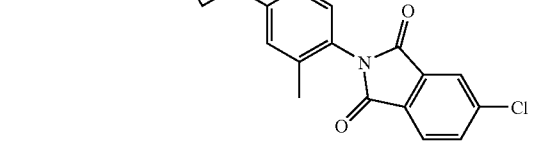

I-217
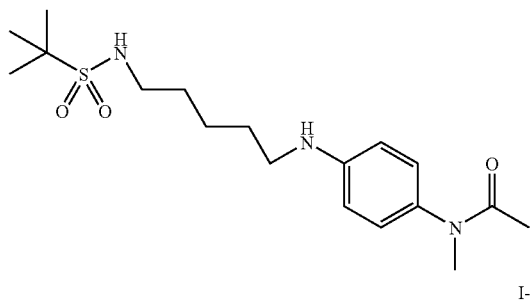
I-218
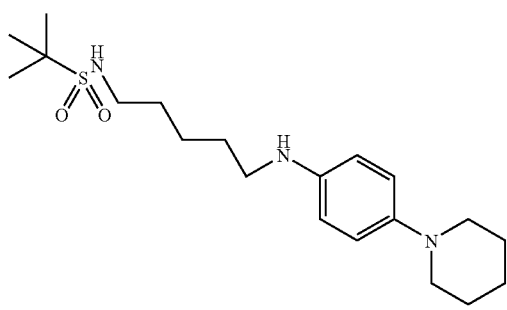
I-219
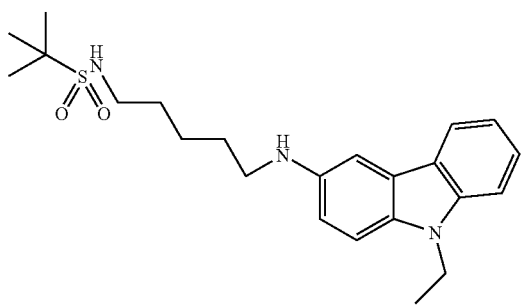
I-220
I-227
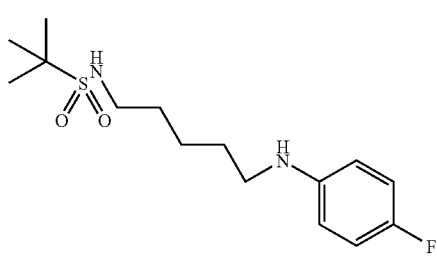
I-228
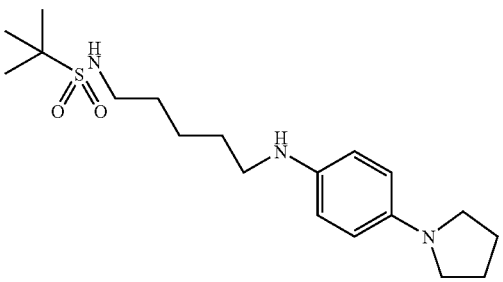
I-229
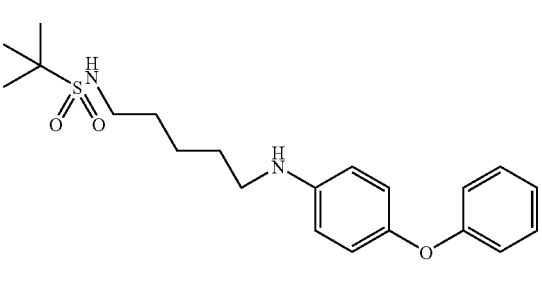
I-230
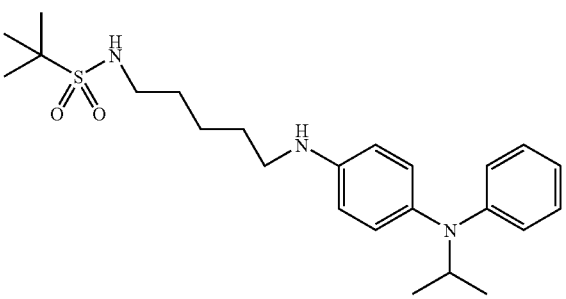
I-231
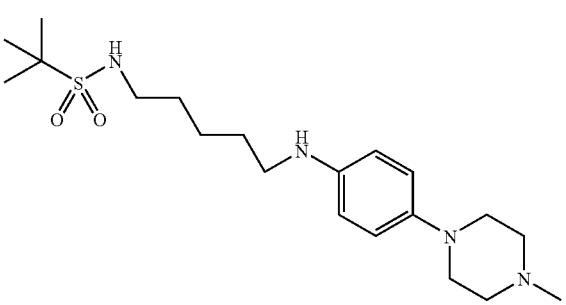
I-232
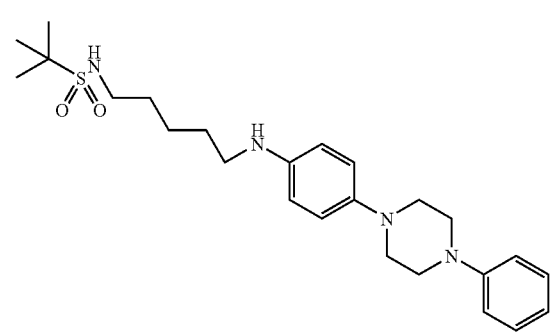

-continued
I-233
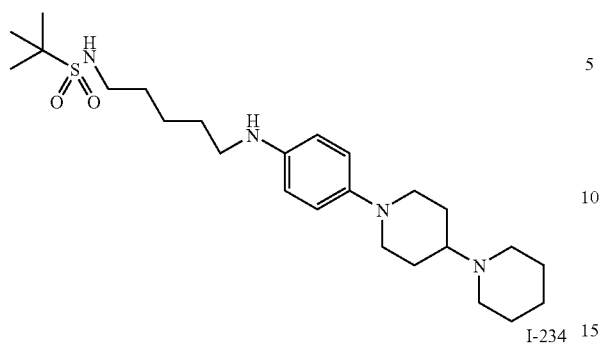
I-234
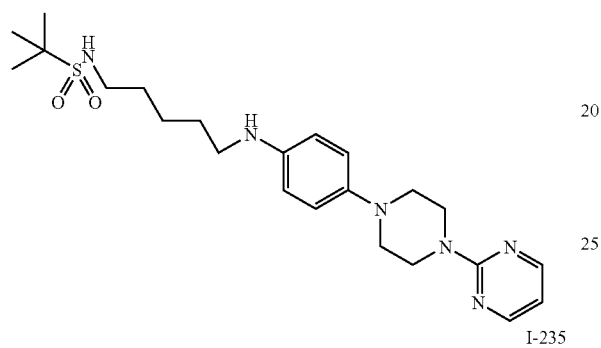
I-235
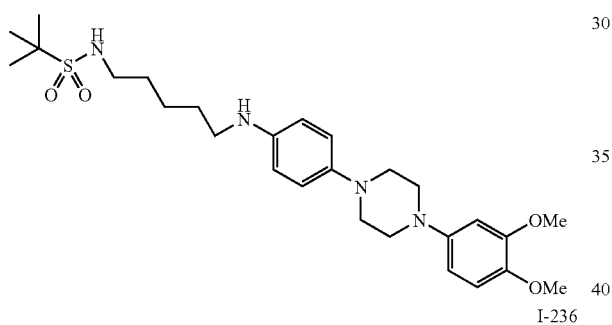
I-236
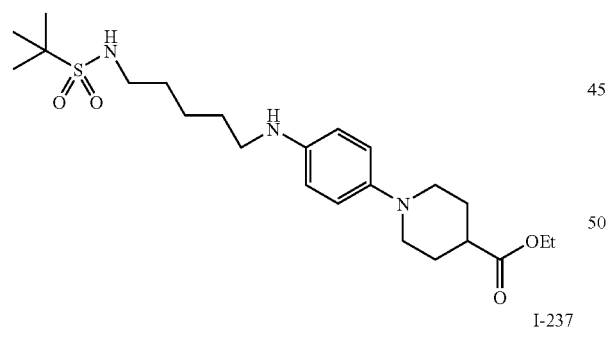
I-237
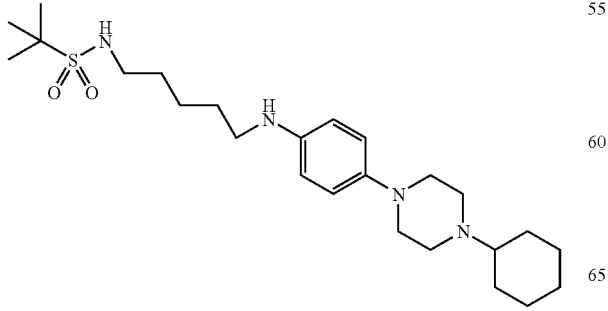
-continued
I-238
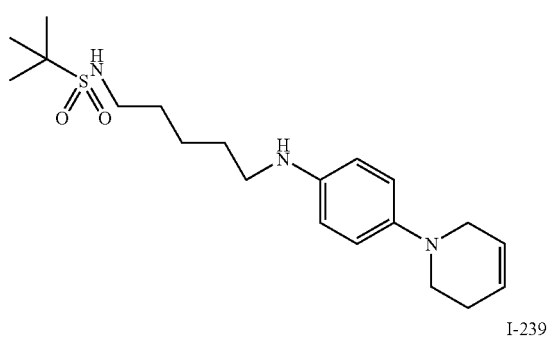
I-239
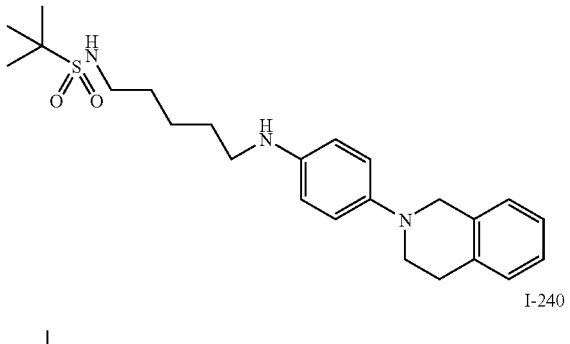
I-240
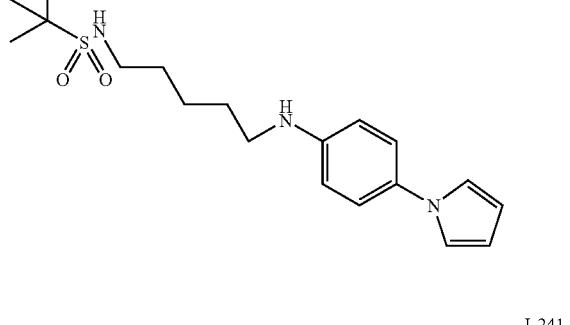
I-241
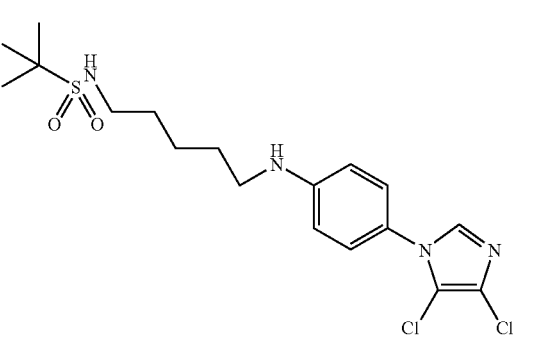
I-242

I-243
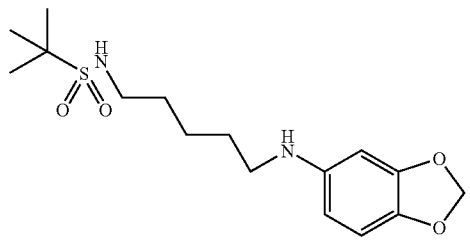
I-244
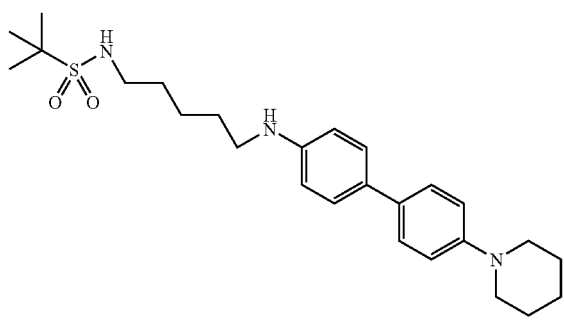
I-245
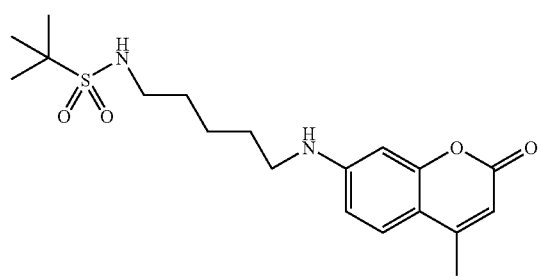
I-246
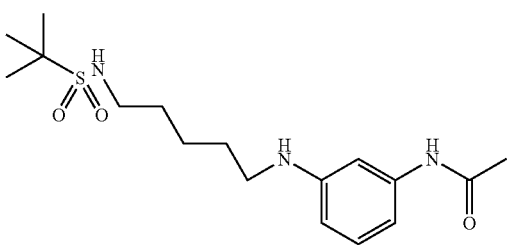
I-247
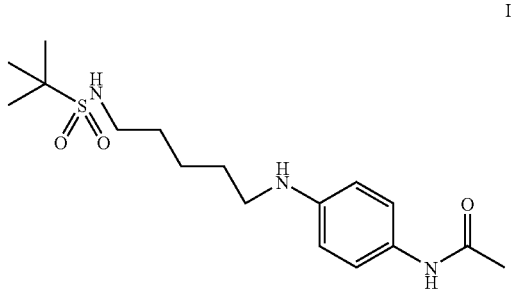
I-248
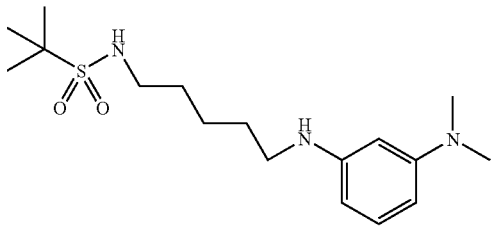
I-249
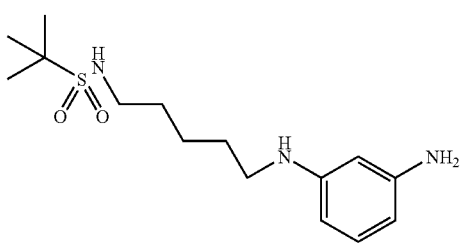
I-250
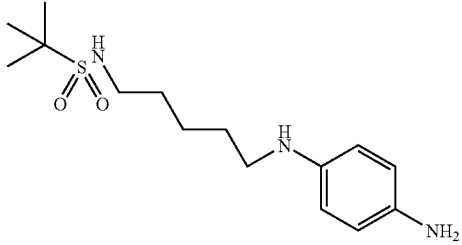
I-251
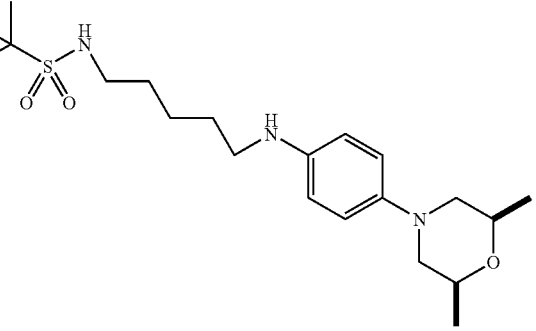
I-252
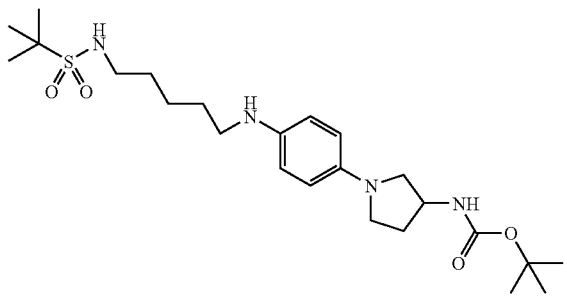

I-253
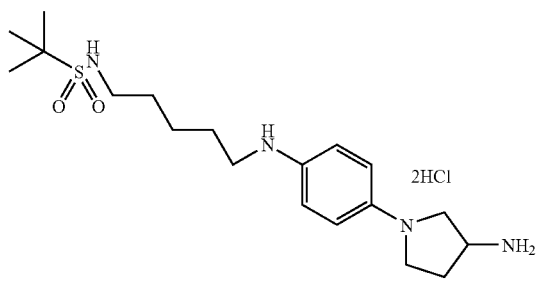
I-254
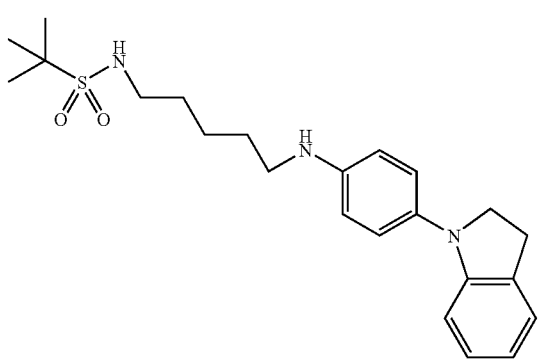
I-25
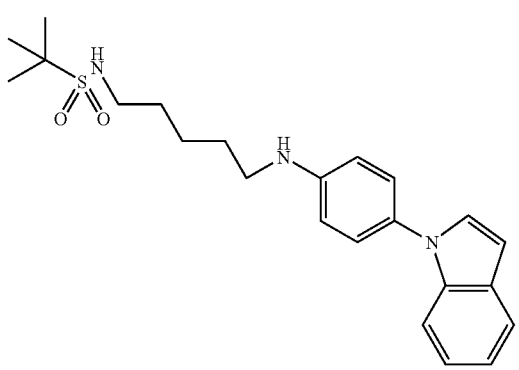
I-256
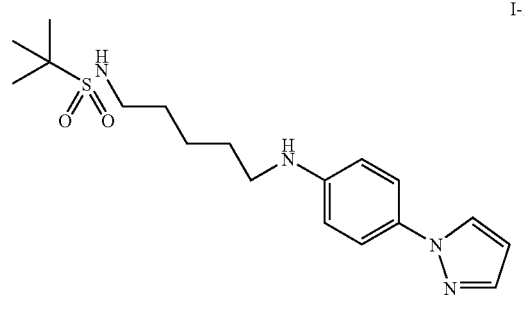
I-257
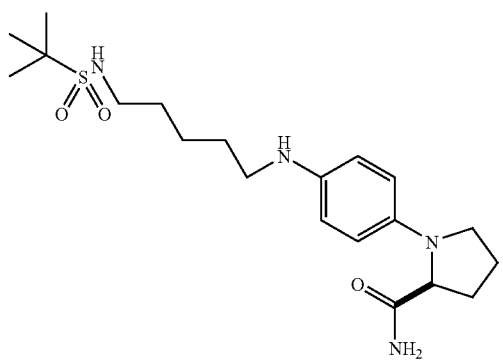
I-258
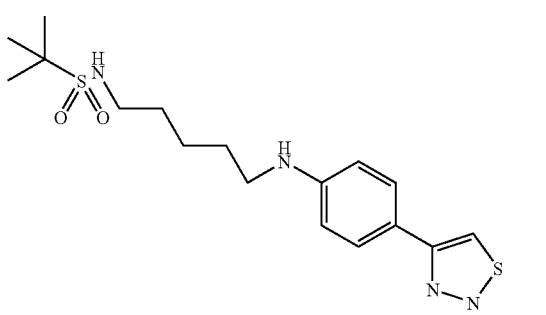
I-259
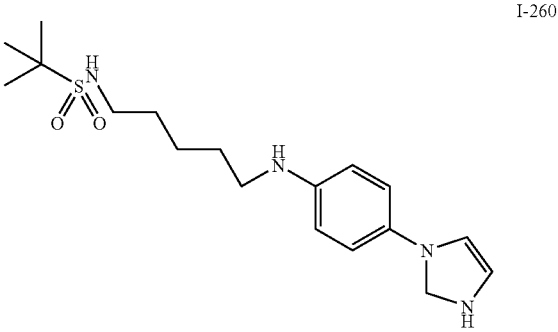
I-260
I-261
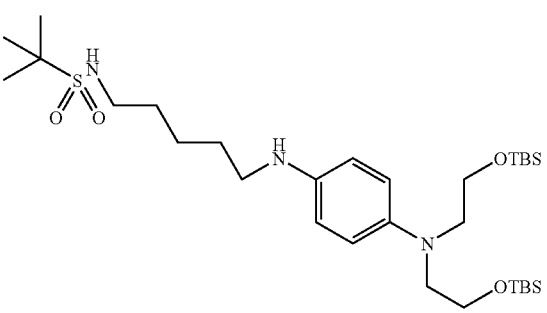

I-262
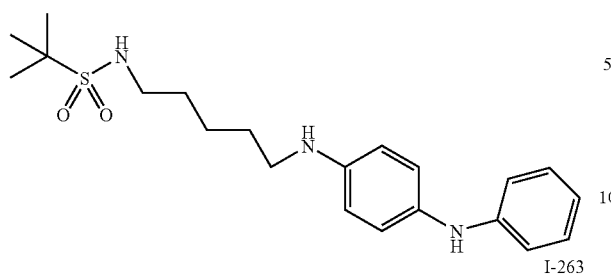
I-263
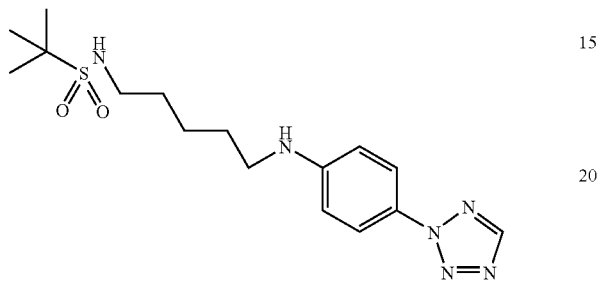
I-264
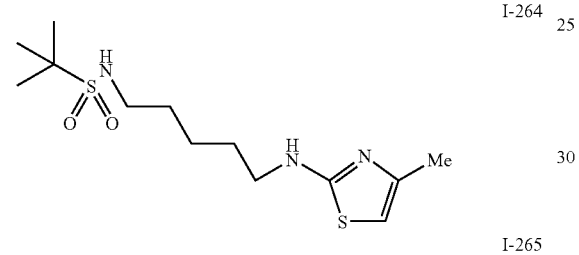
I-265
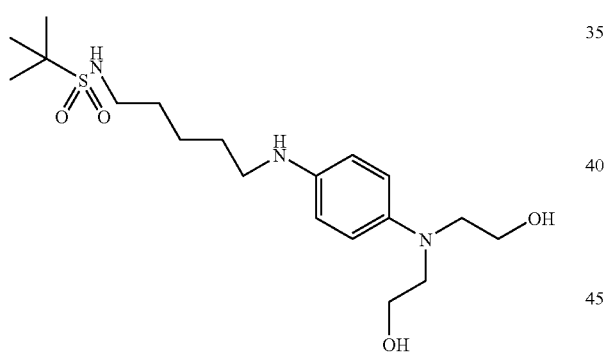
I-266
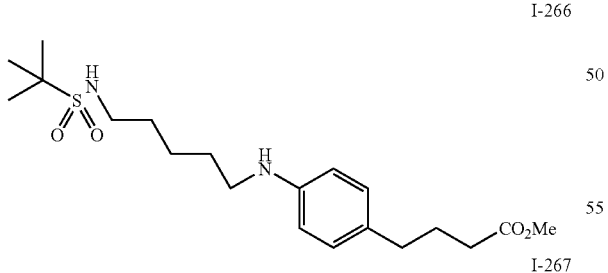
I-267
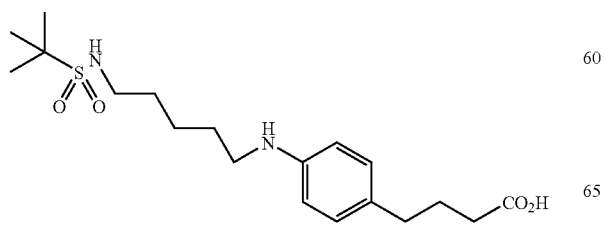
I-268
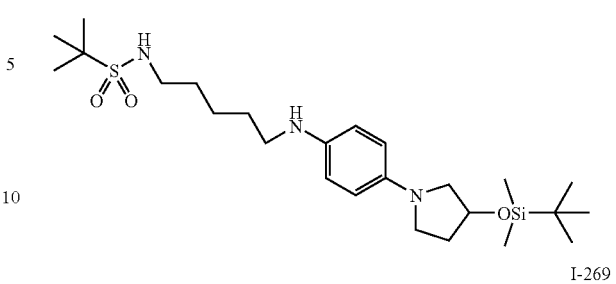
I-269
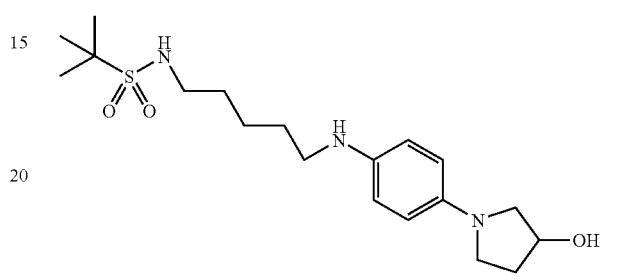
I-270
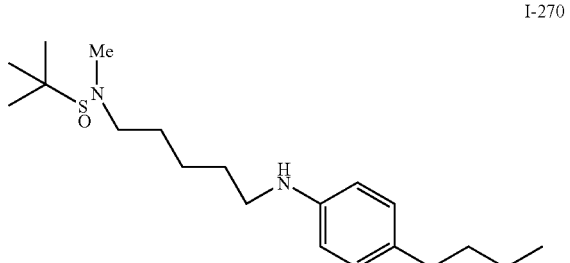
I-271
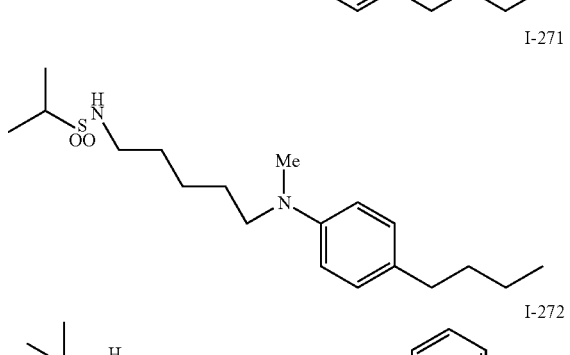
I-272
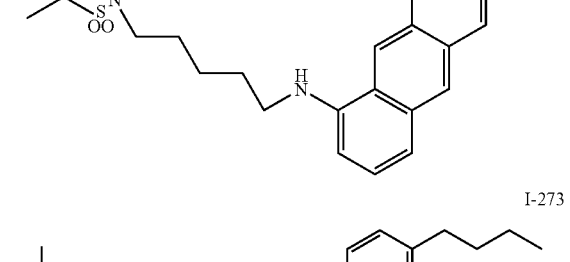
I-273
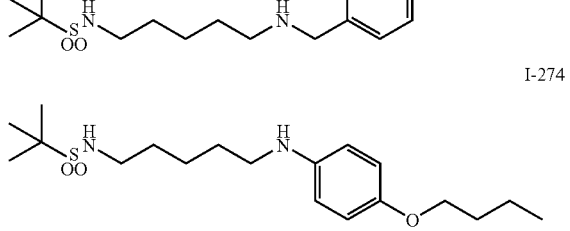
I-274

I-275
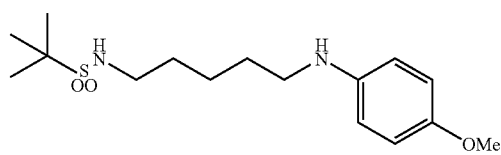
I-276
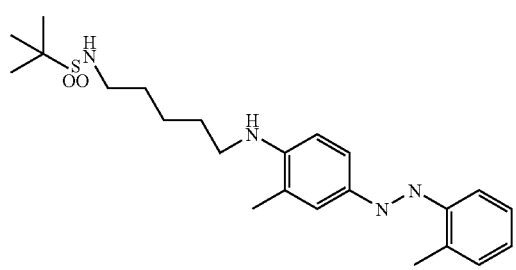
I-277
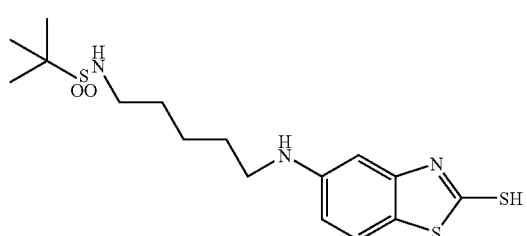
I-278
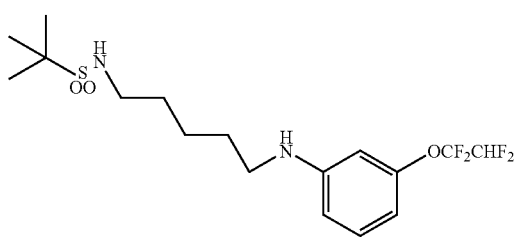
I-279
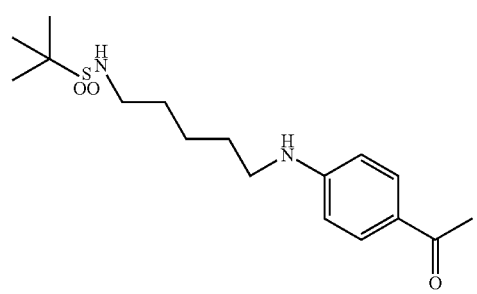
I-280
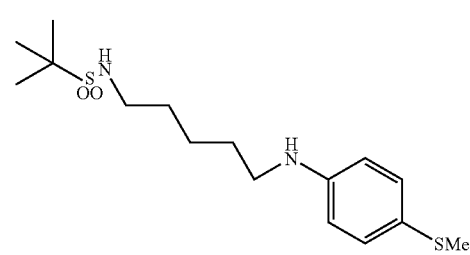
I-282
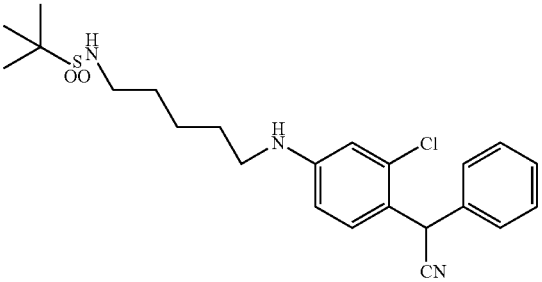
I-283
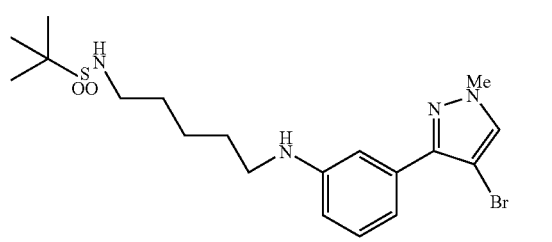
I-284
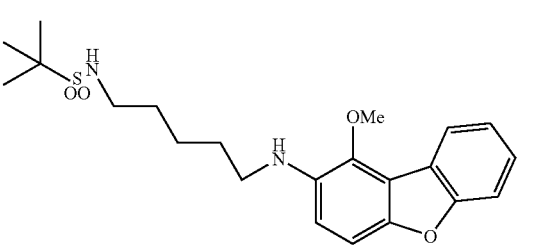
I-285
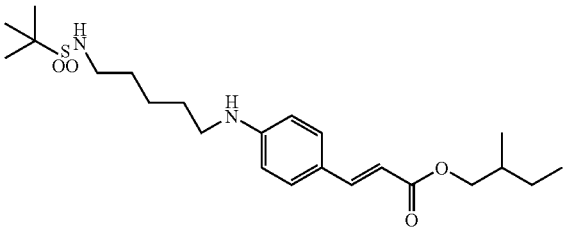
I-286
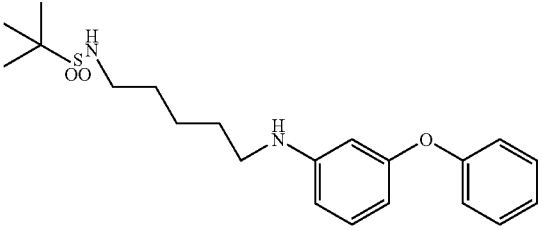
I-287
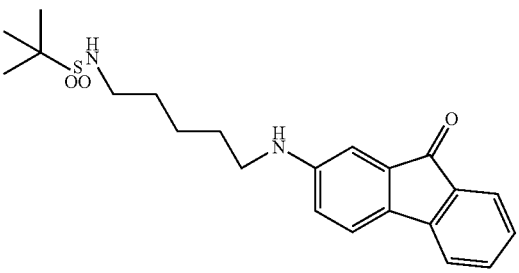

I-288
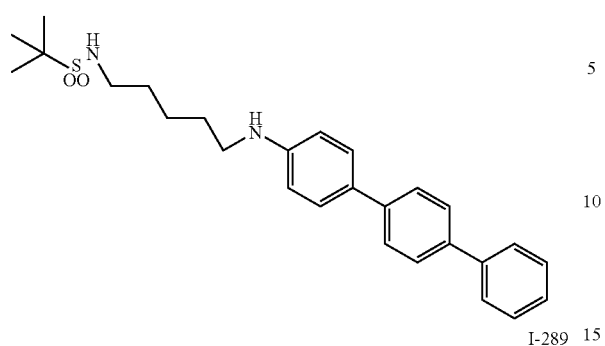
I-294
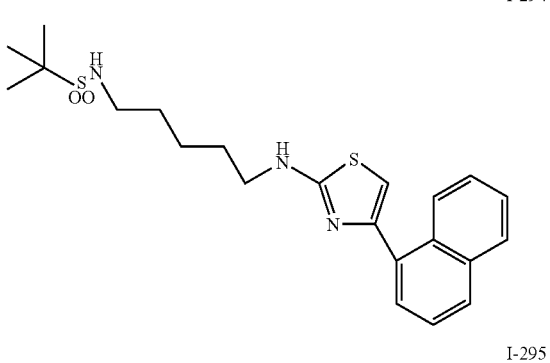
I-289
I-295
I-290
I-296
I-291
I-297
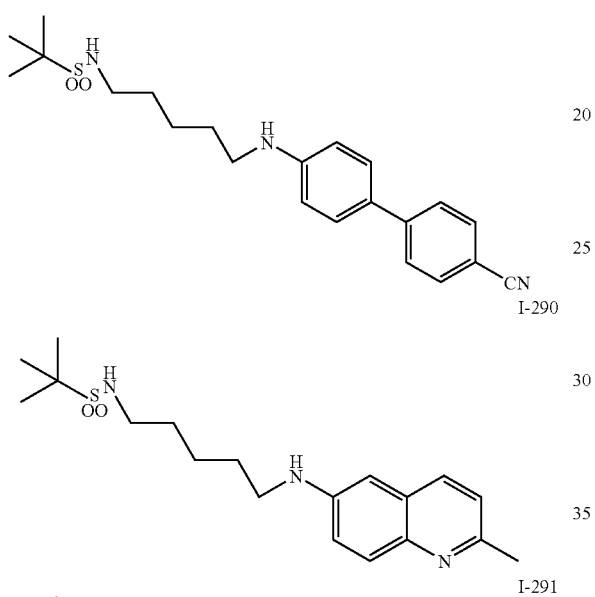
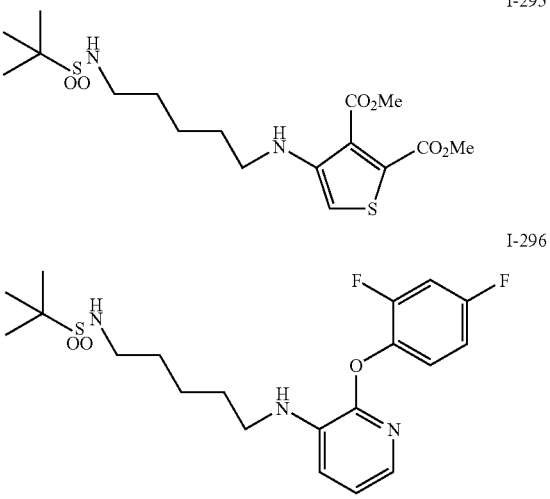
I-292
I-298
I-293
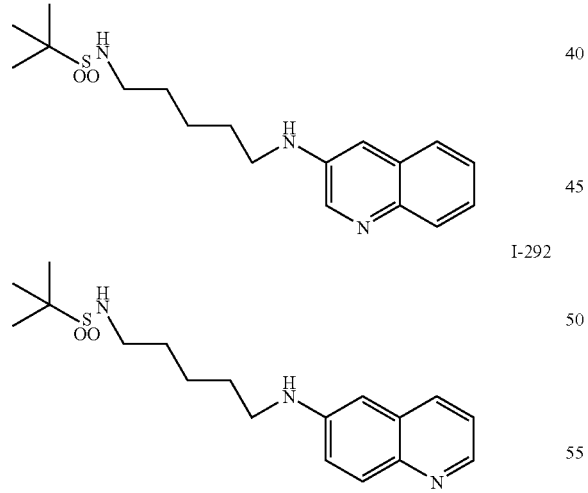
I-299
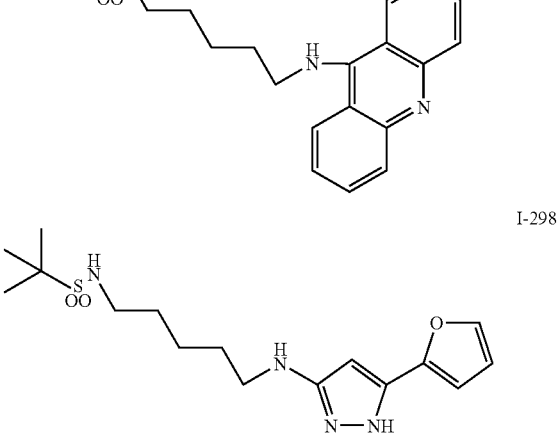
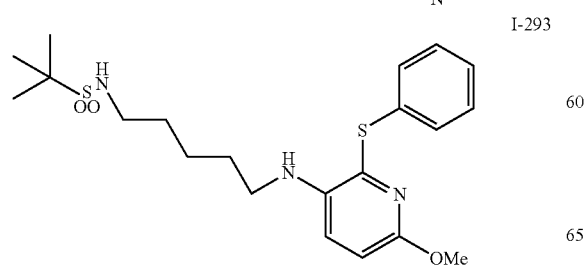
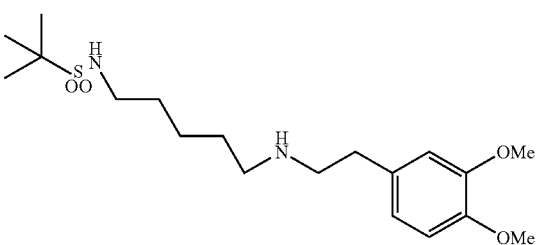

I-300
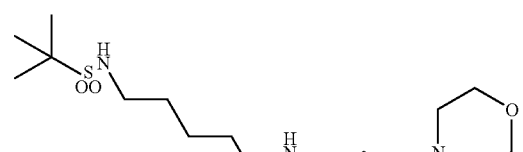
I-301
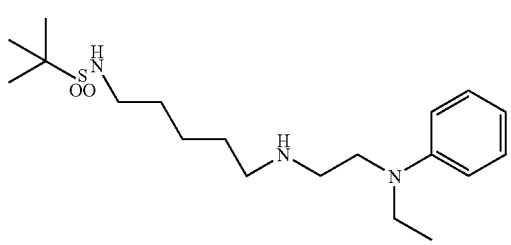
I-302
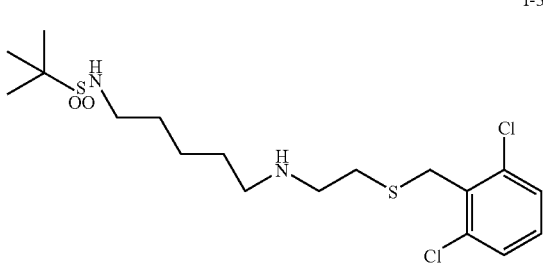
I-303
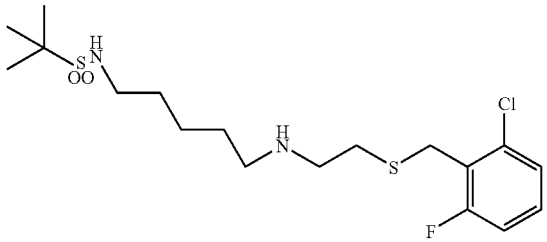
I-304
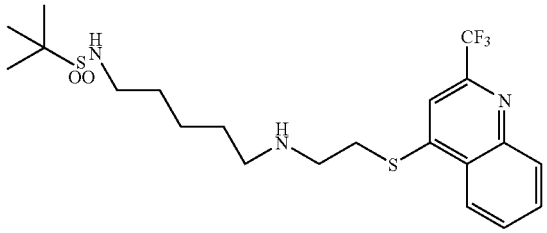
I-305
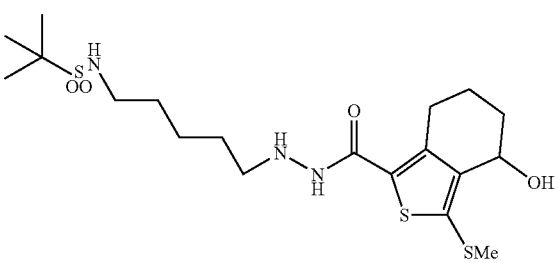
I-306
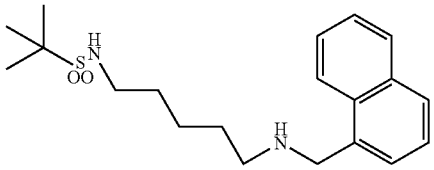
I-307
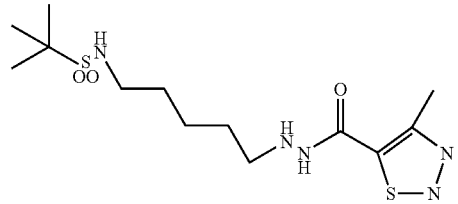
I-308
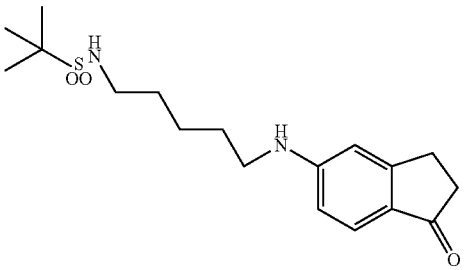
I-309
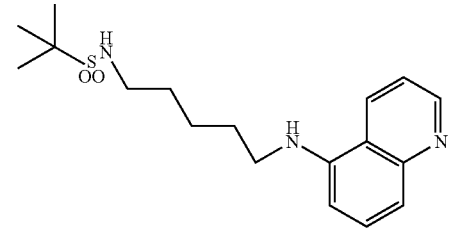
I-310
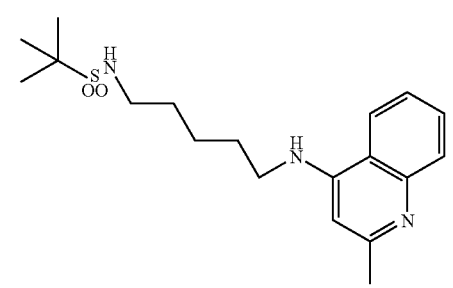
I-311
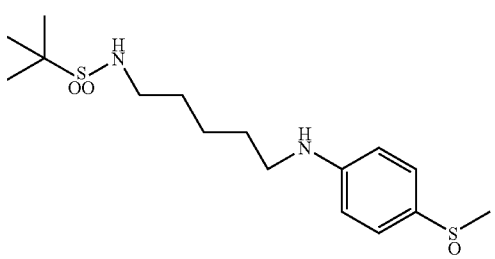

I-312
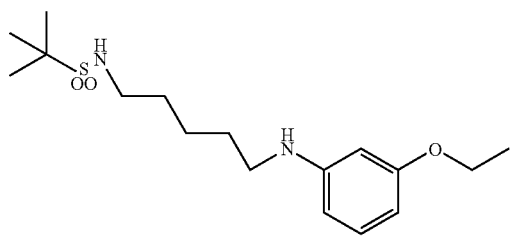
I-313
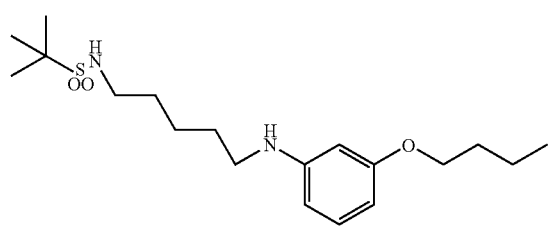
I-314
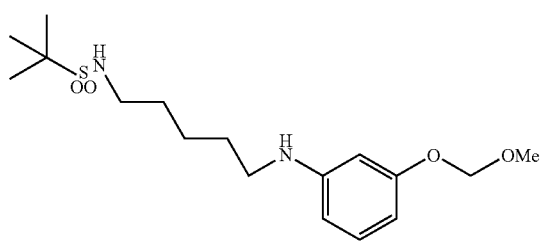
I-315
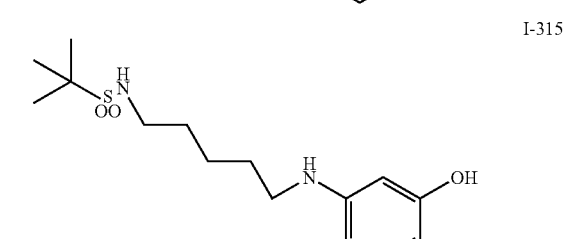
I-316
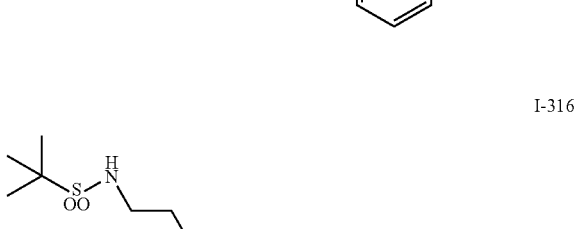
I-317
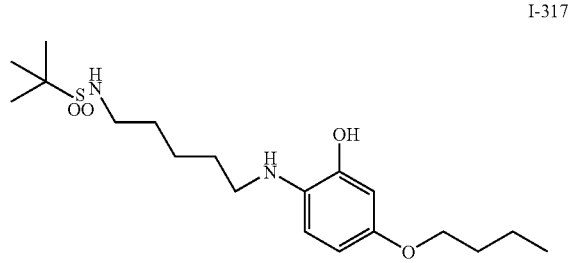
I-318
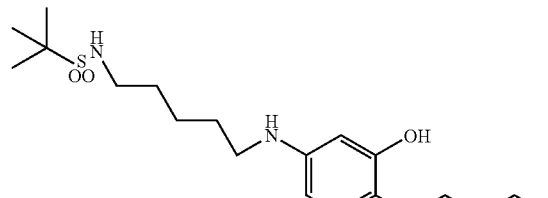
I-319
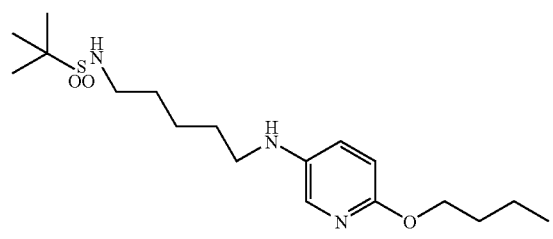
I-320
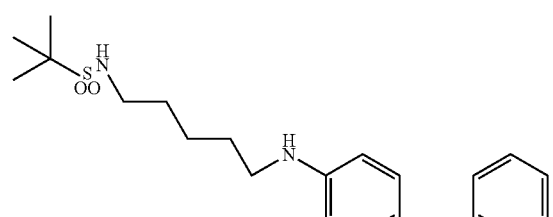
I-321
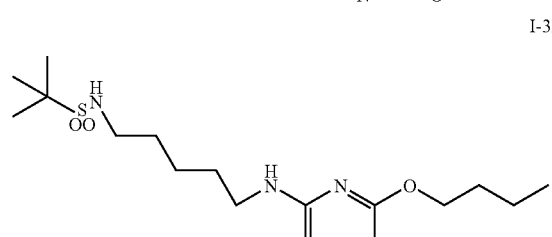
I-322
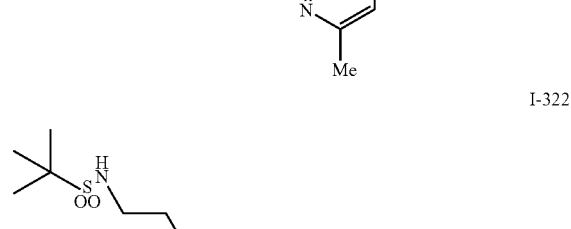
I-323
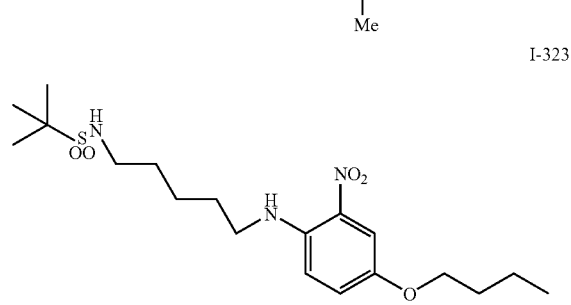

I-324
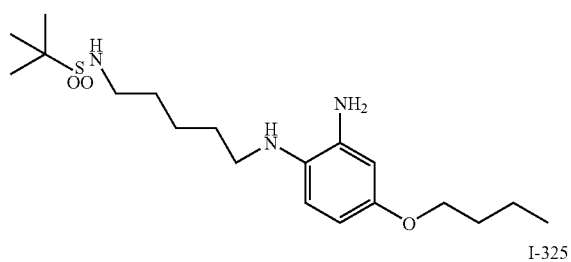
I-325
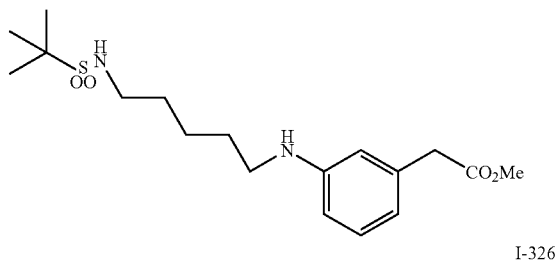
I-326
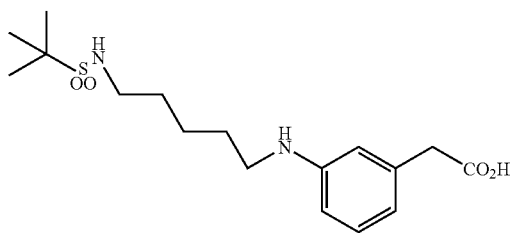
I-327
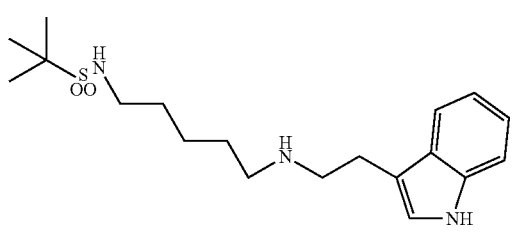
I-328
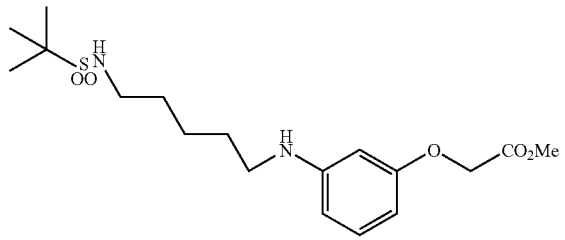
I-329
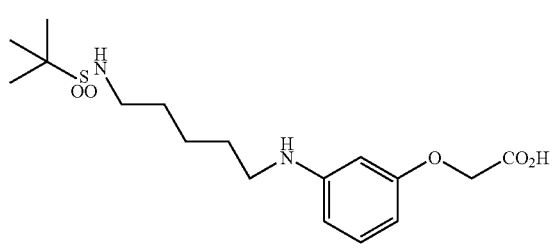
I-330

I-331

I-332

I-333

I-334
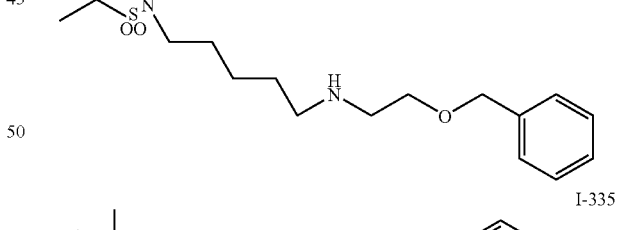
I-335
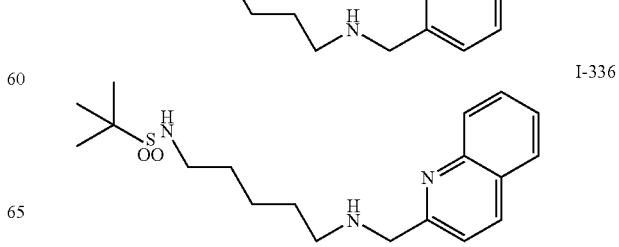
I-336

I-337 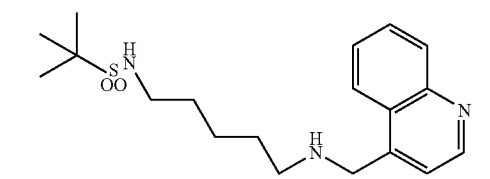
I-338 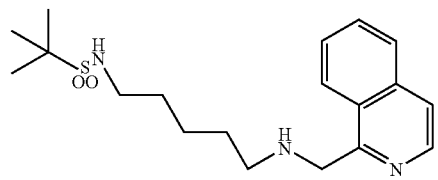
I-339 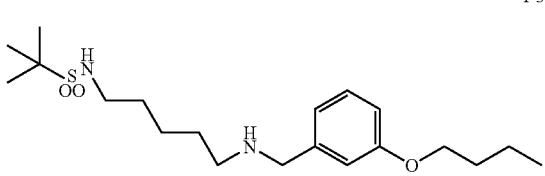
I-340 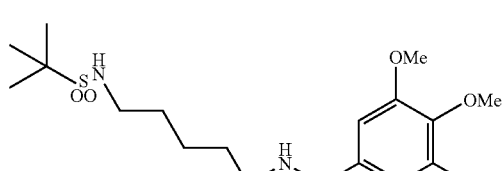
I-341 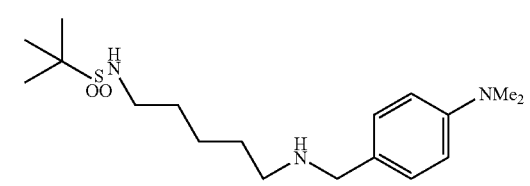
I-342 
I-343 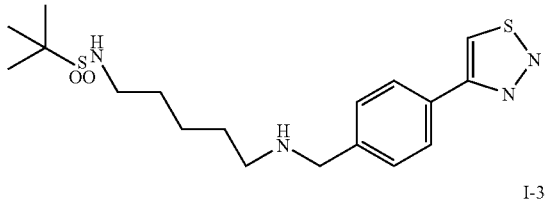
I-344 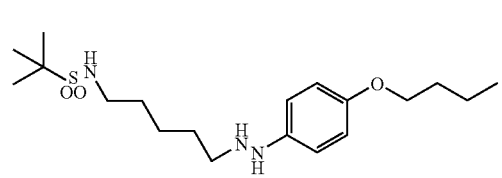
I-345 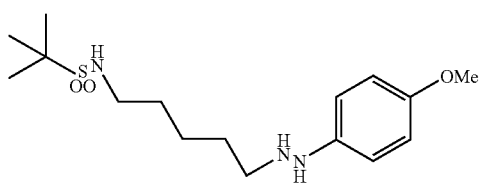
I-346 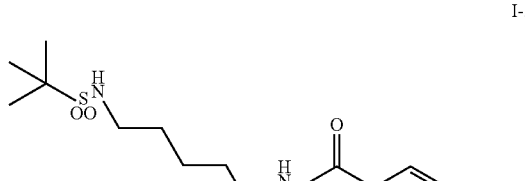
I-347 
I-348 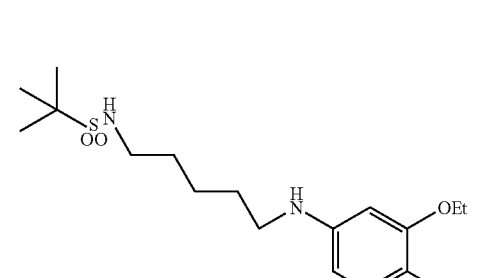
I-349 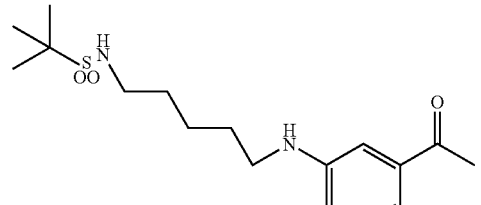
I-350 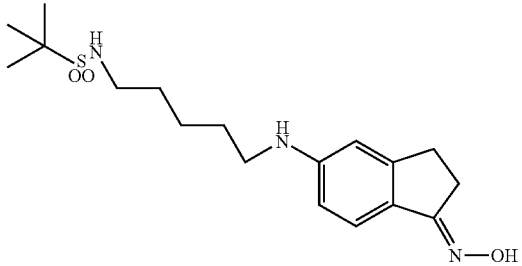

I-351
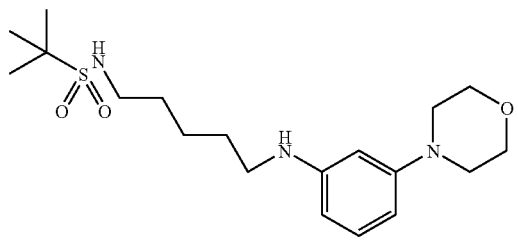
I-352
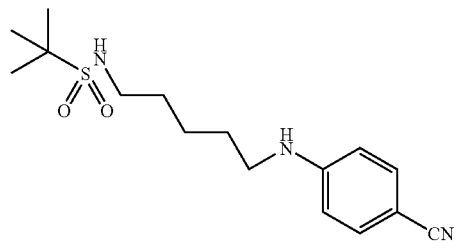
I-353
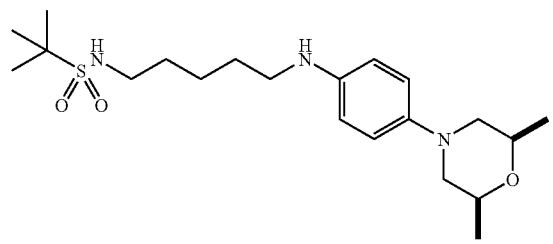
I-354
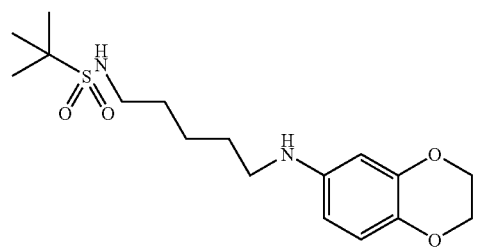
I-355
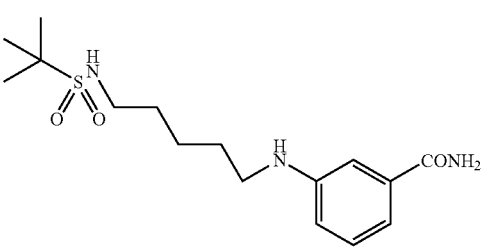
I-356
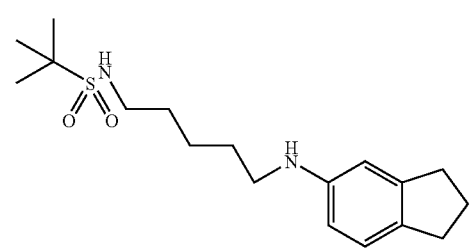
I-357
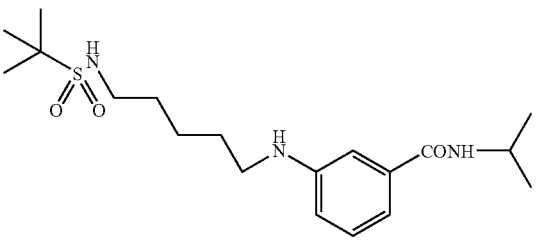
I-358
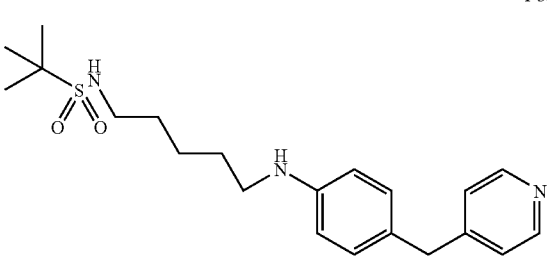
I-359
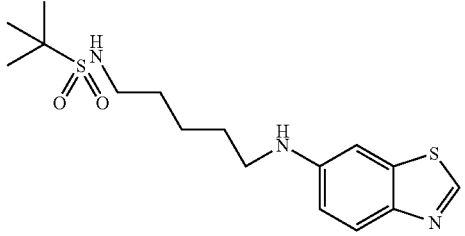
I-360
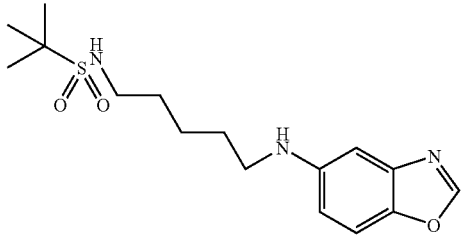
I-361
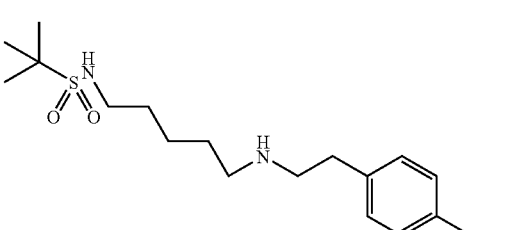
I-362
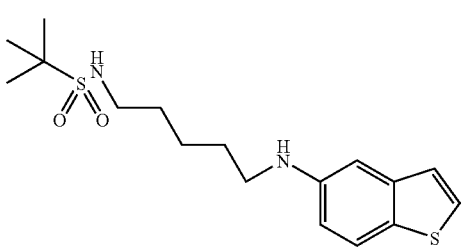

I-363
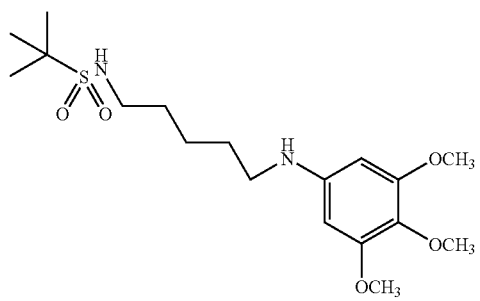
I-364
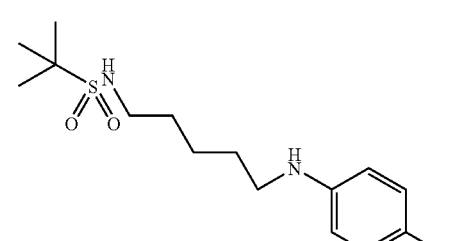
I-365
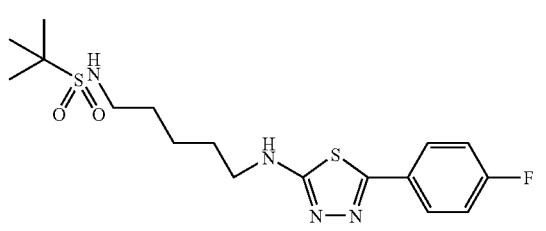
I-366
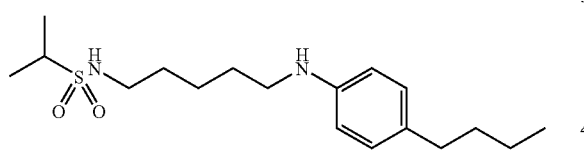
I-367
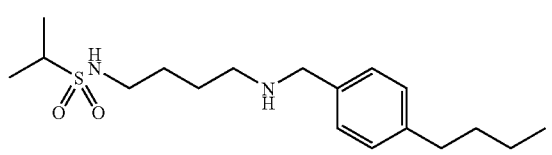
I-368
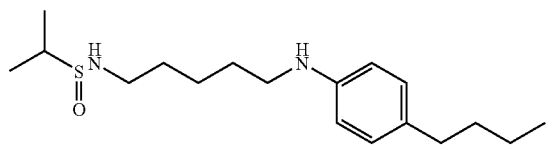
I-369
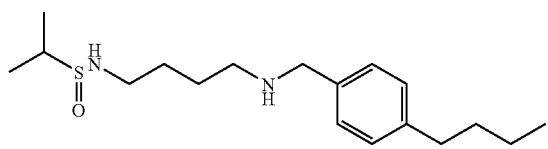
I-370
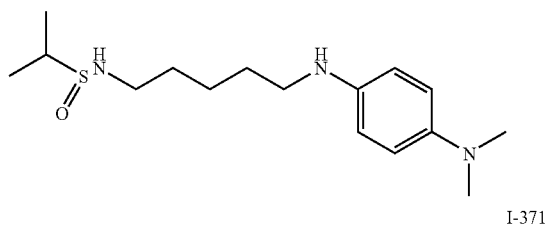
I-371
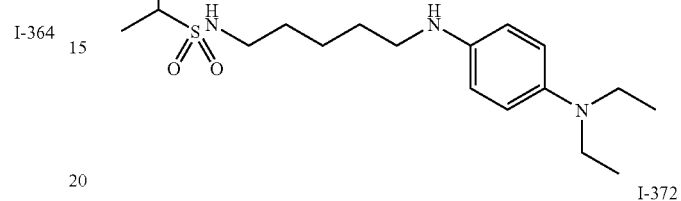
I-372
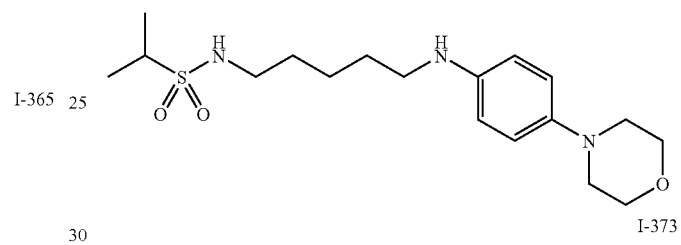
I-373
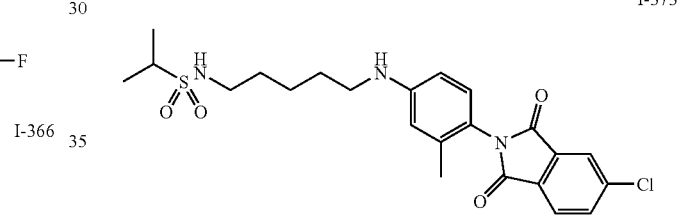
I-374
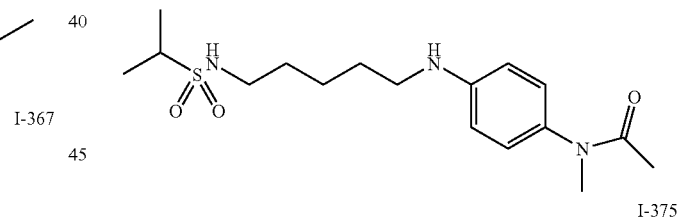
I-375
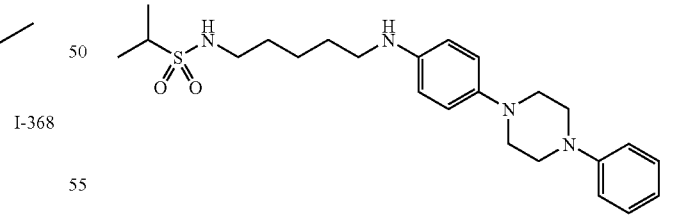
I-376
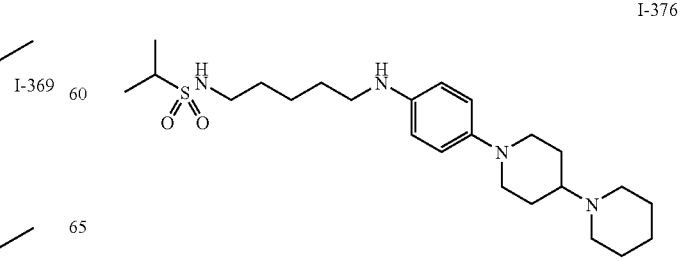

I-377
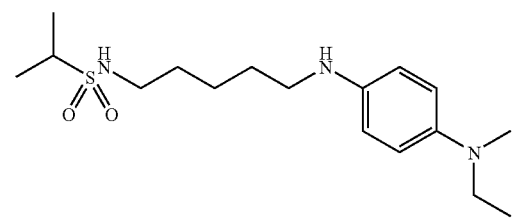
I-378
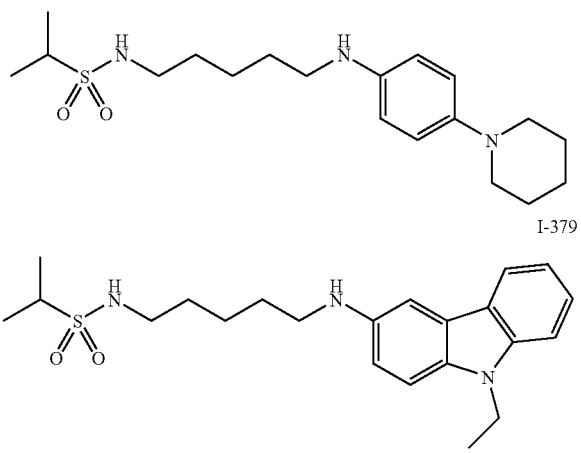
I-379
I-380
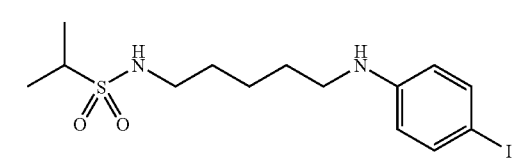
I-381
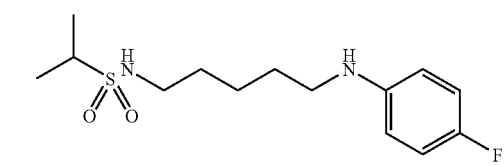
I-382
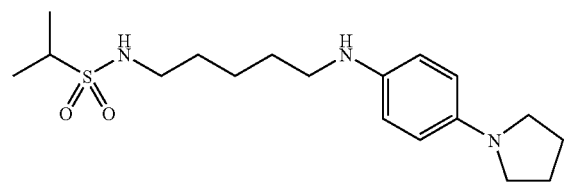
I-383
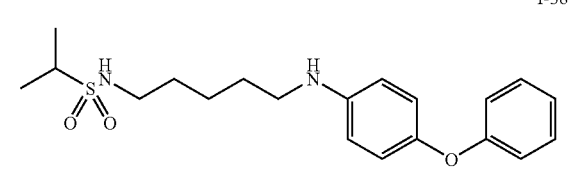
I-384
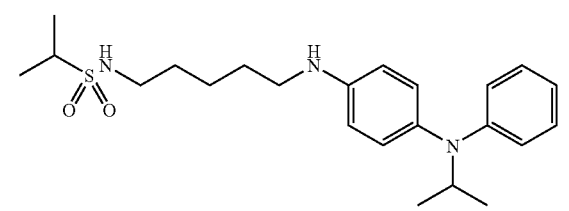
I-385
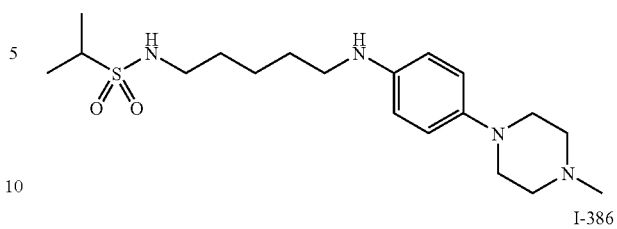
I-386
I-387
I-388
I-389
I-390
I-391

I-392 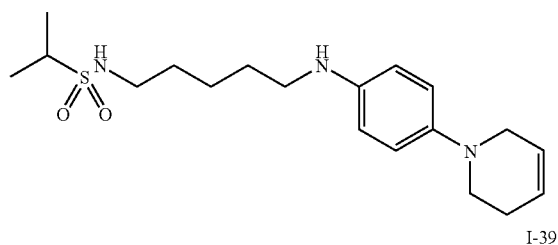
I-393 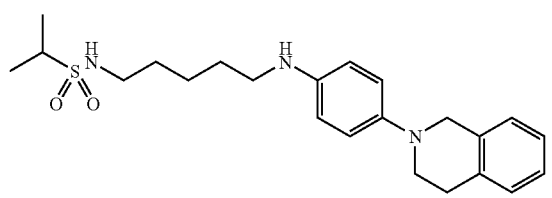
I-394 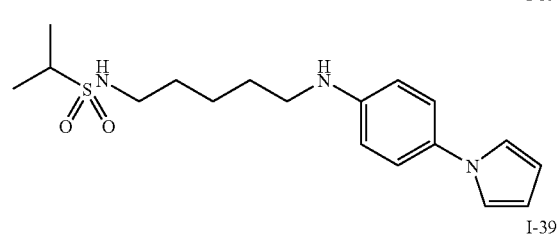
I-395 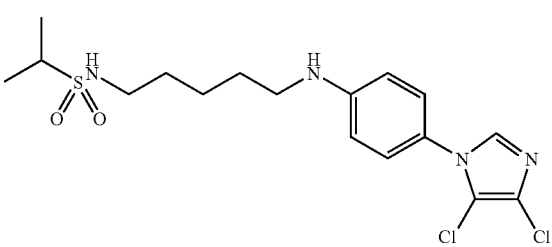
I-396 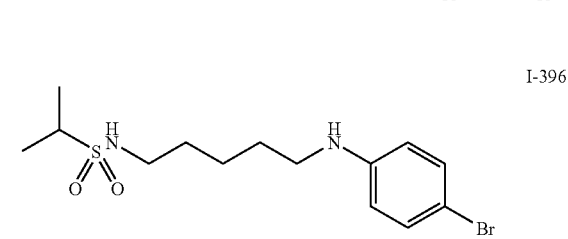
I-397 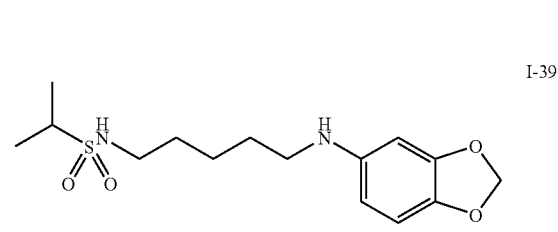
I-398 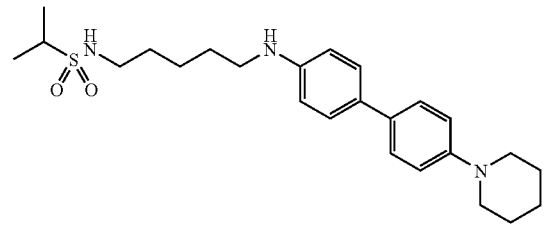
I-399 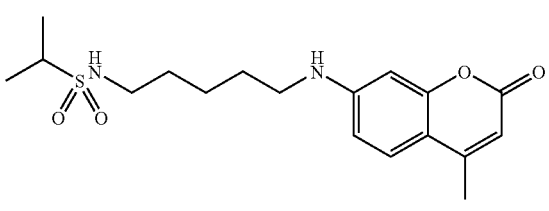
I-400 
I-401 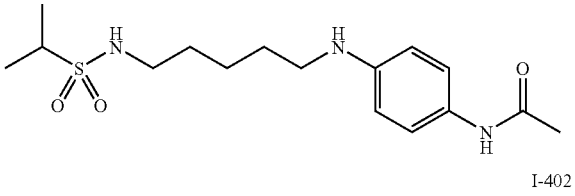
I-402 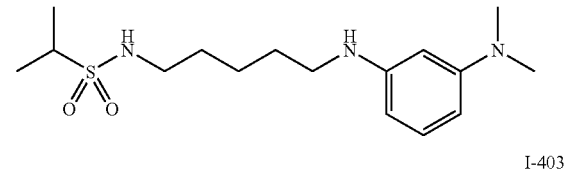
I-403 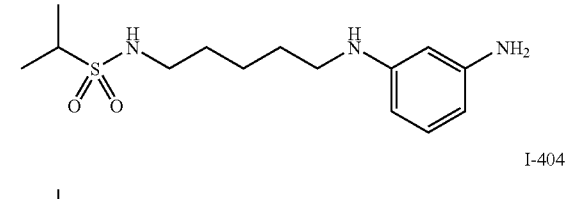
I-404 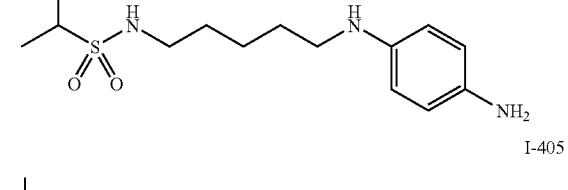
I-405 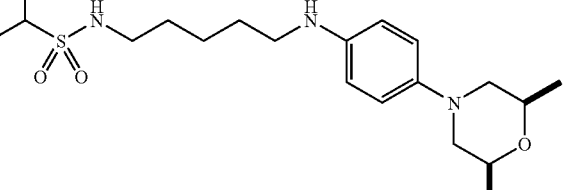
I-406 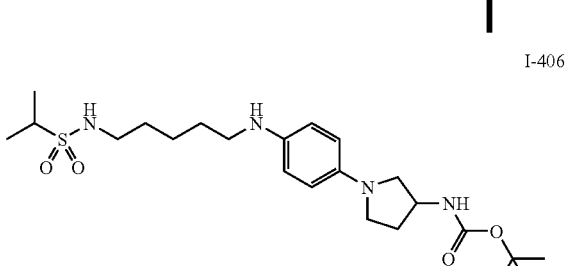

I-407
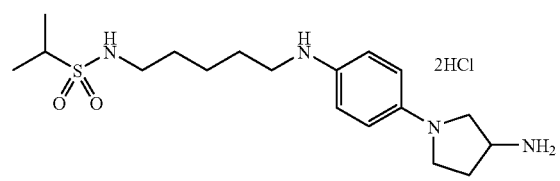
I-408
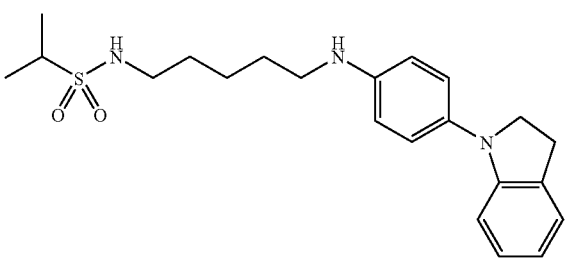
I-409
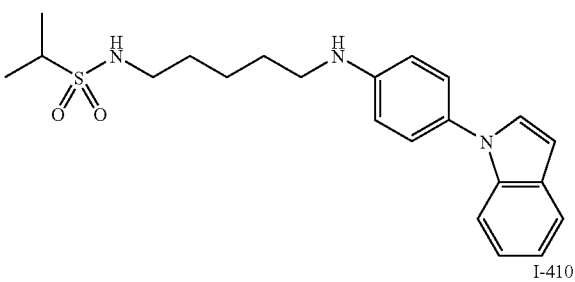
I-410
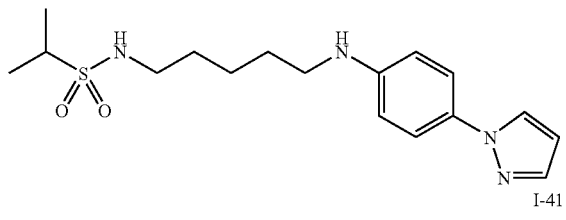
I-411
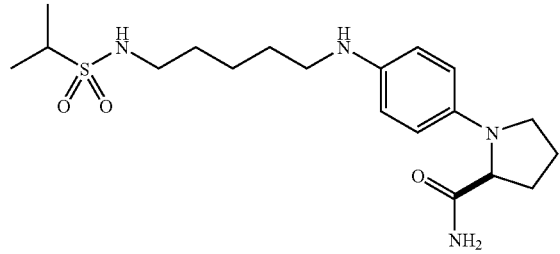
I-412
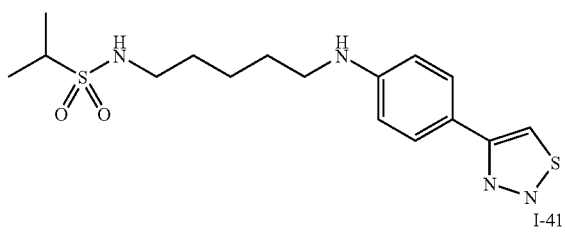
I-413
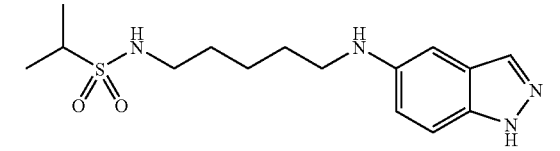
I-414
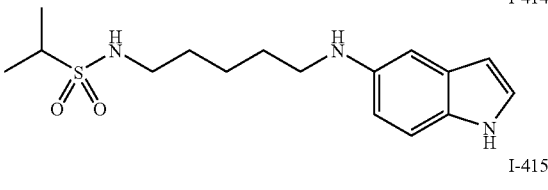
I-415
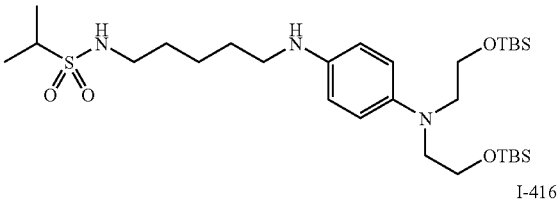
I-416
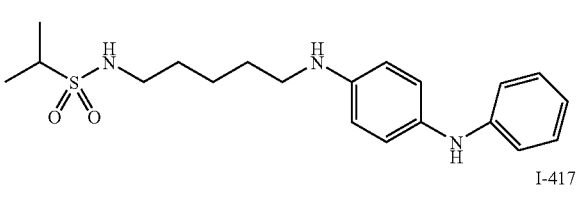
I-417
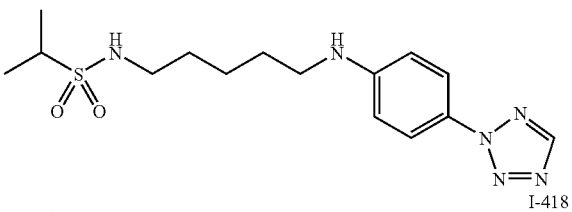
I-418
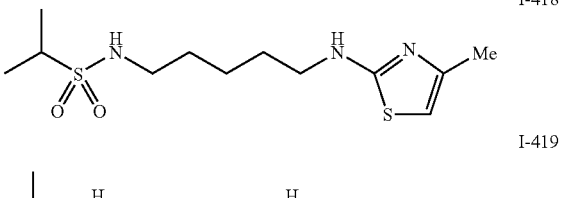
I-419
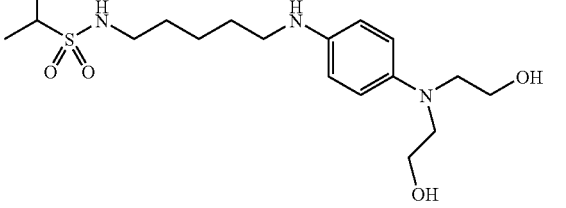
I-420
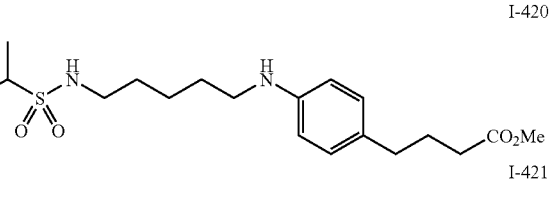
I-421
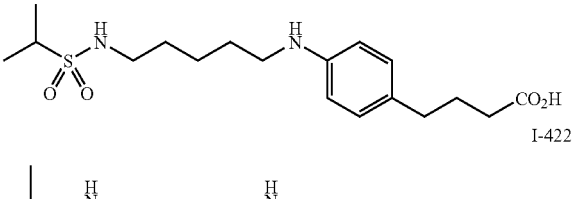
I-422
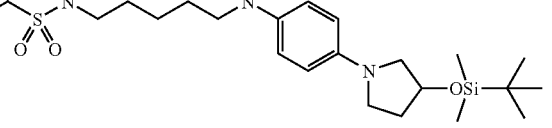

I-423
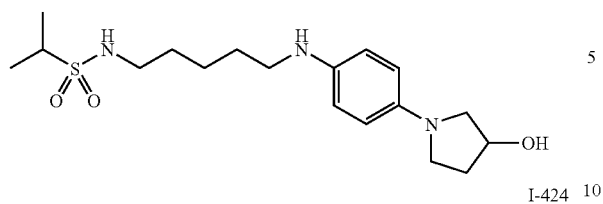
I-424
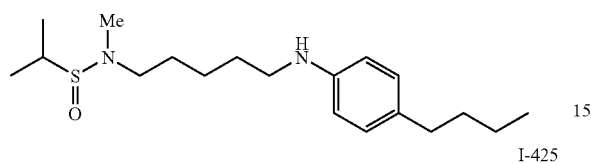
I-425
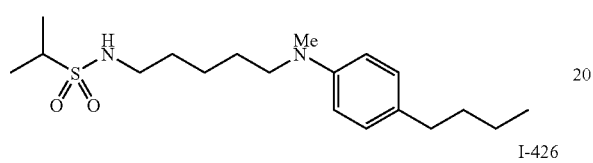
I-426
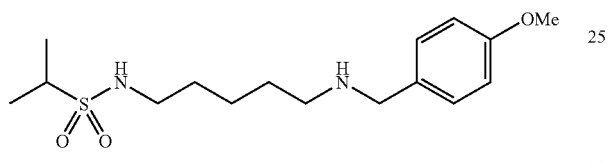
I-427
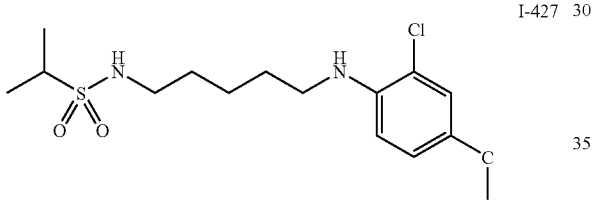
I-432
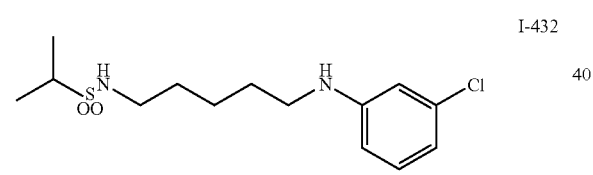
I-433

I-434
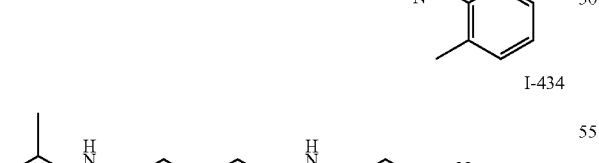
I-435
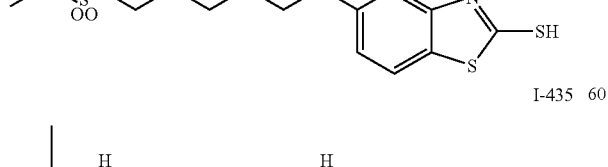

I-436
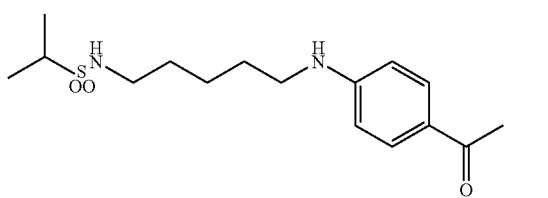
I-437
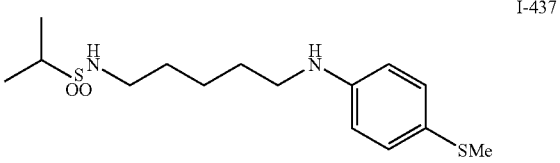
I-438
I-439
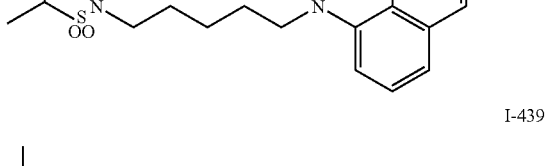
I-440
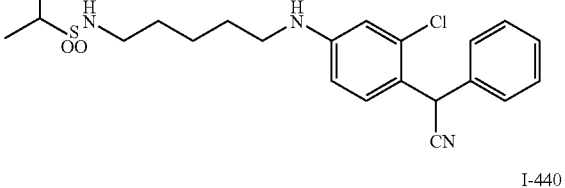
I-441
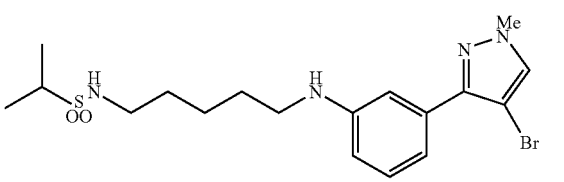
I-442

I-443
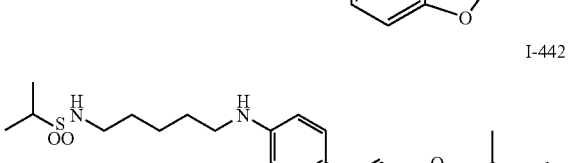
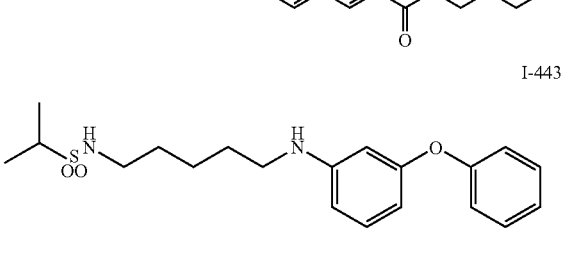

I-444
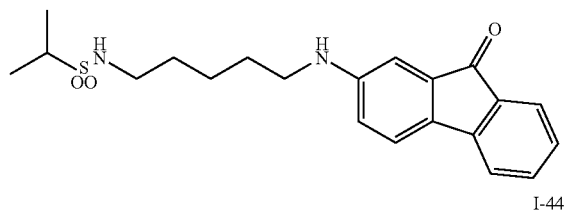
I-445
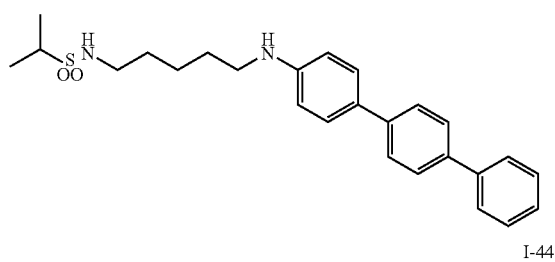
I-446
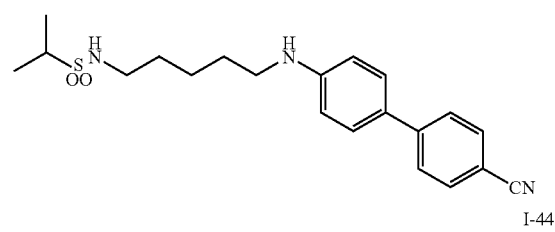
I-447
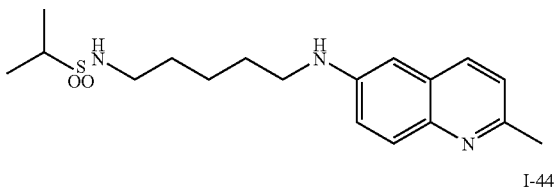
I-448
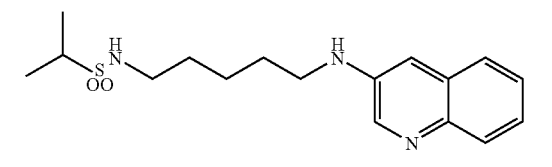
I-449
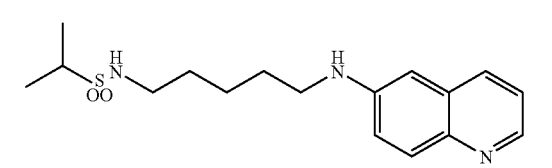
I-450
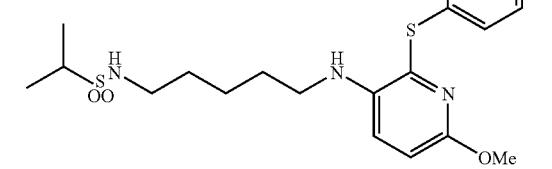
I-451
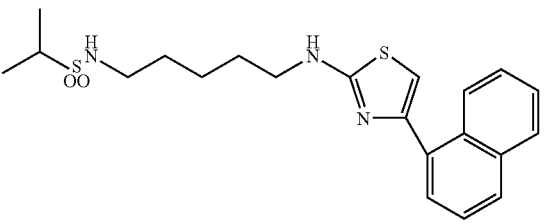
I-452
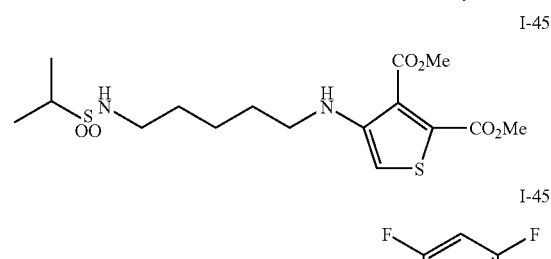
I-453
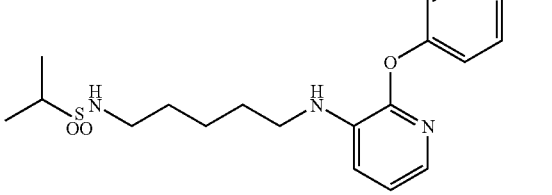
I-454
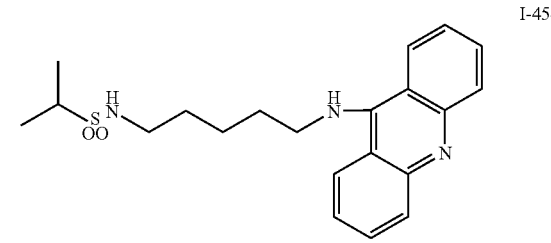
I-455
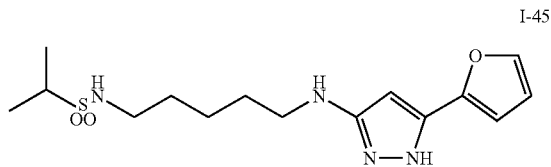
I-456
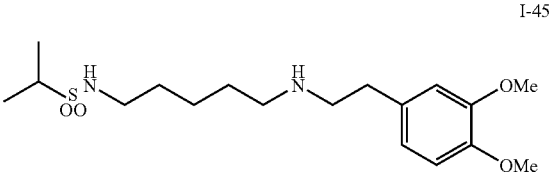
I-457
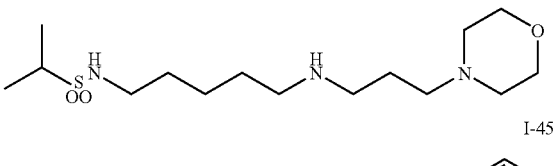

I-459
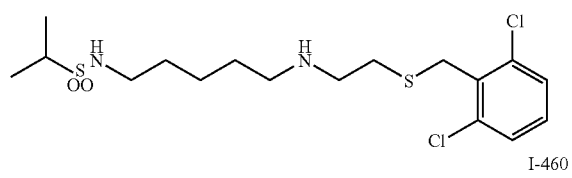
I-460
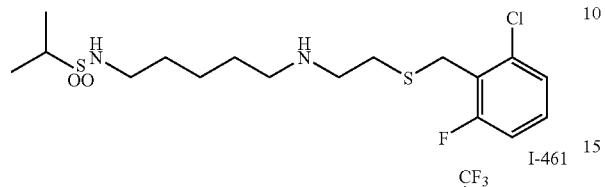
I-461
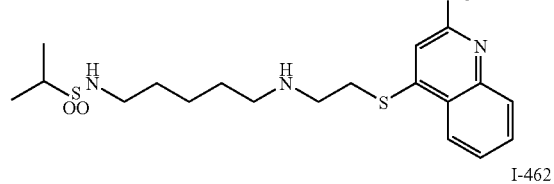
I-462
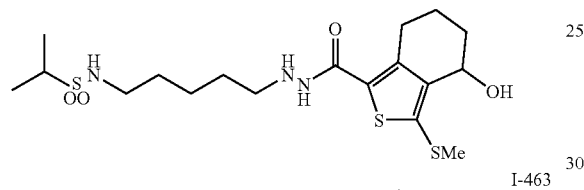
I-463

I-464
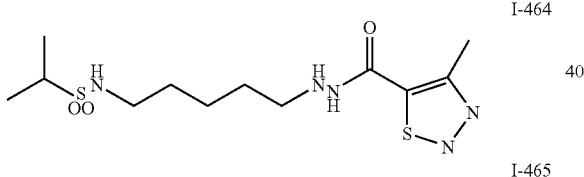
I-465
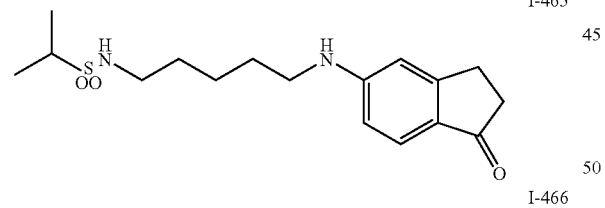
I-466
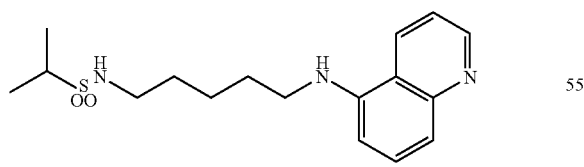
I-467
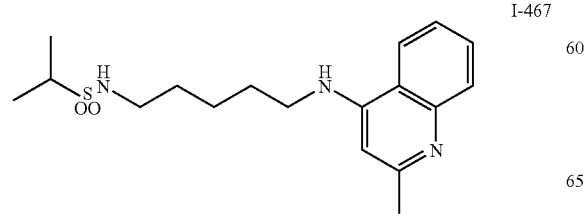
I-468
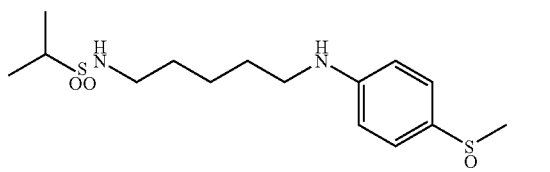
I-469
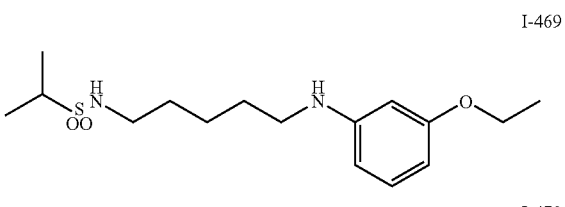
I-470
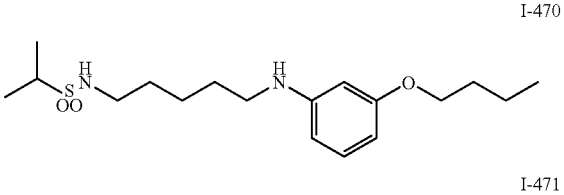
I-471
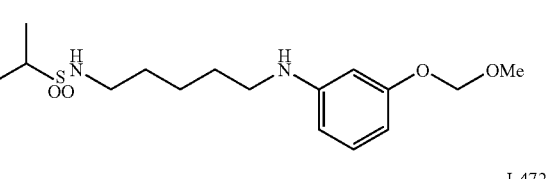
I-472
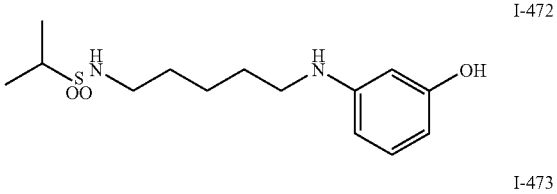
I-473
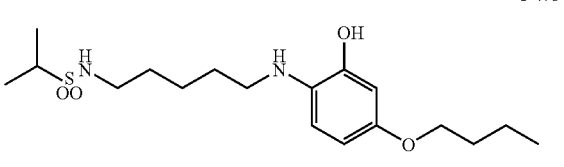
I-474
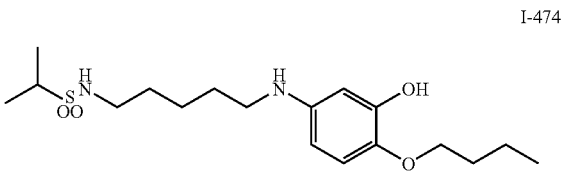
I-475
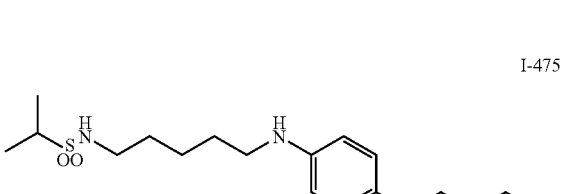
I-476

I-477
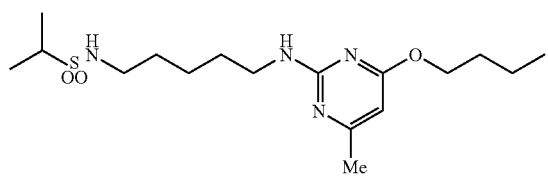
I-478
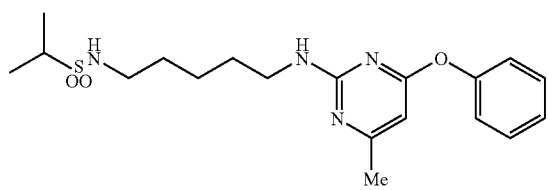
I-479
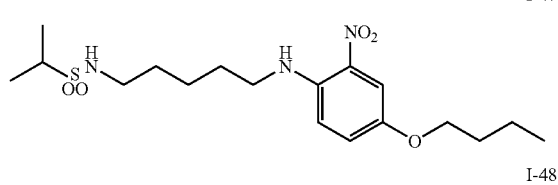
I-480
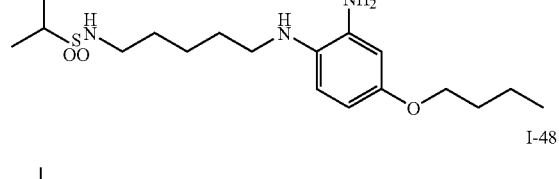
I-481
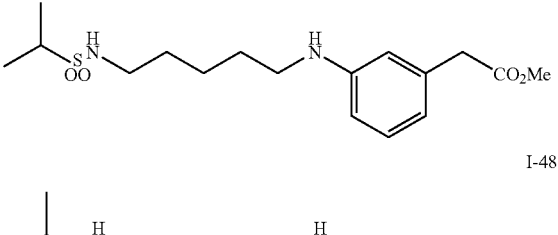
I-482
I-483
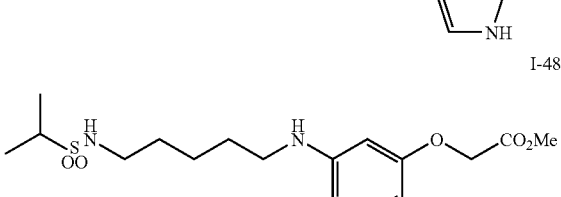
I-484
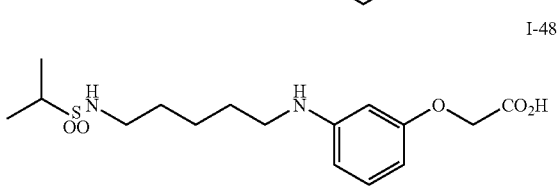
I-486
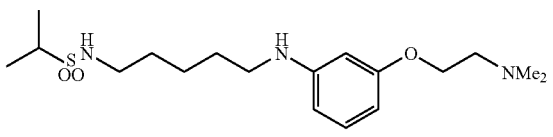
I-487
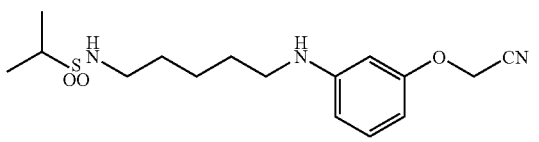
I-488
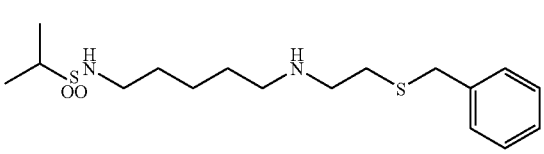
I-489
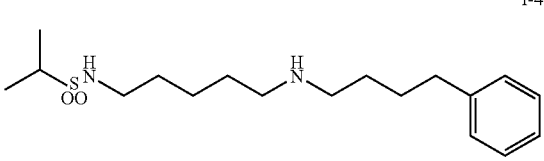
I-490
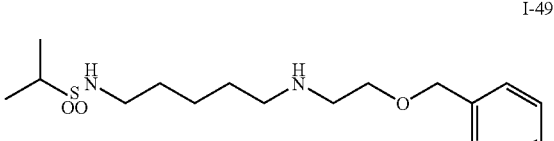
I-491
I-492
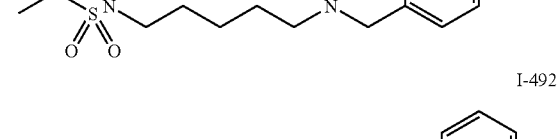
I-493
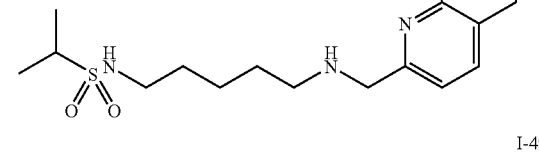
I-494
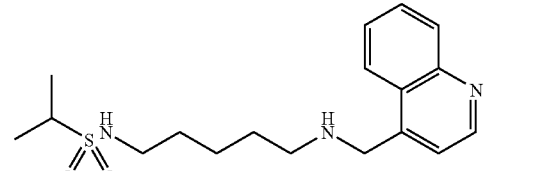

I-495
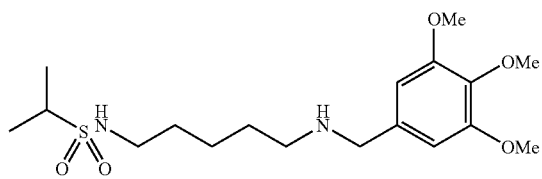
I-496
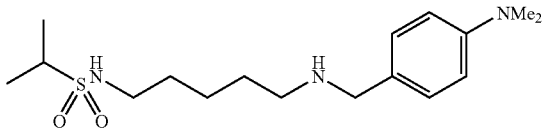
I-497
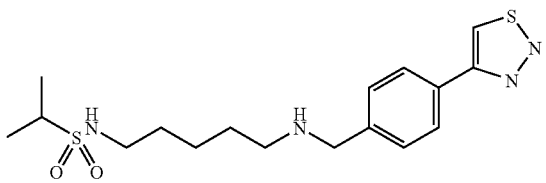
I-498
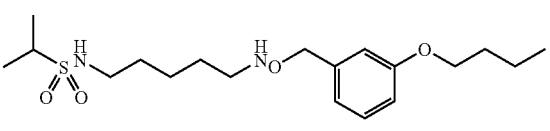
I-499
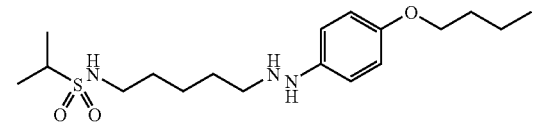
I-500
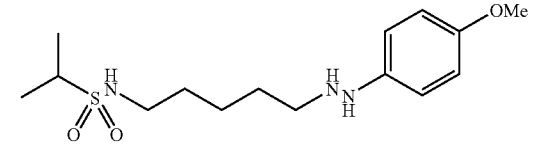
I-501
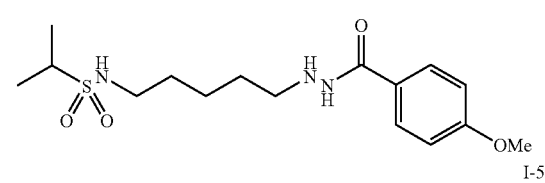
I-502
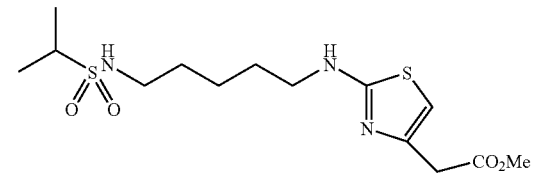
I-503
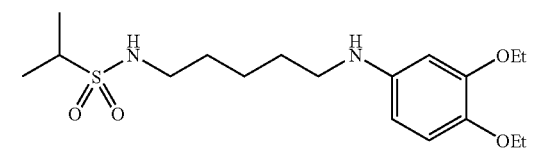
I-504
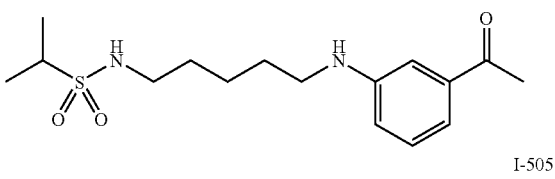
I-505
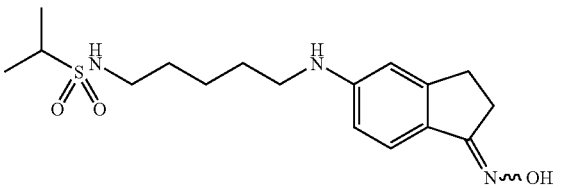
I-506
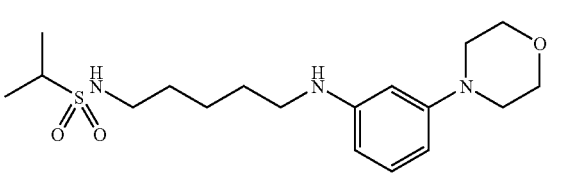
I-507
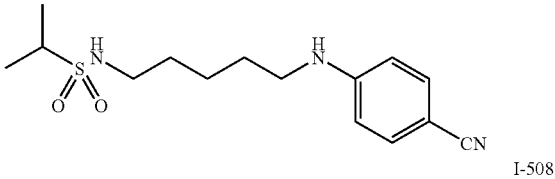
I-508
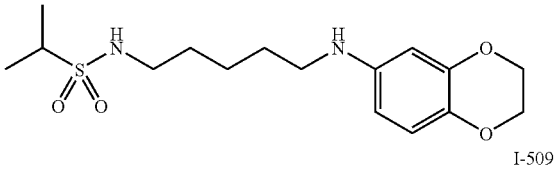
I-509
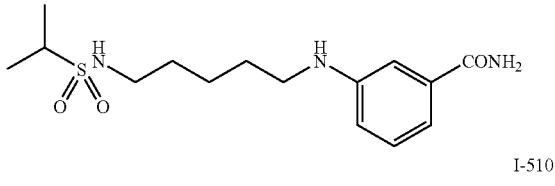
I-510
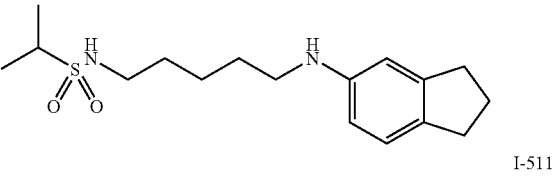
I-511
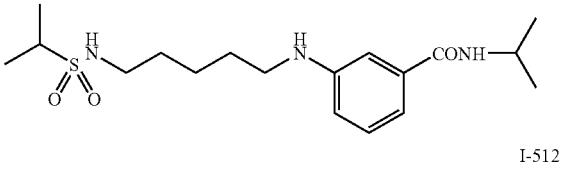
I-512
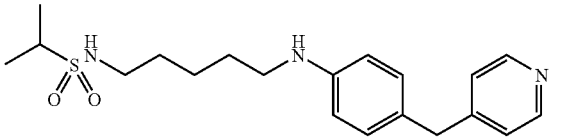

121
-continued
I-513
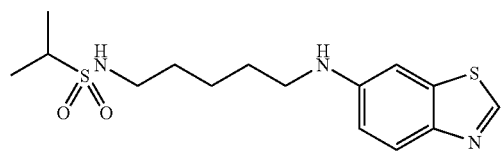
I-514
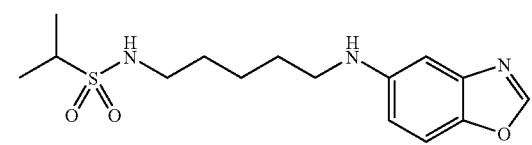
I-515
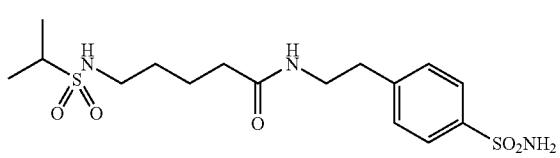
I-516
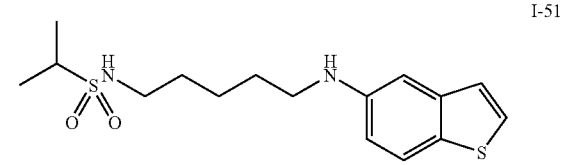
I-517
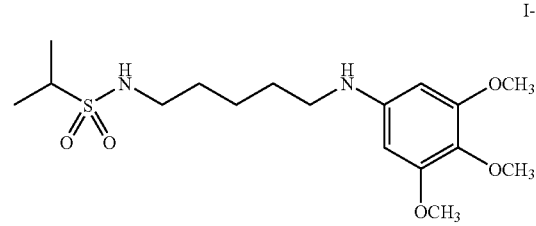
I-518
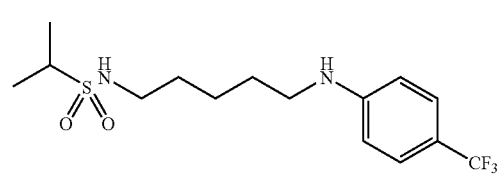
I-519
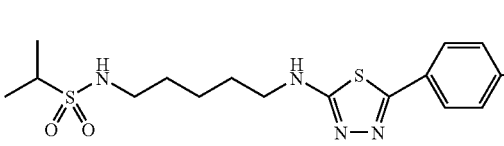
I-520
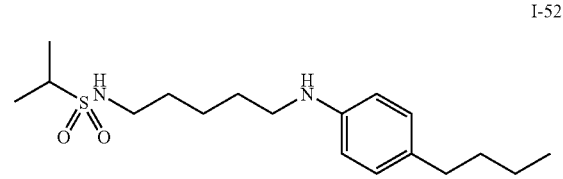
I-521
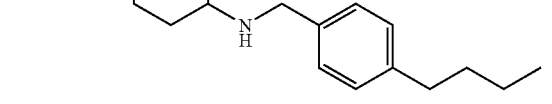
122
-continued
I-522
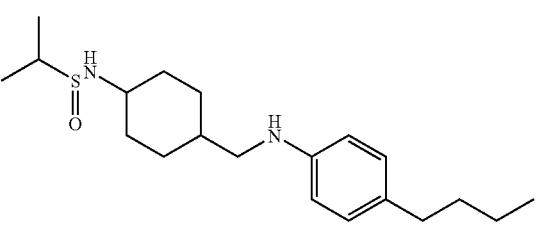
I-523
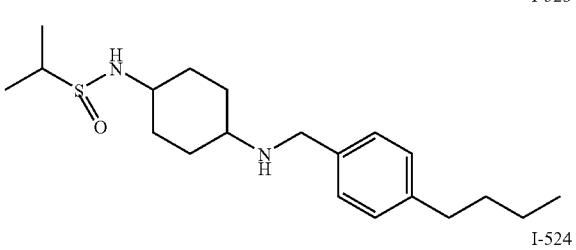
I-524
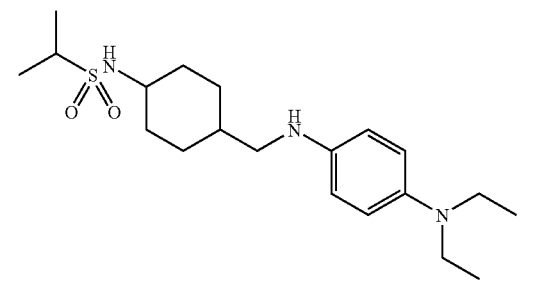
I-525
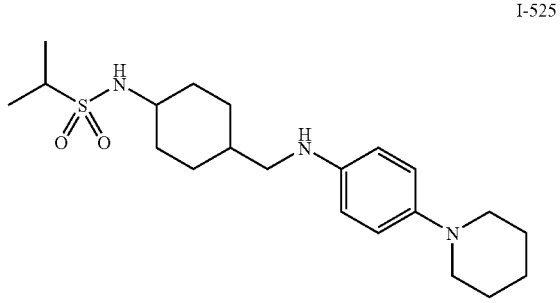
I-526
I-527
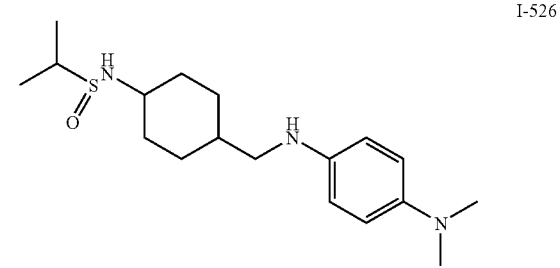

I-528
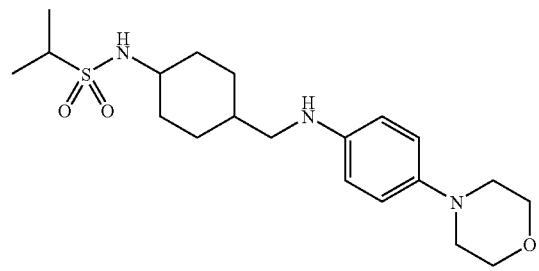
I-529
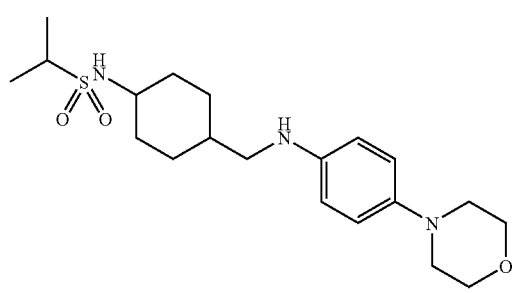
I-530
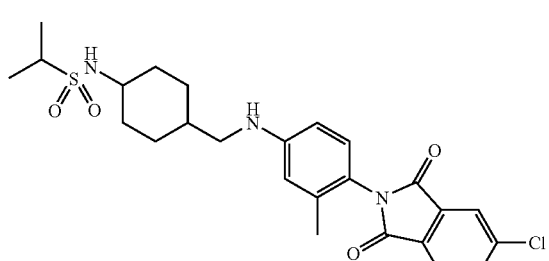
I-531
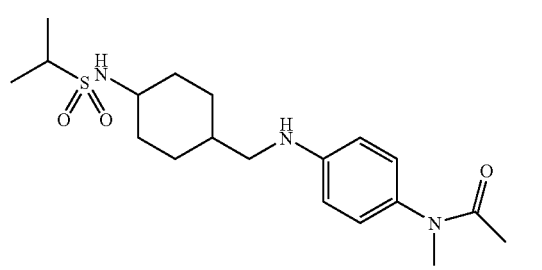
I-532
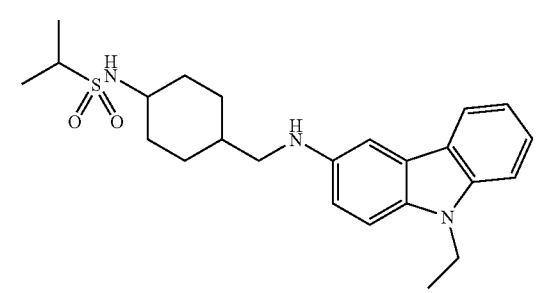
I-533
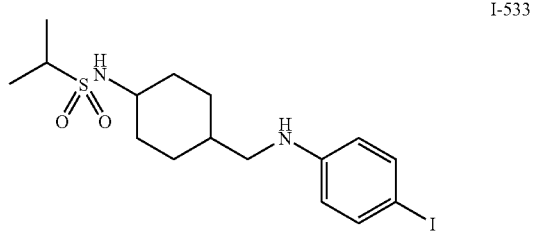
I-534
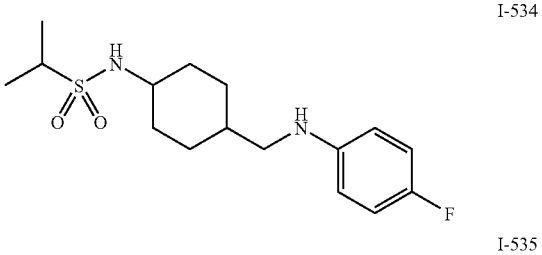
I-535
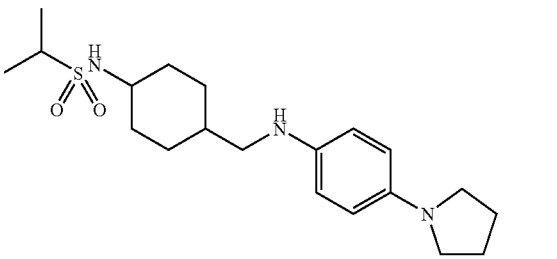
I-536
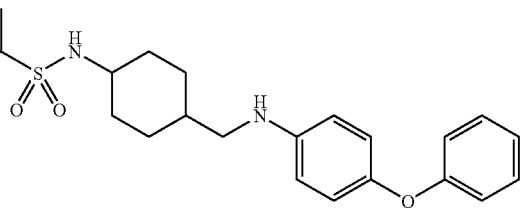
I-537
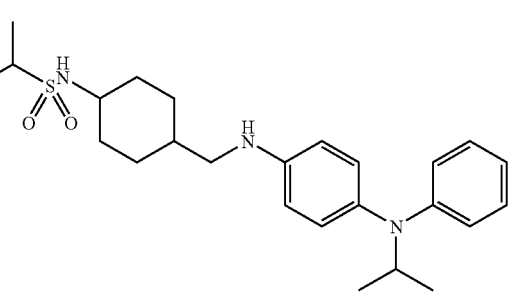
I-538
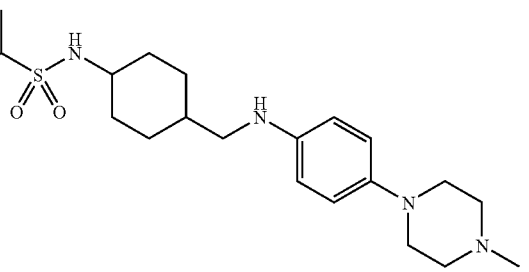

I-539
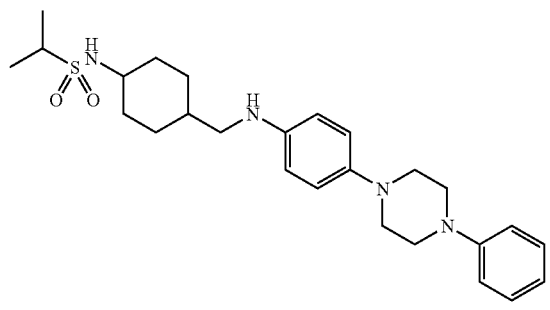
I-540
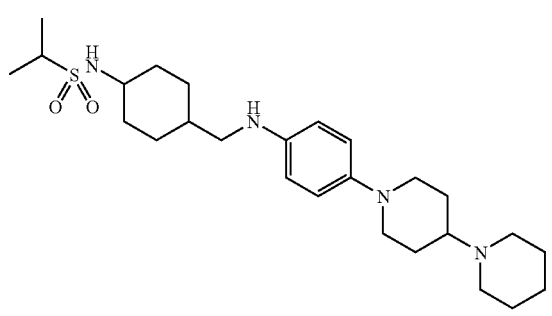
I-543
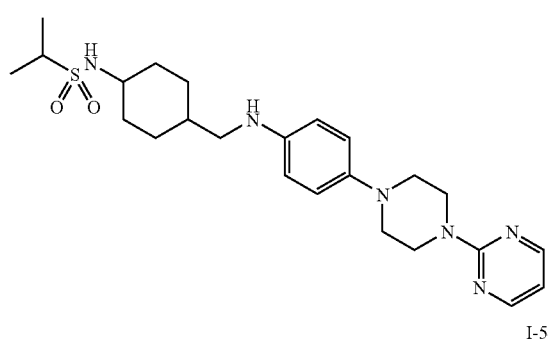
I-544
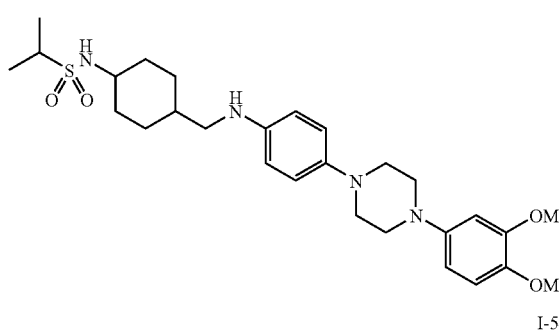
I-545
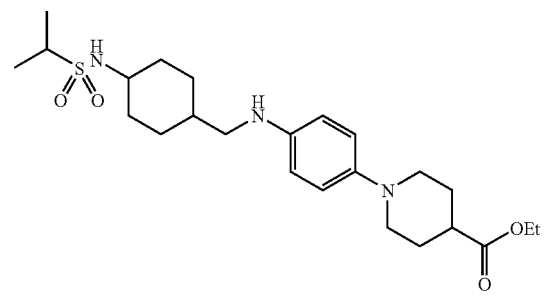
I-546
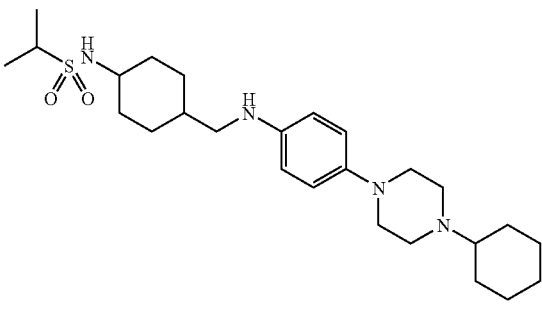
I-547
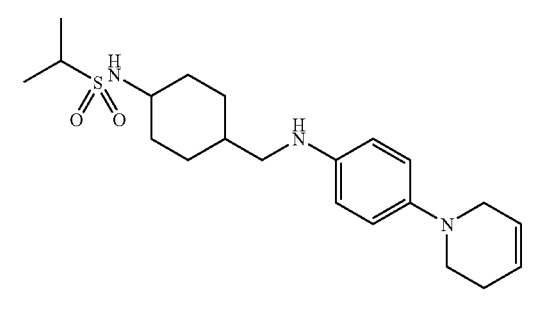
I-548
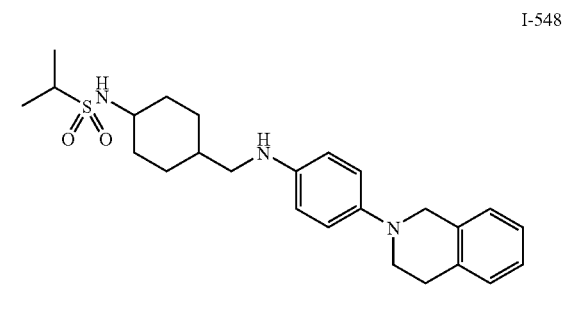
I-549
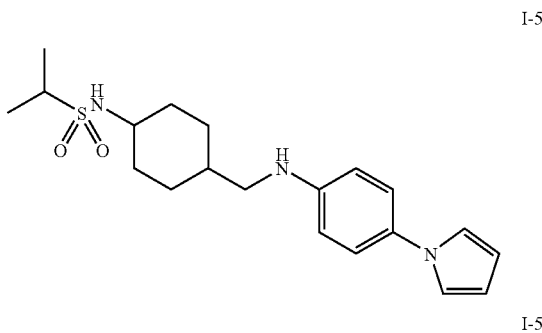
I-550
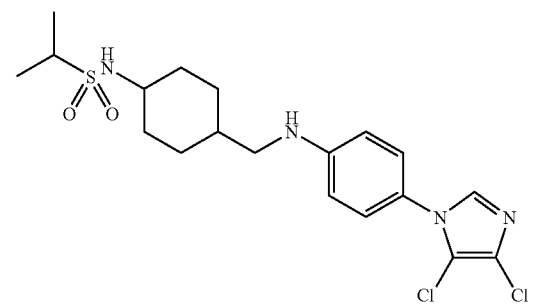

127
-continued
128
-continued
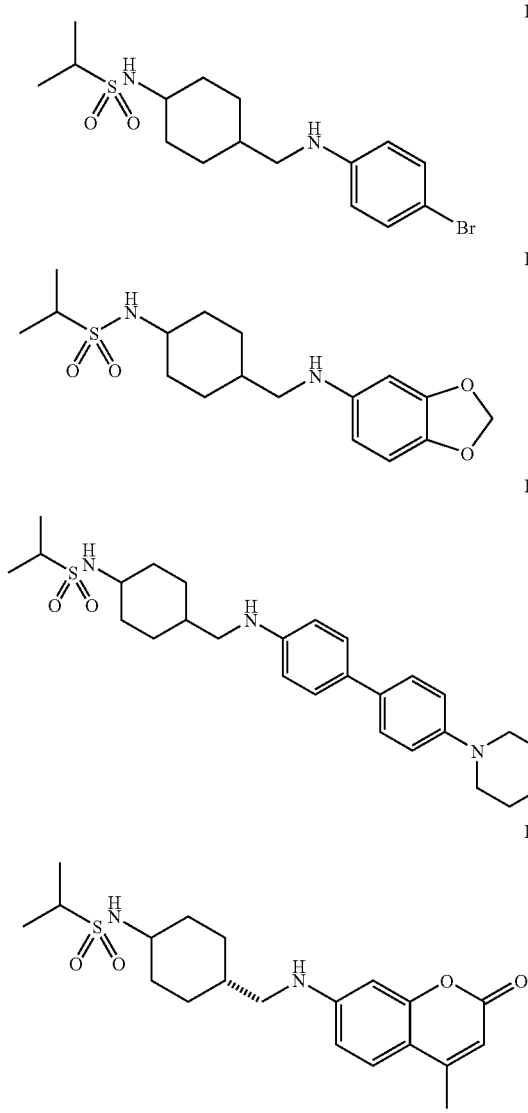
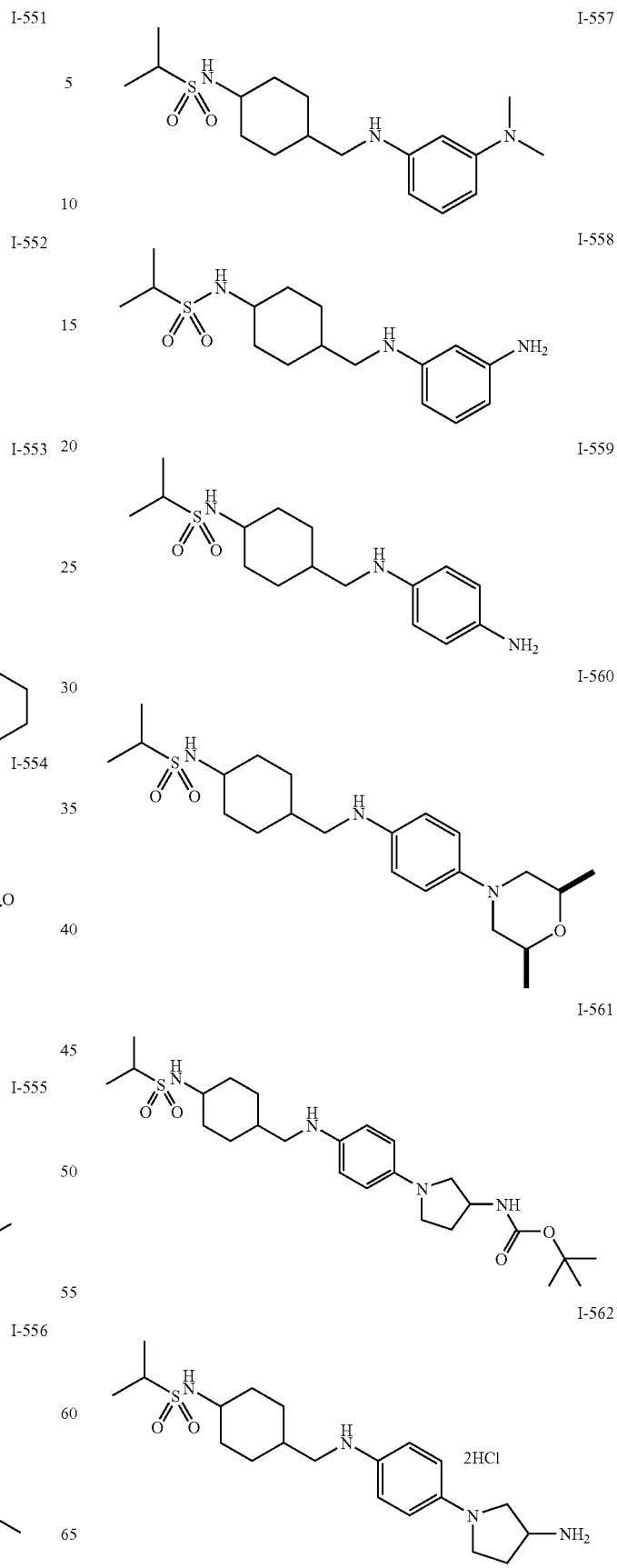

I-563
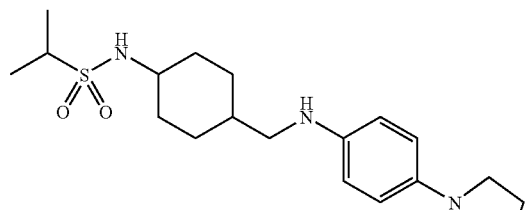
I-564
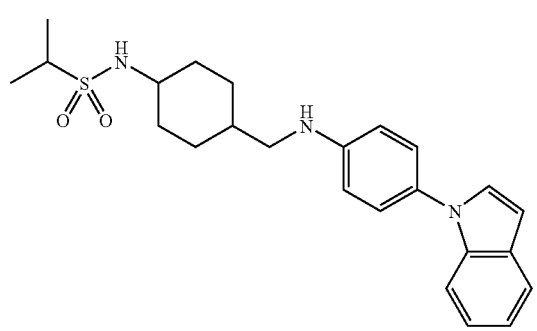
I-565
I-566
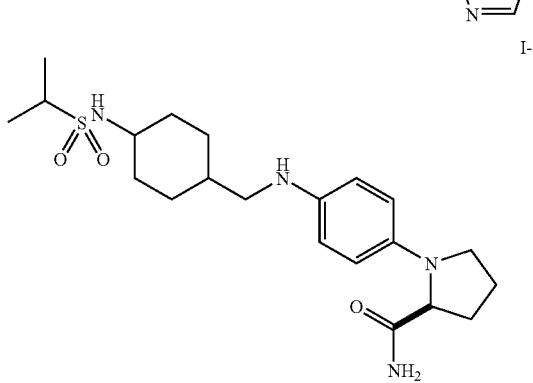
I-567
I-568
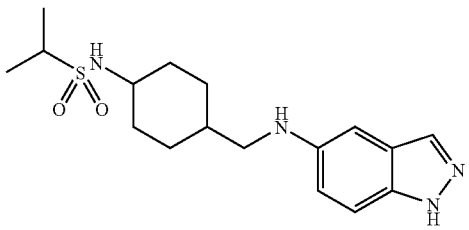
I-569
I-570
I-571
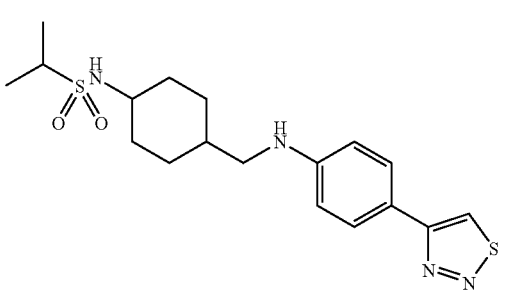
I-572
I-573

I-574
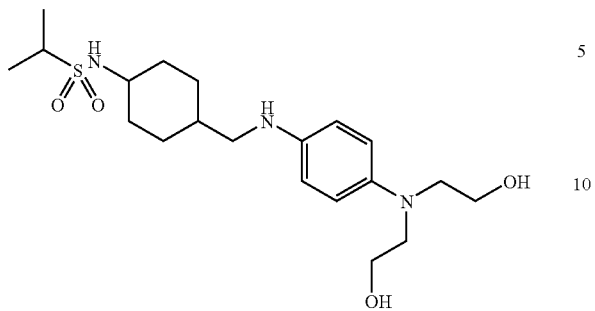
I-575
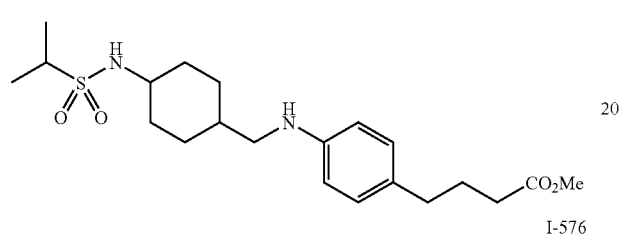
I-576
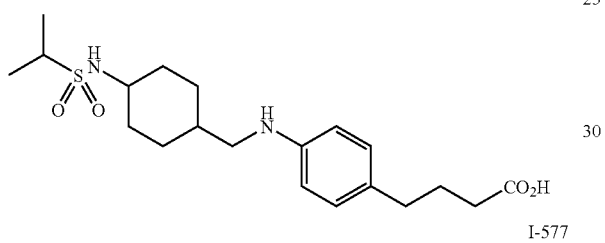
I-577
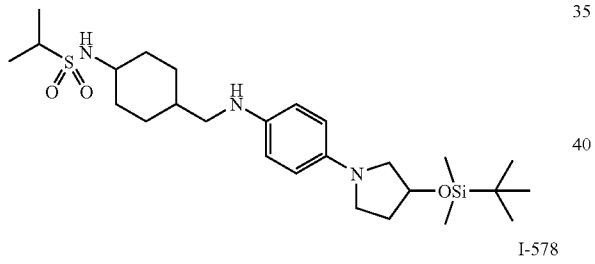
I-578
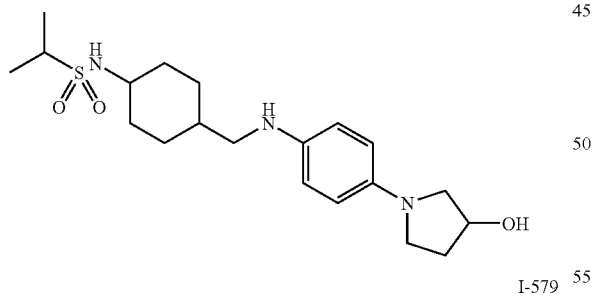
I-579
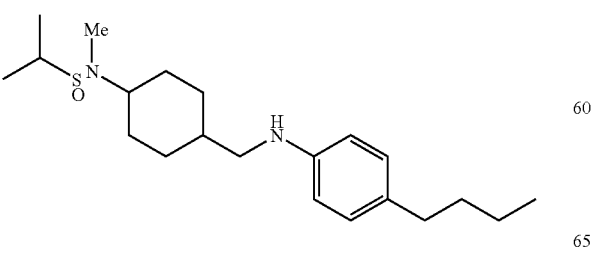
I-580
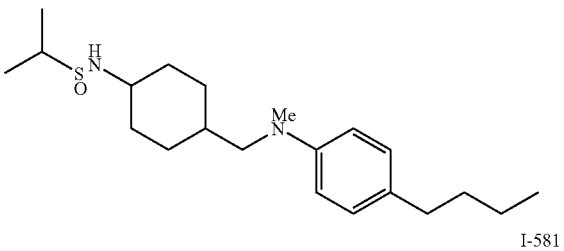
I-581
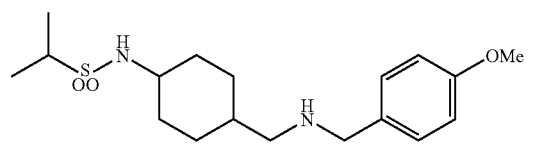
I-582
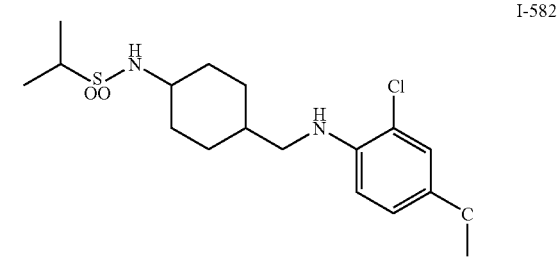
I-583
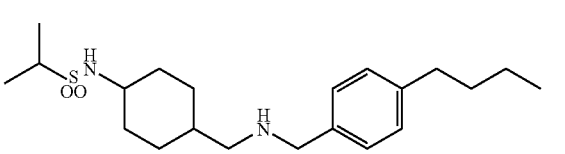
I-584
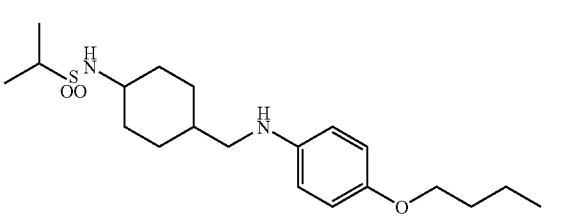
I-585
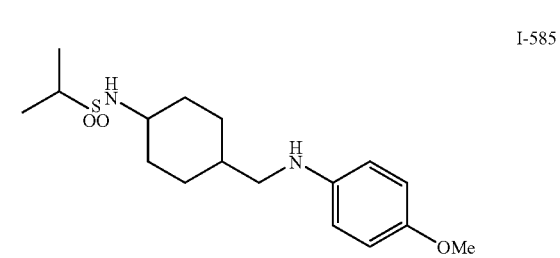
I-587
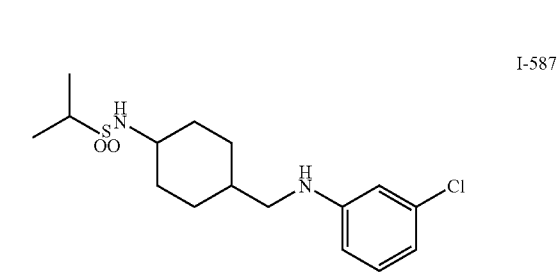

I-589
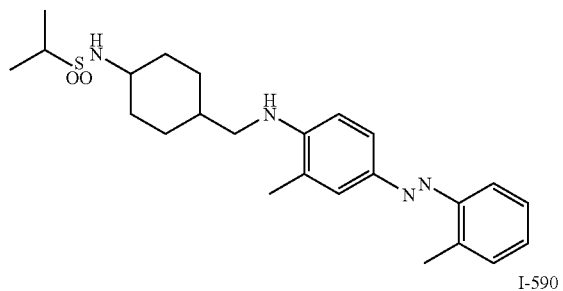
I-590
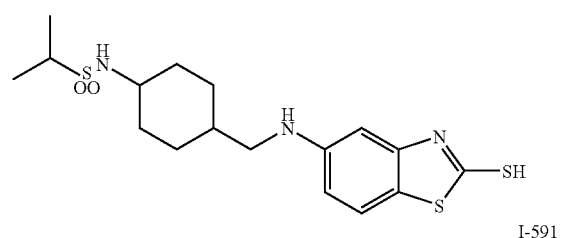
I-591
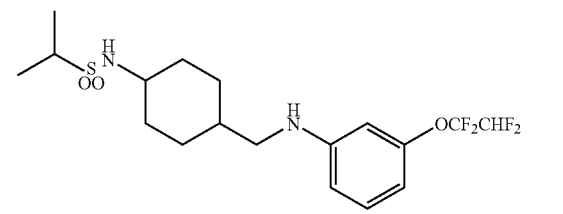
I-592
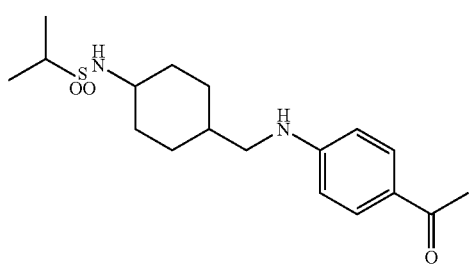
I-593
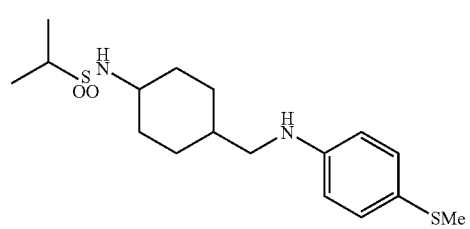
I-594
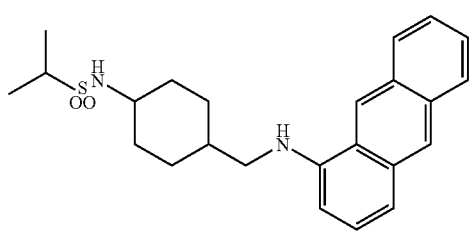
I-595
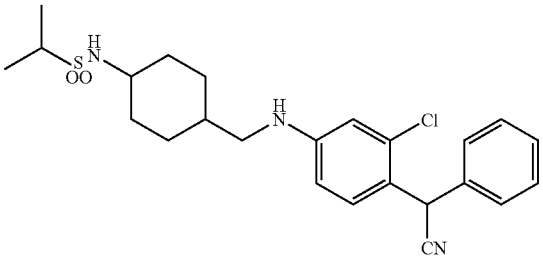
I-596
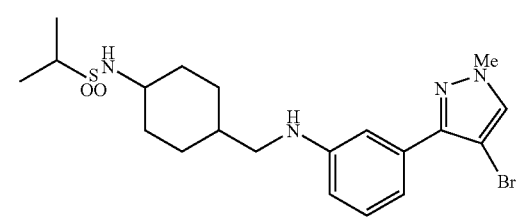
I-597
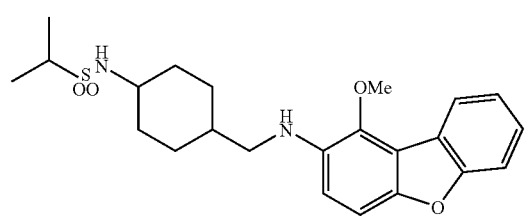
I-598
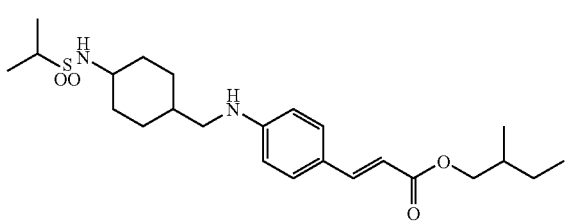
I-599
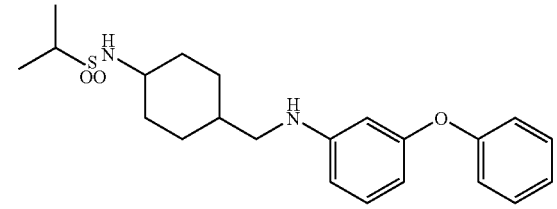
I-600
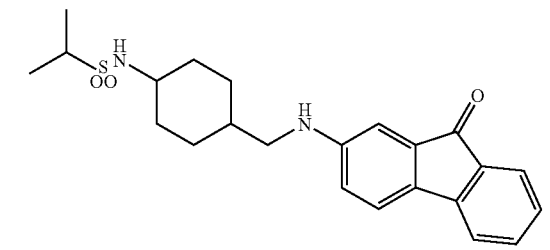

I-601
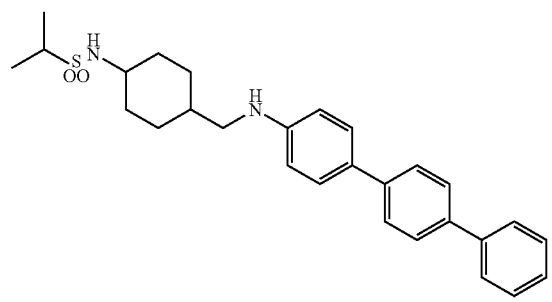
I-602
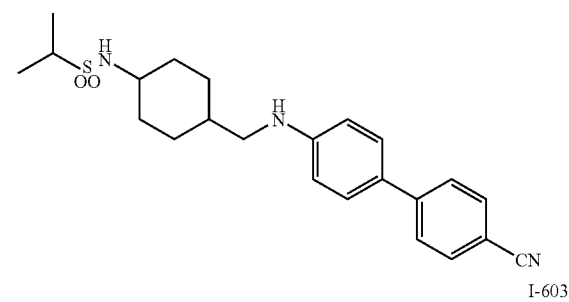
I-603
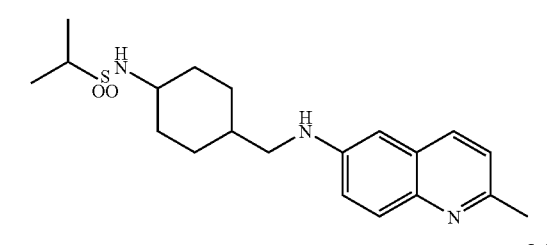
I-604
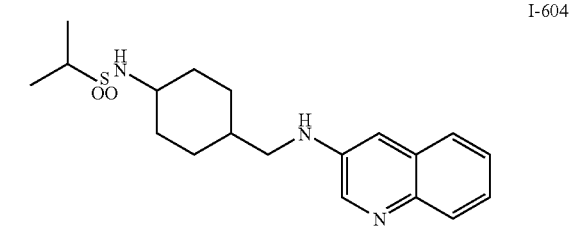
I-605
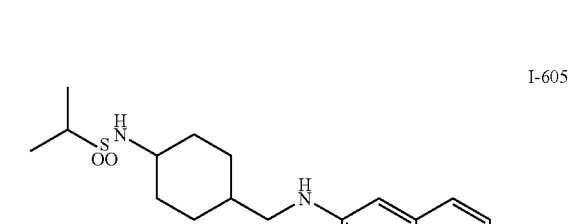
I-606
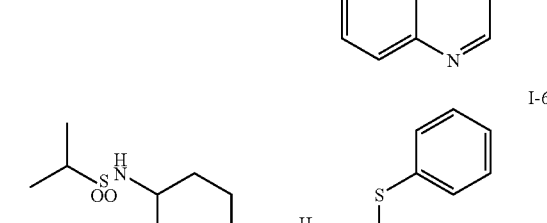
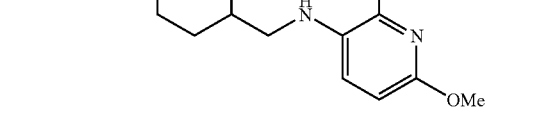
I-607
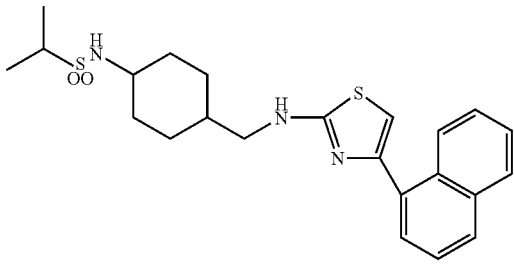
I-608
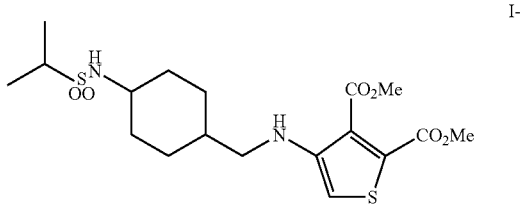
I-609
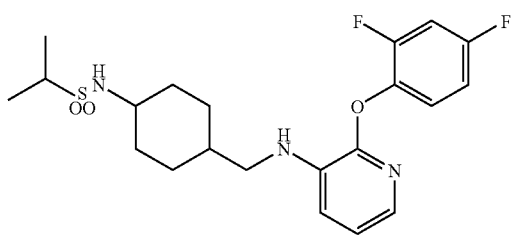
I-610
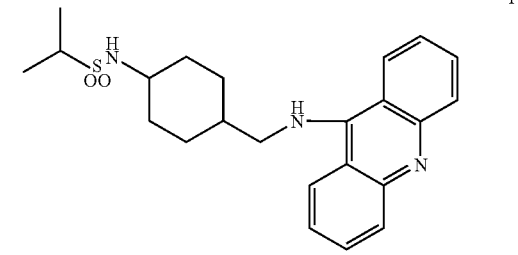
I-611
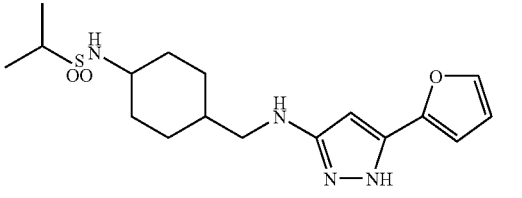
I-612
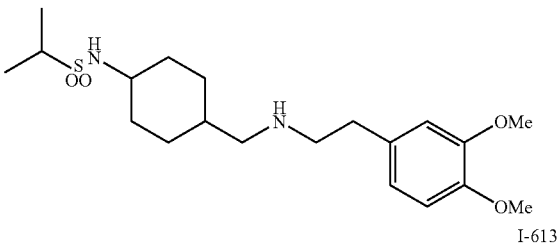
I-613

I-614
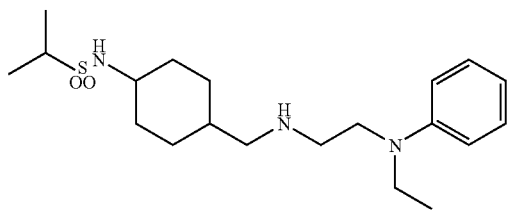
I-615
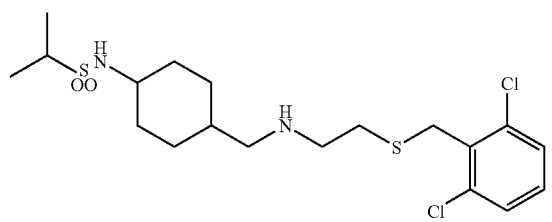
I-616
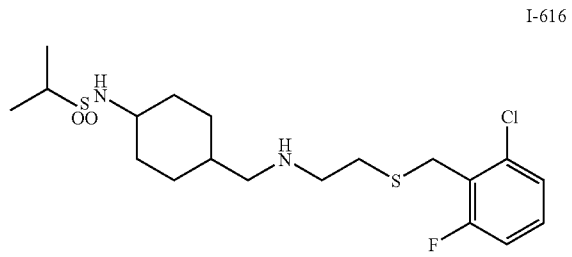
I-617
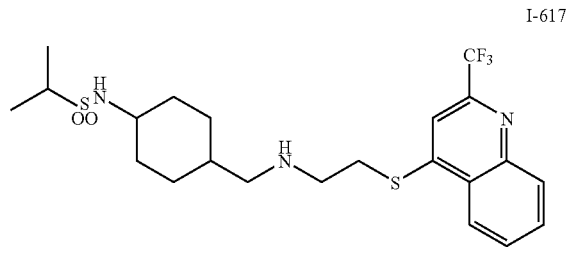
I-618
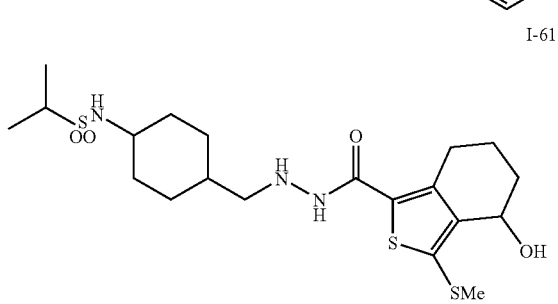
I-619
I-620
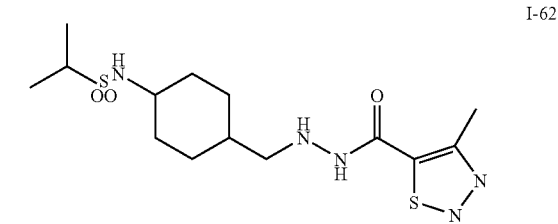
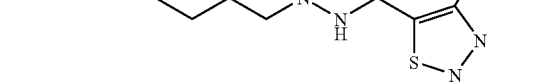
I-621
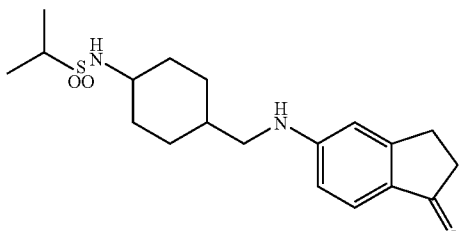
I-622
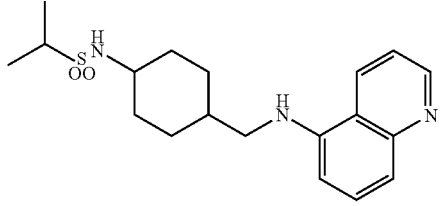
I-623
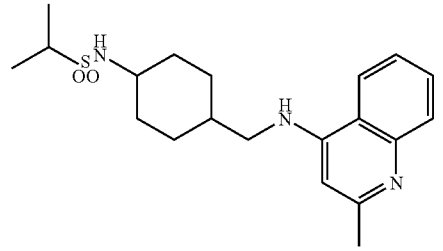
I-624
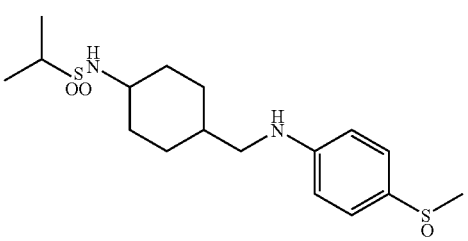
I-625
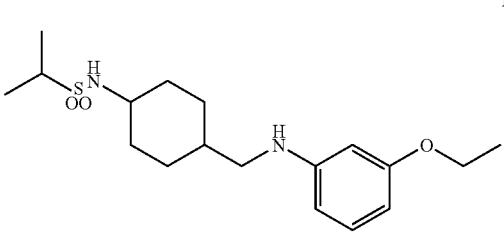
I-626
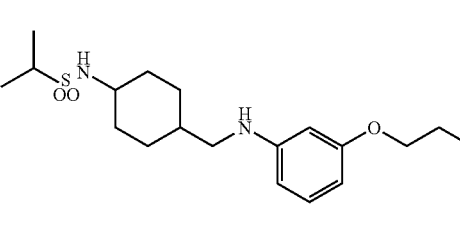
I-627
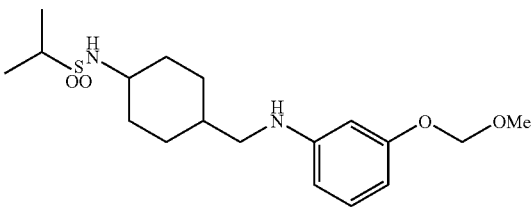

I-628
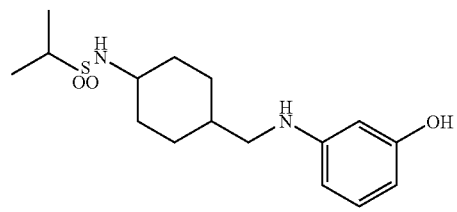
I-629
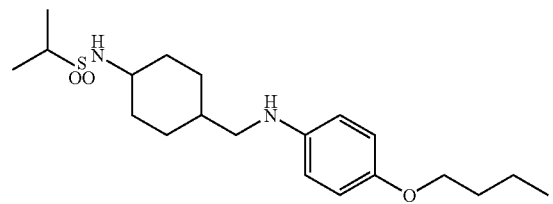
I-630
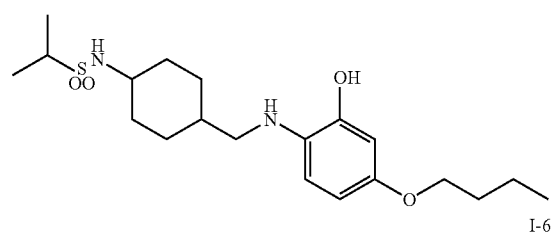
I-631
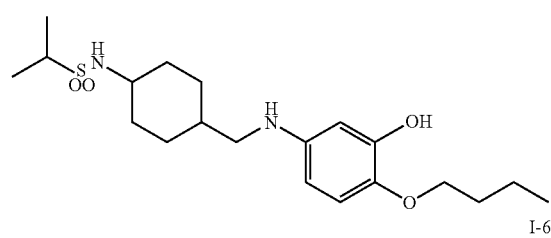
I-632
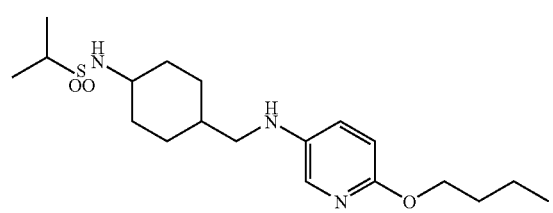
I-633
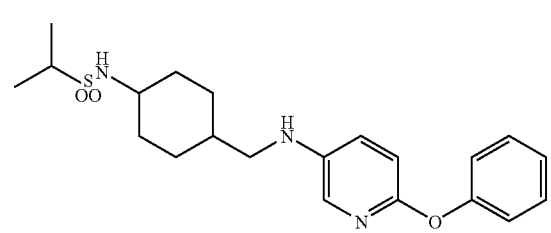
I-634
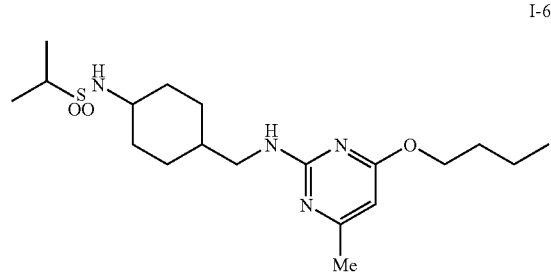
I-635
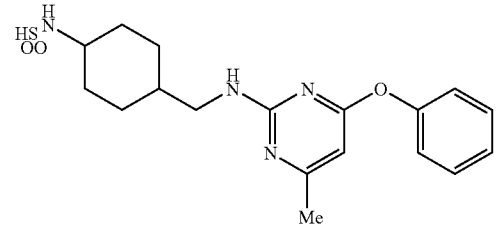
I-636
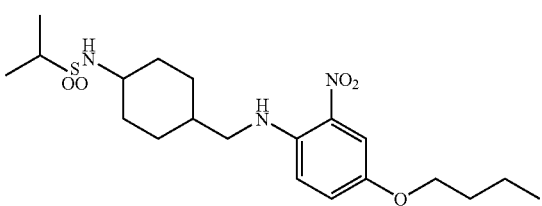
I-637
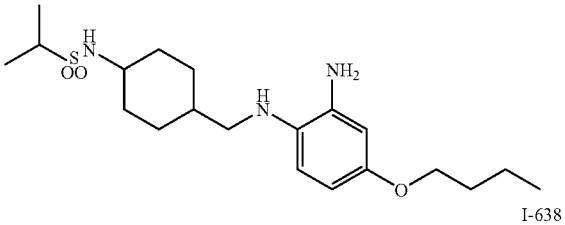
I-638
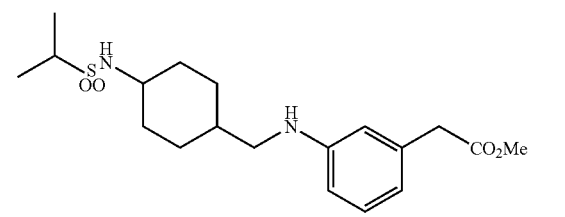
I-639
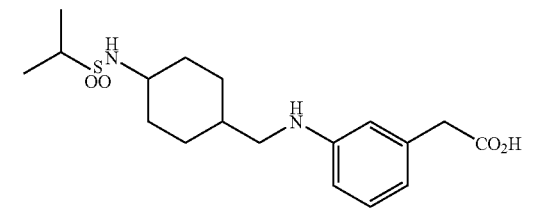
I-640
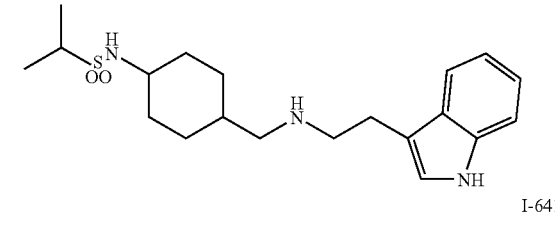
I-641
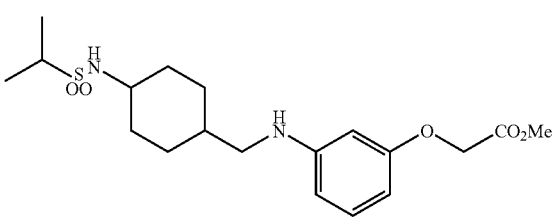

I-642
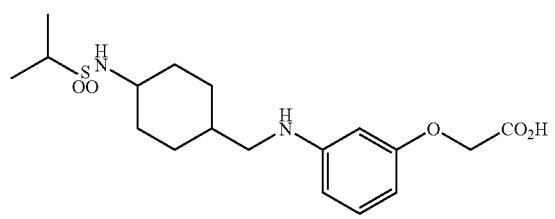
I-643
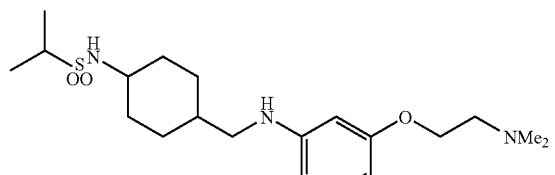
I-644
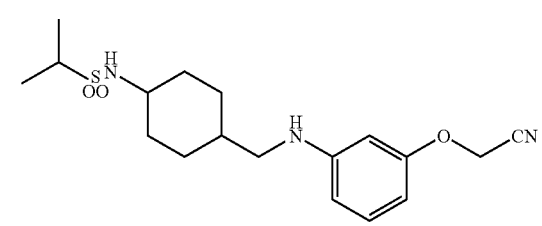
I-645
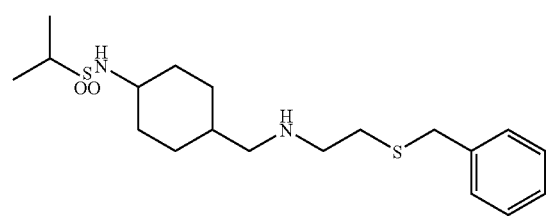
I-646
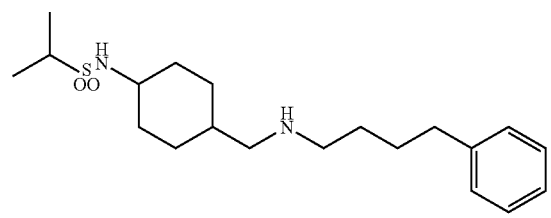
I-647
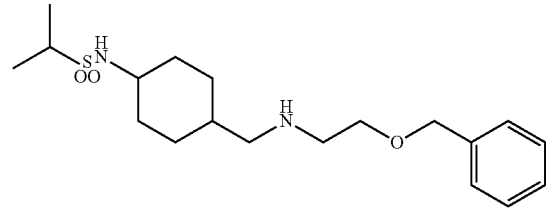
I-648
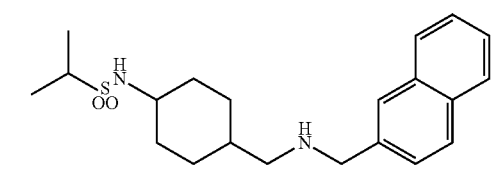
I-649
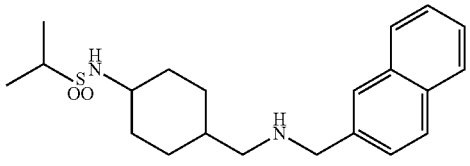
I-650
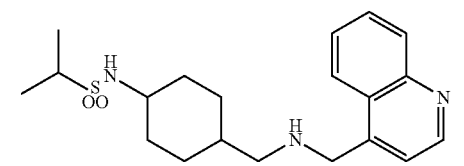
I-651
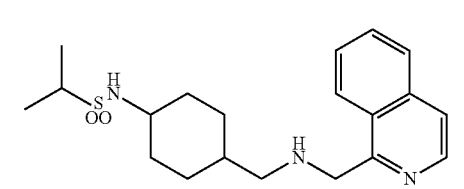
I-652
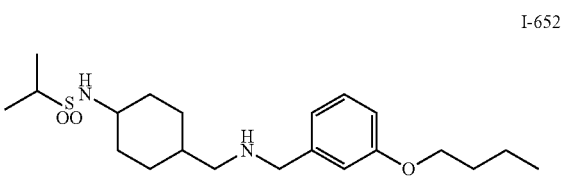
I-653
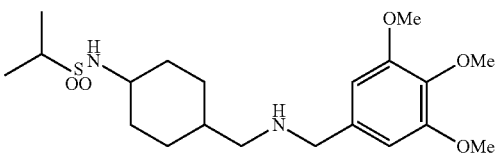
I-654
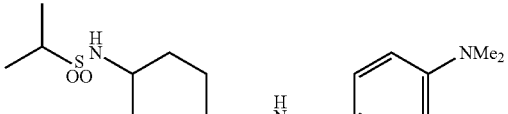
I-655
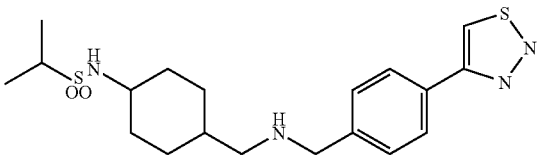
I-656
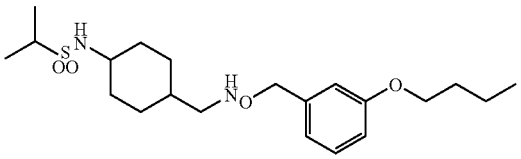
I-657
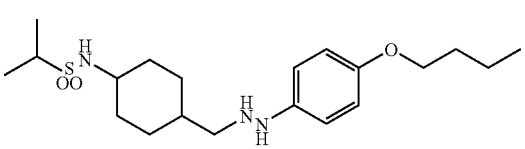

I-658
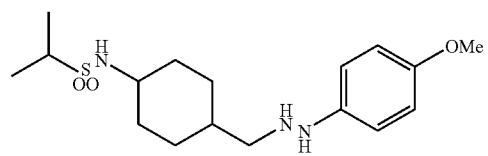
I-659
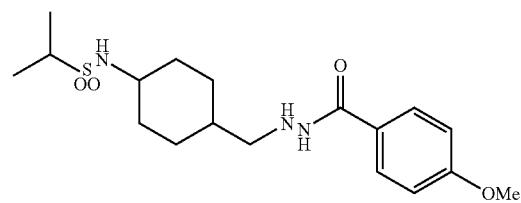
I-660
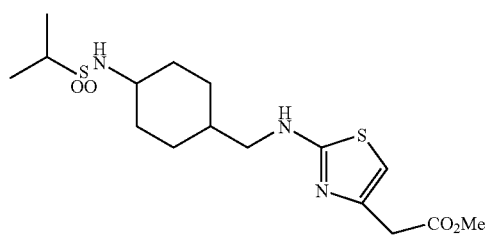
I-661
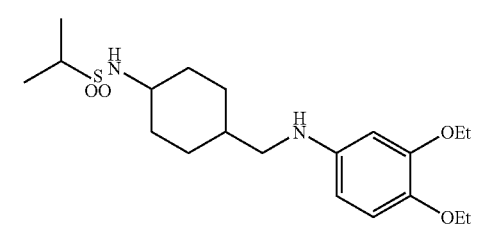
I-662
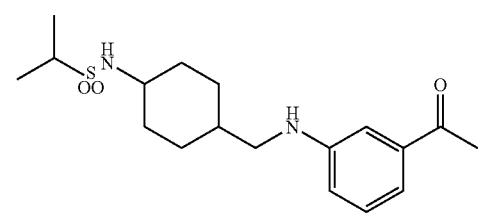
I-663
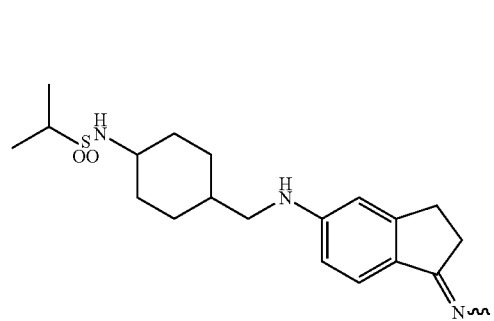
I-664
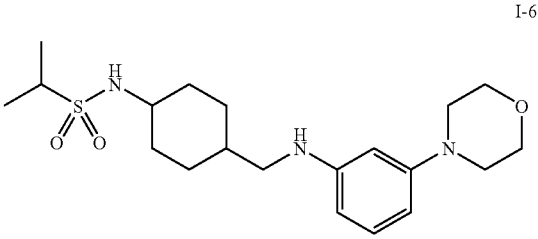
I-665
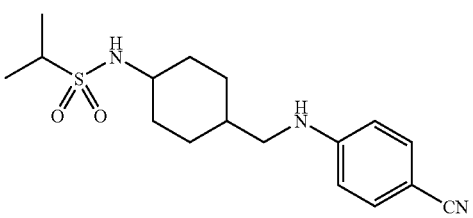
I-666
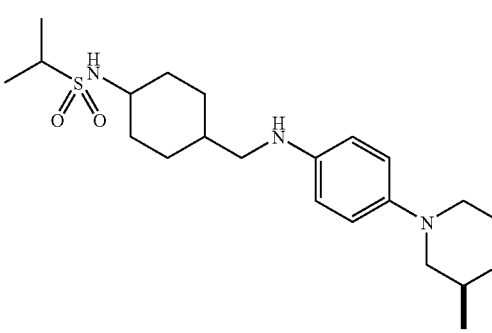
I-667
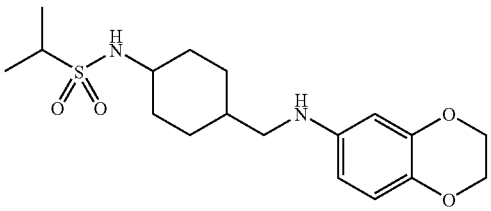
I-668
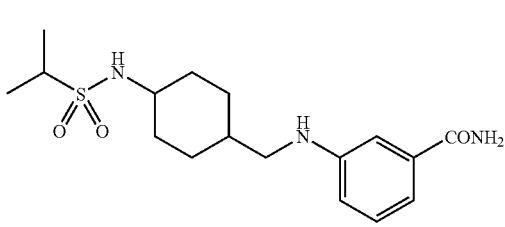
I-669
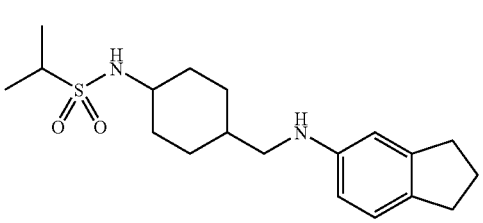
I-670
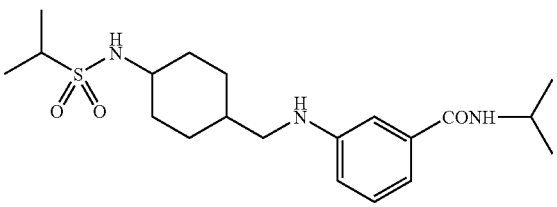

I-671
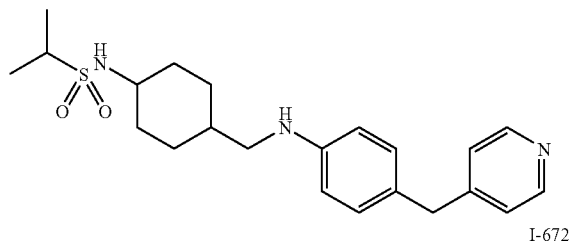
I-672
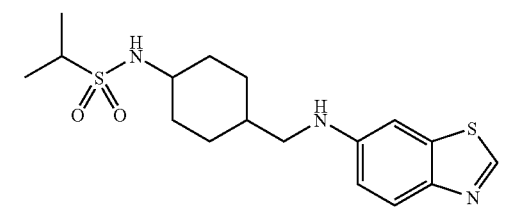
I-673
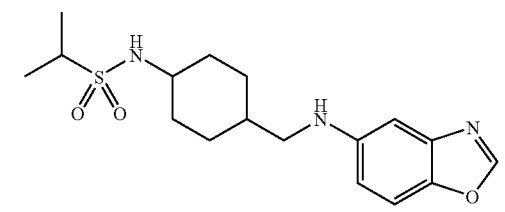
I-674
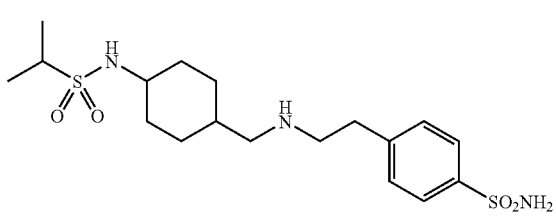
I-675
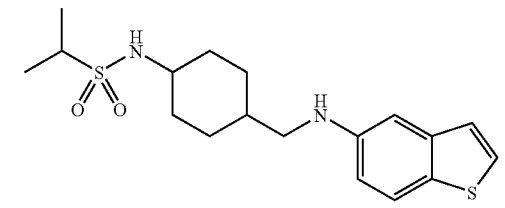
I-676
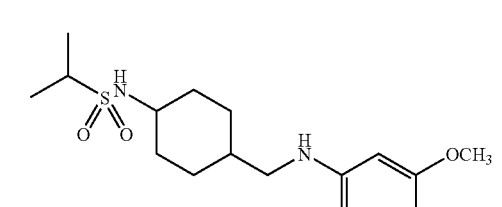
I-677
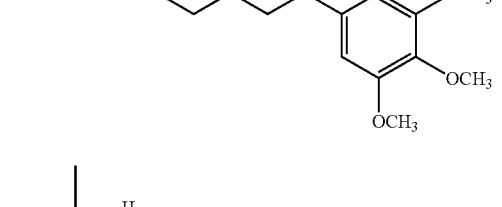
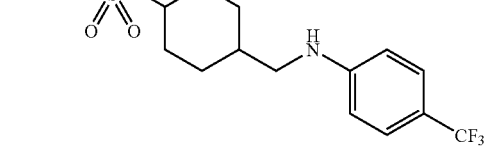
I-678
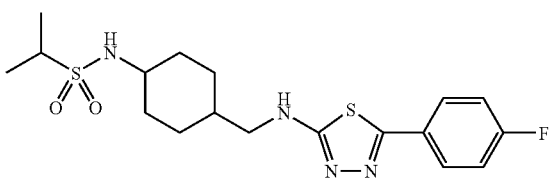
I-679
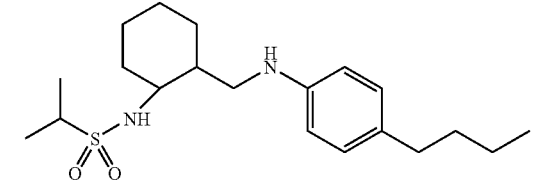
I-680
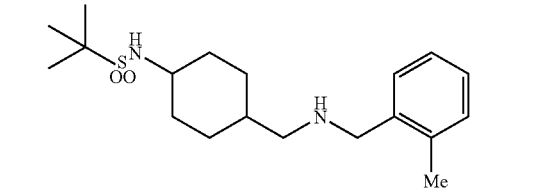
I-681
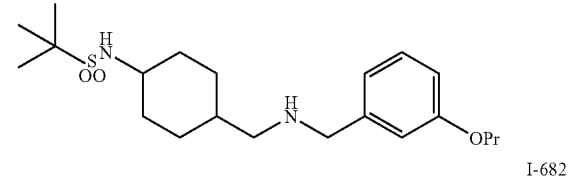
I-682
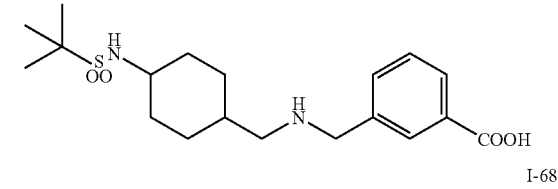
I-683
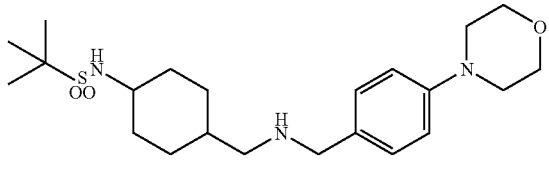
I-684
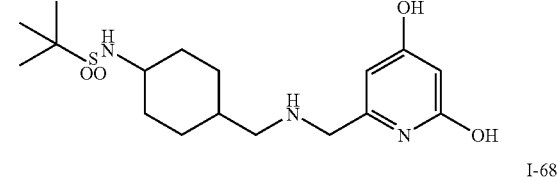
I-685
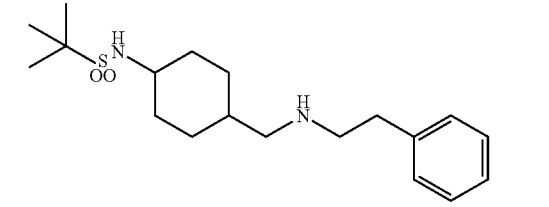

I-686
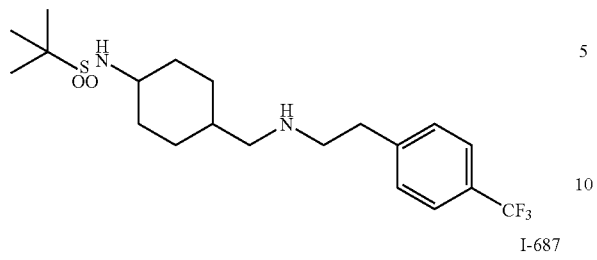
I-687
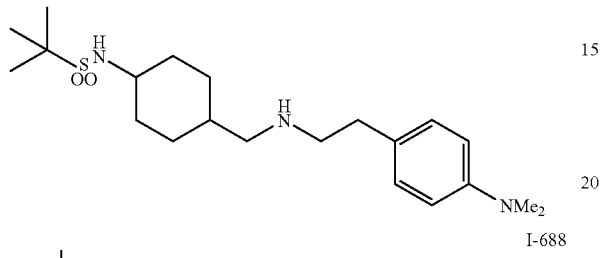
I-688
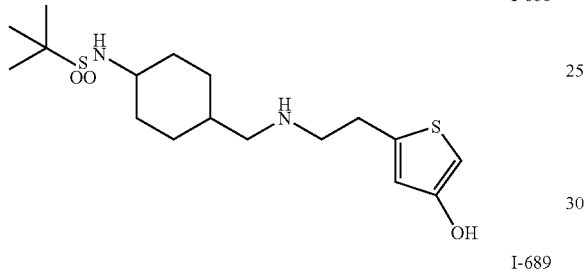
I-689
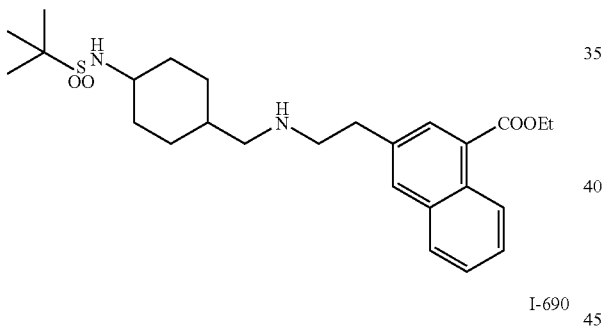
I-690
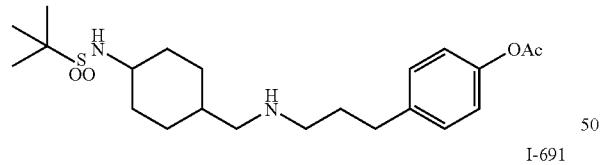
I-691
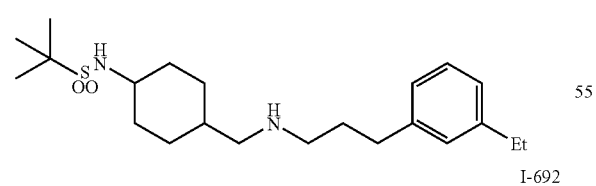
I-692
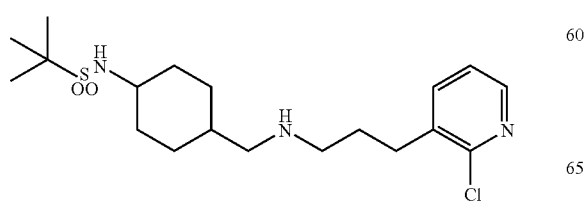
I-693
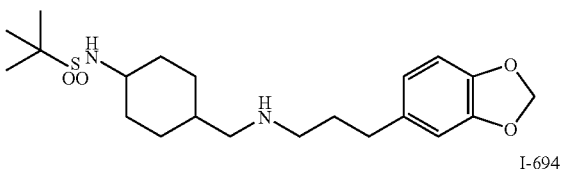
I-694
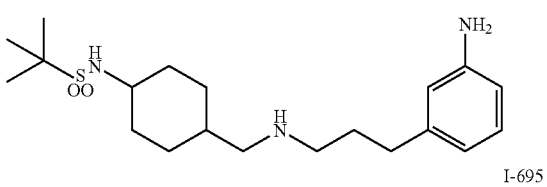
I-695
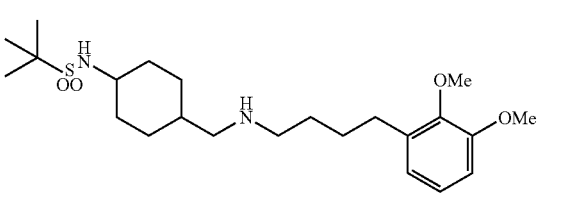
I-696
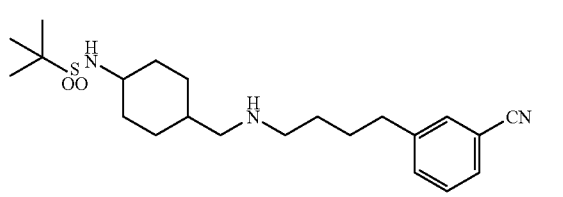
I-697
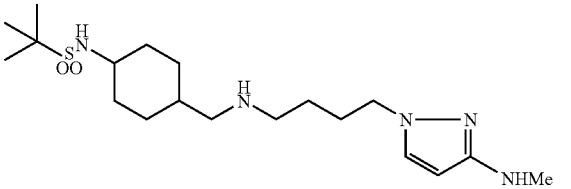
I-698
I-699
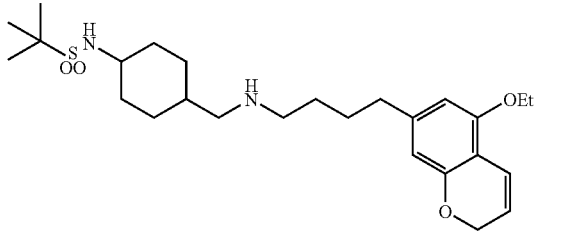

I-700
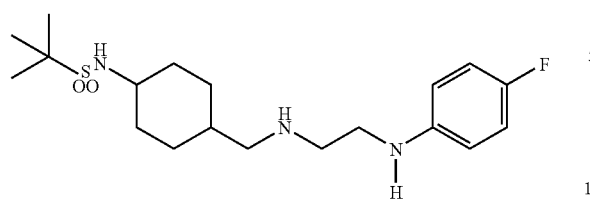
I-701
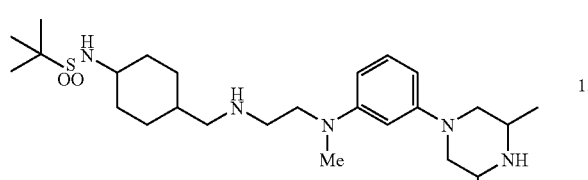
I-702
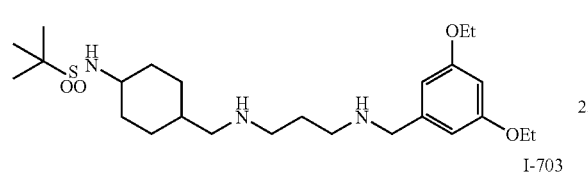
I-703
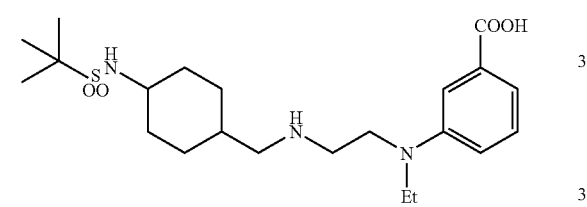
I-704
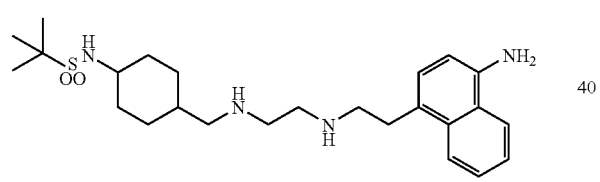
I-705
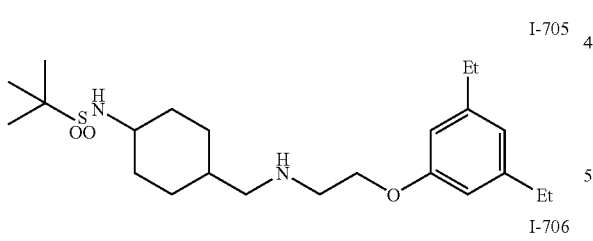
I-706
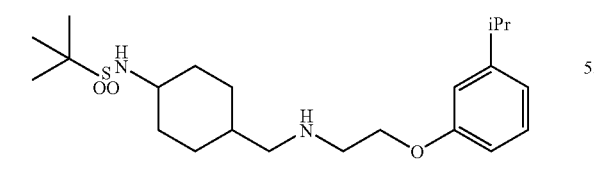
I-707
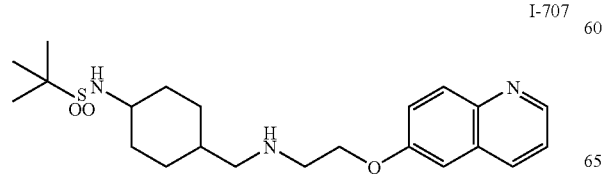
I-708
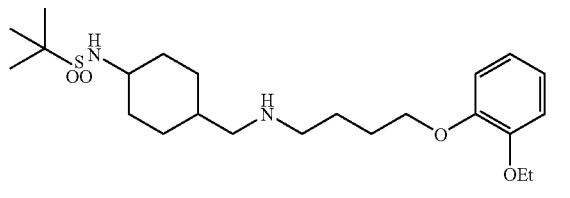
I-709
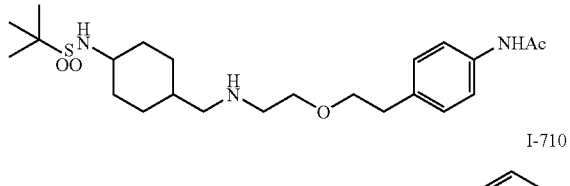
I-710
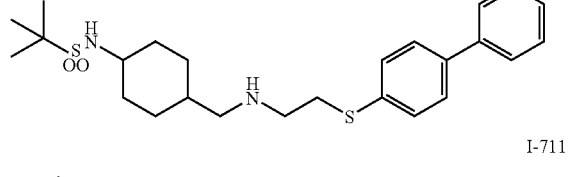
I-711
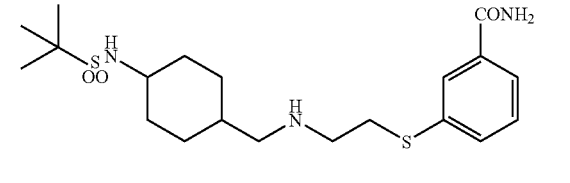
I-712
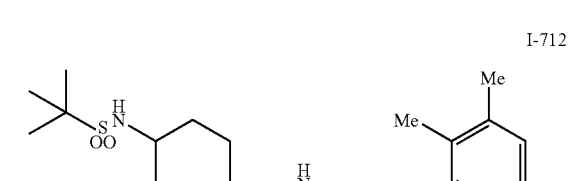
I-713
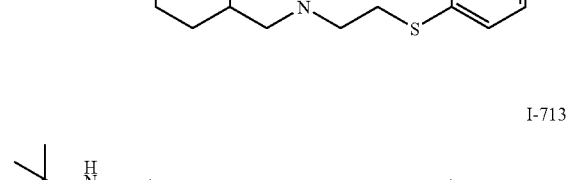
I-714
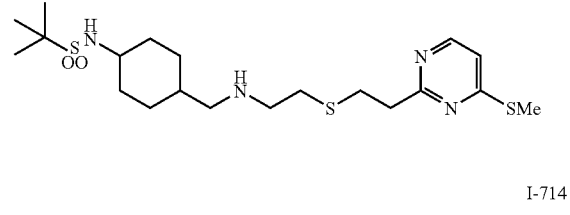
I-715
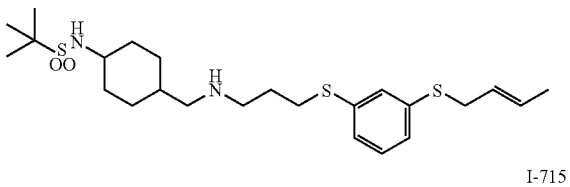
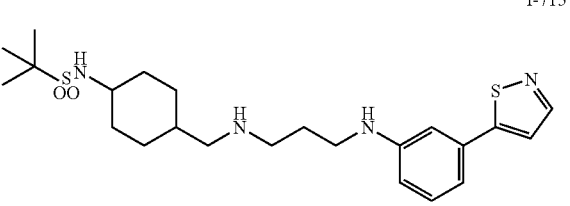

I-716
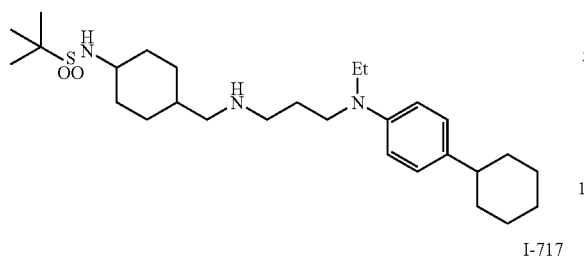
I-717

I-718

I-719
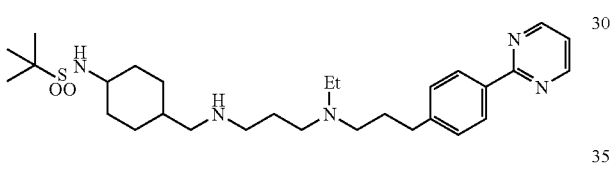
I-720
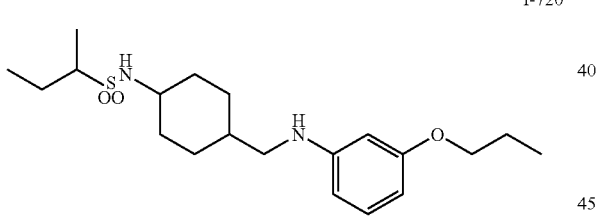
I-721
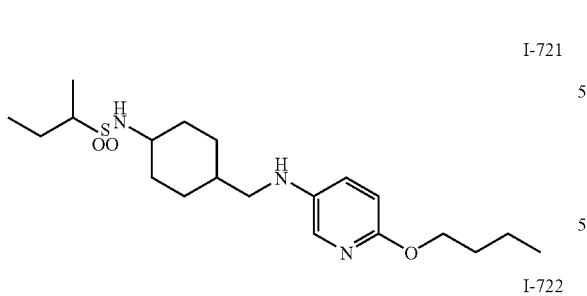
I-722
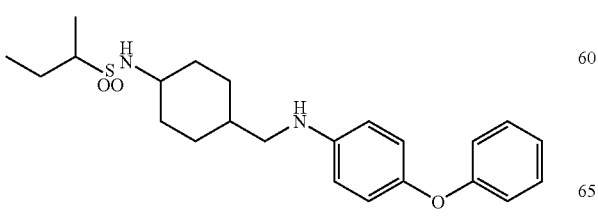
I-723
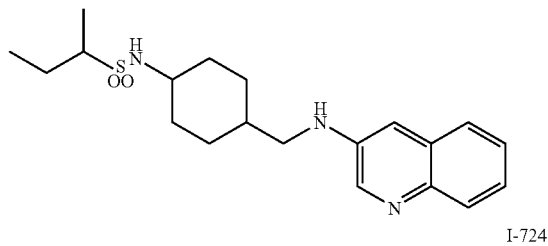
I-724
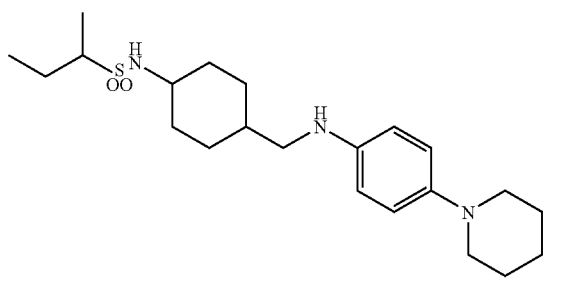
I-725
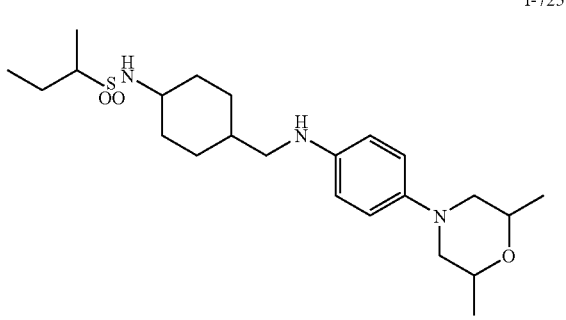
I-726
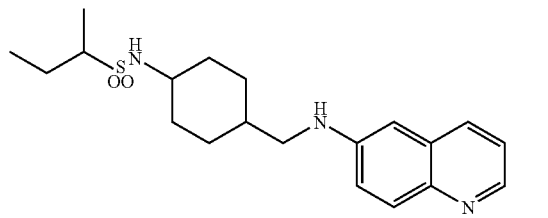
I-727
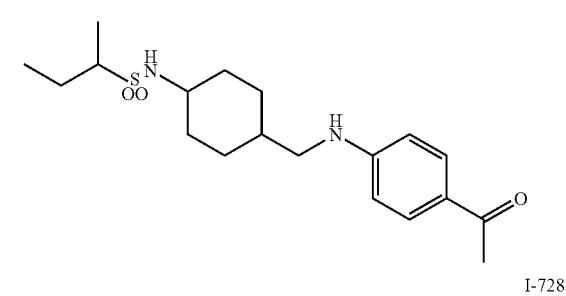
I-728
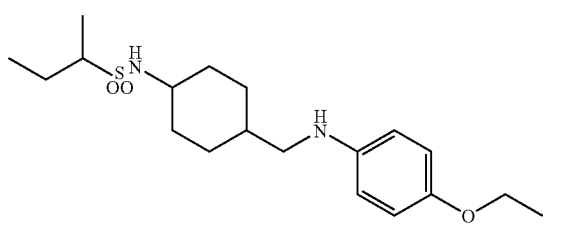

I-729
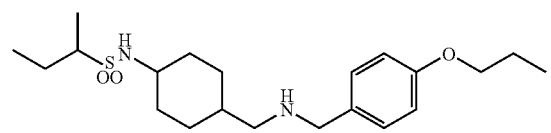
I-730
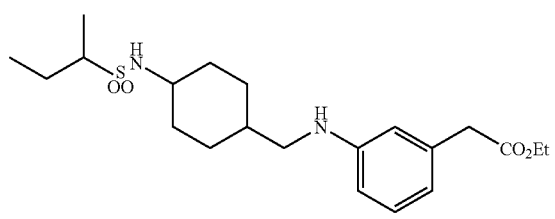
I-731
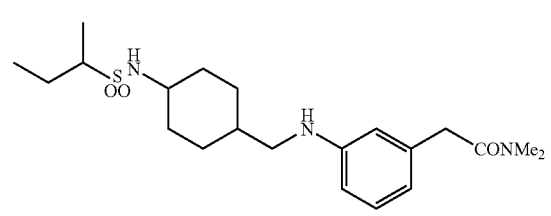
I-732
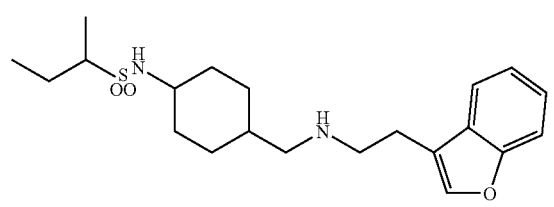
I-733
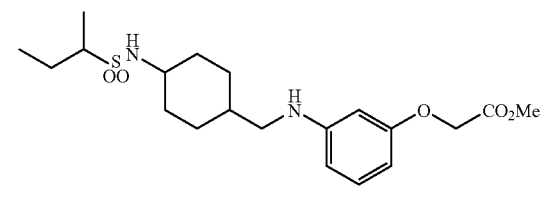
I-734
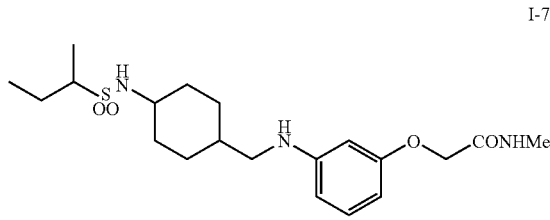
I-735
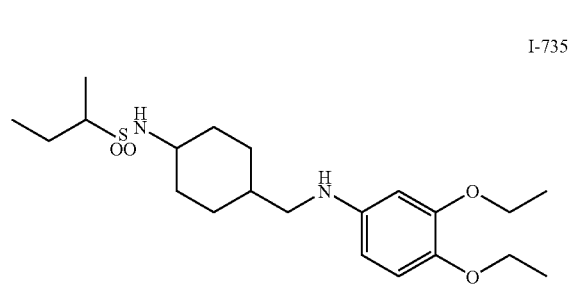
I-736
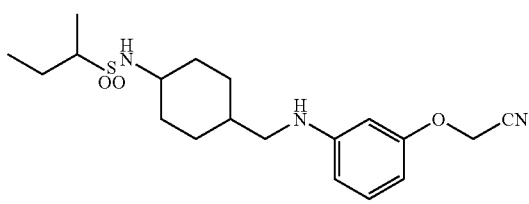
I-737
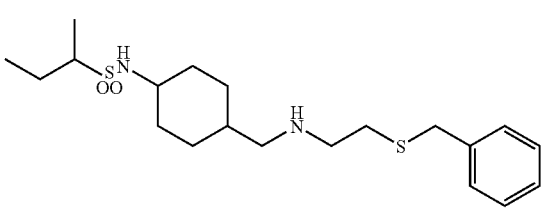
I-738
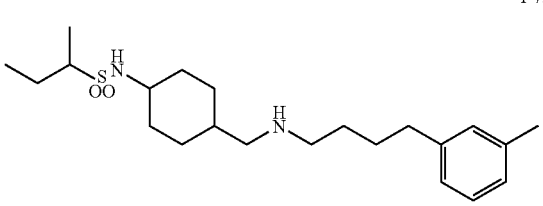
I-739
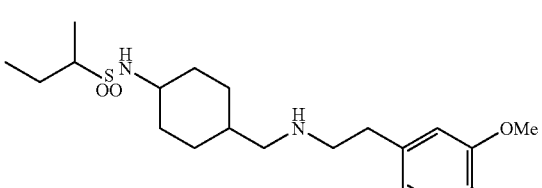
I-740
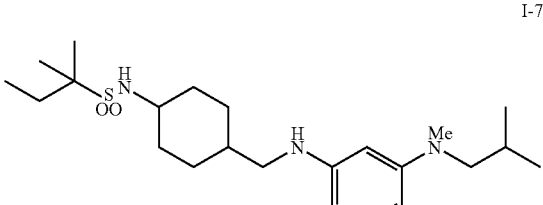
I-741
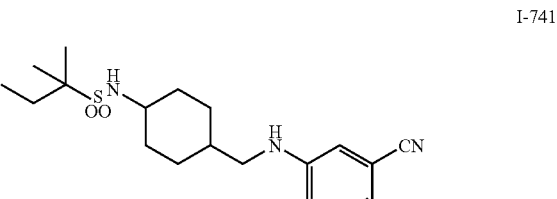
I-742
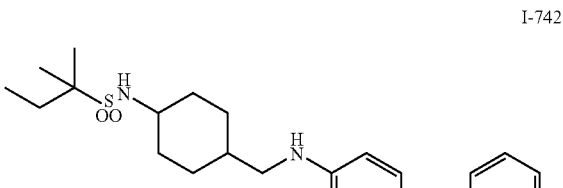

I-743
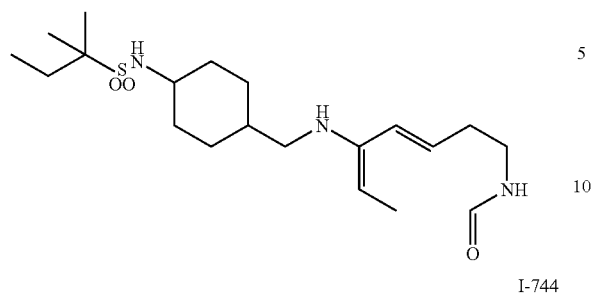
I-744
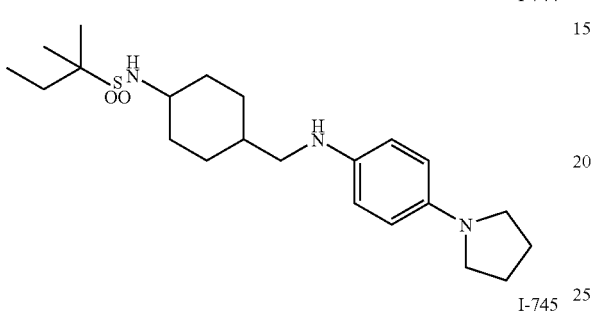
I-745
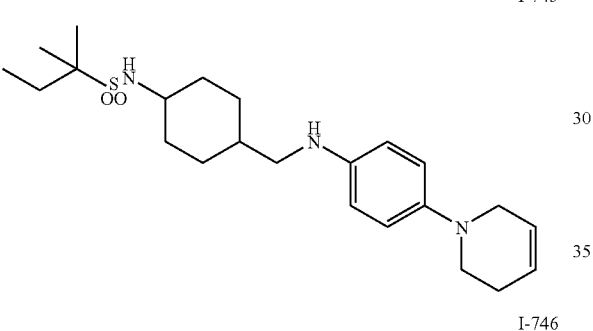
I-746
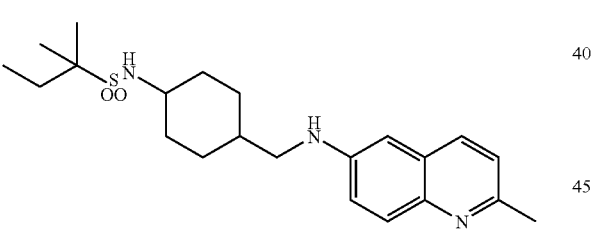
I-747
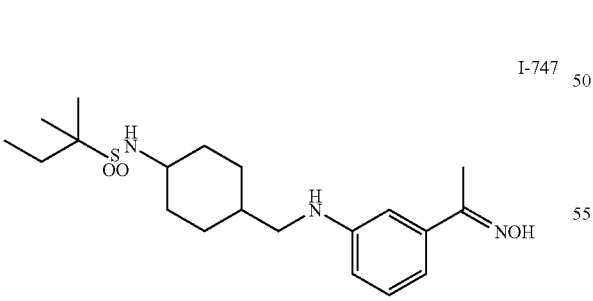
I-748
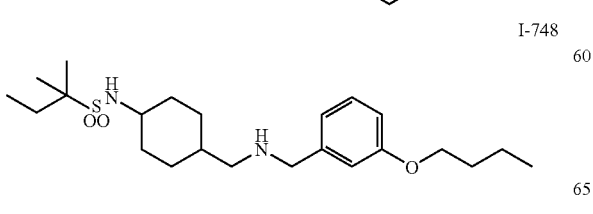
I-749
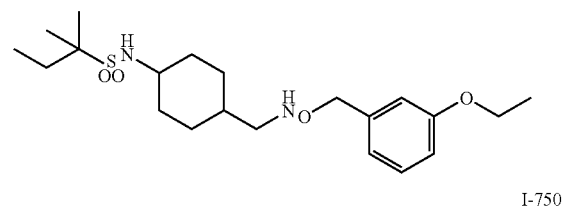
I-750
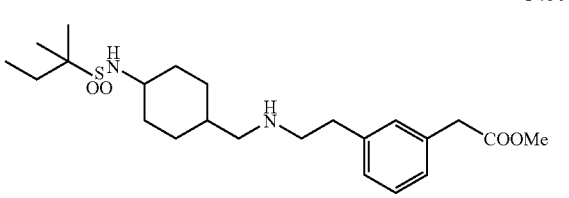
I-751
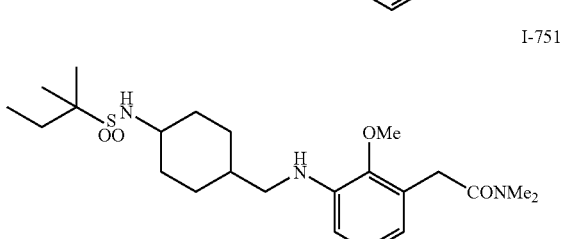
I-752
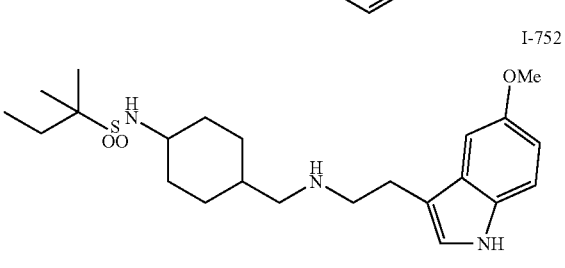
I-753
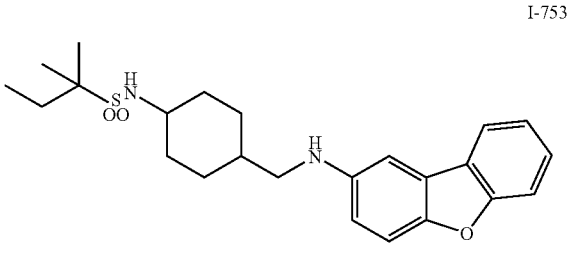
I-754
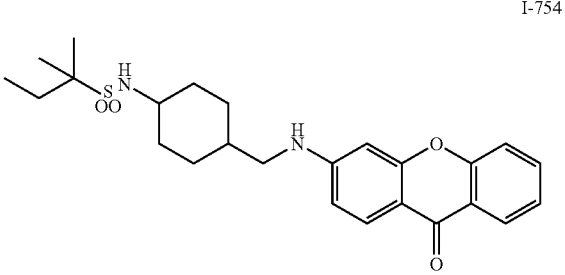
I-755
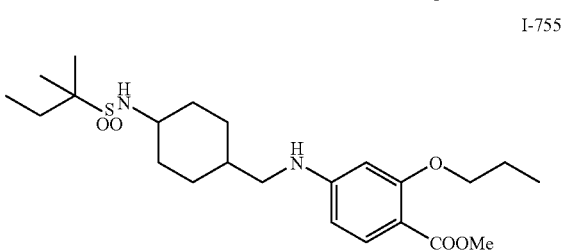

I-756
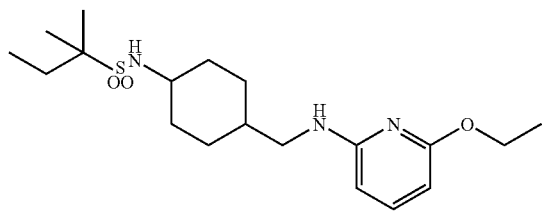
Ia-4
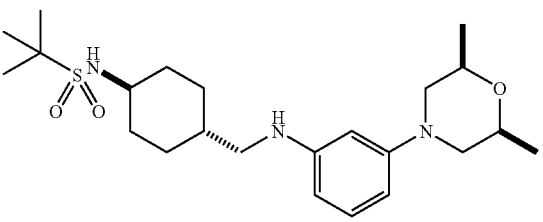
I-757
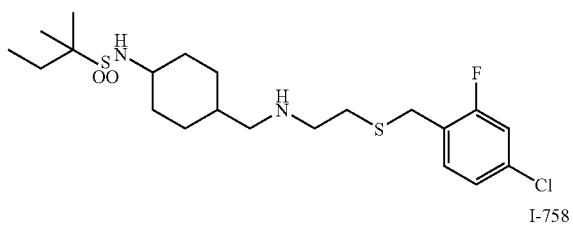
Ia-5
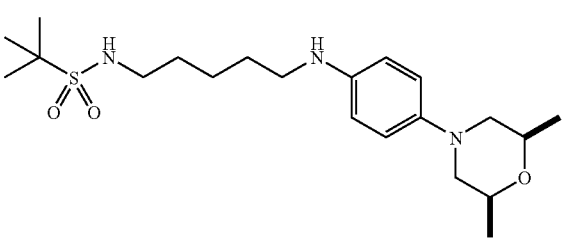
I-758
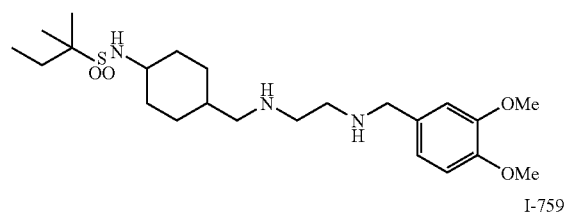
I-759
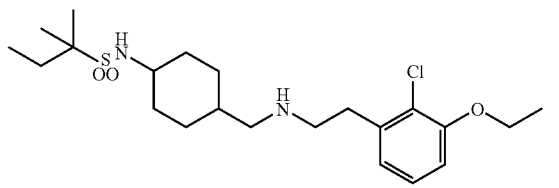
Ia-6
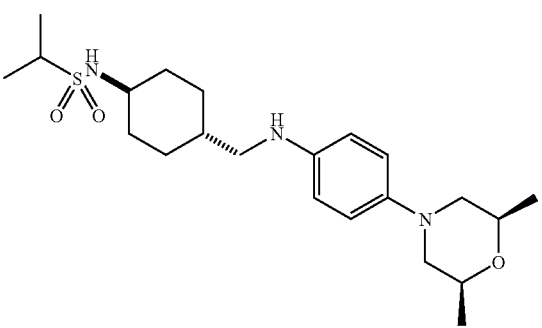
Ia-1
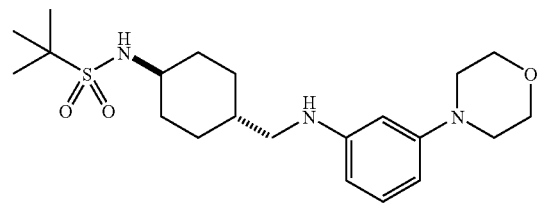
Ia-7
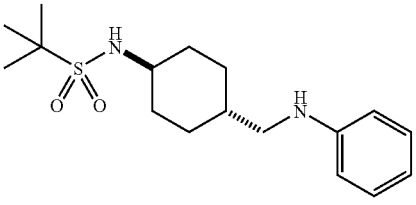
Ia-2
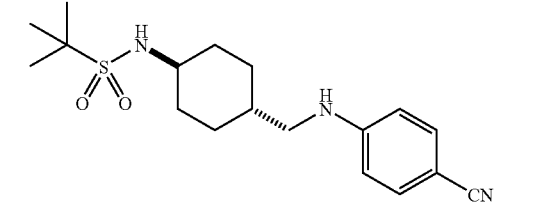
Ia-8
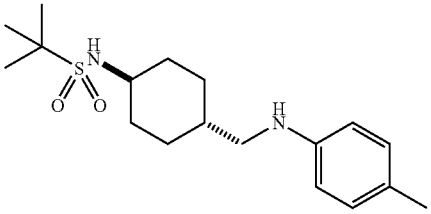
Ia-3
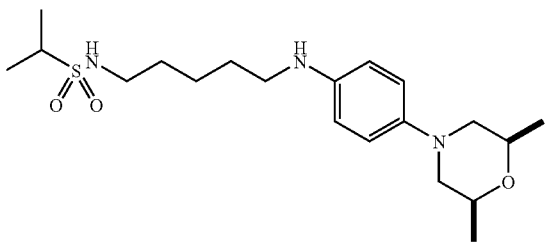
Ia-9

Ia-10
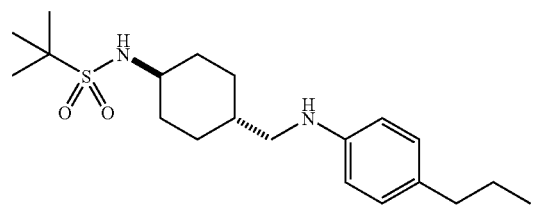
Ia-11
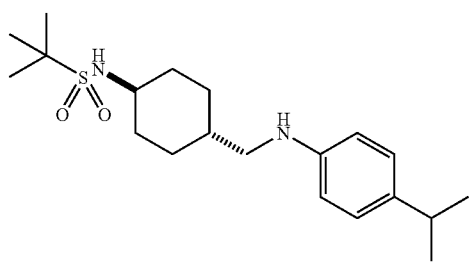
Ia-12
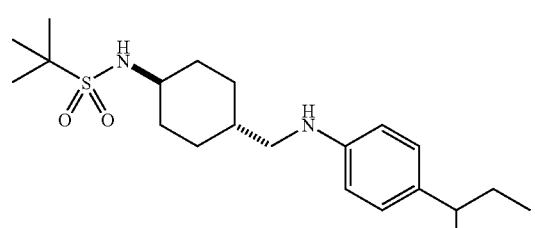
Ia-13
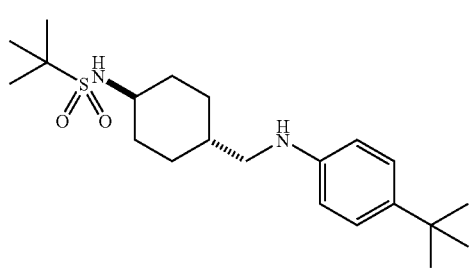
Ia-14
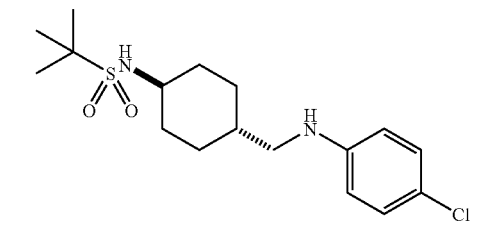
Ia-15
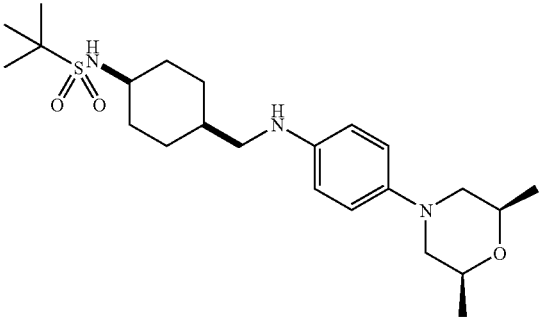
Ia-16
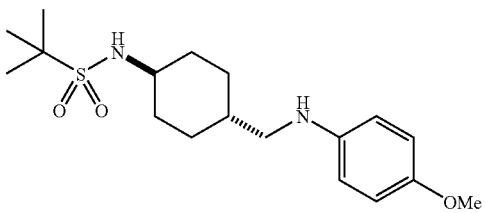
Ia-17
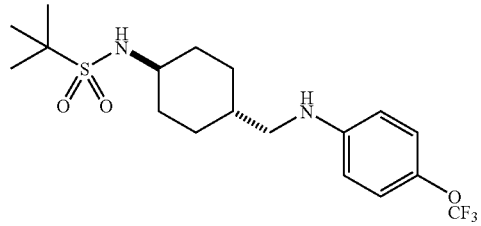
Ia-18
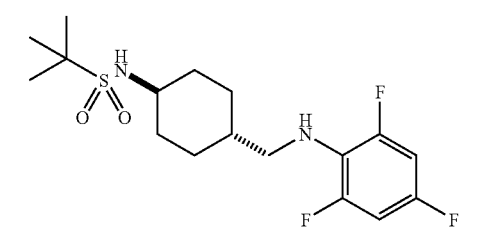
Ia-19
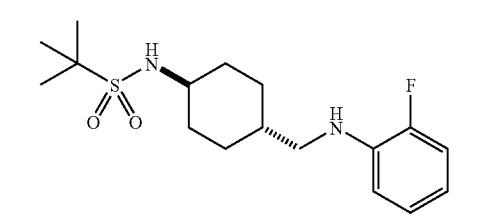
Ia-20
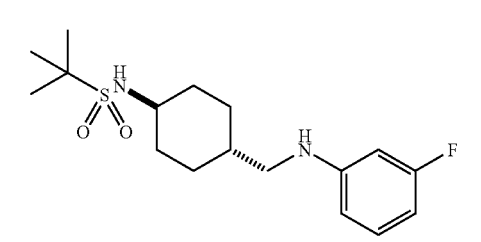
Ia-21
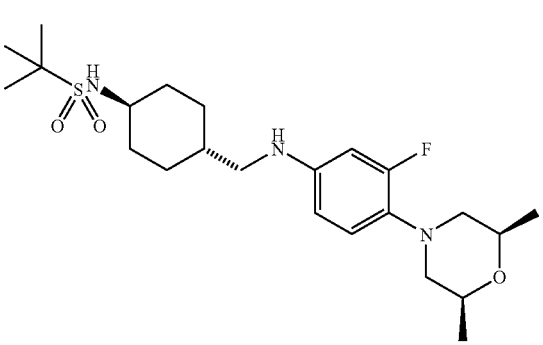

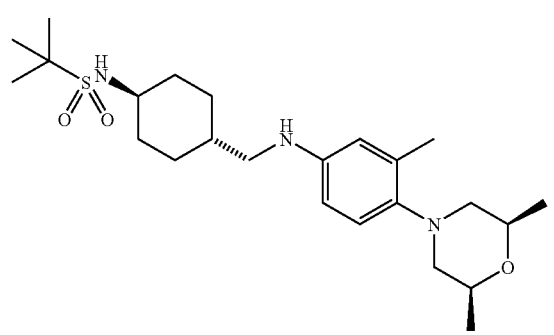
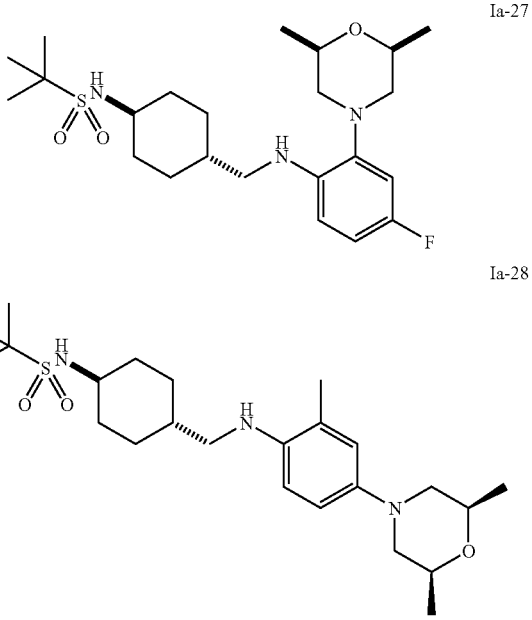
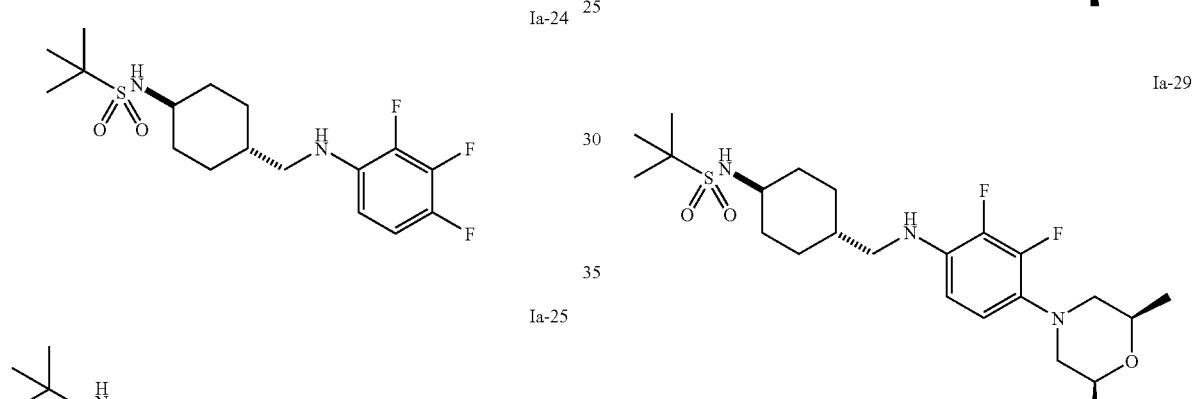
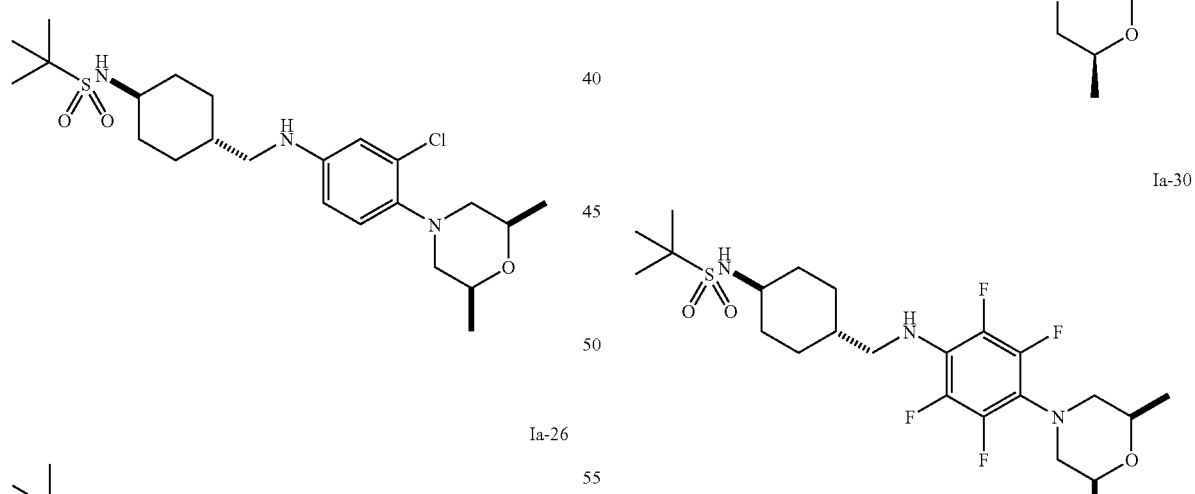
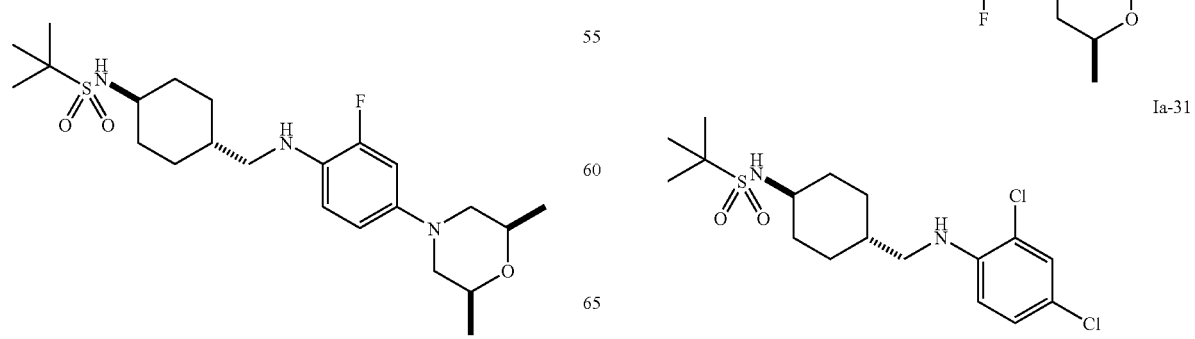

163
-continued
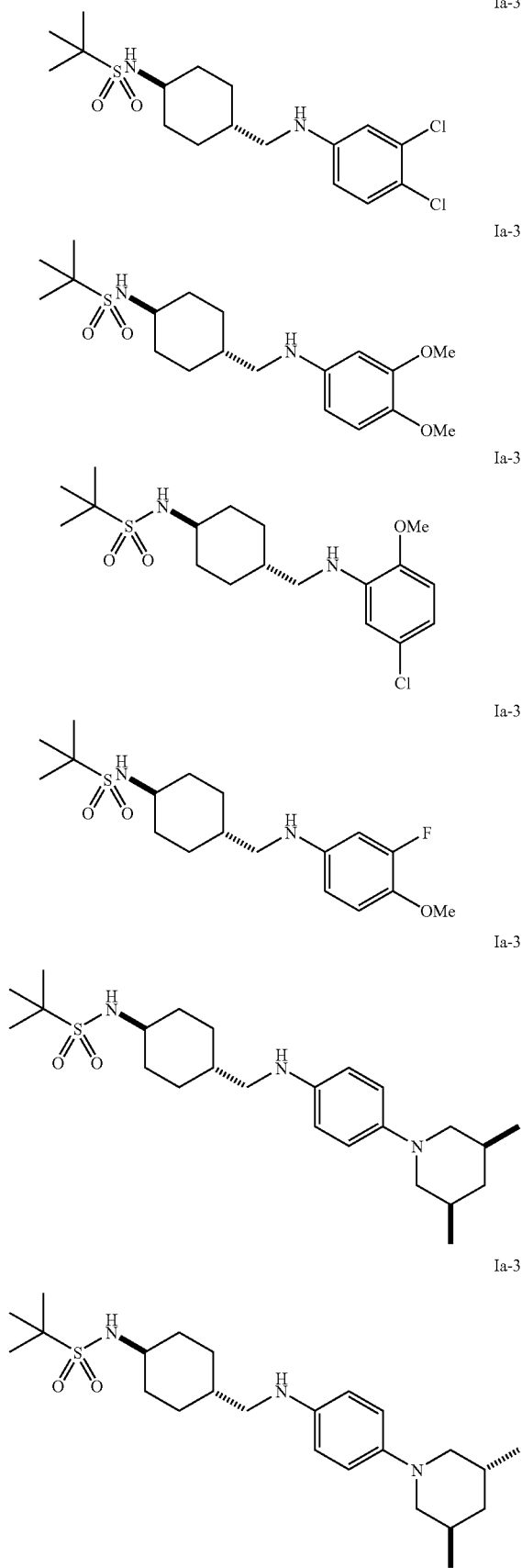
164
-continued
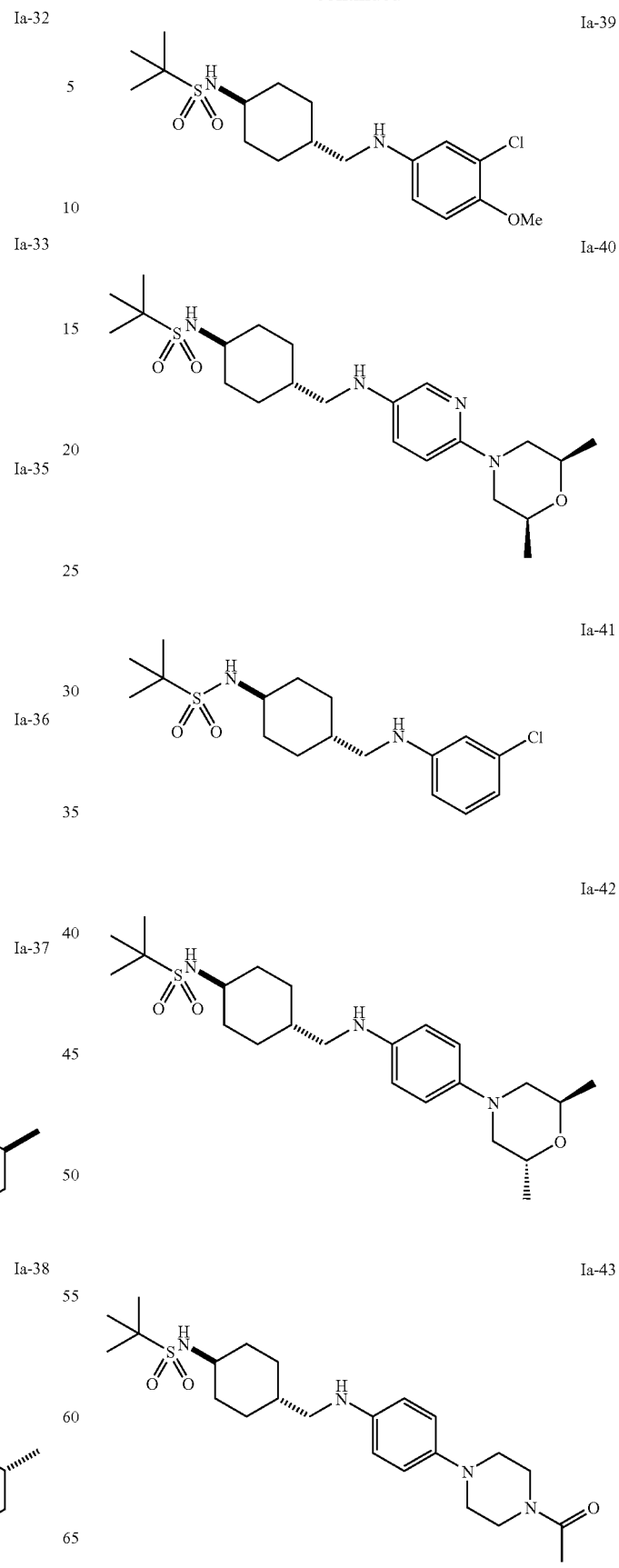

Ia-44
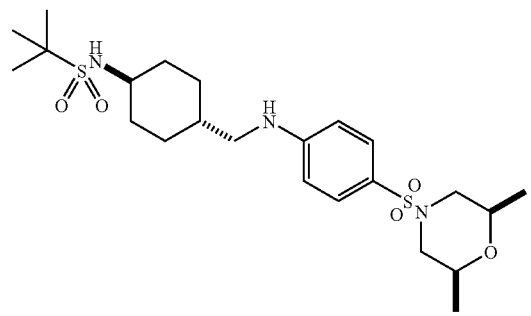
Ia-45
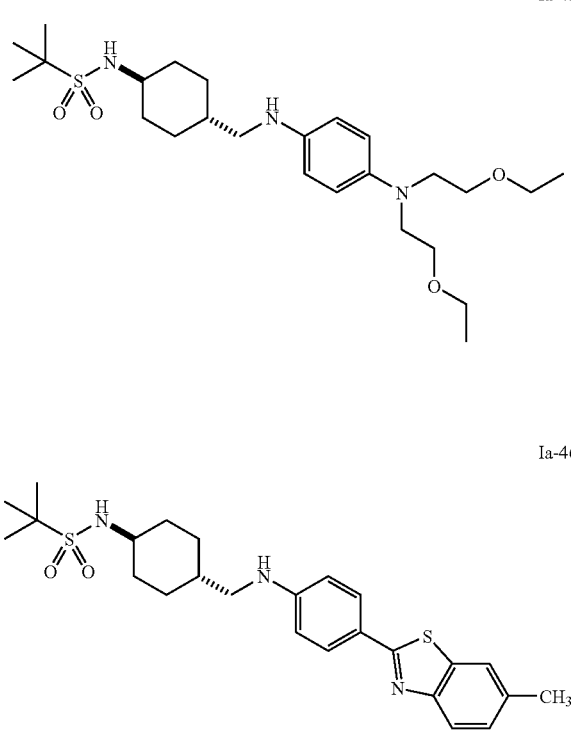
Ia-46
Ia-47
Ia-48
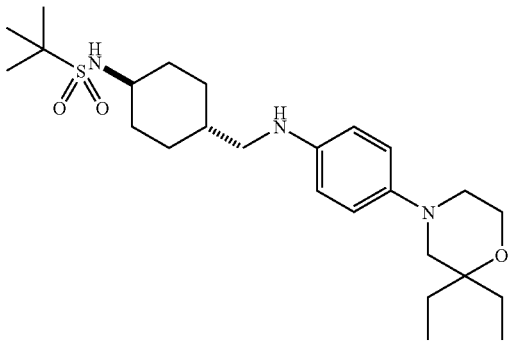
Ia-49
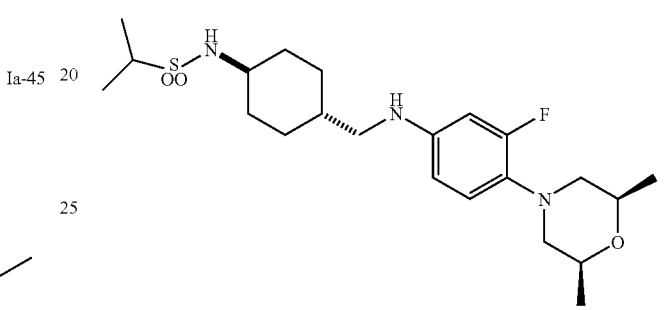
Ia-50
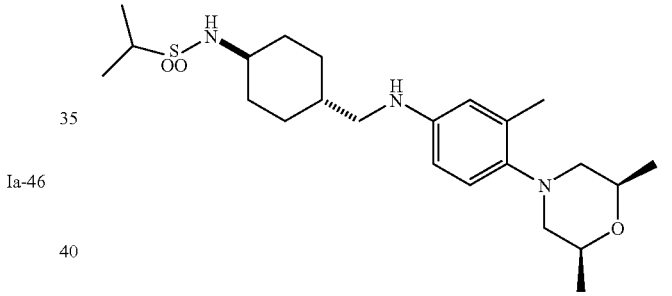
Ia-51
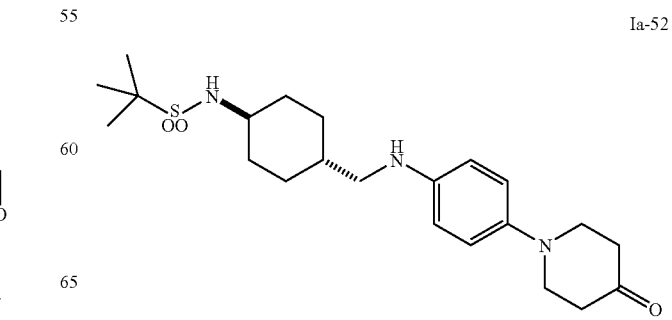
Ia-52
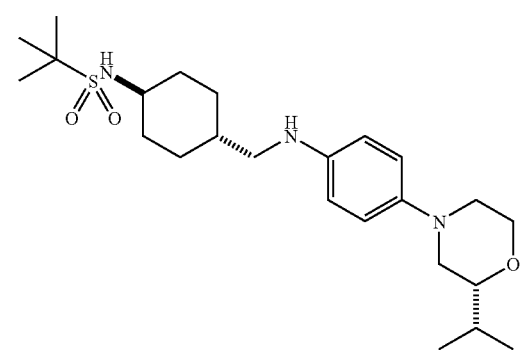

Ia-53
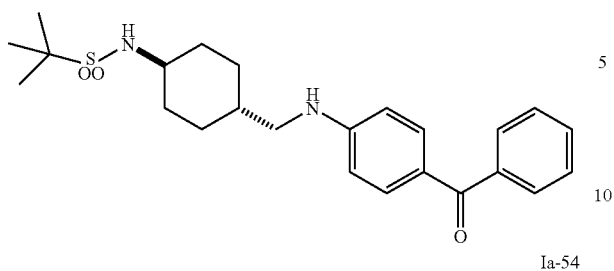
Ia-54
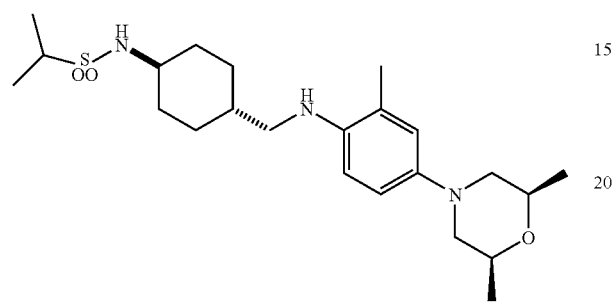
Ia-55
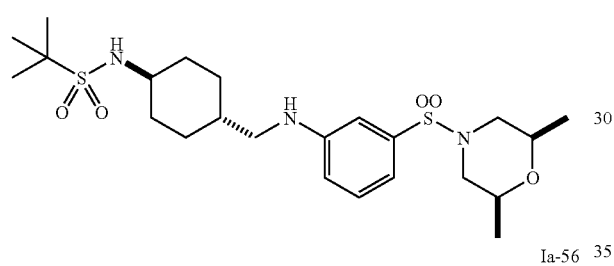
Ia-56
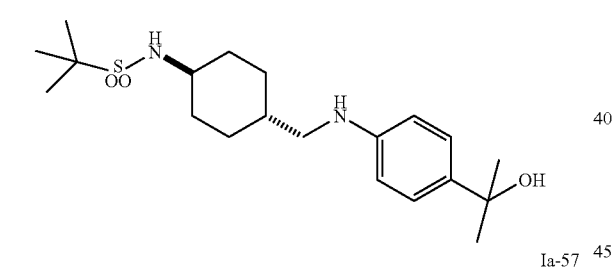
Ia-57
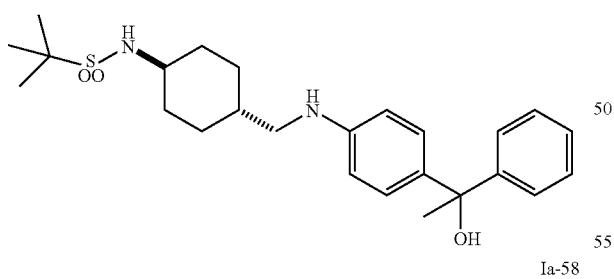
Ia-58
Ia-59
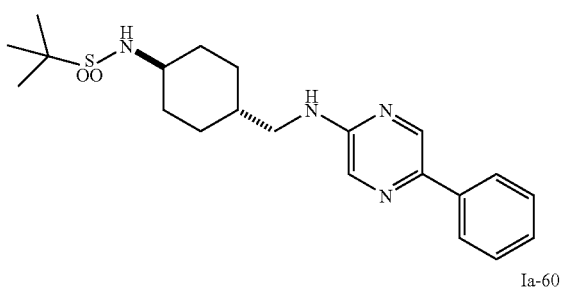
Ia-60
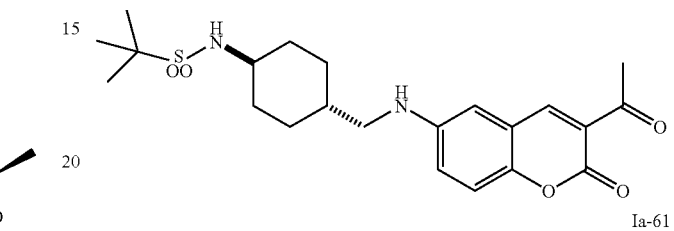
Ia-61
Ia-62
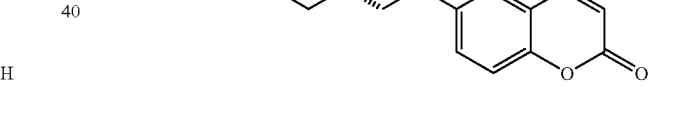
Ia-63
Ia-64
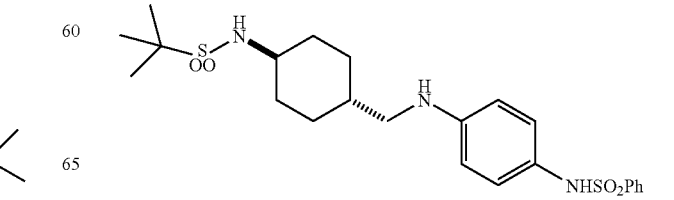

Ia-65
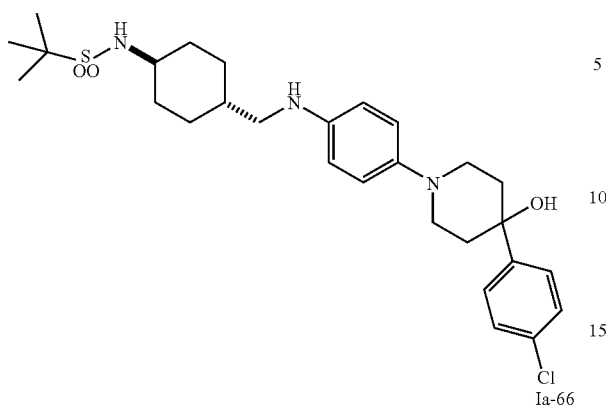
Ia-66
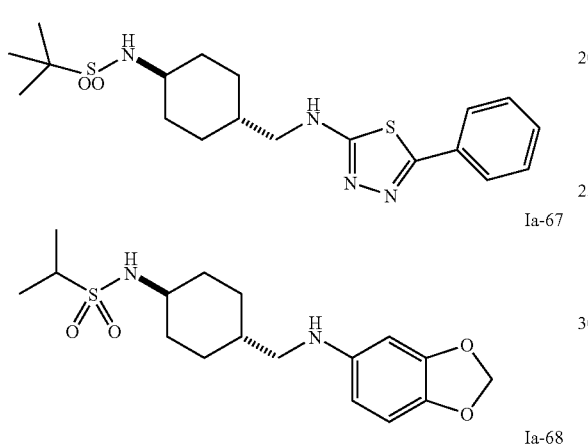
Ia-67
Ia-68
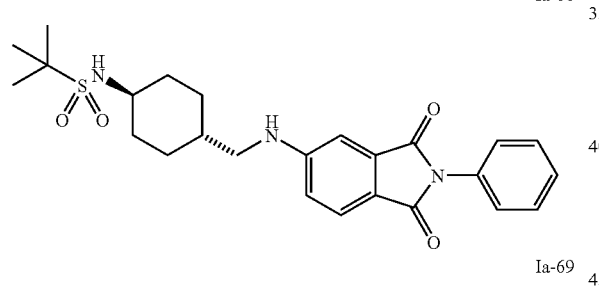
Ia-69
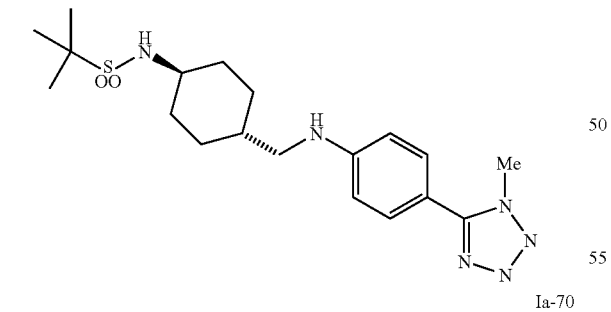
Ia-70
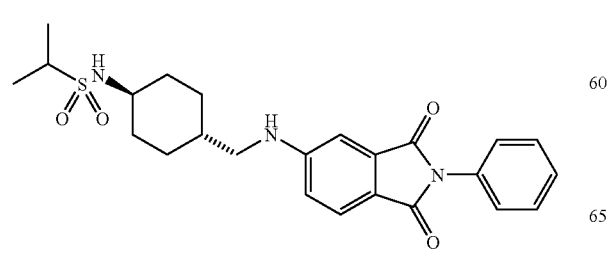
Ia-71
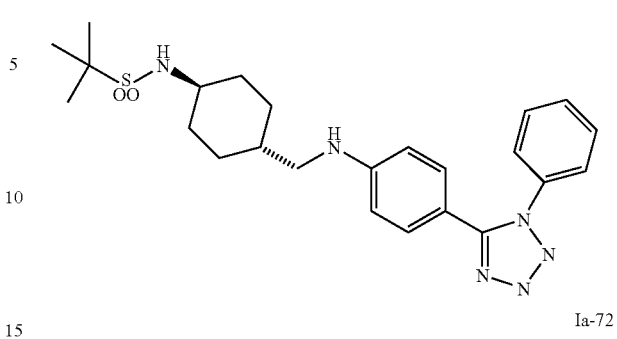
Ia-72
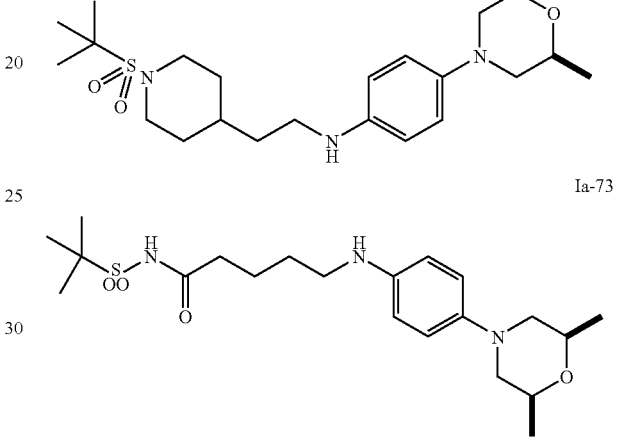
Ia-73
Ia-74
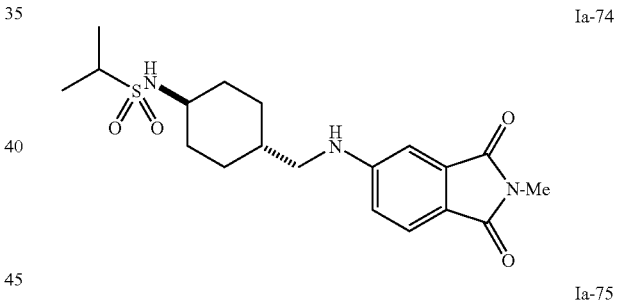
Ia-75
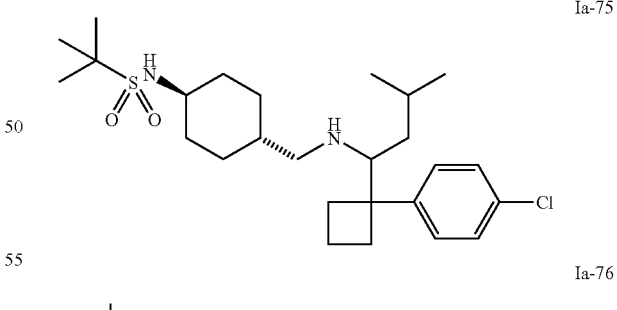
Ia-76

Ia-77
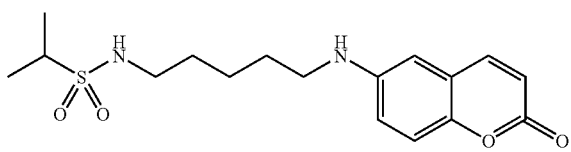
Ia-78
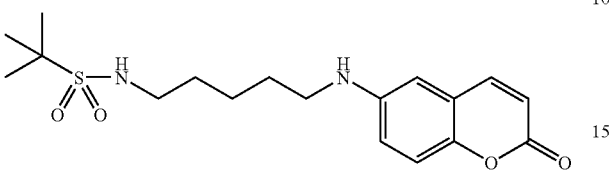
Ia-79
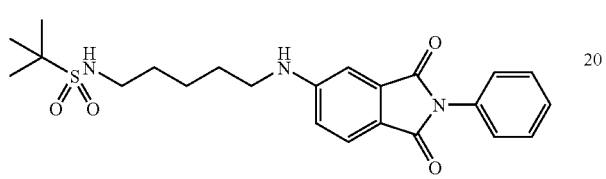
Ia-80
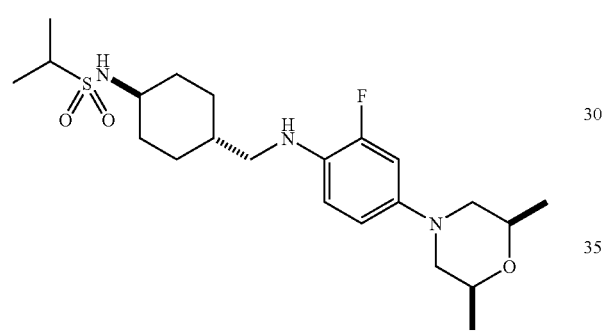
Ia-81
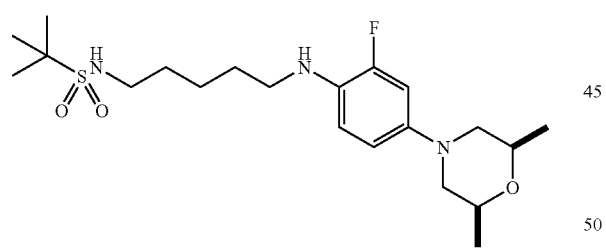
Ia-82
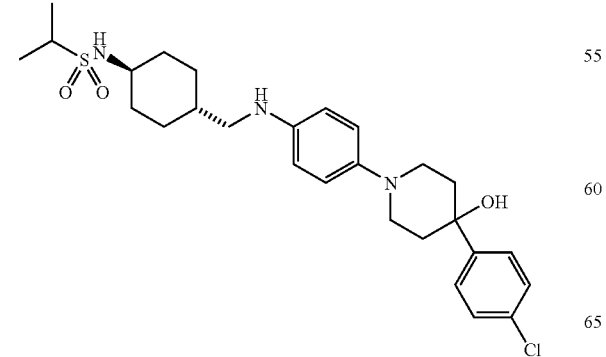
Ia-83
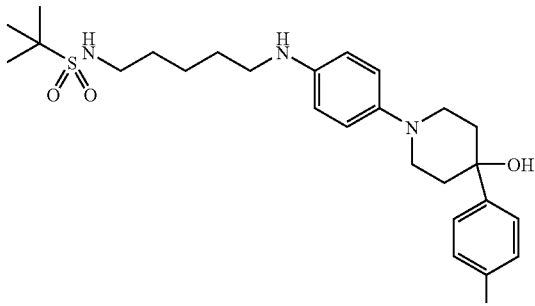
Ia-84
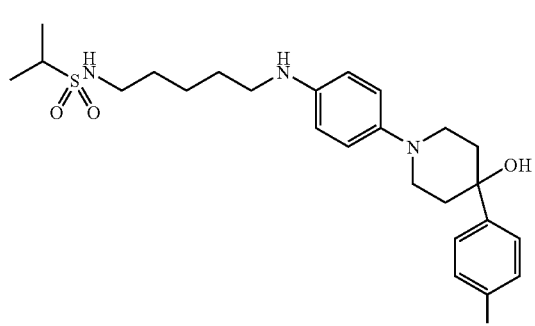
Ia-89
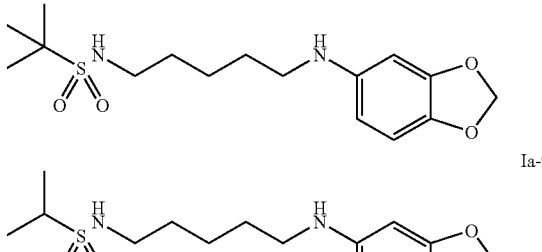
Ia-90
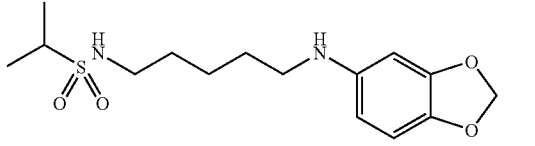
Ia-91
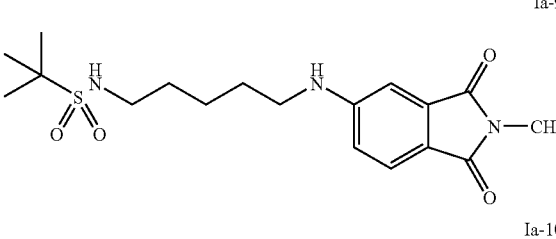
Ia-104
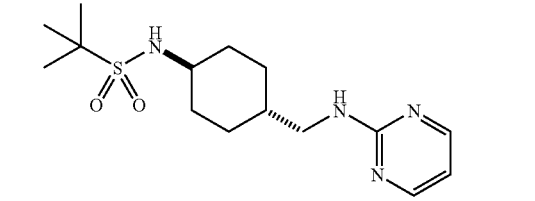
Ia-105
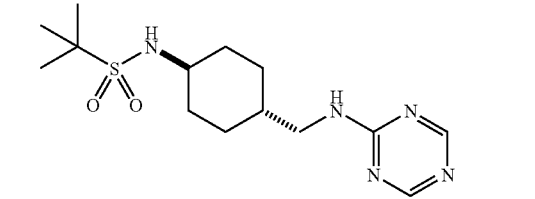

Ia-106
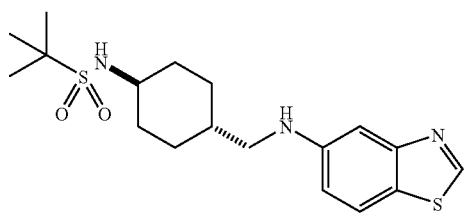
Ia-107
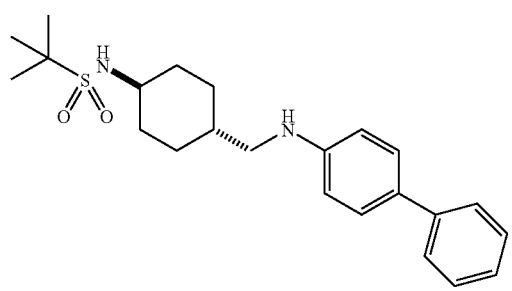
Ia-108
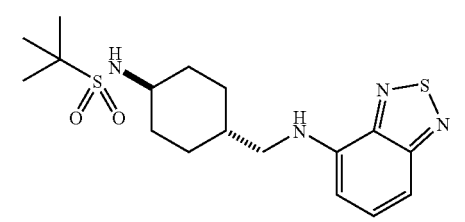
Ia-109
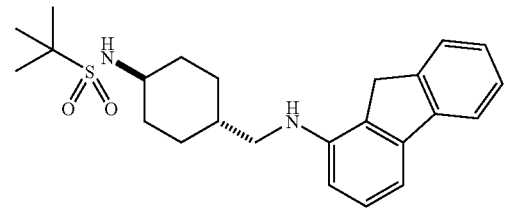
Ia-110
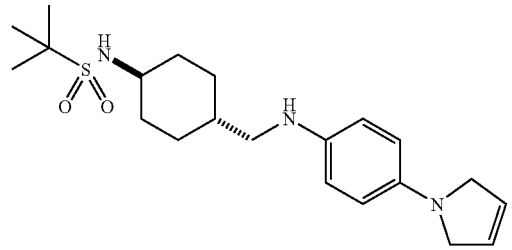
Ia-111
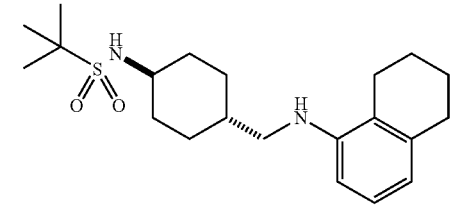
Ia-122
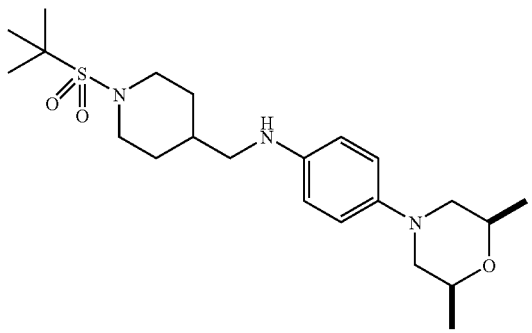
Ia-123
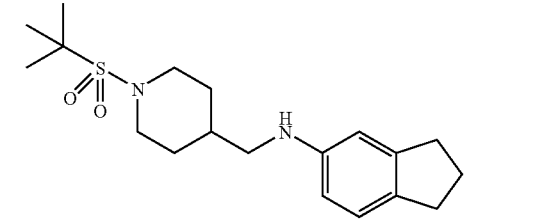
Ia-124
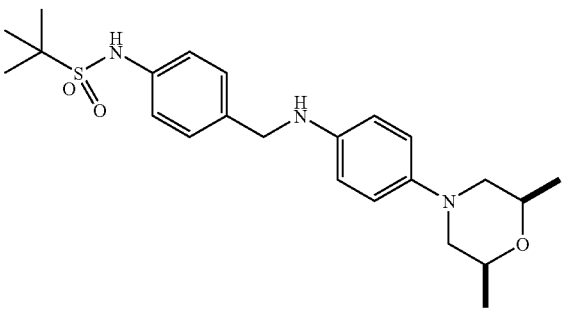
Ia-125
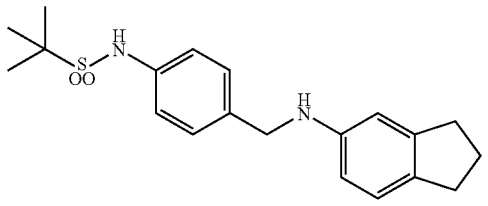
Ia-126
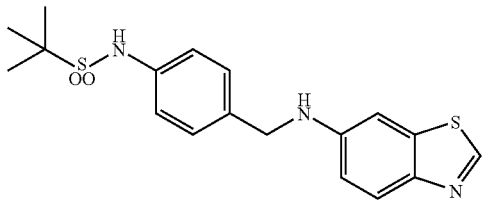
Ia-127
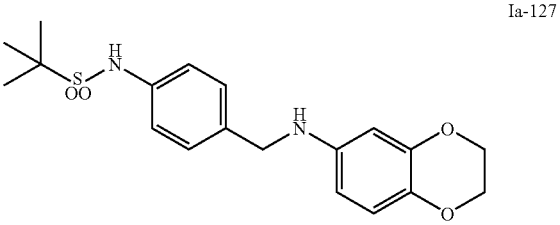

Ia-128
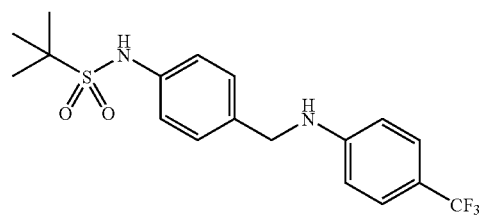
Ia-129
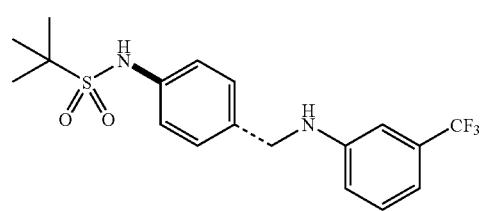
Ia-130
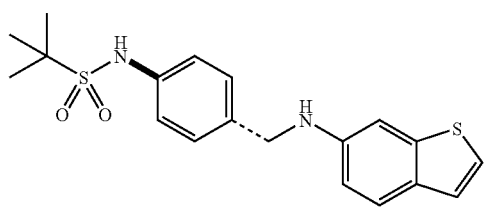
Ia-131
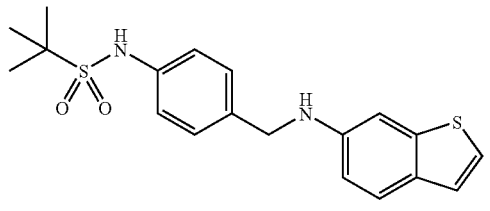
Ia-132
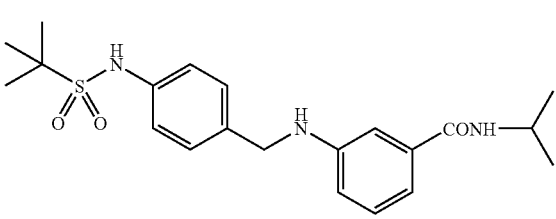
Ia-133
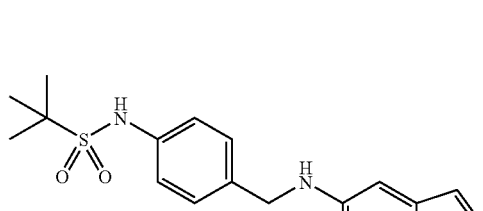
Ia-134
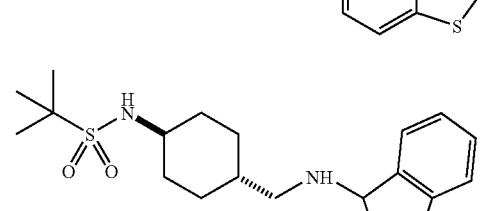
Ia-135
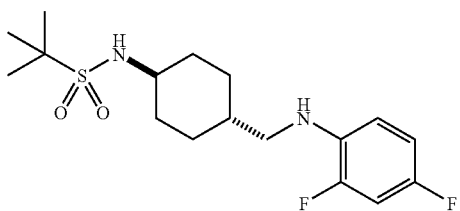
Ia-136
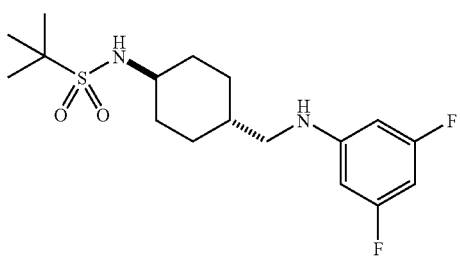
Ia-137
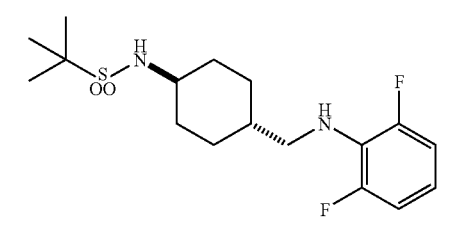
Ia-138
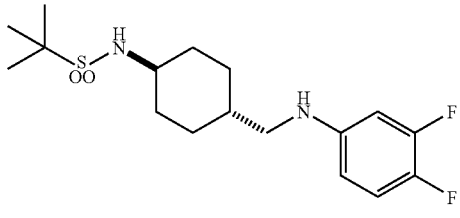
Ia-139
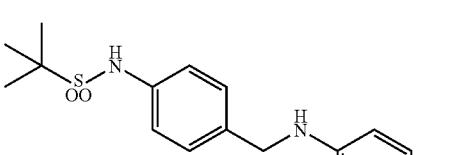
Ia-140
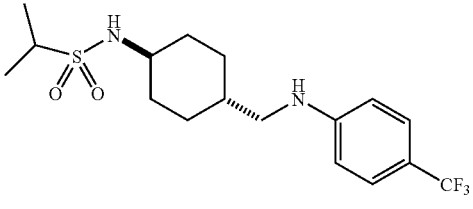
Ia-141
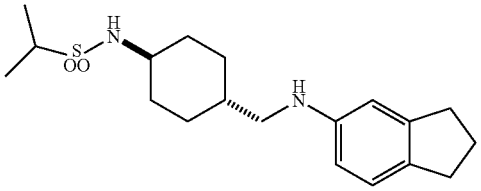

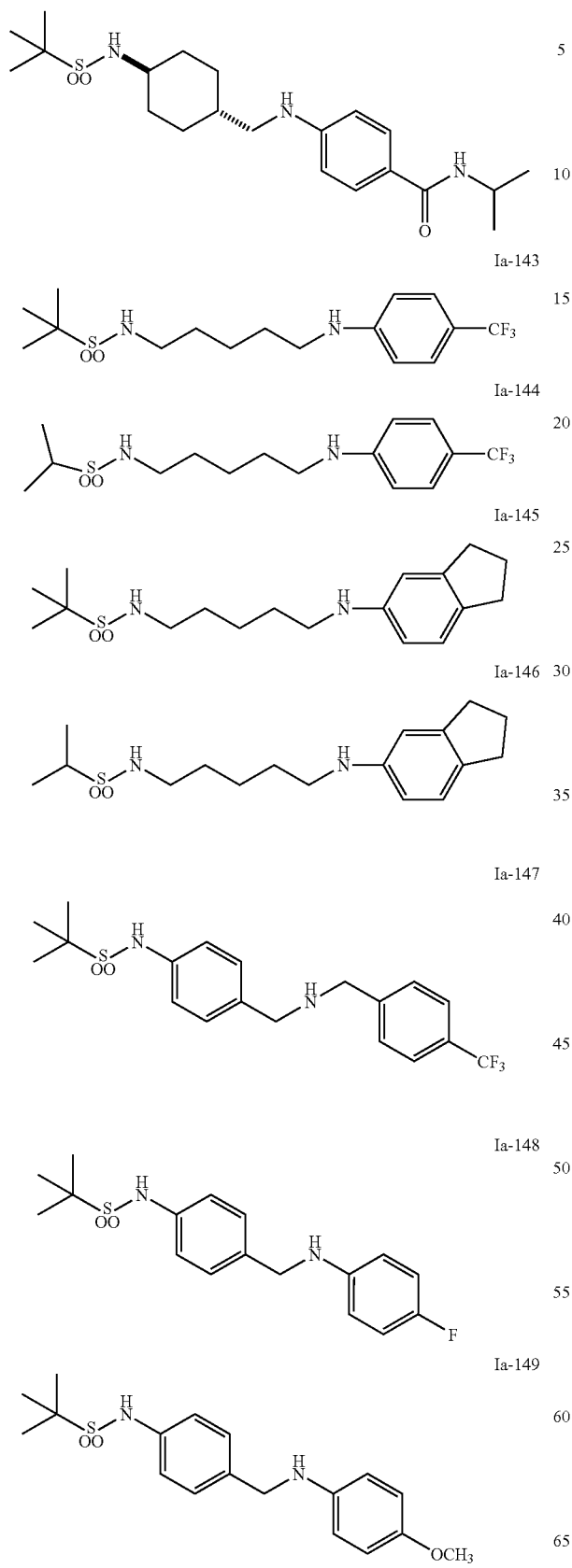
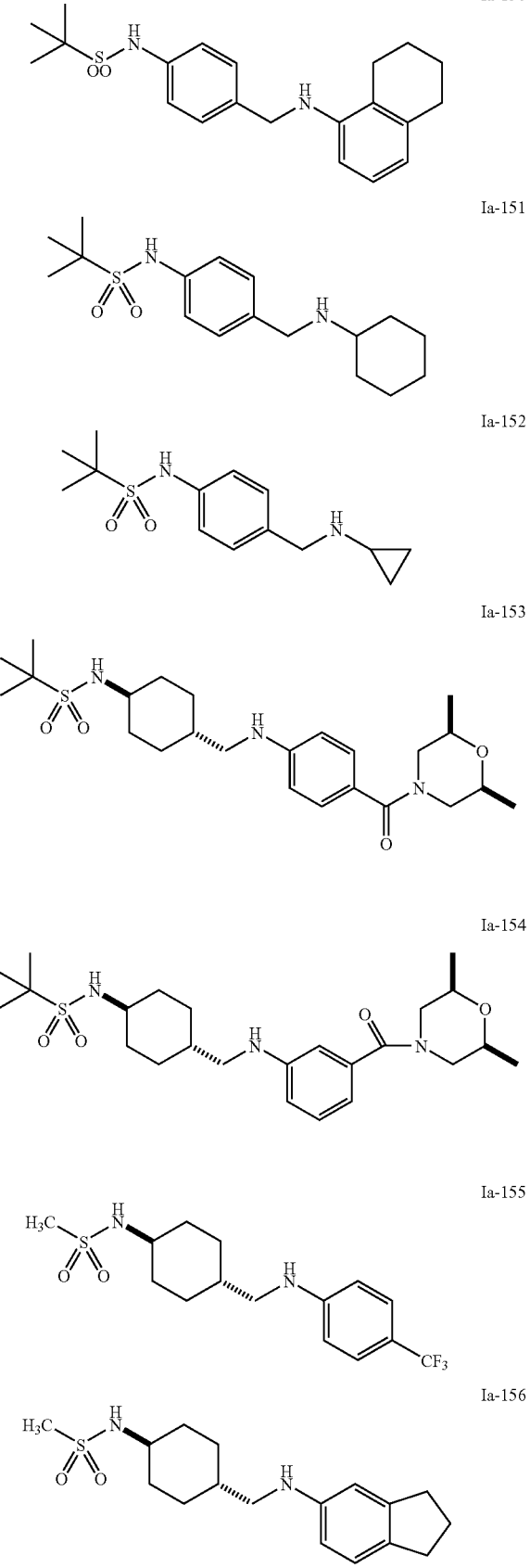

Ia-157
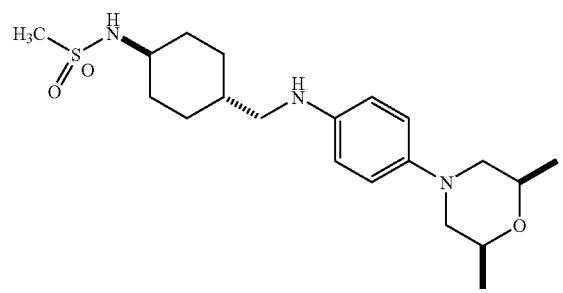
Ia-158
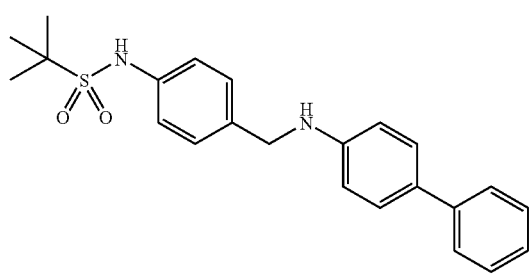
Ia-159
Ia-160
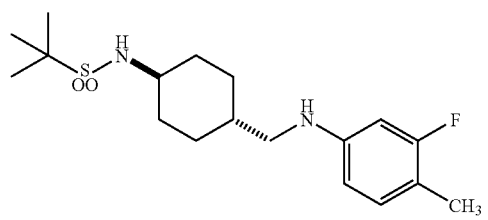
Ia-161
Ia-162
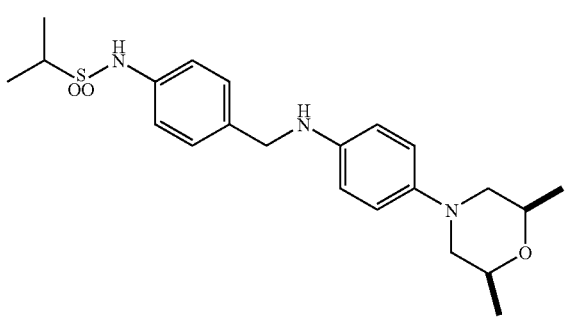
Ia-163
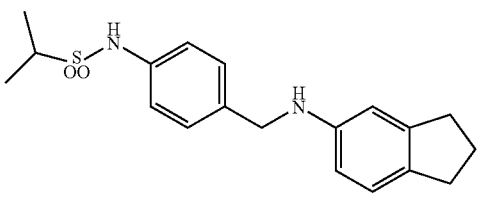
Ia-164
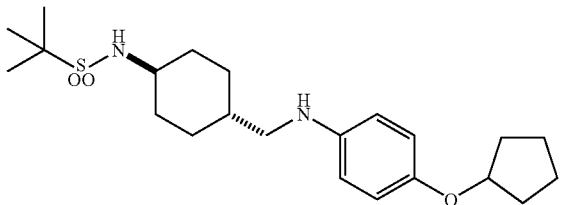
Ia-165
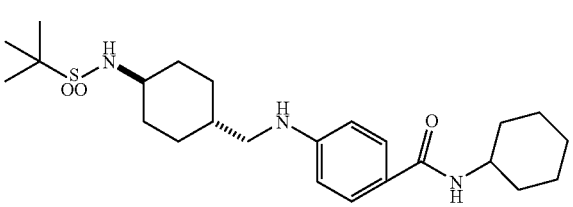
Ia-166
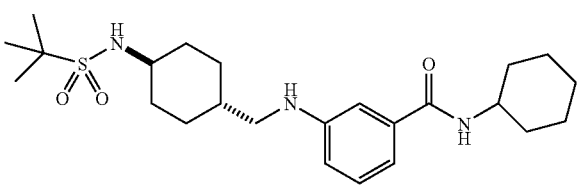
Ia-167
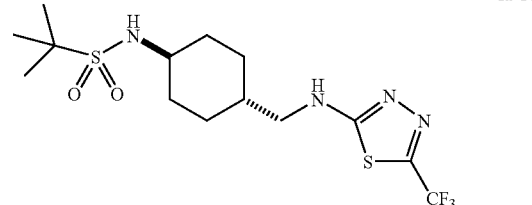
Ia-168
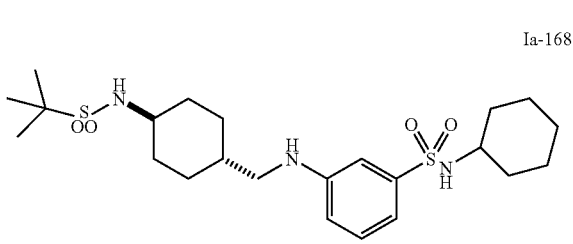
Ia-169
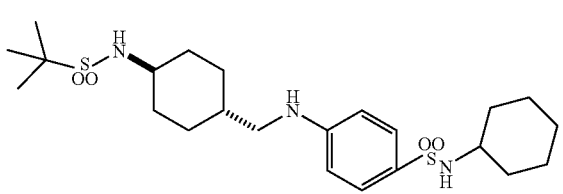

Ia-171
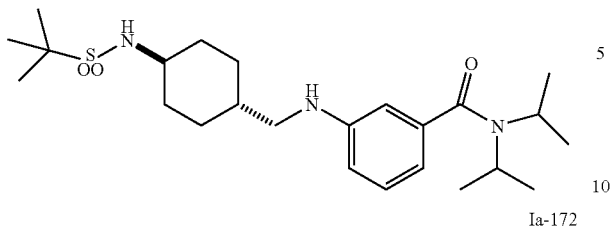
Ia-172
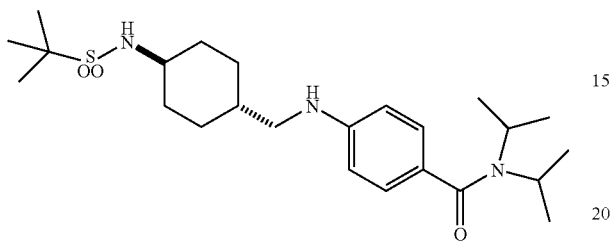
Ia-173
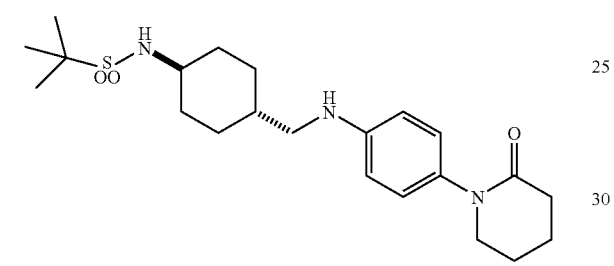
Ia-174
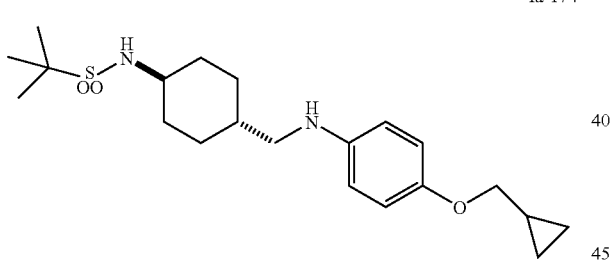
Ia-175
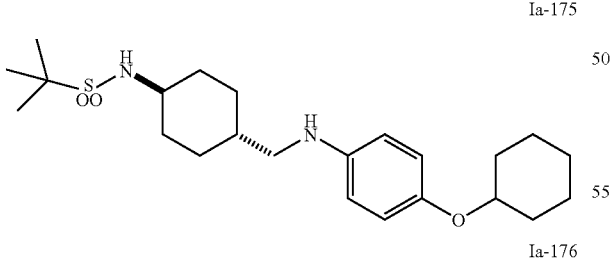
Ia-176
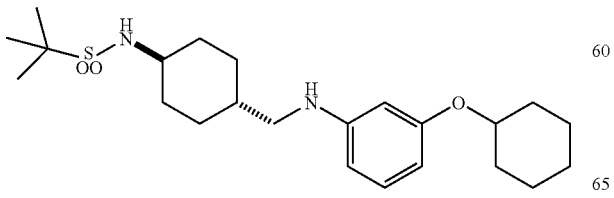
Ia-177
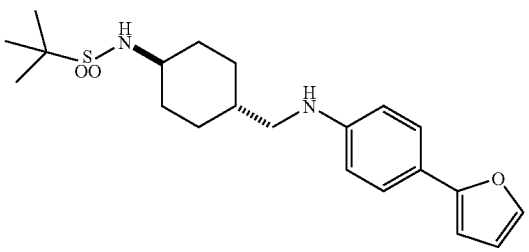
Ia-178
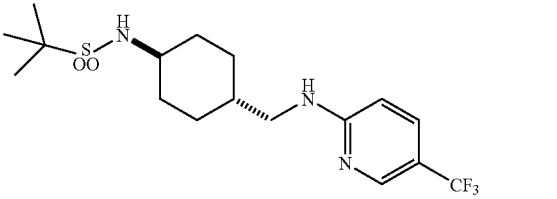
Ia-179
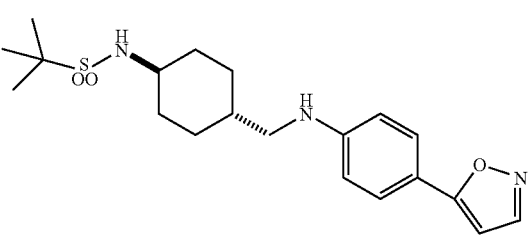
Ia-180
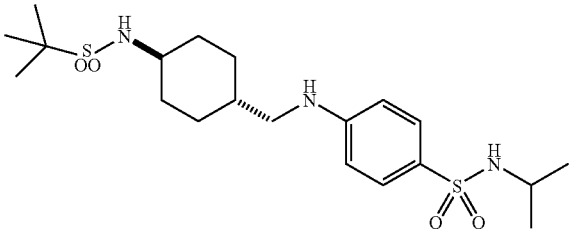
Ia-181
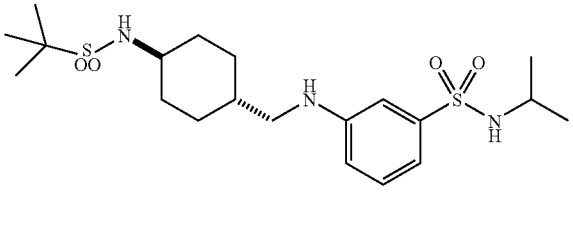
Ia-182
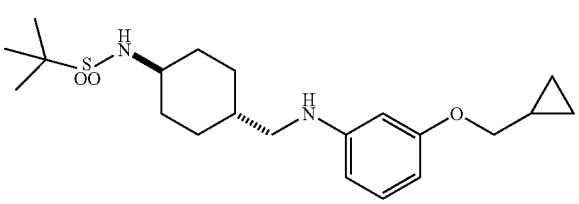

Ia-183
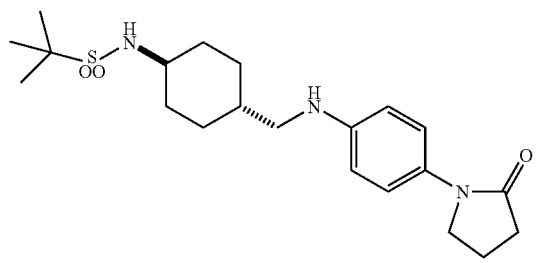
Ia-184
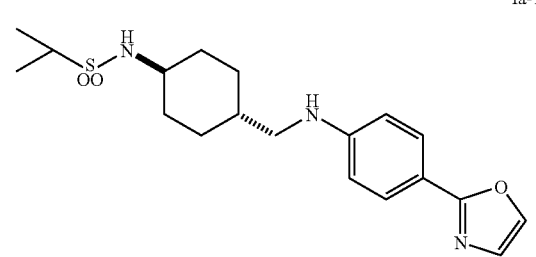
Ia-185
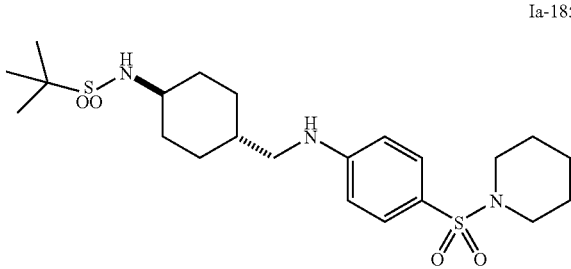
Ia-186
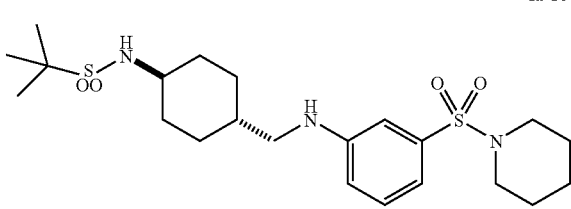
Ia-187
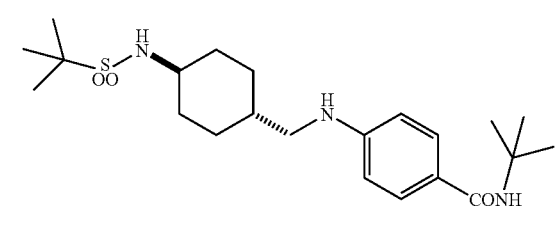
Ia-188
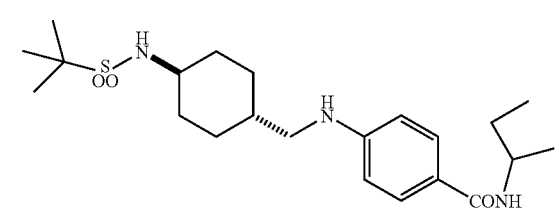
Ia-189
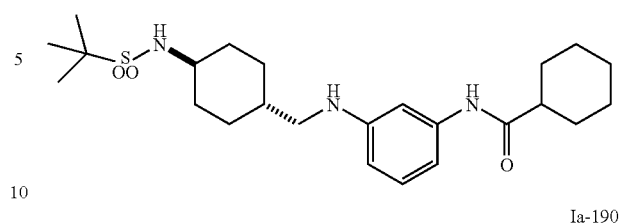
Ia-190
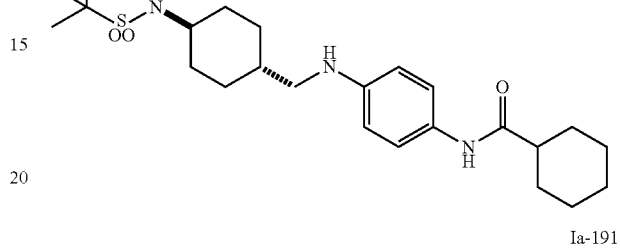
Ia-191
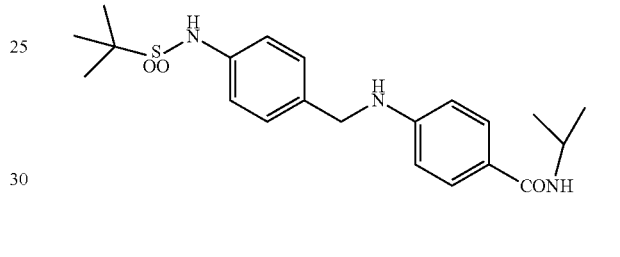
Ia-192
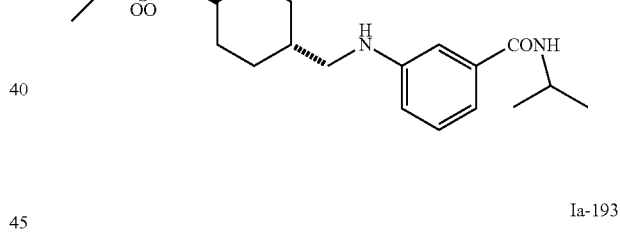
Ia-193
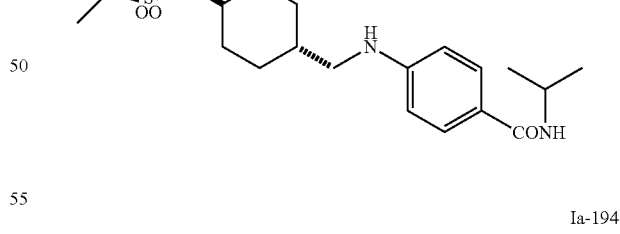
Ia-194
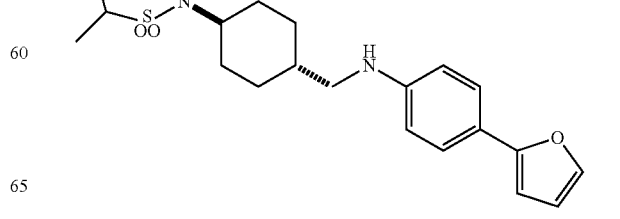

Ia-195
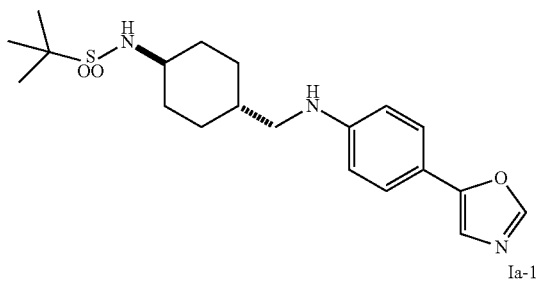
Ia-196
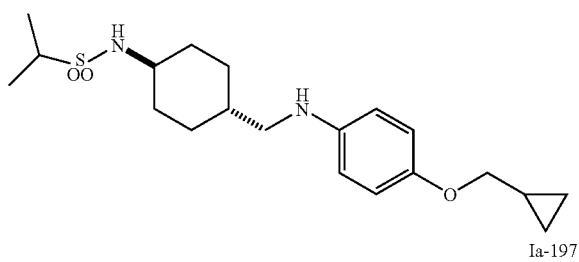
Ia-197
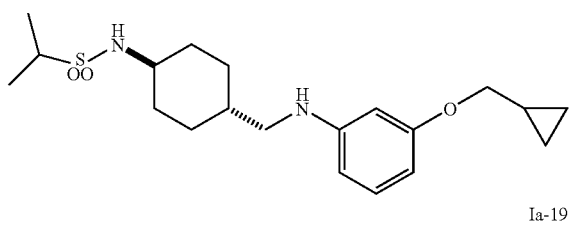
Ia-198
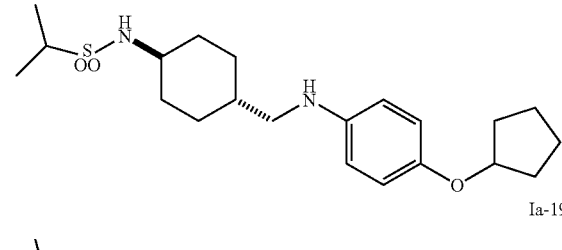
Ia-199
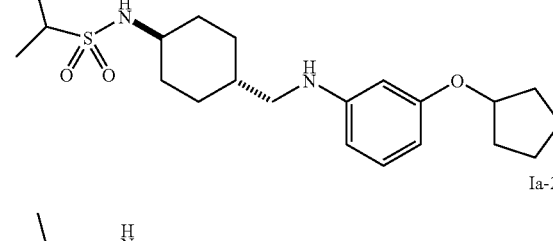
Ia-200
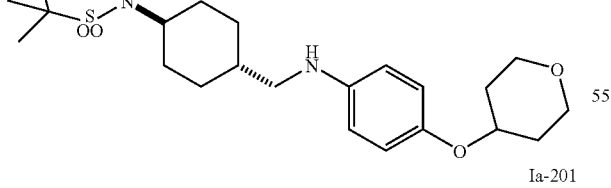
Ia-201
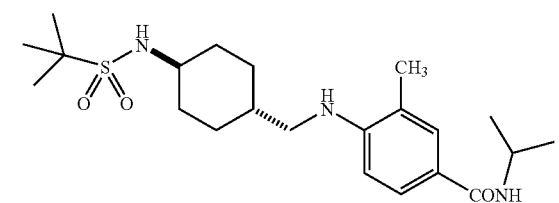
Ia-202
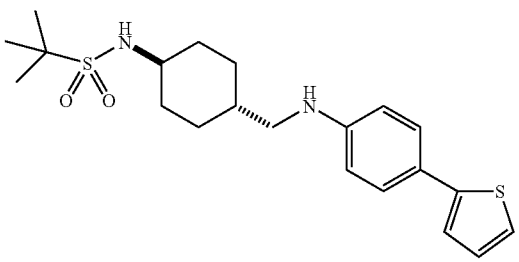
Ia-203
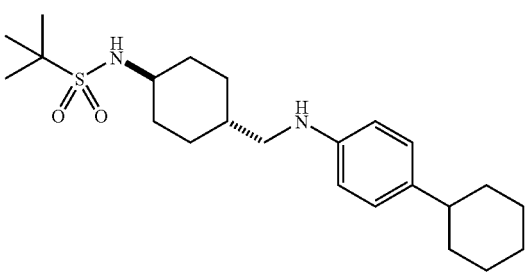
Ia-204
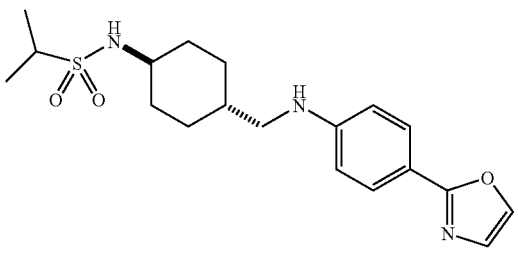
Ia-205
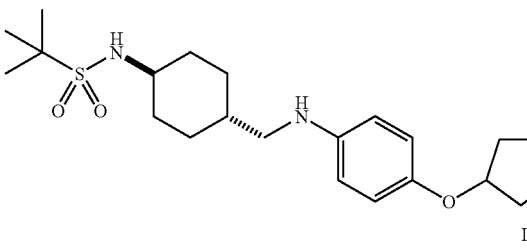
Ia-206
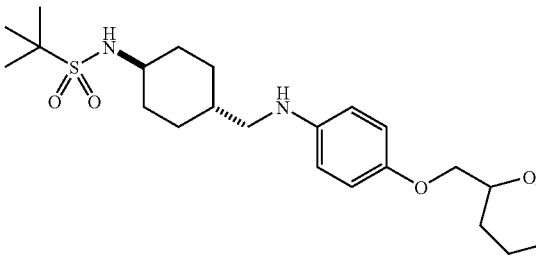
Ia-207
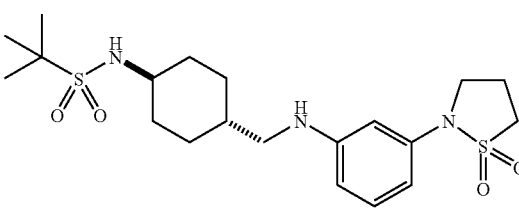

Ia-208
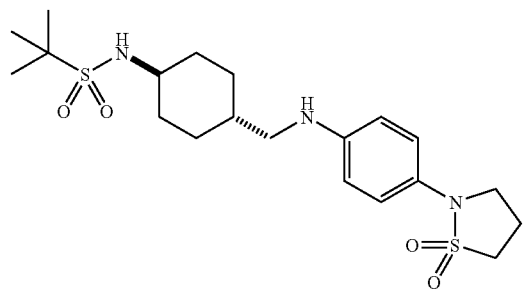
Ia-209
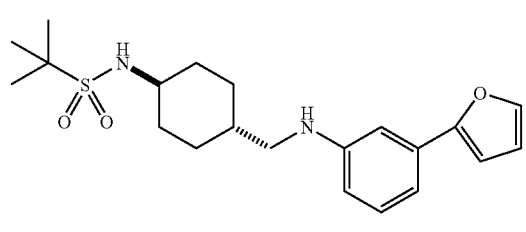
Ia-210
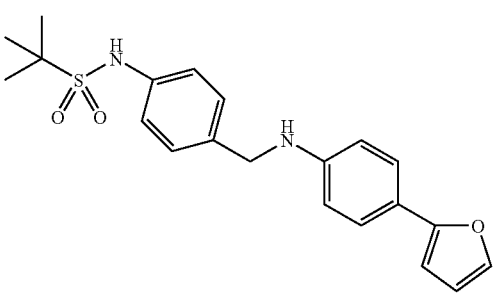
Ia-211
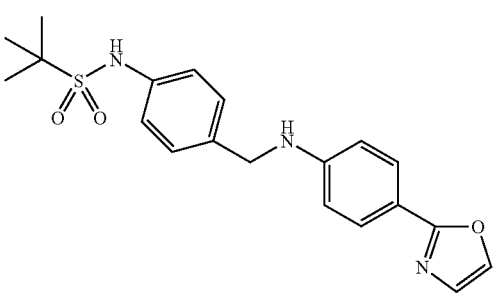
Ia-212
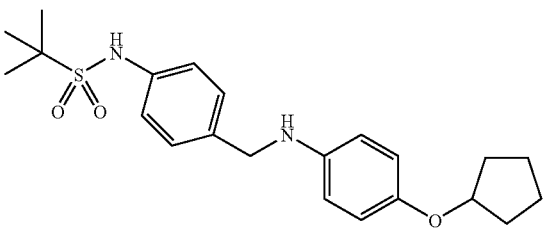
Ia-213
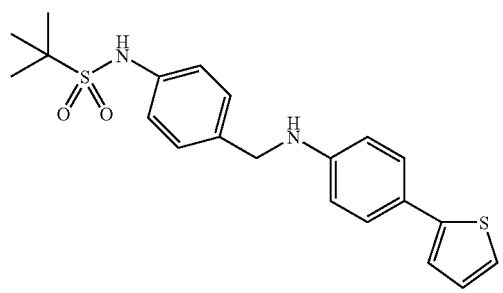
Ia-214
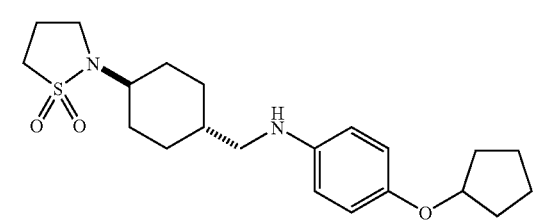
Ia-215
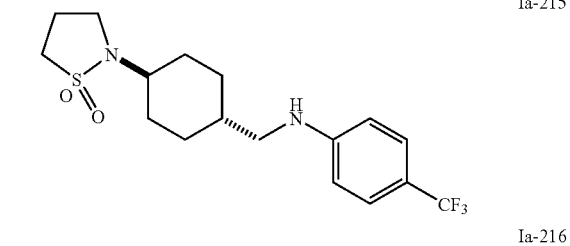
Ia-216
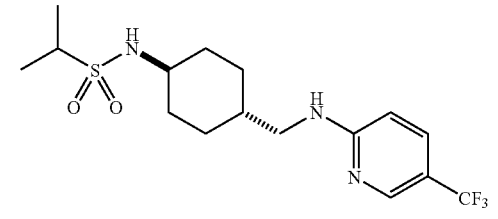
Ia-219
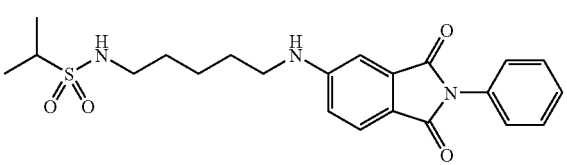
Ia-220
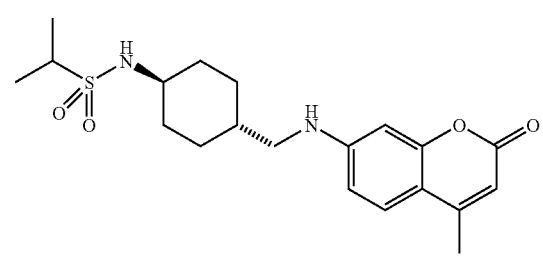
Ia-221
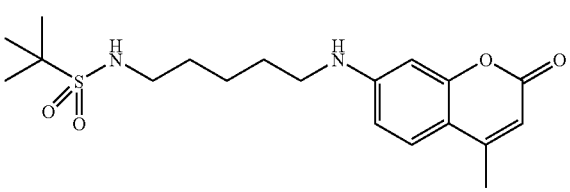

-continued
Ia-222
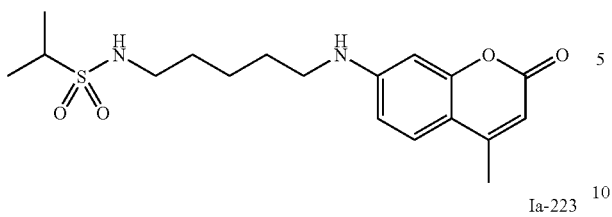
Ia-223
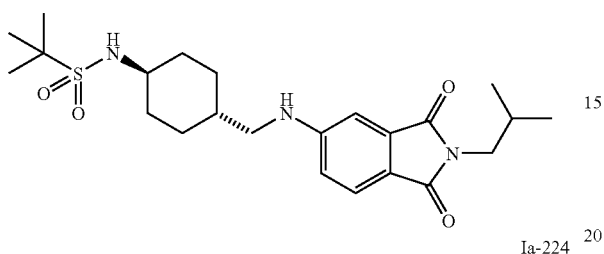
Ia-224
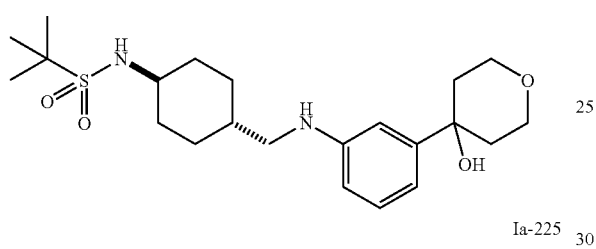
Ia-225
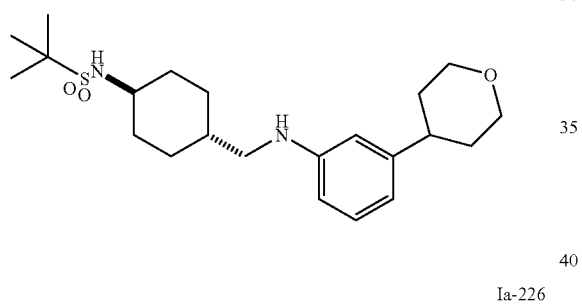
Ia-226
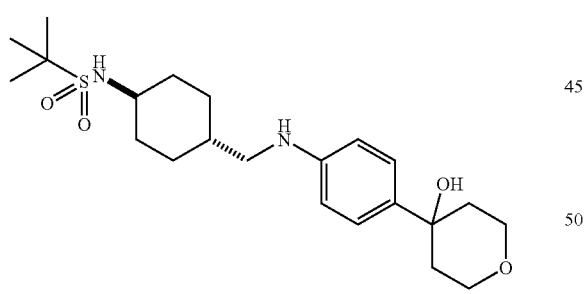
Ia-227
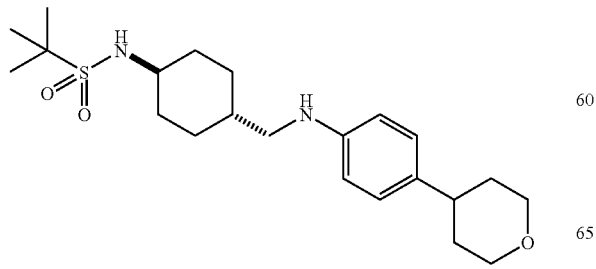
-continued
Ia-228
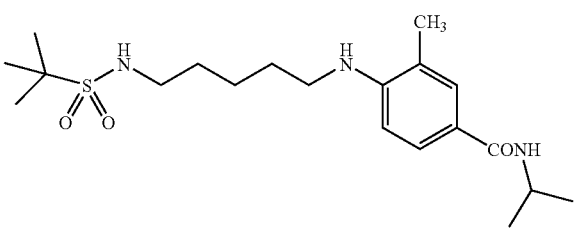
Ia-229
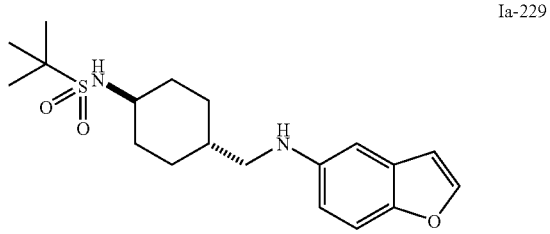
Ia-230
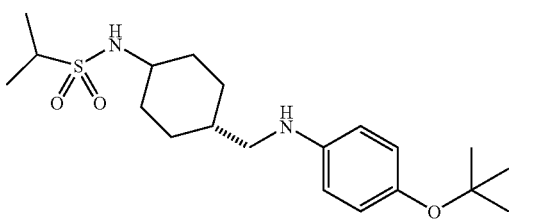
Ia-231
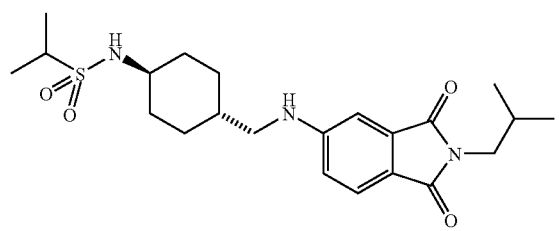
Ia-232
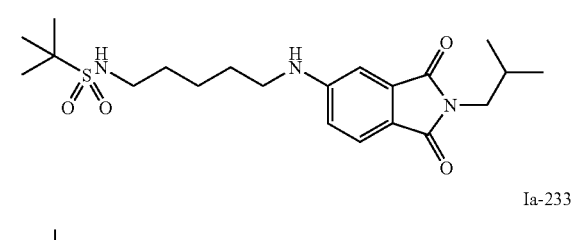
Ia-233
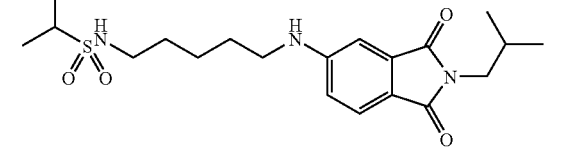
Ia-234
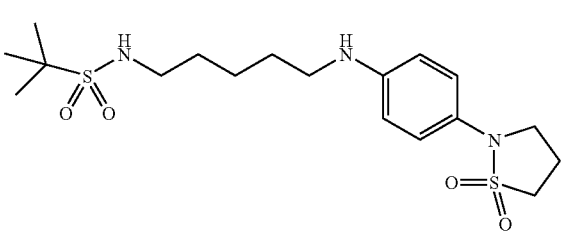

Ia-235
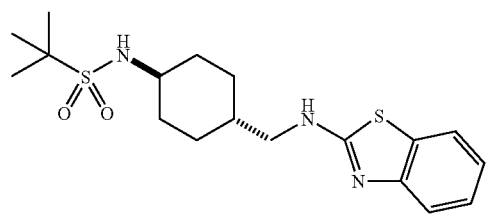
Ia-236
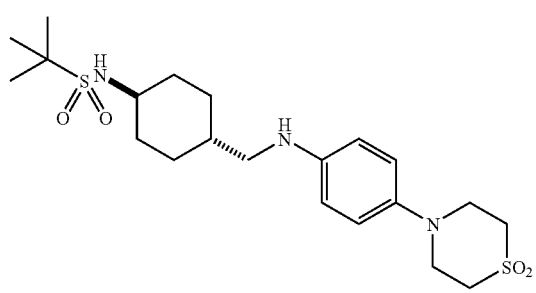
Ia-237
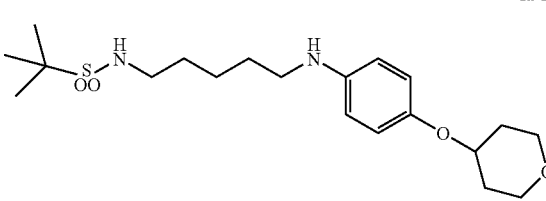
Ia-238
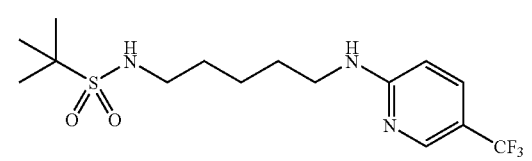
Ia-239
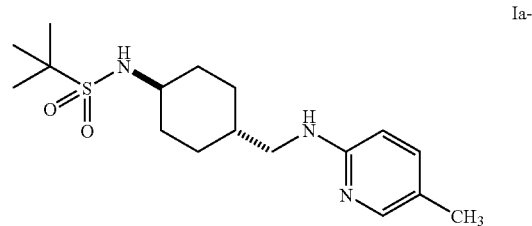
Ia-240
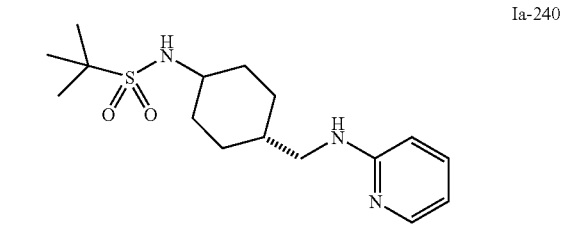
Ia-241
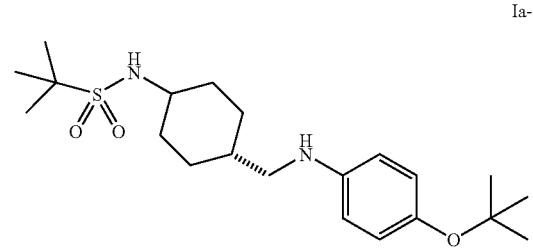
Ia-242
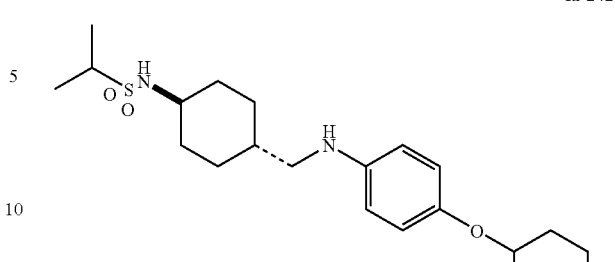
Ia-244
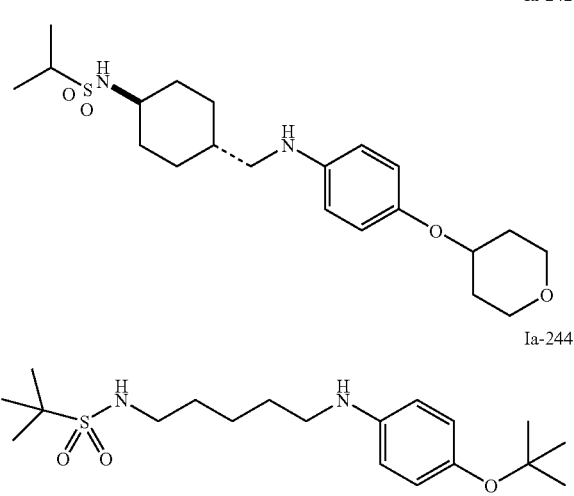
Ib-1
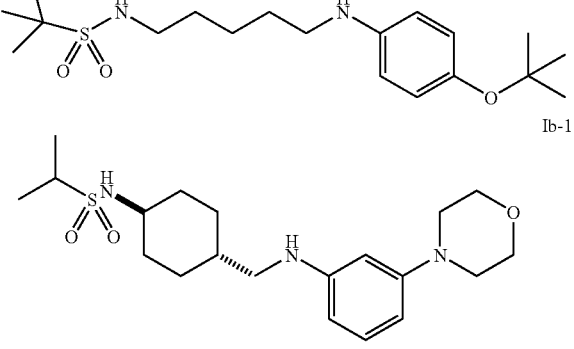
Ib-2
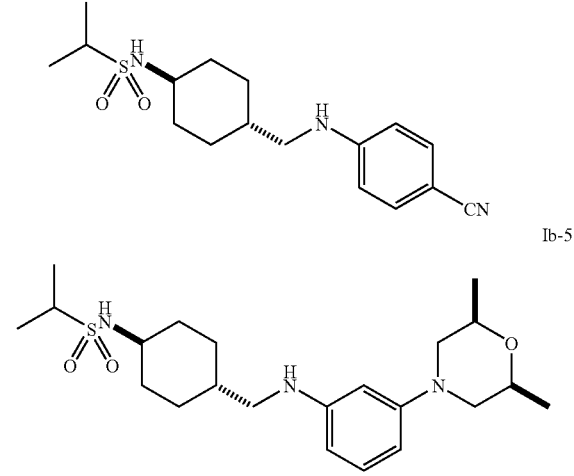
Ib-5
Ib-7
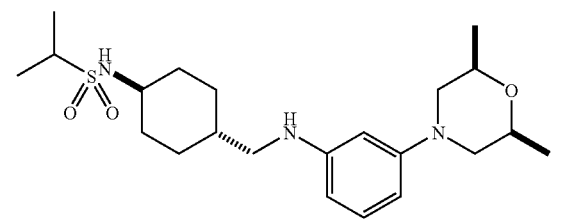
Ib-8
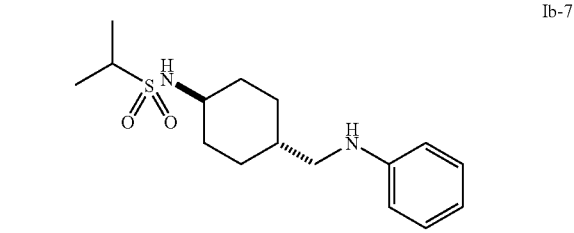

-continued
Ib-9
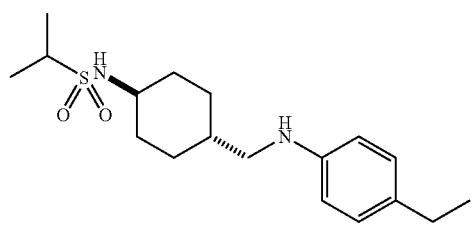
Ib-10
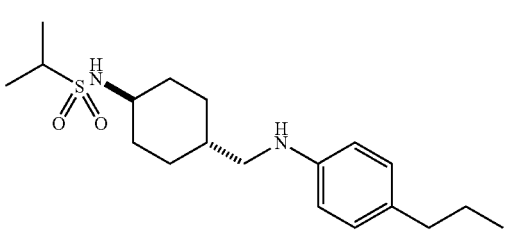
Ib-11
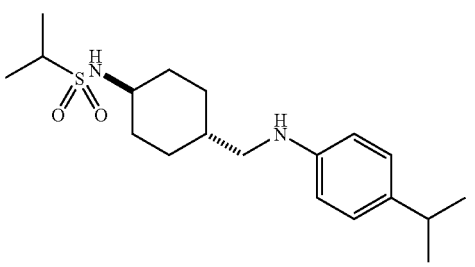
Ib-12
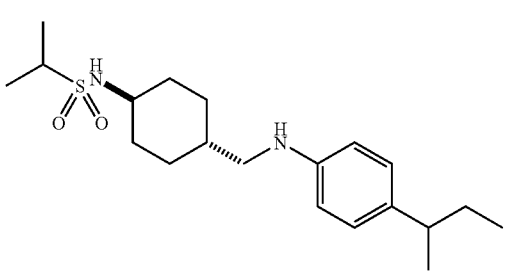
Ib-13
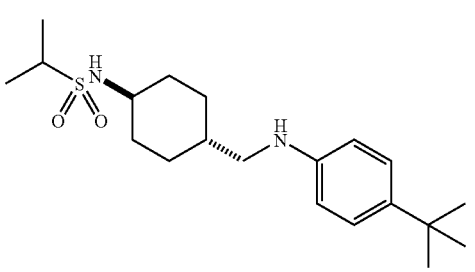
Ib-14
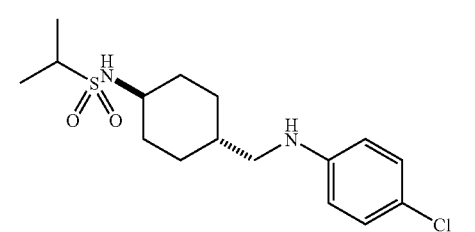
-continued
Ib-15
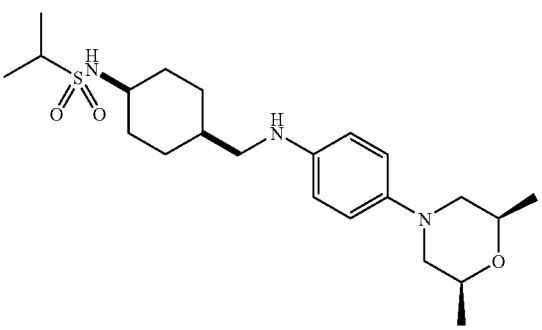
Ib-16
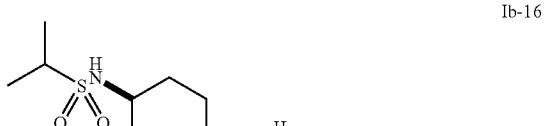
Ib-17
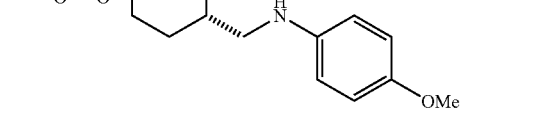
Ib-18
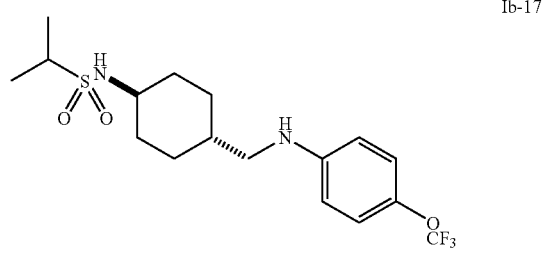
Ib-19
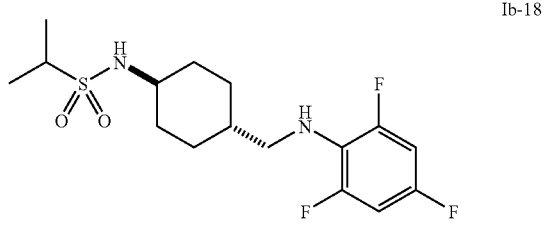
Ib-20
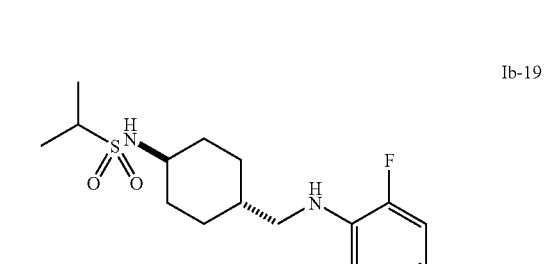

Ib-21
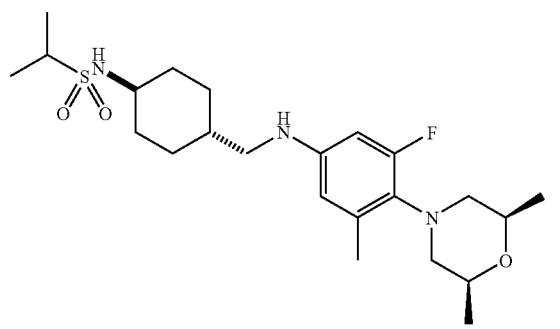
Ib-22
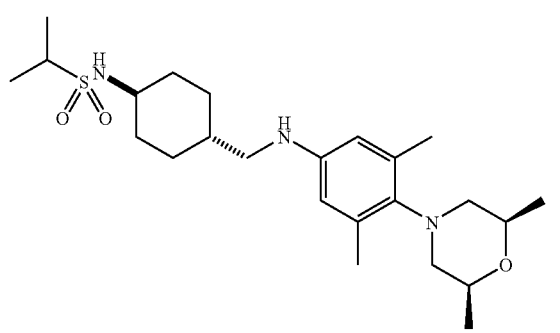
Ib-23
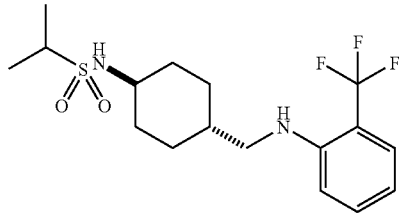
Ib-24
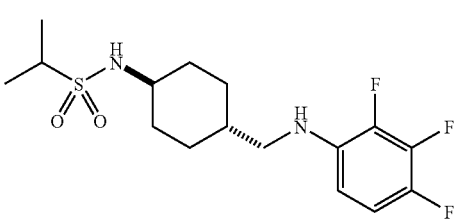
Ib-25
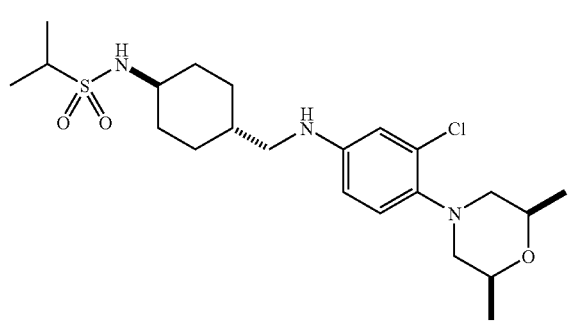
Ib-26
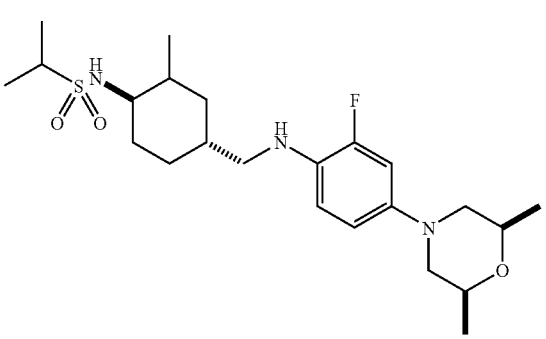
Ib-27
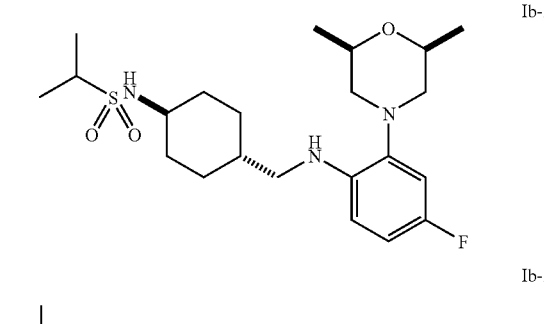
Ib-28
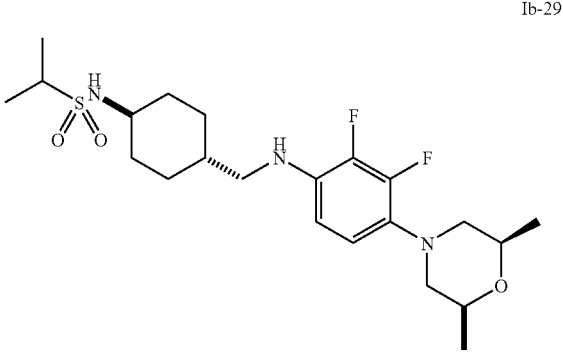
Ib-29
Ib-30
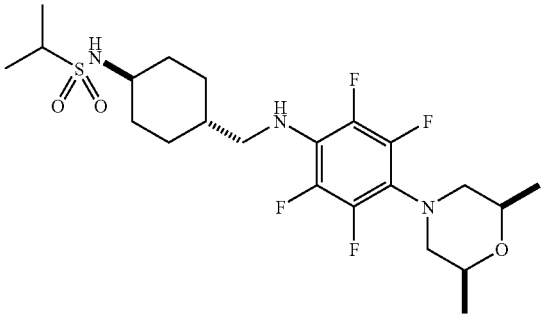

Ib-31
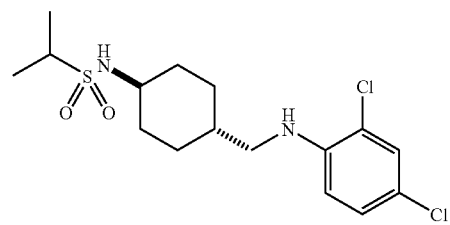
Ib-32
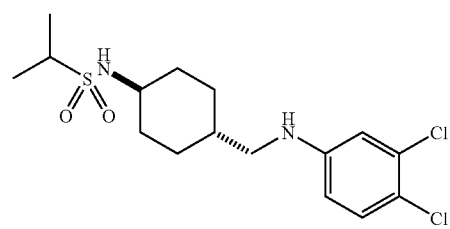
Ib-33
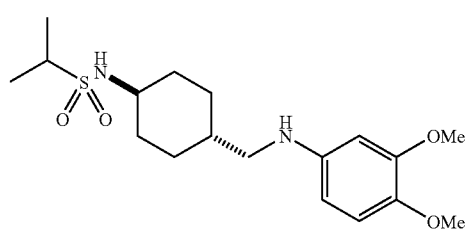
Ib-35
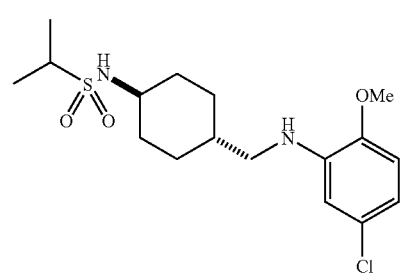
Ib-36
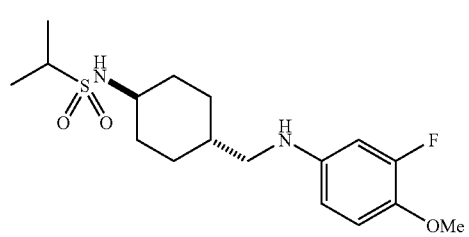
Ib-37
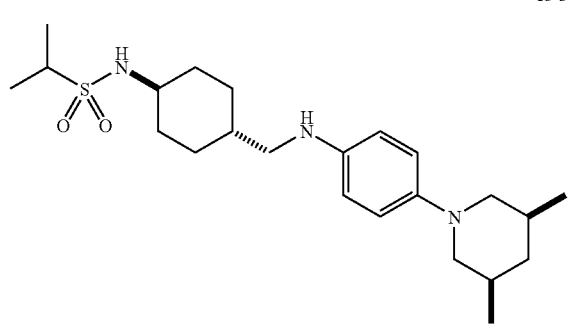
Ib-38
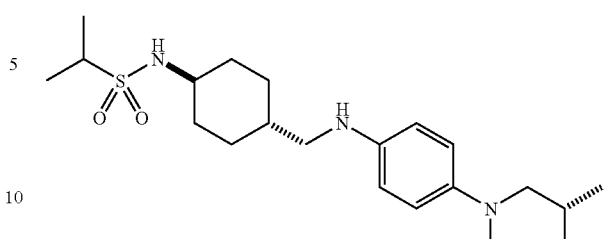
Ib-39
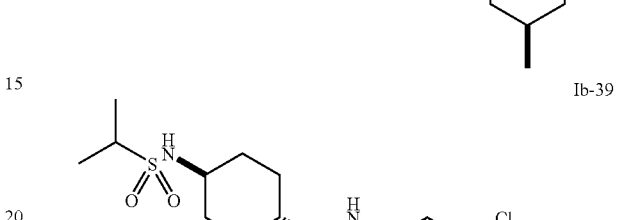
Ib-40
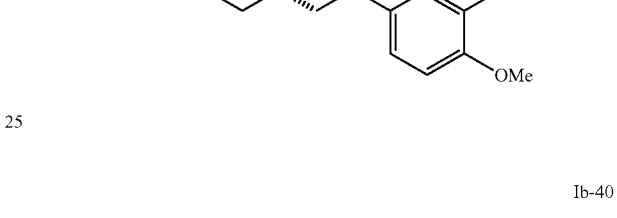
Ib-41
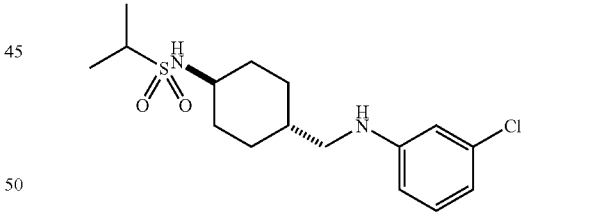
Ib-42
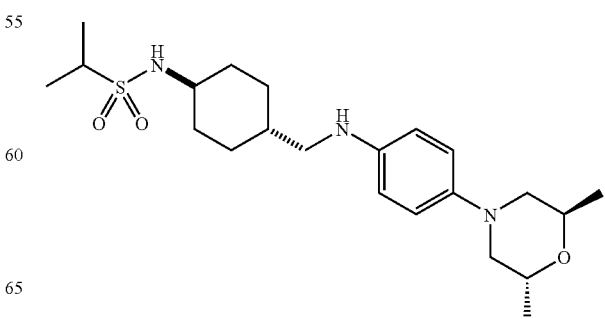

199
-continued
Ib-43
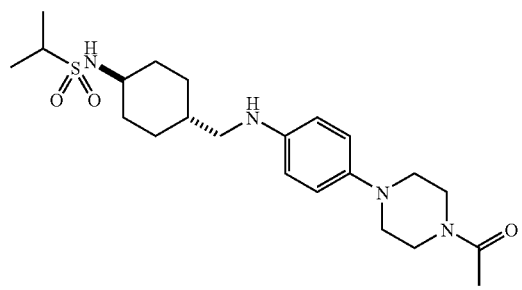
Ib-44
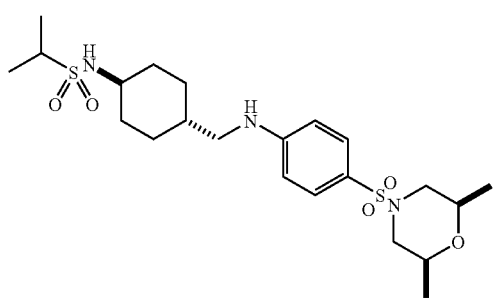
Ib-45
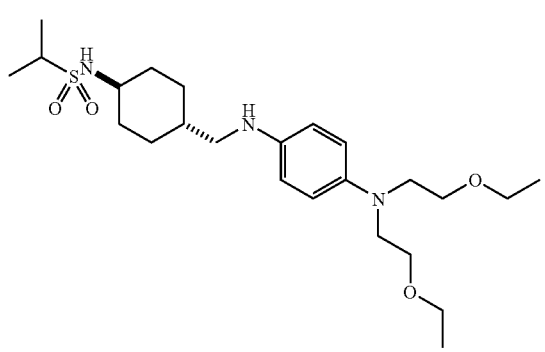
Ib-46
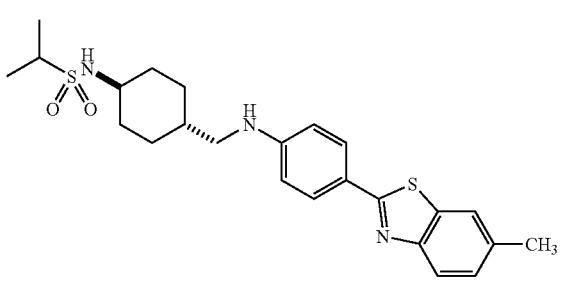
Ib-47
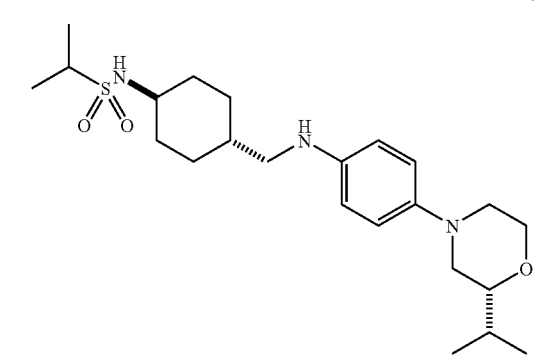
200
-continued
Ib-48
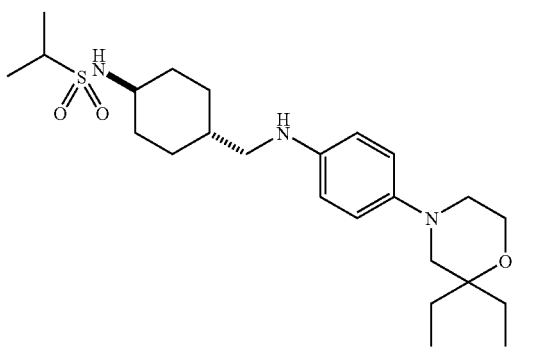
Ib-49
Ib-50
Ib-51
Ib-52

Ib-53
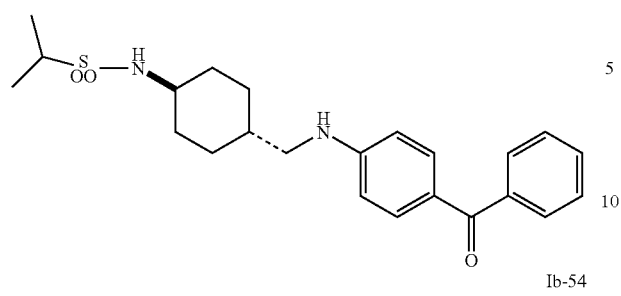
Ib-54
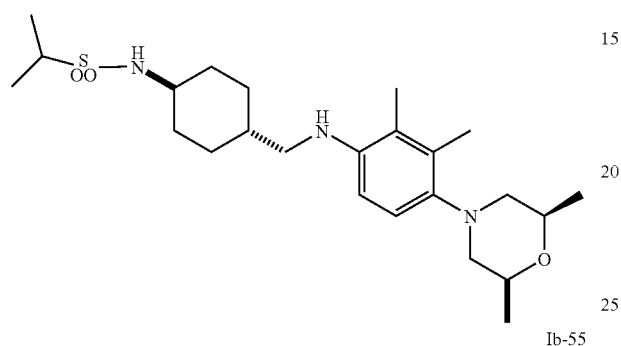
Ib-55
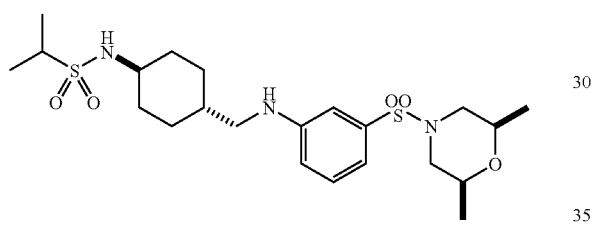
Ib-56
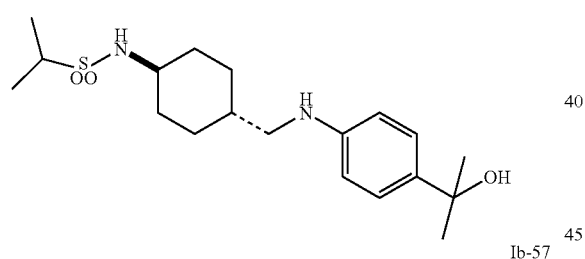
Ib-57
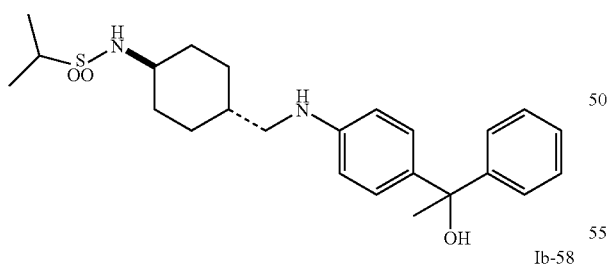
Ib-58
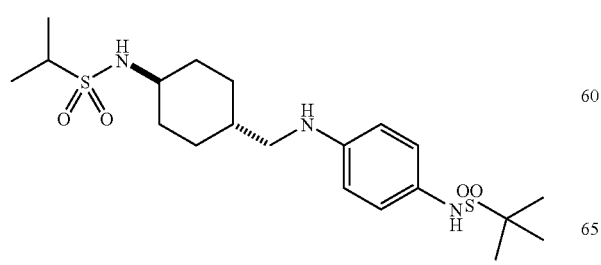
Ib-59
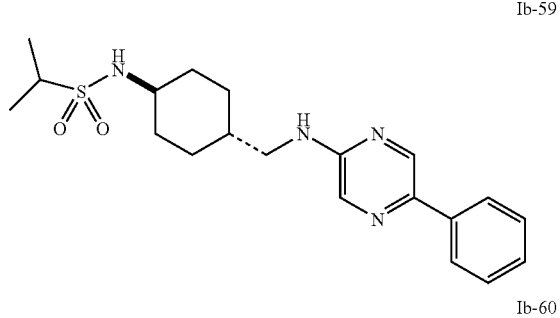
Ib-60
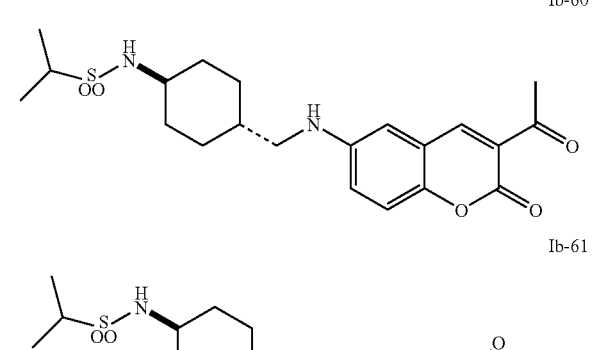
Ib-61
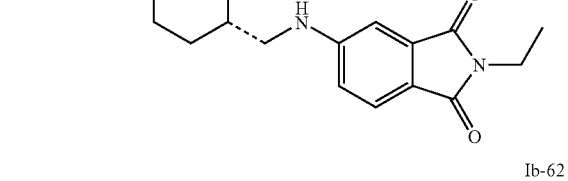
Ib-62
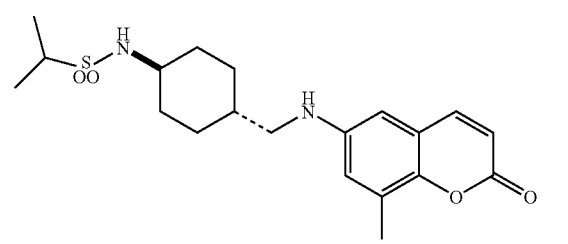
Ib-63
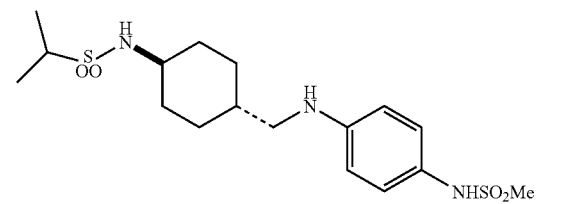
Ib-64
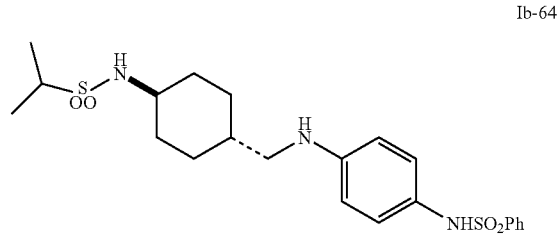

Ib-65
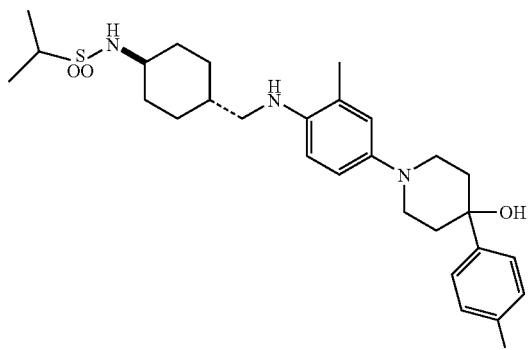
Ib-66
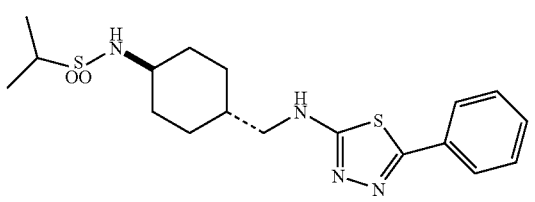
Ib-68
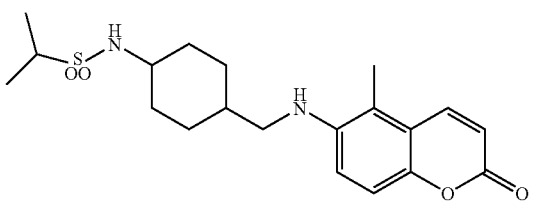
Ib-69
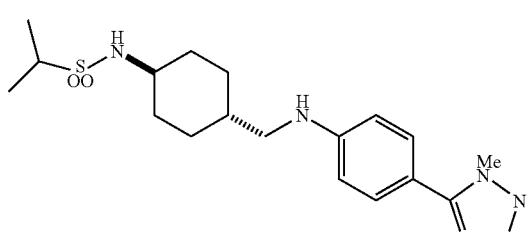
Ib-70
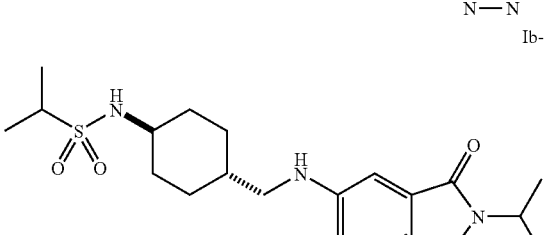
Ib-71
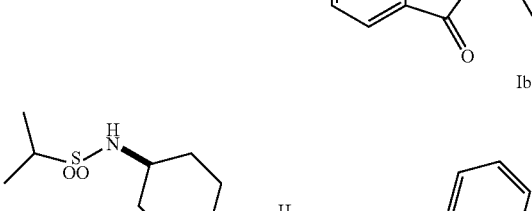
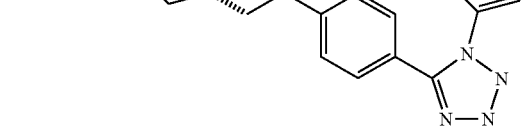
Ib-72
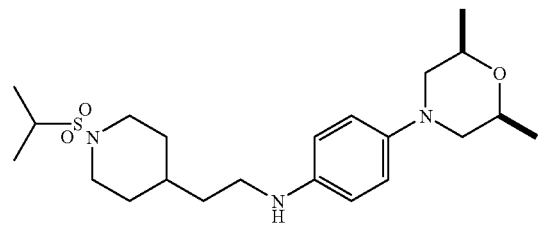
Ib-73
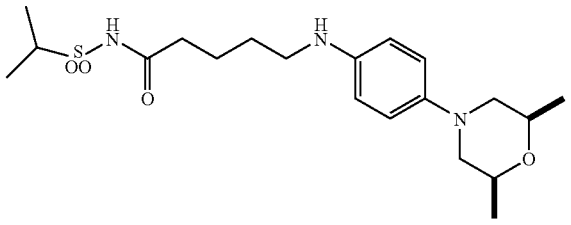
Ib-74
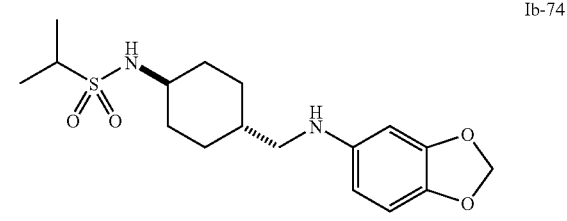
Ib-75
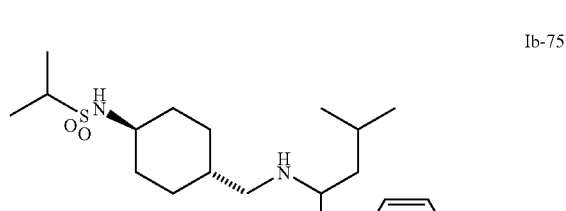
Ib-76
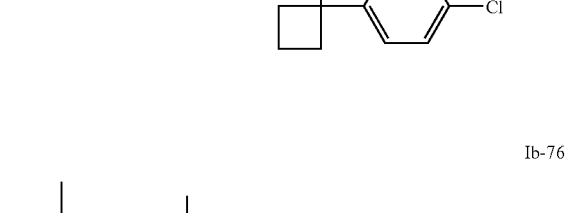
Ib-77
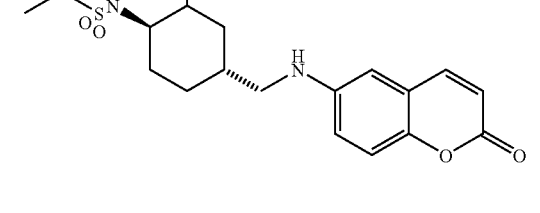

Ib-78
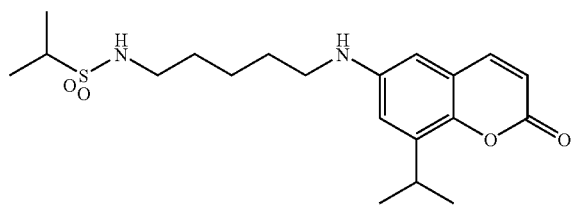
Ib-79
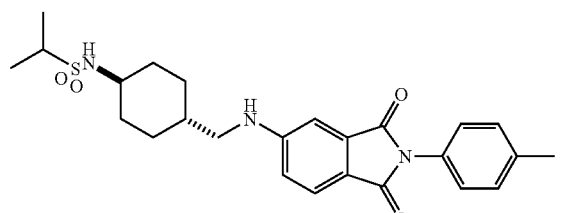
Ib-80
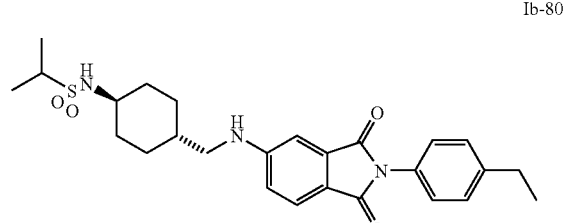
Ib-81
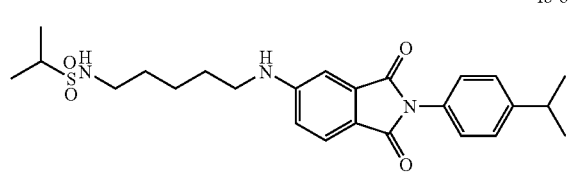
Ib-82
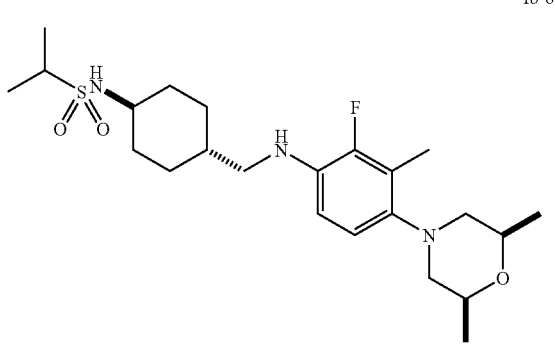
Ib-83
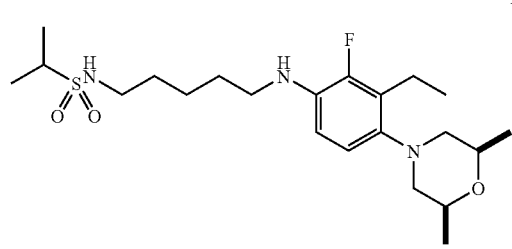
Ib-84
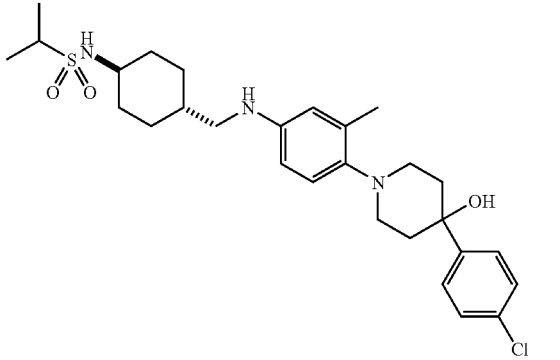
Ib-85
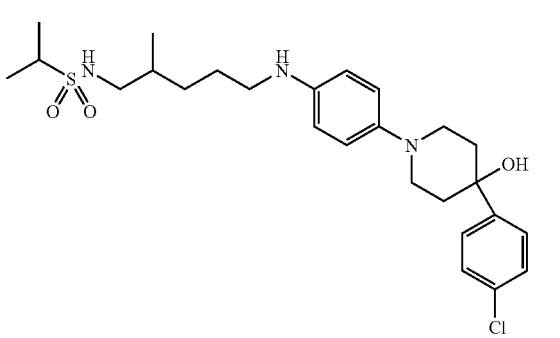
Ib-86
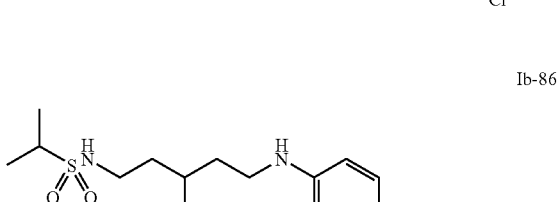
Ib-87
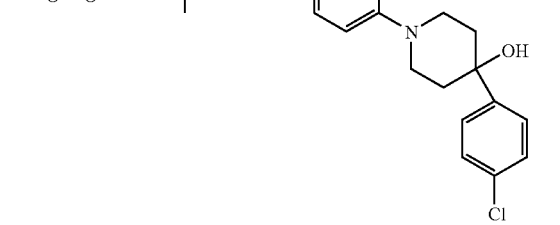
Ib-88
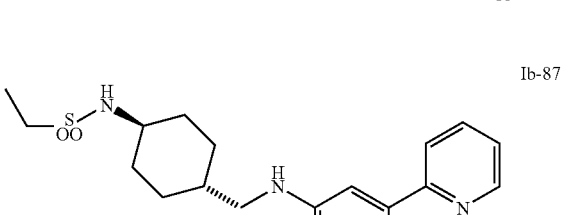
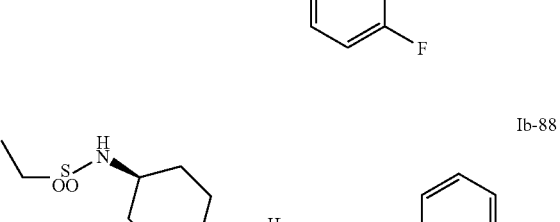

Ib-89
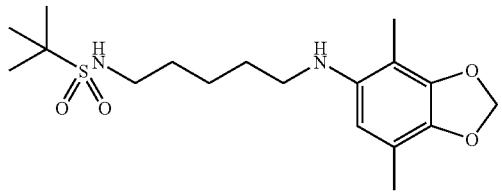
Ib-90
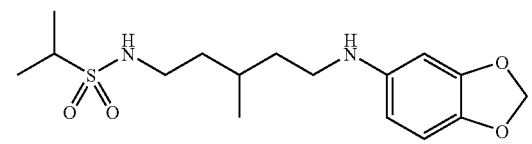
Ib-91
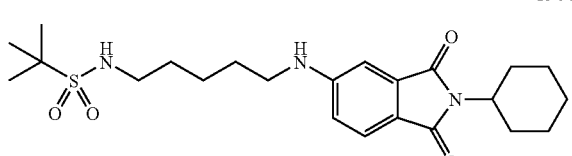
Ib-92
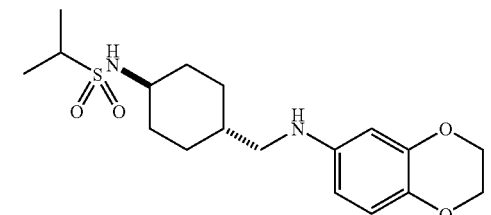
Ib-93
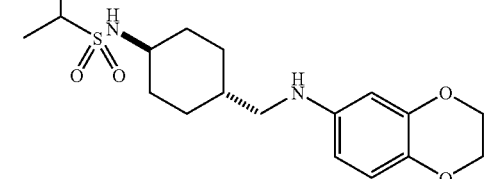
Ib-94
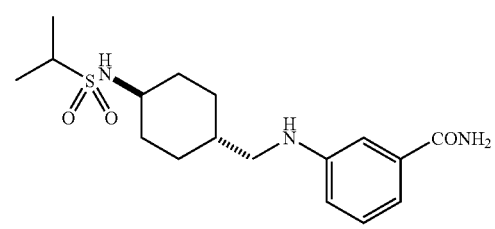
Ib-95
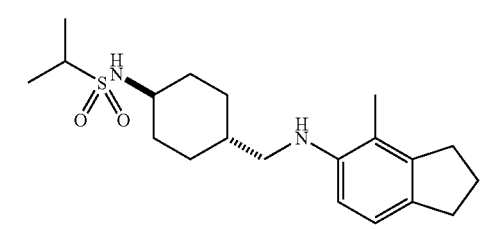
Ib-96
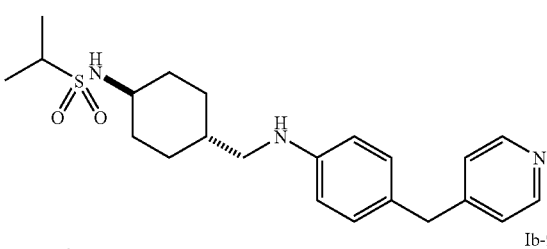
Ib-97
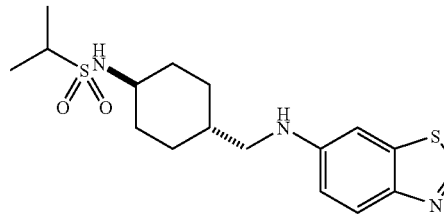
Ib-98
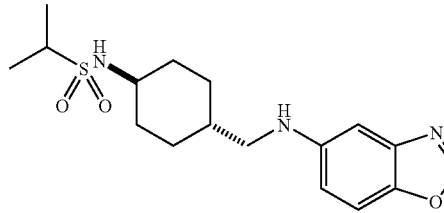
Ib-99
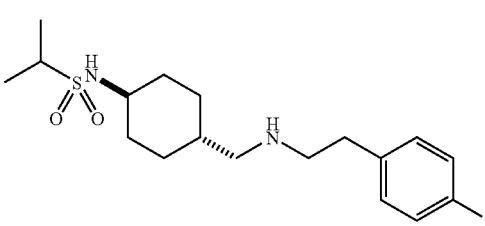
Ib-100
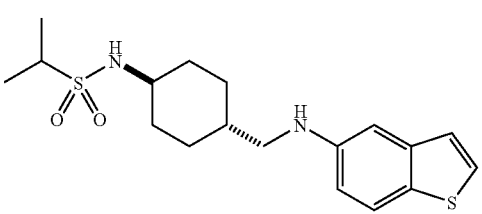
Ib-101
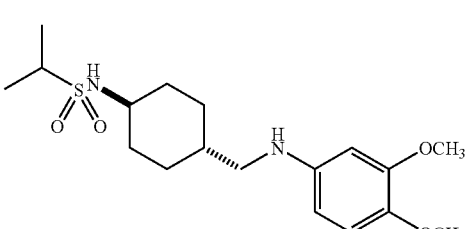
Ib-102
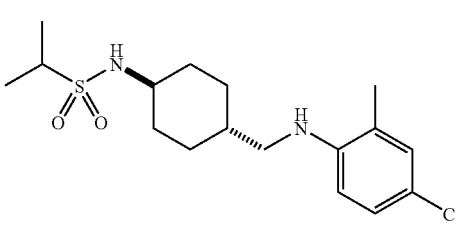

Ib-103
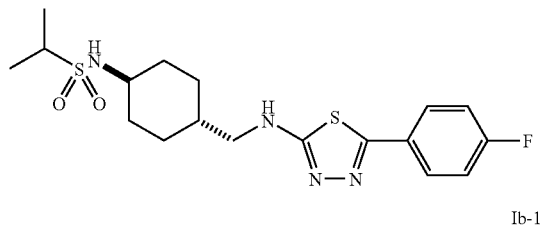
Ib-104
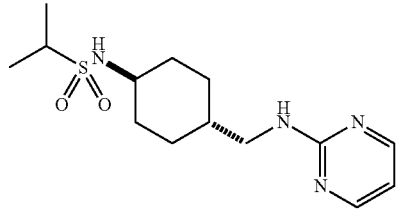
Ib-105
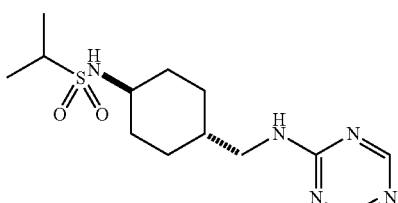
Ib-106
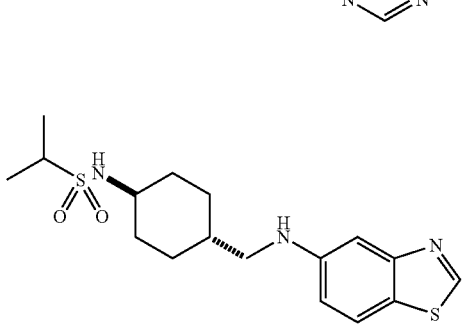
Ib-107
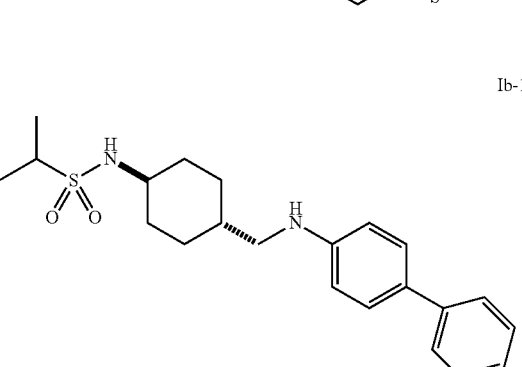
Ib-108
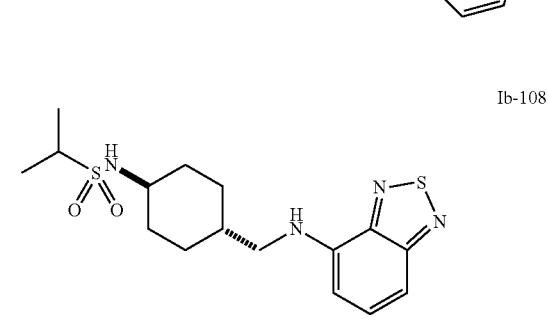
Ib-109
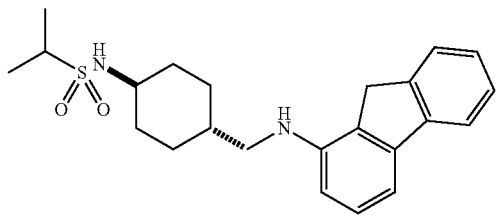
Ib-110
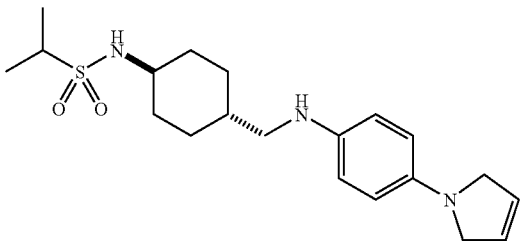
Ib-111
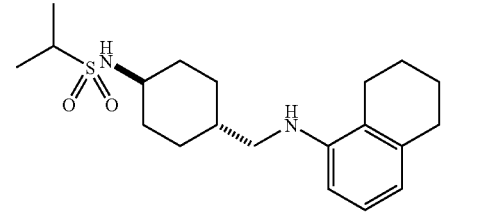
Ib-112
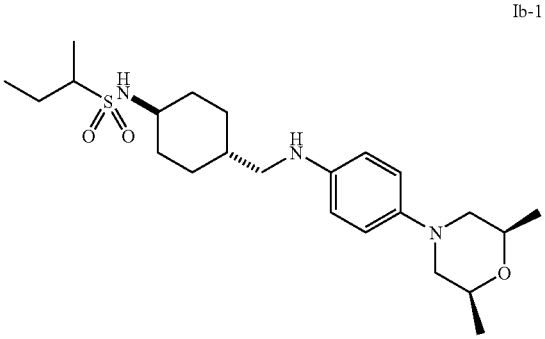
Ib-113
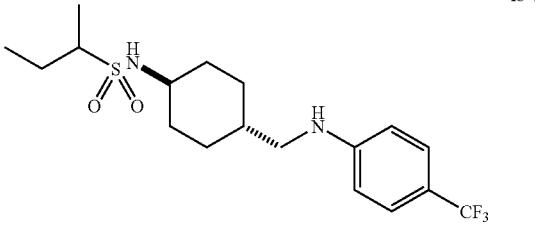
Ib-114
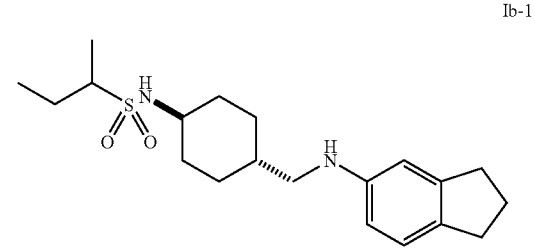

Ib-115
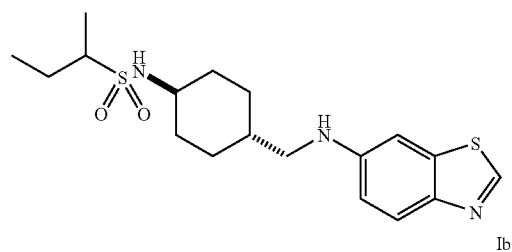
Ib-116
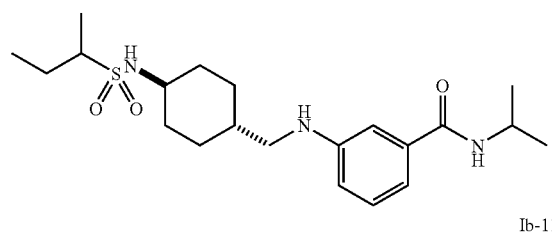
Ib-117
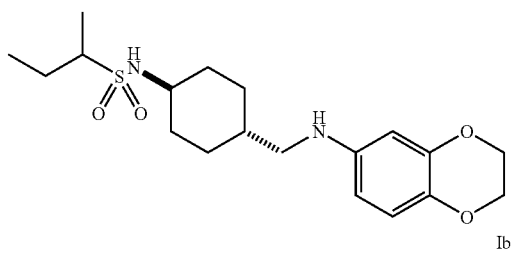
Ib-118
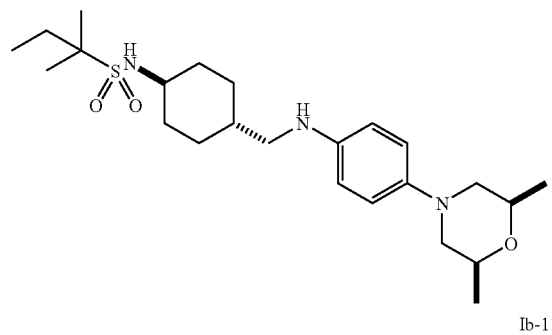
Ib-119
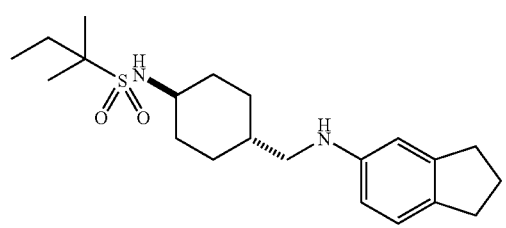
Ib-120
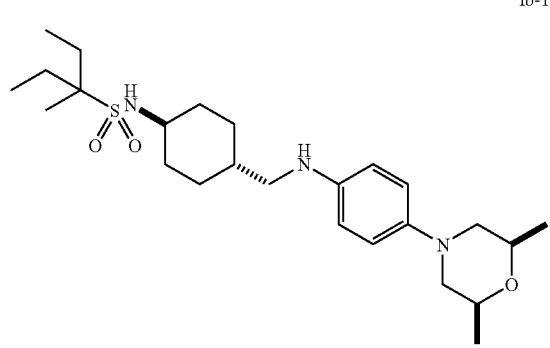
Ib-121
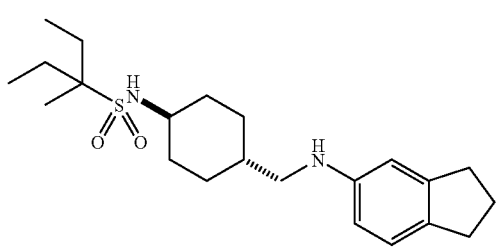
Ib-122
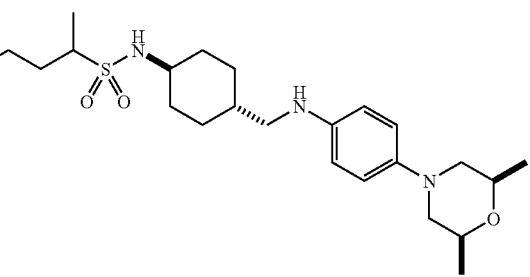
Ib-123
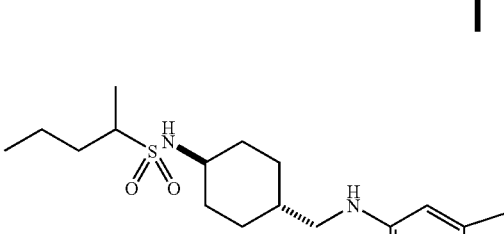
Ib-124
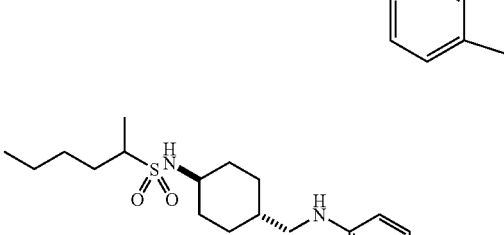
Ib-125
Ib-126

-continued

Ib-139, Ib-140, Ib-141, Ib-142, Ib-143, Ib-144, Ib-145, Ib-146, Ib-147, Ib-148, Ib-149, Ib-150, Ib-151

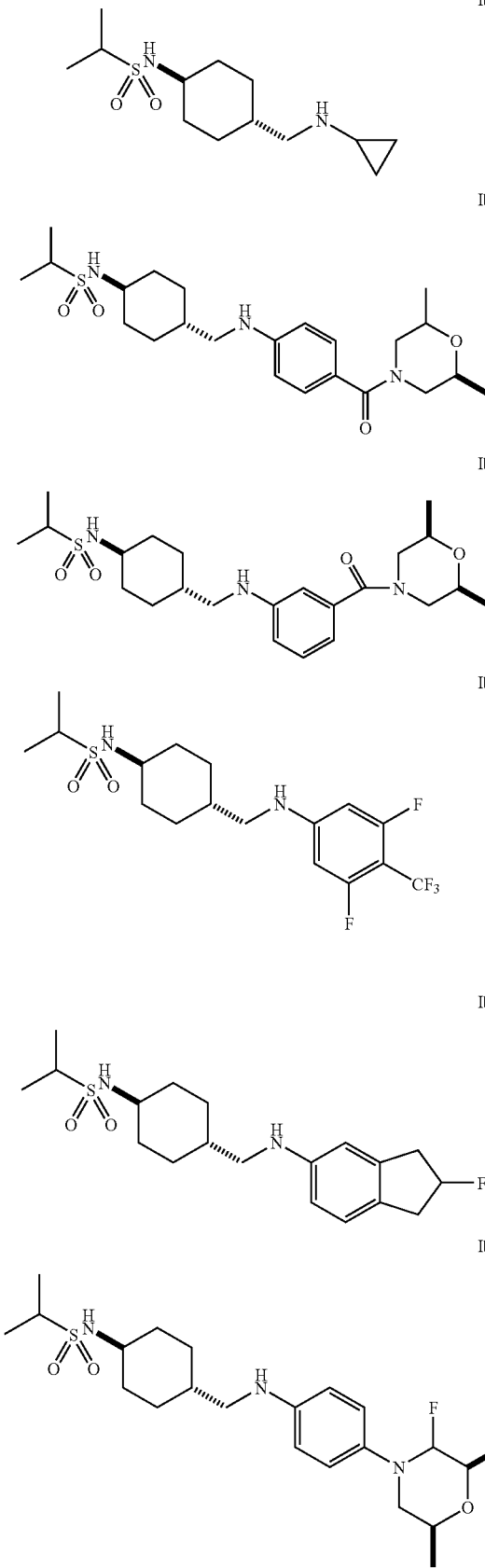
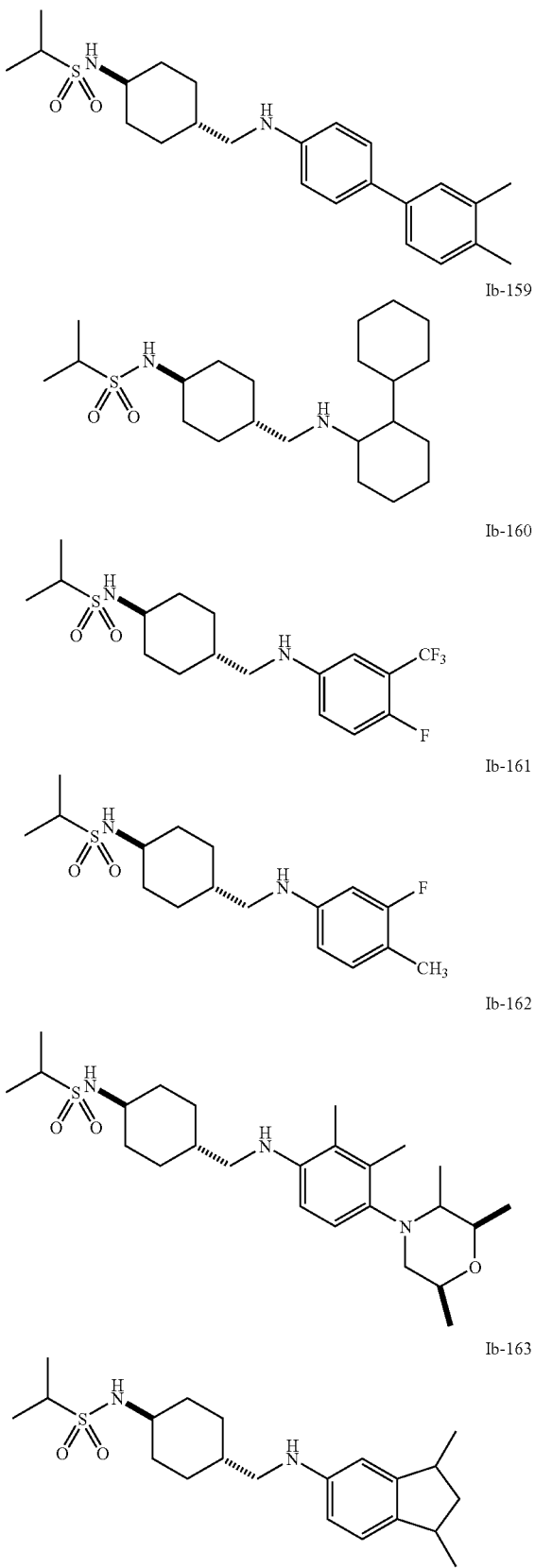

Ib-164
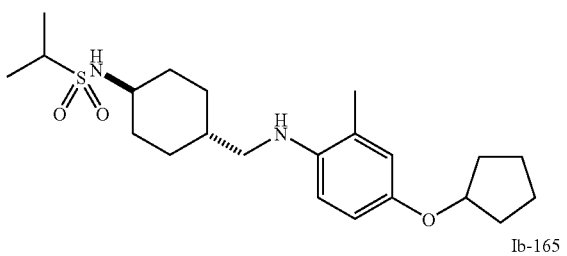
Ib-165
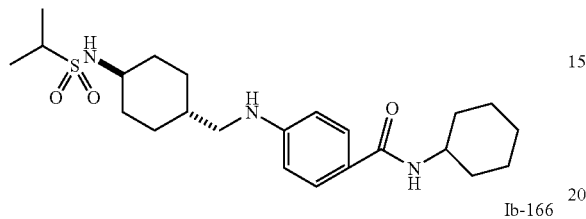
Ib-166
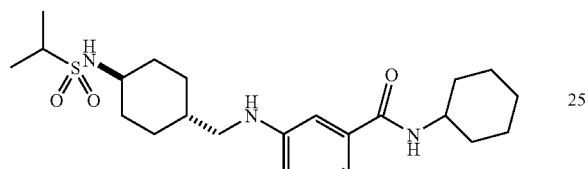
Ib-167
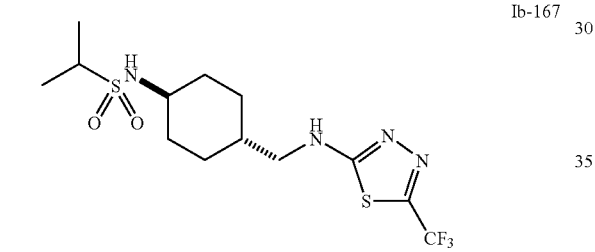
Ib-168
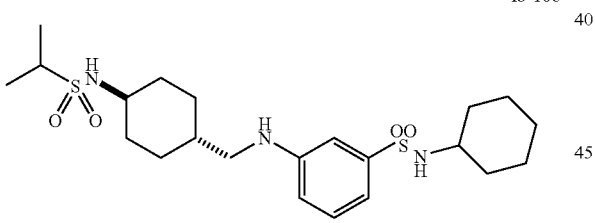
Ib-169
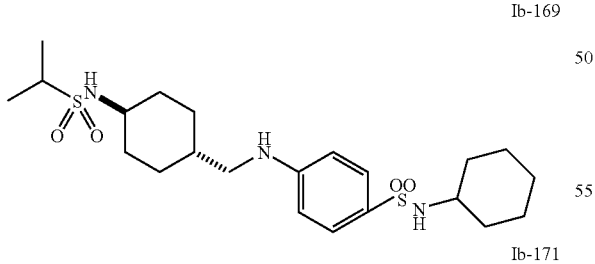
Ib-171
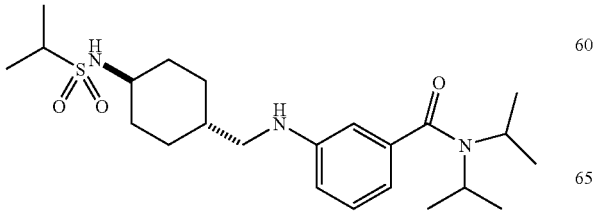
Ib-172
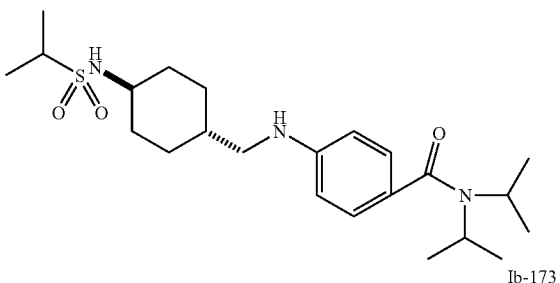
Ib-173
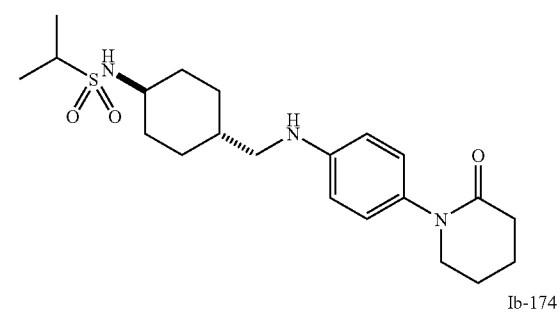
Ib-174
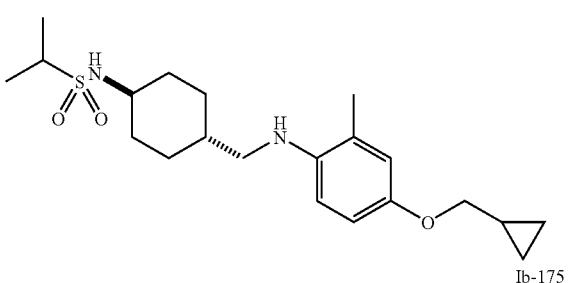
Ib-175
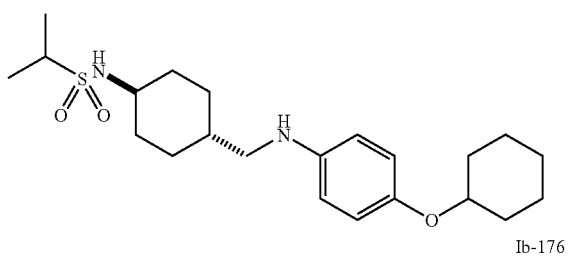
Ib-176
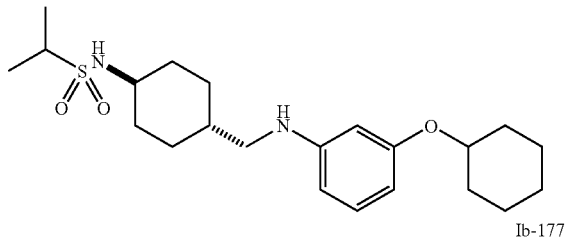
Ib-177
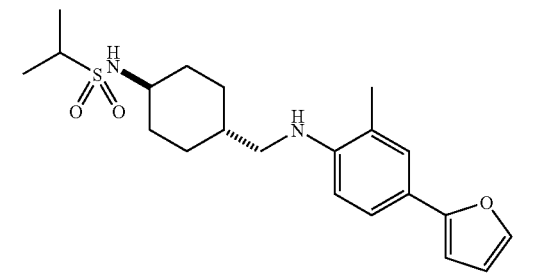

Ib-178
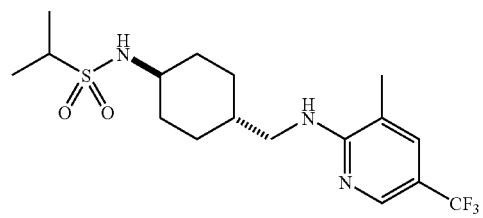
Ib-179
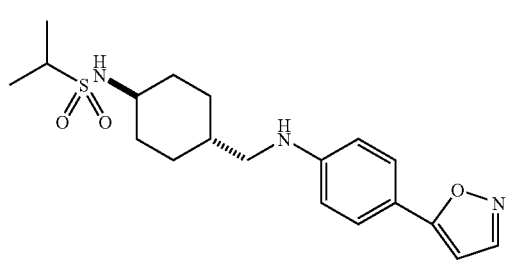
Ib-180
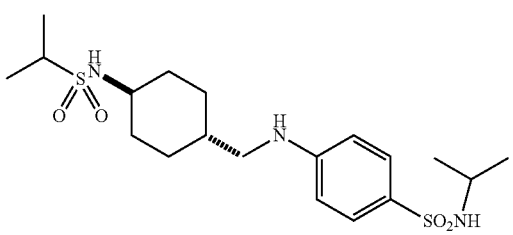
Ib-181
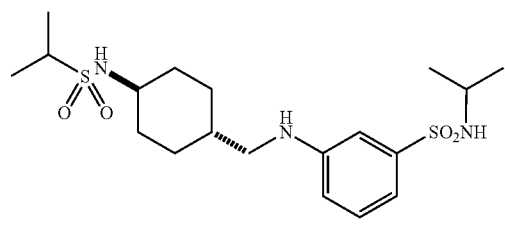
Ib-182
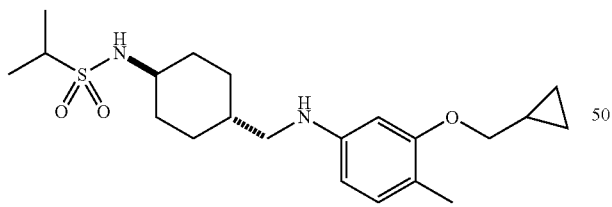
Ib-183
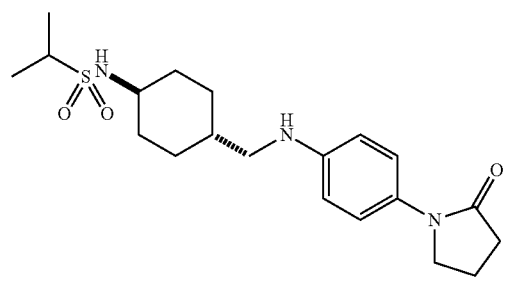
Ib-184
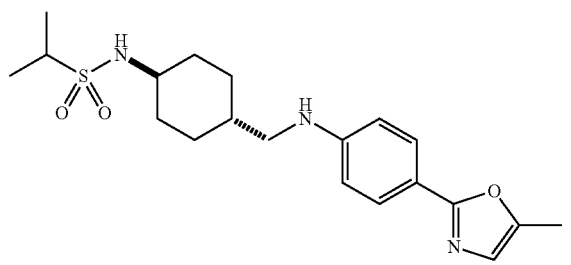
Ib-185
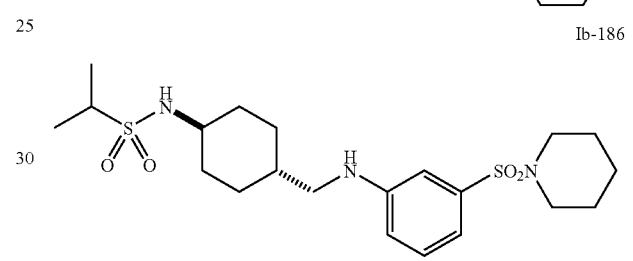
Ib-186
Ib-187
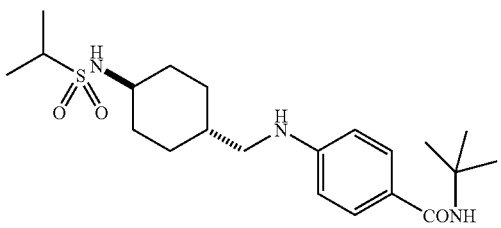
Ib-188
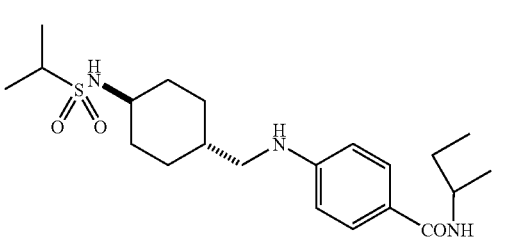
Ib-189
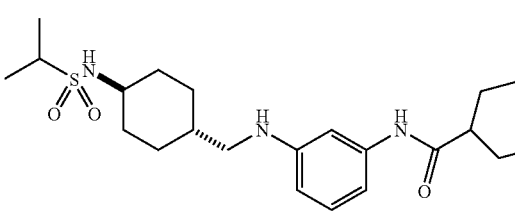

Ib-190
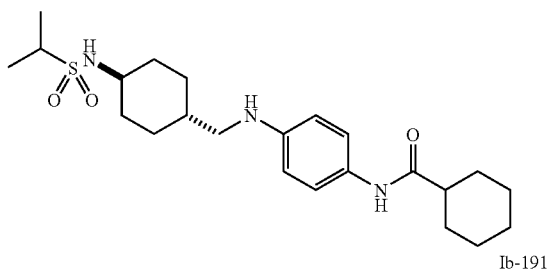
Ib-191
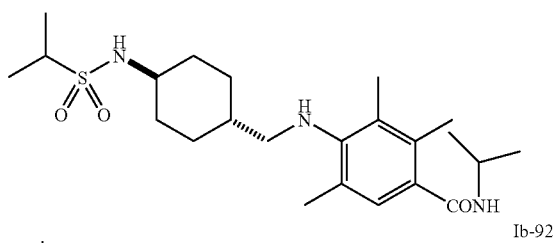
Ib-92
Ib-193
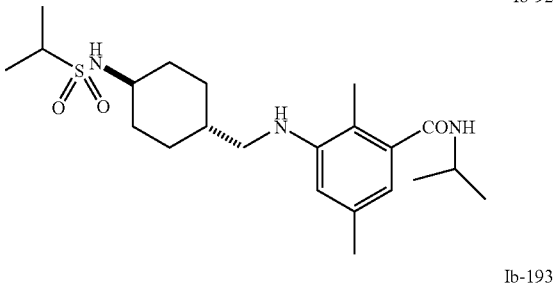
Ib-194
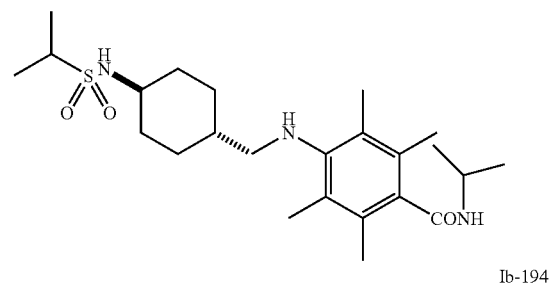
Ib-195

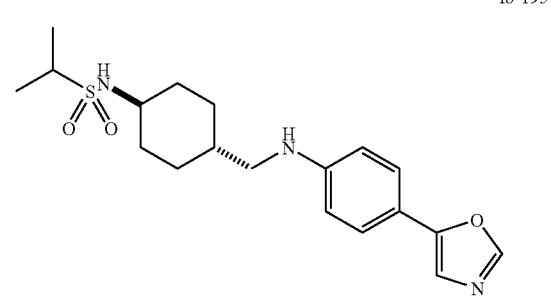
Ib-196
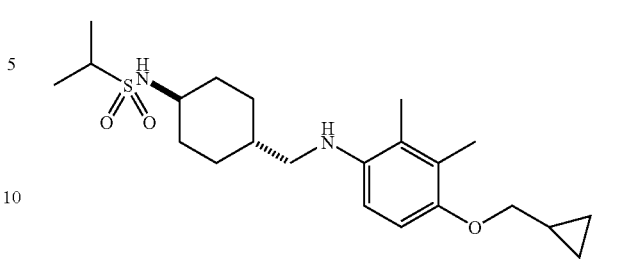
Ib-197
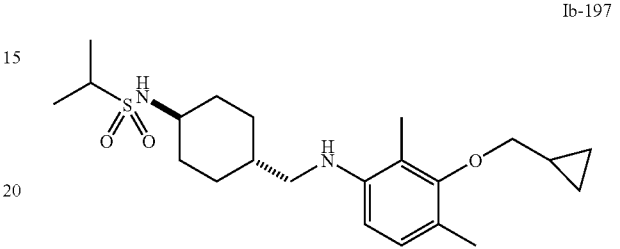
Ib-198
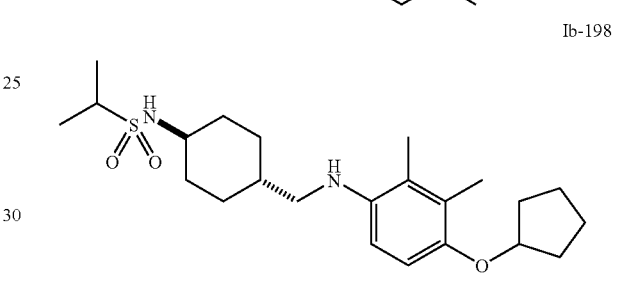
Ib-199

Ib-200
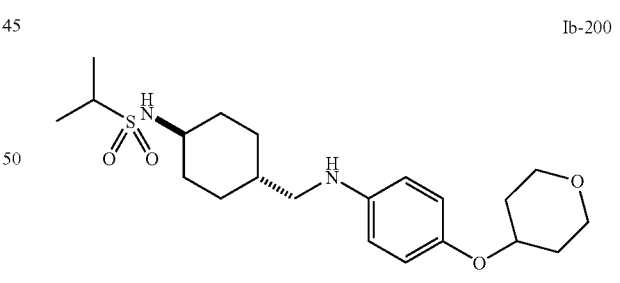
Ib-201
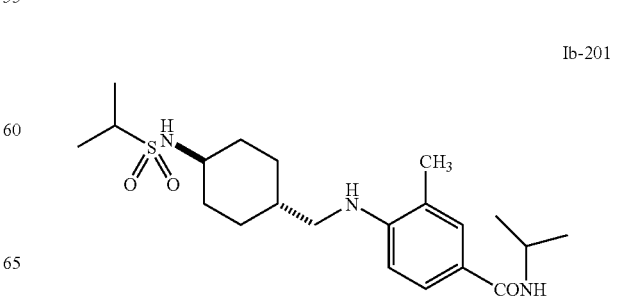

Ib-202
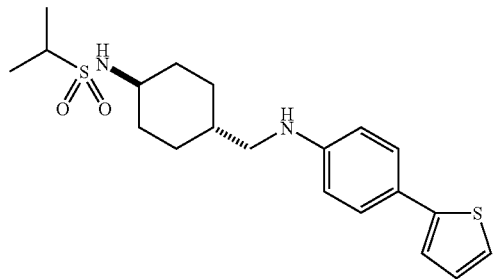
Ib-203
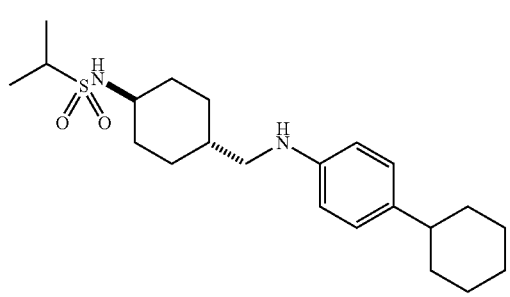
Ib-204
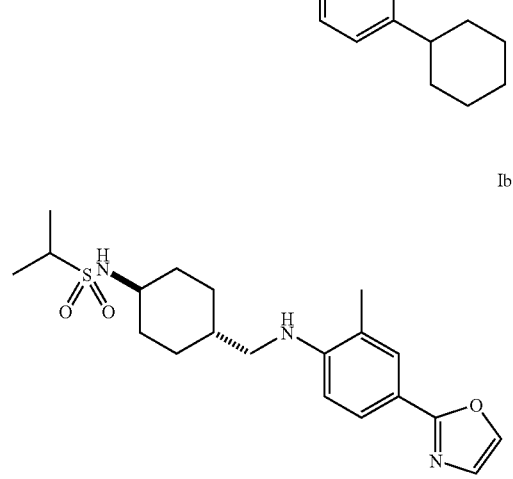
Ib-205
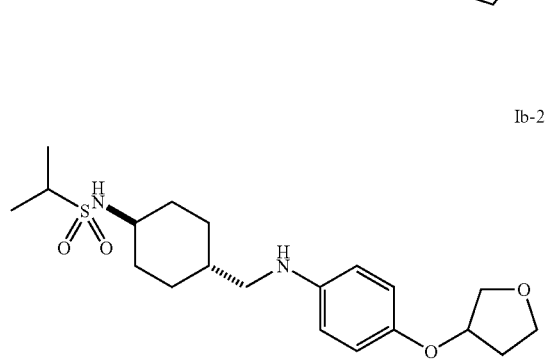
Ib-206
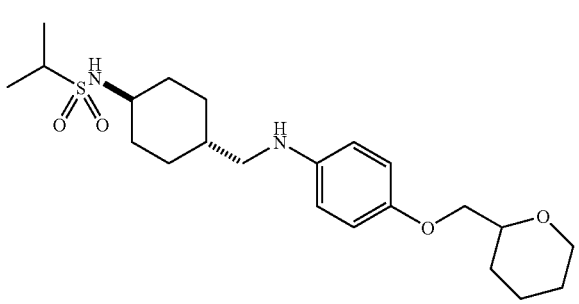
Ib-207
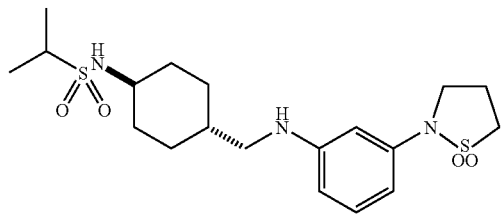
Ib-208
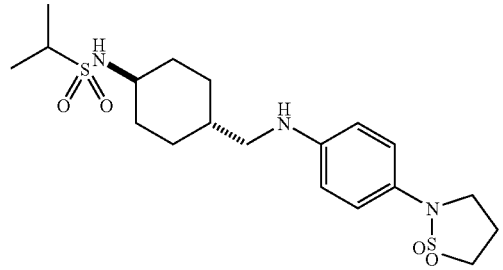
Ib-209
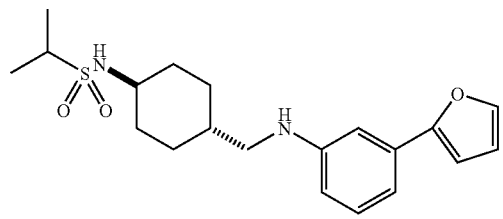
Ib-210
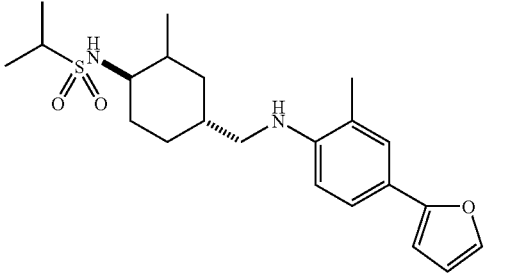
Ib-211
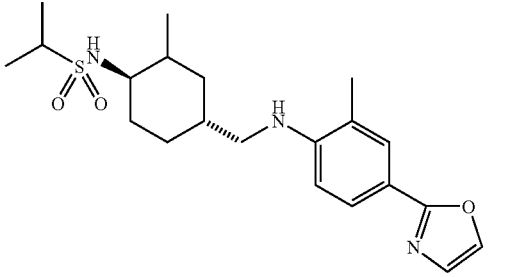
Ib-212

Ib-213 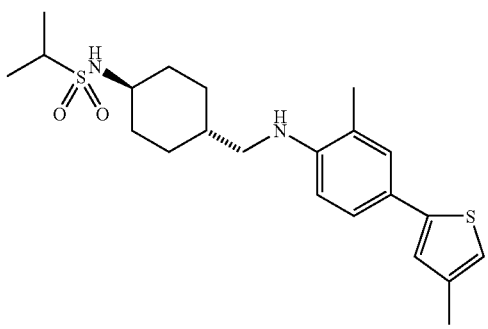
Ib-214 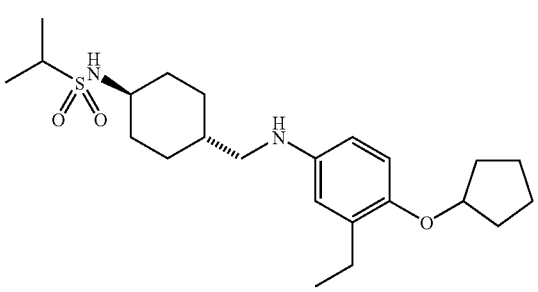
Ib-215 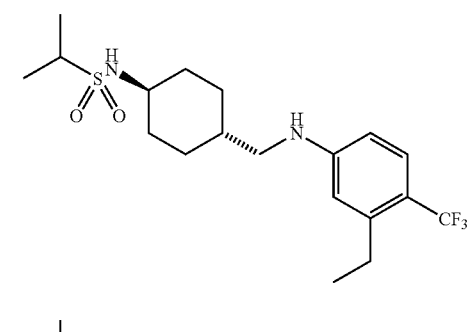
Ib-216 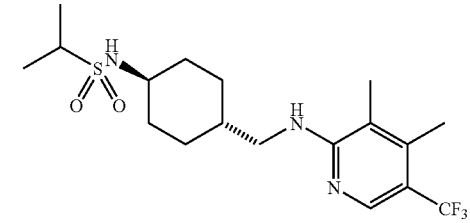
Ib-219 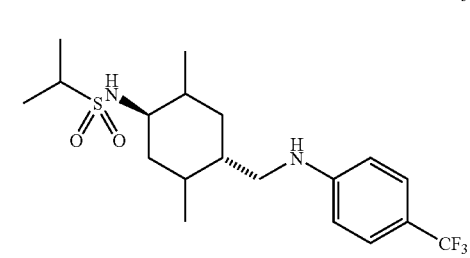
Ib-220 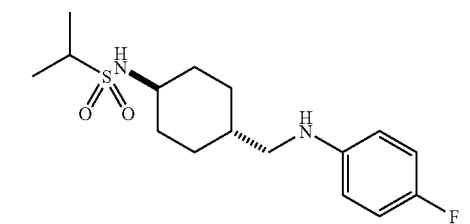
Ib-221 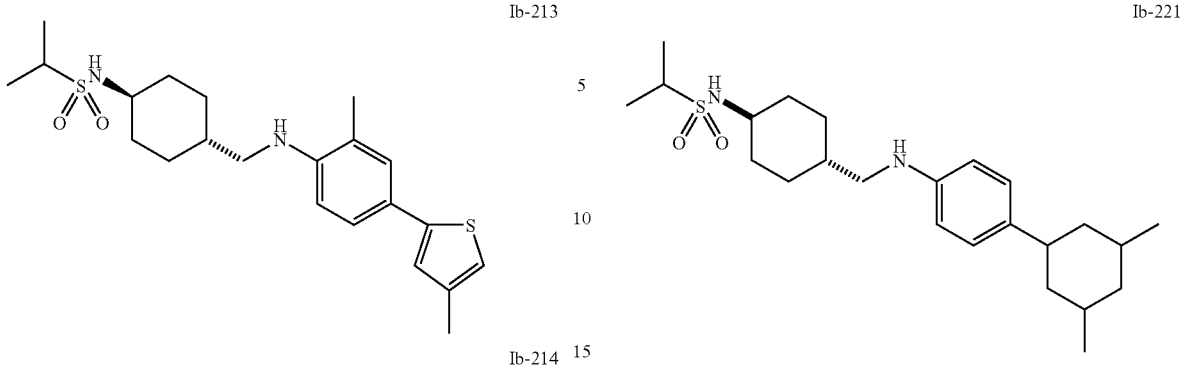
Ib-222 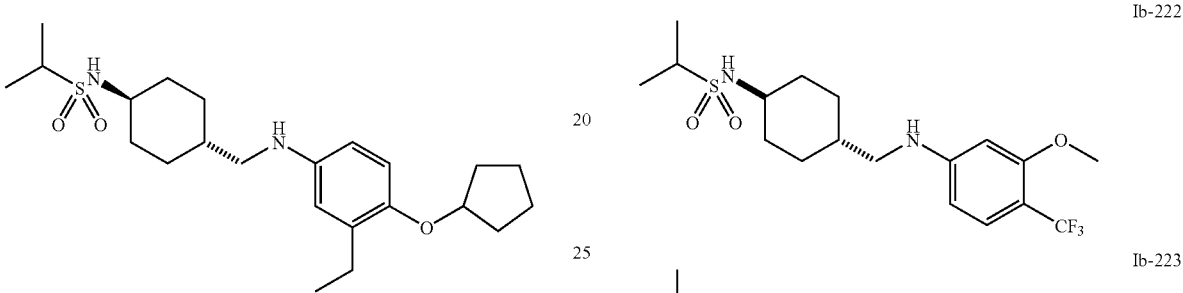
Ib-223 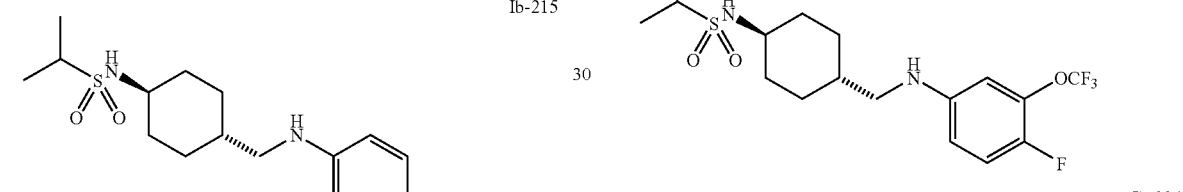
Ib-224 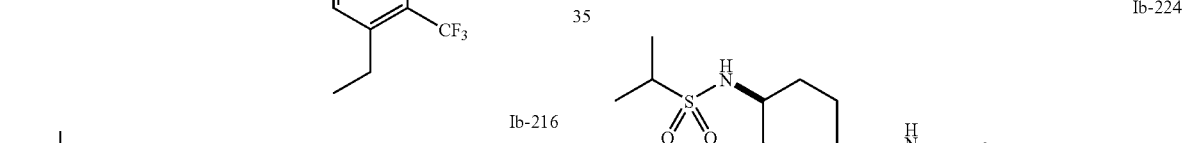
Ib-225 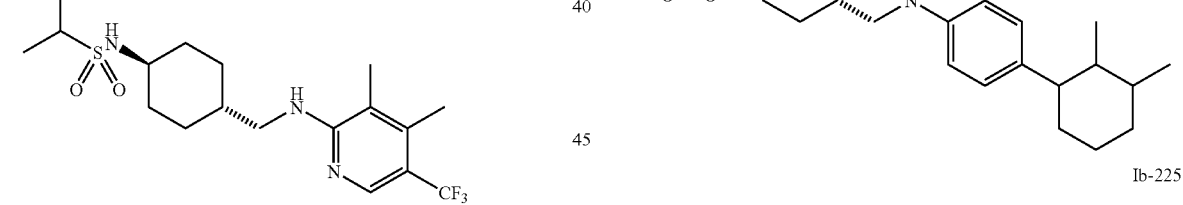
Ib-226 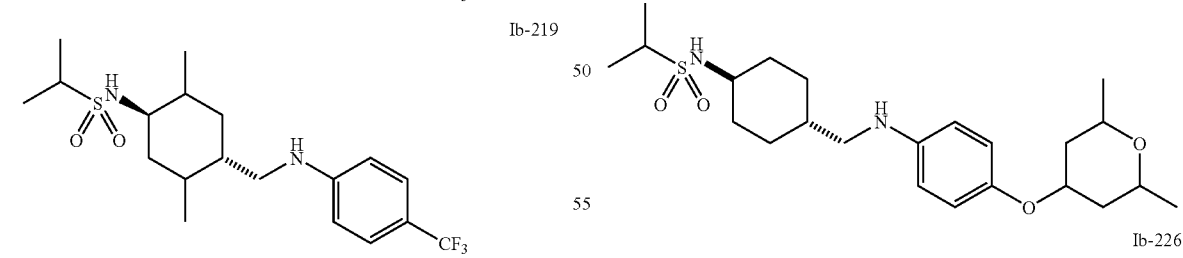
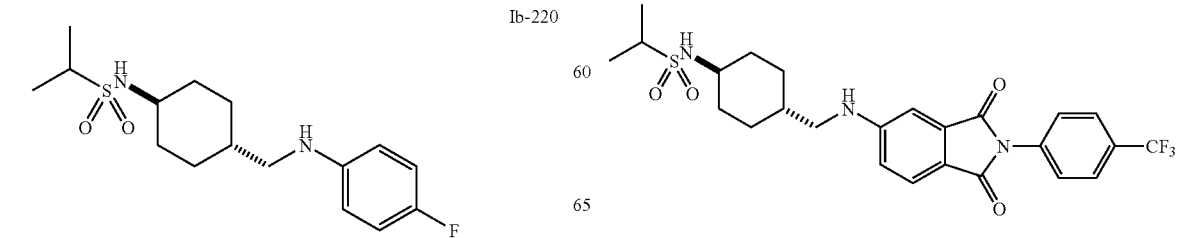

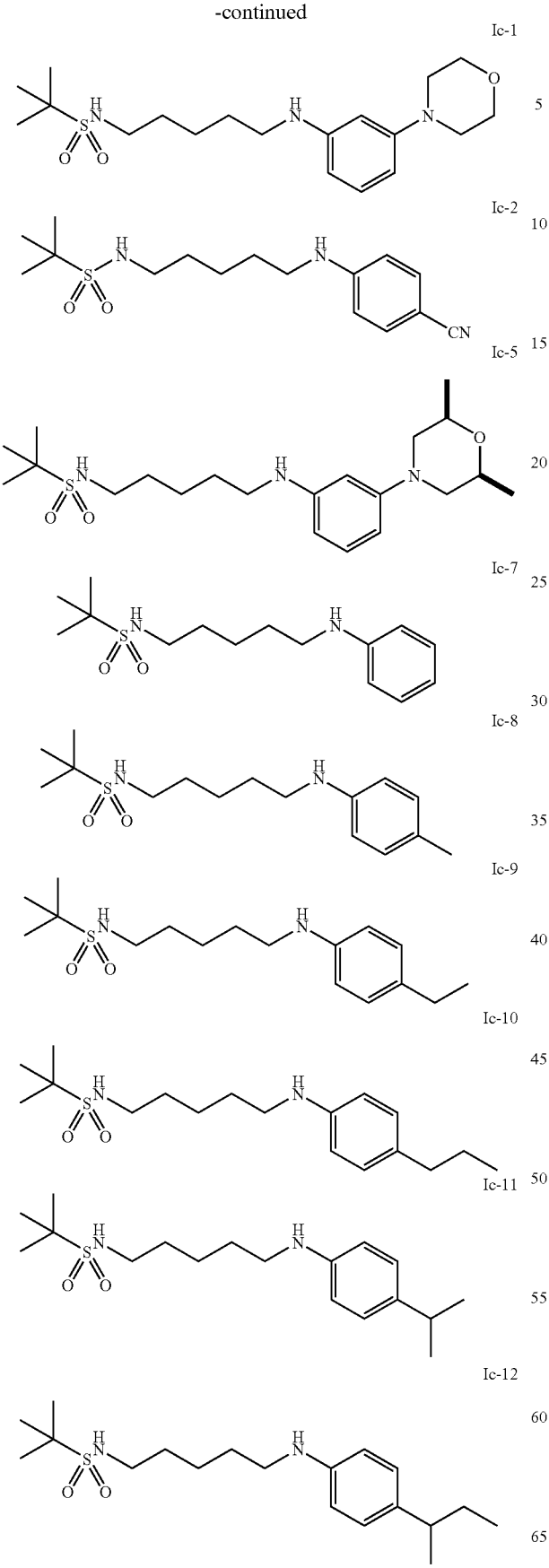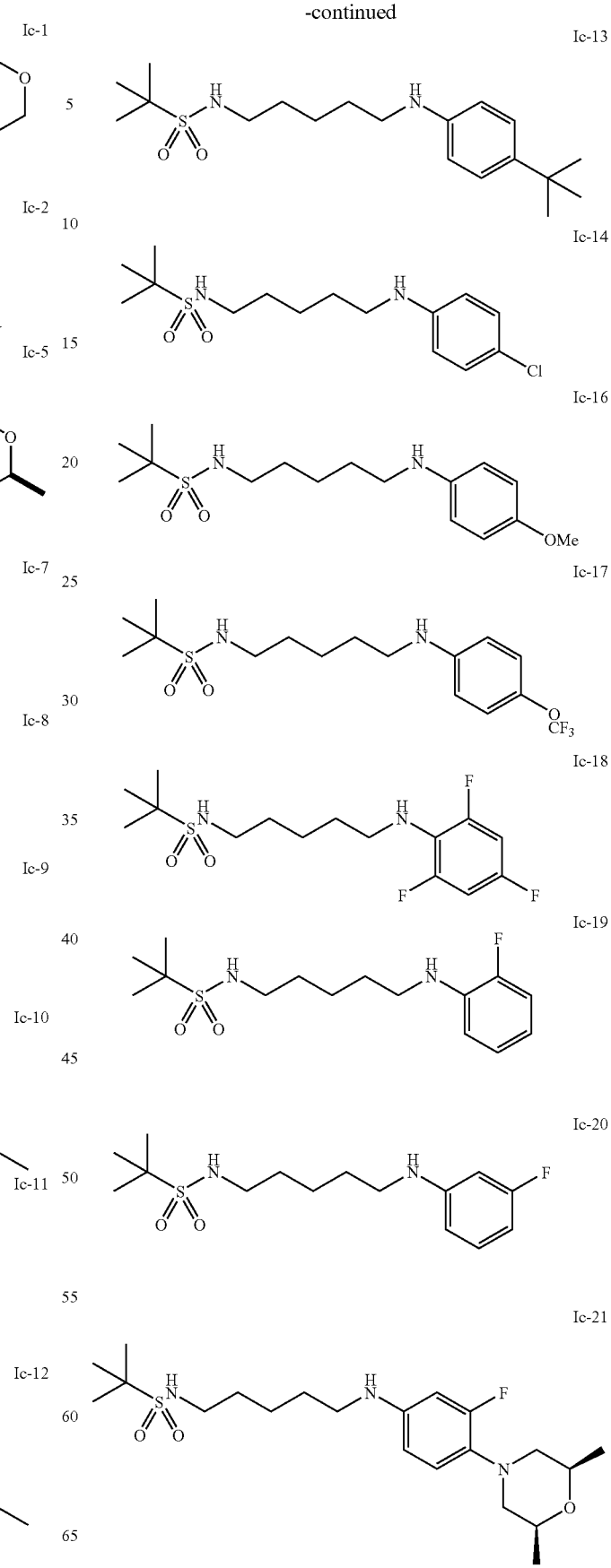

-continued
Ic-22
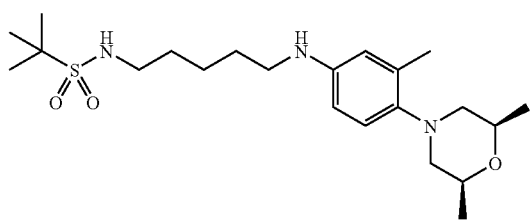
Ic-23
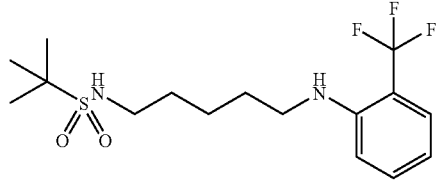
Ic-24
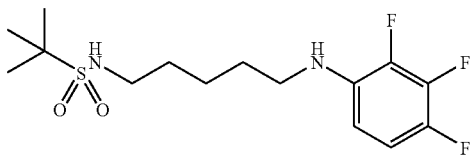
Ic-25
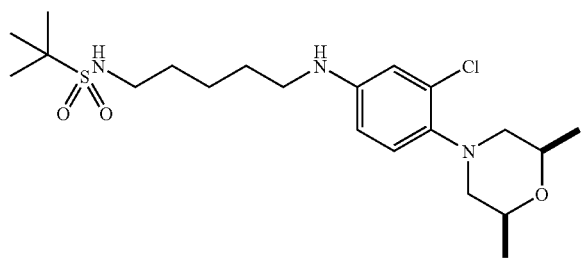
Ic-26
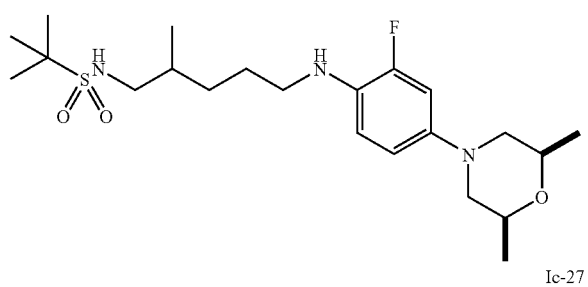
Ic-27
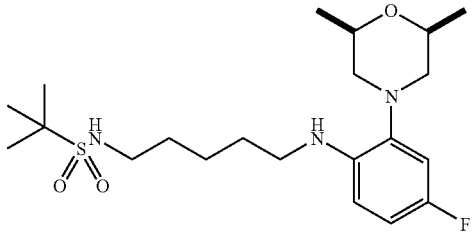
Ic-28
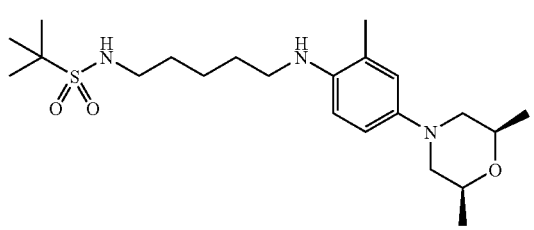
-continued
Ic-29
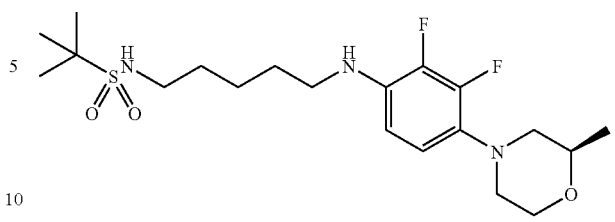
Ic-30
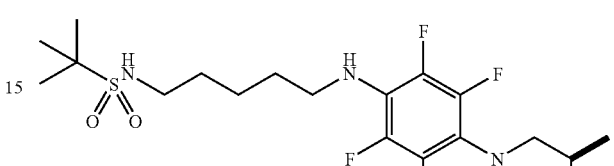
Ic-31
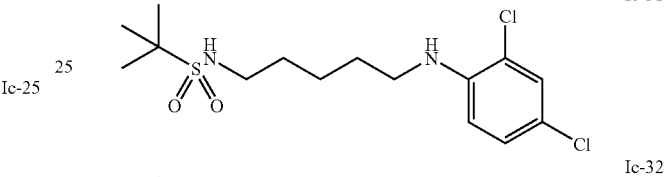
Ic-32
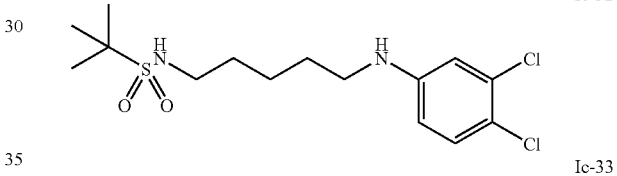
Ic-33
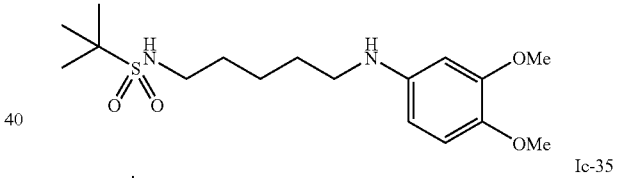
Ic-35
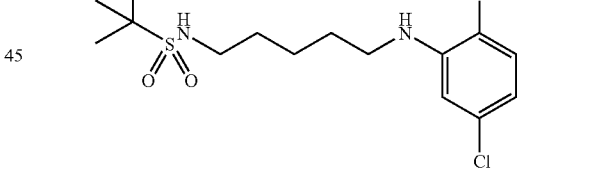
Ic-36
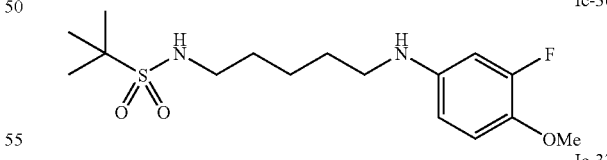
Ic-37
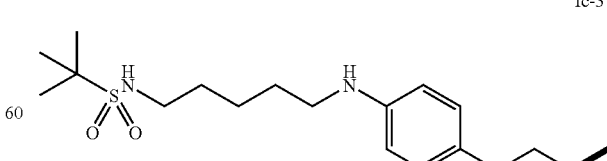

Ic-38
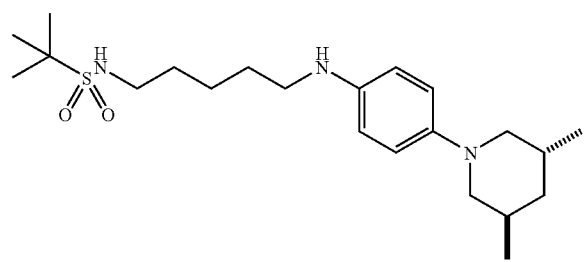
Ic-39
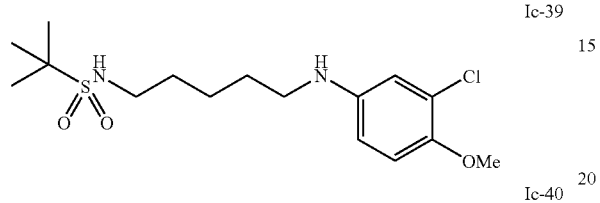
Ic-40
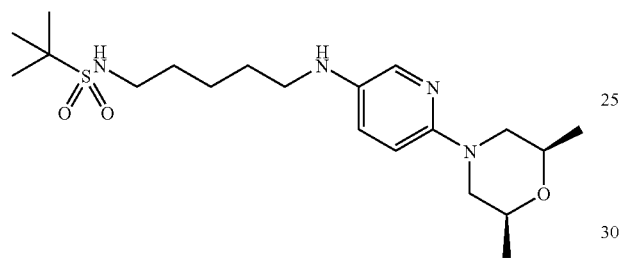
Ic-41
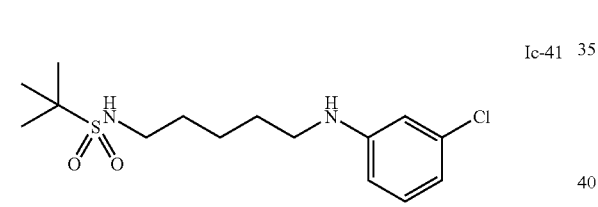
Ic-42
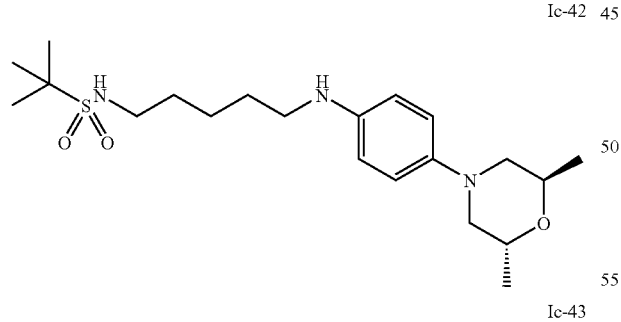
Ic-43
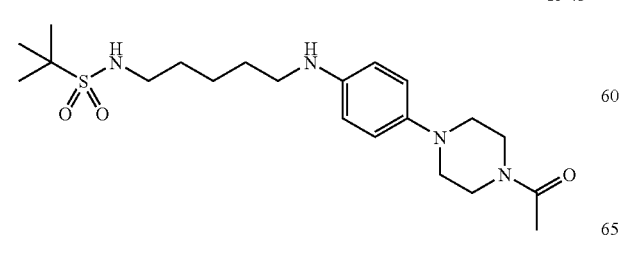
Ic-44
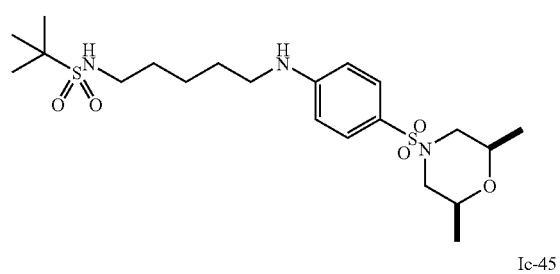
Ic-45
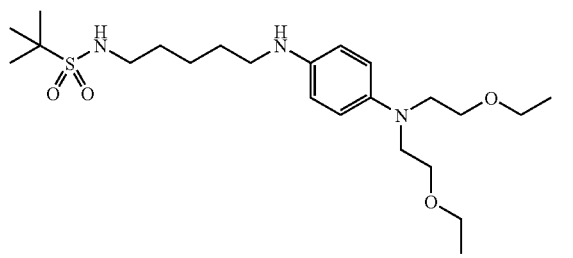
Ic-46
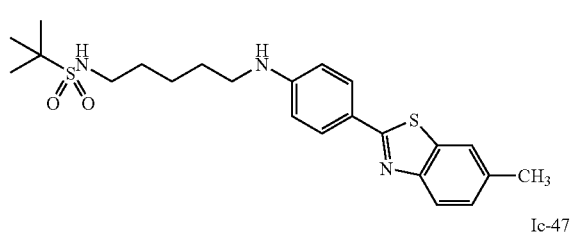
Ic-47
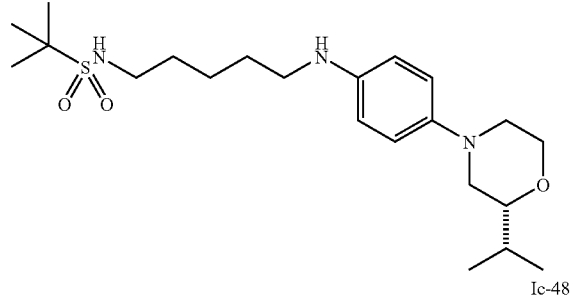
Ic-48
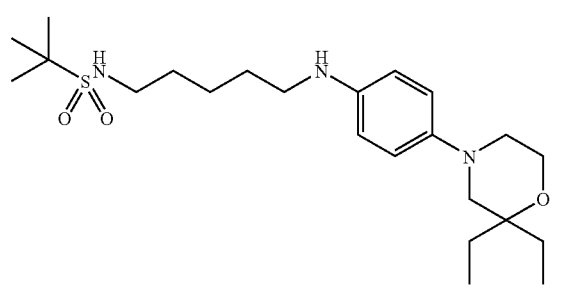
Ic-49
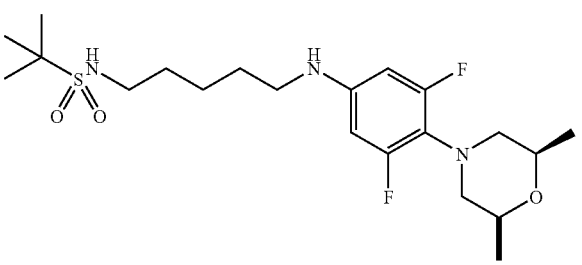

Ic-50
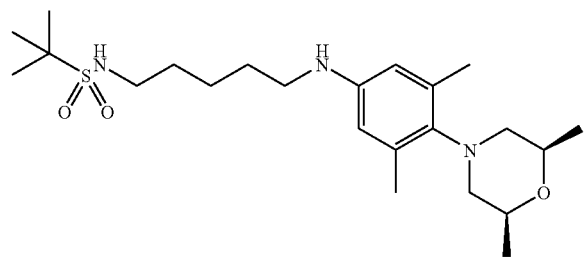
Ic-51
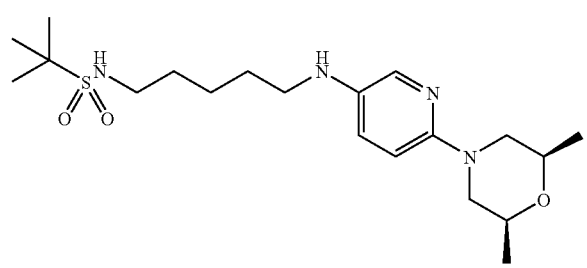
Ic-52
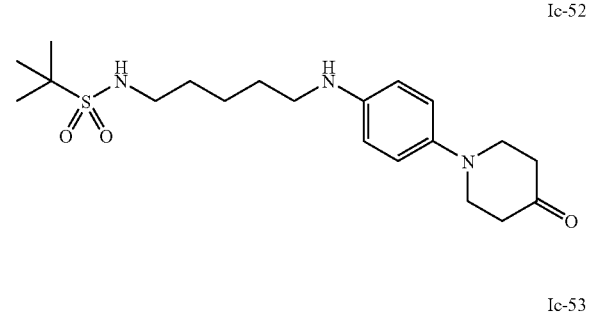
Ic-53
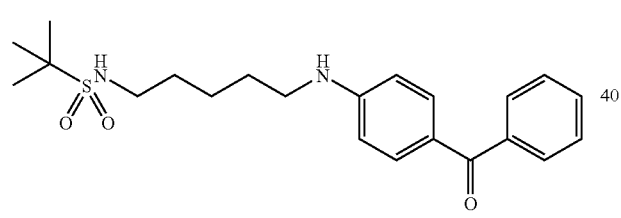
Ic-54
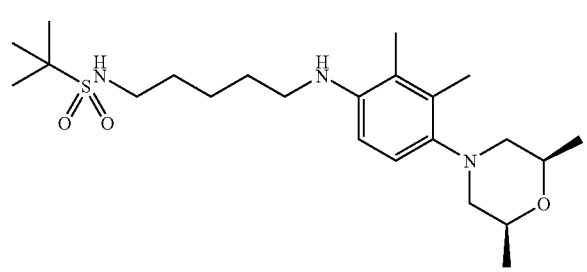
Ic-55
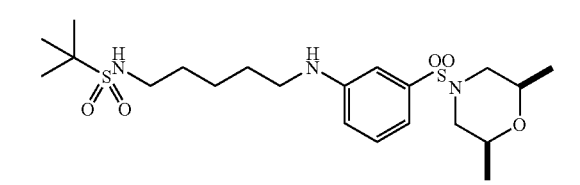
Ic-56
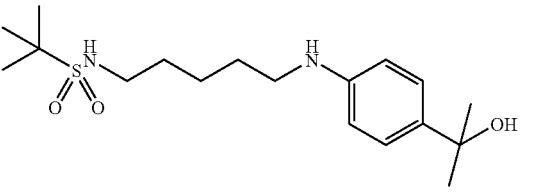
Ic-57
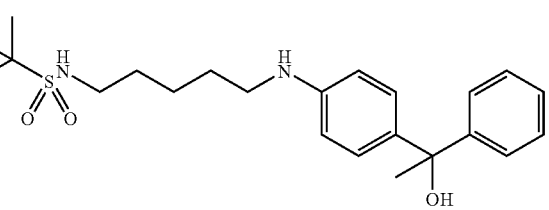
Ic-58
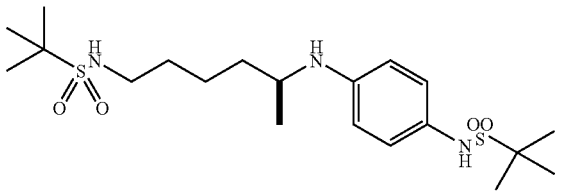
Ic-59
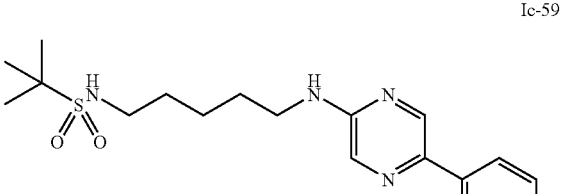
Ic-60
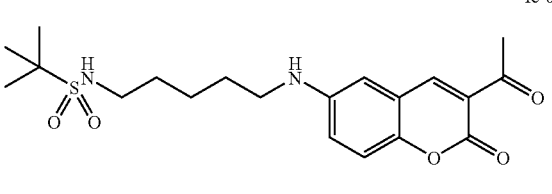
Ic-61
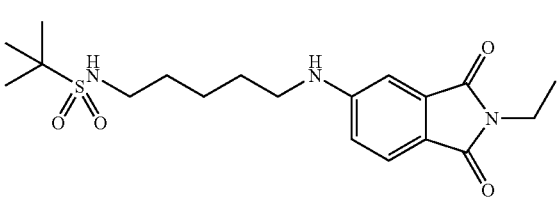
Ic-62
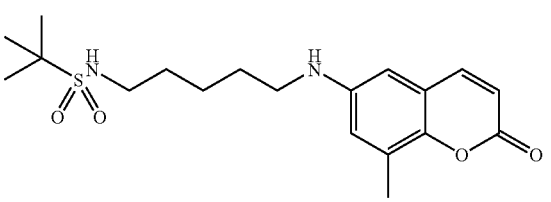

Ic-63
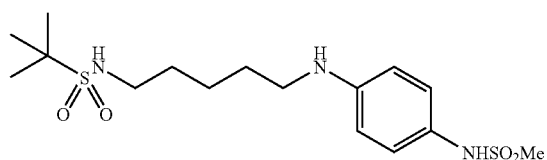
Ic-64
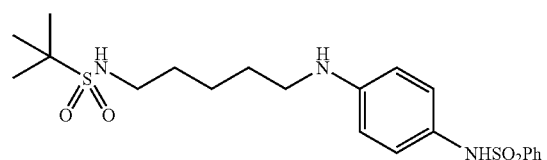
Ic-65
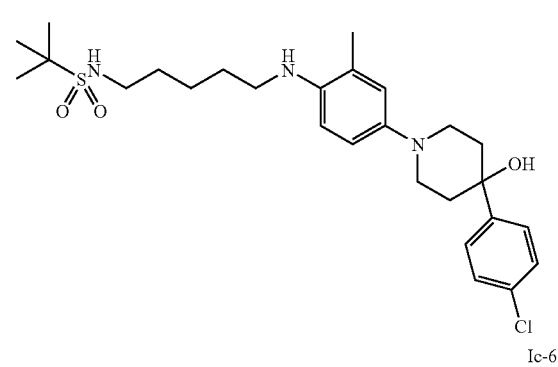
Ic-66
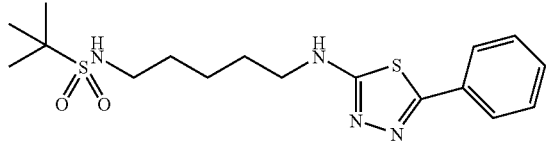
Ic-67
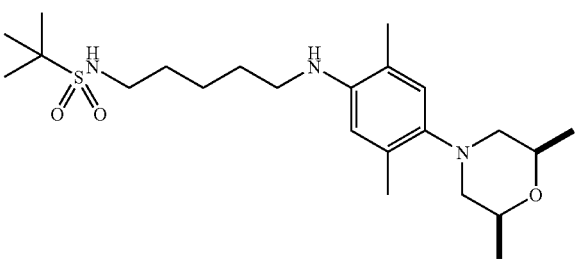
Ic-68
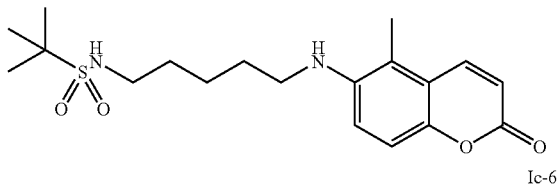
Ic-69
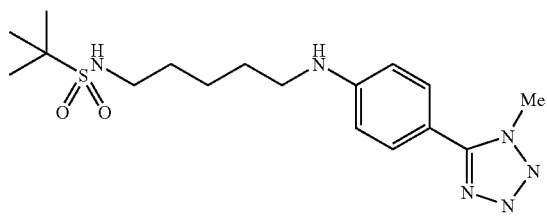
Ic-70
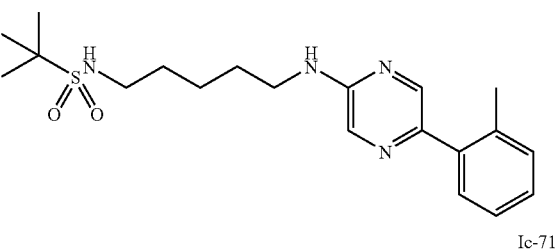
Ic-71
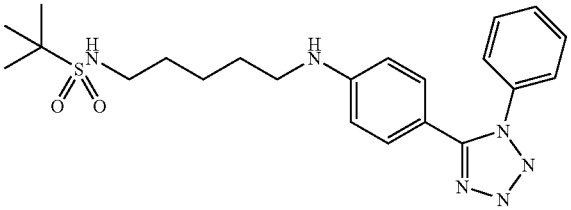
Ic-73
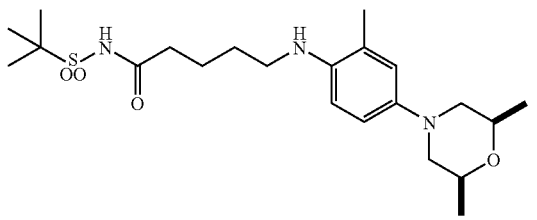
Ic-74
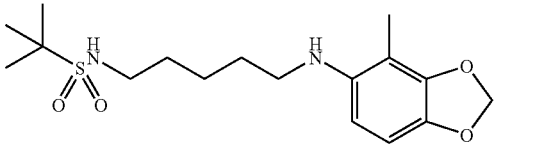
Ic-75
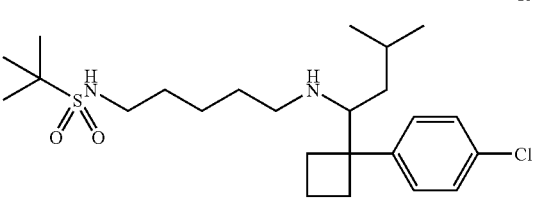
Ic-76
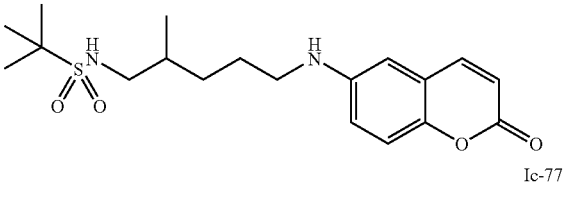
Ic-77
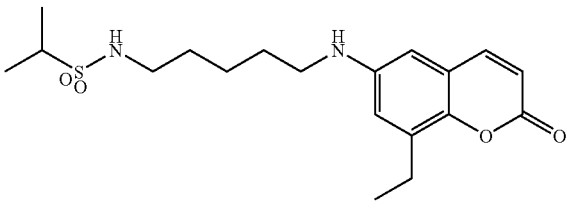

Ic-78
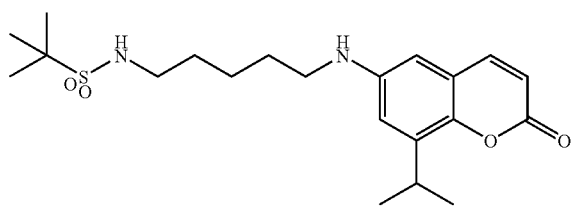
Ic-79
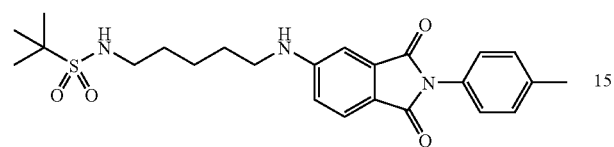
Ic-80
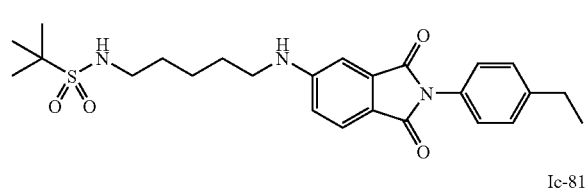
Ic-81
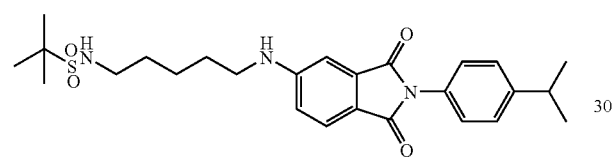
Ic-82
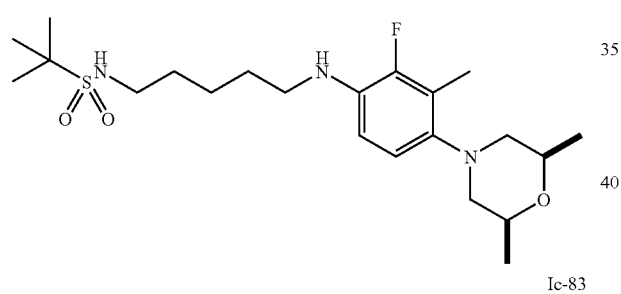
Ic-83
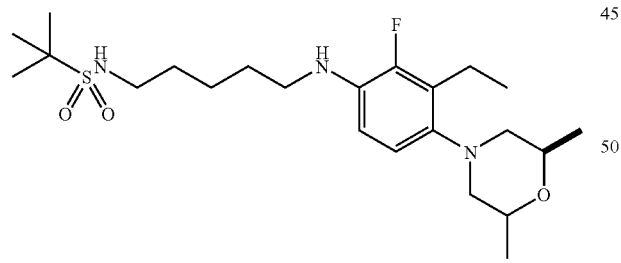
Ic-84
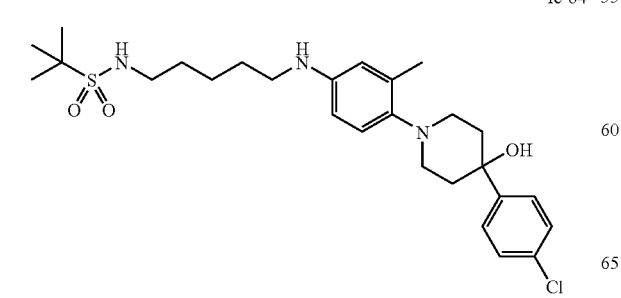
Ic-85
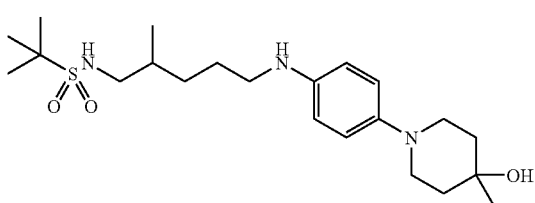
Ic-86
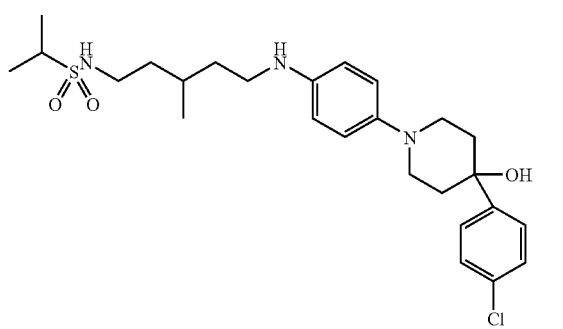
Ic-87
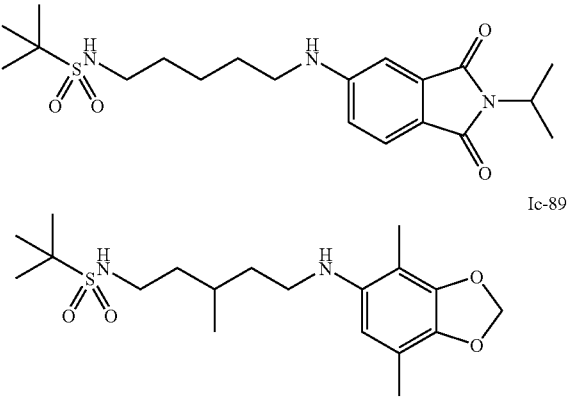
Ic-89
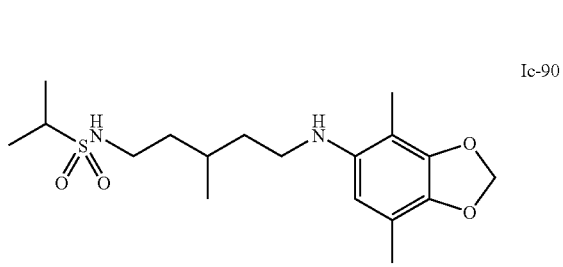
Ic-90
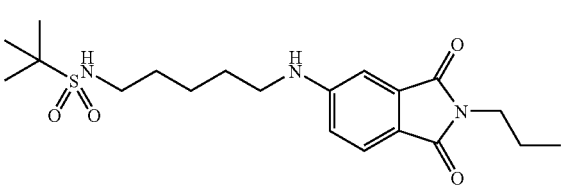
Ic-91

-continued
Ic-92
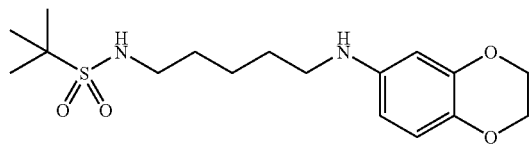
Ic-93
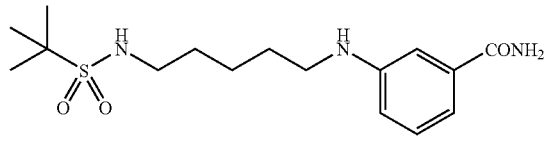
Ic-94
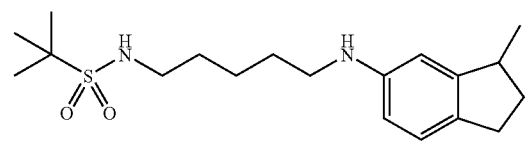
Ic-95
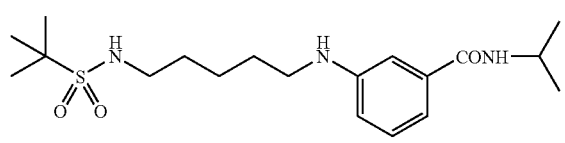
Ic-96
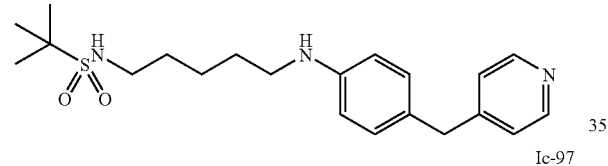
Ic-97
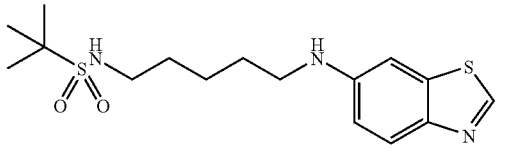
Ic-98
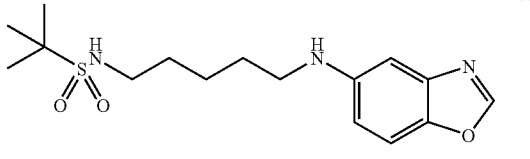
Ic-99
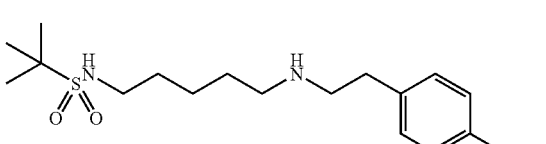
Ic-100
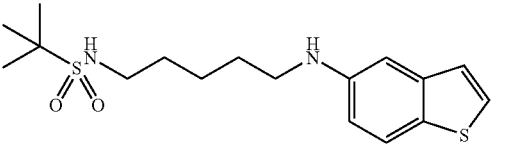
-continued
Ic-101
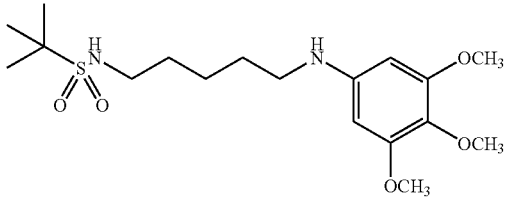
Ic-102
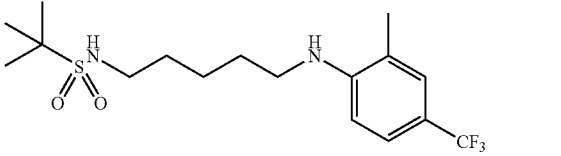
Ic-103
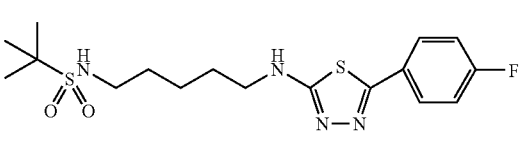
Ic-104
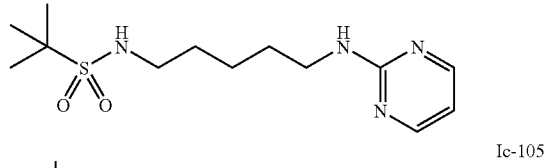
Ic-105
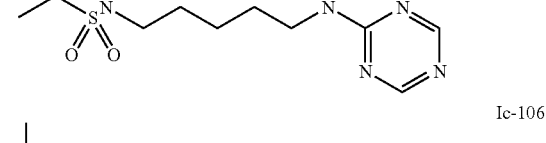
Ic-106
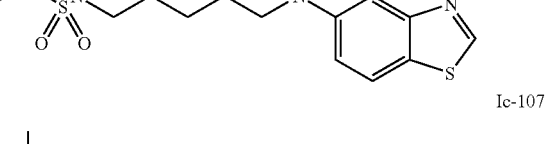
Ic-107
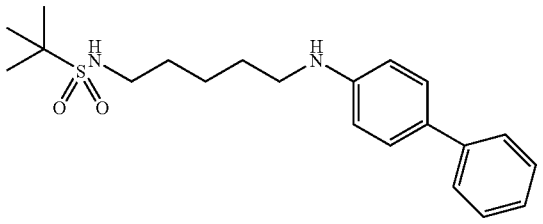
Ic-108
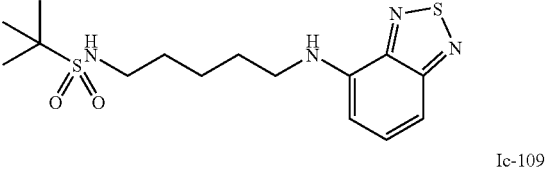
Ic-109

Ic-110
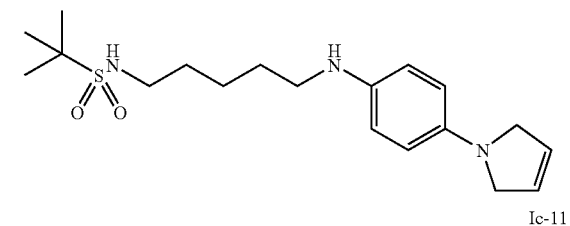
Ic-111
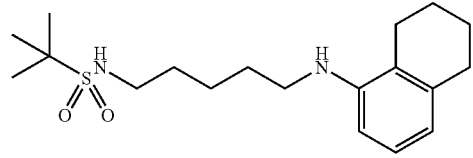
Ic-112
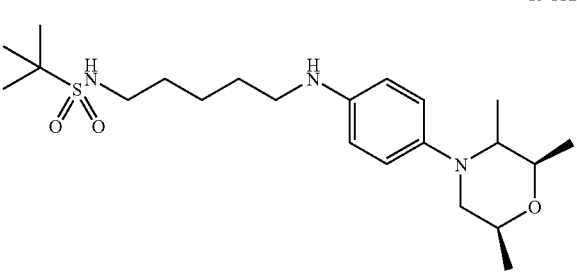
Ic-113
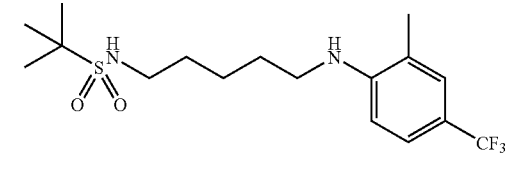
Ic-114
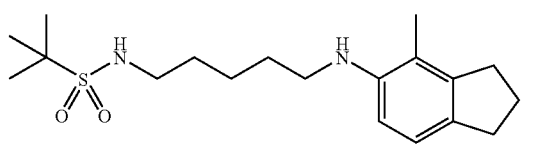
Ic-115
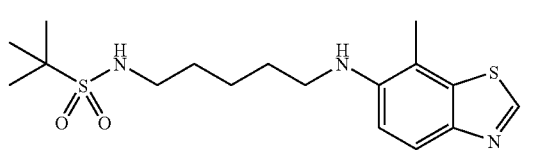
Ic-116
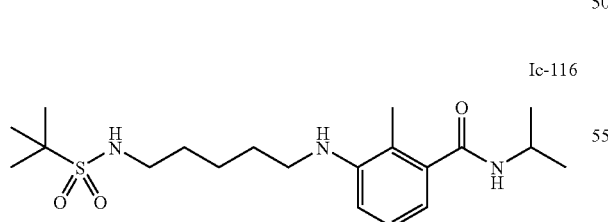
Ic-117
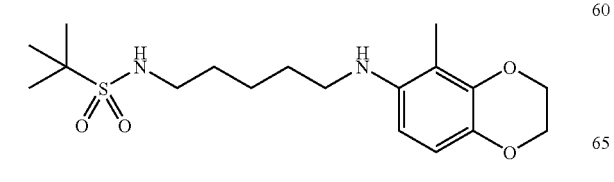
Ic-118
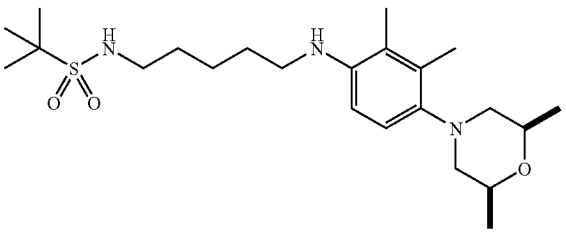
Ic-119
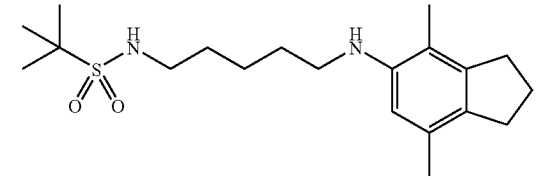
Ic-120
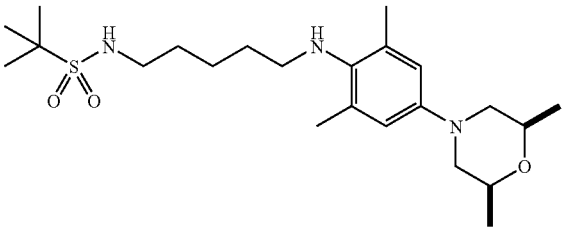
Ic-121
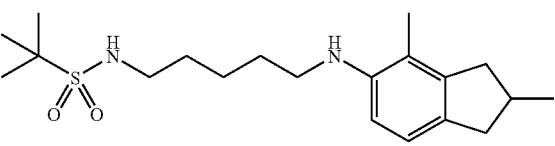
Ic-122
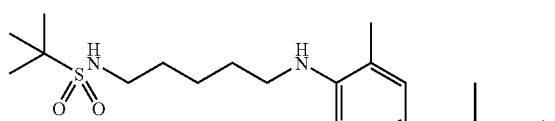
Ic-123
Ic-124
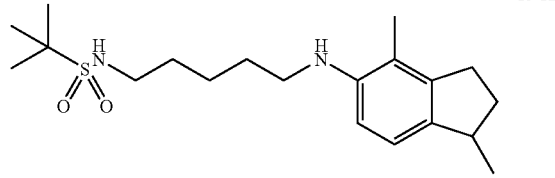

Ic-125
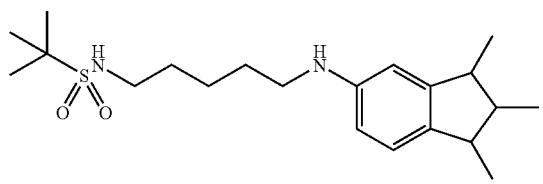
Ic-126
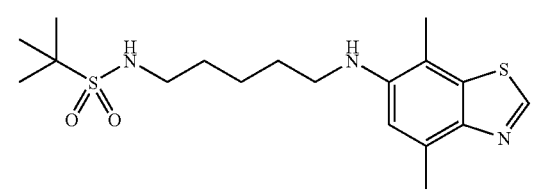
Ic-127
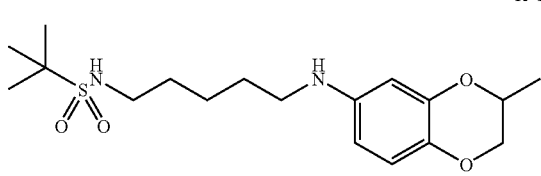
Ic-128
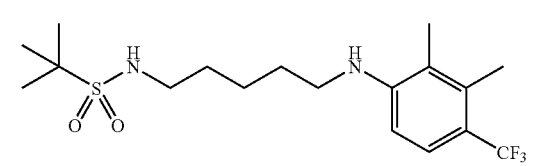
Ic-129
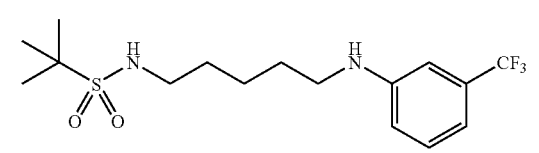
Ic-130
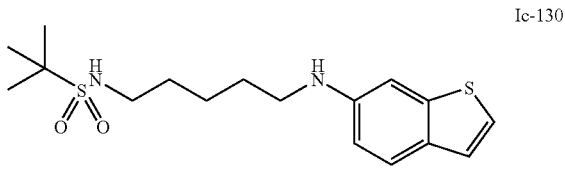
Ic-131
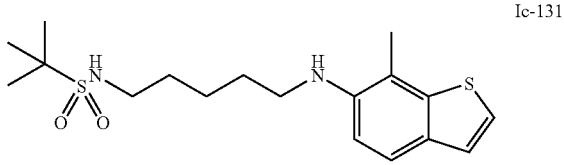
Ic-132
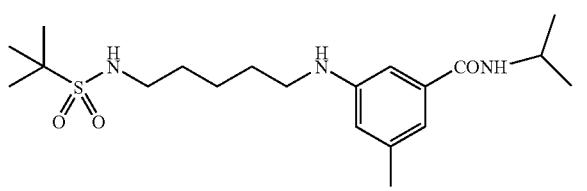
Ic-133
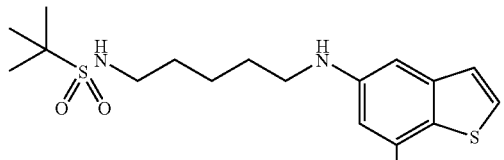
Ic-134
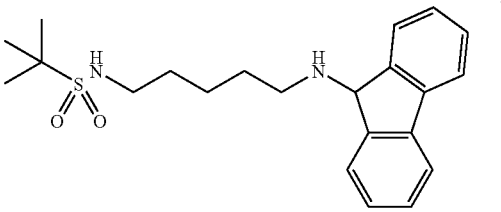
Ic-135
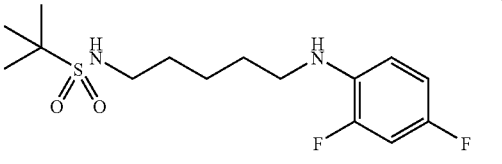
Ic-136
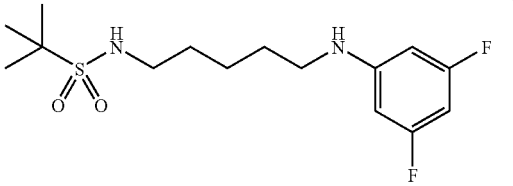
Ic-137
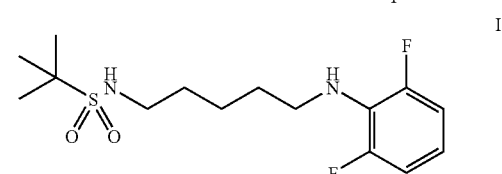
Ic-138
Ic-139
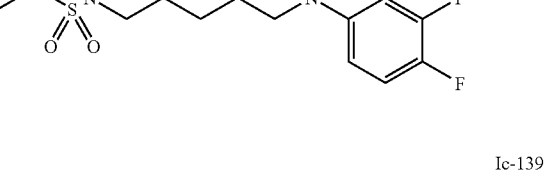
Ic-140
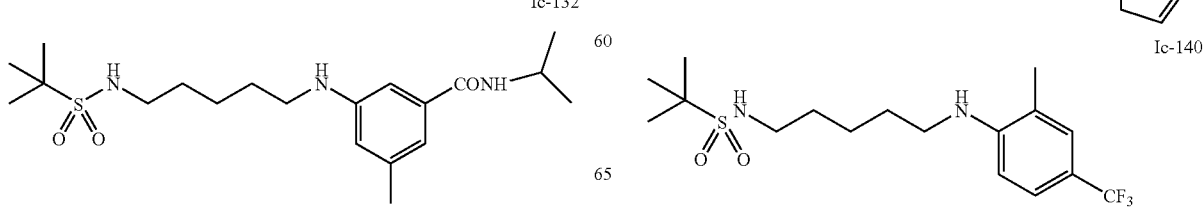

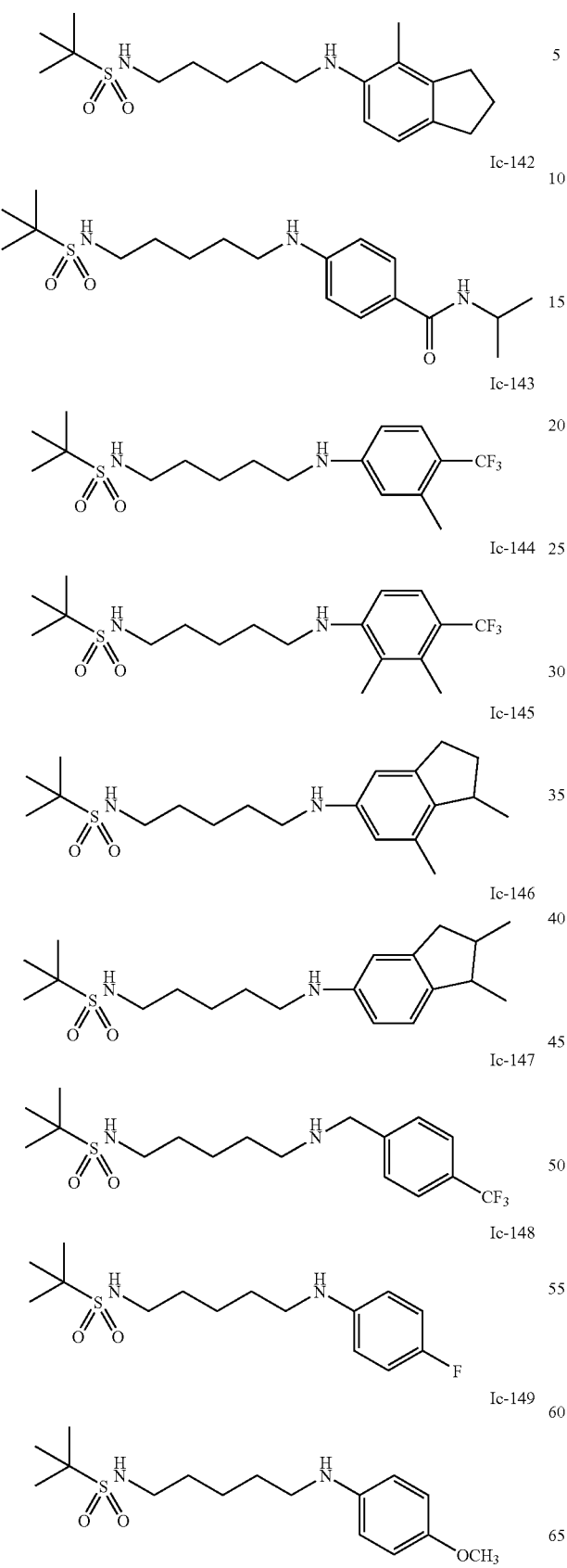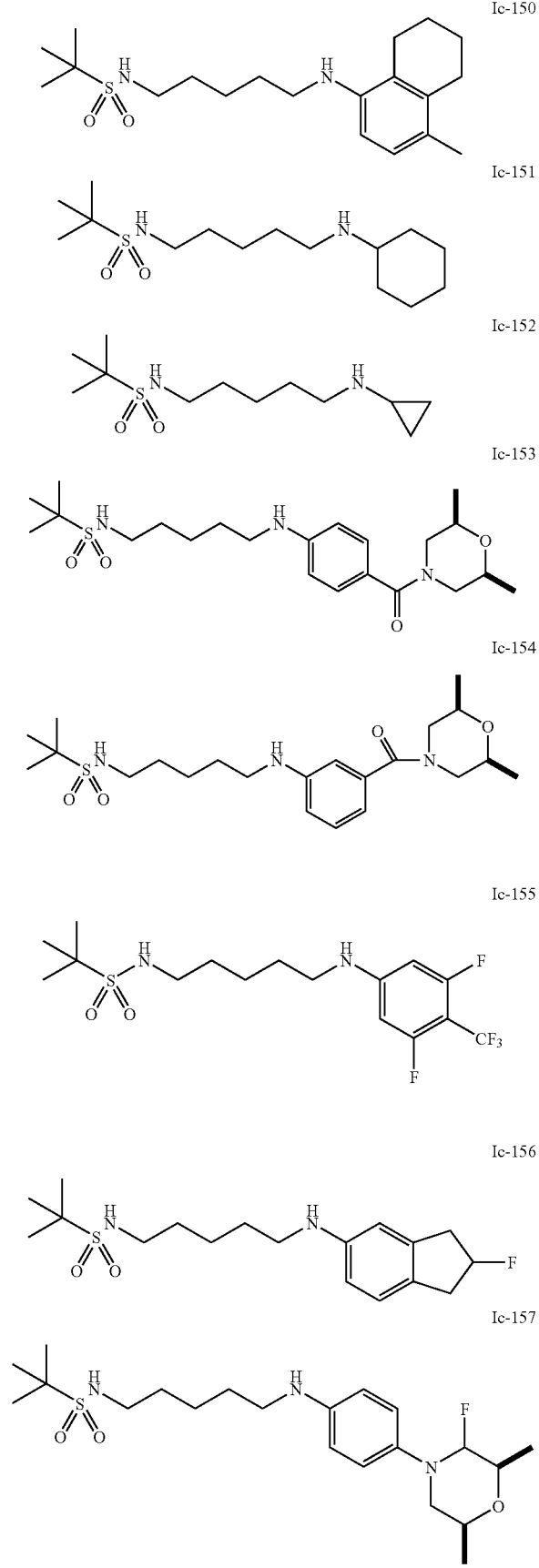

Ic-158
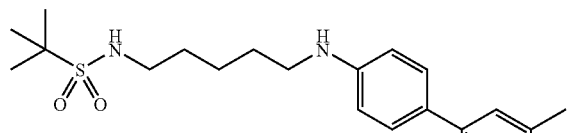
Ic-159
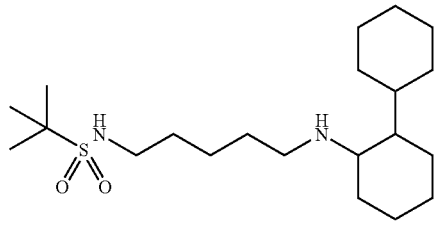
Ic-160
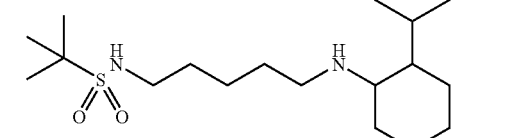
Ic-161
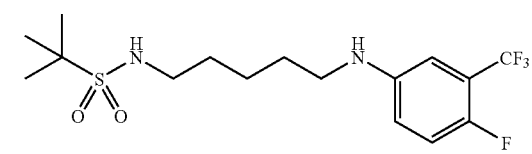
Ic-162
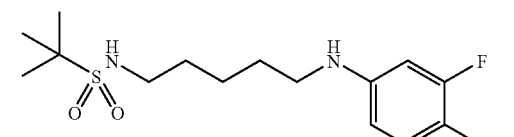
Ic-163
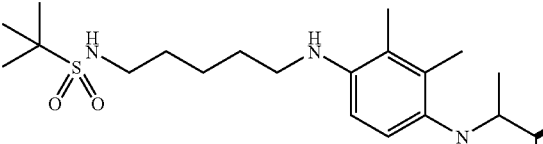
Ic-164
Ic-165
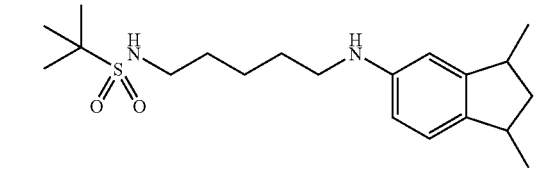
Ic-166
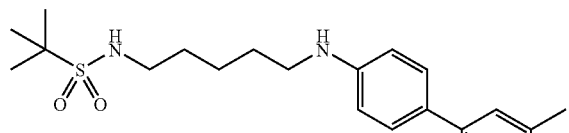
Ic-167
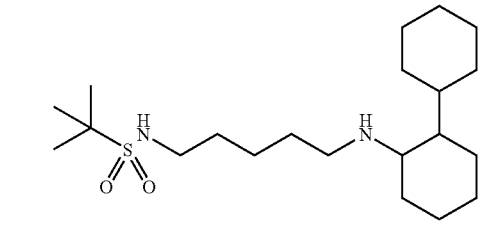
Ic-168
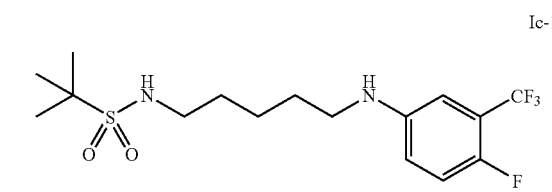
Ic-169
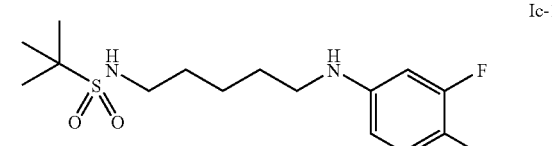
Ic-171
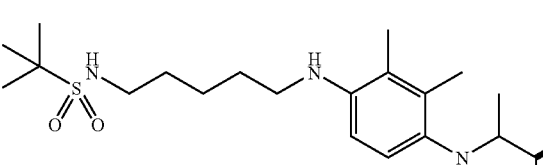
Ic-172
Ic-173
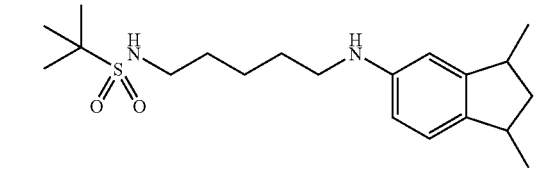
Ic-174
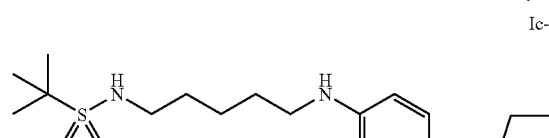

Ic-175
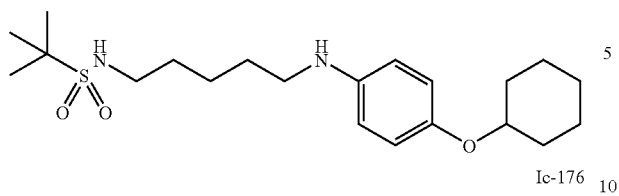
Ic-176
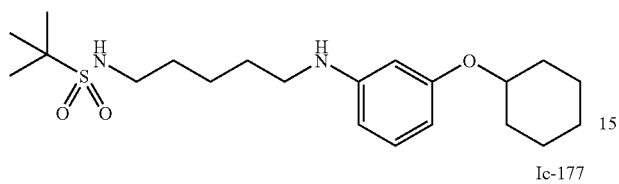
Ic-177
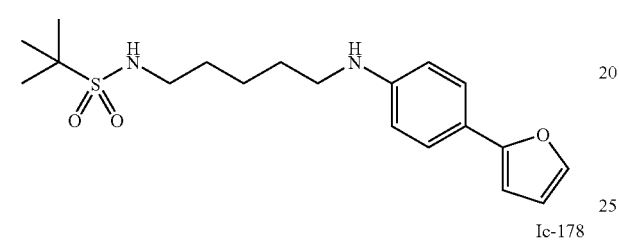
Ic-178
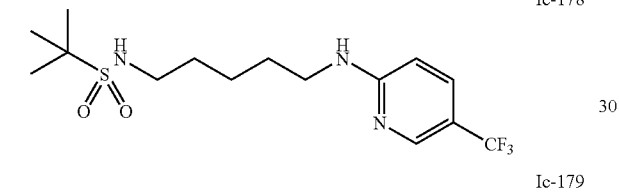
Ic-179
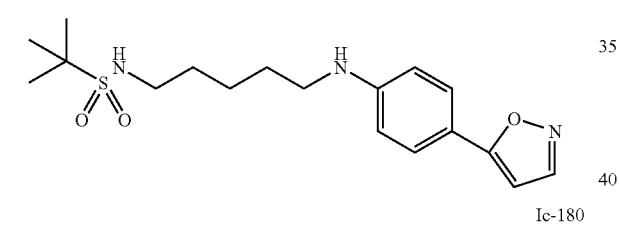
Ic-180
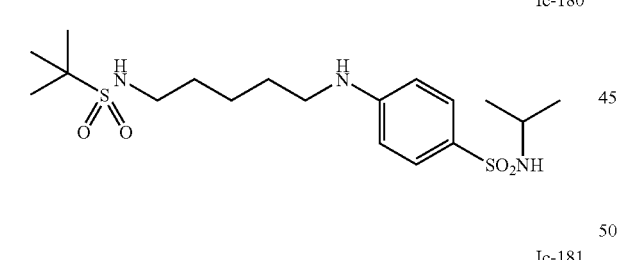
Ic-181
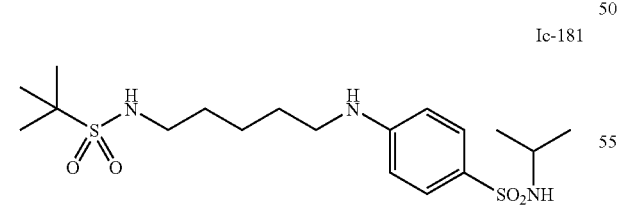
Ic-182
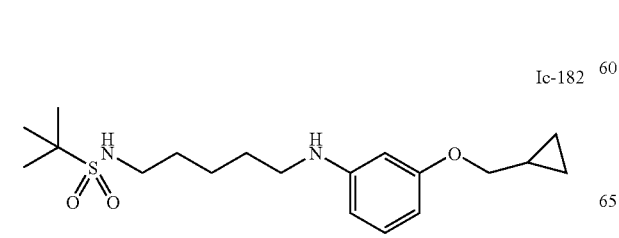
Ic-183
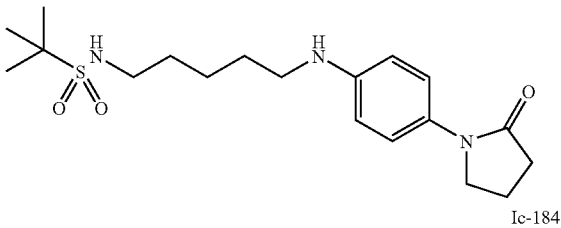
Ic-184
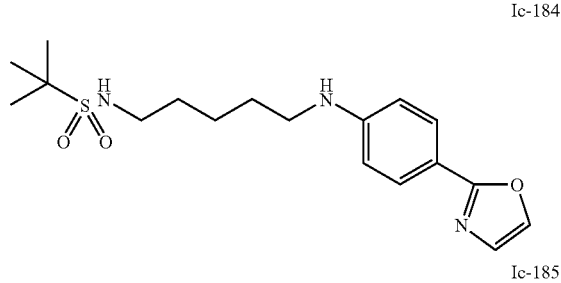
Ic-185
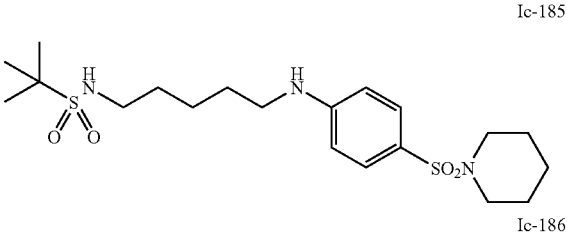
Ic-186
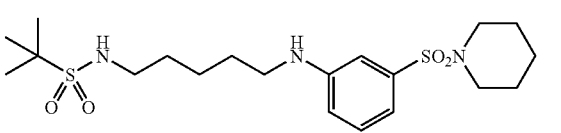
Ic-187
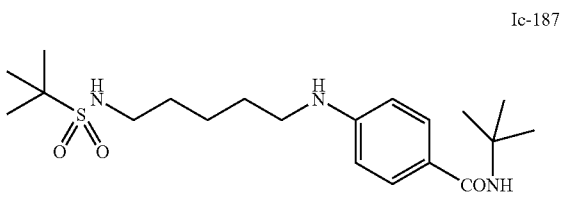
Ic-188
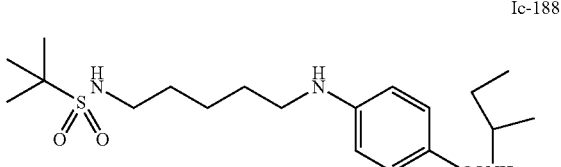
Ic-189
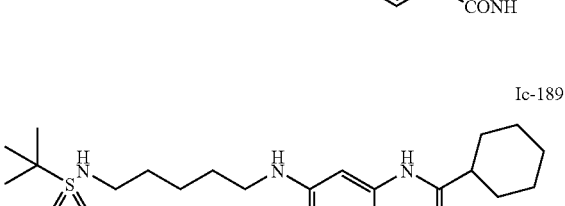
Ic-190
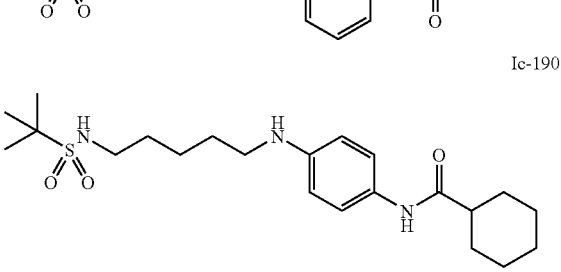

-continued
Ic-191
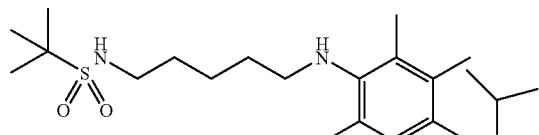
Ic-192
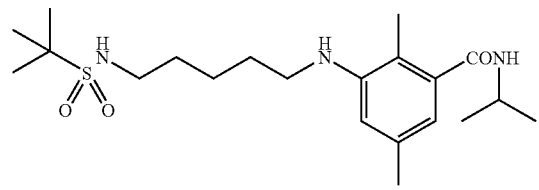
Ic-193
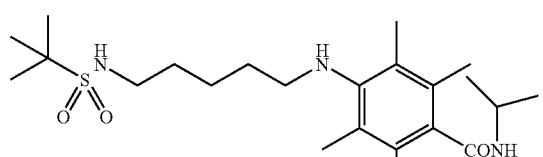
Ic-194
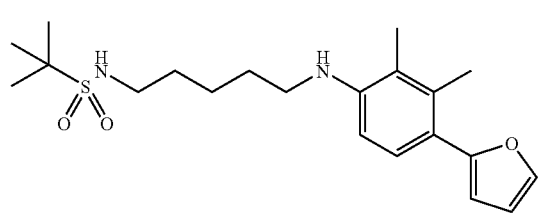
Ic-195
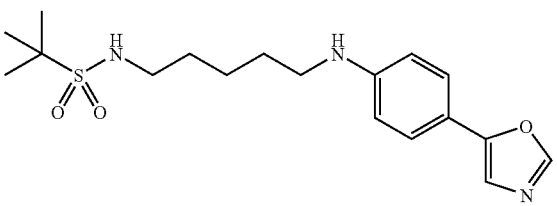
Ic-196
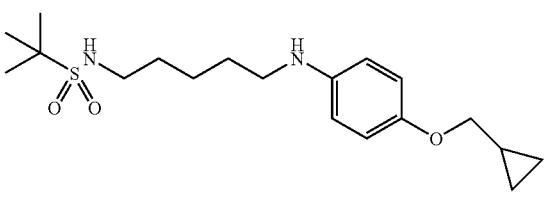
Ic-197
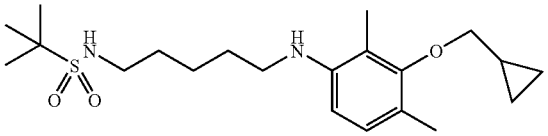
Ic-198
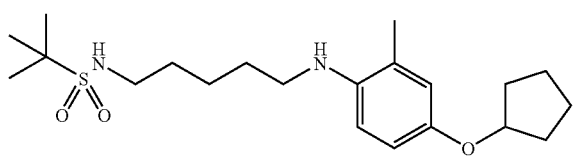
-continued
Ic-199
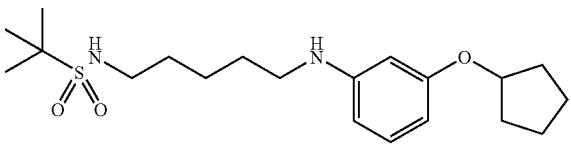
Ic-200
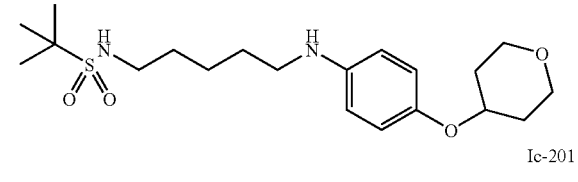
Ic-201
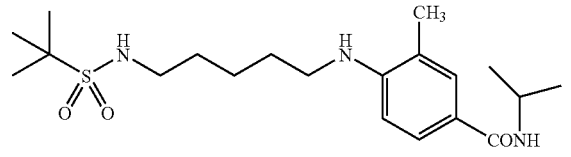
Ic-202
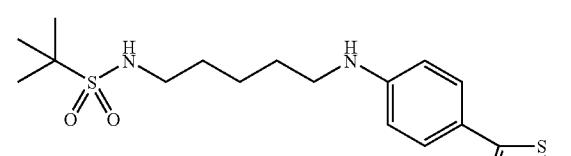
Ic-203
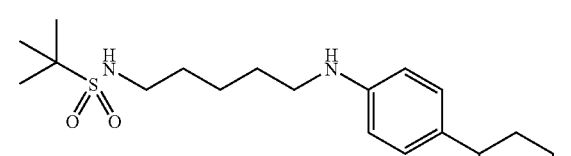
Ic-204
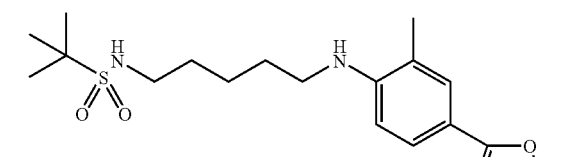
Ic-205
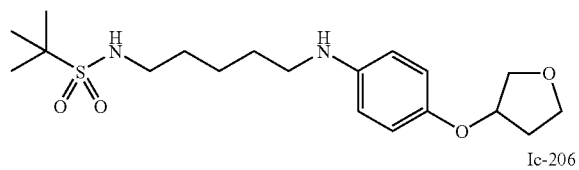
Ic-206
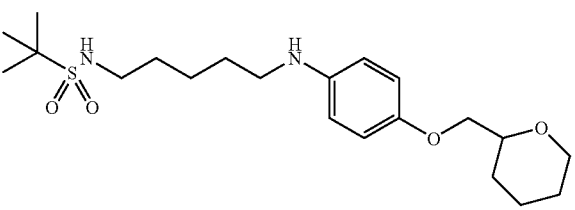

Ic-207
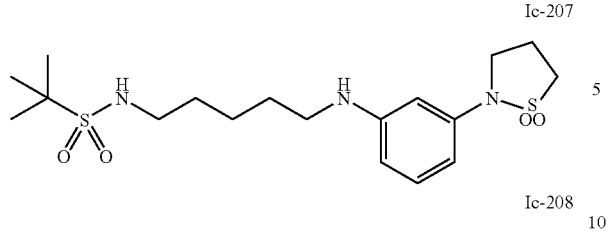
Ic-208
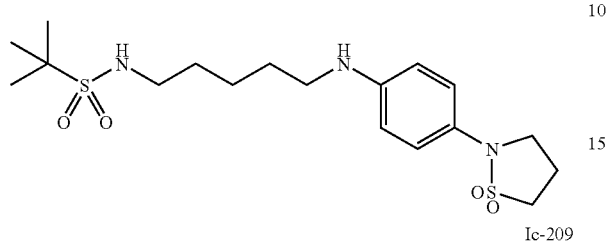
Ic-209
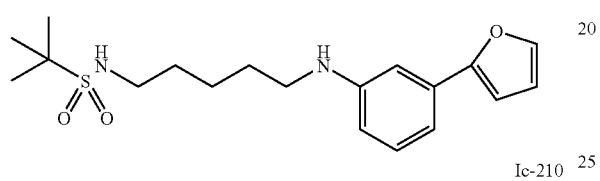
Ic-210
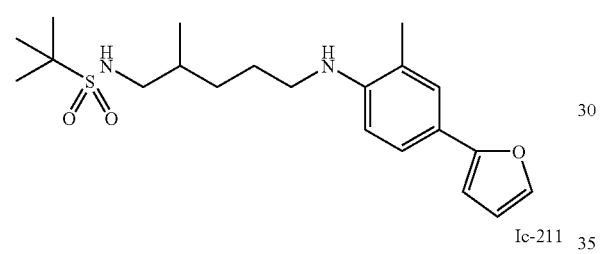
Ic-211
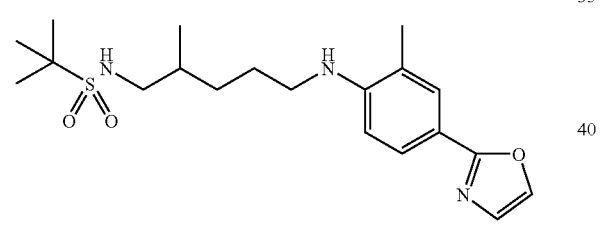
Ic-212
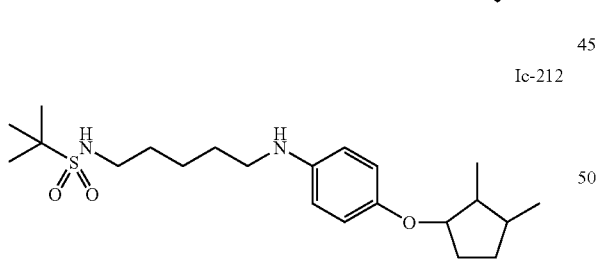
Ic-213
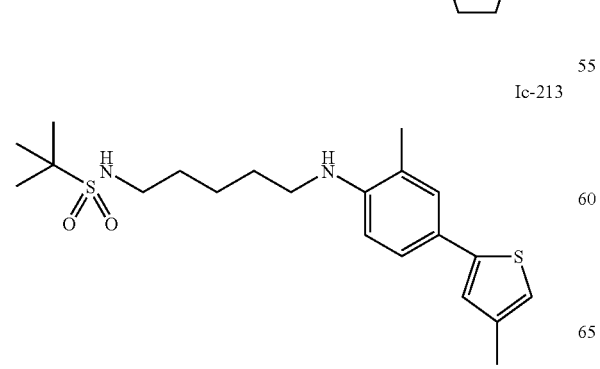
Ic-214
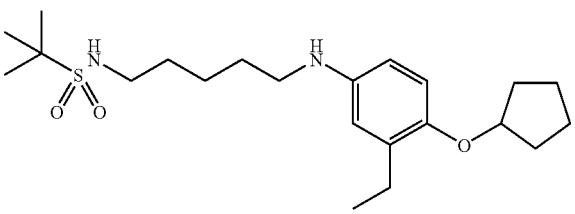
Ic-215
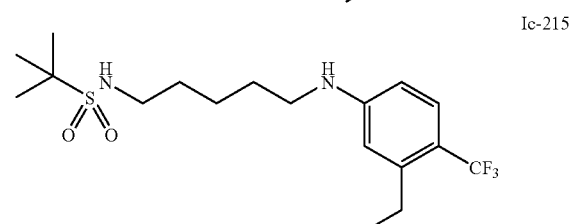
Ic-216
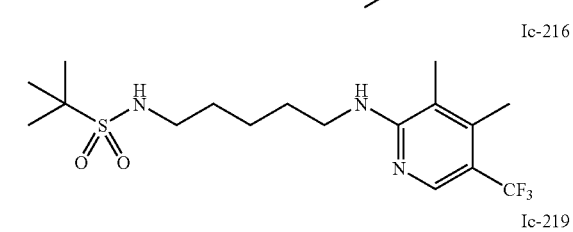
Ic-219
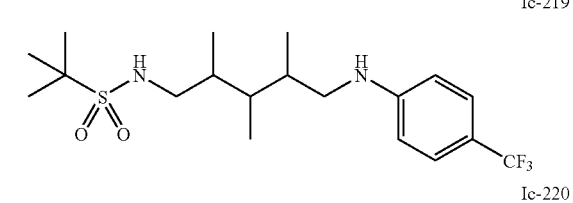
Ic-220
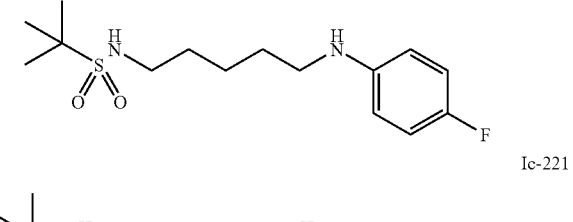
Ic-221
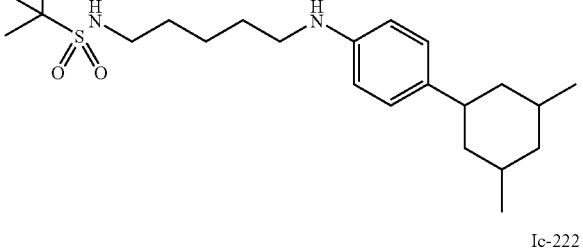
Ic-222
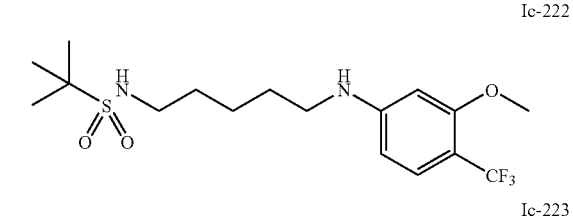
Ic-223
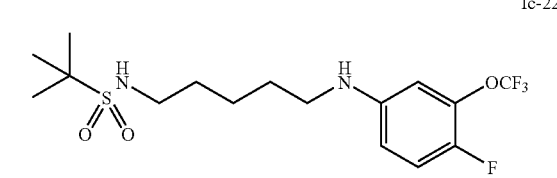

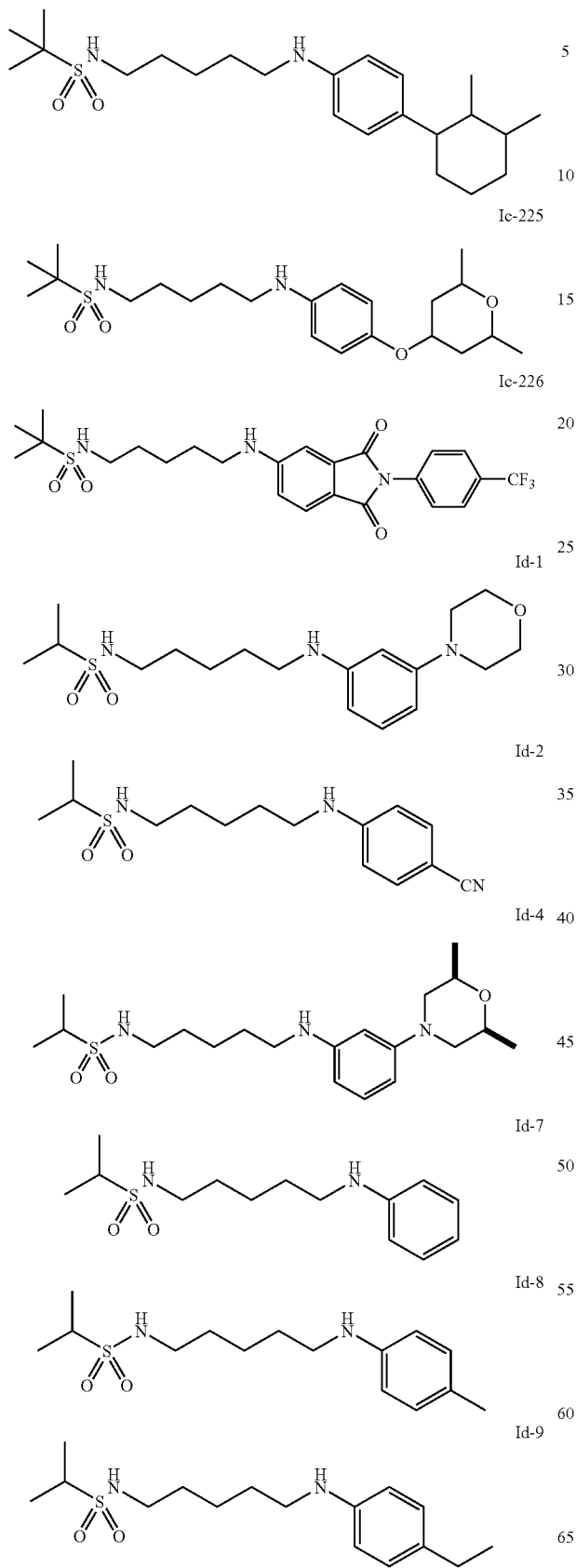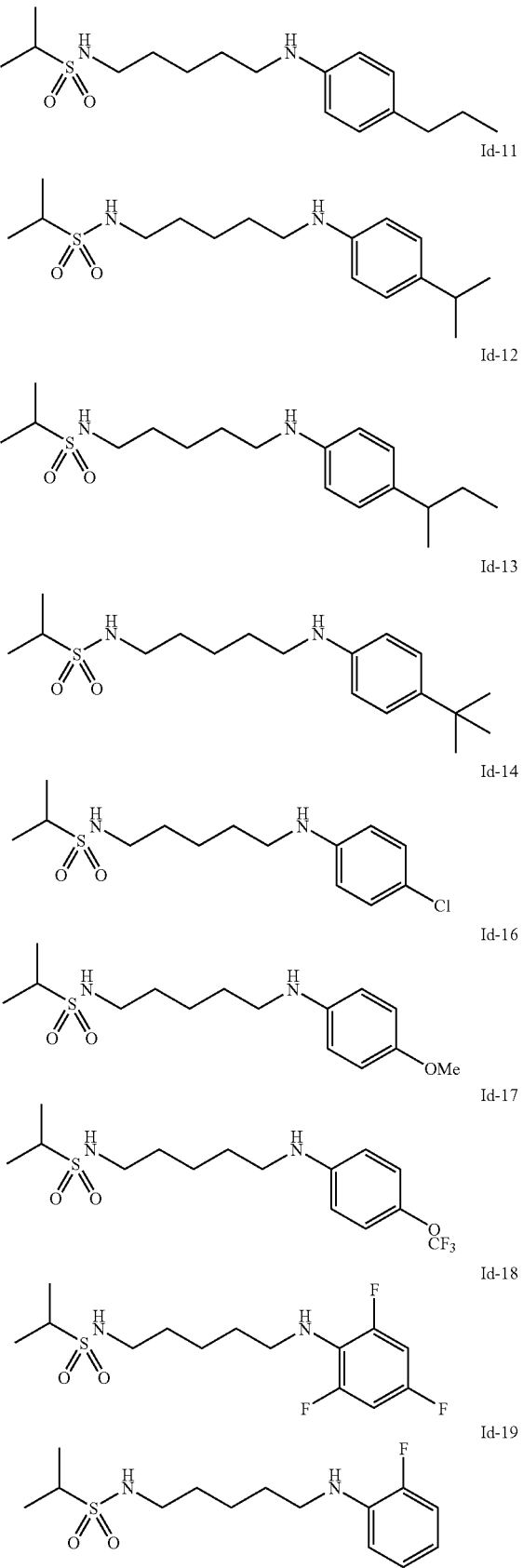

Id-20
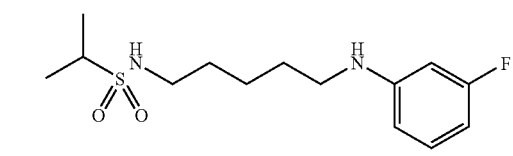
Id-21
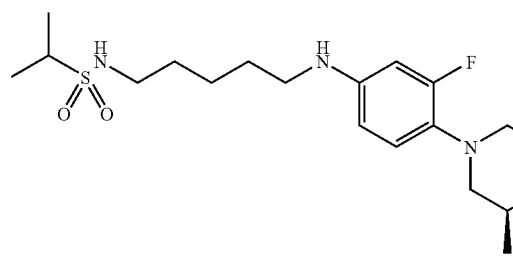
Id-22
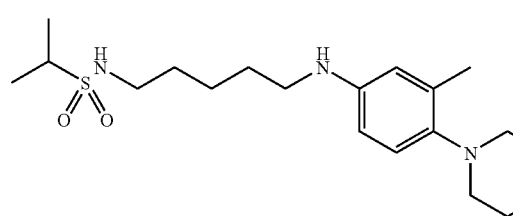
Id-23
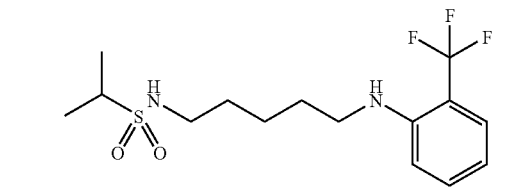
Id-24
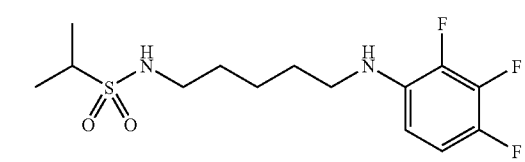
Id-25
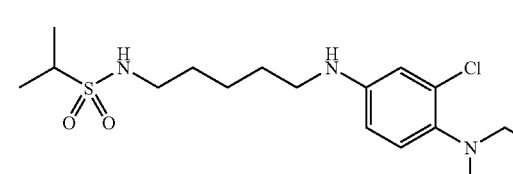
Id-26
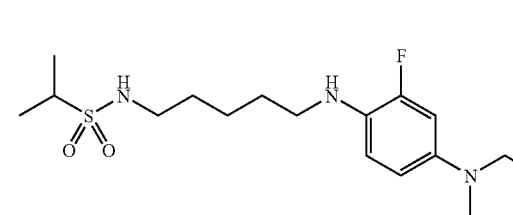
Id-27
Id-28
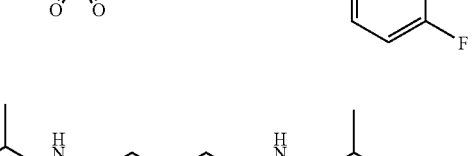
Id-29
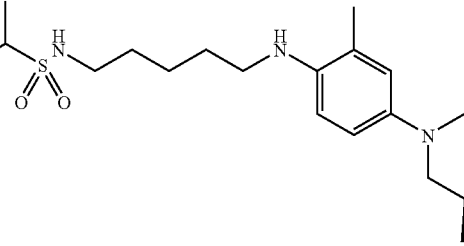
Id-30
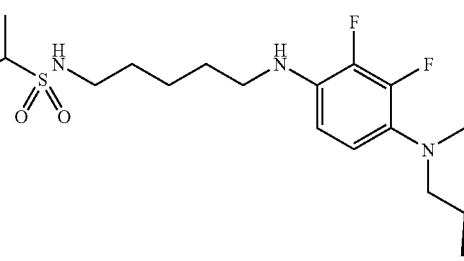
Id-31
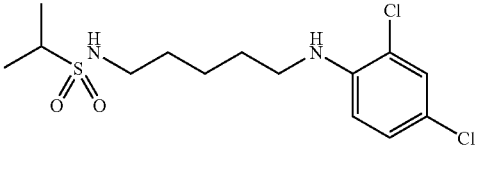
Id-32
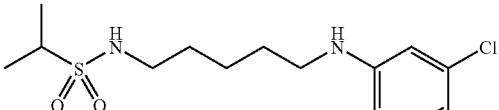
Id-33
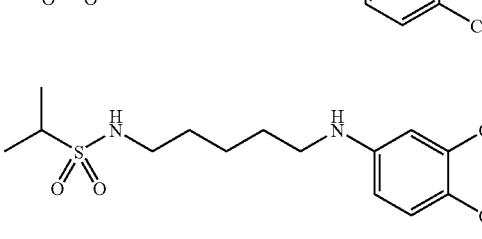

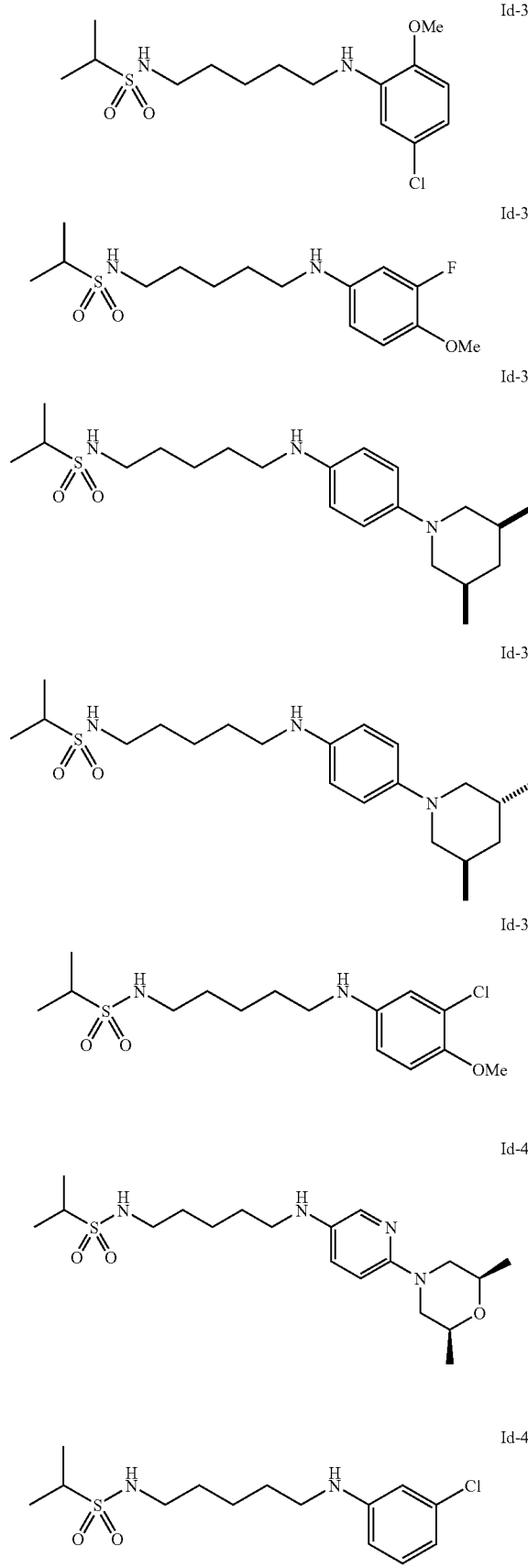

Id-48
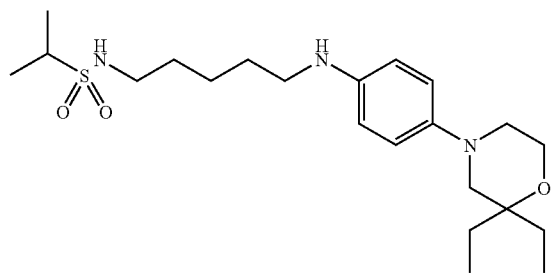
Id-49
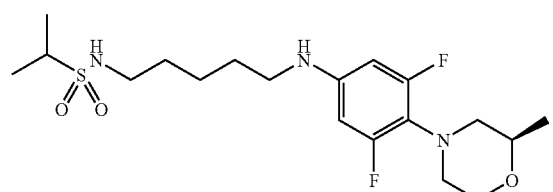
Id-50
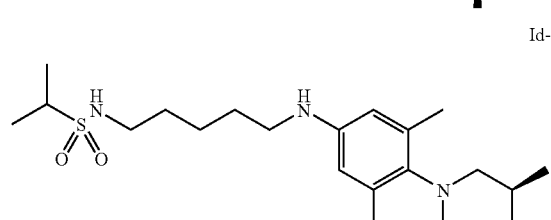
Id-51
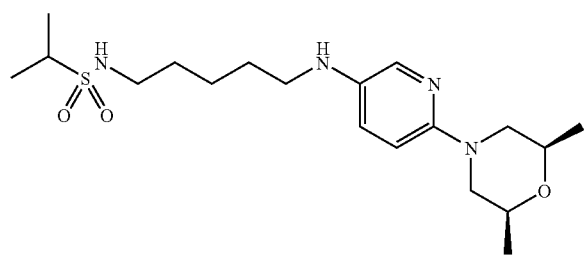
Id-52
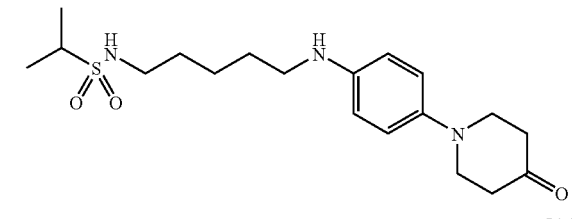
Id-53
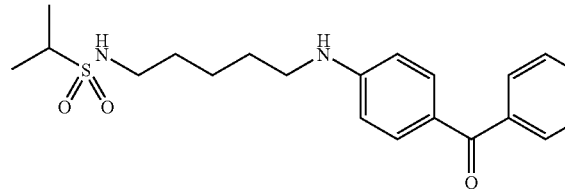
Id-54
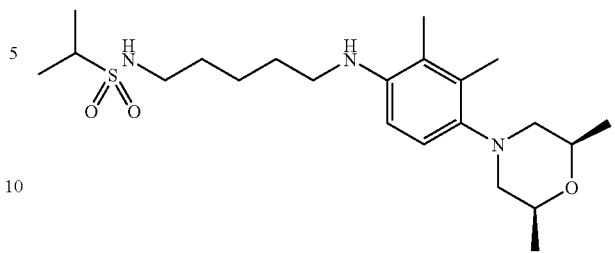
Id-55
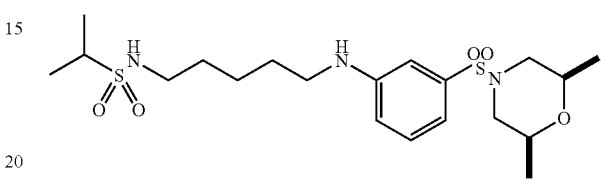
Id-56
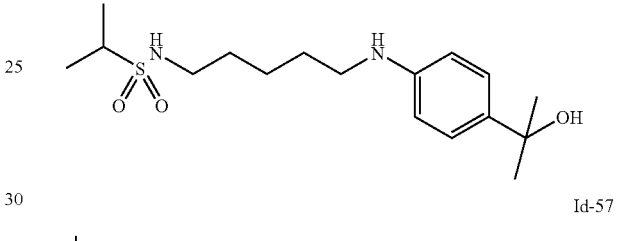
Id-57
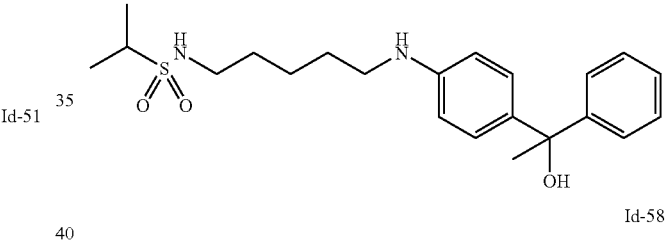
Id-58
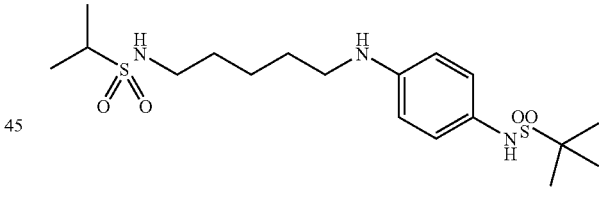
Id-59
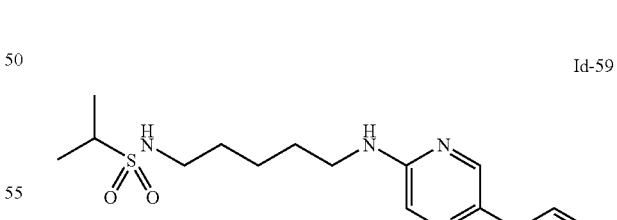
Id-60
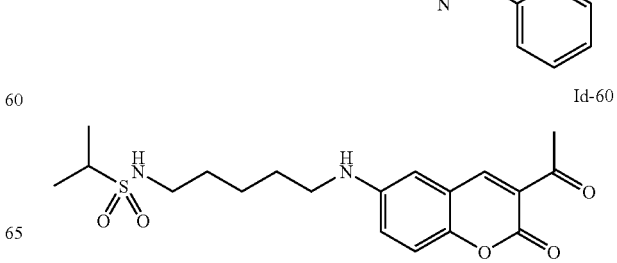

Id-61 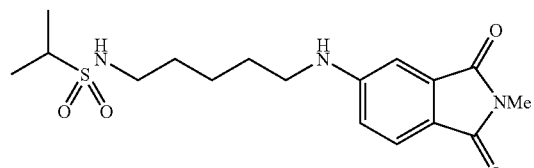
Id-62 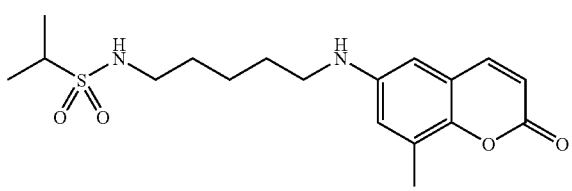
Id-63 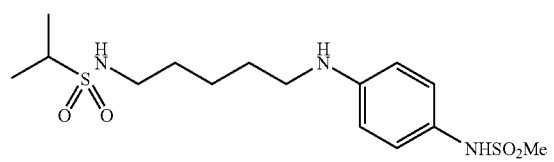
Id-64 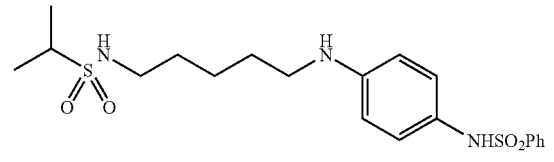
Id-65 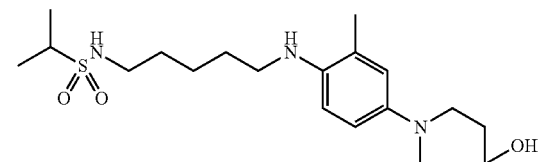
Id-66 
Id-67 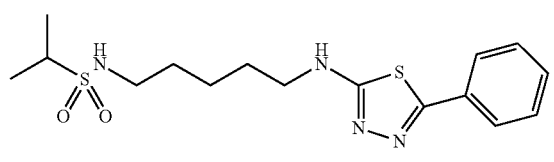
Id-68 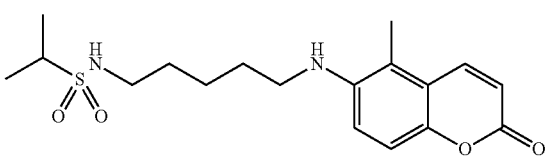
Id-69 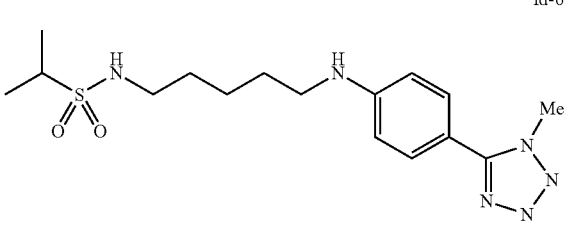
Id-70 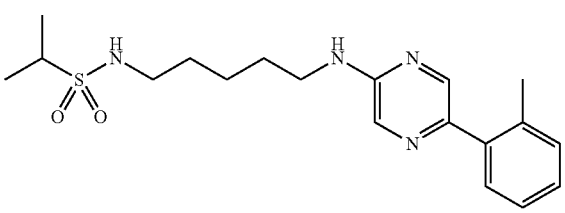
Id-71 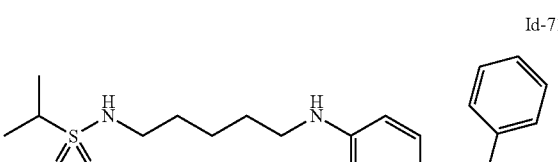
Id-73 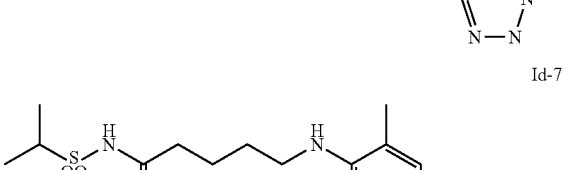
Id-74 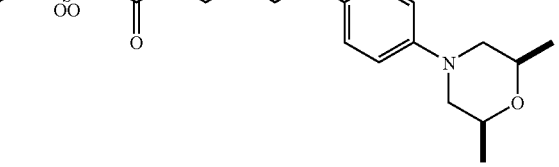
Id-75 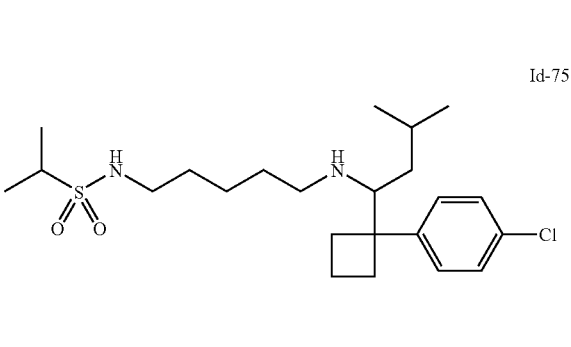

Id-76
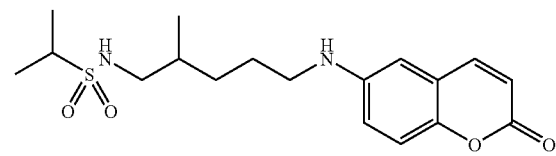
Id-77
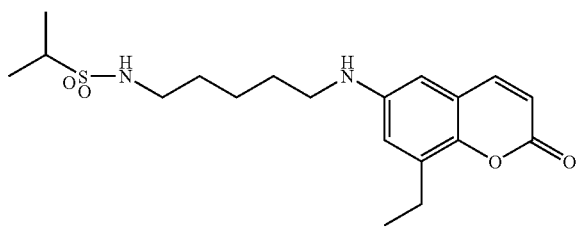
Id-78
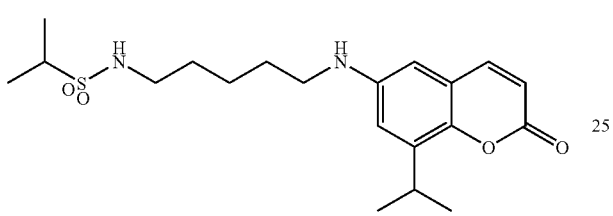
Id-79
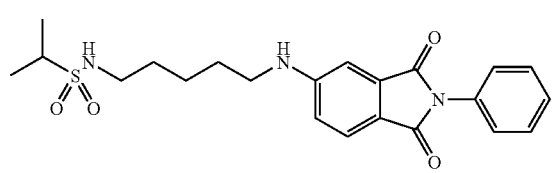
Id-80
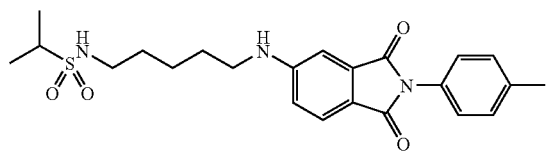
Id-81
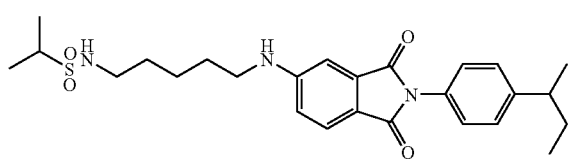
Id-82
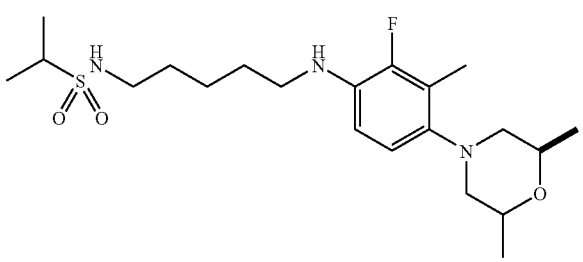
Id-83
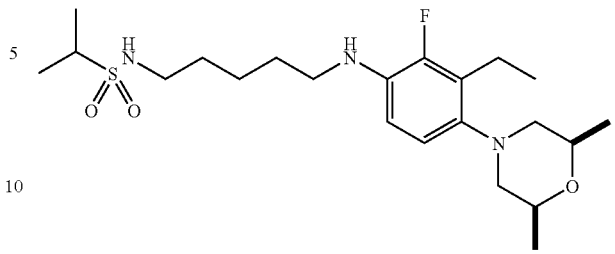
Id-84
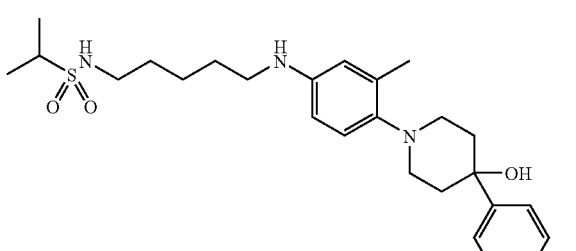
Id-85
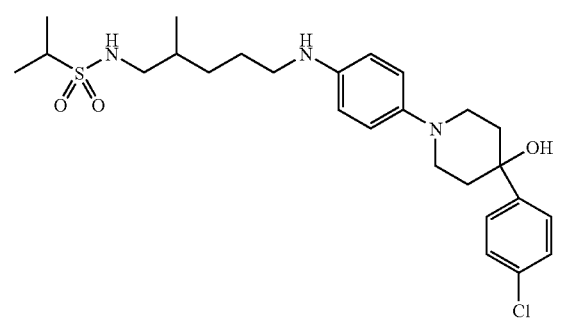
Id-86
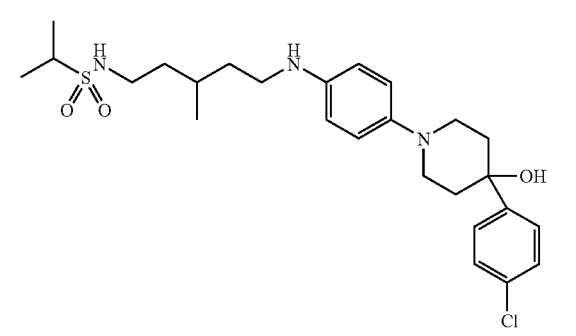
Id-87
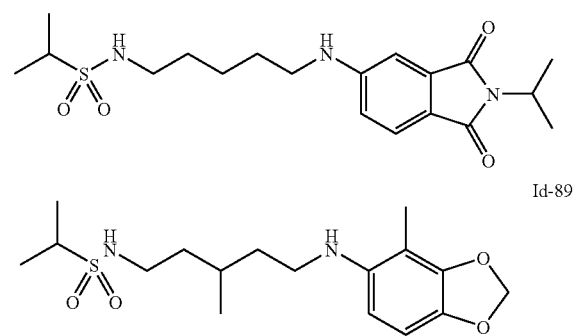
Id-89

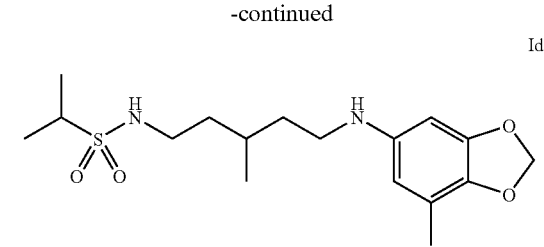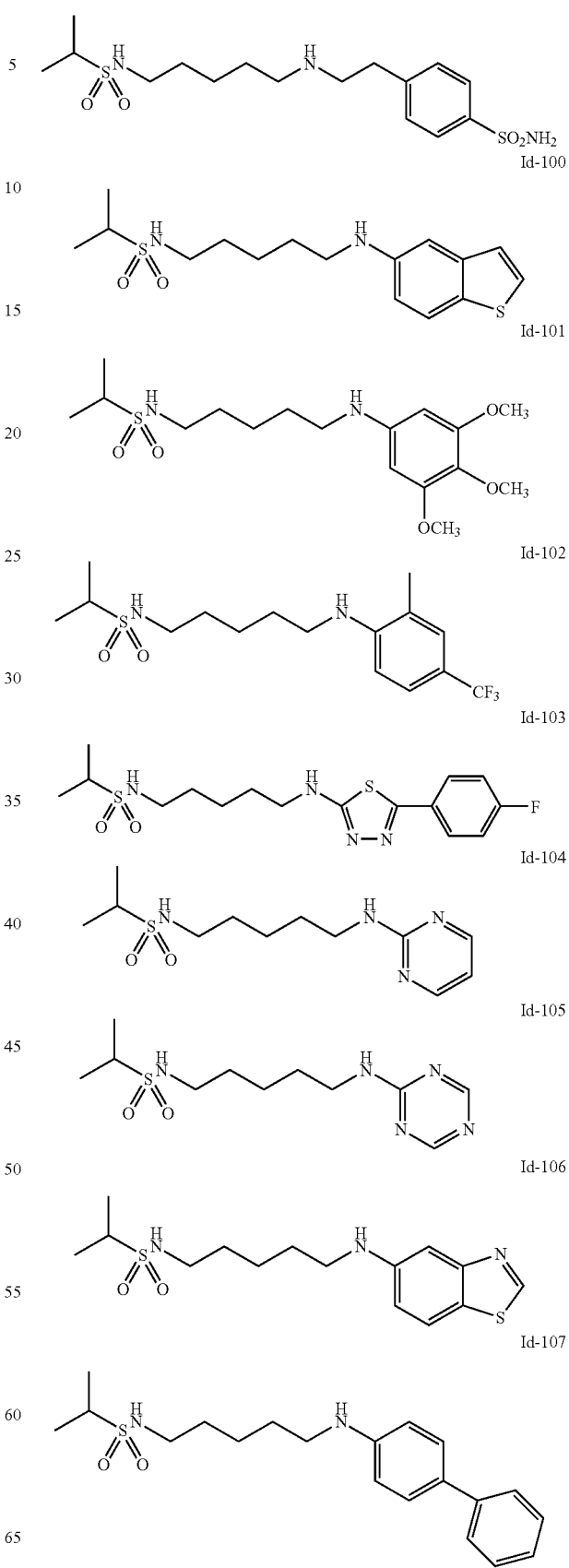

Id-108
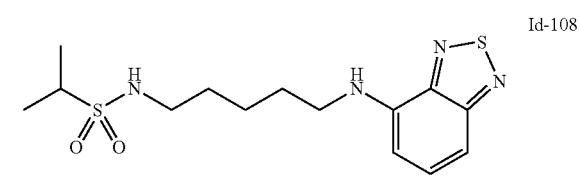
Id-109
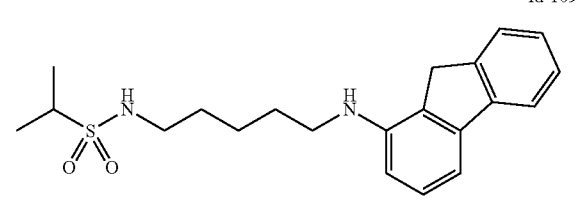
Id-110
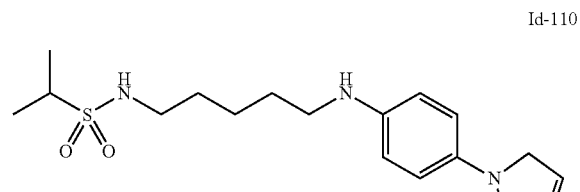
Id-111
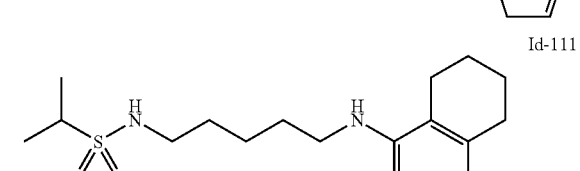
Id-112
Id-113
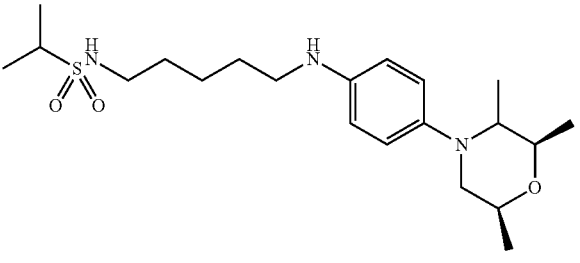
Id-114
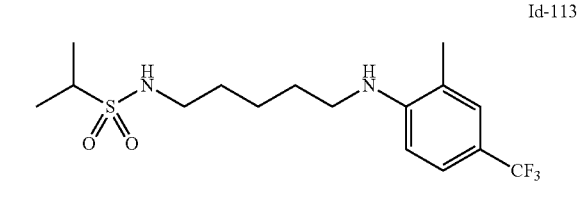
Id-115
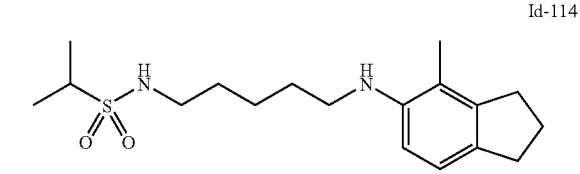
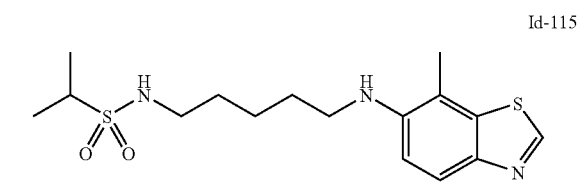
Id-116
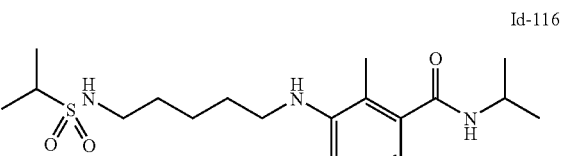
Id-117
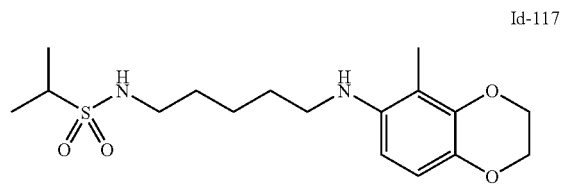
Id-118
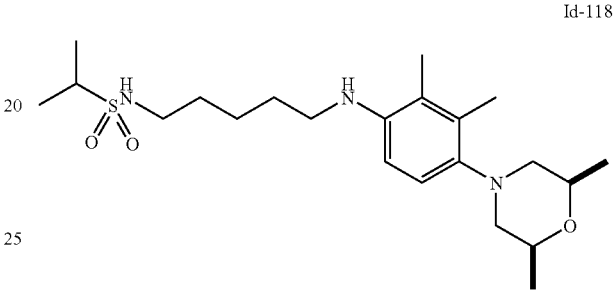
Id-119
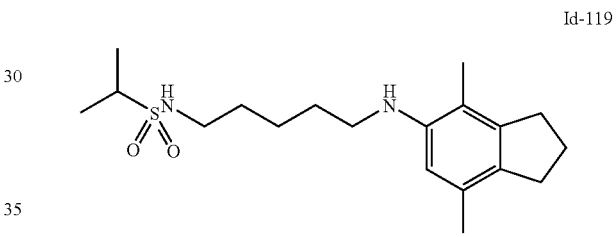
Id-120
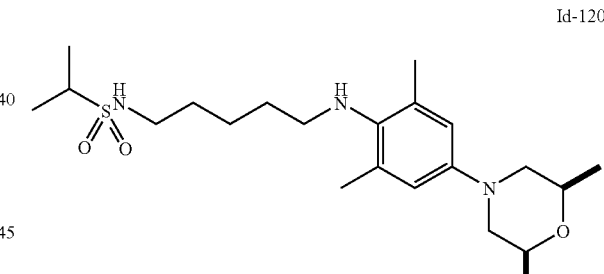
Id-121
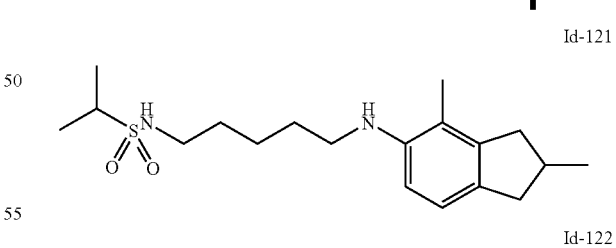
Id-122
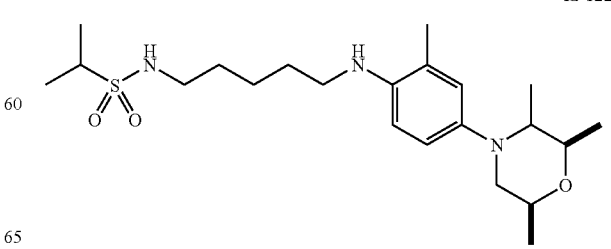

Id-123
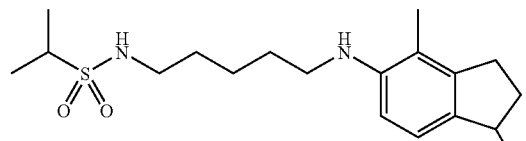
Id-124
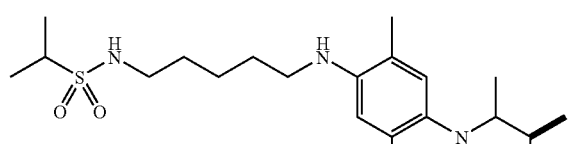
Id-125
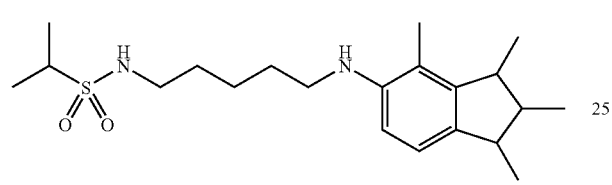
Id-126
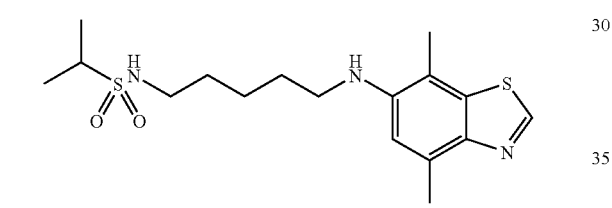
Id-127
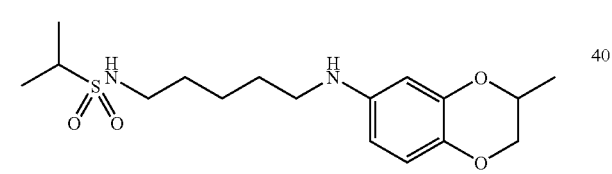
Id-128
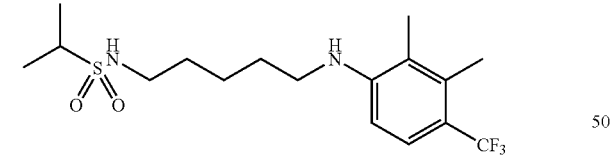
Id-129
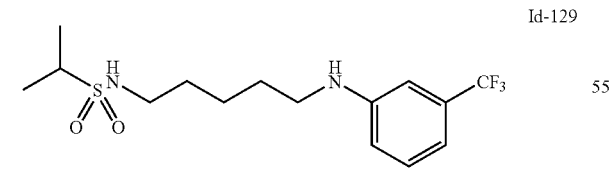
Id-130
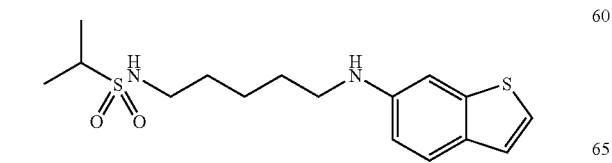
Id-131
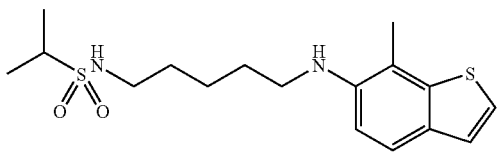
Id-132
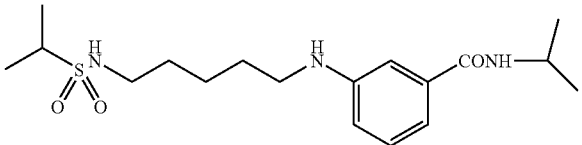
Id-133
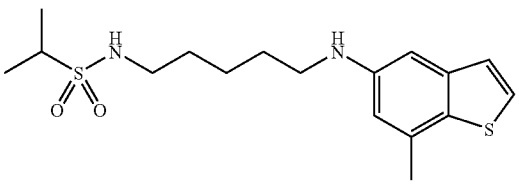
Id-134
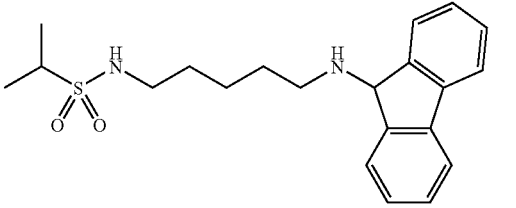
Id-135
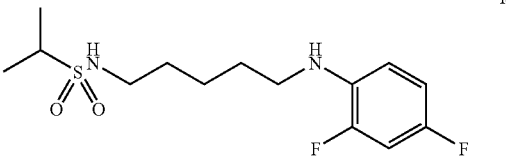
Id-136
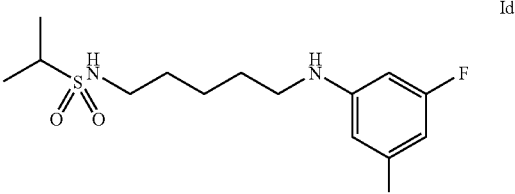
Id-137
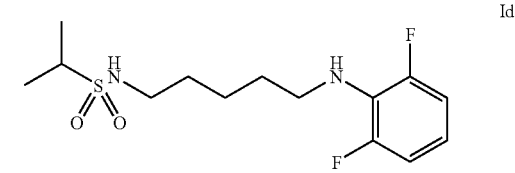
Id-138

275
-continued
Id-139
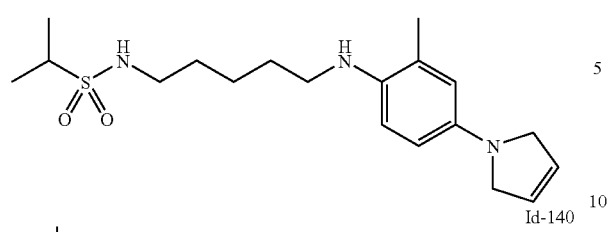
Id-140
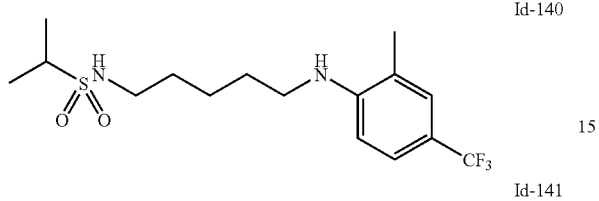
Id-141
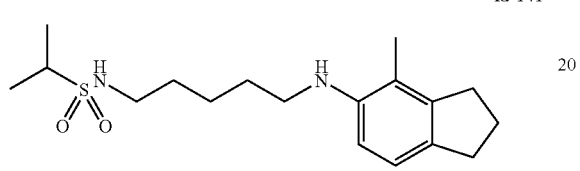
Id-142
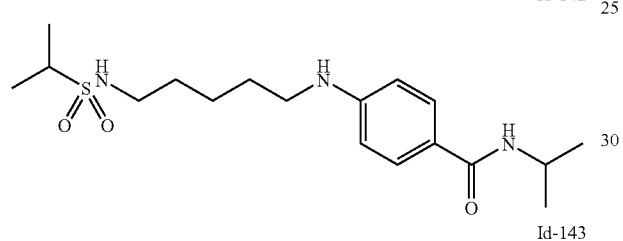
Id-143
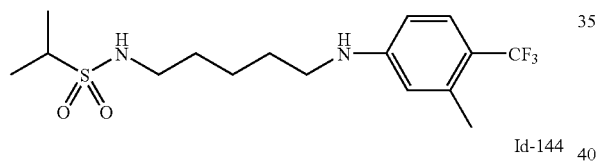
Id-144
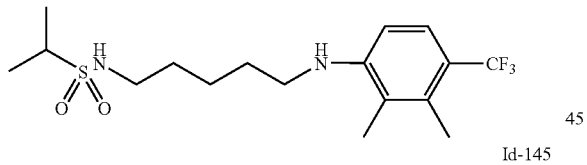
Id-145
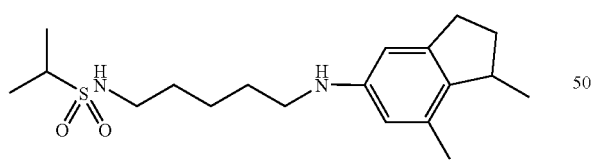
Id-146
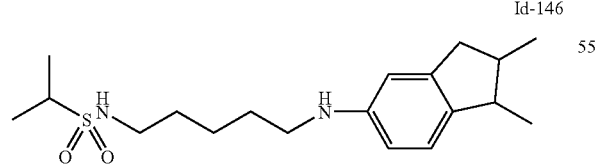
Id-147
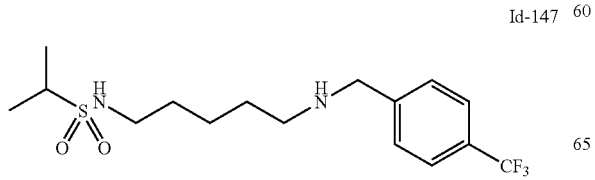
276
-continued
Id-148
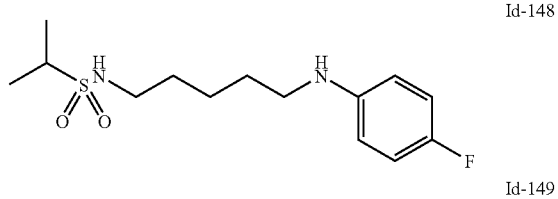
Id-149
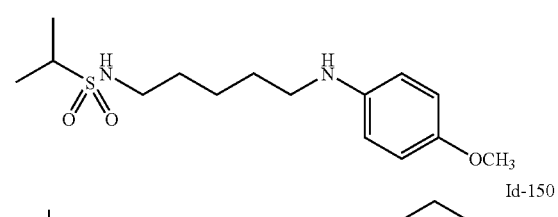
Id-150
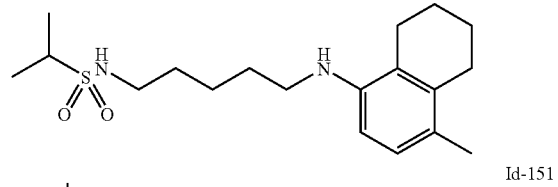
Id-151
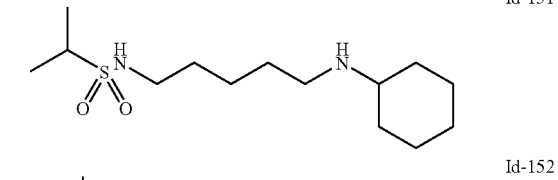
Id-152
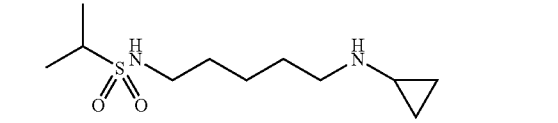
Id-153
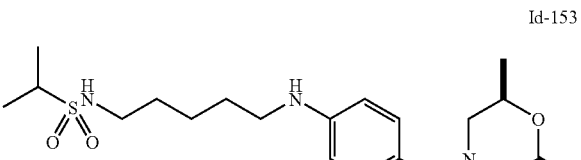
Id-154
Id-155
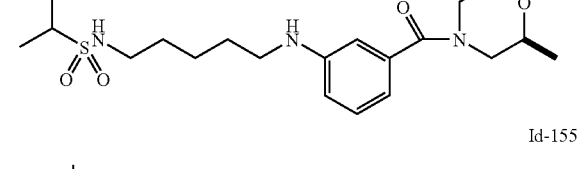
Id-156
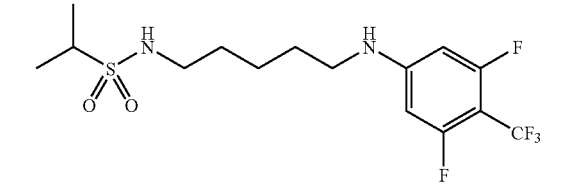
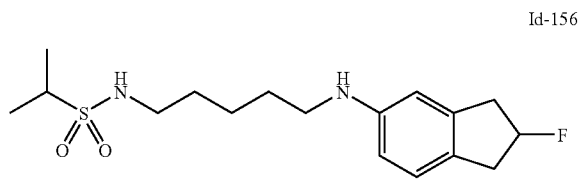

Id-157
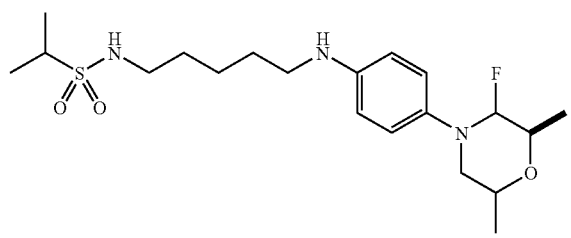
Id-158
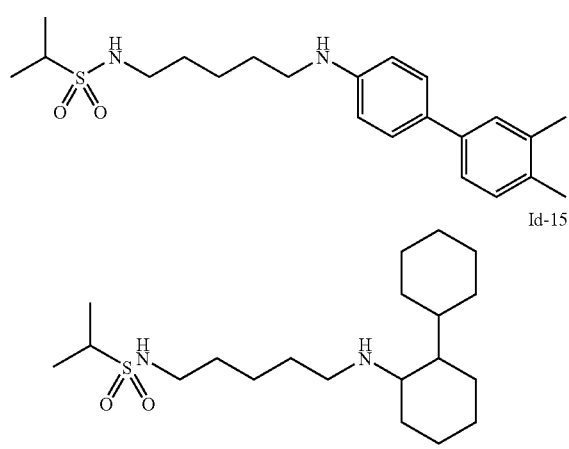
Id-159
Id-160
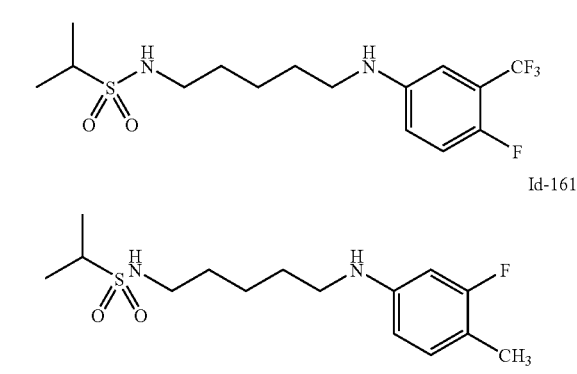
Id-161
Id-162
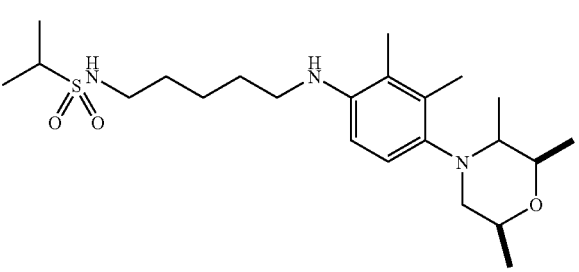
Id-163
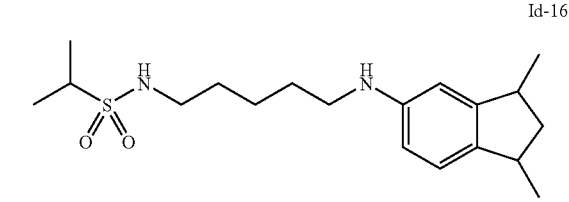
Id-164
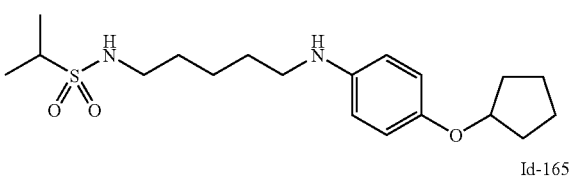
Id-165
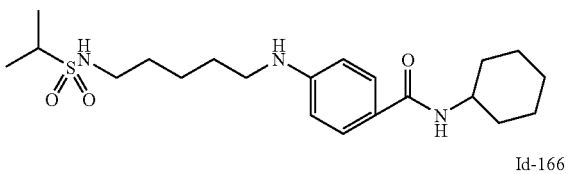
Id-166
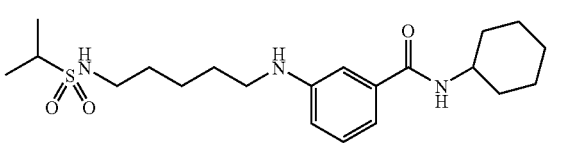
Id-167
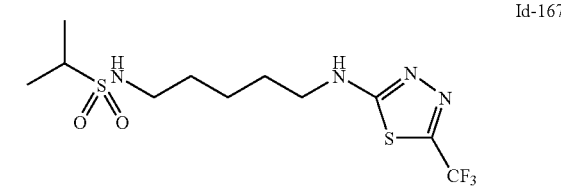
Id-168
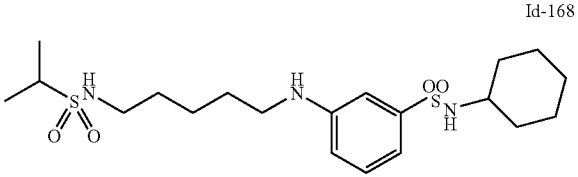
Id-169
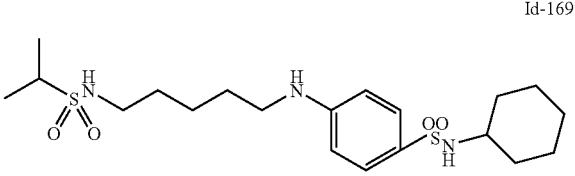
Id-171
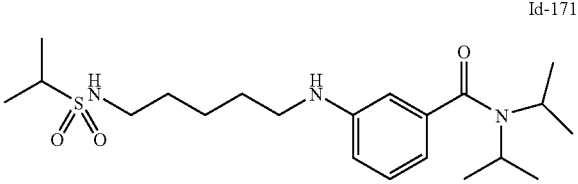
Id-172
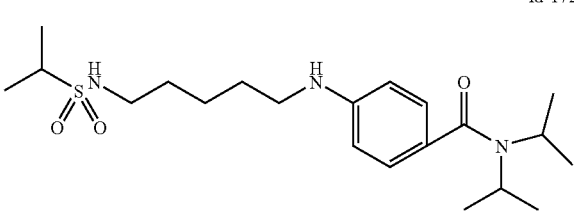

Id-173
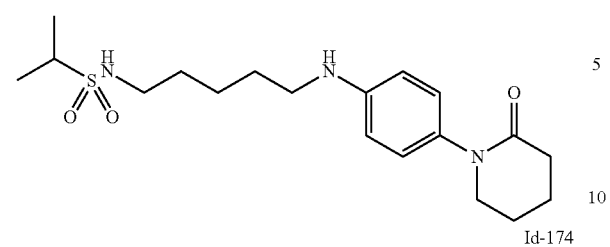
Id-174
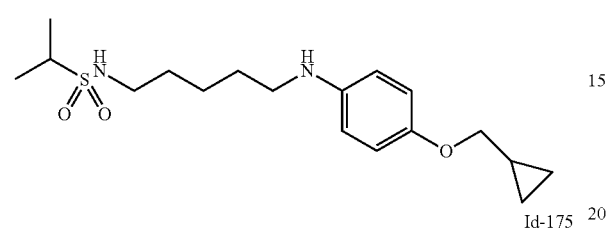
Id-175
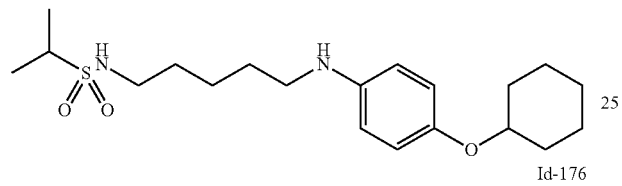
Id-176
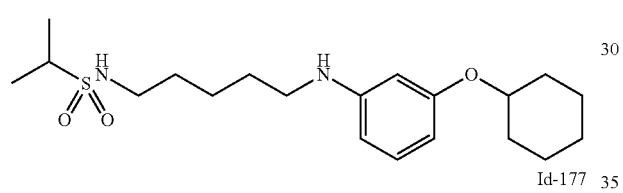
Id-177
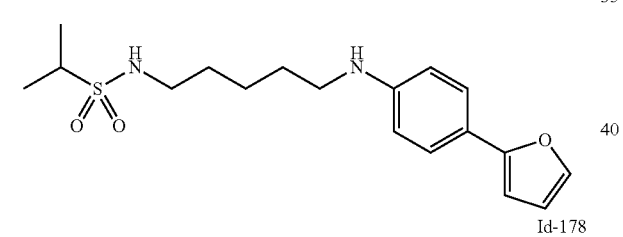
Id-178
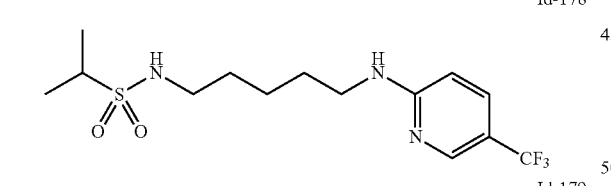
Id-179
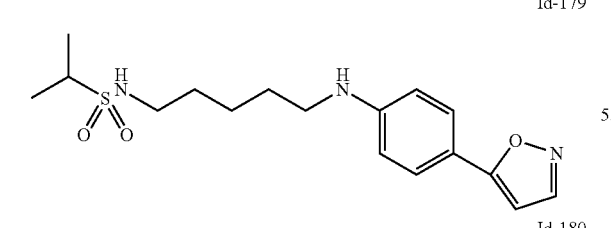
Id-180
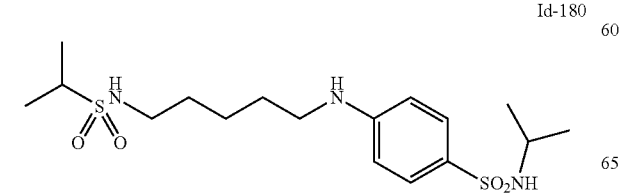
Id-181
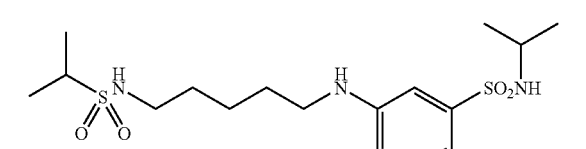
Id-182
Id-183
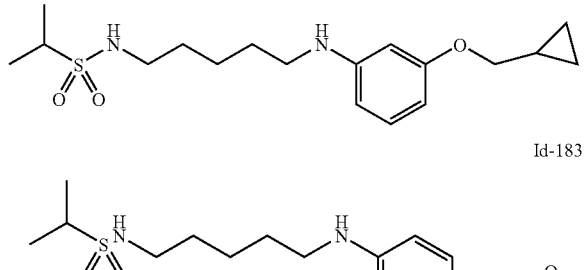
Id-184
Id-185
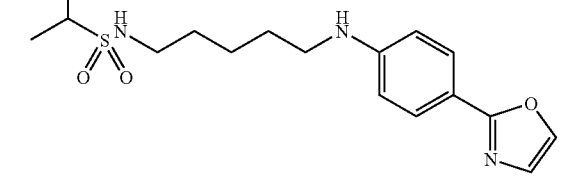
Id-186
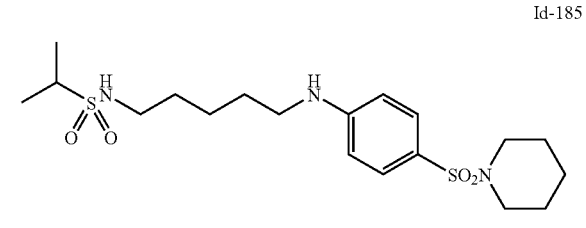
Id-187
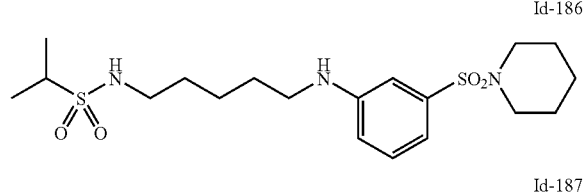
Id-188
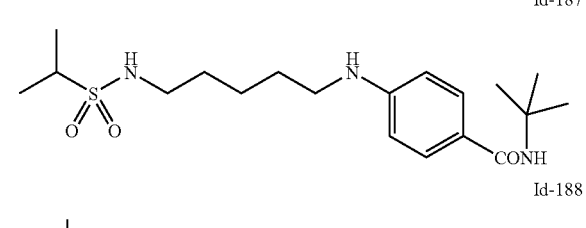
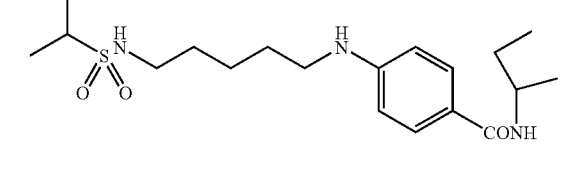

Id-189
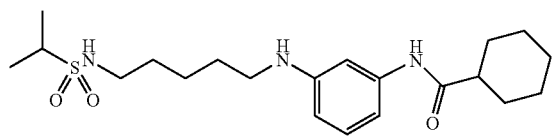
Id-196
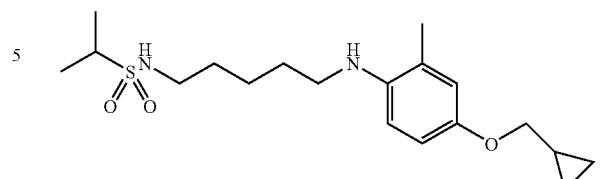
Id-190
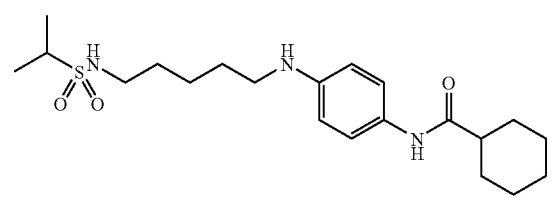
Id-197
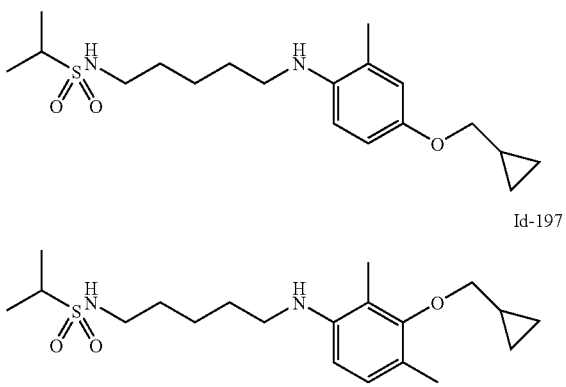
Id-191
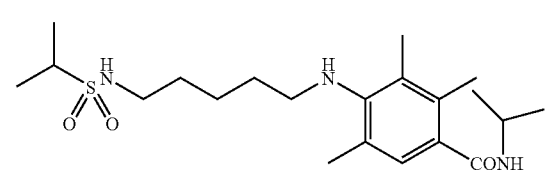
Id-198
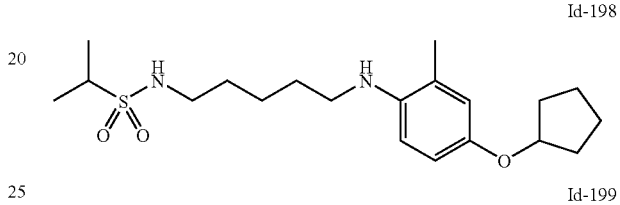
Id-192
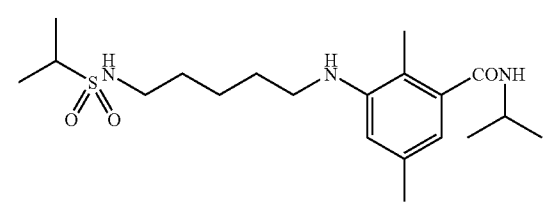
Id-199
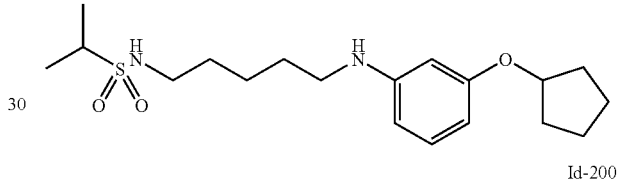
Id-193
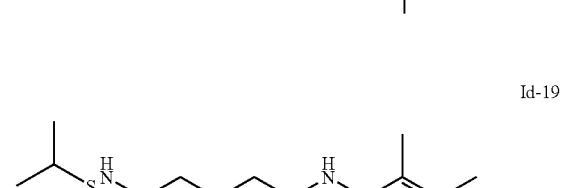
Id-200
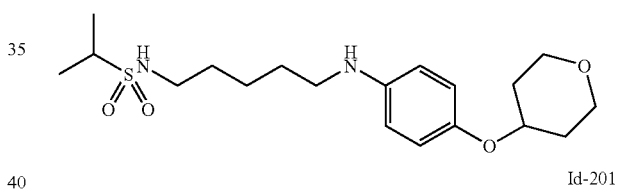
Id-194
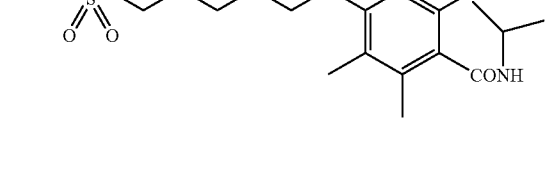
Id-201
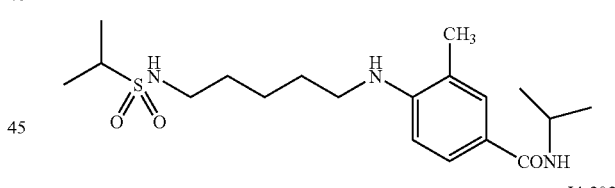
Id-195
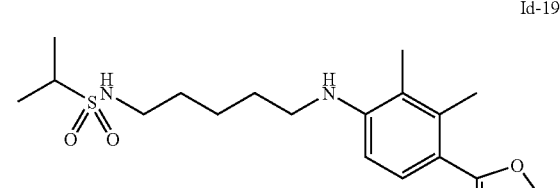
Id-202
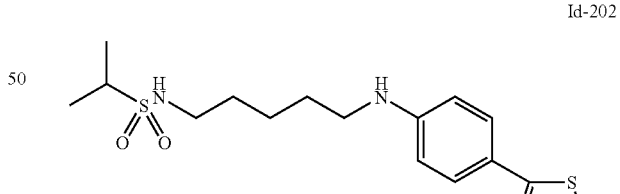
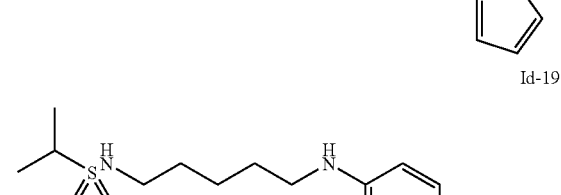
Id-203
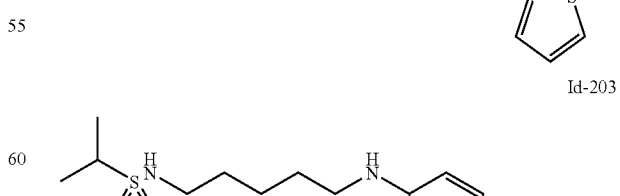

Id-204
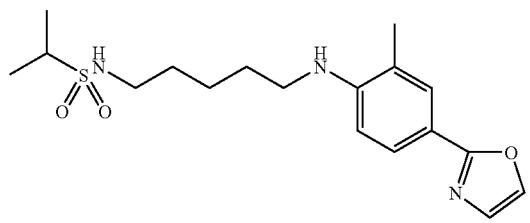
Id-205
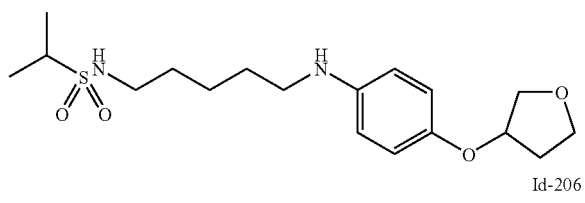
Id-206
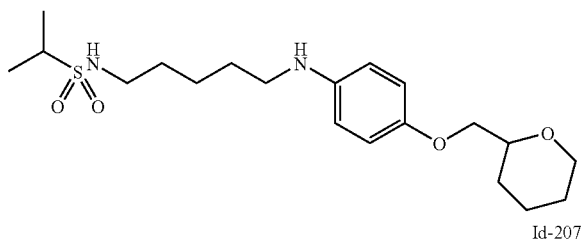
Id-207
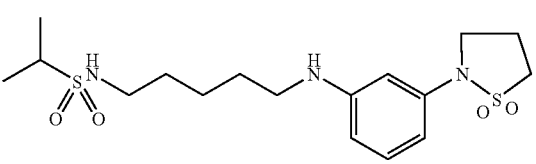
Id-208
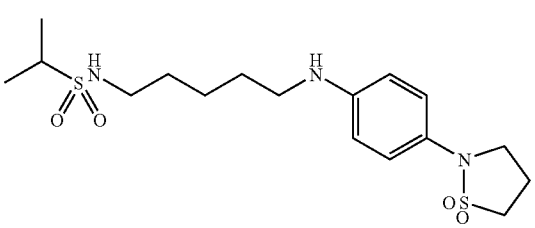
Id-209
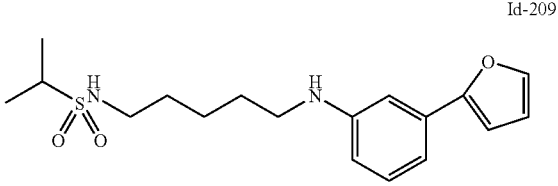
Id-210
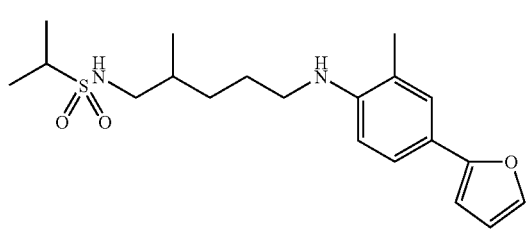
Id-211
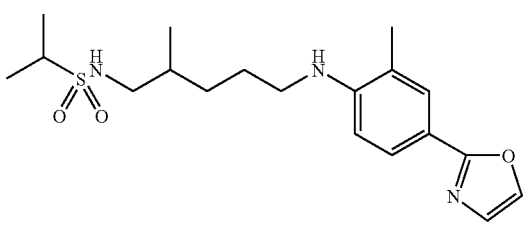
Id-212
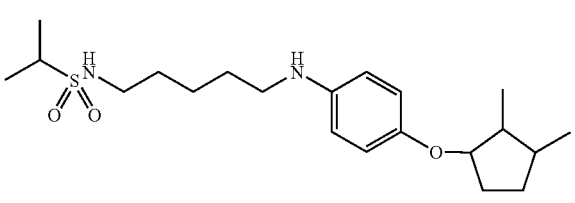
Id-213
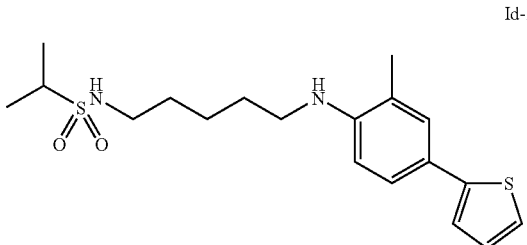
Id-214
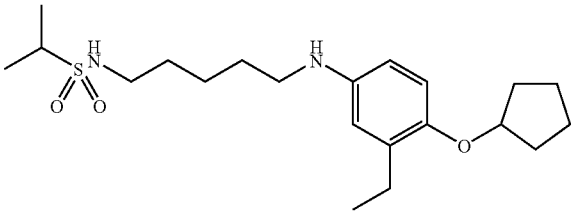
Id-215
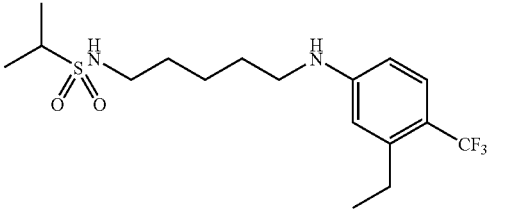
Id-216
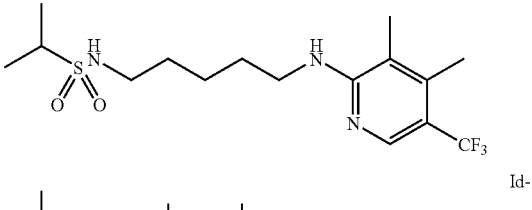
Id-219
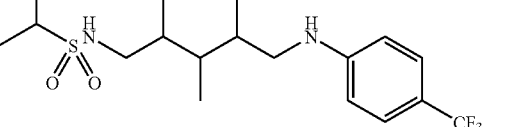

Id-220
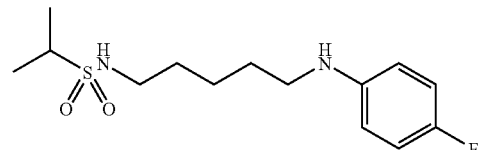
Id-221
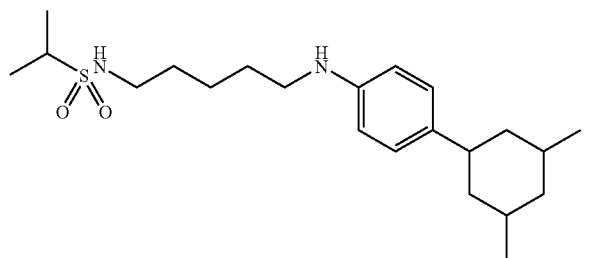
Id-222
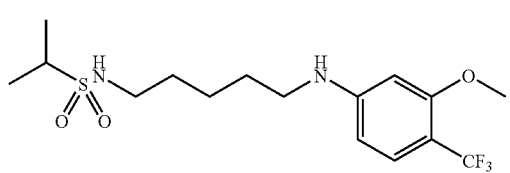
Id-223
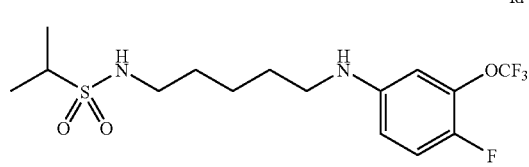
Id-224
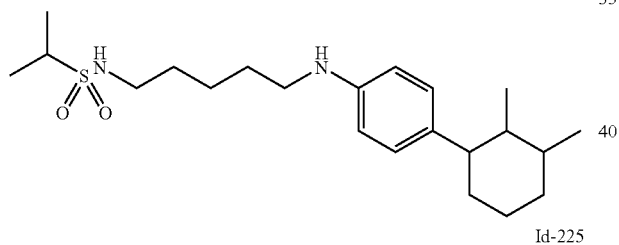
Id-225
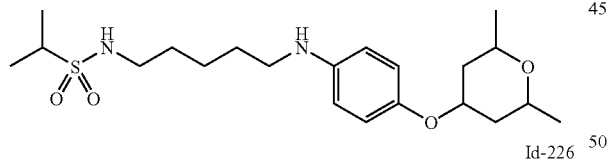
Id-226
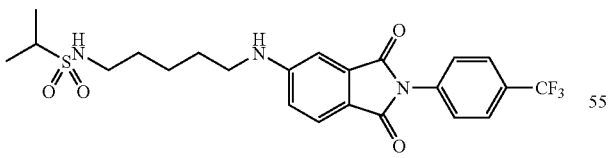
Ig-1
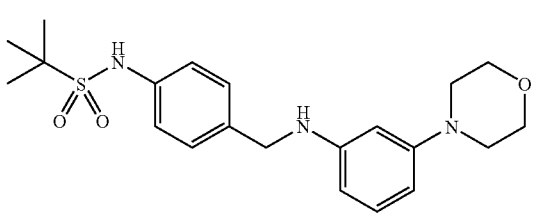
Ig-2
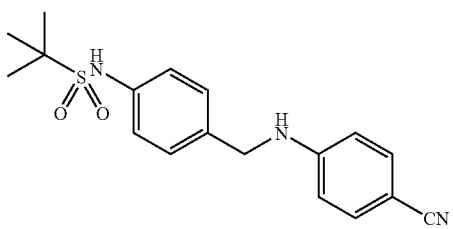
Ig-3
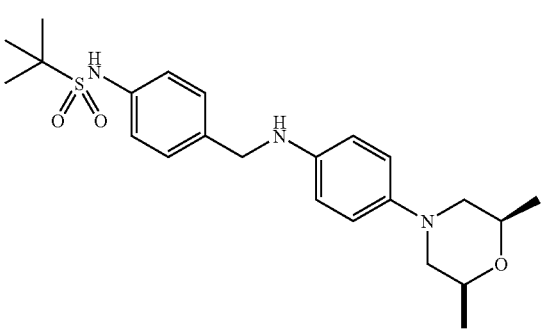
Ig-4
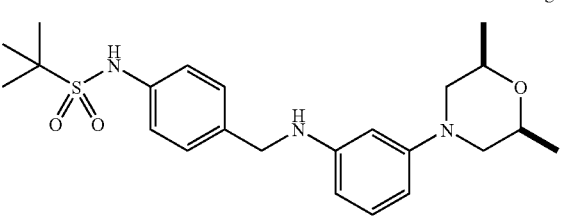
Ig-7
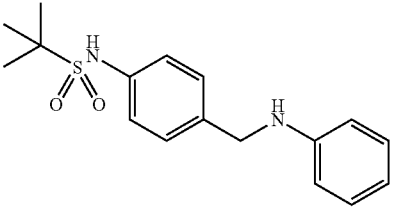
Ig-8
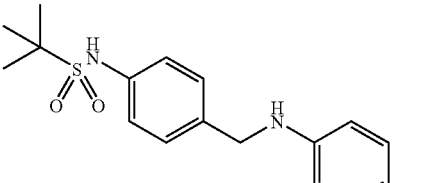
Ig-9
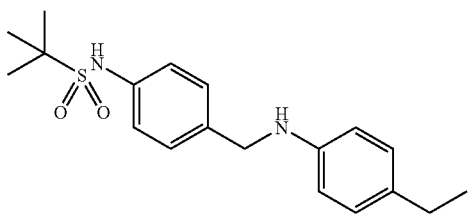

287 -continued
Ig-10
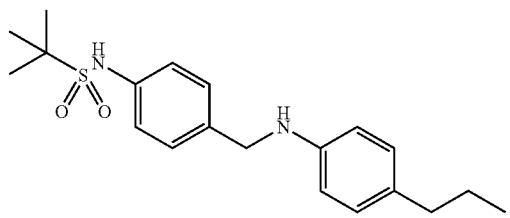
Ig-11
Ig-12
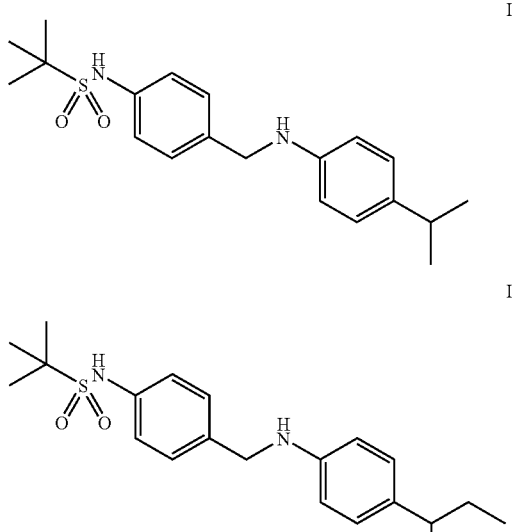
Ig-13
Ig-14
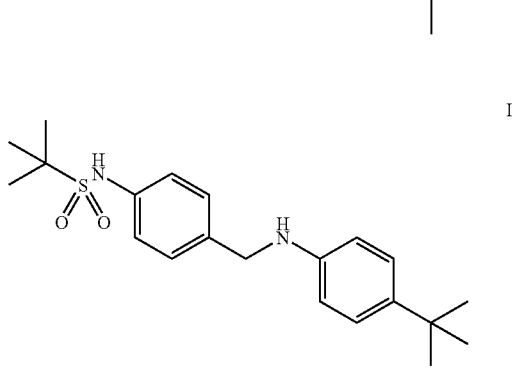
Ig-16
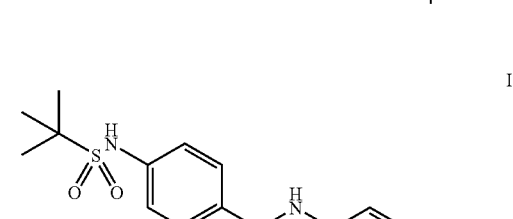
288 -continued
Ig-17
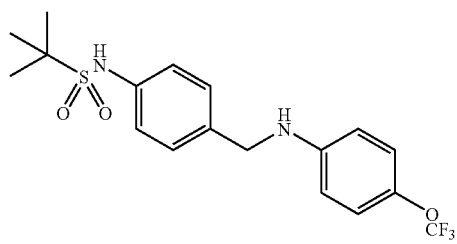
Ig-18
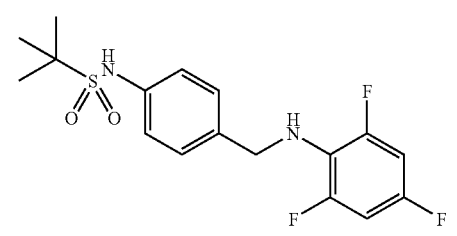
Ig-19
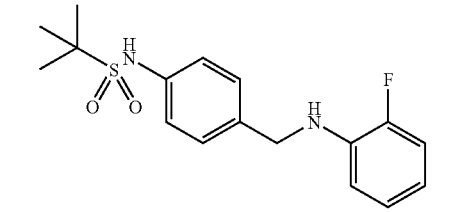
Ig-20
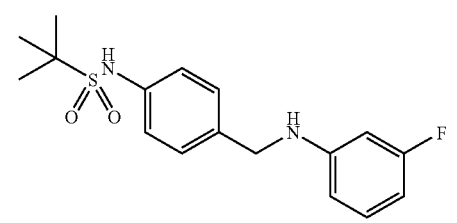
Ig-21
Ig-22
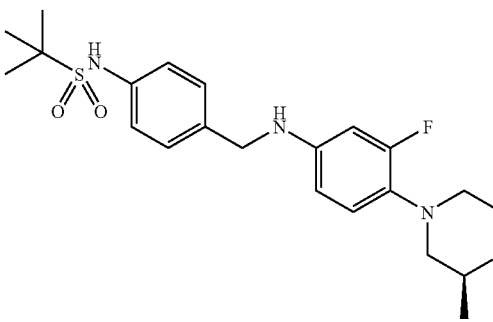

Ig-23
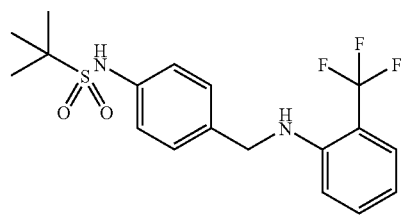
Ig-24
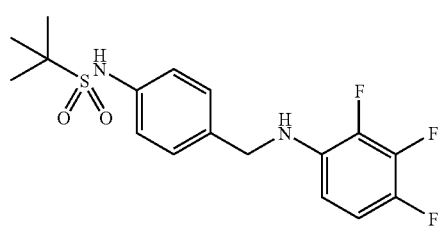
Ig-25
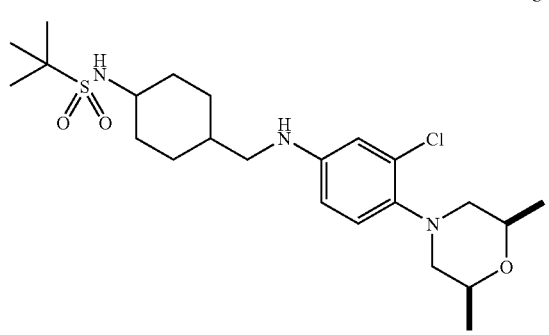
Ig-26
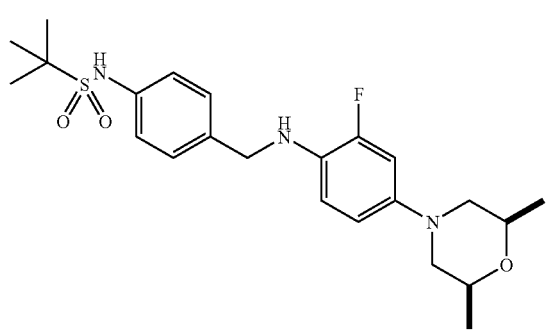
Ig-27
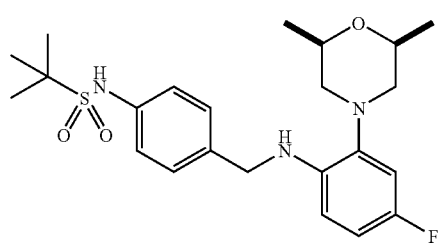
Ig-28
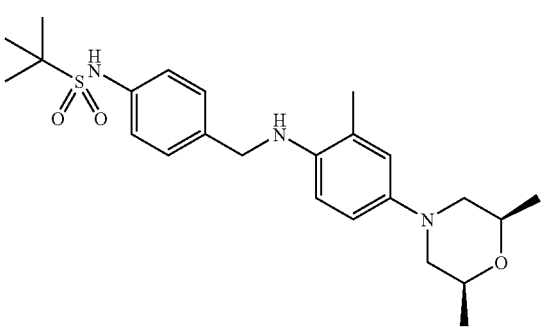
Ig-29
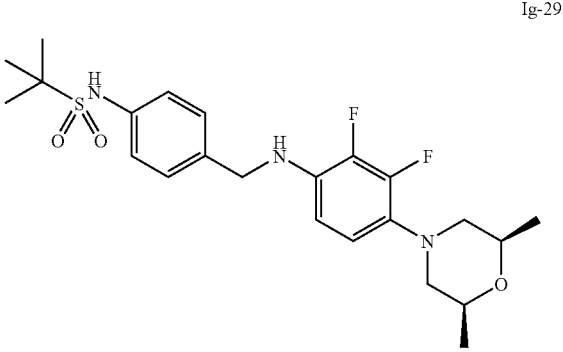
Ig-30
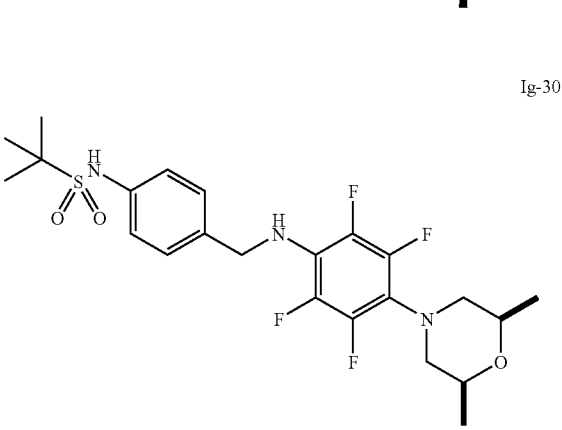
Ig-31
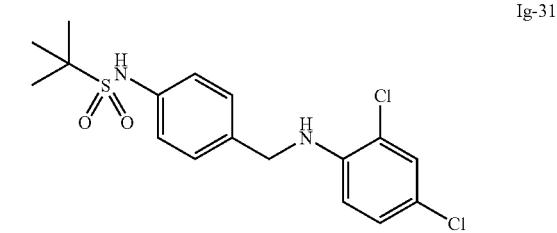
Ig-32
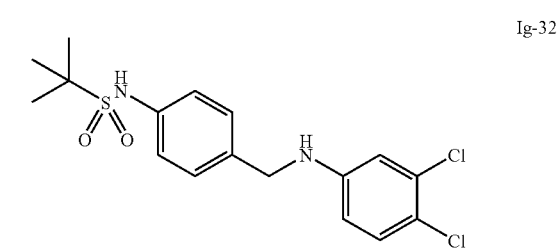

Ig-33
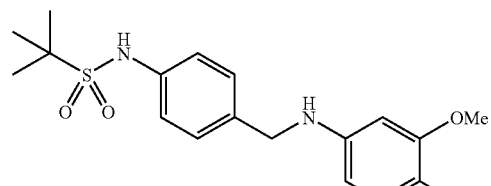
Ig-35
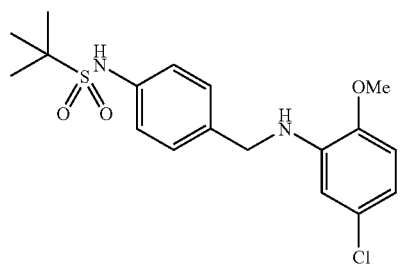
Ig-36
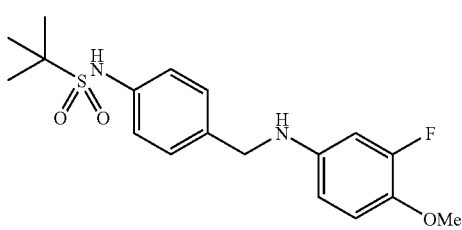
Ig-37
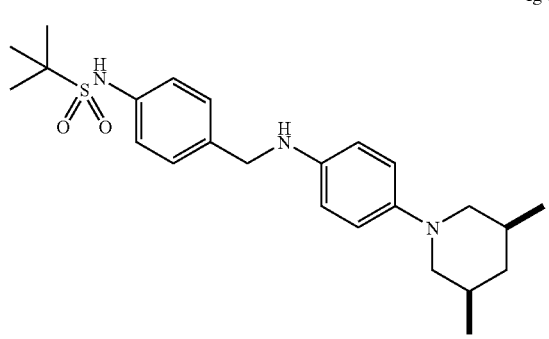
Ig-38
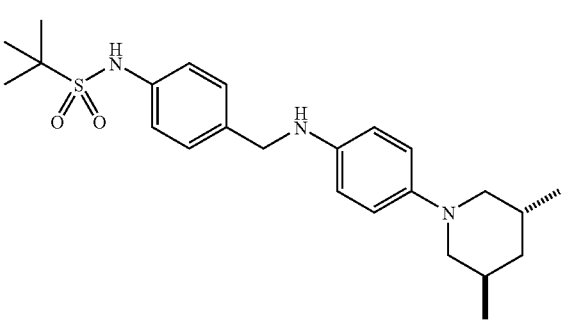
Ig-39
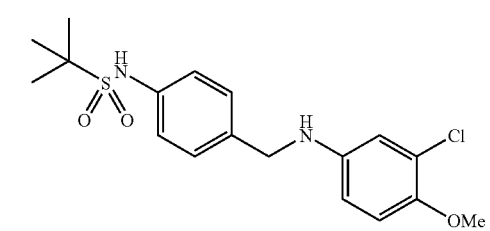
Ig-40
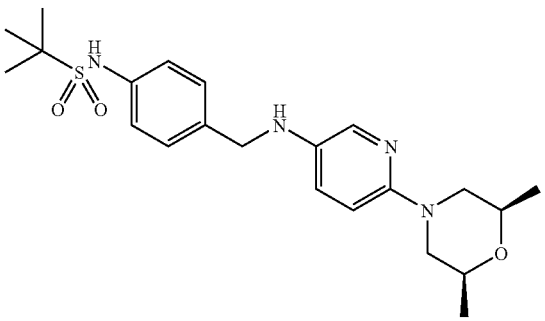
Ig-41
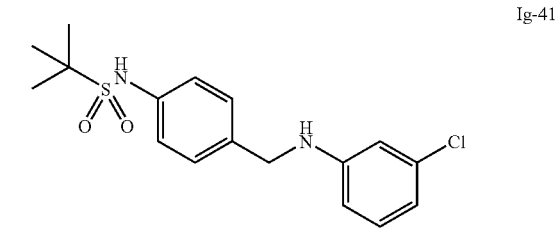
Ig-42
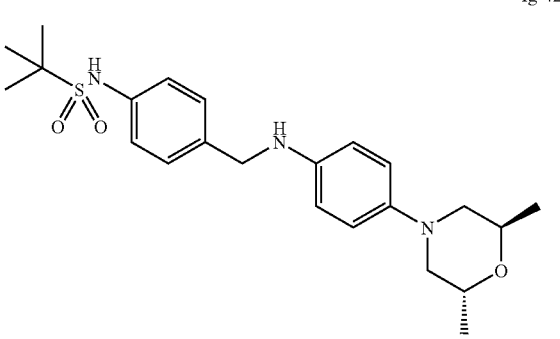
Ig-43
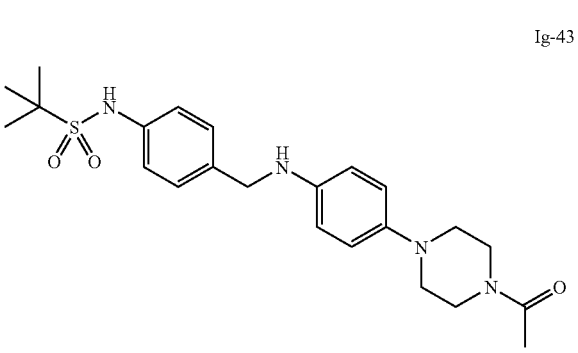
Ig-44
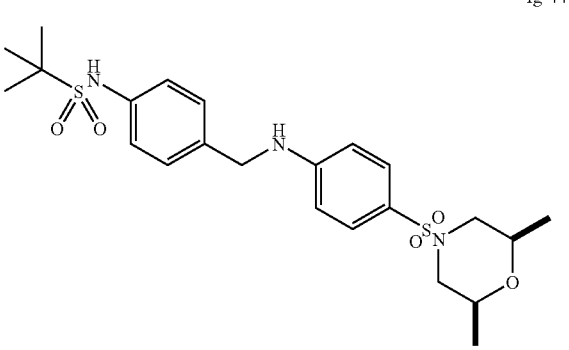

Ig-45
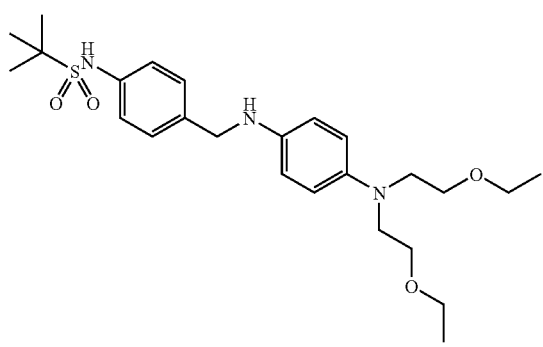
Ig-46
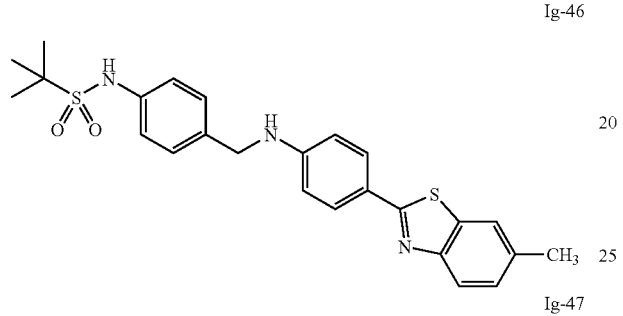
Ig-47
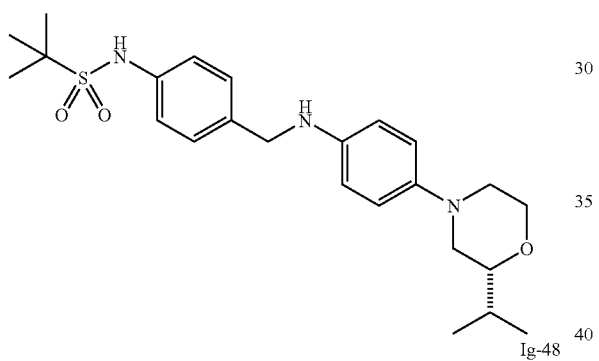
Ig-48
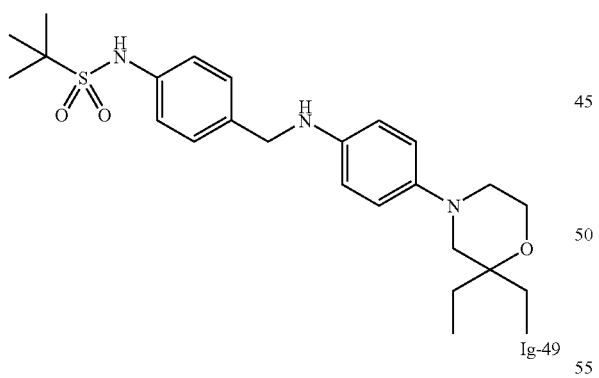
Ig-49
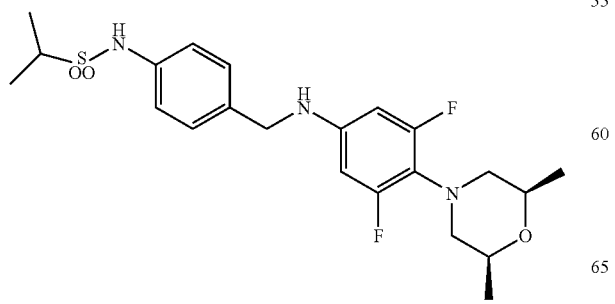
Ig-50
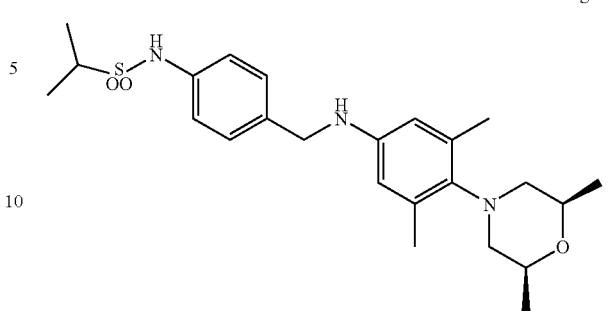
Ig-51
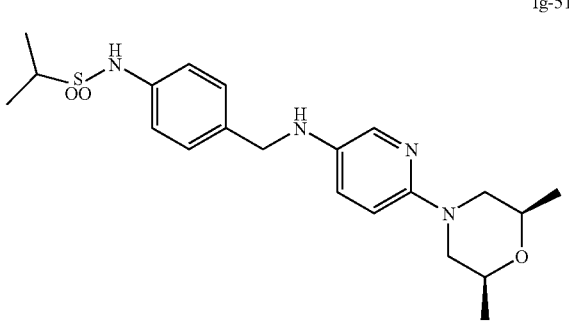
Ig-52
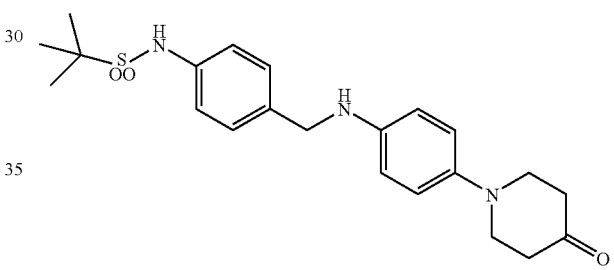
Ig-53
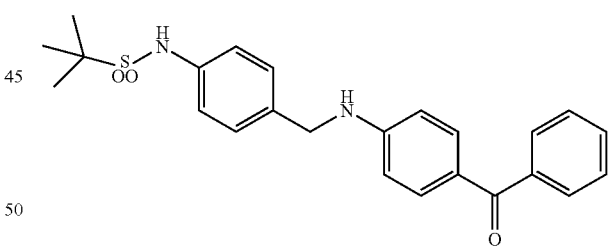
Ig-54
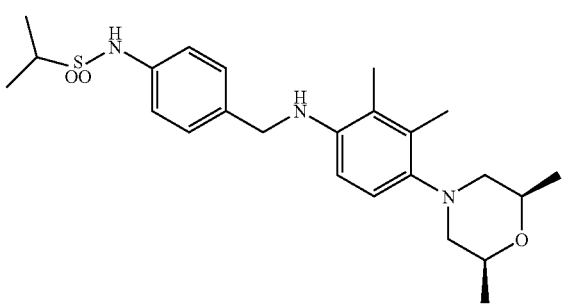

Ig-55
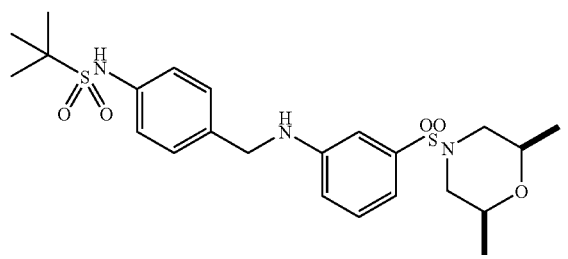
Ig-56
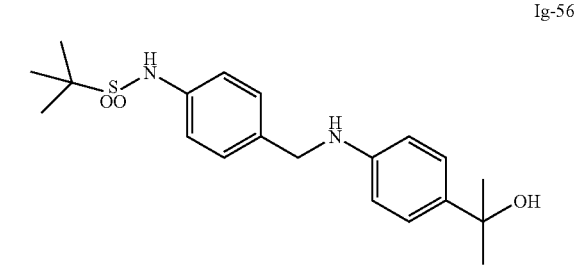
Ig-57
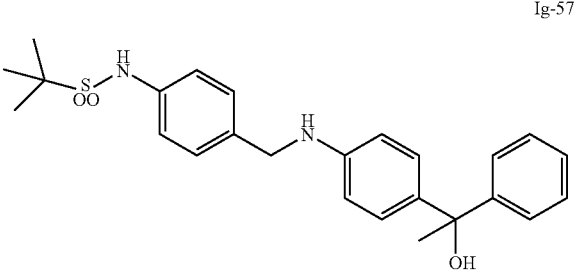
Ig-58
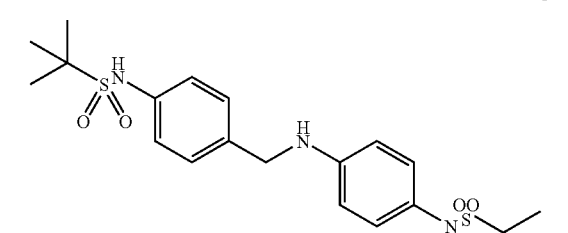
Ig-59
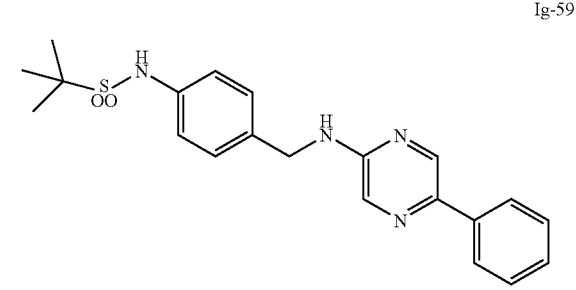
Ig-60
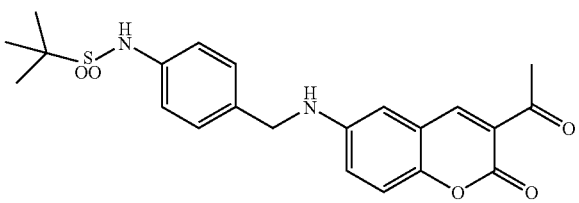
Ig-61
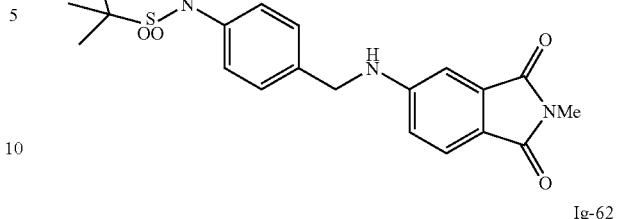
Ig-62
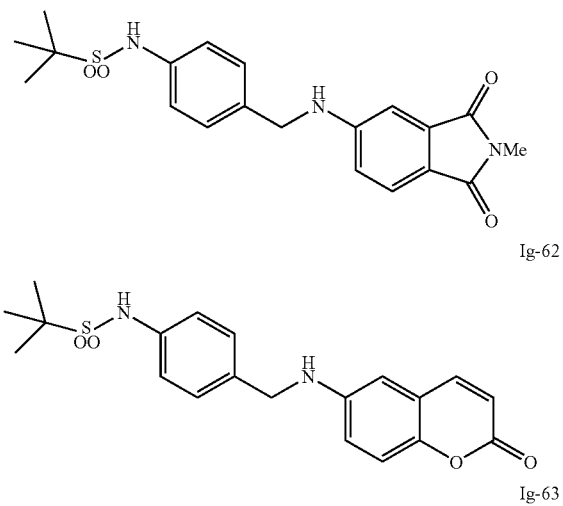
Ig-63
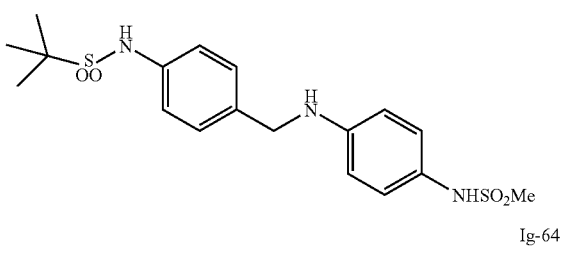
Ig-64
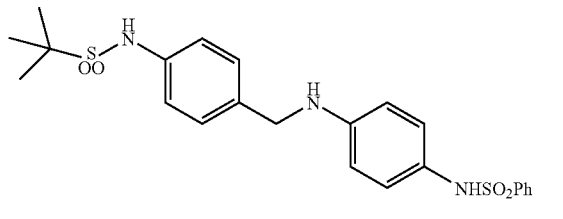
Ig-65
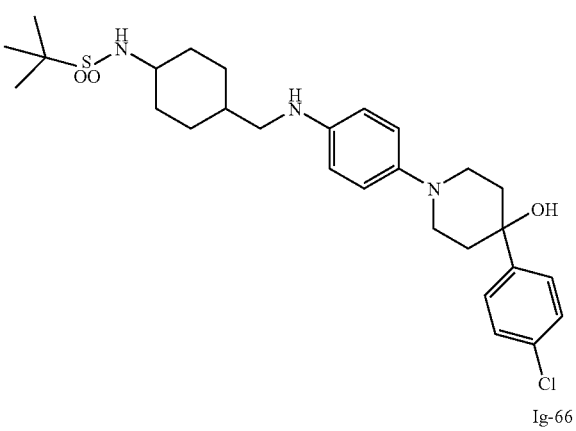
Ig-66
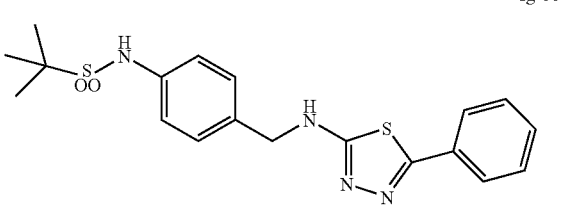

Ig-67
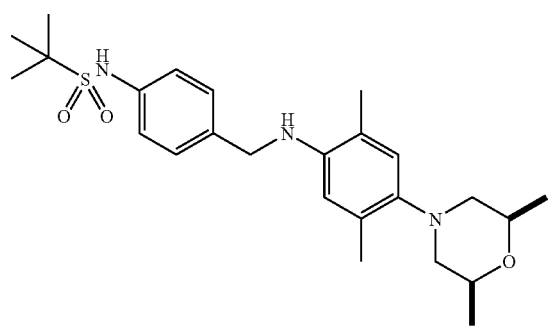
Ig-68
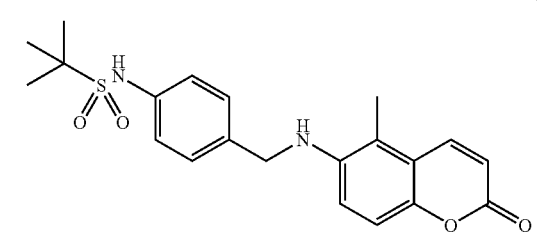
Ig-69
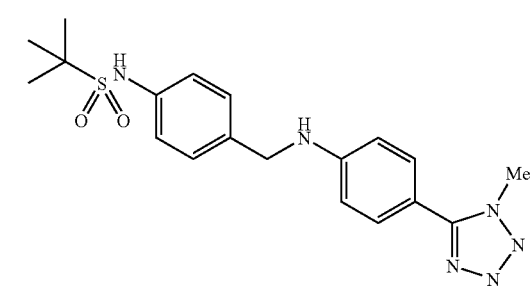
Ig-70
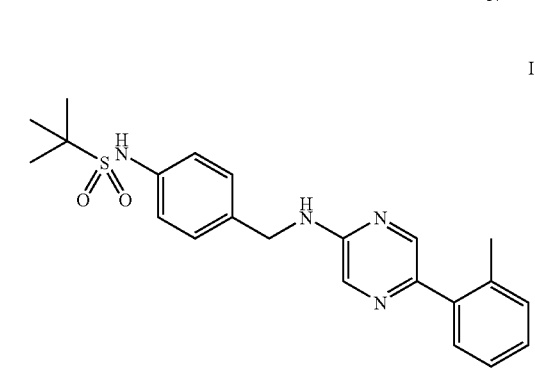
Ig-71
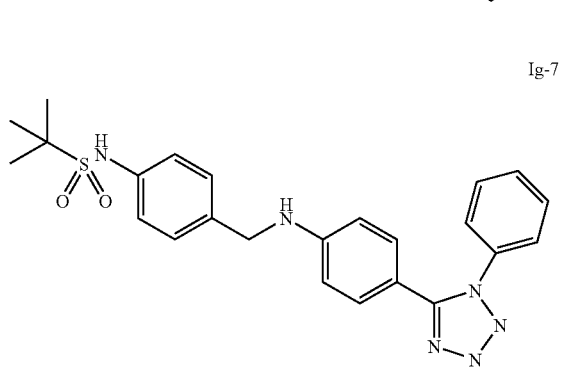
Ig-74
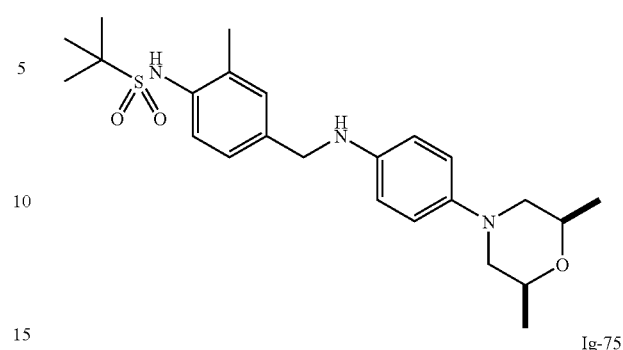
Ig-75
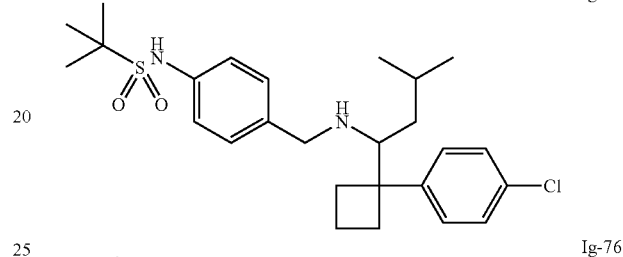
Ig-76
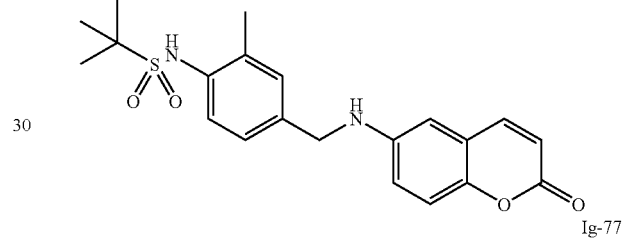
Ig-77
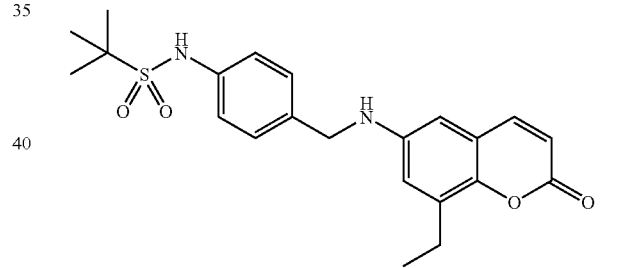
Ig-78
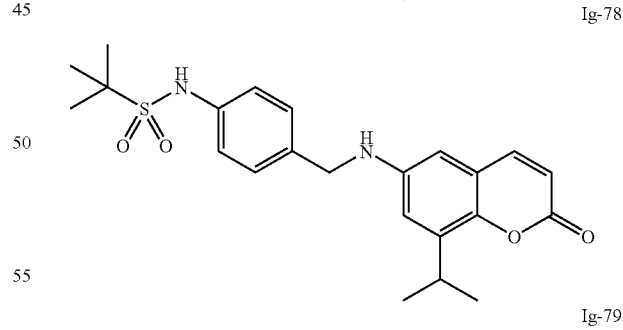
Ig-79
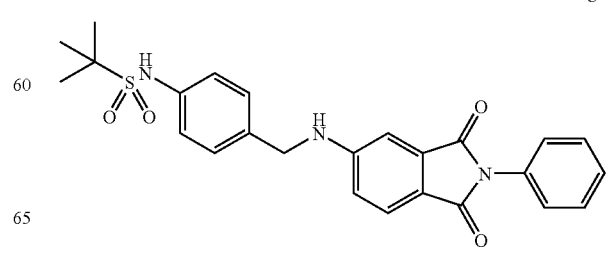

-continued
Ig-80
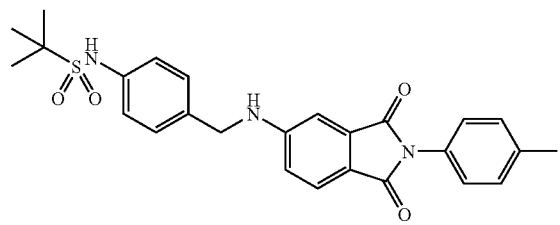
Ig-81
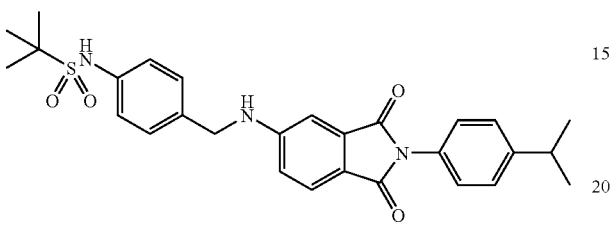
Ig-82
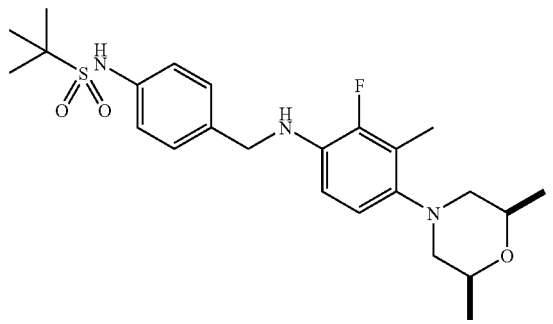
Ig-83
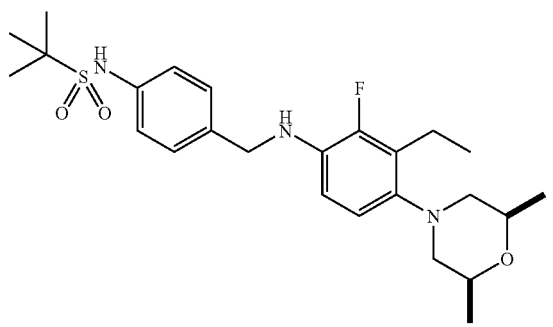
Ig-84
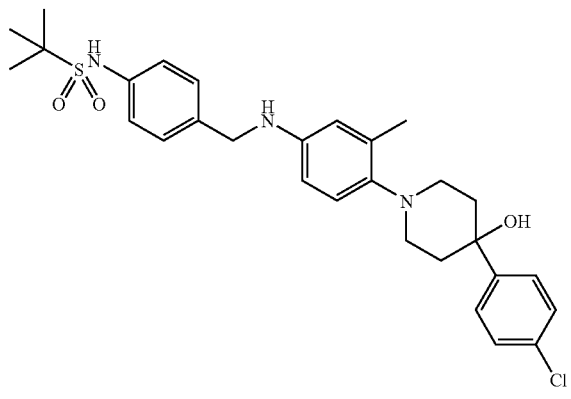
-continued
Ig-85
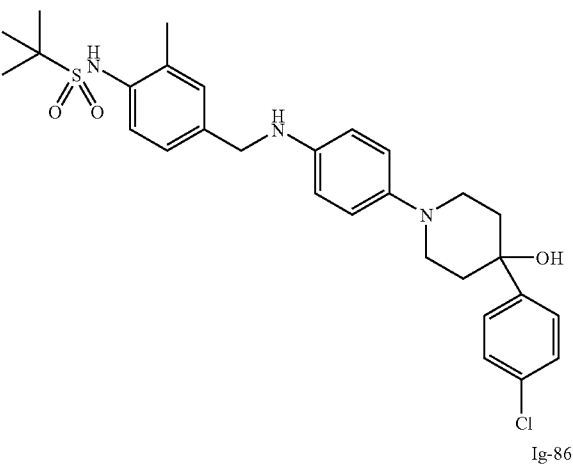
Ig-86
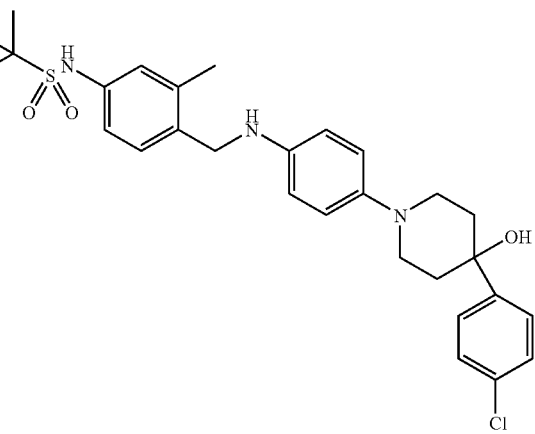
Ig-87
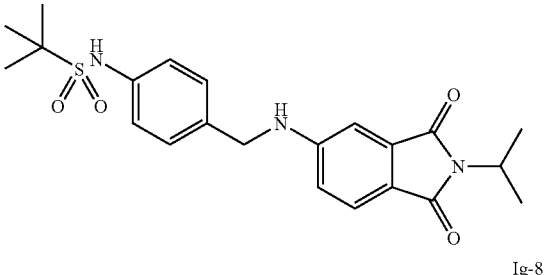
Ig-88
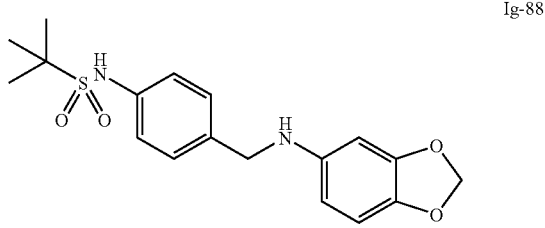
Ig-89

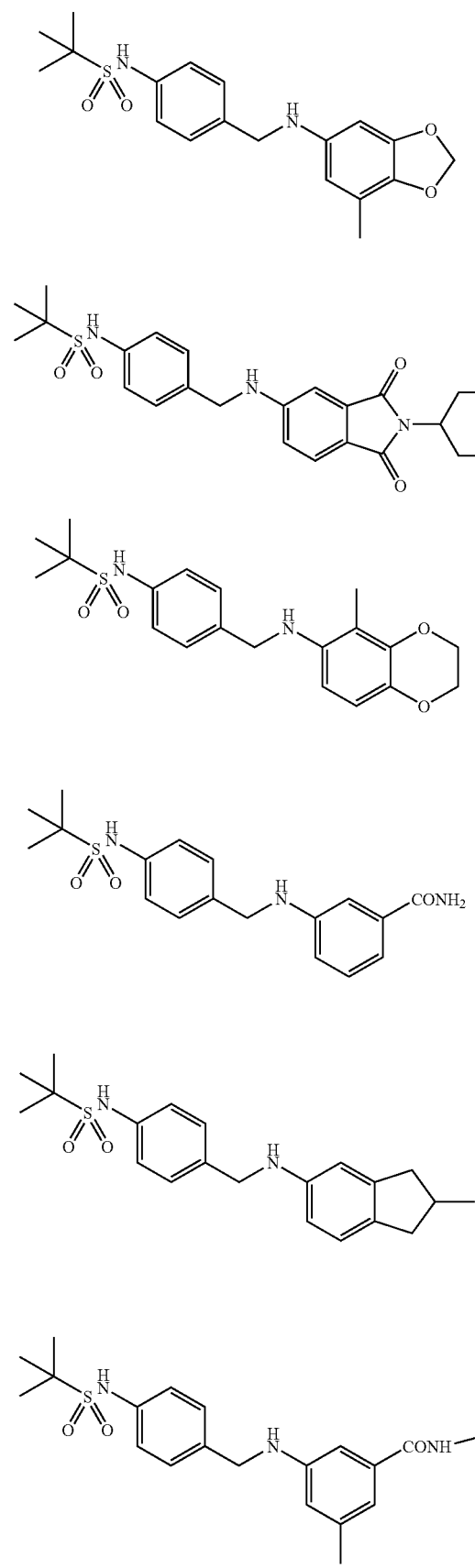
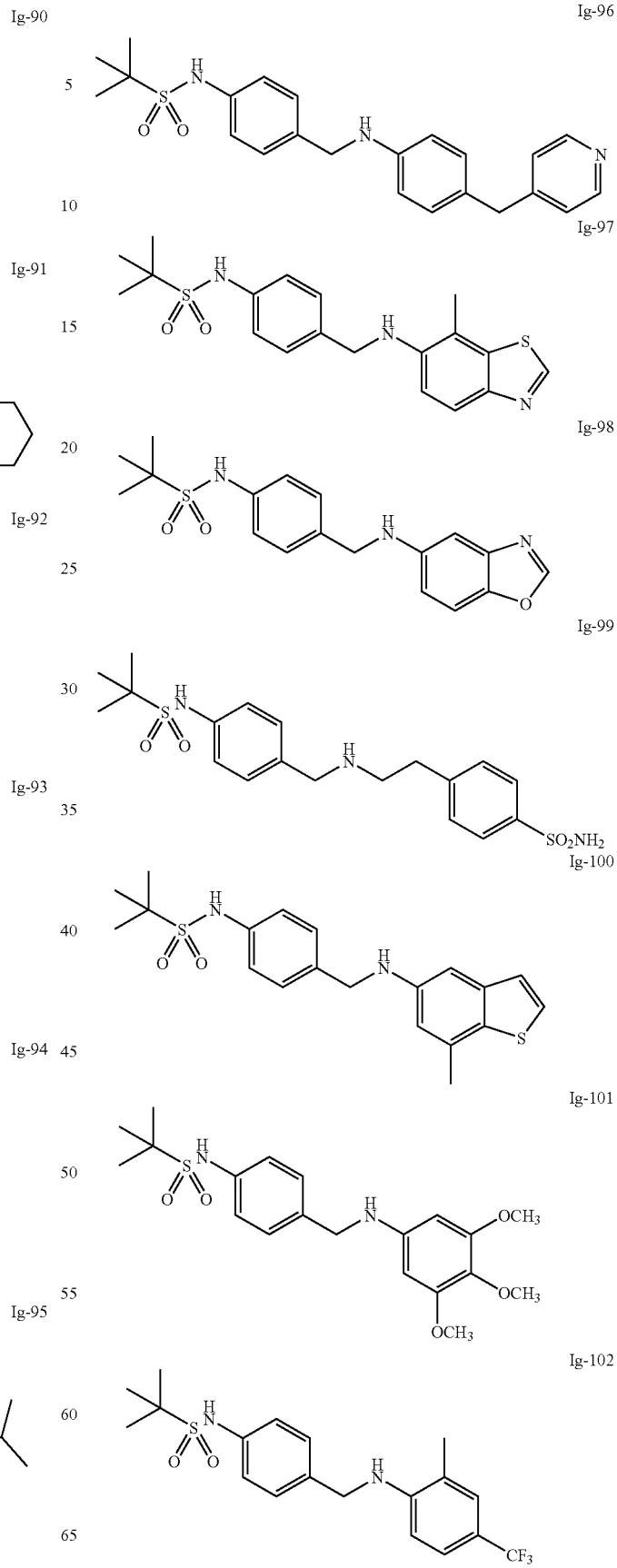

Ig-103
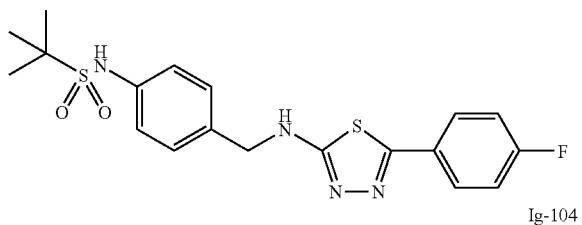
Ig-104
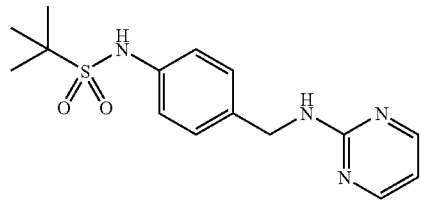
Ig-105
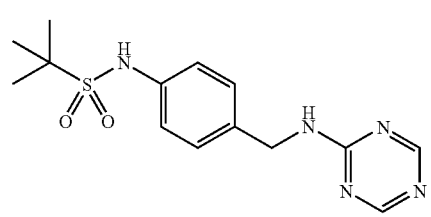
Ig-106
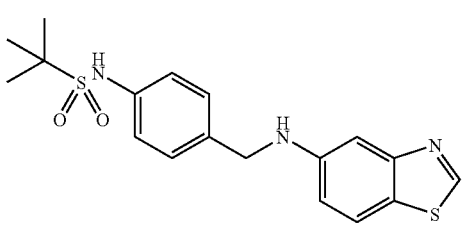
Ig-107
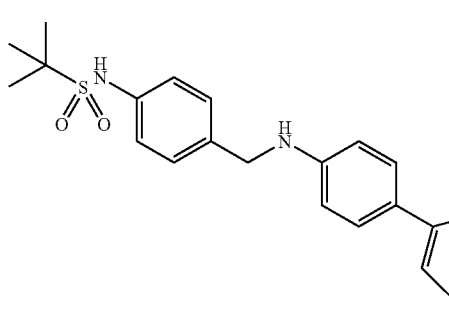
Ig-108
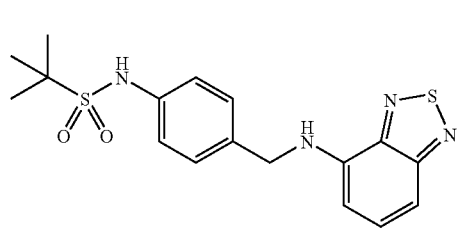
Ig-109
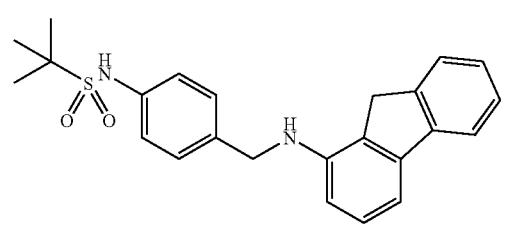
Ig-110
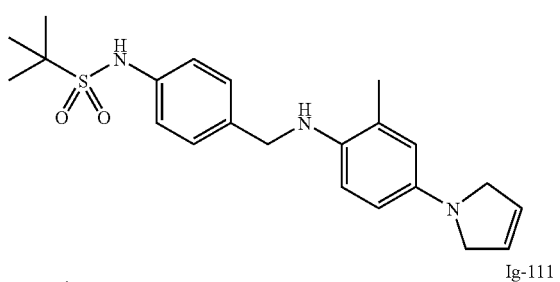
Ig-111
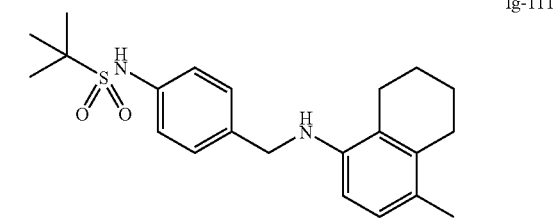
Ig-112
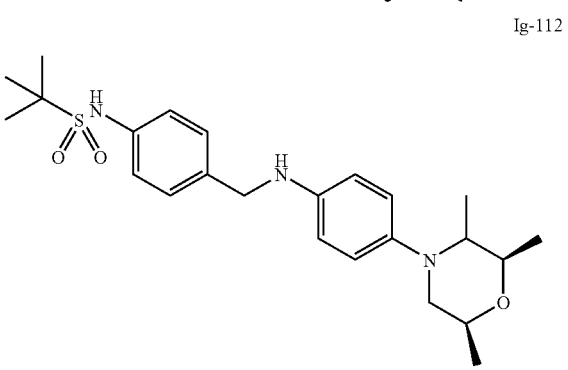
Ig-113
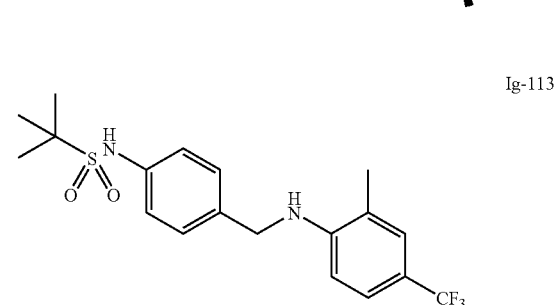
Ig-114
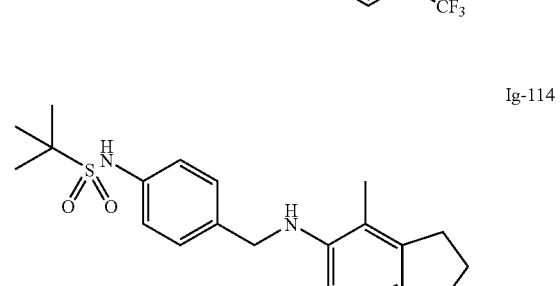
Ig-115

Ig-116
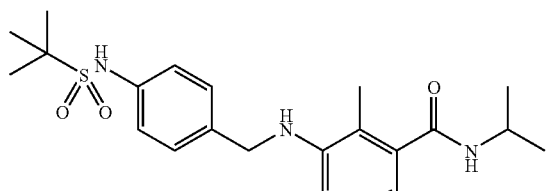
Ig-117
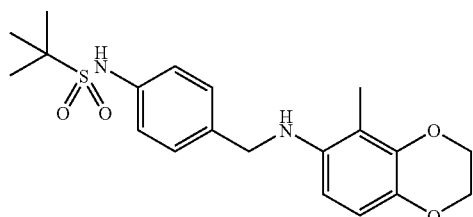
Ig-118
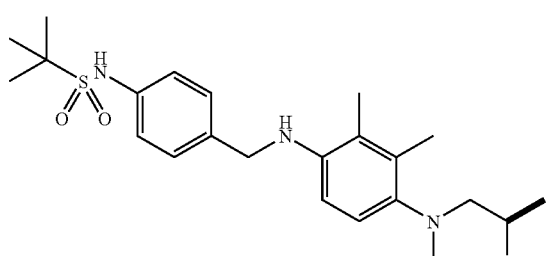
Ig-119
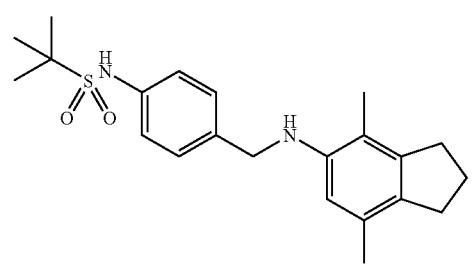
Ig-120
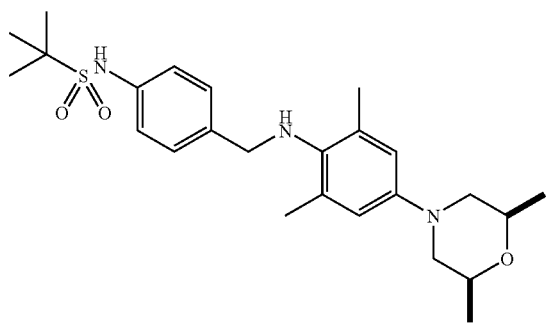
Ig-121
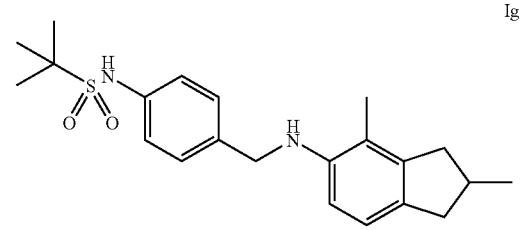
Ig-122
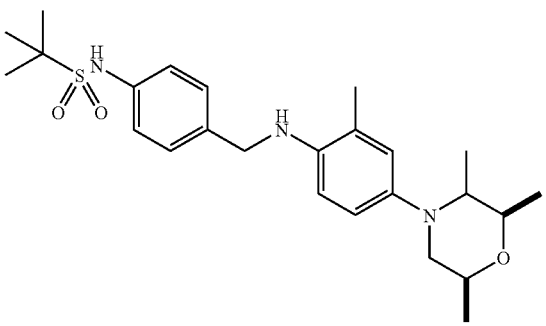
Ig-123
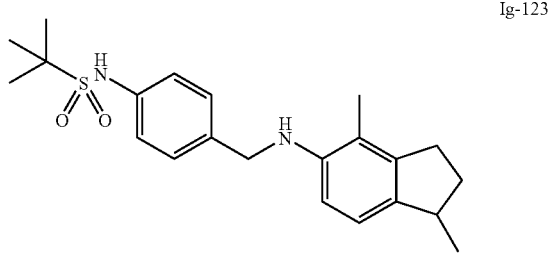
Ig-124
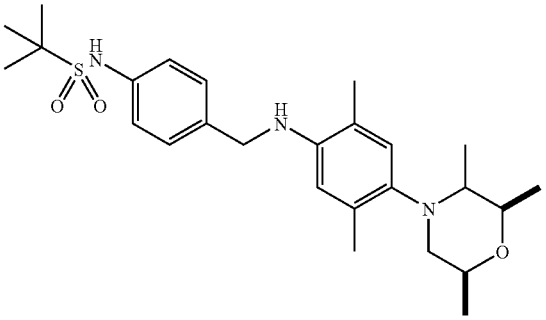
Ig-125
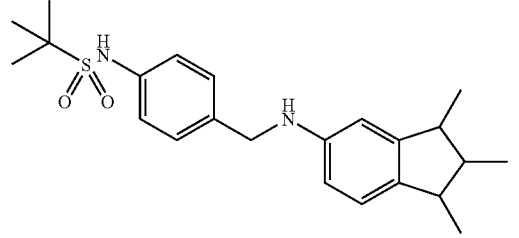
Ig-126

Ig-127
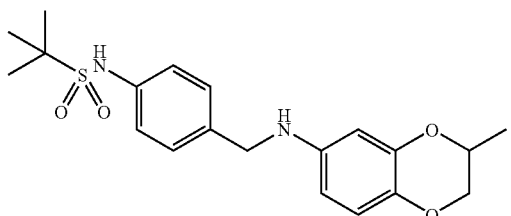
Ig-128
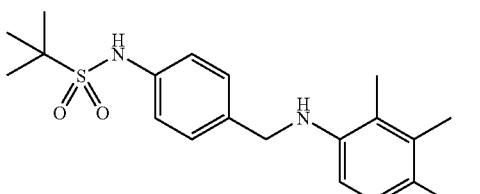
Ig-129
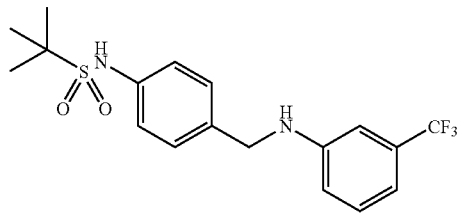
Ig-30
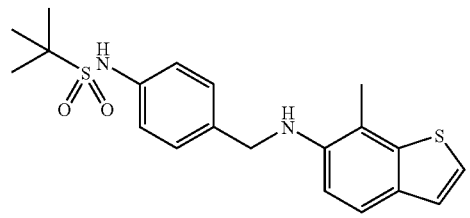
Ig-131
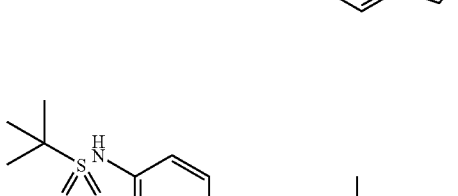
Ig-132
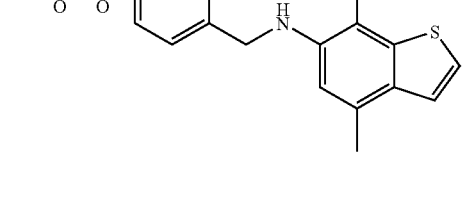
Ig-133
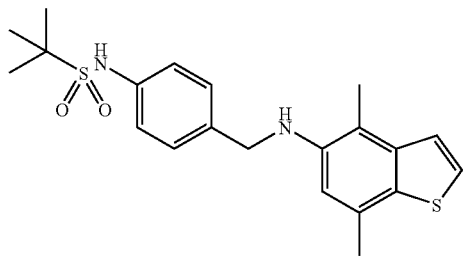
Ig-134
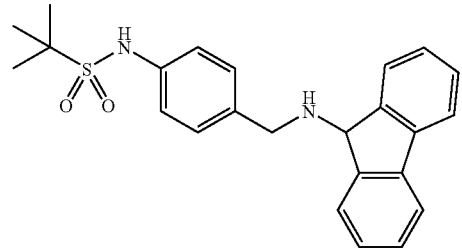
Ig-135
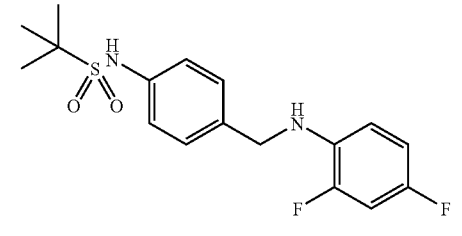
Ig-136
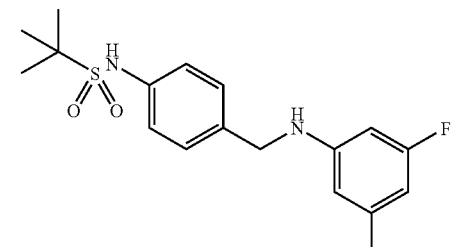
Ig-137
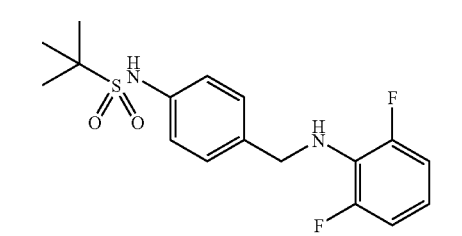
Ig-138
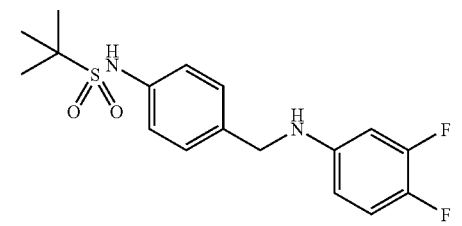
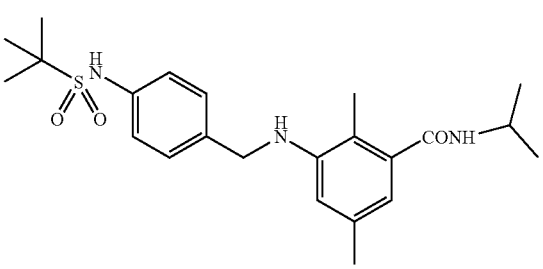

Ig-139
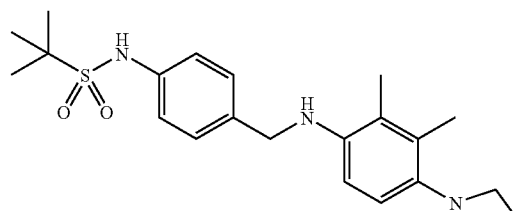
Ig-140
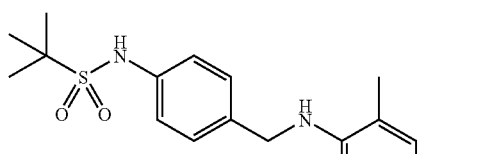
Ig-141
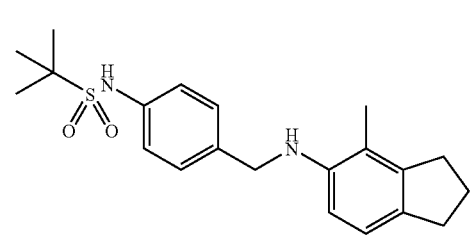
Ig-142
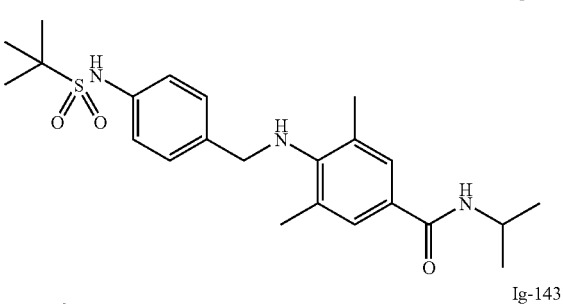
Ig-143
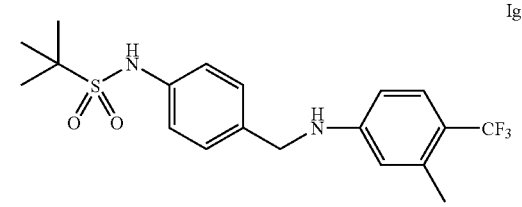
Ig-144
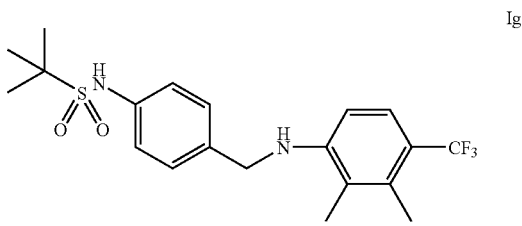
Ig-145
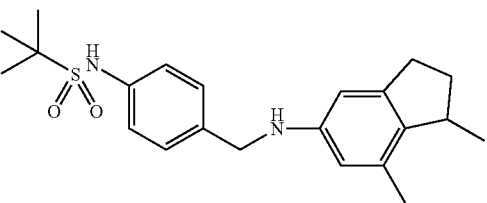
Ig-146
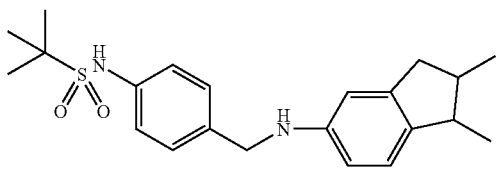
Ig-147
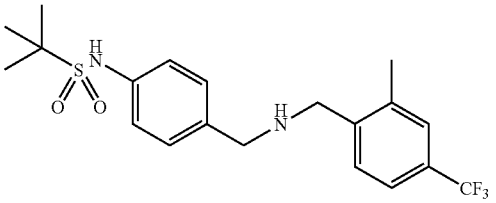
Ig-148
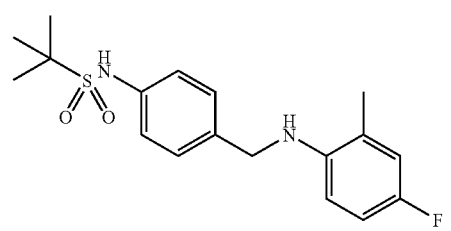
Ig-149
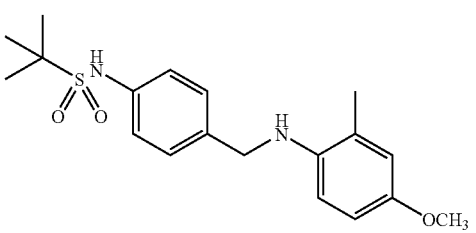
Ig-150
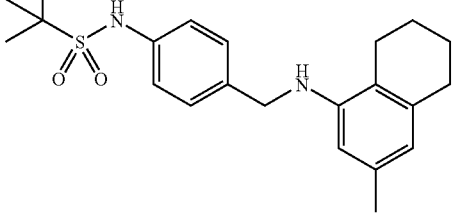
Ig-151
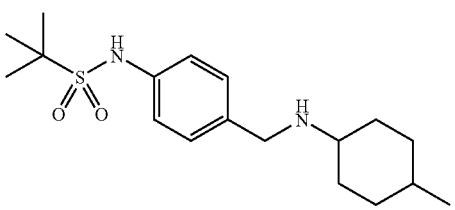
Ig-152
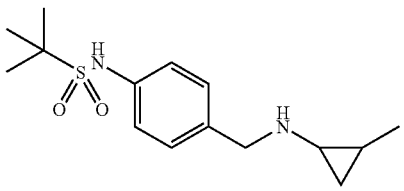

Ig-153
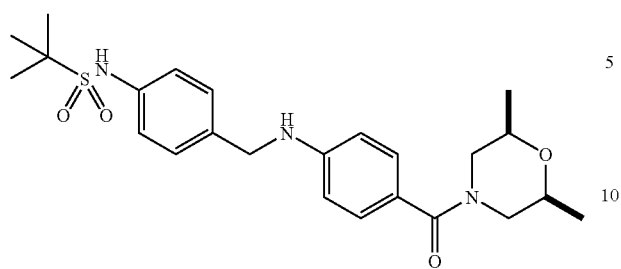
Ig-154
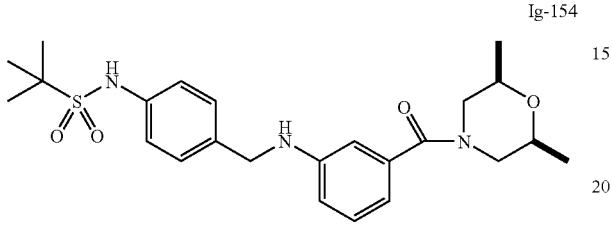
Ig-155
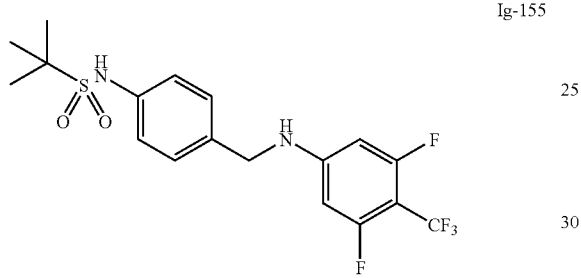
Ig-156
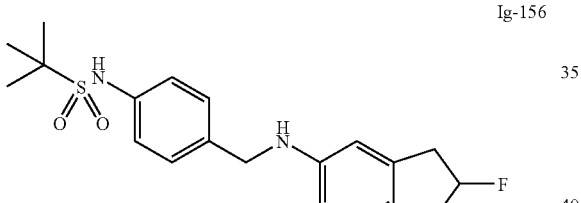
Ig-157
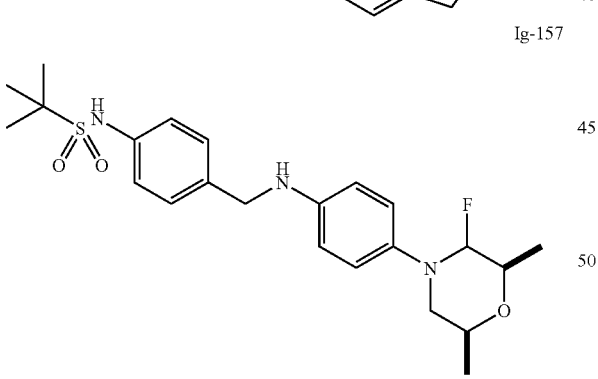
Ig-158
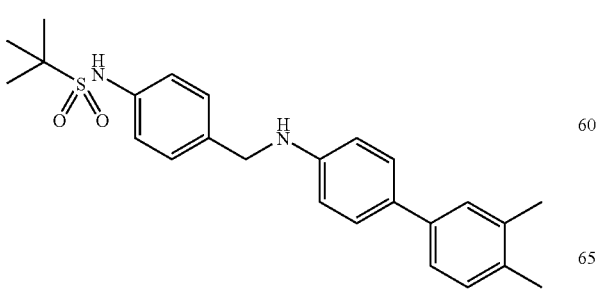
Ig-159
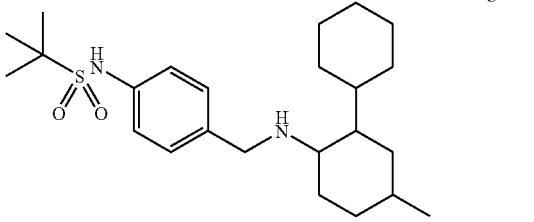
Ig-160
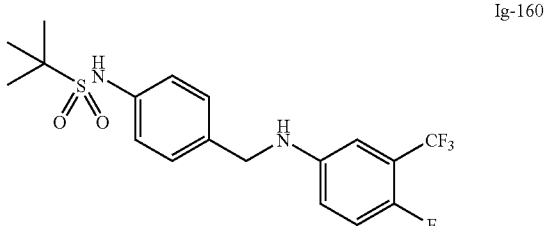
Ig-161
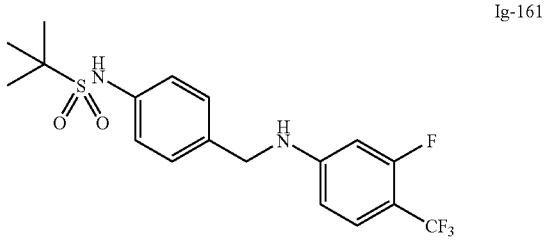
Ig-162
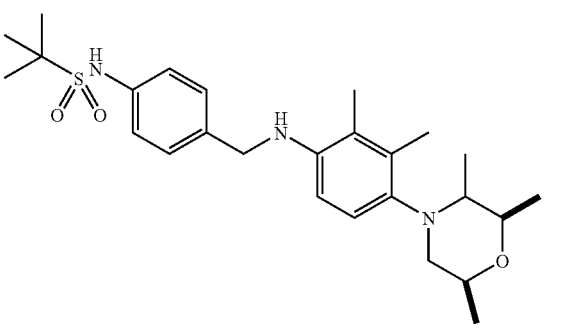
Ig-163
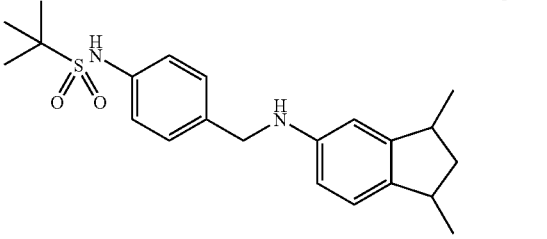
Ig-164
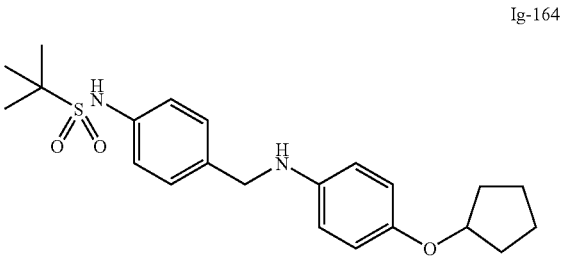

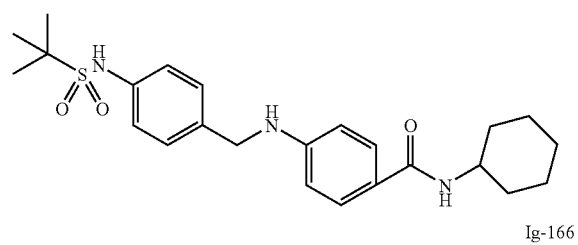
Ig-165
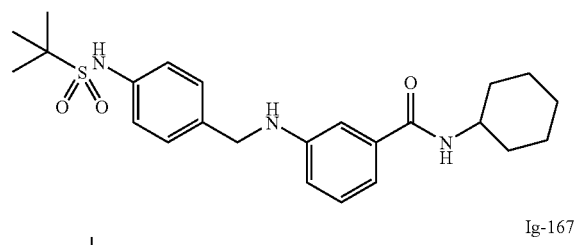
Ig-166
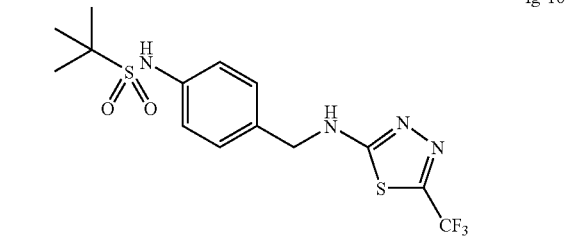
Ig-167
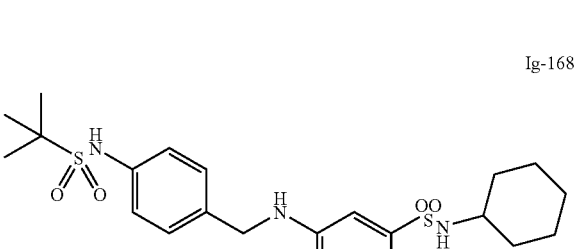
Ig-168
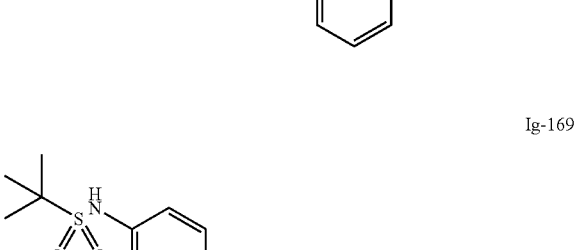
Ig-169
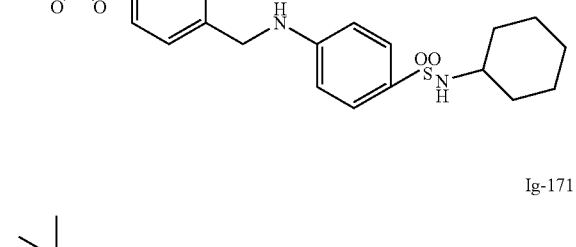
Ig-171
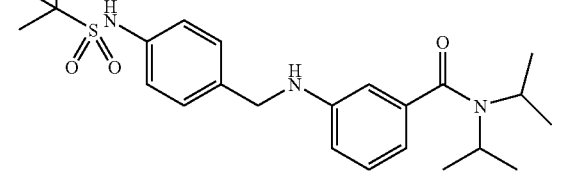
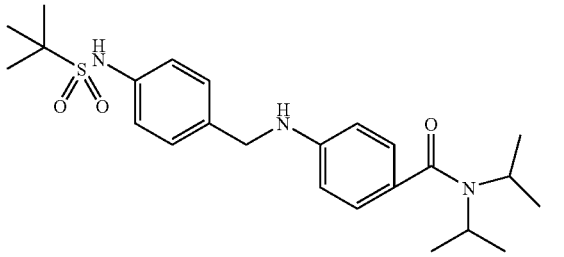
Ig-172
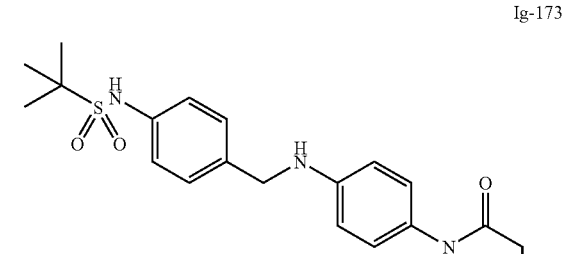
Ig-173
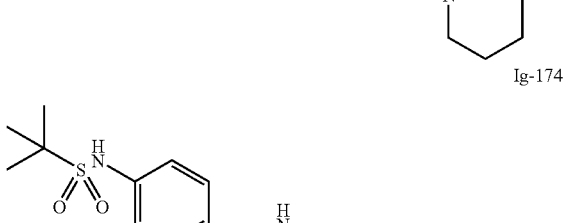
Ig-174
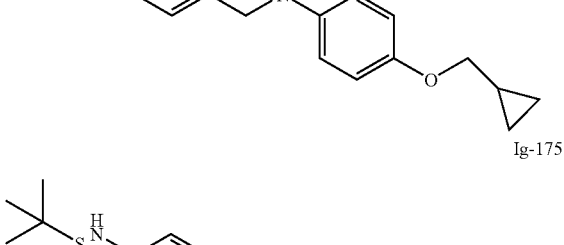
Ig-175
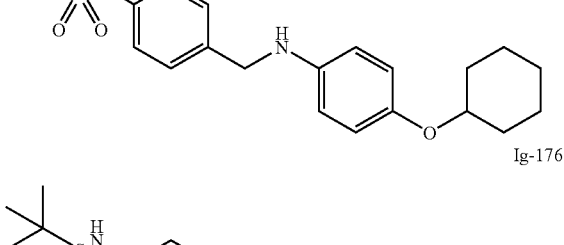
Ig-176
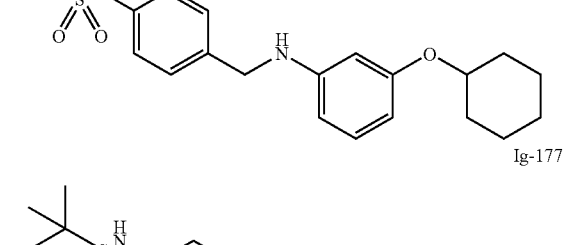
Ig-177
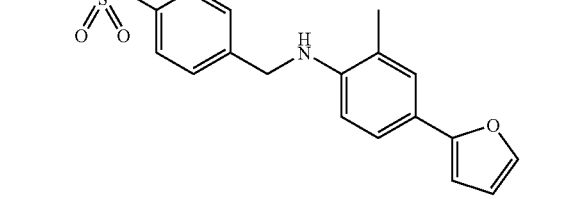

Ig-178
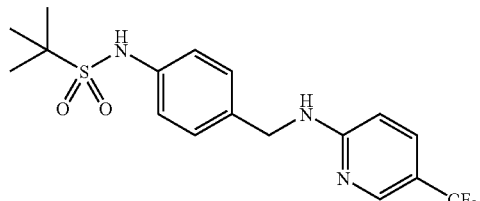
Ig-179
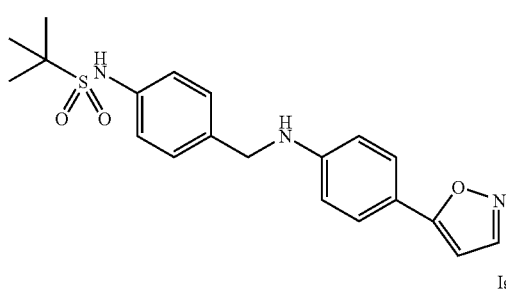
Ig-180
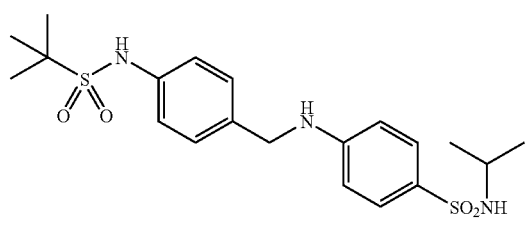
Ig-181
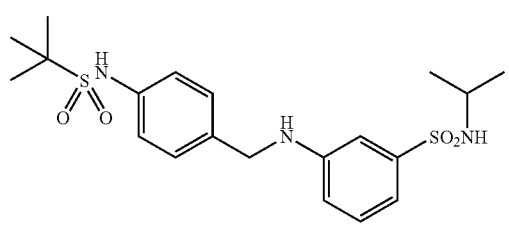
Ig-182
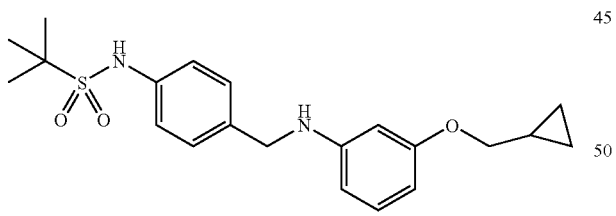
Ig-183
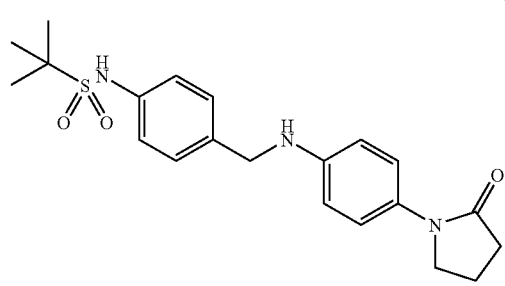
Ig-184
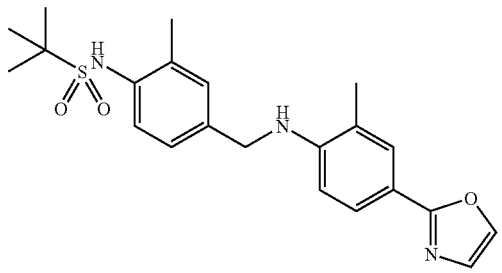
Ig-185
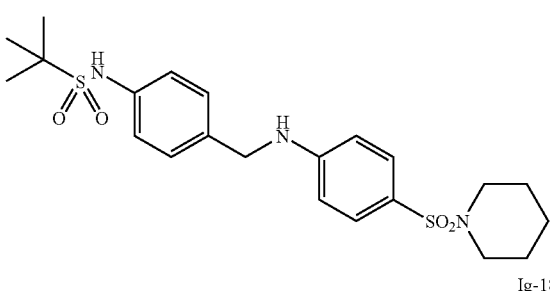
Ig-186
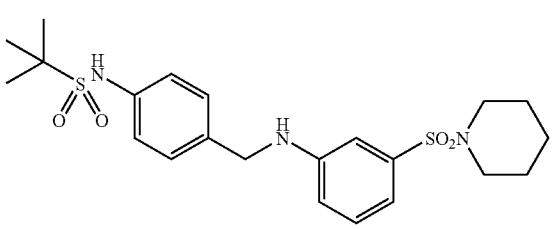
Ig-187
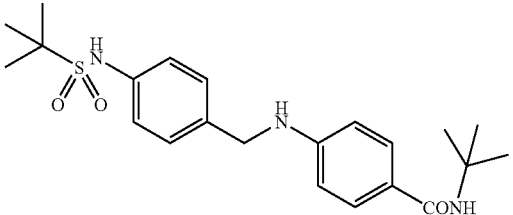
Ig-188
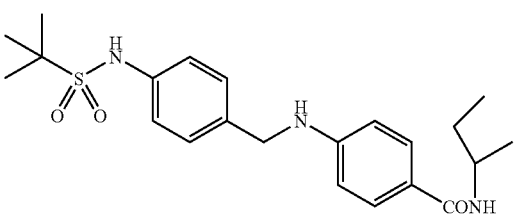
Ig-189
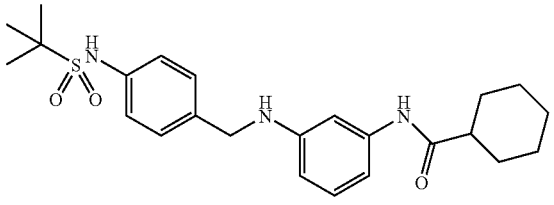

Ig-190
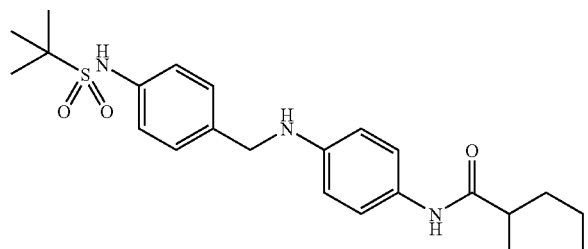
Ig-191
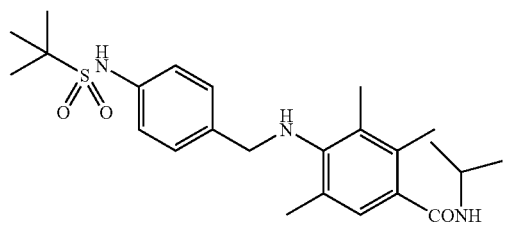
Ig-192
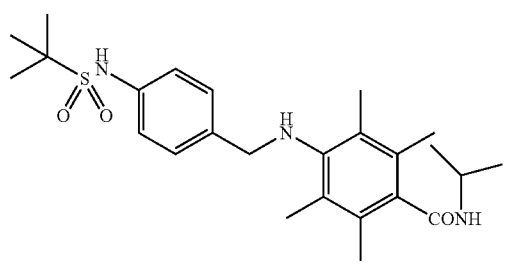
Ig-193
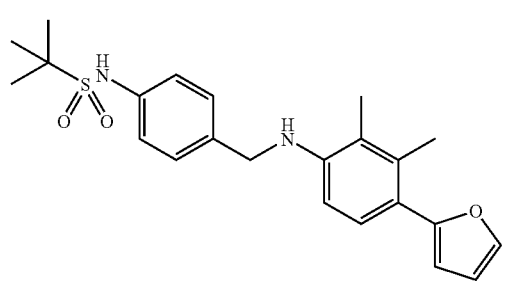
Ig-194
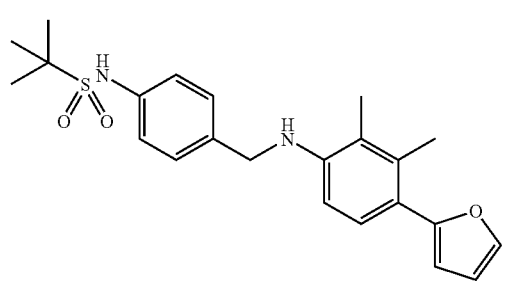
Ig-195
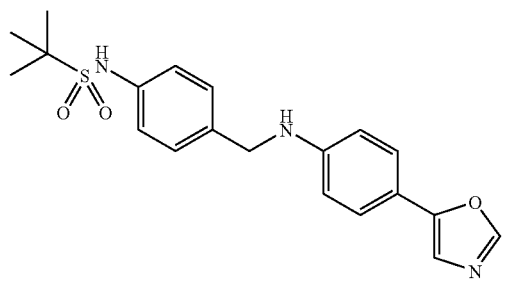
Ig-196
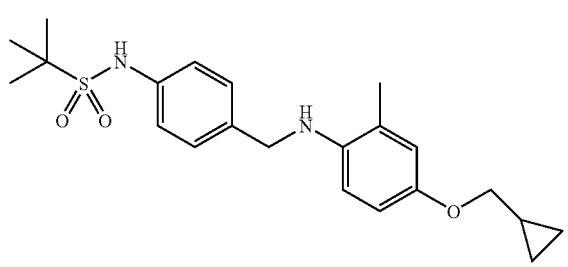
Ig-197
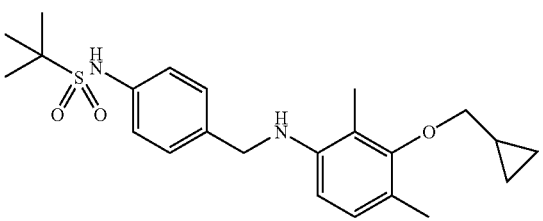
Ig-198
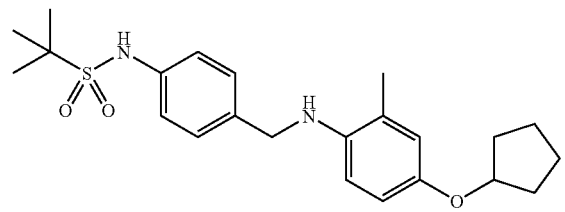
Ig-199
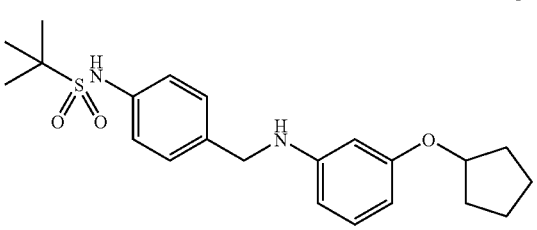
Ig-200
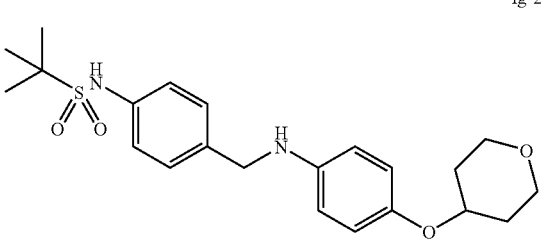

Ig-201
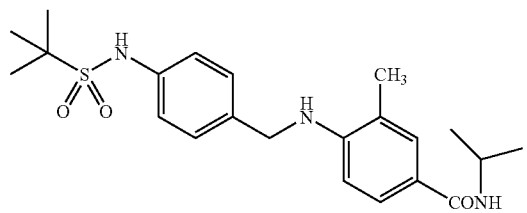
Ig-202
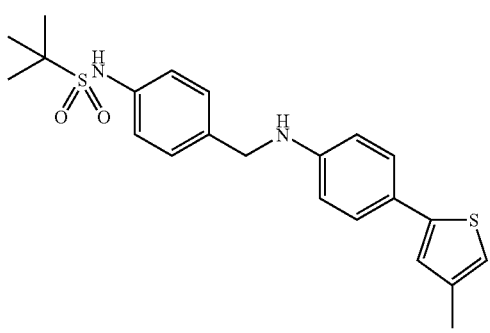
Ig-203
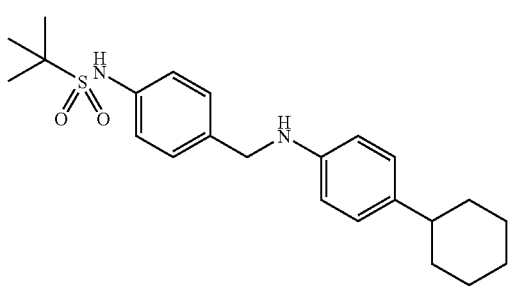
Ig-204
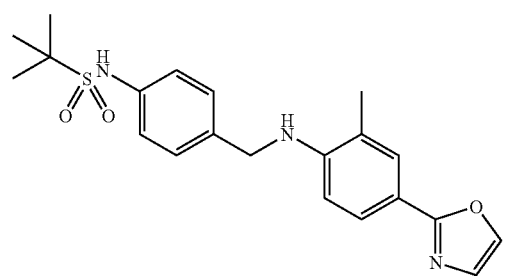
Ig-205
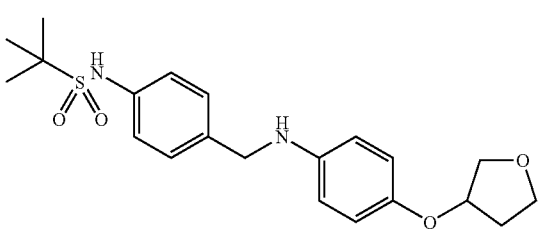
Ig-206
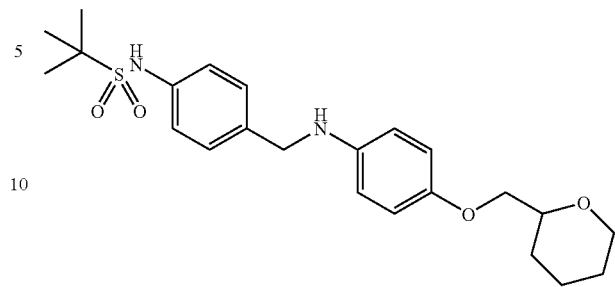
Ig-207
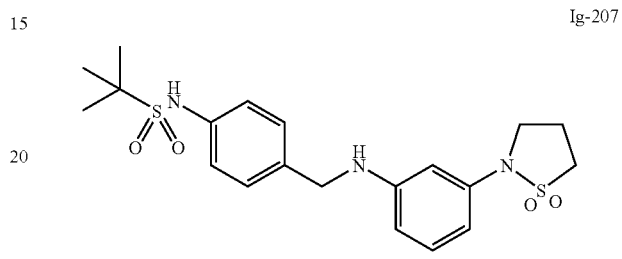
Ig-208
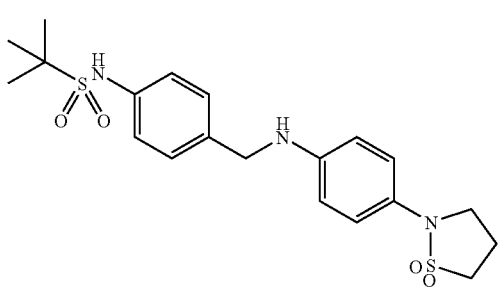
Ig-209
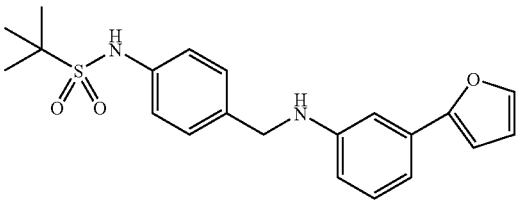
Ig-210
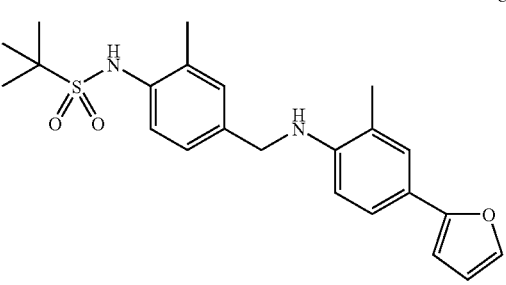

Ig-211
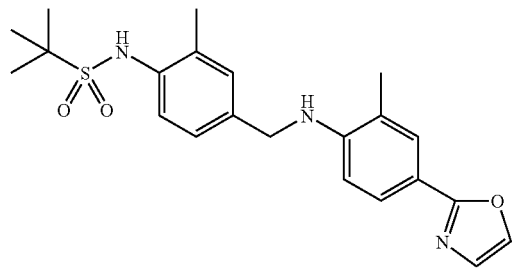
Ig-212
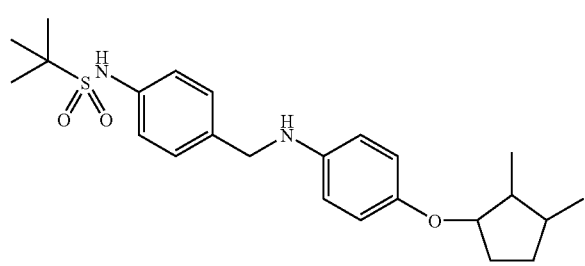
Ig-213
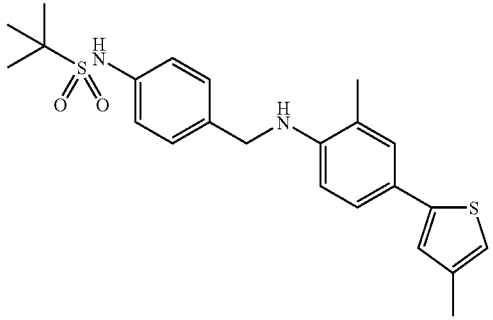
Ig-214
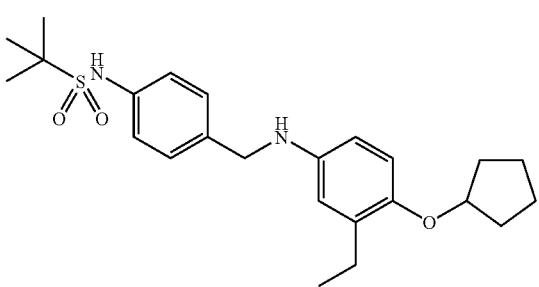
Ig-215
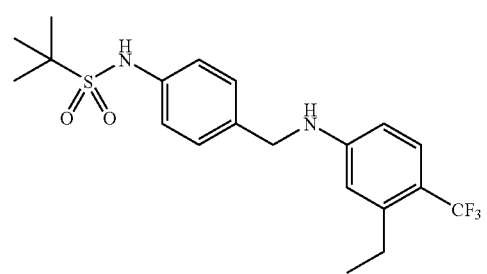
Ig-216
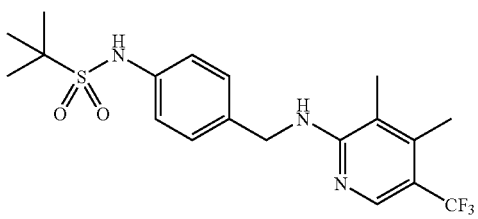
Ig-217
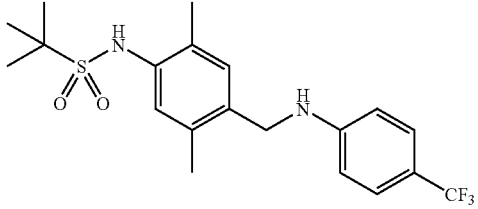
Ig-220
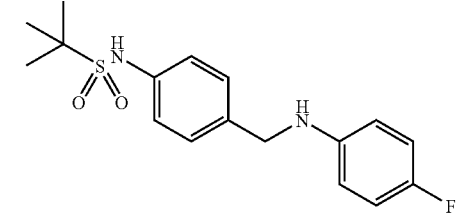
Ig-221
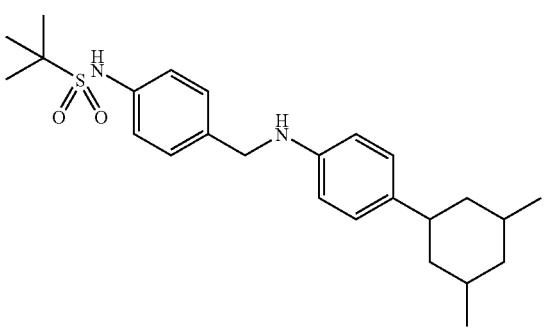
Ig-222
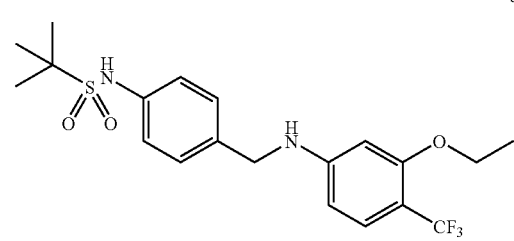
Ig-223
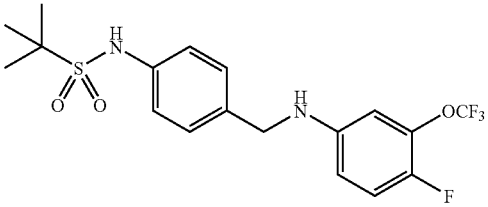

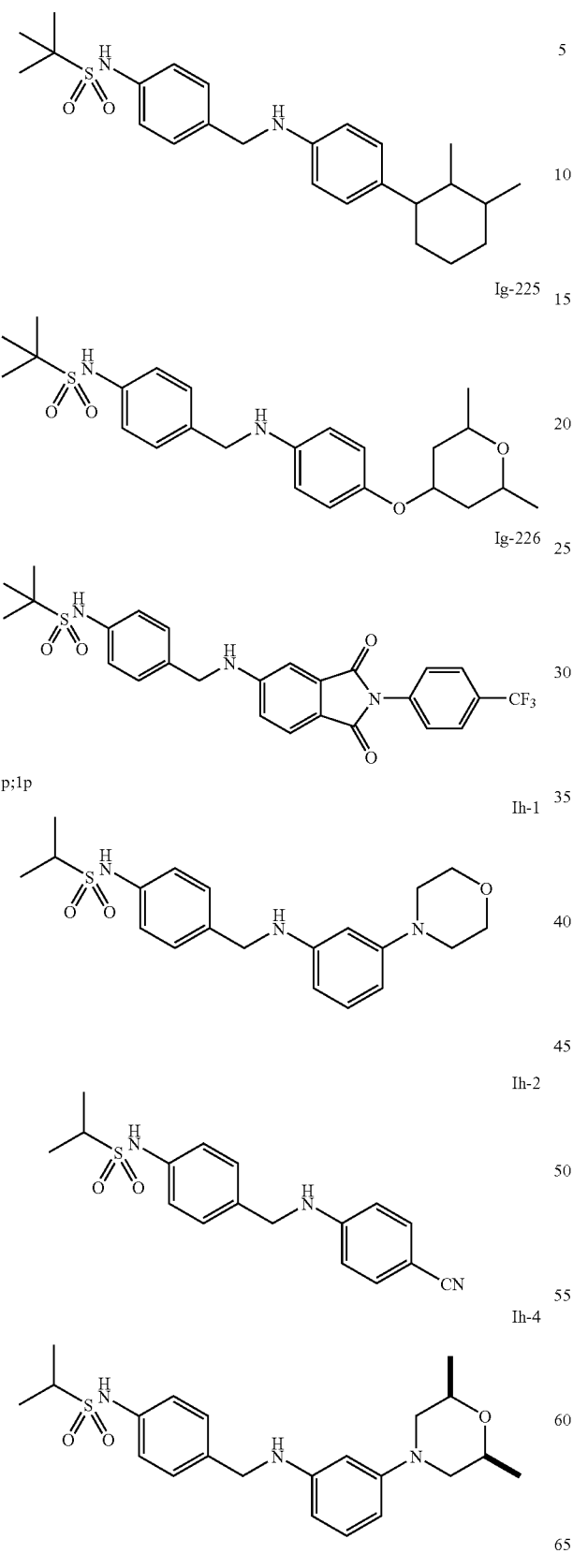

Ih-13 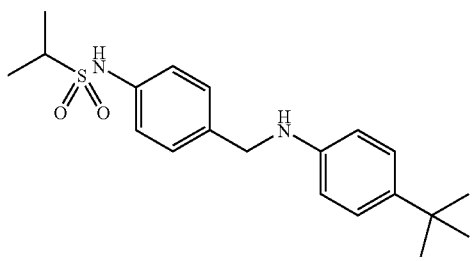
Ih-14 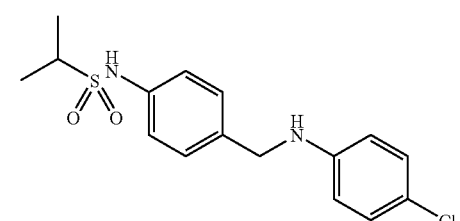
Ih-16 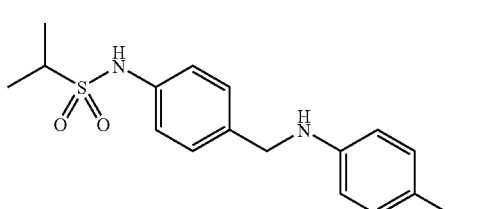
Ih-17 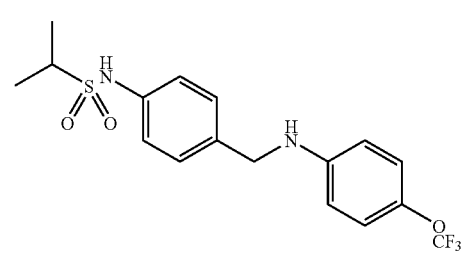
Ih-18 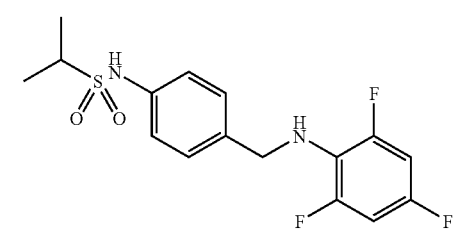
Ih-19 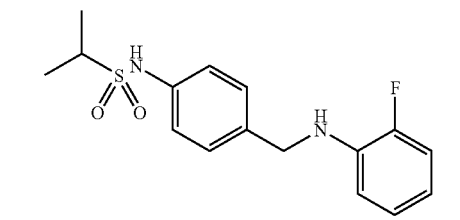
Ih-20 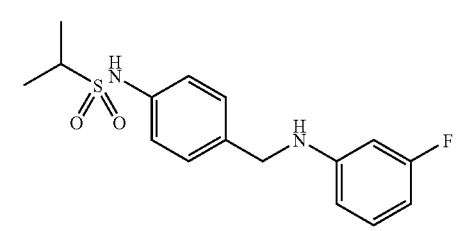
Ih-21 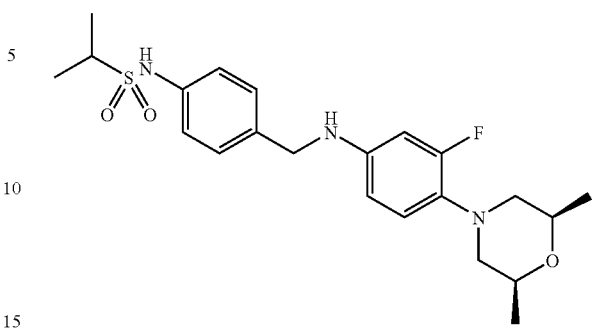
Ih-22 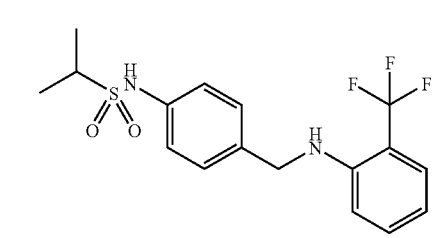
Ih-23 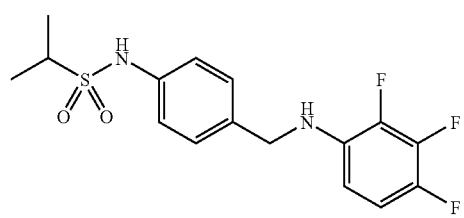
Ih-24 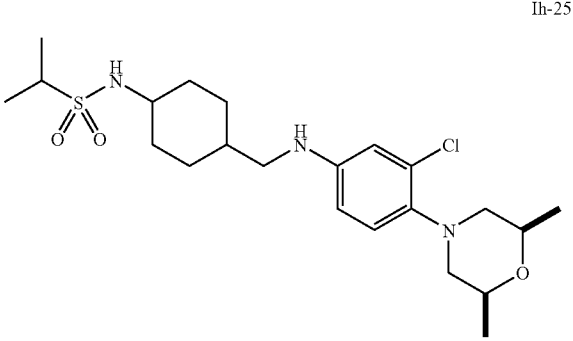
Ih-25

Ih-26
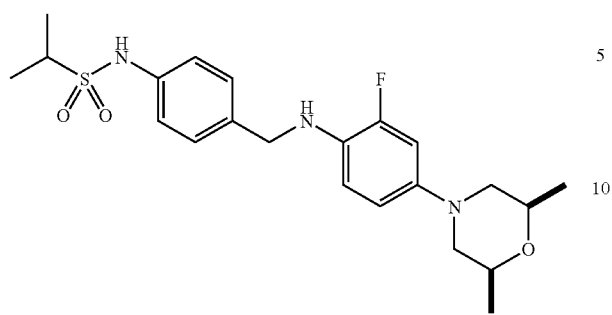
Ih-27
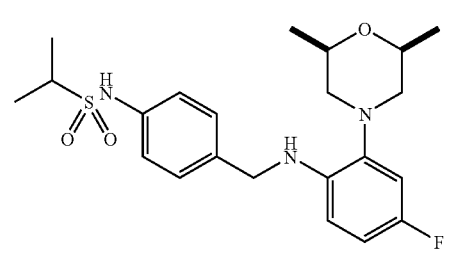
Ih-28
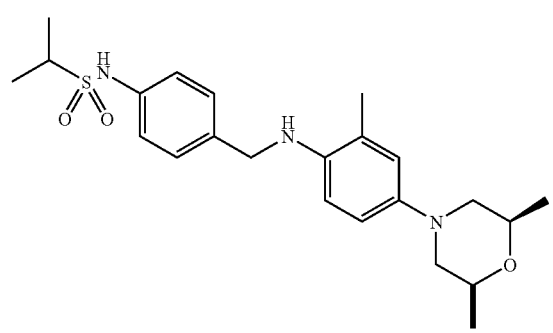
Ih-29
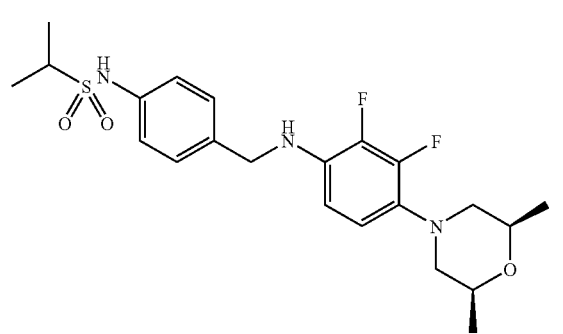
Ih-30
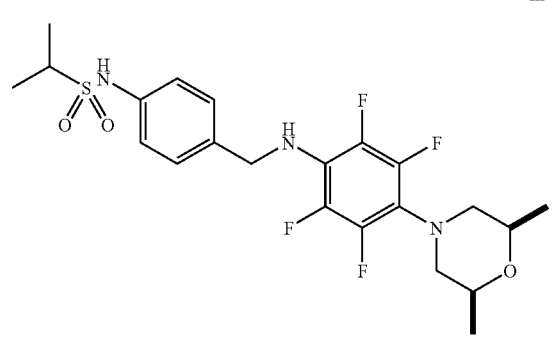
Ih-31
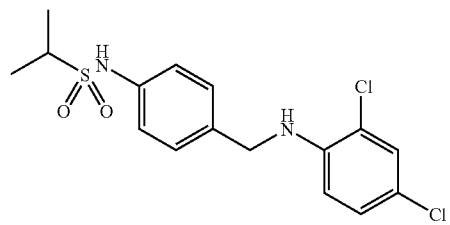
Ih-32
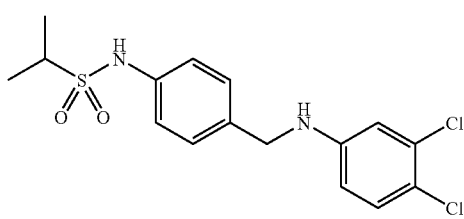
Ih-33
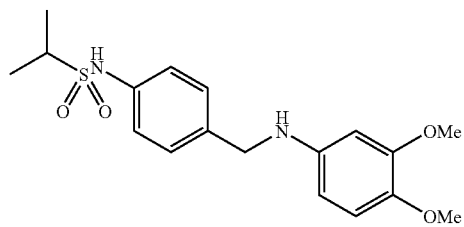
Ih-35
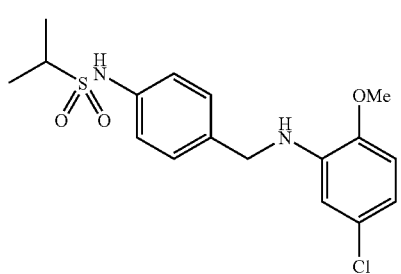
Ih-36
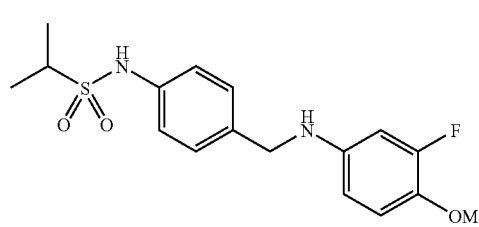
Ih-37
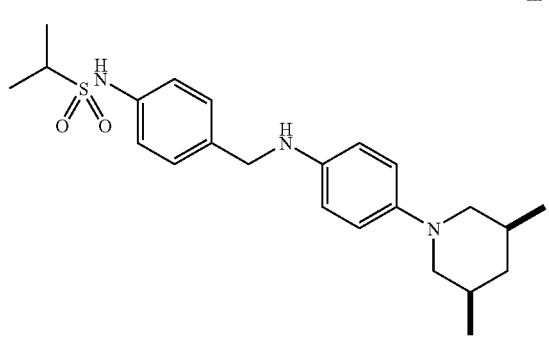

329
-continued
Ih-38
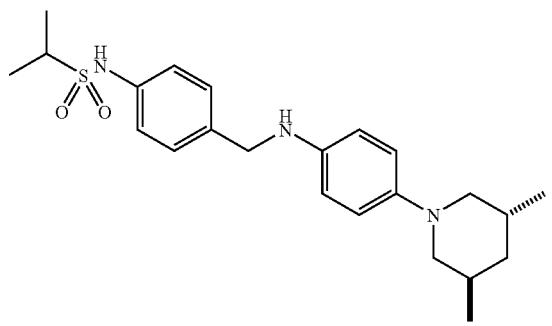
Ih-39
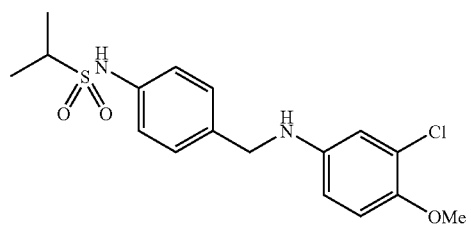
Ih-40
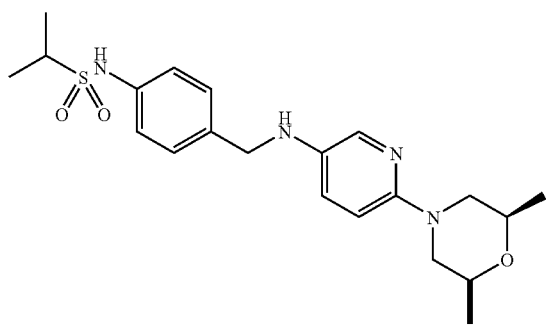
Ih-41
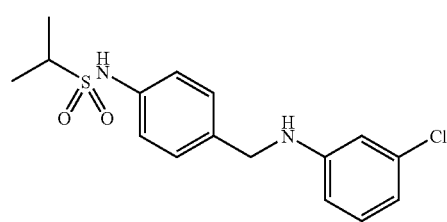
Ih-42
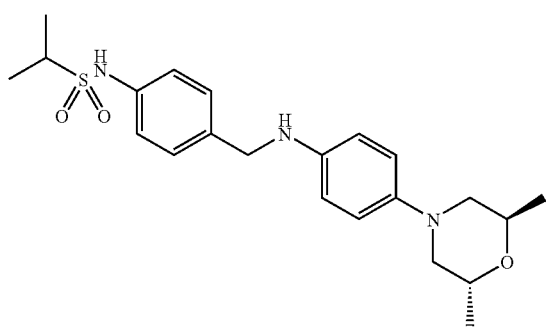
330
-continued
Ih-43
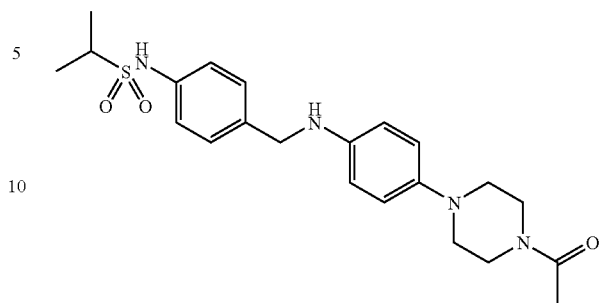
Ih-44
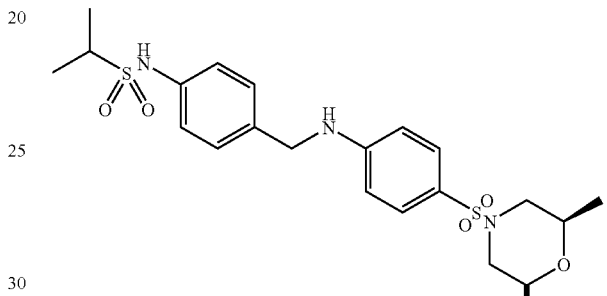
Ih-45
Ih-46
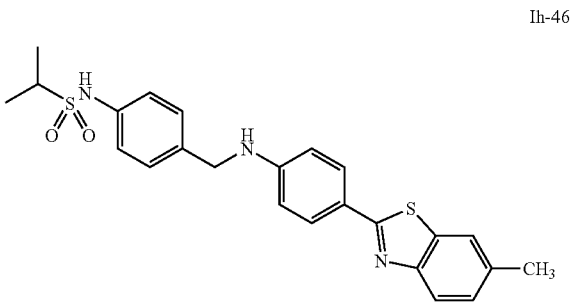

Ih-47
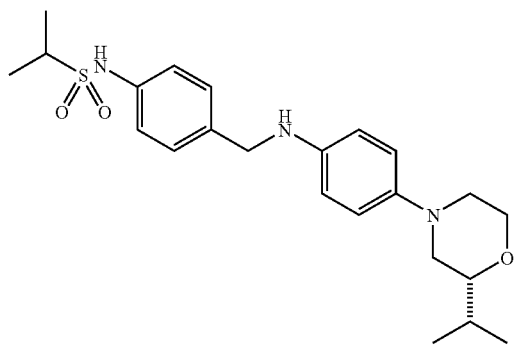
Ih-48
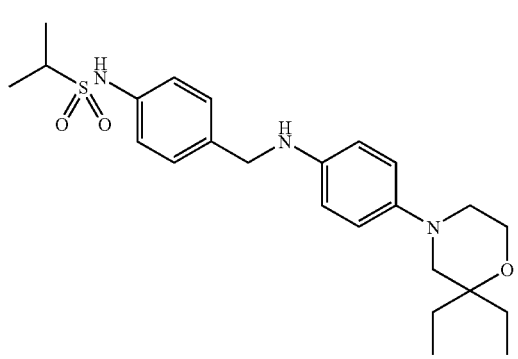
Ih-49
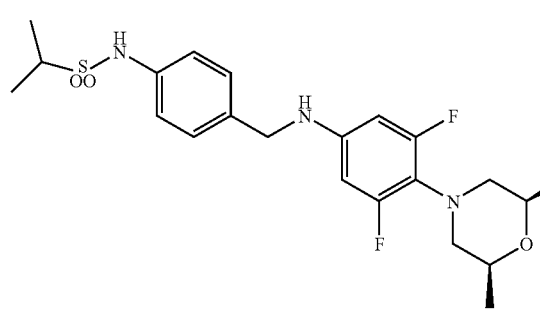
Ih-50
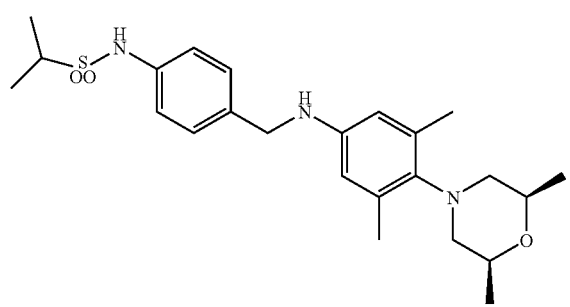
Ih-51
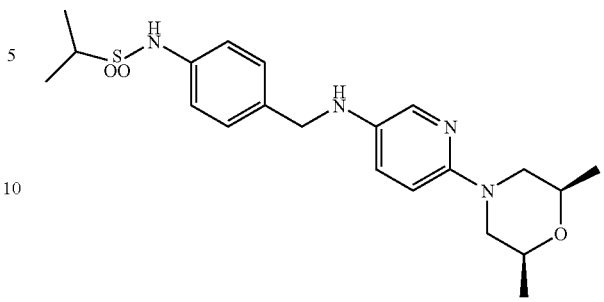
Ih-52
Ih-53
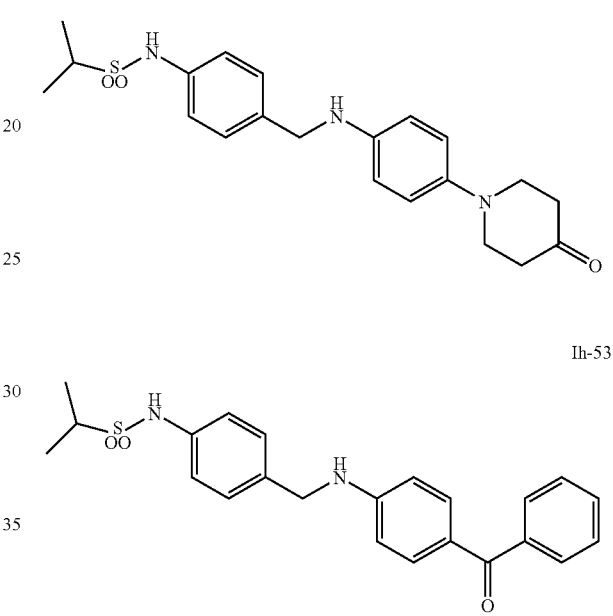
Ih-54
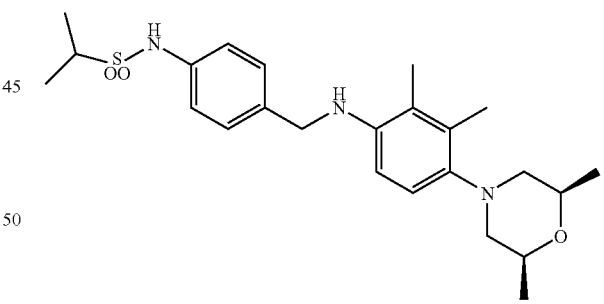
Ih-55
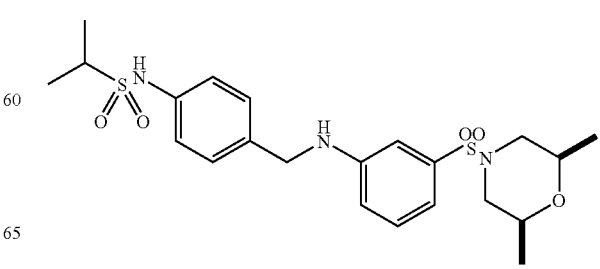

Ih-56
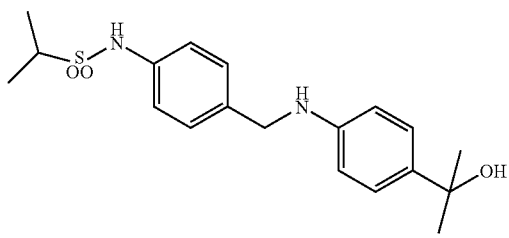
Ih-57
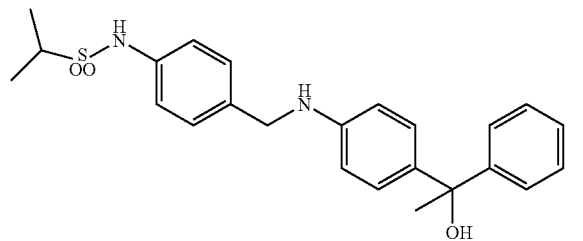
Ih-58
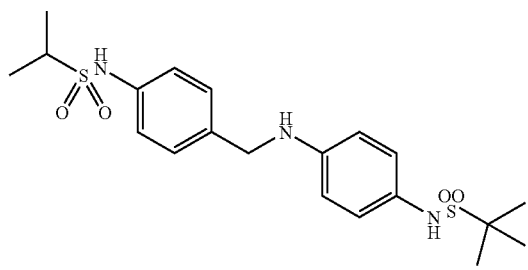
Ih-59
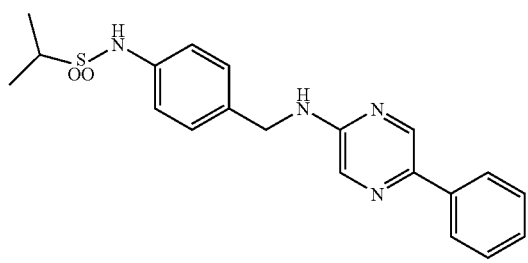
Ih-60
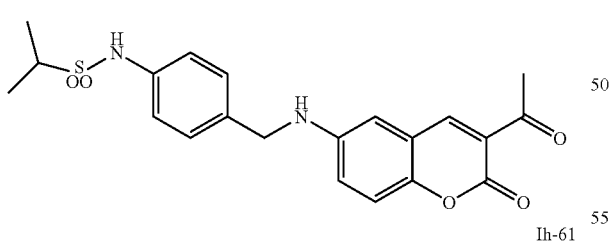
Ih-61
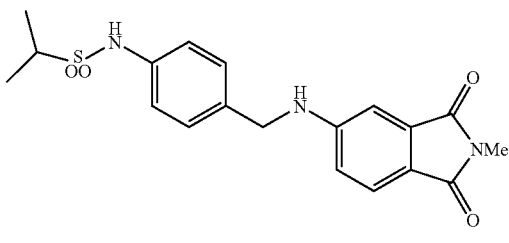
Ih-62
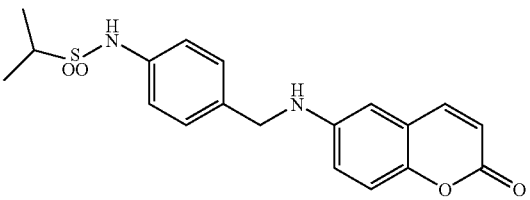
Ih-63
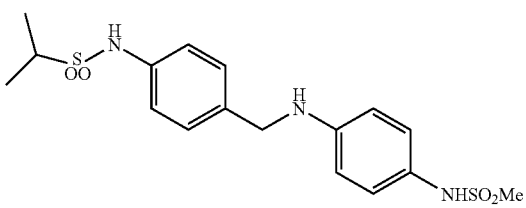
Ih-64
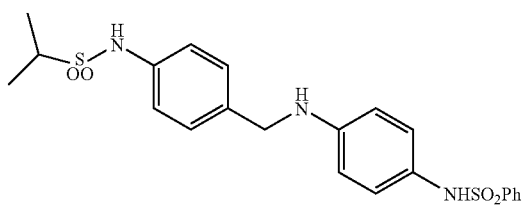
Ih-65
Ih-66
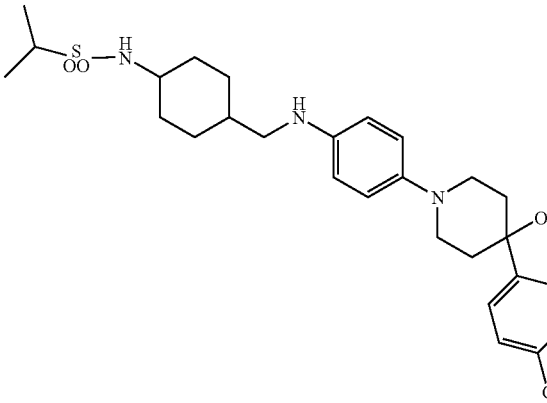

Ih-67
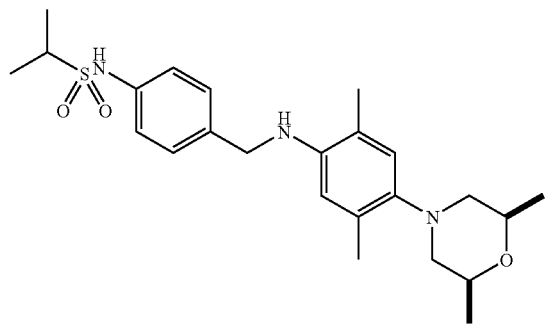
Ih-68
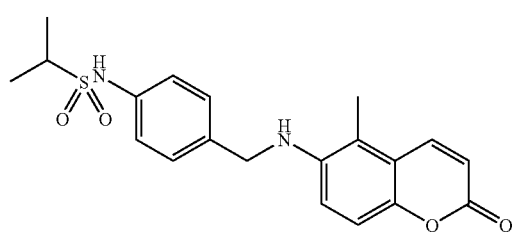
Ih-69
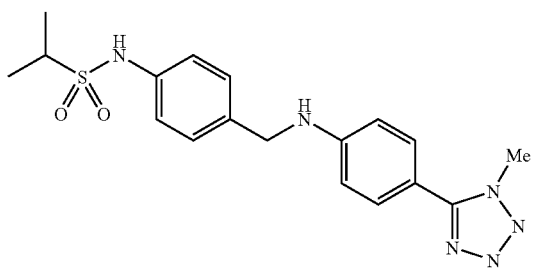
Ih-70
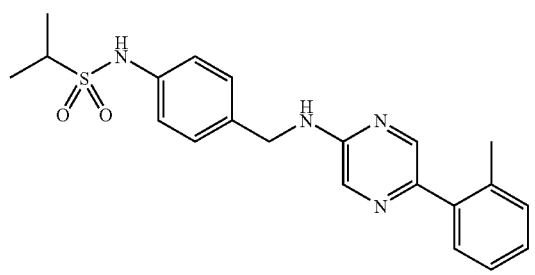
Ih-71
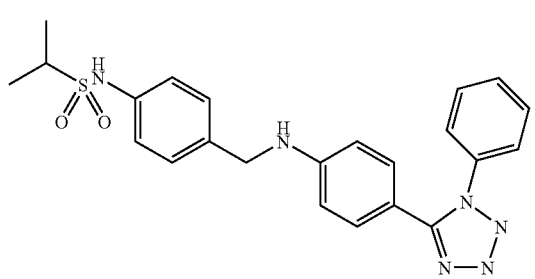
Ih-72
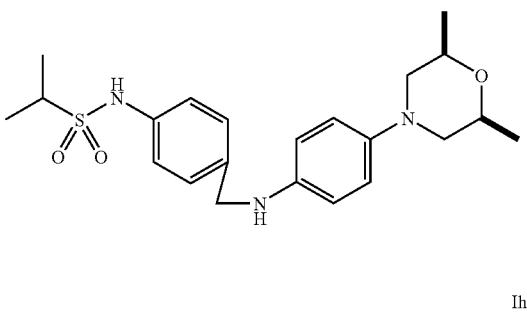
Ih-74
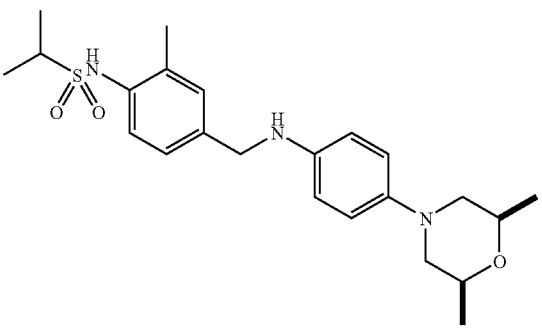
Ih-75
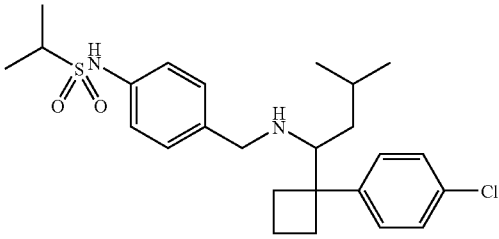
Ih-76
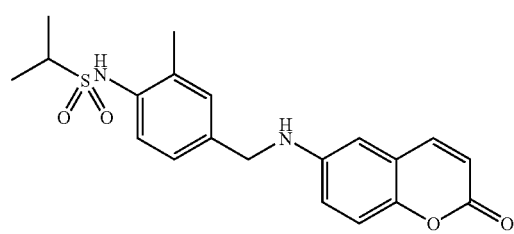
Ih-77
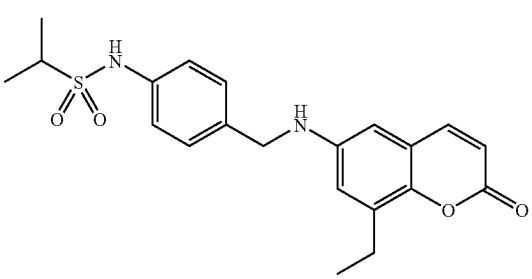

Ih-78
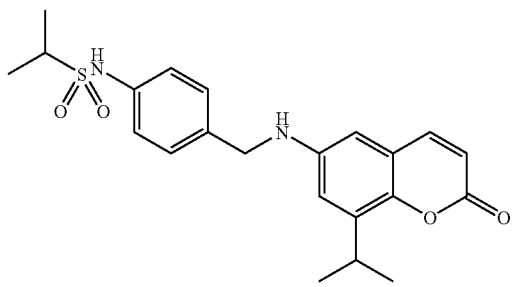
Ih-79
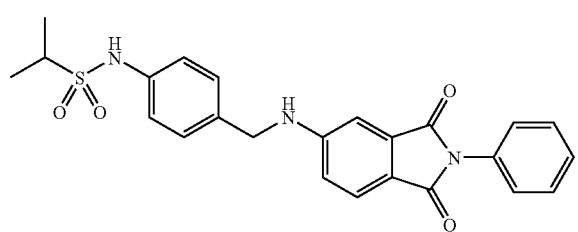
Ih-80
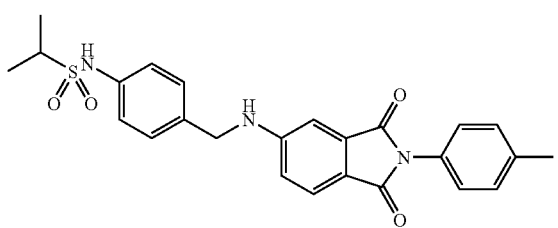
Ih-81
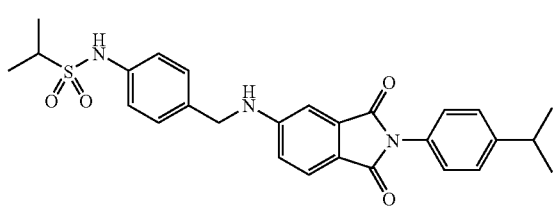
Ih-82
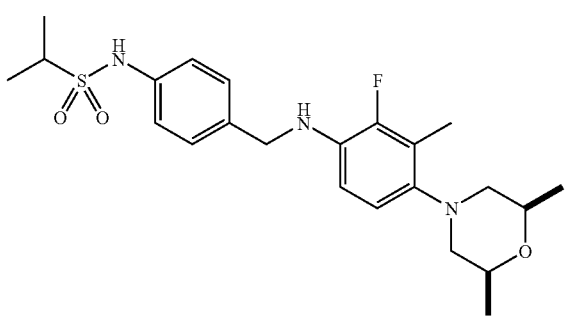
Ih-83
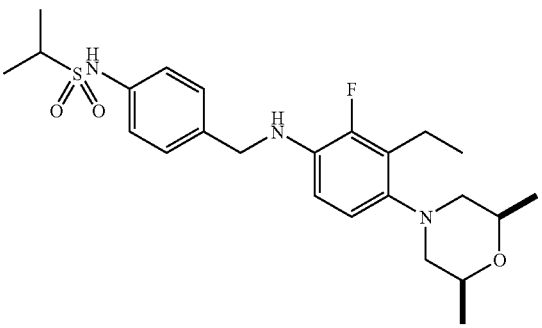
Ih-84
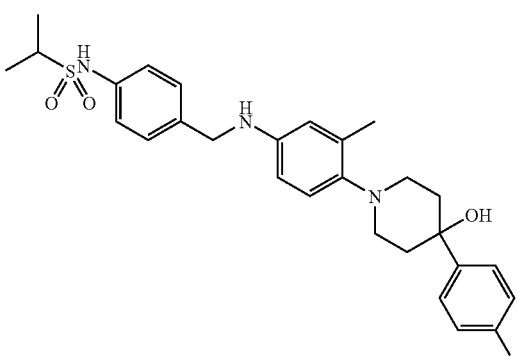
Ih-85
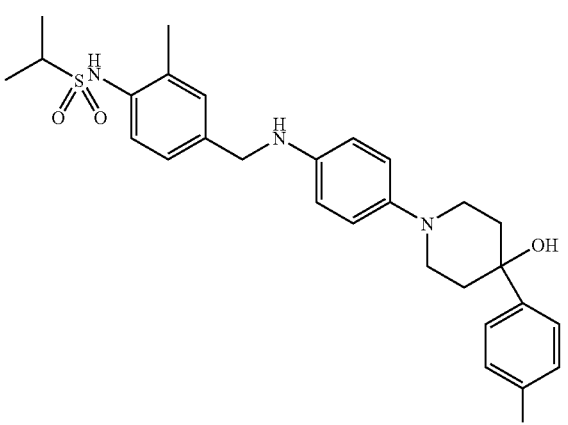
Ih-86
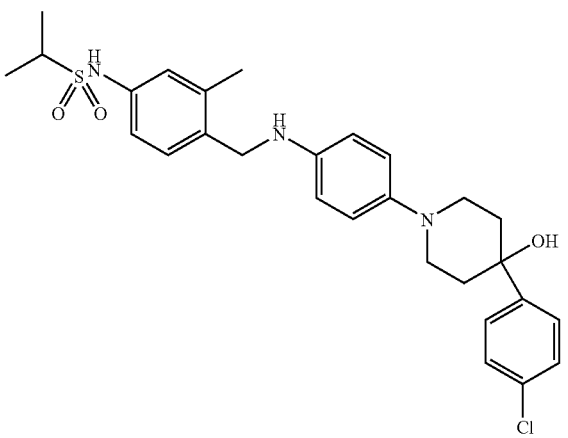

Ih-87
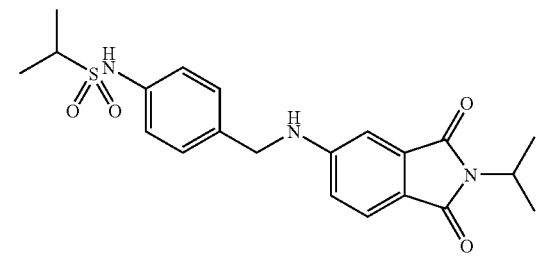
Ih-88
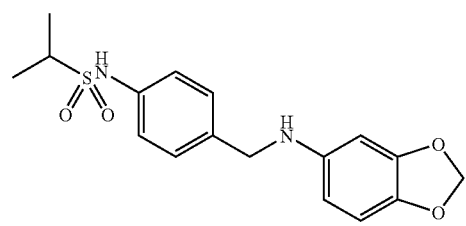
Ih-89
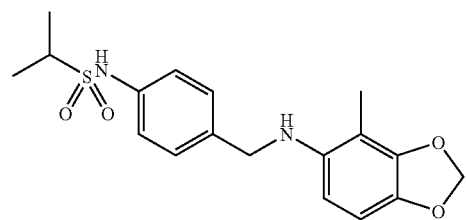
Ih-90
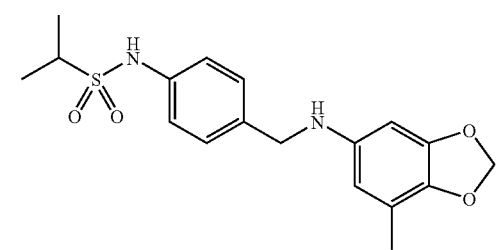
Ih-91
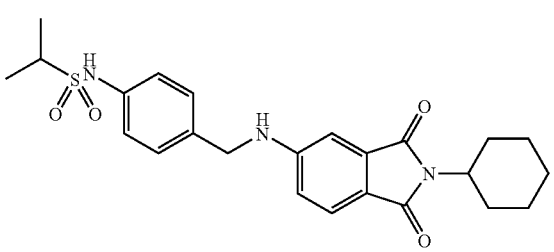
Ih-92
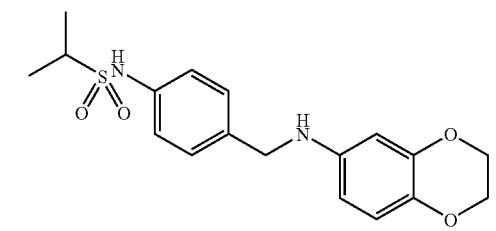
Ih-93
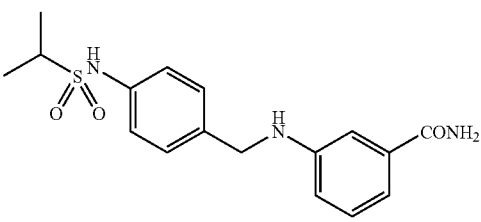
Ih-94
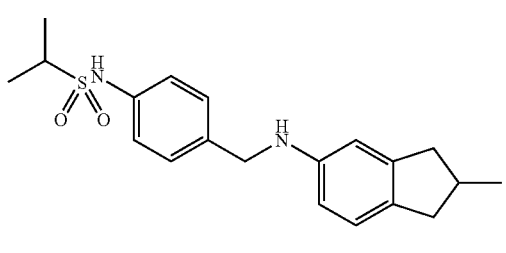
Ih-95
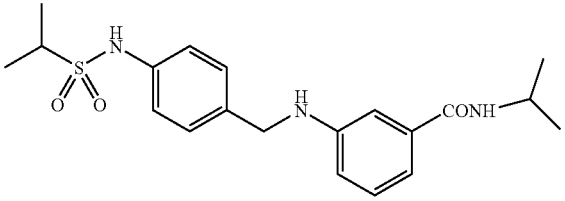
Ih-96
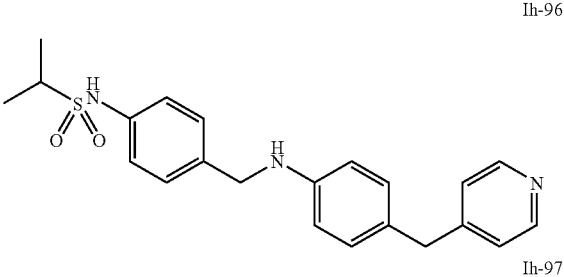
Ih-97
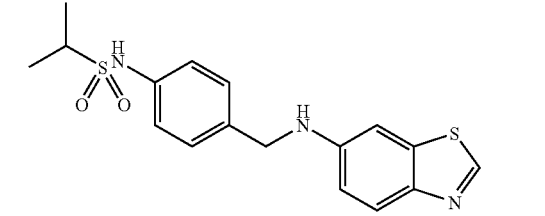
Ih-98
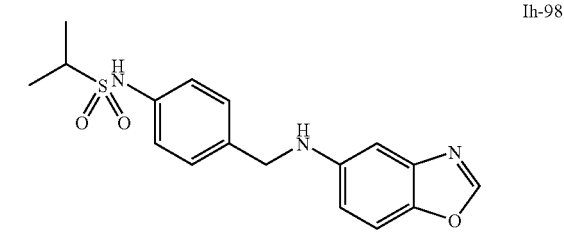
Ih-99
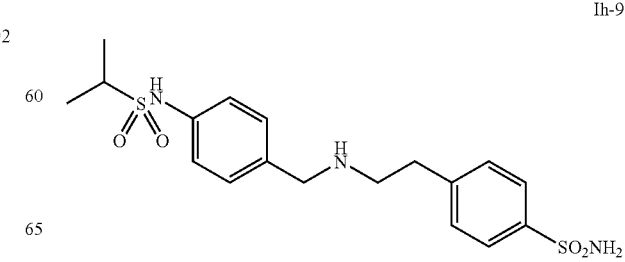

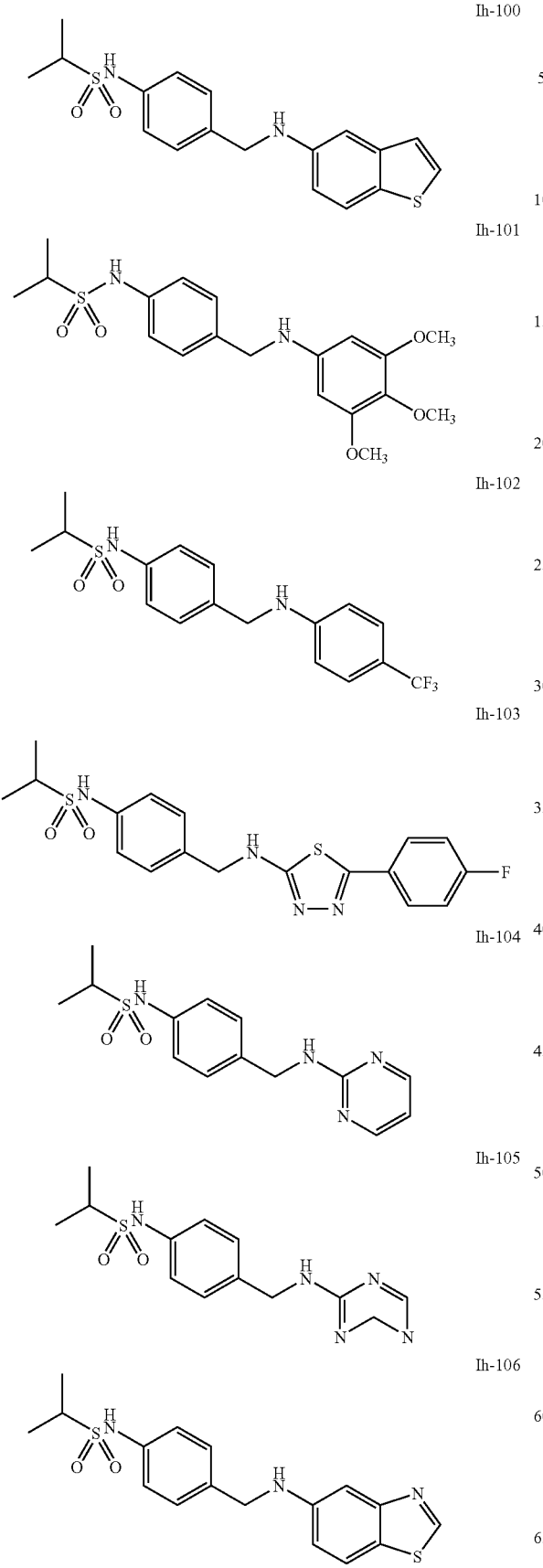
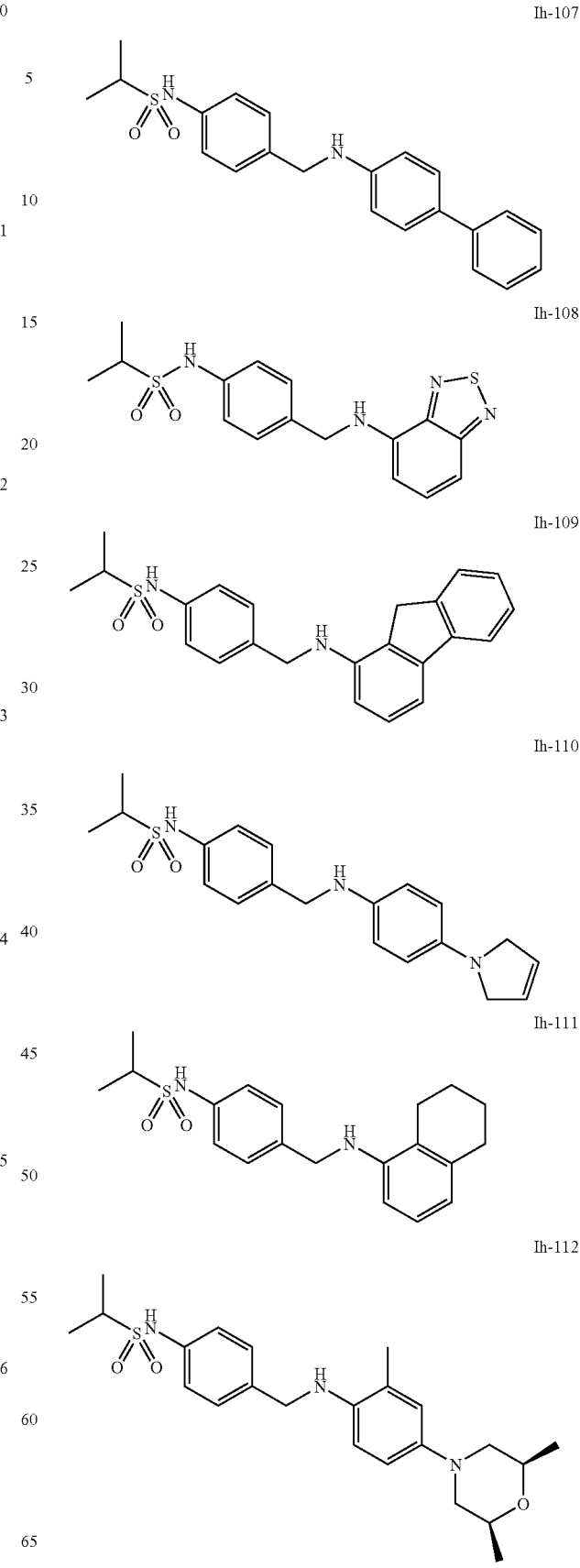

Ih-113
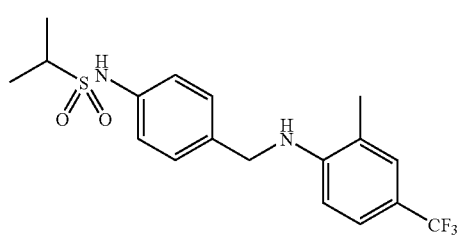
Ih-114
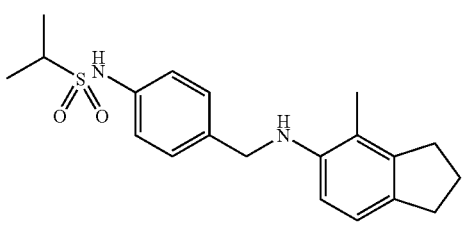
Ih-115
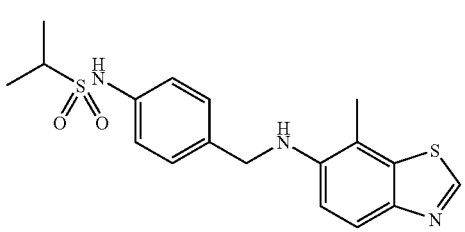
Ih-116
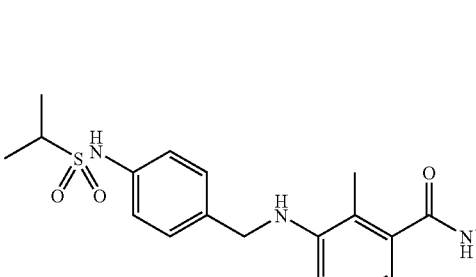
Ih-117
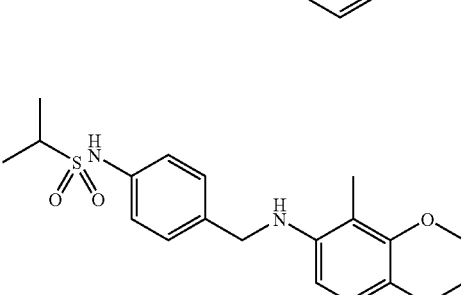
Ih-118
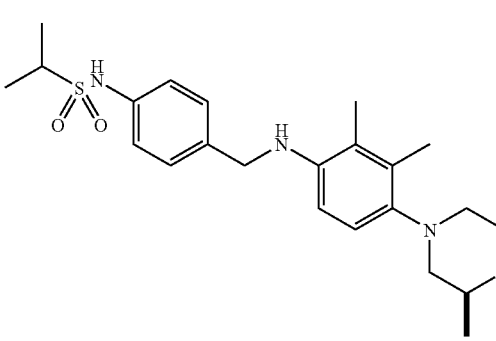
Ih-119
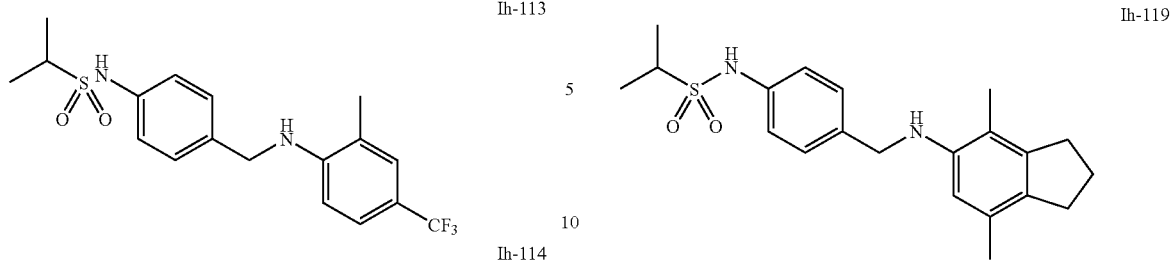
Ih-120
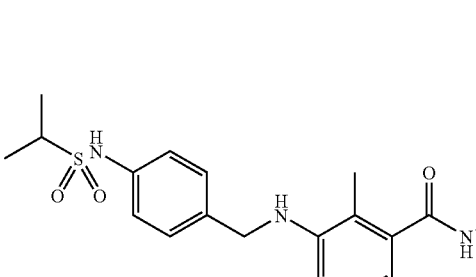
Ih-121
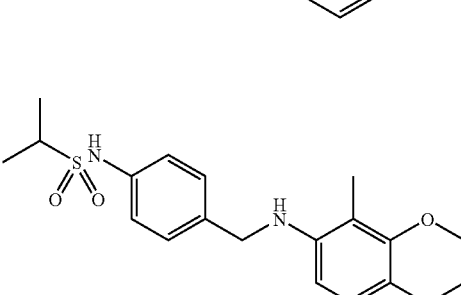
Ih-122
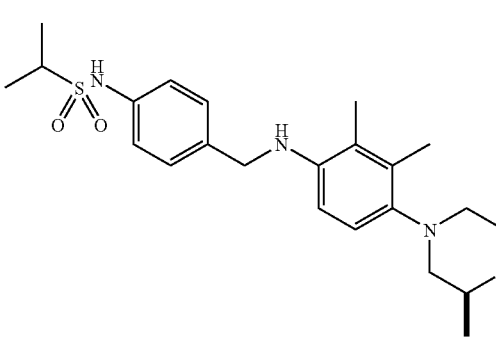
Ih-123
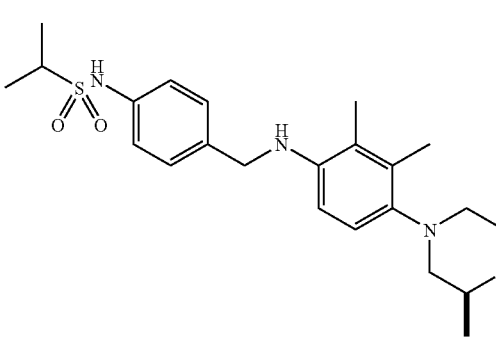

Ih-124
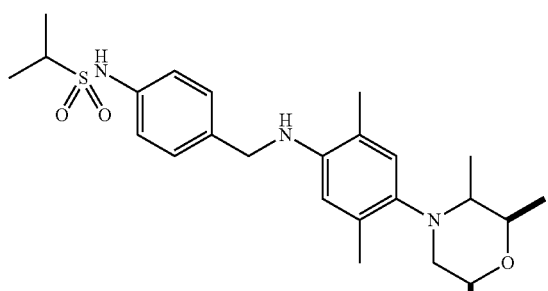
Ih-125
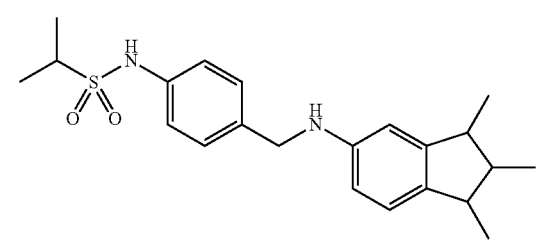
Ih-126
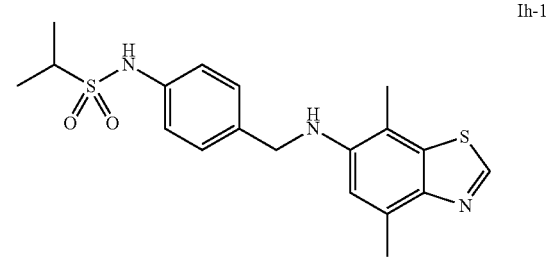
Ih-127
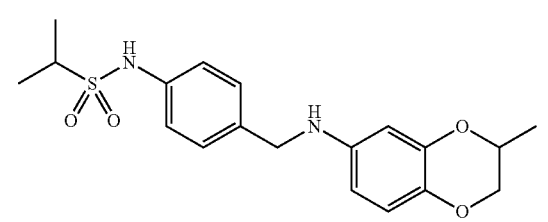
Ih-128
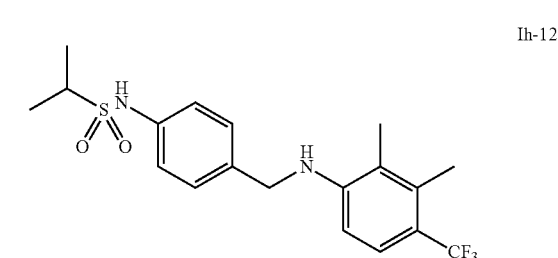
Ih-129
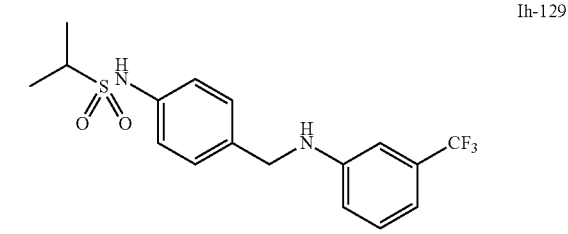
Ih-131
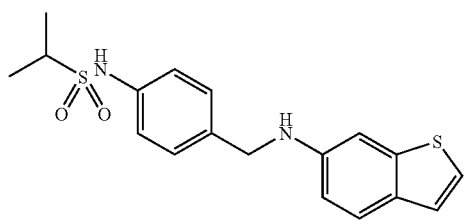
Ih-132
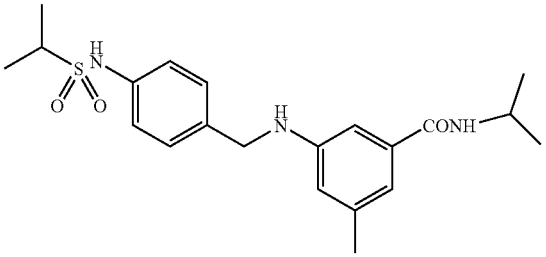
Ih-133
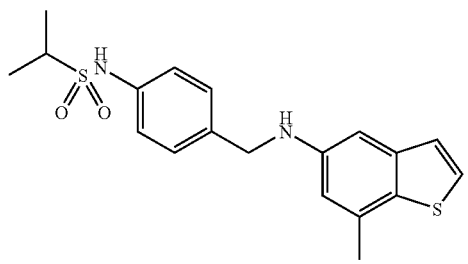
Ih-134
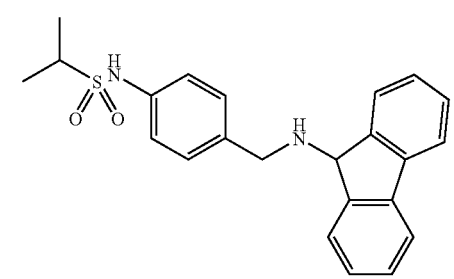
Ih-135
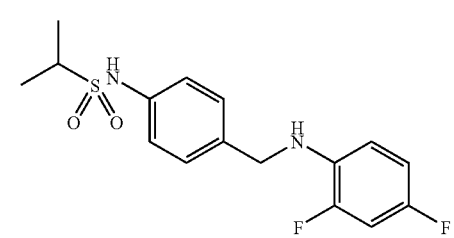
Ih-136
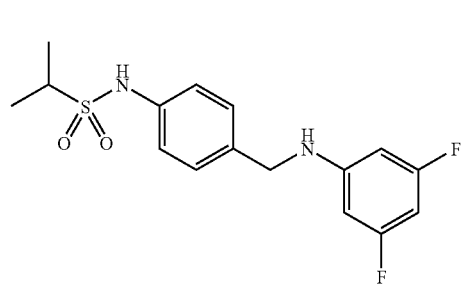

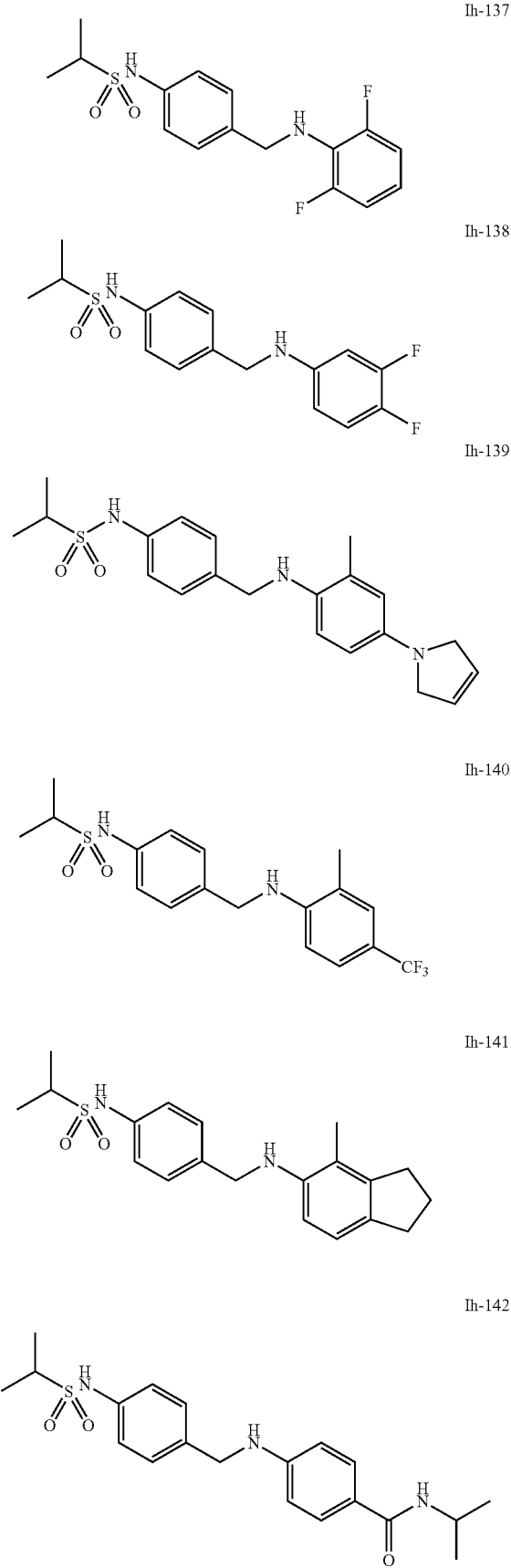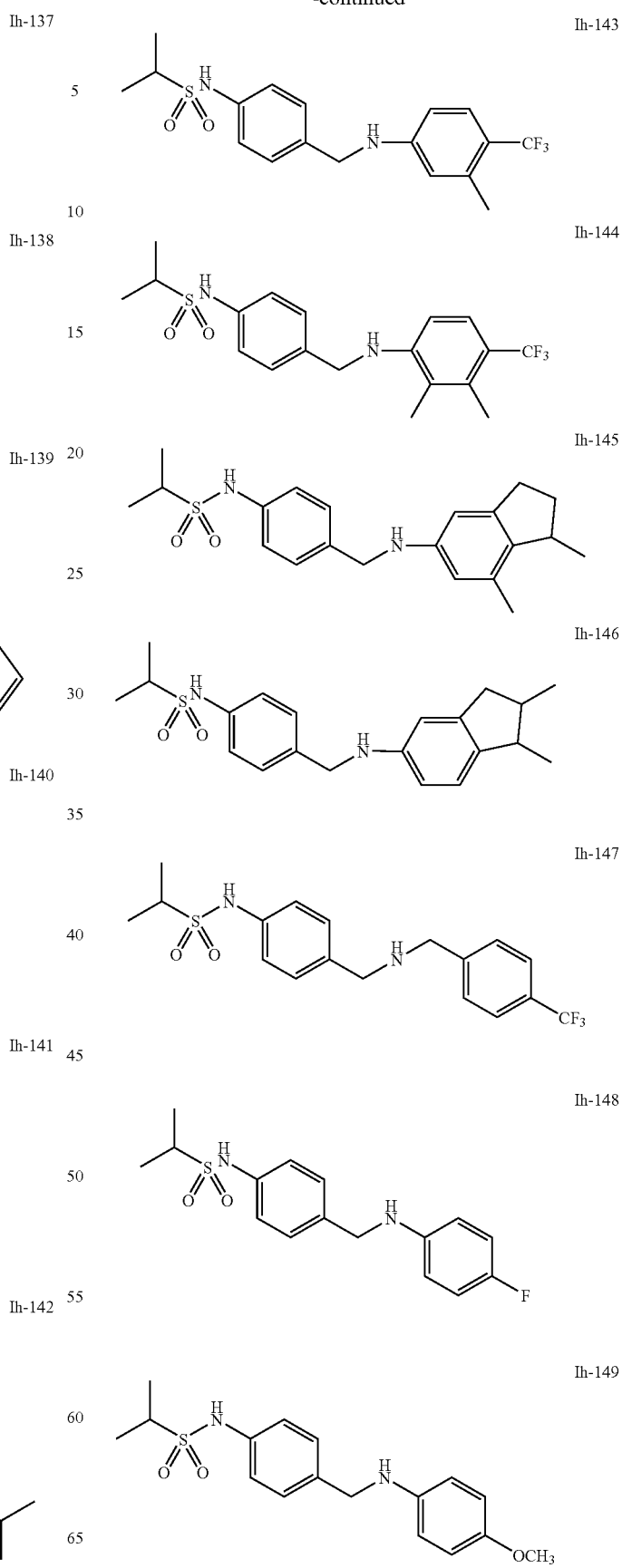

Ih-150 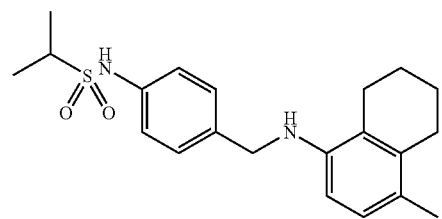
Ih-151 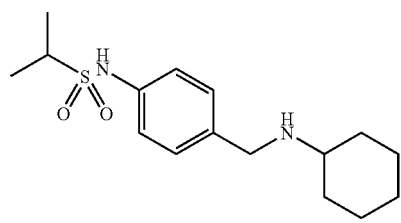
Ih-152 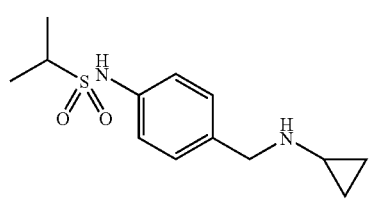
Ih-153 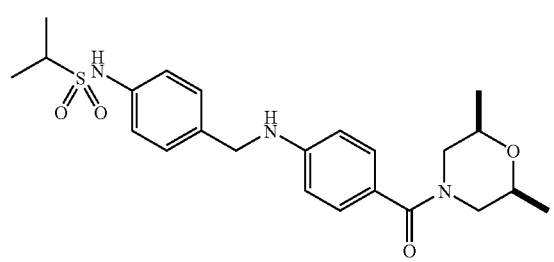
Ih-154 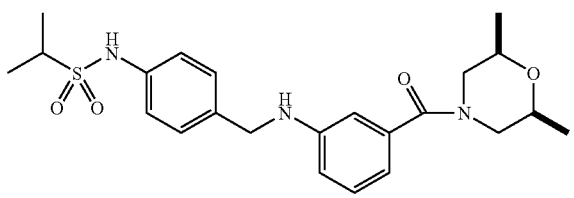
Ih-155 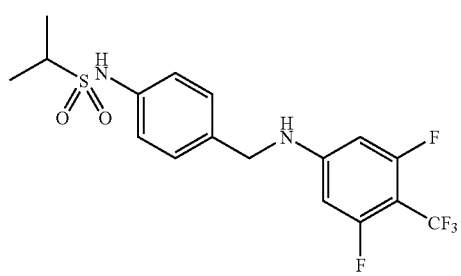
Ih-156 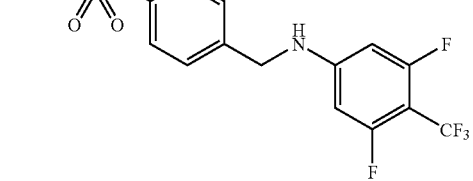
Ih-157 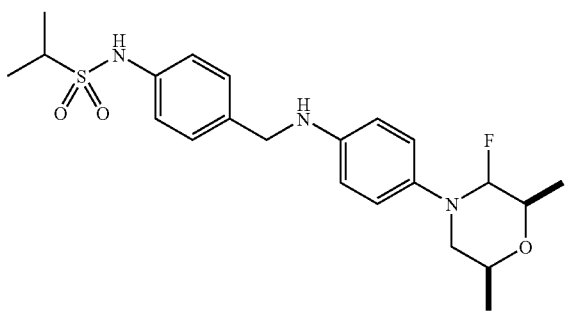
Ih-158 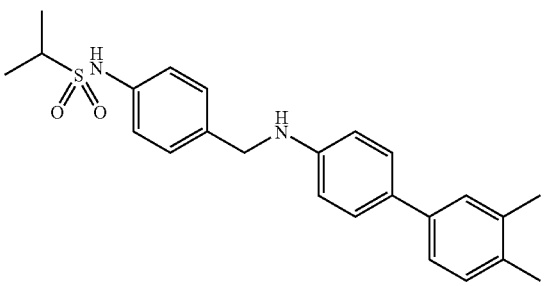
Ih-159 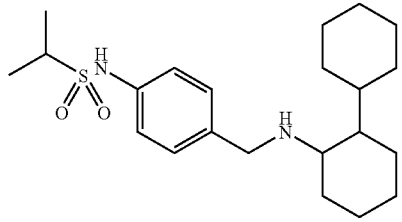
Ih-160 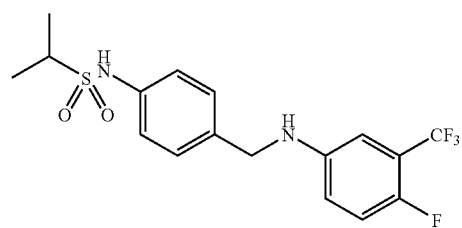
Ih-161 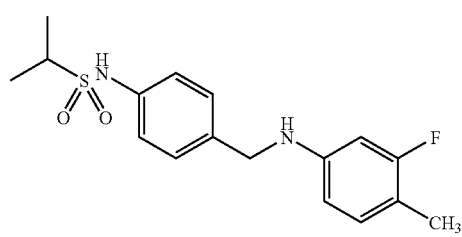

Ih-162
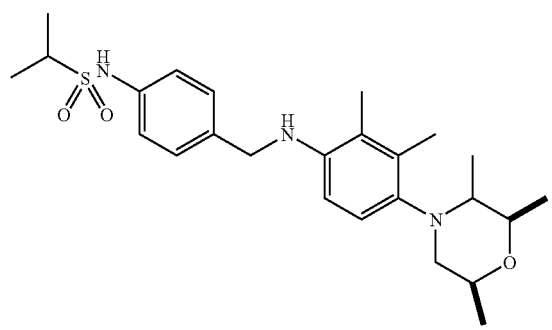
Ih-163
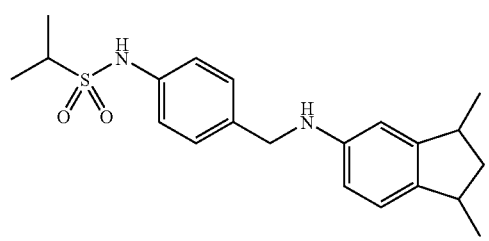
Ih-164
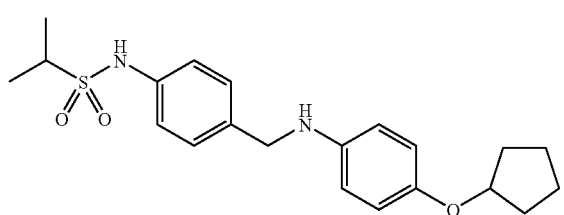
Ih-165
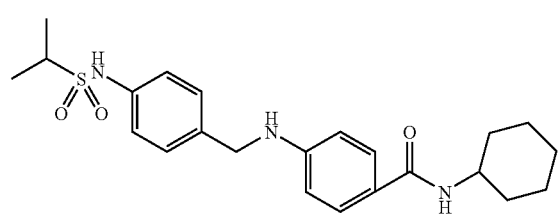
Ih-166
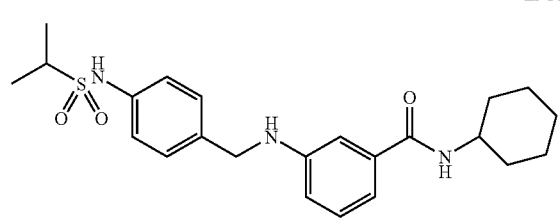
Ih-167
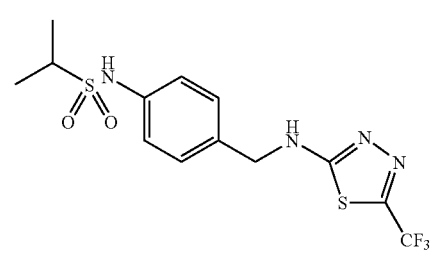
Ih-168
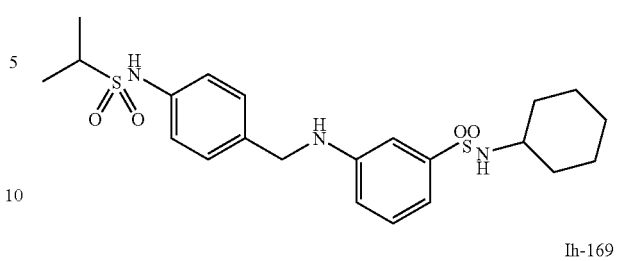
Ih-169
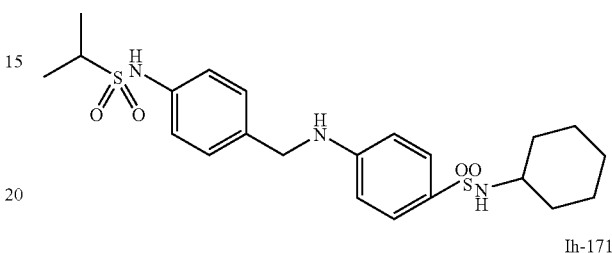
Ih-171
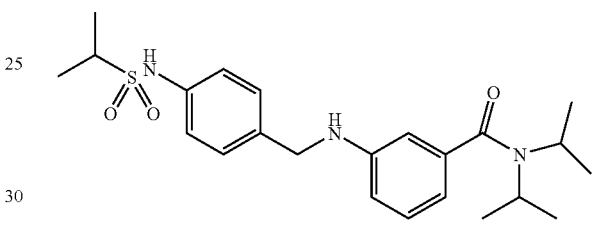
Ih-172
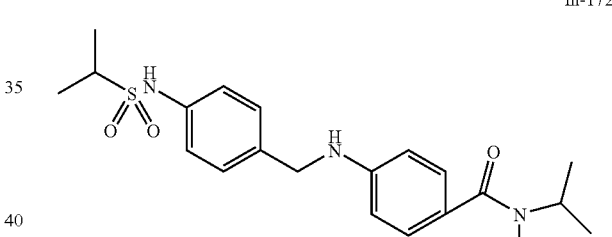
Ih-173
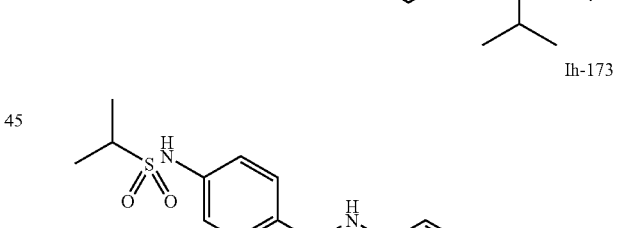
Ih-174
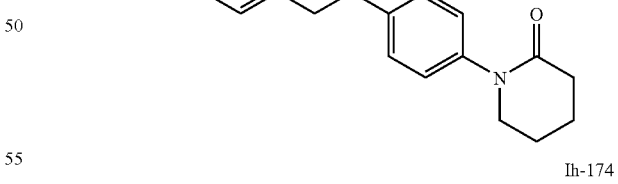
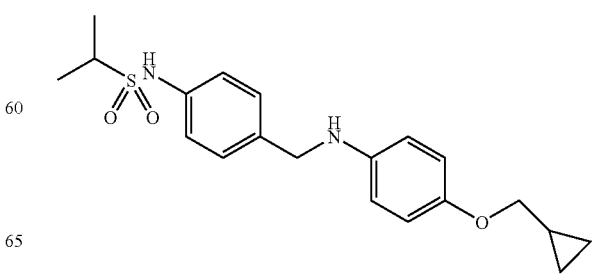

Ih-175
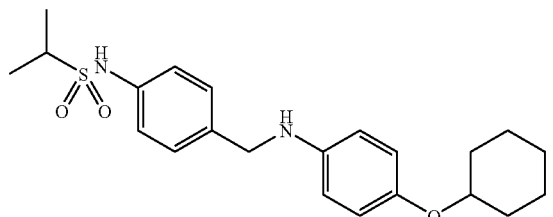
Ih-176
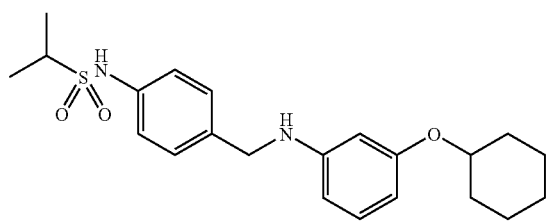
Ih-177
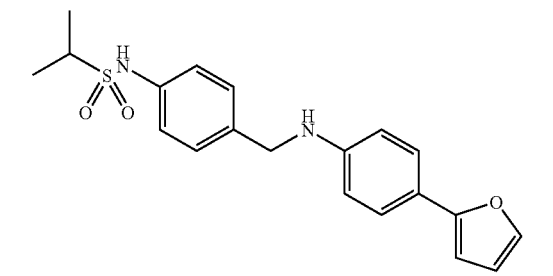
Ih-178
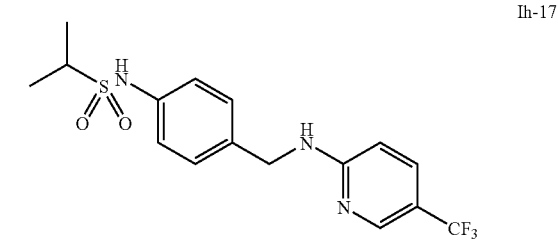
Ih-179
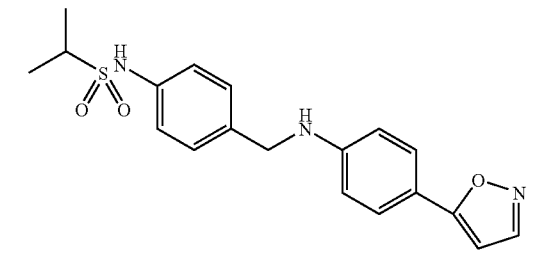
Ih-180
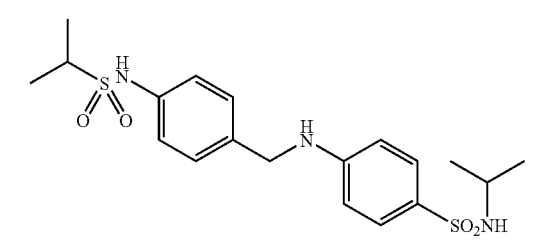
Ih-181
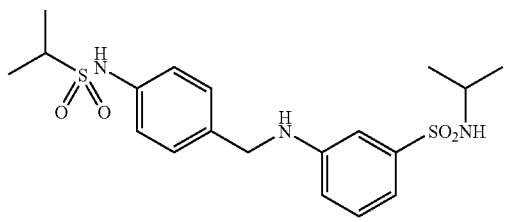
Ih-182
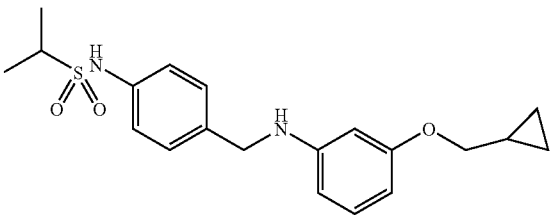
Ih-183
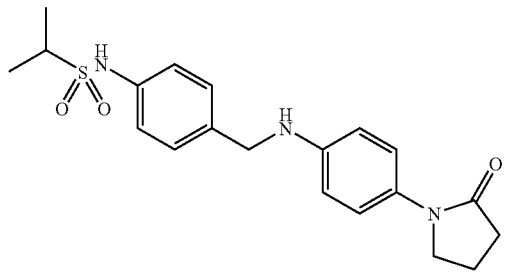
Ih-184
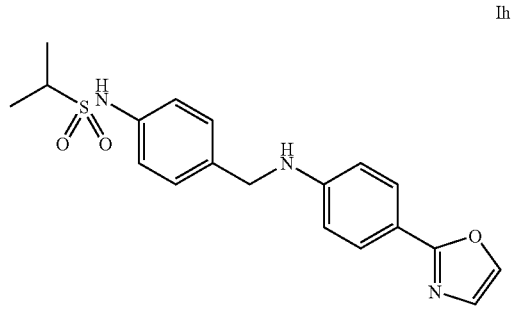
Ih-185
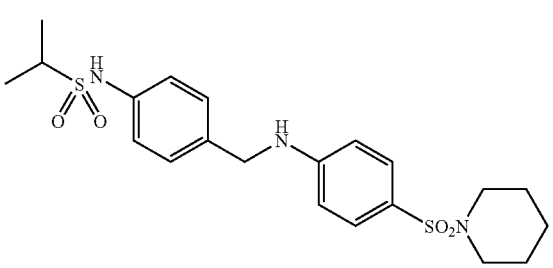
Ih-186
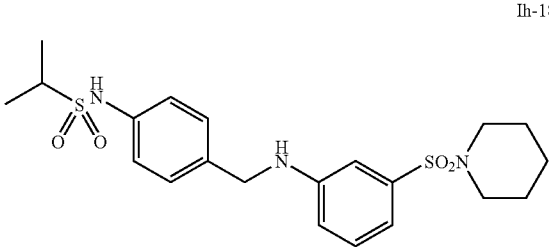

355
-continued
Ih-187
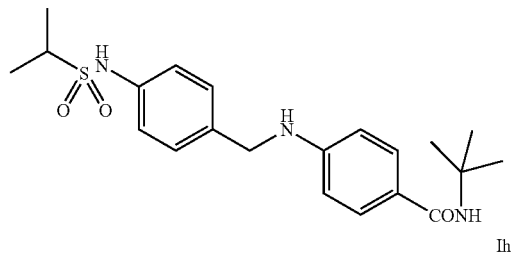
Ih-188
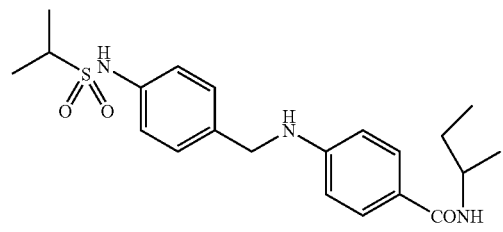
Ih-189
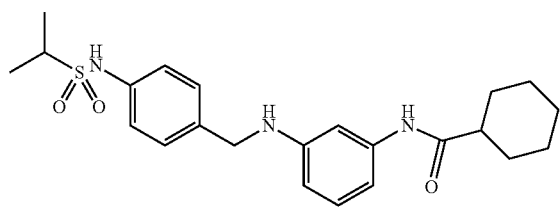
Ih-190
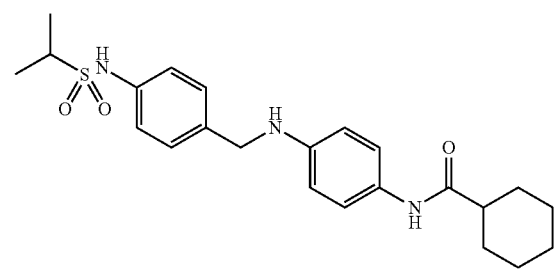
Ih-191
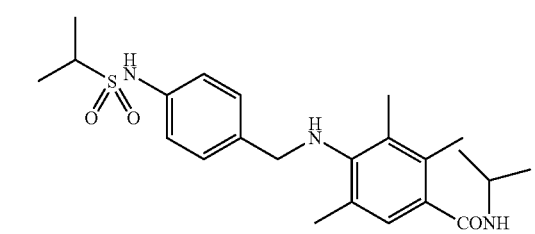
Ih-192
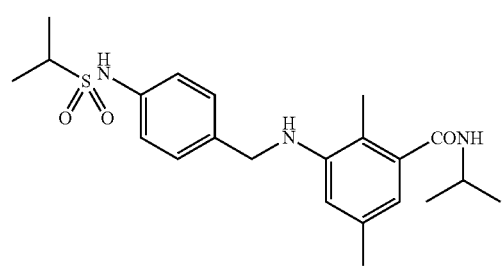
356
-continued
Ih-193
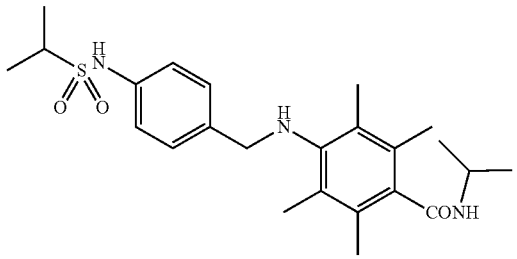
Ih-194
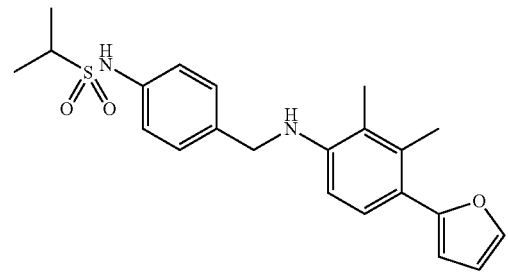
Ih-195
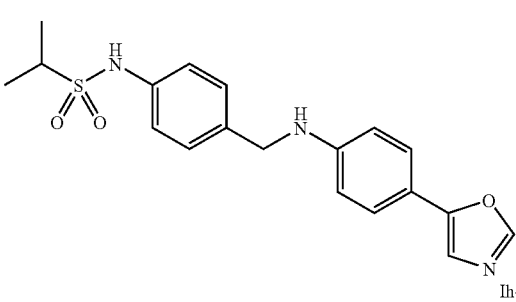
Ih-196
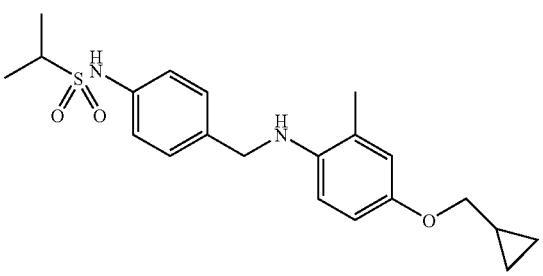
Ih-197
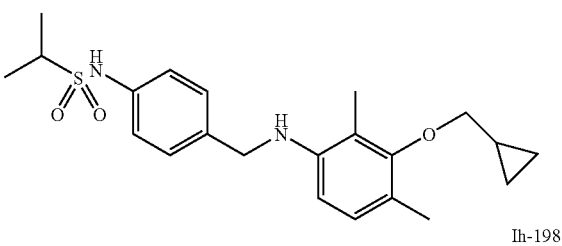
Ih-198

Ih-199
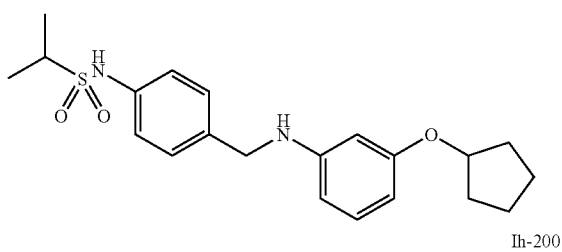
Ih-200
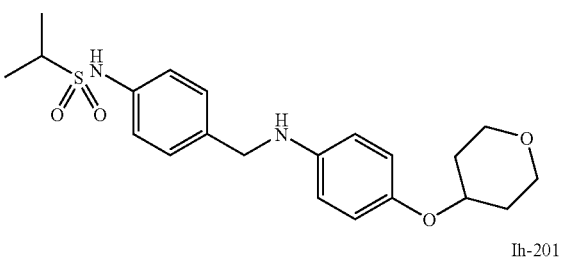
Ih-201
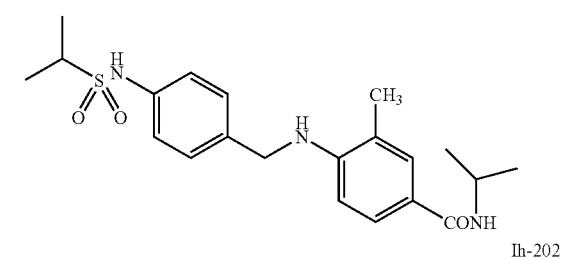
Ih-202
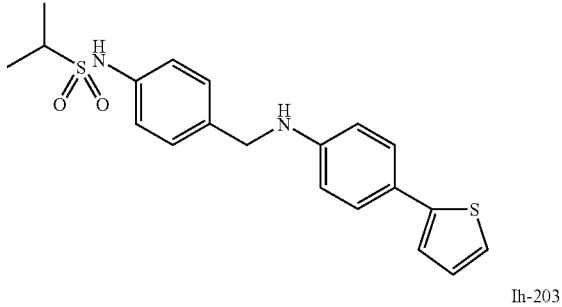
Ih-203
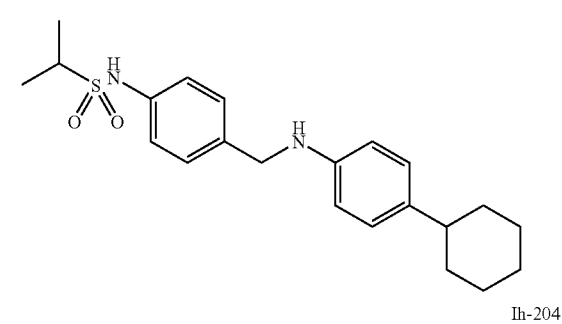
Ih-204
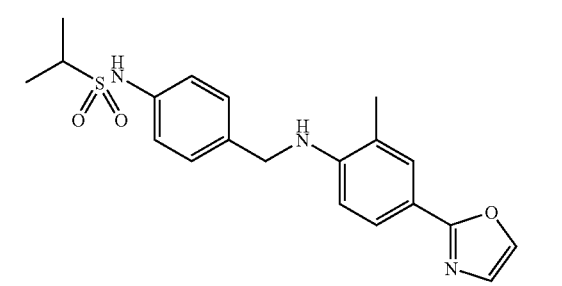
Ih-205
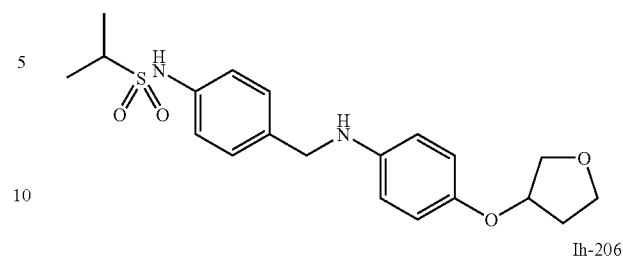
Ih-206
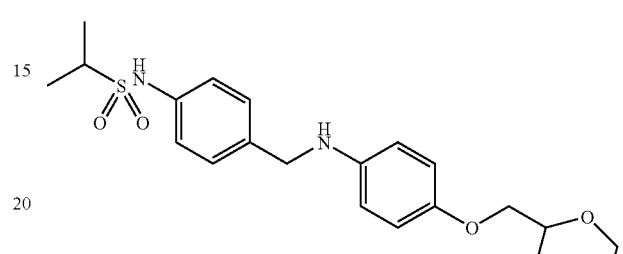
Ih-207
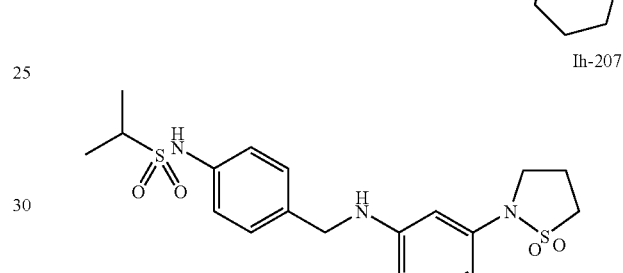
Ih-208
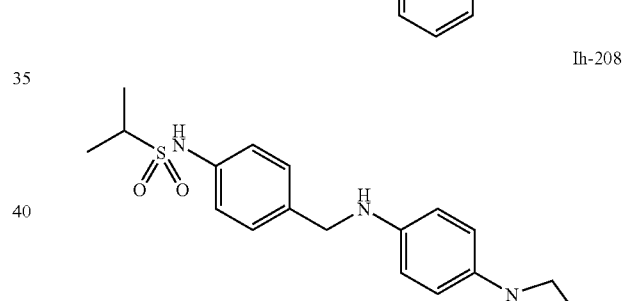
Ih-209
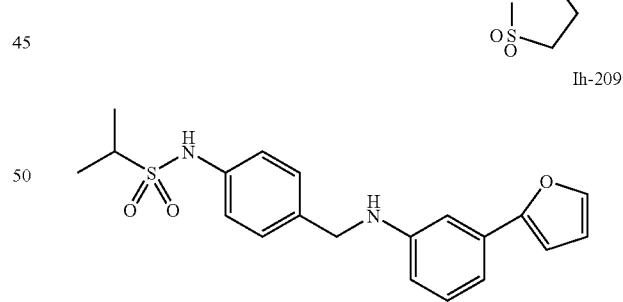
Ih-210
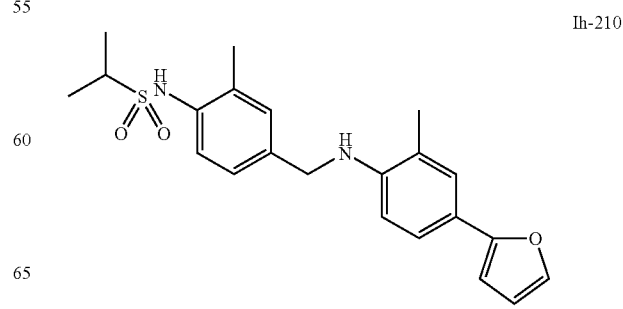

Ih-211
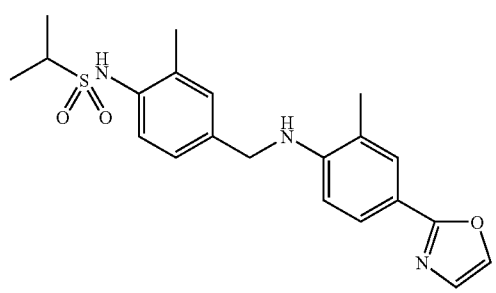
Ih-212
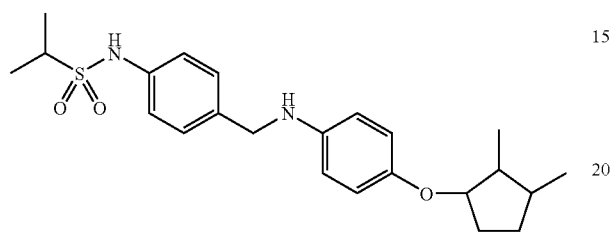
Ih-213
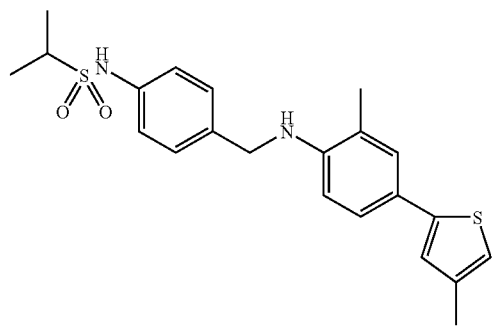
Ih-214
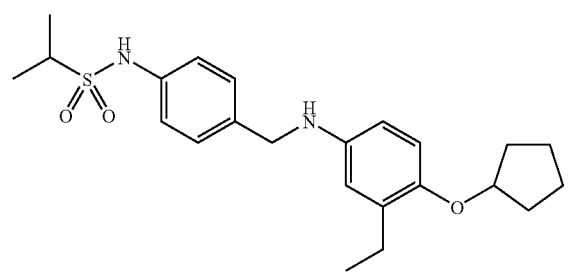
Ih-215
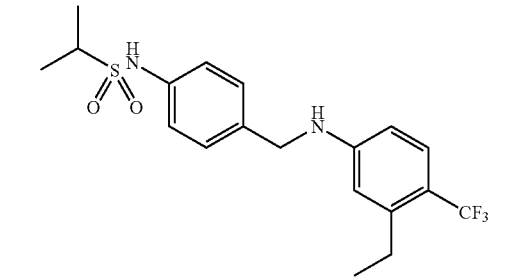
Ih-216
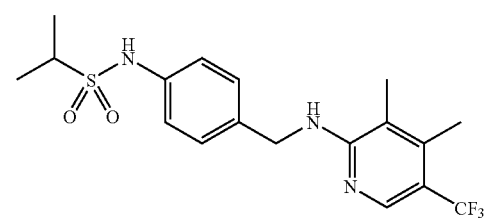
Ih-219
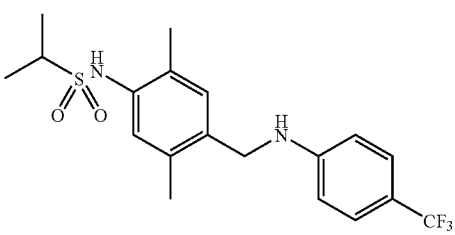
Ih-220
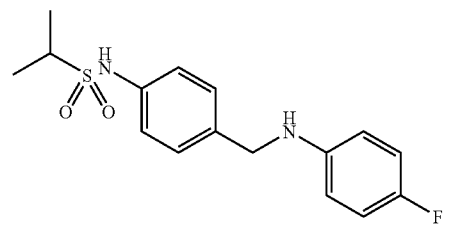
Ih-221
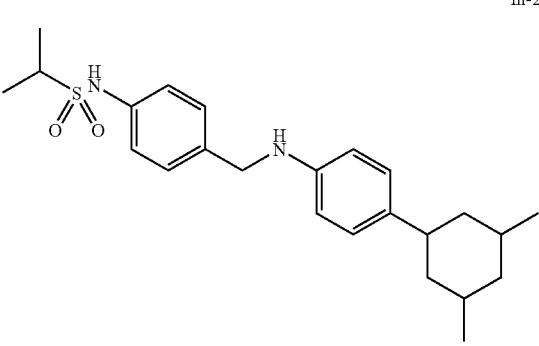
Ih-222
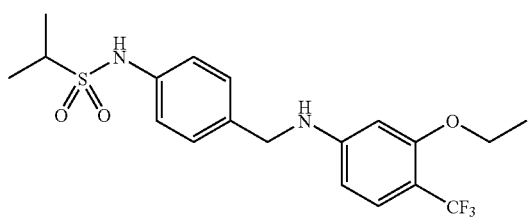
Ih-223
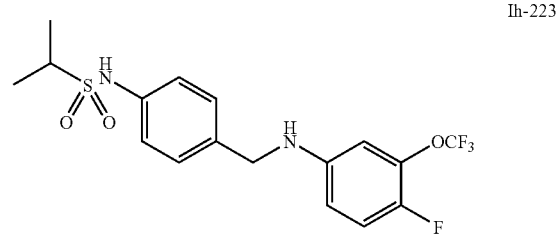
Ih-224
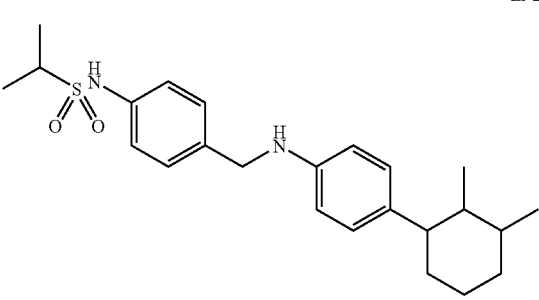

Ih-225

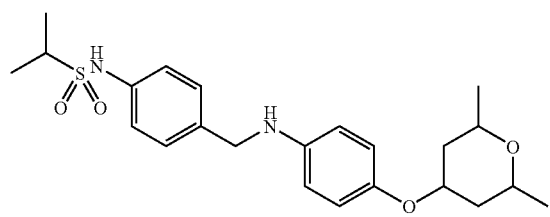

Ih-226

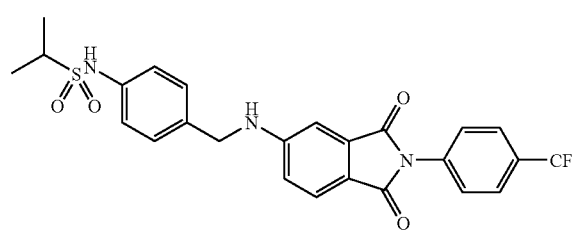

Compound I-72

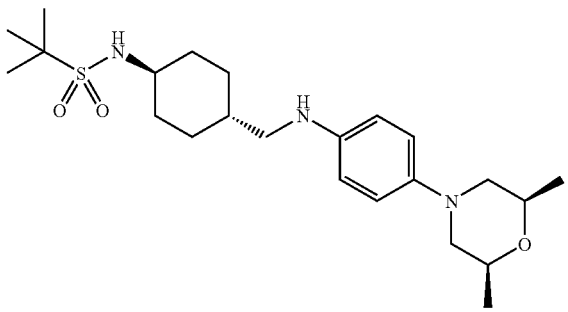

¹H-NMR (DMSO-d₆) δ: 0.90-1.05 (m, 2H), 1.05-1.15 (m, 6H), 1.25 (5, 9H,), 1.15-1.32 (m, 3H), 1.41 (m, 1H), 1.75-1.98 (m, 4H), 2.11 (m, 1H), 2.58-3.38 (m, 5H), 3.58-3.76 (m, 2H), 5.17 (m, 1H), 6.25-6.92 (m, 5H) Melting point: 147 to 149° C.

Compound Ia-140

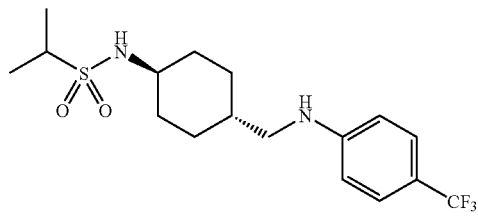

¹H-NMR (CDCl₃) δ: 1.02-1.20 (m, 2H), 1.17-1.32 (m, 2H), 1.37 (d, 6H, J=6.9 Hz), 1.46-1.70 (m, 4H), 1.86-1.95 (m, 2H), 2.08-2.18 (m, 2H), 3.01 (d, 2H, J=6.9 Hz), 3.13 (m, 1H), 3.25 (m, 1H), 3.87 (d, 1H, J=8.4 Hz), 6.61 (d, 2H, J=8.7 Hz), 7.39 (d, 2H, J=8.7 Hz)

Compound Ia-141

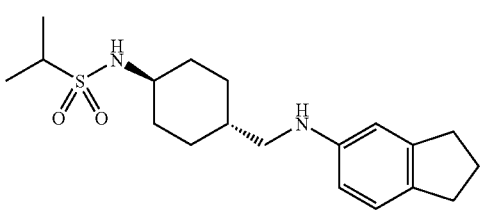

¹H-NMR (CDCl₃) δ: 1.00-1.30 (m, 4H), 1.37 (d, 6H, J=6.9 Hz), 1.59 (m, 1H), 1.87-1.98 (m, 2H), 1.99-2.18 (m, 5H), 2.85 (q, 3H, J=7.5 Hz), 2.97 (d, 2H, J=6.9 Hz), 3.12 (m, 1H), 3.23 (m, 1H), 3.88 (d, 1H, J=8.1 Hz), 6.53 (d, 1H, J=7.8 Hz), 6.63 (brs, 1H), 7.04 (d, 1H, J=7.8 Hz) Mass: 351[M+H]

Compound Ia-178

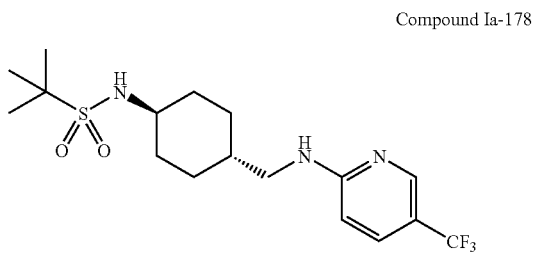

¹H-NMR (CDCl₃) δ: 1.08-1.36 (m, 4H), 1.39 (s, 9H), 1.59 (m, 1H), 1.90-1.99 (m, 2H), 2.16-2.26 (m, 2H), 3.17-3.34 (m, 3H), 3.69 (d, 1H, J=9.3 Hz), 6.68 (d, 1H, J=9.3 Hz), 7.77 (dd, 1H, J=2.1 Hz and 9.3 Hz), 8.49 (brs, 1H) Mass: 394[M+H]+

Compound Ib-138

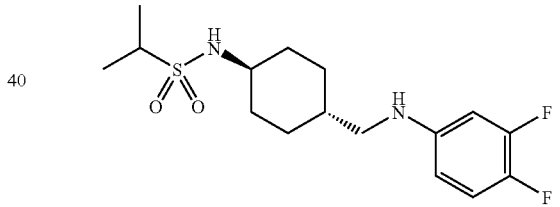

¹H-NMR (CDCl₃) δ: 1.02-1.34 (m, 4H), 1.37 (d, 6H, J=6.6 Hz), 1.57 (m, 1H), 1.87-1.97 (m, 2H), 2.07-2.18 (m, 2H), 2.93 (d, 2H, J=6.6 Hz), 3.13 (m, 1H), 3.25 (m, 1H), 3.99 (d, 1H, J=8.4 Hz), 6.38 (m, 1H), 6.49 (brs, 1H), 6.97 (q, 1H, J=9.3 Hz) Mass: 347[M+H]

Compound Ii-2

¹H-NMR (DMSO-d₆) δ: 0.91-1.06 (m, 2H), 1.12-1.28 (m, 11H), 1.31-1.47 (m, 1H), 1.75-1.94 (m, 4H), 2.19 (t, 2H,

J=11.3 Hz), 2.79 (t, 2H, J=6.0 Hz), 2.93-3.08 (m, 1H), 2.97 (q, 2H, J=7.42 Hz), 3.46 (m, 2H), 3.57-3.69 (m, 2H), 5.71 (t, 1H, J=5.2 Hz), 5.77 (d, 1H, J=11.5 Hz), 5.88-5.96 (m, 2H), 7.01 (d, 1H, J=7.4 Hz).

Compound Ii-3

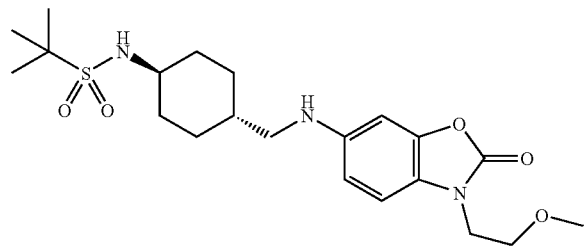

¹H-NMR (DMSO-d₆) δ: 0.90-1.07 (m, 2H), 1.15-1.21 (m, 1H), 1.27 (s, 9H), 1.40-1.49 (m, 2H), 1.82 (d, 2H, J=11.6 Hz), 1.92 (d, 2H, J=11.6 Hz), 2.79-2.84 (m, 2H), 2.97-3.10 (m, 1H), 3.24 (s, 3H), 3.55-3.62 (m, 2H), 3.84-3.91 (m, 2H), 5.50-5.59 (m, 1H), 6.40 (d, 1H, J=8.0 Hz), 6.56 (s, 1H), 6.72 (d, 1H, J=8.4 Hz), 6.97 (d, 1H, J=8.4 Hz). Melting point: 166 to 168° C.

Compound Ii-4

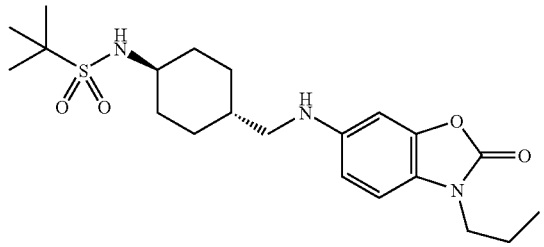

¹H-NMR (DMSO-d₆) δ: 0.87 (t, 3H, J=7.2 Hz), 0.93-1.06 (m, 2H), 1.13-1.21 (m, 1H), 1.26 (s, 9H), 1.37-1.49 (m, 2H), 1.61-1.72 (m, 2H), 1.82 (d, 2H, J=12.0 Hz), 1.91 (d, 2H, J=12.0 Hz), 2.78-2.84 (m, 2H), 2.97-3.08 (m, 1H), 3.61-3.71 (m, 2H), 5.52-5.60 (m, 1H), 6.40 (d, 1H, J=8.4 Hz), 6.56 (s, 1H), 6.73 (d, 1H, J=8.8 Hz), 6.97 (d, 1H, J=8.8 Hz). Melting point: 185 to 186° C.

Compound Ii-5

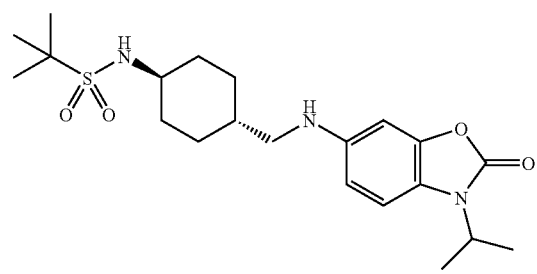

¹H-NMR (DMSO-d₆) δ: 0.90-1.05 (m, 2H), 1.26 (s, 9H), 1.28-1.31 (m, 1H), 1.35-1.47 (m, 8H), 1.81 (d, 2H, J=12.4 Hz), 1.91 (d, 2H, J=12.4 Hz), 2.77-2.84 (m, 2H), 2.96-3.07 (m, 1H), 4.30-4.42 (m, 1H), 5.51-5.64 (m, 1H), 6.39 (d, 1H, J=8.0 Hz), 6.55 (s, 1H), 6.72 (d, 1H, J=8.8 Hz), 7.07 (d, 1H, J=8.8 Hz). Melting point: 156 to 157° C.

Compound Ii-6

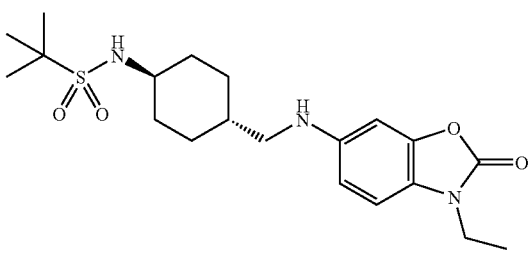

1H-NMR (DMSO-d₆) δ: 0.91-1.07 (m, 2H), 1.19-1.25 (m, 4H), 1.26 (s, 9H), 1.38-1.49 (m, 2H), 1.82 (d, 2H, J=8.8 Hz), 1.91 (d, 2H, J=8.8 Hz), 2.79-2.84 (m, 2H), 2.97-3.07 (m, 1H), 3.69-3.80 (m, 2H), 5.51-5.63 (m, 1H), 6.41 (d, 1H, J=8.0 Hz), 6.56 (s, 1H), 6.72 (d, 1H, J=8.8 Hz), 6.97 (d, 1H, J=8.8 Hz). Melting point: 178 to 179° C.

Compound Ii-7

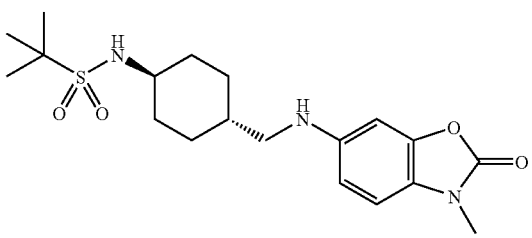

¹H-NMR (DMSO-d₆) δ: 0.92-1.07 (m, 2H), 1.19-1.22 (m, 1H), 1.26 (s, 9H), 1.38-1.48 (m, 2H), 1.82 (d, 2H, J=11.6 Hz), 1.91 (d, 2H, J=11.6 Hz), 2.79-2.84 (m, 2H), 2.95-3.09 (m, 1H), 3.25 (s, 3H), 5.52-5.60 (m, 1H), 6.41 (d, 1H, J=8.4 Hz), 6.56 (s, 1H), 6.72 (d, 1H, J=8.4 Hz), 6.92 (d, 1H, J=8.4 Hz). Melting point: 206 to 207° C.

Compound Ii-8

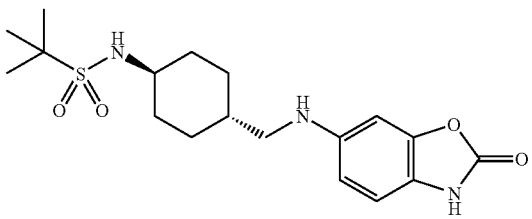

¹H-NMR (DMSO-d₆) δ: 0.91-1.05 (m, 2H), 1.16-1.24 (m, 1H), 1.26 (s, 9H), 1.37-1.47 (m, 2H), 1.81 (d, 2H, J=12.8 Hz), 1.90 (d, 2H, J=12.8 Hz), 2.75-2.81 (m, 2H), 2.96-3.08 (m, 1H), 5.45-5.52 (m, 1H), 6.33 (d, 1H, J=8.4 Hz), 6.50 (s, 1H), 6.68-6.80 (m, 2H), 11.02 (brs, 1H). Melting point: 213 to 214° C.

Compound Ii-9

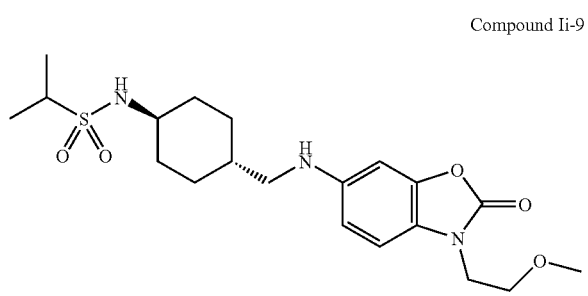

¹H-NMR (DMSO-d₆) δ: 0.91-1.08 (m, 2H), 1.17-1.30 (m, 8H), 1.44 (brs, 1H), 1.82 (d, 2H, J=12.4 Hz), 1.89 (d, 2H, J=12.4 Hz), 2.78-2.82 (m, 2H), 2.97-3.15 (m, 2H), 3.23 (s, 3H), 3.55-3.62 (m, 2H), 3.83-3.90 (m, 2H), 5.52-5.59 (m, 1H), 6.40 (d, 1H, J=8.0 Hz), 6.55 (s, 1H), 6.92 (d, 1H, J=8.0 Hz), 6.97 (d, 1H, J=8.4 Hz). Melting point: 120 to 121° C.

Compound Ii-10

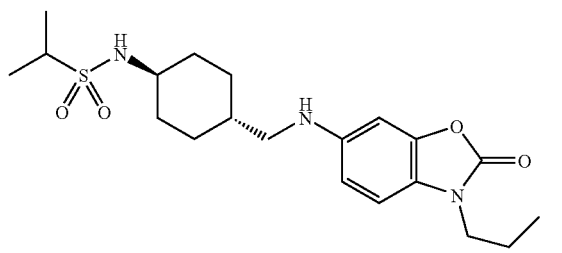

¹H-NMR (DMSO-d₆) δ: 0.88 (t, 3H, J=7.2 Hz), 0.93-1.08 (m, 2H), 1.17-1.30 (m, 8H), 1.44 (brs, 1H), 1.52-1.61 (m, 2H), 1.83 (d, 2H, J=12.0 Hz), 1.90 (d, 2H, J=12.0 Hz), 2.78-2.84 (m, 2H), 2.98-3.15 (m, 2H), 3.62-3.71 (m, 2H), 5.52-5.60 (m, 1H), 6.41 (d, 1H, J=8.4 Hz), 6.57 (s, 1H), 6.92 (d, 1H, J=8.0 Hz), 6.97 (d, 1H, J=8.4 Hz). Melting point: 144 to 145° C.

Compound Ii-11

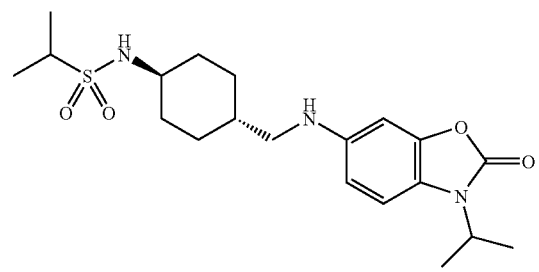

¹H-NMR (DMSO-d₆) δ: 0.90-1.08 (m, 2H), 1.15-1.30 (m, 8H), 1.33-1.50 (m, 7H), 1.82 (d, 2H, J=12.0 Hz), 1.89 (d, 2H, J=12.0 Hz), 2.78-2.86 (m, 2H), 2.96-3.14 (m, 2H), 4.30-4.45 (m, 1H), 5.50-5.61 (m, 1H), 6.40 (d, 1H, J=7.6 Hz), 6.55 (s, 1H), 6.92 (d, 1H, J=7.2 Hz), 7.07 (d, 1H, J=7.6 Hz). Melting point: 137 to 138° C.

Compound Ii-12

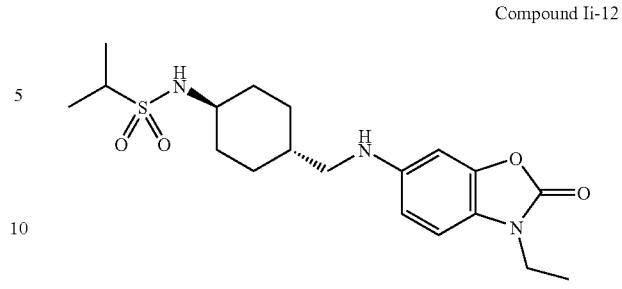

¹H-NMR (DMSO-d₆) δ: 0.92-1.07 (m, 2H), 1.14-1.30 (m, 11H), 1.36-1.50 (m, 1H), 1.82 (d, 2H, J=12.0 Hz), 1.89 (d, 2H, J=12.0 Hz), 2.78-2.85 (m, 2H), 2.97-3.15 (m, 2H), 3.69-3.79 (m, 2H), 5.52-5.60 (m, 1H), 6.41 (d, 1H, J=8.4 Hz), 6.56 (s, 1H), 6.92 (d, 1H, J=7.2 Hz), 6.98 (d, 1H, J=8.4 Hz). Melting point: 158 to 159° C.

Compound Ii-13

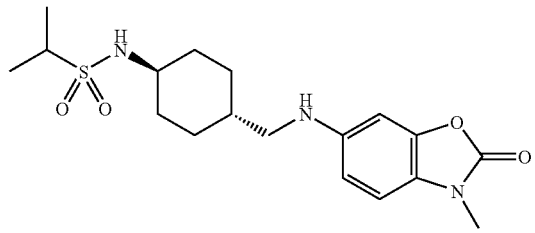

¹H-NMR (DMSO-d₆) δ: 0.90-1.06 (m, 2H), 1.12-1.30 (m, 8H), 1.34-1.51 (m, 1H), 1.82 (d, 2H, J=12.0 Hz), 1.88 (d, 2H, J=12.0 Hz), 2.77-2.83 (m, 2H), 2.95-3.12 (m, 2H), 3.25 (s, 3H), 5.51-5.59 (m, 1H), 6.41 (d, 1H, J=8.8 Hz), 6.56 (s, 1H), 6.86-6.97 (m, 2H). Melting point: 157 to 158° C.

Compound Ii-14

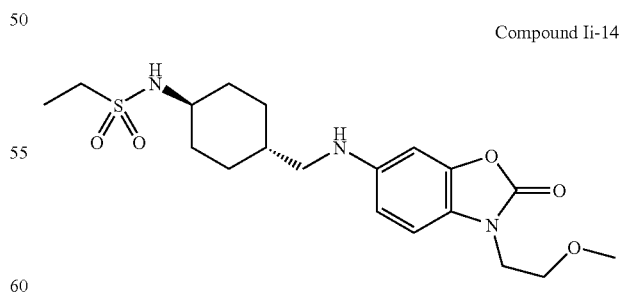

¹H-NMR (DMSO-d₆) δ: 0.91-1.08 (m, 2H), 1.12-1.30 (m, 5H), 1.38-1.50 (m, 1H), 1.82 (d, 2H, J=12.0 Hz), 1.88 (d, 2H, J=12.0 Hz), 2.77-2.85 (m, 2H), 2.90-3.09 (m, 3H), 3.23 (s, 3H), 3.55-3.61 (m, 2H), 3.84-3.91 (m, 2H), 5.52-5.60 (m, 1H), 6.40 (d, 1H, J=8.4 Hz), 6.55 (s, 1H), 6.89-7.00 (m, 2H). Melting point: 150 to 151° C.

Compound Ii-15

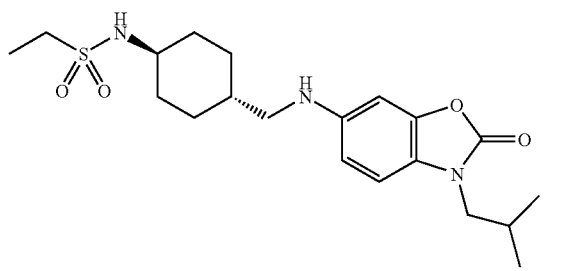

¹H-NMR (DMSO-d₆) δ: 0.88 (s, 3H), 0.90 (s, 3H), 0.92-1.08 (m, 2H), 1.12-1.30 (m, 5H), 1.35-1.51 (m, 1H), 1.83 (d, 2H, J=12.4 Hz), 1.89 (d, 2H, J=12.4 Hz), 2.00-2.16 (m, 1H), 2.77-2.84 (m, 2H), 2.90-3.10 (m, 3H), 3.42-3.55 (m, 2H), 5.50-5.65 (m, 1H), 6.40 (d, 1H, J=8.4 Hz), 6.56 (s, 1H), 6.88-7.01 (m, 2H) Melting point: 132 to 133° C.

Compound Ii-16

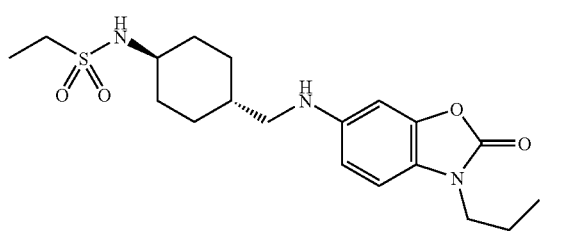

¹H-NMR (DMSO-d₆) δ: 0.87 (t, 3H, J=6.8 Hz), 0.90-1.08 (m, 2H), 1.10-1.28 (m, 5H), 1.35-1.50 (m, 1H), 1.59-1.72 (m, 2H), 1.82 (d, 2H, J=12.0 Hz), 1.89 (d, 2H, J=12.0 Hz), 2.77-2.85 (m, 2H), 2.90-3.09 (m, 3H), 3.61-3.71 (m, 2H), 5.52-5.61 (m, 1H), 6.40 (d, 1H, J=8.0 Hz), 6.56 (s, 1H), 6.97 (d, 2H, J=8.0 Hz). Melting point: 136 to 137° C.

Compound Ii-17

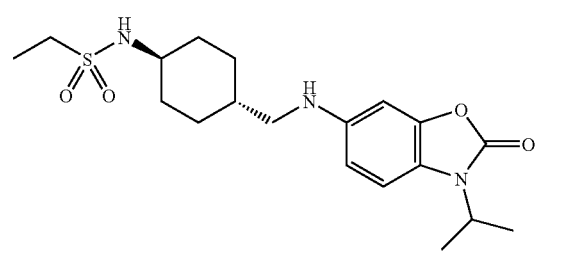

¹H-NMR (DMSO-d₆) δ: 0.92-1.06 (m, 2H), 1.12-1.28 (m, 5H), 1.33-1.50 (m, 7H), 1.81 (d, 2H, J=12.0 Hz), 1.88 (d, 2H, J=12.0 Hz), 2.78-2.84 (m, 2H), 2.90-3.08 (m, 3H), 4.28-4.44 (m, 1H), 5.49-5.79 (m, 1H), 6.39 (d, 1H, J=8.0 Hz), 6.55 (s, 1H), 6.97 (d, 1H, J=7.6 Hz), 7.07 (d, 1H, J=8.0 Hz). Melting point: 124 to 125° C.

Compound Ii-18

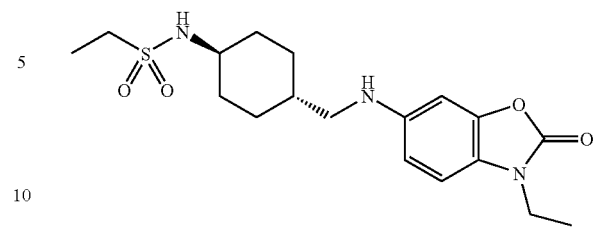

¹H-NMR (DMSO-d₆) δ: 0.90-1.07 (m, 2H), 1.12-1.29 (m, 8H), 1.36-1.51 (m, 1H), 1.82 (d, 2H, J=12.0 Hz), 1.89 (d, 2H, J=12.0 Hz), 2.78-2.86 (m, 2H), 2.90-3.09 (m, 3H), 3.68-3.80 (m, 2H), 5.51-5.61 (m, 1H), 6.41 (d, 1H, J=8.4 Hz), 6.57 (s, 1H), 6.97 (d, 2H, J=8.4 Hz). Melting point: 163 to 164° C.

Compound Ii-19

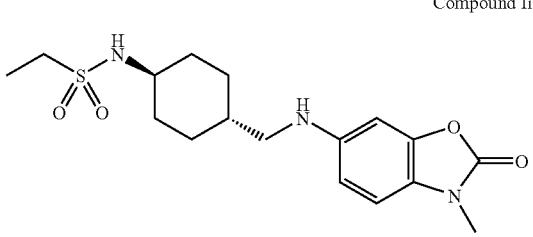

¹H-NMR (DMSO-d₆) δ: 0.89-1.08 (m, 2H), 1.11-1.30 (m, 5H), 1.35-1.51 (m, 1H), 1.82 (d, 2H, J=10.8 Hz), 1.89 (d, 2H, J=10.8 Hz), 2.75-2.88 (m, 2H), 2.89-3.10 (m, 3H), 3.25 (s, 3H), 5.48-5.60 (m, 1H), 6.42 (d, 1H, J=7.6 Hz), 6.56 (s, 1H), 6.92 (d, 1H, J=7.6 Hz), 6.98 (d, 1H, J=5.6 Hz). Melting point: 189 to 190° C.

Compound Ii-20

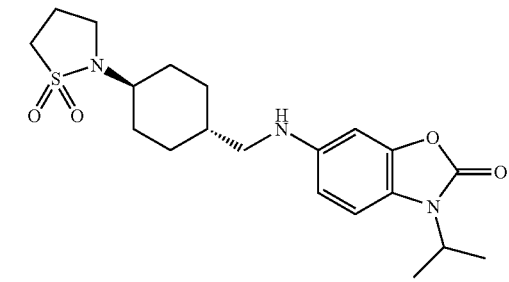

¹H-NMR (DMSO-d₆) δ: 0.95-1.13 (m, 2H), 1.31-1.59 (m, 10H), 1.73-1.92 (m, 4H), 2.12-2.26 (m, 2H), 2.84 (d, 2H, J=6.0 Hz), 3.07-3.30 (m, 4H), 4.30-4.46 (m, 1H), 5.64 (brs, 1H), 6.41 (d, 1H, J=8.4 Hz), 6.57 (s, 1H), 7.08 (d, 1H, J=8.4 Hz). Melting point: 165 to 166° C.

Compound Ii-21

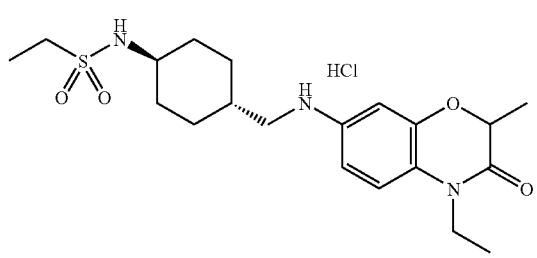

¹H-NMR (DMSO-d₆) δ: 0.86-1.25 (m, 10H), 1.40 (d, 3H, J=6.9 Hz), 1.52 (m, 1H), 1.82-1.93 (m, 4H), 2.95-3.00 (m, 5H), 3.63-3.91 (m, 2H), 4.61-4.68 (m, 1H), 6.73 (brs, 2H), 7.01 (d, 2H, J=7.8 Hz), 7.11 (d, 1H, J=8.1 Hz,).

Compound Ii-22

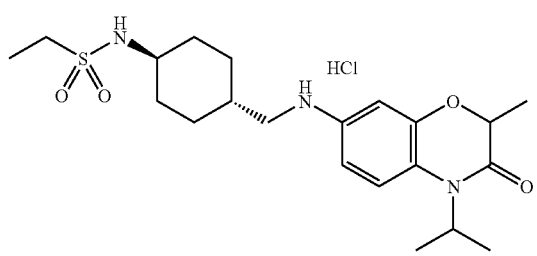

¹H-NMR (DMSO-d₆) δ: 0.98-1.10 (m, 2H), 1.15-1.34 (m, 5H), 1.36-1.43 (m, 9H), 1.53 (m, 1H), 1.82-1.93 (m, 4H), 2.94-3.01 (m, 6H), 4.52 (m, 1H), 4.63 (m, 1H), 6.73 (brs, 2H), 7.02 (d, 1H, J=7.5 Hz), 7.21-7.25 (m, 1H).

Compound Ii-23

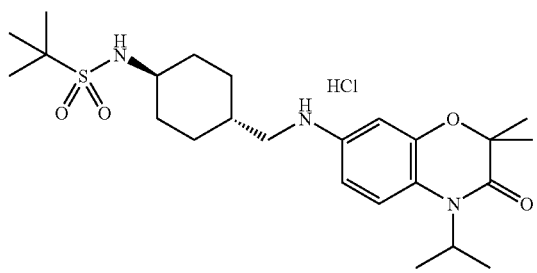

¹H-NMR (DMSO-d₆) δ: 0.86-1.04 (m, 4H), 1.25 (s, 10H), 1.30 (s, 6H), 1.38 (s, 3H), 1.40 (s, 3H), 178-1.92 (m 4H), 2.76-2.80 (m, 2H), 3.03 (m, 1H), 4.54-4.63 (m, 1H), 5.57 (m, 1H), 6.16 (s, 1H), 6.22 (d, 1H, J=8.4 Hz), 6.76 (d, 1H, J=8.4 Hz), 6.98 (d, 1H, J=8.4 Hz).

Compound Ii-24

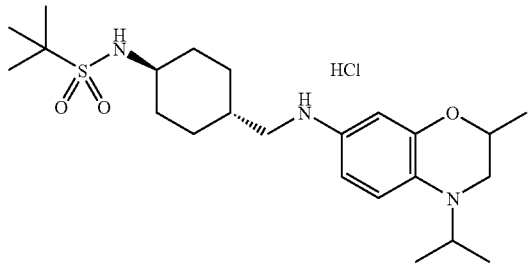

¹H-NMR (DMSO-d₆) δ: 0.98-1.11 (m, 5H), 1.15-1.31 (m, 20H), 1.57 (m, 1H), 1.82-1.93 (m, 4H), 2.74-2.81 (m, 1H), 3.01-3.06 (m, 2H), 3.35 (m, 1H), 3.40 (m, 1H), 4.04-4.17 (m, 3H), 6.77 (d, 1H, J=9.0 Hz),

Compound Ii-25

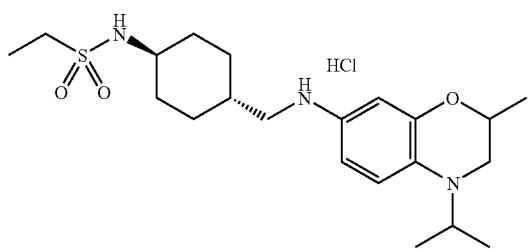

¹H-NMR (DMSO-d₆) δ: 0.98-1.20 (m, 13H), 1.30 (d, 3H, J=3H), 1.59 (m, 1H), 1.81-1.91 (m, 4H), 2.73-2.83 (m, 1H), 2.94-3.04 (m, 4H), 3.35-3.45 (m, 2H), 4.08-4.19 (m, 3H), 6.88 (brs, 3H), 7.03 (d, 1H, J=8.4 Hz).

Compound Ii-26

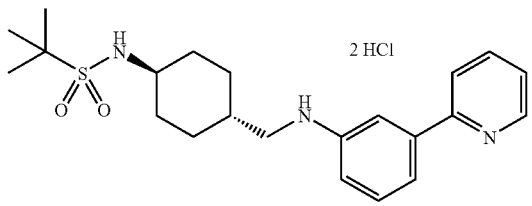

¹H-NMR (DMSO-d₆) δ: 1.02-1.10 (m, 2H), 1.19-1.32 (m, 2H), 1.26 (s, 9H), 1.55 (m, 1H), 1.86-1.93 (m, 4H), 3.01-3.04 (m, 3H), 6.76 (d, 1H, J=8.7 Hz), 7.03 (m, 1H), 7.37-7.43 (m, 3H), 7.76-7.80 (m, 1H), 8.20-8.23 (m, 1H), 8.34-8.40 (m, 1H), 8.78-8.79 (m, 1H)

Compound Ii-27

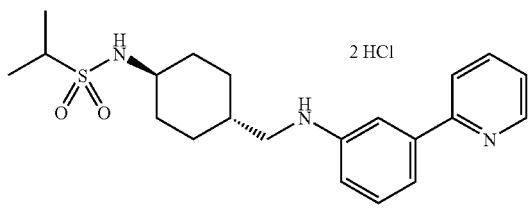

¹H-NMR (DMSO-d₆) δ: 1.03-1.10 (m, 2H), 1.20-1.30 (m, 2H), 1.21 (d, 6H, J=6.9 Hz), 1.53 (m, 1H), 1.88 (m, 4H), 2.99-3.15 (m, 3H), 7.33-7.35 (m, 3H), 7.71-7.75 (m, 1H), 8.16-8.18 (m, 1H), 829-8.32 (m, 1H), 8.76-8.78 (m, 1H)

Compound Ii-28

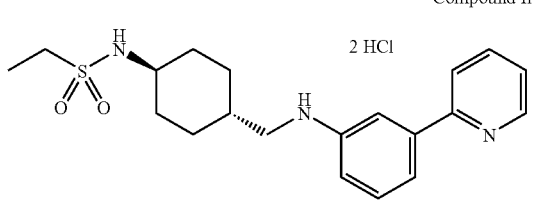

$^1$H-NMR (DMSO-$d_6$) δ: 1.04-1.11 (m, 2H), 1.15-1.28 (m, 2H), 1.19 (t, 3H, J=7.2 Hz), 1.59 (m, 1H), 1.87-1.91 (m, 4H), 2.93-3.08 (m, 2H), 2.97 (q, 2H, J=7.2 Hz), 3.06-3.08 (m, 2H), 7.01 (m, 1H), 7.17 (d, 1H, J=7.5 Hz), 7.43 (d, 1H, J=7.5 Hz), 7.50-7.57 (m, 2H), 7.80-7.84 (m, 1H), 8.25-8.27 (m, 1H), 8.39-8.44 (m, 1H), 8.80-8.82 (m, 1H)

Compound Ii-29

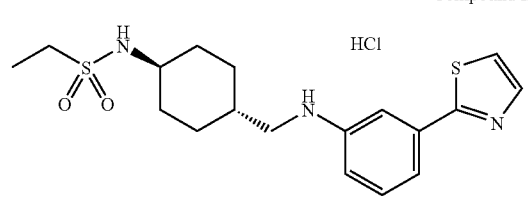

$^1$H-NMR (DMSO-$d_6$) δ: 0.99-1.10 (m, 2H), 1.15-1.28 (m, 2H), 1.19 (t, 3H, J=7.5 Hz), 1.52 (m, 1H), 1.84-1.91 (m, 4H), 2.94-3.01 (m, 5H), 6.88 (m, 1H), 7.00 (d, 1H, J=7.8 Hz), 7.26-7.28 (m, 2H), 7.38 (m, 1H), 7.76 (d, 1H, J=3.3 Hz), 7.90 (d, 1H, J=3.3 Hz)

Compound Ii-30

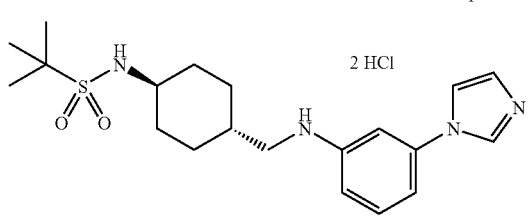

$^1$H-NMR (DMSO-$d_6$) δ: 0.93-1.08 (m, 2H), 1.18-1.33 (m, 2H), 1.26 (s, 9H), 1.45 (m, 1H), 1.78-1.97 (m, 4H), 2.86-2.94 (m, 2H), 2.95-3.10 (m, 1H), 5.91 (m, 1H), 6.55 (d, 1H, J=7.6 Hz), 6.63-6.71 (m, 2H), 6.73 (d, 1H, J=8.0 Hz), 7.06 (s, 1H), 7.15 (t, 1H, J=8.0 Hz), 7.60 (s, 1H), 8.11 (s, 1H), 8.31 (s, 1H)

Compound Ii-31

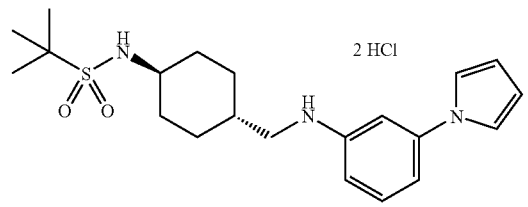

$^1$H-NMR (DMSO-$d_6$) δ: 0.93-1.08 (m, 2H), 1.13-1.28 (m, 2H), 1.26 (s, 9H), 1.43 (m, 1H), 1.76-1.97 (m, 4H), 2.83-3.18 (m, 3H), 5.79 (m, 1H), 6.21 (s, 2H), 6.44 (d, 1H, J=6.8 Hz), 6.58-6.67 (m, 2H), 6.73 (d, 1H, J=8.0 Hz), 7.10 (t, 1H, J=8.0 Hz), 7.21 (s, 2H) Melting point: 205 to 206° C.

Compound Ii-32

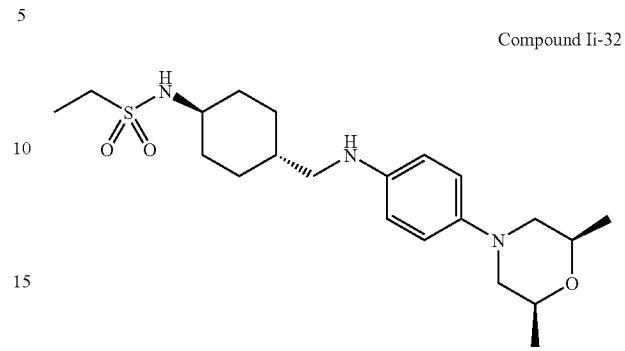

$^1$H-NMR (DMSO-$d_6$) δ: 0.90-1.05 (m, 2H), 1.05-1.28 (m, 11H), 1.41 (m, 1H), 1.75-1.92 (m, 4H), 2.11 (t, 2H, J=10.0 Hz), 2.73-2.82 (m, 2H), 2.91-3.08 (m, 3H), 3.24 (d, 2H, J=11.2 Hz), 3.62-3.72 (m, 2H), 5.07 (m, 1H), 6.47 (d, 2H, J=7.2 Hz), 6.72 (d, 2H, J=7.2 Hz), 6.97 (d, 1H, J=7.6 Hz) Melting point: 165 to 166° C.

Compound Ii-33

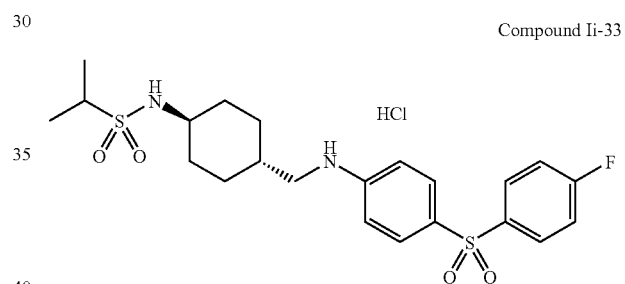

$^1$H-NMR (DMSO-$d_6$) δ: 0.91-1.06 (m, 2H), 1.15-1.26 (m, 8H), 1.33-1.48 (m, 1H), 1.71-1.93 (m, 4H), 2.88 (d, 2H, J=6.5 Hz), 2.93-3.15 (m, 2H), 5.70 (brs, 2H), 6.63 (d, 2H, J=9.1 Hz), 6.93-6.96 (m, 1H), 7.38-7.42 (m, 2H), 7.57 (d, 2H, J=9.1 Hz), 7.88-7.93 (m, 2H)

Compound Ii-34

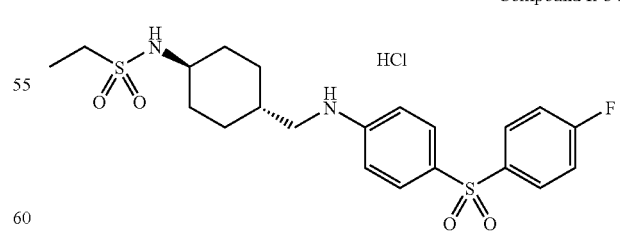

$^1$H-NMR (DMSO-$d_6$) δ: 0.98-1.02 (m, 2H), 1.16-1.18 (m, 5H), 1.42 (s, 1H), 1.75-1.91 (m, 4H), 2.88 (d, 2H, J=6.6 Hz), 2.96 (q, 3H, J=7.3 Hz), 6.63 (d, 2H, J=8.9 Hz), 6.99-7.02 (m, 1H), 7.38-7.41 (m, 2H), 7.57 (d, 2H, J=8.9 Hz), 7.89-7.92 (m, 2H).

Compound Ii-35

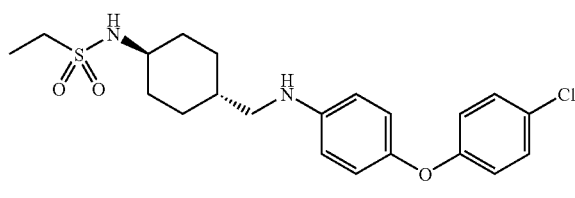

¹H-NMR (DMSO-d₆) δ: 0.90-1.52 (m, 5H), 1.19 (t, 3H, J=7.2 Hz), 1.75-1.96 (m, 4H), 2.50-3.10 (m, 3H), 2.62 (q, 2H, J=7.2 Hz), 5.55-5.70 (m, 1H), 6.57 (d, 2H, J=8.7 Hz), 6.80-7.04 (m, 4H), 7.01 (d, 1H, J=7.8 Hz), 7.34 (d, 2H, J=8.7 Hz)

Compound Ii-36

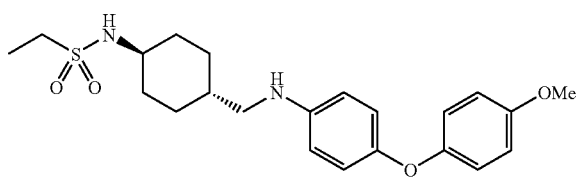

¹H-NMR (DMSO-d₆) δ: 0.90-1.50 (m, 5H), 1.19 (t, 3H, J=7.2 Hz), 1.75-1.95 (m, 4H), 2.70-3.10 (m, 3H), 2.97 (q, 2H, J=7.2 Hz), 3.70 (s, 3H), 5.40-5.50 (m, 1H), 6.53 (d, 2H, J=8.7 Hz), 6.74 (d, 2H, J=8.7 Hz), 6.78-6.90 (m, 4H), 6.99 (d, 1H, J=7.8 Hz)

Compound Ii-37

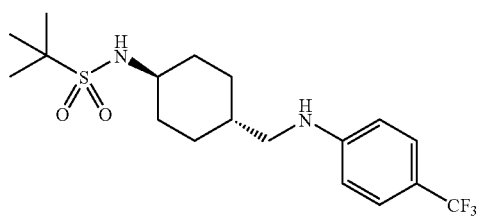

¹H-NMR (CDCl₃) δ: 1.02-1.32 (m, 4H), 139 (s, 9H,), 1.58 (m, 1H), 1.86-1.96 (m, 2H), 2.12-2.22 (m, 2H), 3.02 (d, 2H, J=6.6 Hz), 3.25 (m, 1H), 3.67 (d, 1H, J=9.3 Hz), 6.67 (d, 2H, J=8.7 Hz), 7.41 (d, 2H, J=8.7 Hz) Mass: 393[M+H]

Compound Ii-38

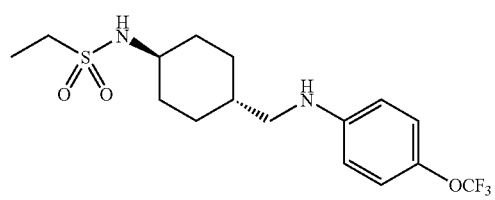

¹H-NMR (DMSO-d₆) δ: 0.93-1.07 (m, 2H), 1.17-1.26 (m, 2H), 1.19 (t, 3H, J=7.1 Hz), 1.43 (s, 1H), 1.77-1.85 (m, 2H), 1.85-1.94 (m, 2H), 2.82 (t, 1H, J=5.8 Hz), 2.98 (m, 1H), 2.97 (q, 2H, J=7.1 Hz), 5.87 (m, 1H), 6.56 (d, 1H, J=8.6 Hz), 6.98 (d, 1H, J=7.6 Hz), 7.02 (d, 2H, J=8.6 Hz).

Compound Ii-39

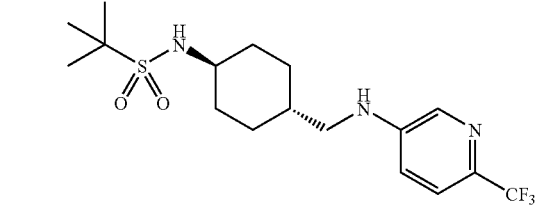

¹H-NMR (DMSO-d₆) δ: 0.98-1.10 (m, 2H), 1.19-1.35 (m, 2H), 1.29 (s, 9H), 1.46 (s, 1H), 1.73-1.98 (m, 4H), 2.93 (m, 1H), 3.04 (m, 1H), 6.60-6.69 (m, 2H), 6.75 (d, 1H, J=8.8 Hz), 6.97 (d, 1H, J=7.6 Hz), 7.49 (d, 1H, J=8.8 Hz), 8.05 (s, 1H).

Compound Ii-40

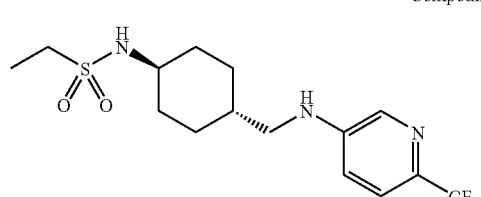

¹H-NMR (DMSO-d₆) δ: 0.96-1.09 (m, 2H), 1.16-1.29 (m, 2H), 1.19 (t, 3H, J=7.3 Hz), 1.45 (s, 1H), 1.76-1.94 (m, 4H), 1.76 (s, 2H), 2.93 (t, 2H, J=5.8 Hz), 2.97 (q, 2H, J=7.3 Hz), 6.66 (s, 1H), 6.94-7.01 (m, 2H), 7.49 (d, 1H, J=8.6 Hz), 8.04 (s, 1H).

Compound Ii-41

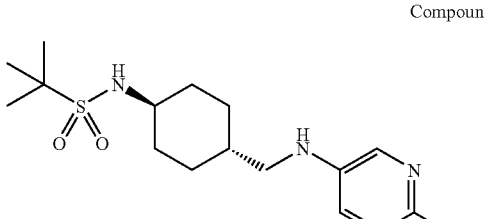

¹H-NMR (DMSO-d₆) δ: 0.91-1.05 (m, 2H), 1.17-1.33 (m, 2H), 1.26 (s, 9H), 1.35-1.48 (m, 1H), 1.76-1.86 (m, 2H), 1.86-1.95 (m, 2H), 2.76-2.82 (m, 1H), 2.96-3.08 (m, 1H), 3.71 (s, 3H), 5.21-5.30 (m, 1H), 6.57 (d, 1H, J=8.6 Hz), 6.73 (d, 1H, J=8.6 Hz), 7.02 (dd, 1H, J=8.6, 2.3 Hz), 7.44 (d, 1H, J=2.3 Hz).

Compound Ii-42

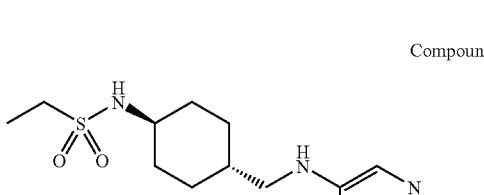

¹H-NMR (DMSO-d₆) δ: 0.98-1.01 (m, 2H), 1.18-1.28 (m, 2H), 1.19 (t, 3H, J=7.1 Hz), 1.42 (s, 1H), 1.76-1.85 (m, 2H), 1.85-1.93 (m, 2H), 2.79 (t, 2H, J=5.9 Hz), 2.97 (q, 2H, J=7.1

Hz), 3.02 (m, 1H), 3.71 (s, 3H), 5.26 (m, 1H), 6.58 (d, 1H, J=8.6 Hz), 6.98 (d, 2H, J=7.8 Hz), 7.02 (d, 2H, J=8.6 Hz), 7.44 (br s, 1H).

Compound Ii-43

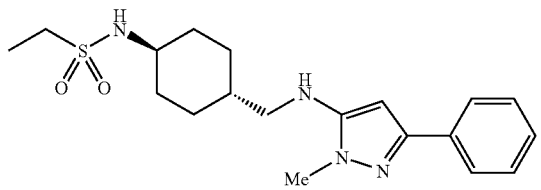

¹H-NMR (DMSO-d₆) δ: 0.98-1.06 (m, 2H), 1.16-1.25 (m, 2H), 1.18 (t, 3H, J=7.5 Hz), 1.51 (m, 1H), 1.83-1.91 (m, 4H), 2.85 (t, 2H, J=6.3 Hz), 2.97 (q, 2H, J=7.5 Hz), 3.04 (m, 1H), 3.56 (s, 3H), 5.46 (t, 1H, J=6.3 Hz), 5.76 (s, 1H), 6.49 (d, 1H, J=7.8 Hz), 7.21 (t, 1H, J=7.5 Hz), 7.32 (t, 2H, J=7.5 Hz), 7.68 (d, 2H, J=7.5 Hz)

Compound Ii-44

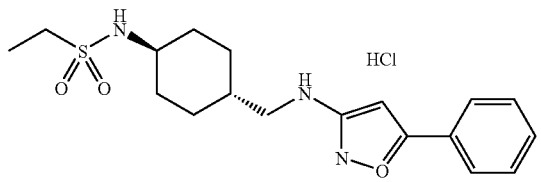

¹H-NMR (DMSO-d₆) δ: 0.96-1.05 (m, 2H), 1.18 (t, 3H, J=7.2 Hz), 1.24 (m, 2H), 1.48 (m, 1H), 1.76-1.91 (m, 4H), 2.91 (d, 2H, J=6.6 Hz), 2.97 (q, 2H, J=7.2 Hz), 6.35 (s, 1H), 6.99 (d, 1H, J=7.8 Hz), 7.46-7.49 (m, 3H), 7.73-7.76 (m, 2H)

Compound Ii-45

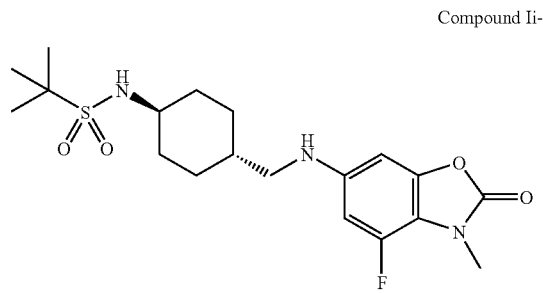

¹H-NMR (DMSO-d₆) δ: 0.92-1.08 (m, 2H), 1.15-1.22 (m, 1H), 1.26 (s, 9H), 1.37-1.51 (m, 2H), 1.81 (d, 2H, J=11.6 Hz), 1.91 (d, 2H, J=11.6 Hz), 2.76-2.86 (m, 2H), 2.97-3.08 (m, 1H), 3.35 (s, 3H), 5.82-5.91 (m, 1H), 6.26 (d, 1H, J=13.6 Hz), 6.39 (s, 1H), 6.73 (brs, 1H). Melting point: 215 to 216° C.

Compound Ii-46

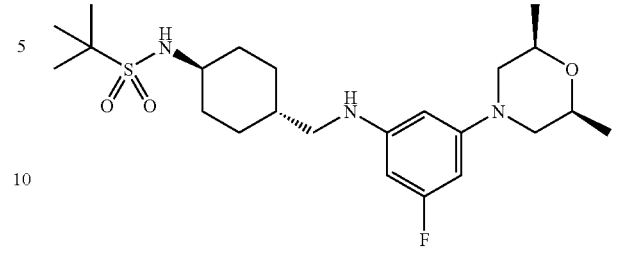

¹H-NMR (CDCl₃) δ: 1.02-1.32 (m, 4H), 1.24 (d, 6H, J=6.0 Hz), 1.39 (s, 9H), 1.54 (m, 1H), 1.84-1.94 (m, 2H), 2.12-2.22 (m, 2H), 2.39 (t, 2H, J=10.5 Hz), 2.94 (d, 2H, J=6.9 Hz), 3.24 (m, 1H), 3.38 (d, 1H, J=9.6 Hz), 3.61 (d, 1H, J=9.6 Hz), 3.72-4.00 (m, 2H), 5.83-5.94 (m, 1H), 5.96-6.10 (m, 2H).

Compound Ii-47

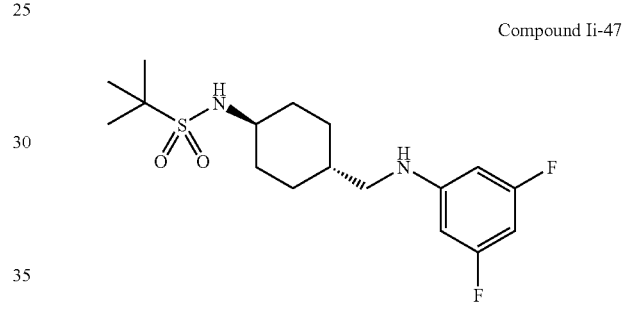

¹H-NMR (DMSO-d₆) δ: 0.91-1.07 (m, 2H), 1.16-1.34 (m, 11H), 1.40 (m, 1H), 1.79 (d, 2H, J=12.5 Hz), 1.90 (d, 2H, J=11.9 Hz), 2.82 (t, 2H, J=5.5 Hz), 3.01 (m, 1H), 6.12-6.18 (m, 3H), 6.30 (t, 1H, J=5.5 Hz), 6.76 (d, 1H, J=8.7 Hz).

Compound Ii-48

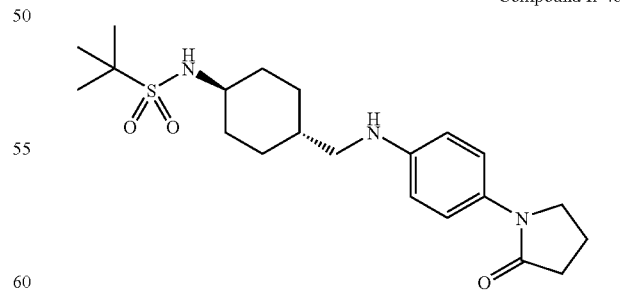

¹H-NMR (CDCl₃) δ: 1.00-1.28 (m, 4H), 1.39 (s, 9H), 1.56 (m, 1H), 1.91 (d, 2H, J=12.4 Hz), 2.08-2.21 (m, 4H), 2.58 (t, 2H, J=8.1 Hz), 2.97 (d, 2H, J=6.0 Hz), 3.23 (m, 1H), 3.70 (d, 1H, J=9.4 Hz), 3.80 (t, 2H, J=7.1 Hz), 6.66 (d, 2H, J=8.7 Hz), 7.36 (d, 2H, J=8.7 Hz).

Compound Ii-49

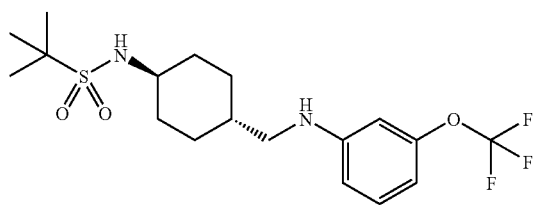

¹H-NMR (DMSO-d₆) δ: 0.92-1.06 (m, 2H), 1.17-1.33 (m, 11H), 1.41 (m, 1H), 1.80 (d, 2H, J=12.9 Hz), 1.90 (d, 2H, J=11.4 Hz), 2.82 (t, 2H, J=6.1 Hz), 3.01 (m, 1H), 6.07 (t, 1H, J=5.3 Hz), 6.34-6.43 (m, 2H), 6.51 (dd, 1H, J1=8.2 Hz, J2=1.8 Hz), 6.75 (d, 1H, J=8.5 Hz), 7.11 (t, 1H, 8.2 Hz).

Compound Ii-50

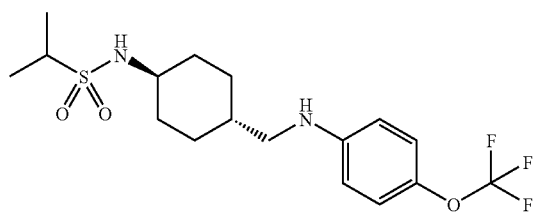

¹H-NMR (DMSO-d₆) δ: 0.92-1.08 (m, 2H), 1.14-1.31 (m, 8H), 1.43 (m, 1H), 1.76-1.94 (m, 4H), 2.82 (t, 2H, J=6.0 Hz), 2.95-3.16 (m, 2H), 5.90 (t, 1H, J=5.5 Hz), 6.56 (d, 2H, J=8.7 Hz), 6.95 (d, 1H, J=7.9 Hz), 7.03 (d, 2H, J=8.6 Hz).

Compound Ii-51

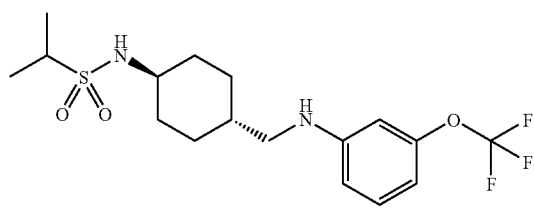

¹H-NMR (DMSO-d₆) δ: 0.90-1.08 (m, 2H), 1.13-1.31 (m, 8H), 1.42 (m, 1H), 1.76-1.94 (m, 4H), 2.83 (t, 2H, J=6.0 Hz), 2.95-3.16 (m, 2H), 6.07 (t, 1H, J=5.4 Hz), 6.36-6.46 (m, 2H), 6.53 (dd, 1H, J1=8.1 Hz, J2=1.9 Hz), 6.95 (d, 1H, J=7.9 Hz), 7.12 (d, 1H, J=8.1 Hz).

Compound Ii-52

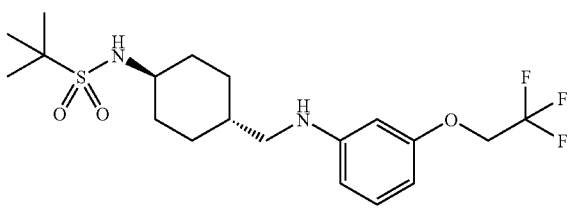

¹H-NMR (DMSO-d₆) δ: 0.91-1.10 (m, 2H), 1.19-1.37 (m, 11H), 1.45 (m, 1H), 1.78-1.90 (m, 4H), 2.84 (t, 2H, J=6.0 Hz), 3.04 (m, 1H), 4.64 (q, 2H, J=9.0 Hz), 5.73 (t, 1H, J=5.4 Hz), 6.13-6.21 (m, 2H), 6.26 (d, 1H, J=7.2 Hz), 6.78 (d, 1H, J=8.4 Hz), 6.99 (t, 1H, 8.0 Hz).

Compound Ii-53

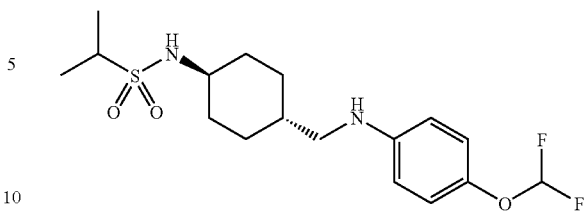

¹H-NMR (DMSO-d₆) δ: 0.90-1.06 (m, 2H), 1.13-1.30 (m, 8H), 1.42 (m, 1H), 1.75-1.93 (m, 4H), 2.80 (t, 2H, J=6.2 Hz), 2.93-3.16 (m, 2H), 5.66 (t, 1H, J=5.5 Hz), 6.53 (d, 2H, J=9.1 Hz), 6.89 (d, 2H, J=8.8 Hz), 6.92 (t, 1H, J_{H-F}=75 Hz), 6.94 (d, 1H, J=8.0 Hz).

Compound Ii-54

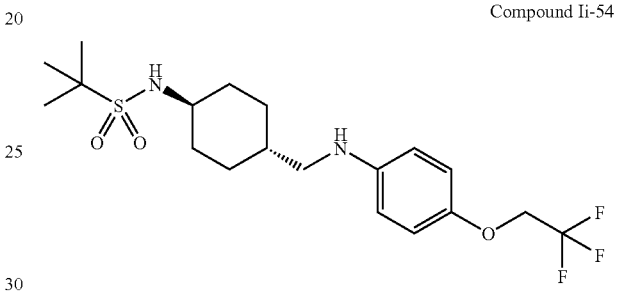

¹H-NMR (DMSO-d₆) δ: 0.88-1.05 (m, 2H), 1.14-1.32 (m, 11H), 1.41 (m, 1H), 1.75-1.94 (m, 4H), 2.77 (t, 2H, J=6.0 Hz), 3.01 (m, 1H), 4.54 (q, 2H, J=9.0 Hz), 5.33 (t, 1H, J=5.8 Hz), 6.49 (d, 2H, J=8.8 Hz), 6.75 (d, 1H, J=8.8 Hz), 6.80 (d, 2H, J=8.8 Hz).

Compound Ii-55

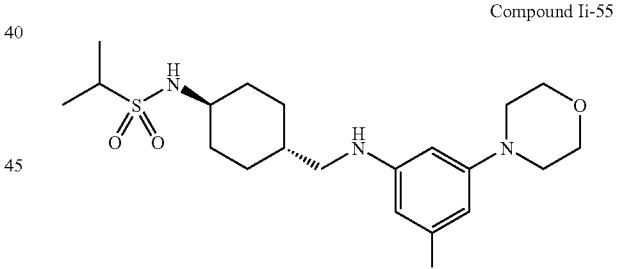

¹H-NMR (DMSO-d₆) δ: 0.90-1.06 (m, 2H), 1.14-1.31 (m, 8H), 1.40 (m, 1H), 1.74-1.93 (m, 4H), 2.79 (t, 2H, J=5.9 Hz), 2.94-3.15 (m, 6H), 3.69 (t, 4H, J=4.8 Hz), 5.70-5.94 (m, 4H), 6.94 (d, 1H, J=8.0 Hz).

Compound Ii-56

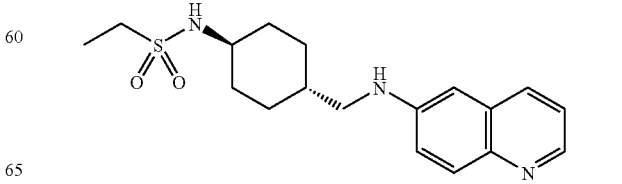

¹H-NMR (DMSO-d₆) δ: 0.98-1.14 (m, 2H), 1.15-1.32 (m, 5H), 1.54 (m, 1H), 1.83-1.96 (m, 4H), 2.89-3.10 (m, 5H), 6.17 (t, 1H, J=5.2 Hz), 6.63 (d, 1H, J=2.2 Hz), 7.02 (d, 1H, J=7.7 Hz), 7.21 (dd, 1H, J1=9.1 Hz, J2=2.5 Hz), 7.27 (dd, 1H, J1=8.2 Hz, J2=4.4 Hz), 7.67 (d, 1H, J=9.1 Hz), 7.97 (d, 1H, J=8.2 Hz), 8.45 (dd, 1H, J1=4.3 Hz, J2=1.5 Hz).

Compound Ii-57

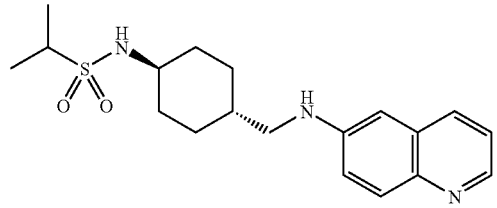

¹H-NMR (DMSO-d₆) δ: 0.97-1.14 (m, 2H), 1.17-1.34 (m, 8H), 1.54 (m, 1H), 1.83-1.96 (m, 4H), 2.94 (t, 2H, J=6.0 Hz), 2.99-3.18 (m, 2H), 6.17 (t, 1H, J=5.4 Hz), 6.63 (d, 1H, J=2.5 Hz), 6.96 (d, 1H, J=7.7 Hz), 7.21 (dd, 1H, J1=9.1 Hz, J2=2.5 Hz), 7.27 (dd, 1H, J1=8.2 Hz, J2=4.1 Hz), 7.67 (d, 1H, J=9.1 Hz), 7.97 (d, 1H, J=8.0 Hz), 8.45 (dd, 1H, J1=4.3 Hz, J2=1.5 Hz).

Compound Ii-58

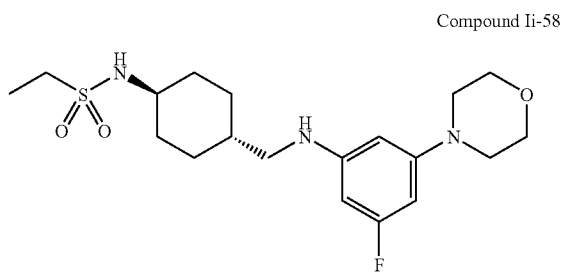

¹H-NMR (DMSO-d₆) δ: 0.90-1.07 (m, 2H), 1.12-1.29 (m, 5H), 1.40 (m, 1H), 1.74-1.93 (m, 4H), 2.80 (t, 2H, J=5.9 Hz), 2.92-3.07 (m, 7H), 3.69 (t, 4H, J=4.8 Hz), 5.69-5.95 (m, 4H), 6.99 (d, 1H, J=7.7 Hz).

Compound Ii-59

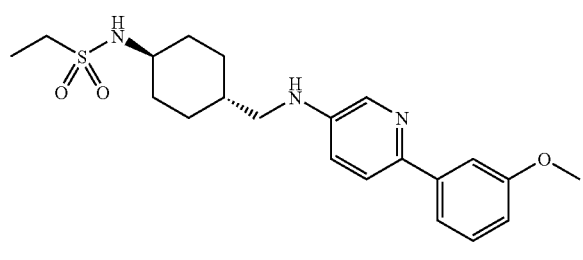

¹H-NMR (DMSO-d₆) δ: 0.94-1.11 (m, 2H), 1.14-1.30 (m, 5H), 1.47 (m, 1H), 1.78-1.95 (m, 4H), 2.88-3.09 (m, 5H), 3.80 (s, 3H), 6.09 (t, 1H, J=5.6 Hz), 6.81-6.86 (m, 1H), 6.96 (dd, 1H, J1=8.8 Hz, J2=2.8 Hz), 7.01 (d, 1H, J=7.4 Hz), 7.29 (t, 1H, J=8.0 Hz), 7.45-7.51 (m, 2H), 7.66 (d, 1H, J=8.5 Hz), 8.04 (d, 1H, J=2.8 Hz).

Compound Ii-60

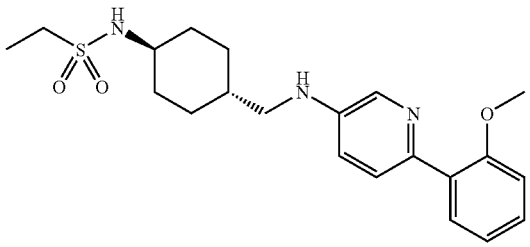

¹H-NMR (DMSO-d₆) δ: 1.03 (m, 2H), 1.19 (t, 2H, J=7.8 Hz), 1.21 (m, 2H), 1.46 (m, 1H), 1.76-1.95 (m, 4H), 2.90 (t, 2H, J=5.8 Hz), 2.97 (q, 2H, J=7.3 Hz), 3.03 (m, 1H), 3.80 (s, 3H), 5.95 (m, 1H), 6.90 (m, 1H), 6.98 (d, 1H, J=7.8 Hz), 6.98 (dd, 1H, J=7.8, 7.8 Hz), 7.06 (d, 1H, J=8.6 Hz), 7.26 (dd, 1H, J=7.8, 7.8 Hz), 7.61 (d, 1H, J=8.6 Hz), 7.69 (d, 1H, J=7.8 Hz), 8.03 (s, 1H).

Compound Ii-61

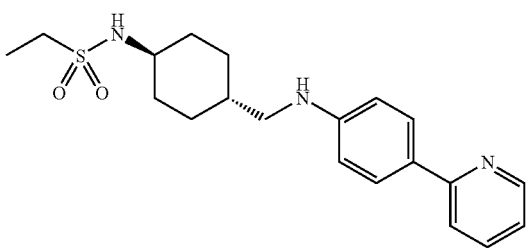

¹H-NMR (DMSO-d₆) δ: 0.96-1.09 (m, 2H), 1.18-1.29 (m, 2H), 1.19 (t, 3H, J=7.6 Hz), 1.47 (m, 1H), 1.87 (m, 5H), 2.90 (t, 2H, J=6.3 Hz), 2.97 (q, 2H, J=7.6 Hz), 3.02 (m, 1H), 5.98 (m, 1H), 6.63 (d, 2H, J=8.3 Hz), 6.98 (d, 1H, J=7.3 Hz), 7.14 (m, 1H), 7.73 (s, 2H), 7.83 (d, 2H, J=8.3 Hz), 8.52 (d, 1H, J=4.0 Hz).

Compound Ii-62

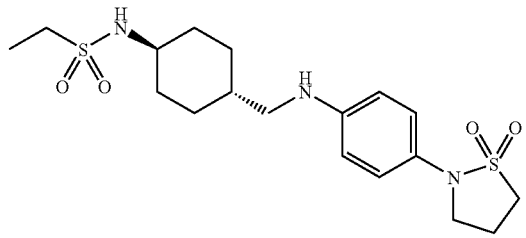

¹H-NMR (DMSO-d₆) δ: 0.98-1.01 (m, 2H), 1.20 (s, 9H), 1.20-1.37 (m, 2H), 1.42 (m, 1H), 1.76-1.96 (m, 4H), 2.28-2.37 (m, 2H), 2.75-2.85 (m, 2H), 3.02 (m, 1H), 3.36 (t, 2H, J=7.8 Hz), 3.57 (t, 2H, J=6.3 Hz), 5.66 (m, 1H), 6.54 (d, 2H, J=8.0 Hz), 6.73 (d, 1H, J=8.6 Hz), 7.00 (d, 1H, J=8.0 Hz).

Compound Ii-63

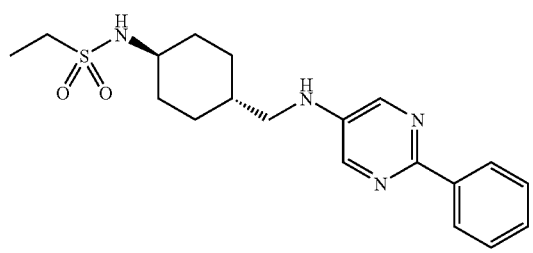

¹H-NMR (DMSO-d₆) δ: 0.96-1.14 (m, 2H), 1.14-1.32 (m, 2H), 1.19 (t, 3H, J=7.2 Hz), 1.50 (m, 1H), 1.76-1.96 (m, 4H), 2.91-3.10 (m, 3H), 2.97 (q, 2H, J=7.2 Hz), 6.28 (m, 1H), 7.02 (d, 1H, J=7.8 Hz), 7.32-7.46 (m, 3H), 8.20 (d, 1H, J=6.9 Hz), 8.22 (s, 2H).

Compound Ii-64

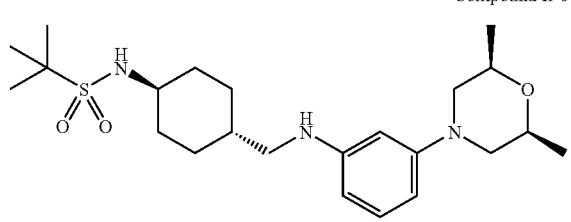

¹H-NMR (DMSO-d₆) δ: 1.03-1.15 (m, 2H), 1.18-1.29 (m, 2H), 1.24 (d, 6H, J=6.3 Hz), 1.52 (m, 1H), 1.86-1.94 (m, 2H), 2.10-2.19 (m, 2H), 2.40 (t, 2H, J=6.0 Hz), 2.95 (d, 2H, J=6.0 Hz), 3.23 (m, 1H), 3.40 (d, 2H, J=11.4 Hz), 3.75-3.85 (m, 2H), 3.86 (d, 1H, J=9.3 Hz), 6.14 (d, 1H, J=8.5 Hz), 6.15 (s, 1H), 6.29 (d, 1H, J=8.5 Hz), 7.06 (d, 1H, J=8.5 Hz).

Compound Ii-65

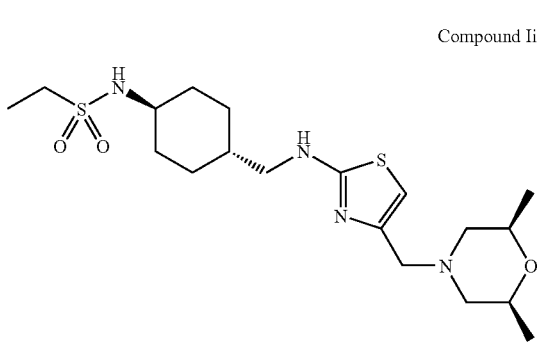

¹H-NMR (CDCl₃) δ: 1.08-1.16 (m, 2H), 1.14 (d, 6H, J=6.8 Hz), 1.21-1.30 (m, 2H), 1.29 (s, 9H), 1.78 (t, 2H, J=10.6 Hz), 1.83-1.92 (m, 2H), 2.11-2.19 (m, 2H), 2.78 (d, 2H, J=10.6 Hz), 3.06 (s, 2H), 3.23 (m, 1H), 3.38 (s, 2H), 3.70-3.80 (m, 2H), 4.02 (d, 1H, J=9.9 Hz), 5.37 (s, 1H), 6.30 (s, 1H).

Compound Ii-66

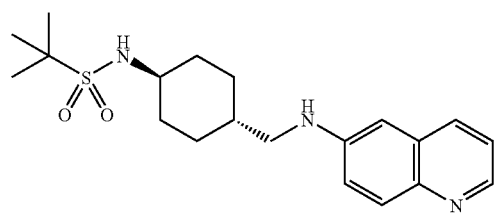

¹H-NMR (DMSO-d₆) δ: 1.01-1.12 (m, 2H), 1.20-1.34 (m, 2H), 1.27 (s, 9H), 1.54 (m, 1H), 1.82-1.99 (m, 4H), 2.91-2.98 (m, 2H), 3.06 (m, 1H), 6.17 (s, 1H), 6.63 (s, 1H), 6.78 (d, 1H, J=9.0 Hz), 7.20 (m, 1H), 7.27 (m, 1H), 7.77 (d, 1H, J=9.0 Hz), 7.98 (d, 1H, J=9.0 Hz), 8.54 (s, 1H).

Compound Ii-67

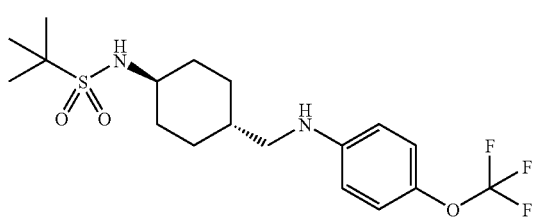

¹H-NMR (DMSO-d₆) δ: 0.92-1.06 (m, 2H), 1.20-1.32 (m, 2H), 1.26 (s, 9H), 1.42 (m, 1H), 1.78-1.88 (m, 2H), 1.88-1.96 (m, 2H), 2.78-2.86 (m, 2H), 3.02 (m, 1H), 5.89 (s, 1H), 6.56 (d, 1H, J=8.4 Hz), 6.76 (d, 1H, J=8.4 Hz), 7.02 (d, 1H, J=8.4 Hz).

Compound Ii-68

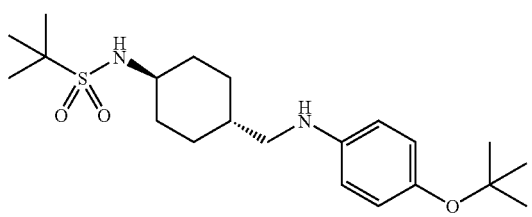

¹H-NMR (DMSO-d₆) δ: 0.92-1.05 (m, 2H), 1.19 (s, 9H), 1.20-1.32 (m, 2H), 1.26 (s, 9H), 1.42 (m, 1H), 1.80-1.96 (m, 4H), 2.77 (s, 2H), 3.04 (m, 1H), 5.29 (s, 1H), 6.44 (d, 1H, J=7.2 Hz), 6.68 (d, 1H, J=7.2 Hz), 6.75 (d, 1H, J=8.4 Hz).

Compound Ii-69

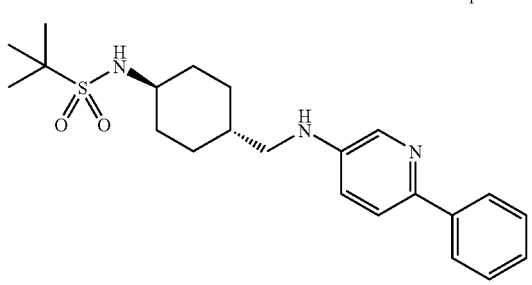

¹H-NMR (DMSO-d₆) δ: 0.95-1.10 (m, 2H), 1.20-1.32 (m, 2H), 1.26 (s, 9H), 1.47 (m, 1H), 1.80-1.88 (m, 2H), 1.88-1.95

(m, 2H), 2.88-2.95 (m, 2H), 3.02 (s, 1H), 6.07 (m, 1H), 6.77 (d, 1H, J=8.4 Hz), 6.97 (d, 1H, J=7.6 Hz), 7.26 (t, 1H, J=7.6 Hz), 7.35-7.42 (m, 2H), 7.46 (d, 1H, J=8.4 Hz), 7.91 (d, 1H, J=7.6 Hz), 8.04 (s, 1H).
Compound Ii-70
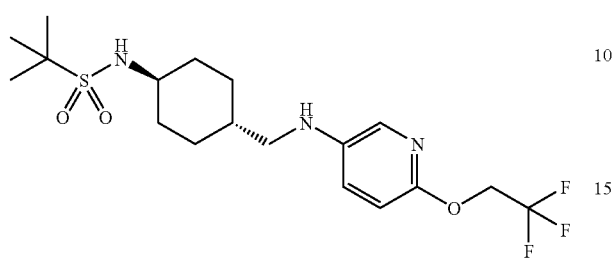
$^1$H-NMR (DMSO-d$_6$) δ: 0.93-1.05 (m, 2H), 1.10-1.32 (m, 2H), 1.26 (s, 9H), 1.42 (m, 1H), 1.78-1.86 (m, 2H), 1.86-1.95 (m, 2H), 2.78-2.83 (m, 2H), 3.03 (m, 1H), 4.80 (q, 2H, J=9.2 Hz), 5.48 (t, 1H, J=5.6 Hz), 6.69-6.76 (m, 2H), 7.08 (dd, 1H, J=8.8, 2.4 Hz), 7.45 (d, 1H, J=2.4 Hz).
Compound Ii-71
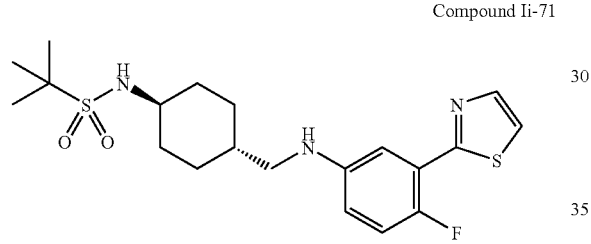
$^1$H-NMR (DMSO-d$_6$) δ: 0.96-1.10 (m, 2H), 1.20-1.32 (m, 2H), 1.27 (s, 9H), 1.82-1.88 (m, 2H), 1.88-1.97 (m, 2H), 2.83-2.88 (m, 2H), 3.04 (m, 1H), 5.82 (s, 1H), 6.69 (m, 1H), 6.76 (d, 1H, J=8.8 Hz), 7.12 (dd, 1H, J=9.2, 8.8 Hz), 7.37 (m, 1H), 7.87 (d, 1H, J=2.8 Hz), 7.99 (s, 1H).
Compound Ii-72
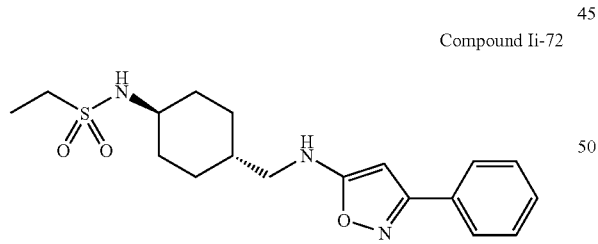
Compound Ii-73
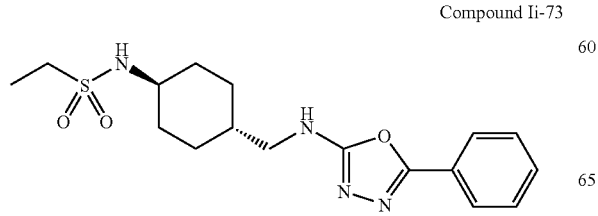
-continued
Compound Ii-74
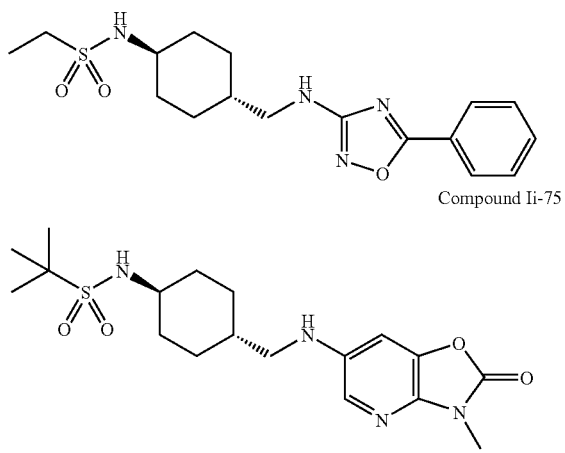
Compound Ii-75
Compound Ii-76
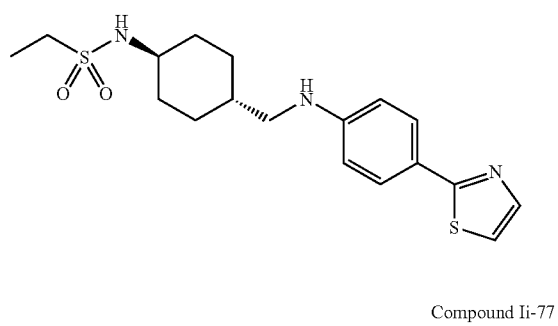
Compound Ii-77
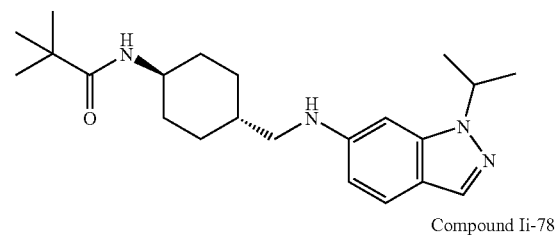
Compound Ii-78
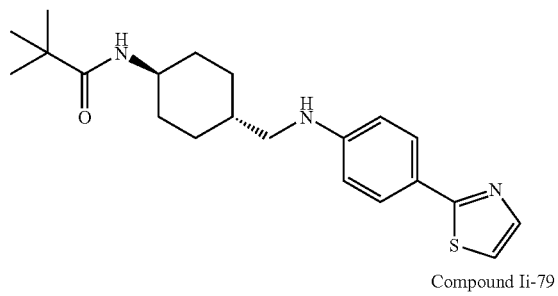
Compound Ii-79
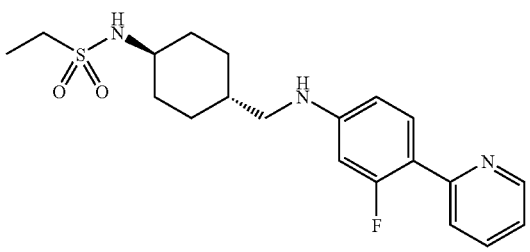

Compound Ii-80
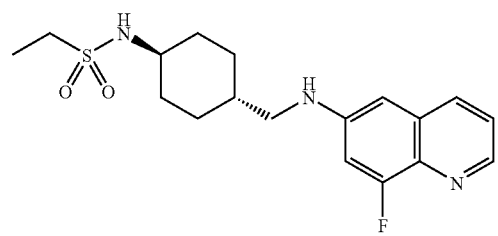
Compound Ii-81
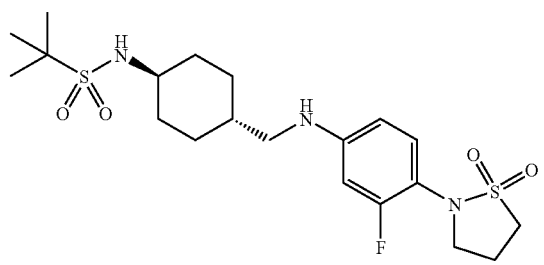
Compound Ii-82
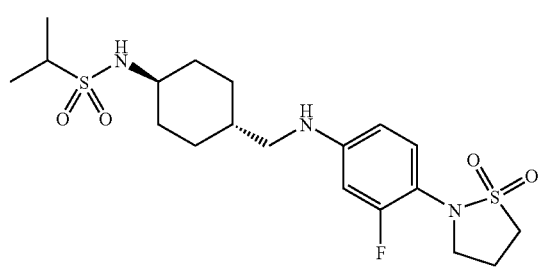
Compound Ii-83
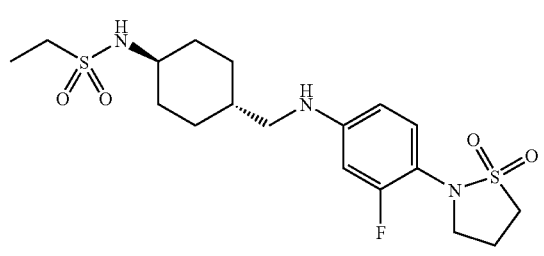
Compound Ii-84
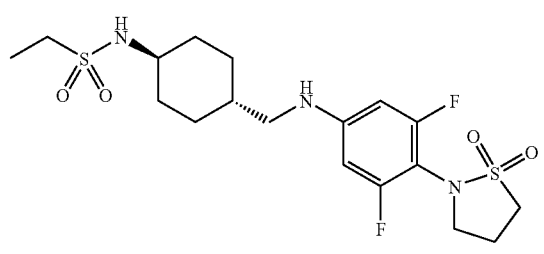
¹H-NMR (DMSO-d₆) δ: 0.91-1.08 (m, 2H), 1.14-1.30 (t, 3H, J=7.5 Hz), 1.41 (m, 1H), 1.73-1.94 (m, 4H), 2.34-2.46 (m, 2H), 2.85 (t, 2H, J=6.6 Hz), 2.97 (q, 2H, J=7.5 Hz), 3.00 (m, 1H), 3.25 (t, 2H, J=7.5 Hz), 3.53 (t, 2H, J=6.6 Hz), 6.27 (d, 2H, J=11.7 Hz), 6.52 (t, 1H, J=5.1 Hz), 7.00 (d, 1H, J=7.2 Hz).
Compound Ii-85
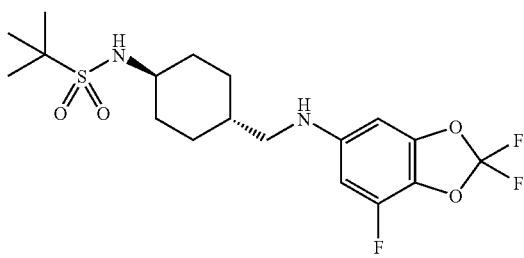
Compound Ii-86
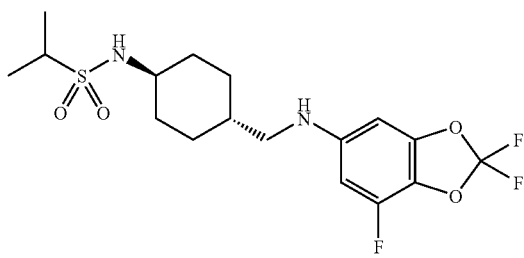
Compound Ii-87
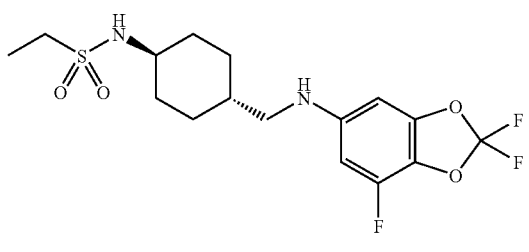
Compound Ii-88
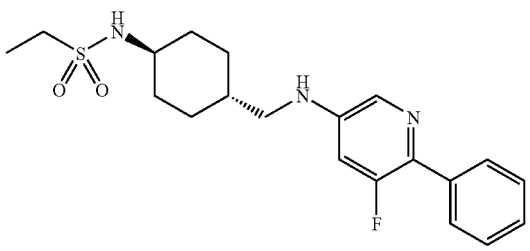
Compound Ii-89
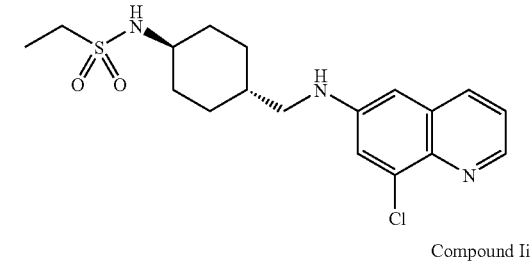
Compound Ii-90
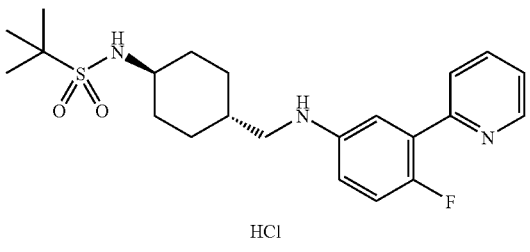
HCl Compound Ii-91

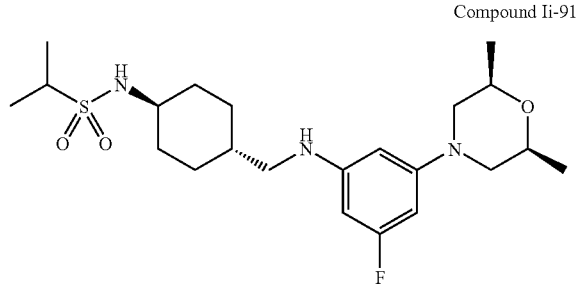

¹H-NMR (DMSO-d₆) δ: 0.92-1.05 (m, 2H), 1.13 (d, 6H, J=6.0 Hz), 1.18-1.30 (m, 2H), 1.21 (d, 6H, J=6.4 Hz), 1.40 (m, 1H), 1.76-1.83 (m, 2H), 1.83-1.93 (m, 2H), 2.19 (dd, 1H, J=11.2, 11.2 Hz), 2.76-2.82 (m, 2H), 3.01 (m, 1H), 3.09 (m, 1H), 3.45 (d, 2H, J=11.2 Hz), 3.58-3.69 (m, 2H), 5.67 (m, 1H), 5.77 (d, 1H, J=12.0 Hz), 5.90 (s, 1H), 5.91 (m, 1H), 6.91 (d, 1H, J=7.6 Hz).

Compound Ii-92

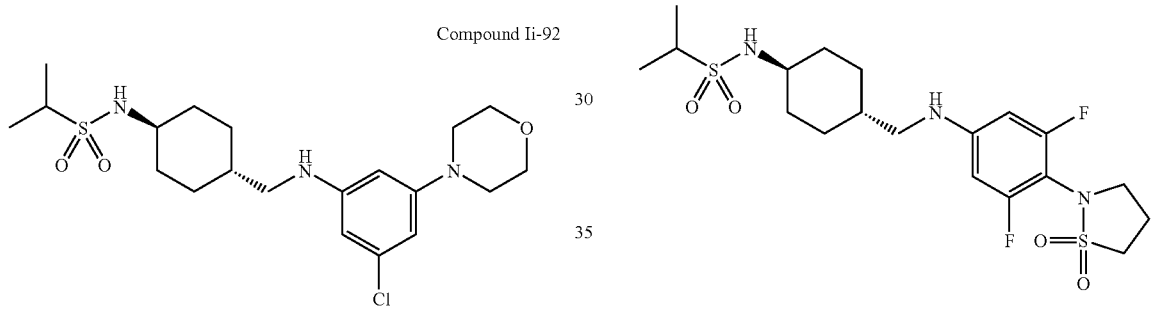

¹H-NMR (DMSO-d₆) δ: 0.90-1.07 (m, 2H), 1.14-1.30 (m, 2H), 1.21 (d, 6H, J=6.6 Hz), 1.32-1.46 (m, 1H), 1.75-1.92 (m, 4H), 2.78-2.83 (m, 2H), 2.95-3.18 (m, 6H), 3.66-3.72 (m, 4H), 5.75 (brs, 1H), 6.00 (s, 1H), 6.04 (s, 1H), 6.11 (s, 1H), 6.95 (d, 1H, J=9.0 Hz).

Compound Ii-93

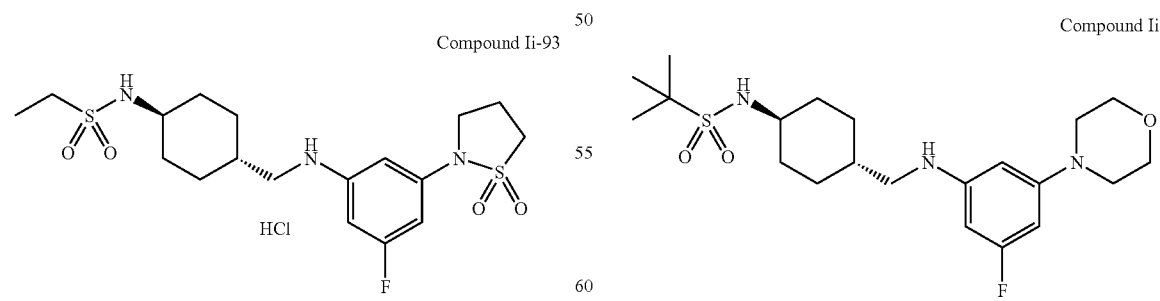

¹H-NMR (DMSO-d₆) δ: 0.90-1.08 (m, 2H), 1.13-1.27 (m, 5H), 1.42 (m, 1H), 1.74-1.93 (m, 4H), 2.30-2.40 (m, 2H), 2.81 (d, 2H, J=6.6 Hz), 2.97 (q, 2H, J=7.5 Hz), 3.00 (m, 1H), 3.49 (t, 2H, J=7.5 Hz), 3.66 (t, 2H, J=6.6 Hz), 5.00-5.50 (brs, 2H), 6.07-6.15 (m, 2H), 6.25 (s, 1H), 7.00 (d, 1H, J=6.6 Hz).

Compound Ii-94

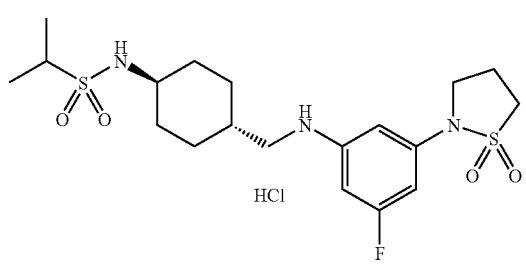

¹H-NMR (DMSO-d₆) δ: 0.92-1.07 (m, 2H), 1.15-1.32 (m, 5H), 1.21 (d, 6H, J=6.9 Hz), 1.42 (m, 1H), 1.74-1.93 (m, 4H), 2.30-2.42 (m, 2H), 2.81 (d, 2H, J=6.6 Hz), 2.92-3.18 (m, 2H), 3.49 (t, 2H, J=7.5 Hz), 3.66 (t, 2H, J=6.6 Hz), 4.70-5.30 (brs, 2H), 6.05-6.16 (m, 2H), 6.25 (s, 1H), 6.95 (d, 1H, J=8.1 Hz).

Compound Ii-95

¹H-NMR (DMSO-d₆) δ: 0.90-1.06 (m, 2H), 1.16-1.31 (d, 6H, J=6.9 Hz), 1.40 (m, 1H), 1.73-1.94 (m, 4H), 2.34-2.46 (m, 2H), 2.84 (t, 2H, J=6.0 Hz), 2.94-3.16 (m, 2H), 3.28 (t, 2H, J=7.5 Hz), 3.53 (t, 2H, J=6.6 Hz), 6.27 (d, 2H, J=11.7 Hz), 6.52 (t, 1H, J=5.4 Hz), 6.94 (d, 1H, J=7.8 Hz).

Compound Ii-96

¹H-NMR (DMSO-d₆) δ: 0.91-1.04 (m, 2H), 1.20-1.32 (m, 2H), 1.26 (s, 9H), 1.40 (m, 1H), 1.76-1.95 (m, 4H), 2.77-2.83 (m, 2H), 2.99-3.04 (m, 5H), 3.67-3.72 (m, 4H), 5.71 (m, 1H), 5.79 (d, 1H, J=11.7 Hz), 5.89 (s, 1H), 5.90 (m, 1H), 6.72 (d, 1H, J=8.4 Hz).

Compound Ii-97

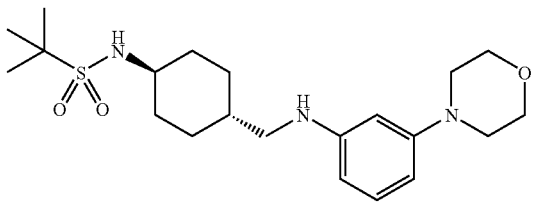

¹H-NMR (DMSO-d₆) δ: 0.92-1.03 (m, 2H), 1.20-1.32 (m, 2H), 1.26 (s, 9H), 1.41 (m, 1H), 1.77-1.93 (m, 4H), 2.78-2.83 (m, 2H), 2.97-3.05 (m, 5H), 3.68-3.72 (m, 4H), 5.36 (m, 1H), 6.04 (d, 1H, J=8.0 Hz), 6.10 (s, 1H), 6.11 (d, 1H, J=8.0 Hz), 6.72 (d, 1H, J=8.0 Hz), 6.89 (dd, 1H, J=8.0, 8.0 Hz).

Compound Ii-98

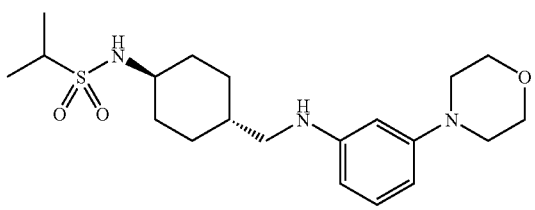

¹H-NMR (DMSO-d₆) δ: 0.92-1.04 (m, 2H), 1.17-1.29 (m, 2H), 1.21 (d, 6H, J=6.4 Hz), 1.41 (m, 1H), 1.75-1.92 (m, 4H), 2.77-2.83 (m, 2H), 2.95-3.05 (m, 5H), 3.09 (m, 1H), 3.67-3.72 (m, 4H), 5.36 (m, 1H), 6.04 (d, 1H, J=8.0 Hz), 6.10 (s, 1H), 6.11 (d, 1H, J=8.0 Hz), 6.89 (dd, 1H, J=8.0, 8.0 Hz), 6.92 (d, 1H, J=8.0 Hz).

Compound Ii-99

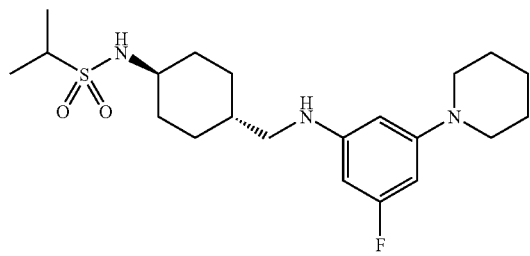

¹H-NMR (DMSO-d₆) δ: 0.90-1.06 (m, 2H), 1.15-1.31 (m, 2H), 1.21 (d, 6H, J=6.9 Hz), 1.39 (m, 1H), 1.47-1.62 (m, 6H), 1.74-1.94 (m, 4H), 2.78 (t, 2H, J=6.0 Hz), 2.93-3.16 (m, 6H), 5.64-5.76 (m, 2H), 5.83-5.92 (m, 2H), 6.94 (d, 1H, J=7.8 Hz).

Compound Ii-100

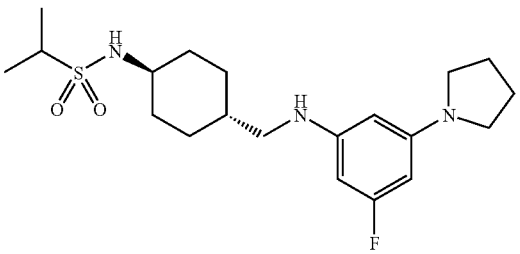

¹H-NMR (DMSO-d₆) δ: 0.90-1.06 (m, 2H), 1.15-1.30 (m, 2H), 1.21 (d, 6H, J=6.9 Hz), 1.40 (m, 1H), 1.74-1.96 (m, 8H), 2.79 (t, 2H, J=6.0 Hz), 2.93-3.18 (m, 6H), 5.48-5.67 (m, 4H), 6.94 (d, 1H, J=8.1 Hz).

Compound Ii-101

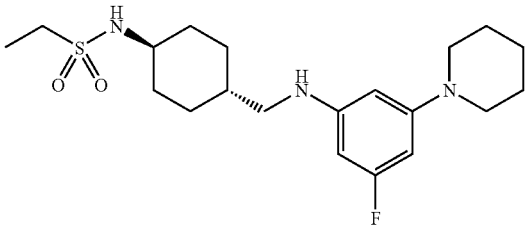

¹H-NMR (DMSO-d₆) δ: 0.90-1.06 (m, 2H), 1.13-1.29 (m, 2H), 1.18 (t, 3H, J=7.5 Hz), 1.39 (m, 1H), 1.47-1.62 (m, 6H), 1.75-1.94 (m, 4H), 2.79 (t, 2H, J=6.0 Hz), 2.97 (q, 2H, J=7.5 Hz), 3.03-3.10 (m, 4H), 5.64-5.75 (m, 2H), 5.83-5.91 (m, 2H), 7.00 (d, 1H, J=7.8 Hz).

Compound Ii-102

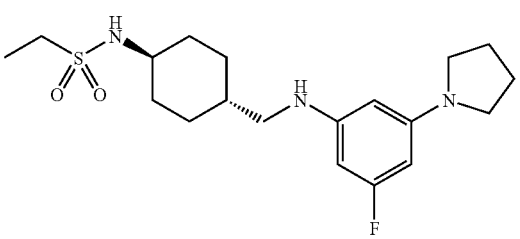

¹H-NMR (DMSO-d₆) δ: 0.90-1.07 (m, 2H), 1.13-1.29 (m, 2H), 1.18 (t, 3H, J=7.5 Hz), 1.41 (m, 1H), 1.74-1.96 (m, 8H), 2.79 (t, 2H, J=6.0 Hz), 2.97 (q, 2H, J=7.5 Hz), 3.00 (m, 1H), 3.09-3.19 (m, 4H), 5.46-5.66 (m, 4H), 6.99 (d, 1H, J=7.2 Hz).

Compound Ii-103

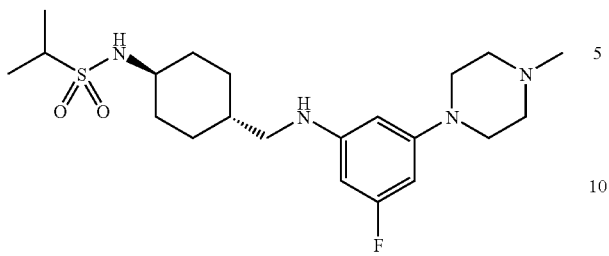

¹H-NMR (DMSO-d₆) δ: 0.91-1.03 (m, 2H), 1.16-1.29 (m, 2H), 1.21 (d, 6H, J=6.8 Hz), 1.40 (m, 1H), 1.75-1.92 (m, 4H), 2.20 (s, 3H), 2.35-2.43 (m, 4H), 2.75-2.82 (m, 2H), 2.88-3.13 (m, 6H), 5.67 (m, 1H), 5.76 (d, 1H, J=11.2 Hz), 5.82-5.92 (m, 2H), 6.91 (d, 1H, J=8.0 Hz).

Compound Ii-104

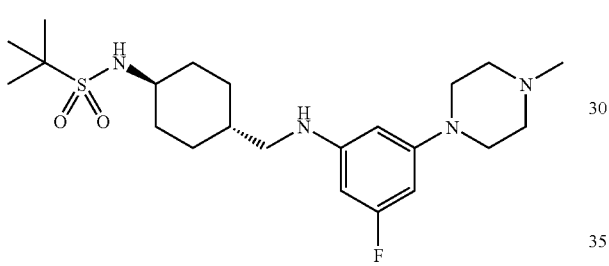

¹H-NMR (DMSO-d₆) δ: 0.92-1.02 (m, 2H), 1.19-1.32 (m, 2H), 1.26 (s, 9H), 1.39 (m, 1H), 1.75-1.95 (m, 4H), 2.19 (s, 3H), 2.38-2.42 (m, 4H), 2.77-2.83 (m, 5H), 2.98-3.09 (m, 5H), 5.67 (m, 1H), 5.76 (d, 1H, J=11.2 Hz), 5.88 (m, 1H), 5.88 (s, 1H), 6.72 (d, 1H, J=8.8 Hz).

Compound Ii-105

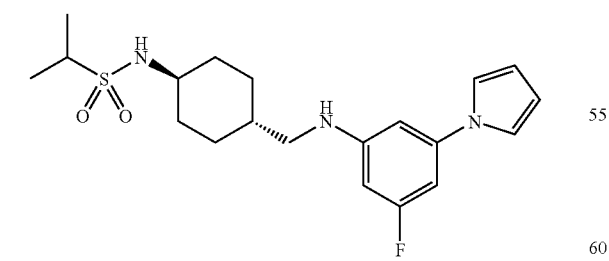

¹H-NMR (DMSO-d₆) δ: 0.95-1.09 (m, 2H), 1.18-1.31 (m, 2H), 1.22 (d, 6H, J=6.8 Hz), 1.44 (m, 1H), 1.78-1.93 (m, 4H), 2.87-2.92 (m, 2H), 3.03 (m, 1H), 3.10 (m, 1H), 6.13 (m, 1H), 6.21 (m, 1H), 6.22 (s, 2H), 6.51 (s, 1H), 6.52 (d, 1H, J=8.0 Hz), 6.92 (d, 1H, J=8.0 Hz), 7.26 (s, 2H).

Compound Ii-106

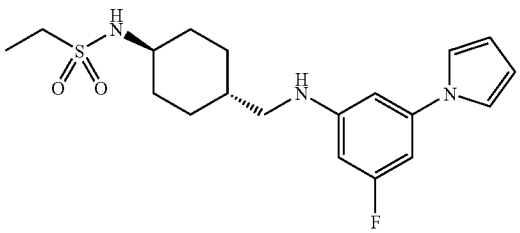

¹H-NMR (DMSO-d₆) δ: 0.97-1.08 (m, 2H), 1.17-1.29 (m, 5H), 1.40-1.68 (m, 3H), 1.80-1.92 (m, 2H), 2.90 (t, 2H, J=6.0 Hz), 2.94-3.06 (m, 3H), 6.12-6.22 (m, 4H), 6.50-6.54 (m, 2H), 6.94-7.00 (m, 1H), 7.26-7.27 (m, 2H).

Compound Ii-107

¹H-NMR (DMSO-d₆) δ: 0.91-1.03 (m, 2H), 1.16-1.29 (m, 2H), 1.21 (d, 6H, J=6.4 Hz), 1.40 (m, 1H), 1.74-1.92 (m, 4H), 2.75-2.81 (m, 2H), 2.84 (s, 3H), 3.00 (m, 1H), 3.09 (m, 1H), 3.25 (s, 3H), 3.35-3.47 (m, 4H), 5.59-5.67 (m, 4H), 6.91 (d, 1H, J=8.0 Hz).

Compound Ii-108

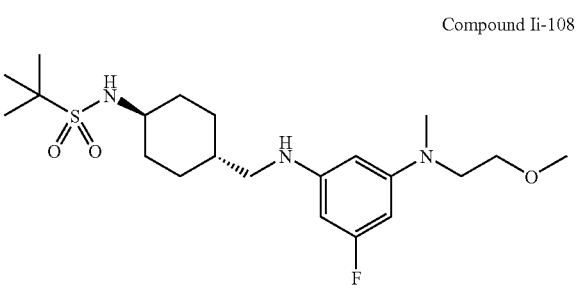

¹H-NMR (DMSO-d₆) δ: 0.92-1.03 (m, 2H), 1.18-1.32 (m, 2H), 1.26 (s, 9H), 1.40 (m, 1H), 1.75-1.94 (m, 4H), 2.75-2.81 (m, 2H), 2.83 (s, 3H), 3.01 (m, 1H), 3.25 (s, 3H), 3.34-3.47 (m, 4H), 5.58-5.70 (m, 4H), 6.72 (d, 1H, J=8.4 Hz).

Compound Ii-109

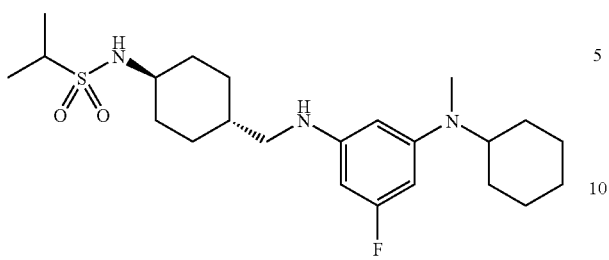

¹H-NMR (DMSO-d₆) δ: 0.90-1.51 (m, 10H), 1.21 (d, 6H, J=6.9 Hz), 1.56-1.67 (m, 3H), 1.71-1.93 (m, 6H), 2.64 (s, 3H), 2.78 (t, 2H, J=6.0 Hz), 2.93-3.17 (m, 2H), 3.44 (m, 1H), 5.56-5.77 (m, 4H), 6.94 (d, 1H, J=7.8 Hz).

Compound Ii-112

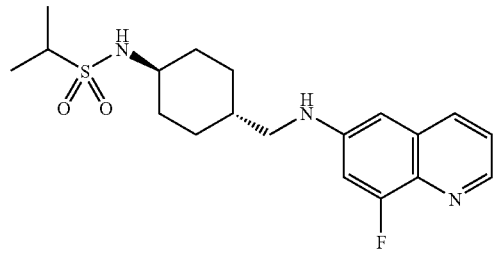

¹H-NMR (DMSO-d₆) δ: 0.97-1.13 (m, 2H), 1.17-1.34 (m, 8H), 1.45-1.59 (m, 1H), 1.81-1.99 (m, 4H), 2.94 (t, 2H, J=5.9 Hz), 2.99-3.21 (m, 2H), 6.33 (t, 1H, J=5.4 Hz), 6.51 (d, 1H, J=2.2 Hz), 6.96 (d, 1H, J=7.7 Hz), 7.02 (dd, 1H, J=13.5, 2.2 Hz), 7.36 (dd, 1H, J=8.2, 4.1 Hz), 8.02 (d, 1H, J=8.5 Hz), 8.48 (dd, 1H, J=4.1, 1.4 Hz).

Compound Ii-110

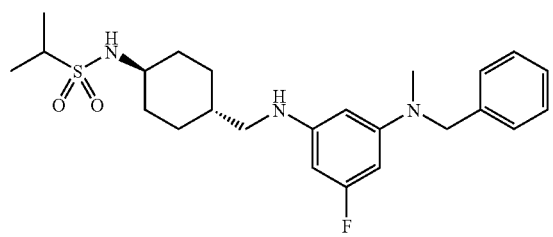

¹H-NMR (DMSO-d₆) δ: 0.83-1.01 (m, 2H), 1.00-1.40 (m, 3H), 1.21 (d, 6H, J=6.9 Hz), 1.68-1.91 (m, 4H), 2.73 (t, 2H, J=6.0 Hz), 2.90-3.15 (m, 2H), 2.95 (s, 3H), 4.48 (s, 2H), 5.60-5.72 (m, 4H), 6.94 (d, 1H, J=7.8 Hz), 7.15-7.35 (m, 5H).

Compound Ii-113

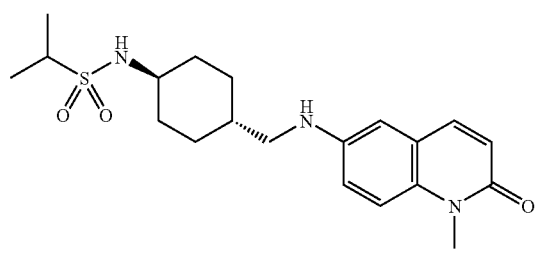

¹H-NMR (DMSO-d₆) δ: 0.93-1.13 (m, 2H), 1.15-1.34 (m, 8H), 1.39-1.57 (m, 1H), 1.79-1.95 (m, 4H), 2.87 (t, 2H, J=6.2 Hz), 2.94-3.16 (m, 2H), 3.54 (s, 3H), 5.66 (t, 1H, J=5.5 Hz), 6.49 (d, 1H, J=9.6 Hz), 6.73 (d, 1H, J=2.8 Hz), 6.91-7.02 (m, 2H), 7.29 (d, 1H, J=9.3 Hz), 7.72 (d, 1H, J=9.3 Hz).

Compound Ii-111

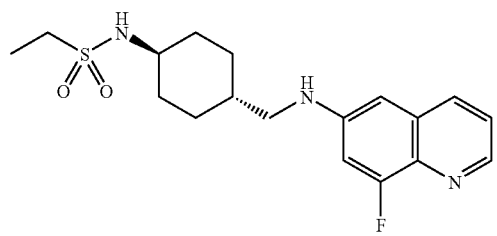

¹H-NMR (DMSO-d₆) δ: 0.97-1.14 (m, 2H), 1.14-1.33 (m, 5H), 1.45-1.61 (m, 1H), 1.81-1.96 (m, 4H), 2.90-3.10 (m, 5H), 6.34 (t, 1H, J=5.2 Hz), 6.51 (d, 1H, J=2.2 Hz), 6.99-7.07 (m, 2H), 7.36 (dd, 1H, J=8.2, 4.1 Hz), 8.02 (d, 1H, J=8.5 Hz), 8.48 (dd, 1H, J=4.1, 1.4 Hz).

Compound Ii-114

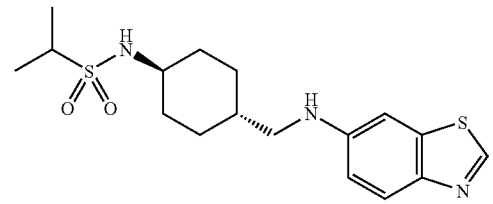

¹H-NMR (DMSO-d₆) δ: 0.93-1.10 (m, 2H), 1.14-1.33 (m, 8H), 1.41-1.56 (m, 1H), 1.79-1.94 (m, 4H), 2.89 (t, 2H, J=6.0 Hz), 2.95-3.16 (m, 2H), 6.00 (t, 1H, J=5.4 Hz), 6.84 (dd, 1H, J=8.8, 2.2 Hz), 6.95 (d, 1H, J=8.0 Hz), 7.07 (d, 1H, J=2.2 Hz), 7.72 (d, 1H, J=8.8 Hz), 8.86 (s, 1H).

Compound Ii-115

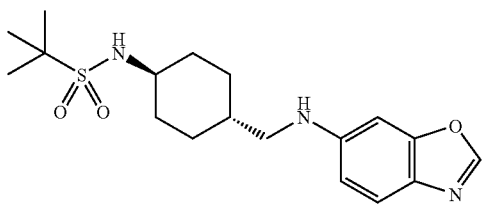

1H-NMR (DMSO-d$_6$) δ: 0.94-1.06 (m, 4H), 1.26 (s, 9H), 1.40-1.51 (m, 1H), 1.84 (d, 2H, J=12.4 Hz), 1.91 (d, 2H, J=12.4 Hz), 2.85-2.90 (m, 2H), 2.97-3.06 (m, 1H), 5.93-5.99 (m, 1H), 6.63-6.79 (m, 3H), 7.40 (d, 1H, J=8.8 Hz), 8.32 (s, 1H).

Compound Ii-116

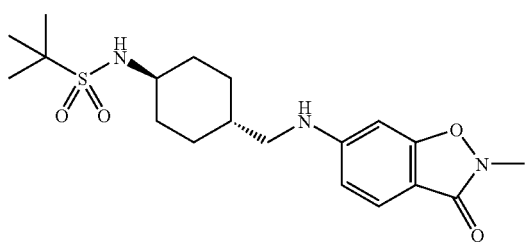

$^1$H-NMR (DMSO-d$_6$) δ: 0.95-1.07 (m, 4H), 1.26 (s, 9H), 1.39-1.47 (m, 1H), 1.80 (d, 2H, J=12.4 Hz), 1.91 (d, 2H, J=12.4 Hz), 2.87-2.93 (m, 2H), 2.98-3.06 (m, 1H), 3.37 (s, 3H), 6.27 (s, 1H), 6.55 (d, 1H, J=8.8 Hz), 6.73 (d, 1H, J=8.8 Hz), 6.80 (t, 1H, J=5.2 Hz), 7.32 (d, 1H, J=8.8 Hz).

Compound Ii-117

$^1$H-NMR (DMSO-d$_6$) δ: 0.94-1.08 (m, 4H), 1.20 (s, 3H), 1.22 (s, 3H), 1.39-1.51 (m, 1H), 1.80 (d, 2H, J=12.4 Hz), 1.88 (d, 2H, J=12.4 Hz), 2.87-2.94 (m, 2H), 2.97-3.07 (m, 1H), 3.08-3.14 (m, 1H), 3.37 (s, 3H), 6.27 (s, 1H), 6.55 (d, 1H, J=8.4 Hz), 6.82 (t, 1H, J=5.6 Hz), 6.94 (d, 1H, J=8.0 Hz), 7.32 (d, 1H, J=8.4 Hz).

Compound Ii-118

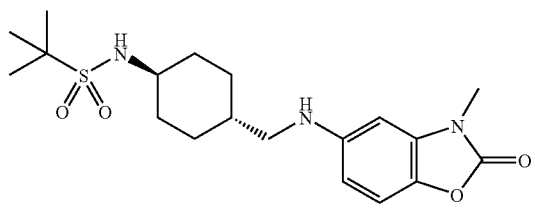

$^1$H-NMR (DMSO-d$_6$) δ: 0.92-1.06 (m, 4H), 1.26 (s, 9H), 1.38-1.50 (m, 1H), 1.83 (d, 2H, J=12.4 Hz), 1.90 (d, 2H, J=12.4 Hz), 2.80-2.86 (m, 2H), 2.96-3.06 (m, 1H), 3.26 (s, 3H), 5.58-5.65 (m, 1H), 6.27 (d, 1H, J=8.4 Hz), 6.38 (s, 1H), 6.75 (d, 1H, J=8.4 Hz), 6.99 (d, 1H, J=8.4 Hz).

Compound Ii-119

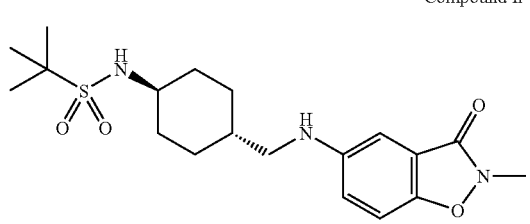

$^1$H-NMR (DMSO-d$_6$) δ: 0.94-1.06 (m, 4H), 1.26 (s, 9H), 1.39-1.50 (m, 1H), 1.84 (d, 2H, J=12.4 Hz), 1.90 (d, 2H, J=12.4 Hz), 2.81-2.89 (m, 2H), 2.96-3.07 (m, 1H), 3.51 (s, 3H), 5.79-5.84 (m, 1H), 6.60 (s, 1H), 6.75 (d, 1H, J=8.8 Hz), 7.03 (d, 1H, J=8.8 Hz), 7.19 (d, 1H, J=8.8 Hz).

Compound Ii-120

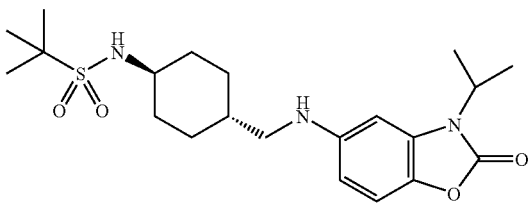

$^1$H-NMR (DMSO-d$_6$) δ: 0.93-1.10 (m, 4H), 1.26 (s, 9H), 1.37-1.40 (m, 1H), 1.42 (s, 3H), 1.44 (s, 3H), 1.83 (d, 2H, J=12.4 Hz), 1.91 (d, 2H, J=12.4 Hz), 2.79-2.96 (m, 2H), 2.97-3.07 (m, 1H), 4.33-4.46 (m, 1H), 5.50-5.59 (m, 1H), 6.25 (d, 1H, J=8.8 Hz), 6.57 (s, 1H), 6.75 (d, 1H, J=8.4 Hz), 7.00 (d, 1H, J=8.4 Hz).

Compound Ii-121

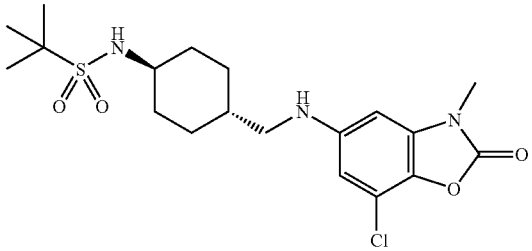

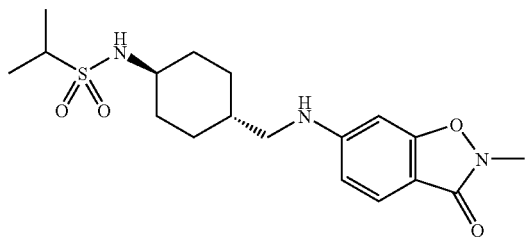

¹H-NMR (DMSO-d₆) δ: 0.90-1.06 (m, 4H), 1.26 (s, 9H), 1.36-1.49 (m, 1H), 1.82 (d, 2H, J=12.4 Hz), 1.90 (d, 2H, J=12.4 Hz), 2.80-2.87 (m, 2H), 2.95-3.97 (m, 1H), 3.27 (s, 3H), 5.85-5.92 (m, 1H), 6.33 (s, 1H), 6.36 (s, 1H), 6.75 (d, 1H, J=8.8 Hz).

Compound Ii-122

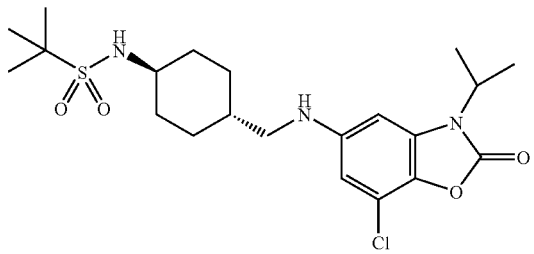

¹H-NMR (DMSO-d₆) δ: 0.92-1.08 (m, 4H), 1.26 (s, 9H), 1.38-1.41 (m, 1H), 1.42 (s, 3H), 1.43 (s, 3H), 1.82 (d, 2H, J=11.8 Hz), 1.90 (d, 2H, J=11.8 Hz), 2.83-2.88 (m, 2H), 2.98-3.06 (m, 1H), 4.33-4.47 (m, 1H), 6.35 (s, 1H), 6.54 (s, 1H), 6.76 (d, 1H, J=8.4 Hz), 8.32 (s, 1H).

Compound Ii-123

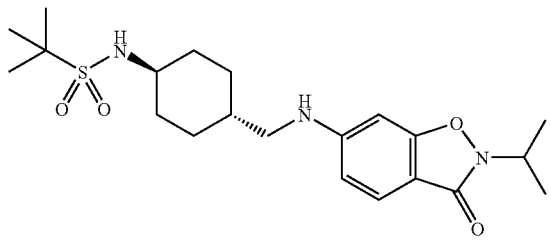

¹H-NMR (DMSO-d₆) δ: 0.93-1.06 (m, 4H), 1.22 (s, 3H), 1.24 (s, 3H), 1.26 (s, 9H), 1.39-1.50 (m, 1H), 1.81 (d, 2H, J=12.4 Hz), 1.90 (d, 2H, J=12.4 Hz), 2.87-2.93 (m, 2H), 2.96-3.07 (m, 1H), 4.39-4.47 (m, 1H), 6.30 (s, 1H), 6.54 (d, 1H, J=8.8 Hz), 6.77 (d, 1H, J=8.8 Hz), 6.86 (t, 1H, J=5.2 Hz), 7.32 (d, 1H, J=8.4 Hz).

Compound Ii-124

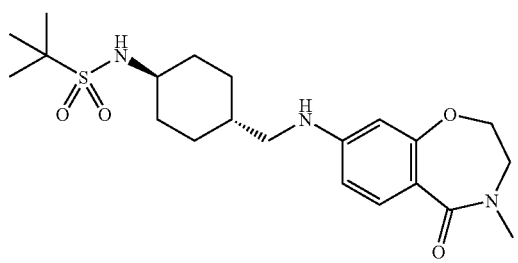

¹H-NMR (DMSO-d₆) δ: 0.90-1.05 (m, 4H), 1.26 (s, 9H), 1.36-1.51 (m, 1H), 1.79 (d, 2H, J=12.4 Hz), 1.90 (d, 2H, J=12.4 Hz), 2.80-2.86 (m, 2H), 3.01 (s, 3H), 3.02-3.05 (m, 1H), 3.49 (t, 2H, J=4.8 Hz), 4.26 (t, 2H, J=4.8 Hz), 6.02 (s, 1H), 6.20 (t, 1H, J=5.6 Hz), 6.31 (d, 1H, J=8.8 Hz), 6.74 (d, 1H, J=8.8 Hz), 7.43 (d, 1H, J=8.4 Hz).

Compound Ii-125

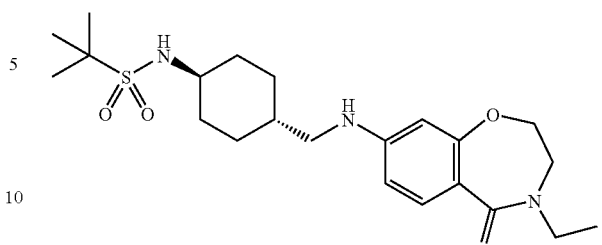

¹H-NMR (DMSO-d₆) δ: 0.92-1.02 (m, 4H), 1.08 (t, 3H, J=7.2 Hz), 1.25 (s, 9H), 1.35-1.42 (m, 1H), 1.79 (d, 2H, J=12.0 Hz), 1.90 (d, 2H, J=12.0 Hz), 2.80-2.86 (m, 2H), 2.96-3.05 (m, 1H), 3.42-3.51 (m, 4H), 4.20-4.26 (m, 2H), 6.03 (s, 1H), 6.20 (s, 1H), 6.31 (d, 1H, J=8.8 Hz), 6.75 (d, 1H, J=8.8 Hz), 7.42 (d, 1H, J=8.8 Hz).

Compound Ii-126

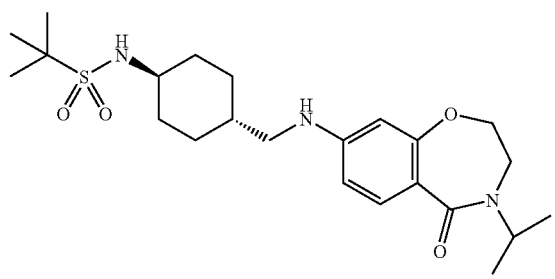

¹H-NMR (DMSO-d₆) δ: 0.92-1.02 (m, 4H), 1.09 (s, 3H), 1.11 (s, 3H), 1.25 (s, 9H), 1.43-1.55 (m, 1H), 1.80 (d, 2H, J=12.4 Hz), 1.91 (d, 2H, J=12.0 Hz), 2.84 (m, 2H), 2.97-3.08 (m, 1H), 3.37 (t, 2H, J=5.2 Hz), 4.18 (t, 2H, J=5.2 Hz), 4.71-4.80 (m, 1H), 6.05 (s, 1H), 6.19 (t, 1H, J=5.2 Hz), 6.32 (d, 1H, J=8.8 Hz), 6.74 (d, 1H, J=8.4 Hz), 7.18 (d, 1H, J=8.4 Hz).

Compound Ii-127

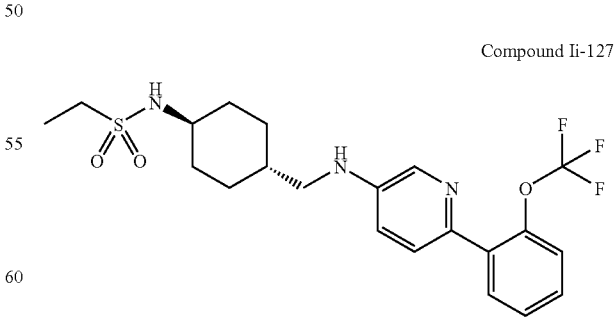

1H-NMR (DMSO-d₆) δ: 0.94-1.12 (m, 2H), 1.14-1.39 (m, 5H), 1.34-1.56 (m, 1H), 1.70-1.97 (m, 4H), 2.87-3.10 (m, 5H), 6.17 (t, 1H, J=5.2 Hz), 6.94-7.06 (m, 2H), 7.35-7.47 (m, 4H), 7.75-7.80 (m, 1H), 8.07 (d, 1H, J=3.0 Hz).

Compound Ii-128

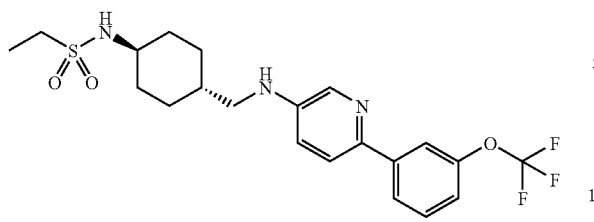

¹H-NMR (DMSO-d₆) δ: 0.96-1.12 (m, 2H), 1.14-1.31 (m, 5H), 1.31-1.55 (m, 1H), 1.70-1.96 (m, 4H), 2.89-3.09 (m, 5H), 6.24 (t, 1H, J=5.4 Hz), 6.94-7.05 (m, 2H), 7.24 (d, 1H, J=6.9 Hz), 7.52 (t, 1H, J=8.0 Hz), 7.75 (d, 1H, J=8.8 Hz), 7.88-7.97 (m, 2H), 8.07 (d, 1H, J=2.5 Hz).

Compound Ii-129

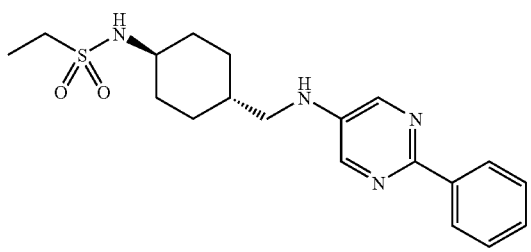

¹H-NMR (DMSO-d₆) δ: 0.98-1.12 (m, 2H), 1.18-1.30 (m, 2H), 1.19 (t, 3H, J=6.8 Hz), 1.48 (m, 1H), 1.79-1.95 (m, 4H), 2.92-3.09 (m, 3H), 2.97 (q, 2H, J=6.8 Hz), 6.27 (m, 1H), 7.01 (d, 1H, J=8.0 Hz), 7.39-7.47 (m, 2H), 7.56 (m, 1H), 8.18-8.25 (m, 2H), 8.23 (s, 2H).

Compound Ii-130

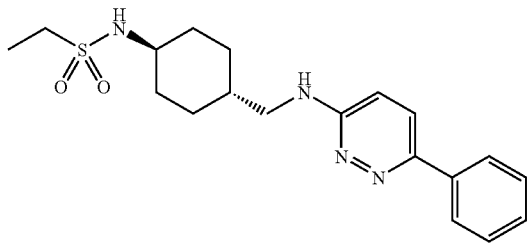

¹H-NMR (DMSO-d₆) δ: 0.96-1.12 (m, 2H), 1.15-1.30 (m, 2H), 1.18 (t, 3H, J=7.2 Hz), 1.45-1.64 (m, 1H), 1.78-1.96 (m, 4H), 2.97 (q, 2H, J=7.2 Hz), 2.95-3.15 (m, 1H), 3.22-3.28 (m, 2H), 6.89 (d, 1H, J=9.0 Hz), 6.94-7.02 (m, 2H), 7.38 (t, 1H, J=6.0 Hz), 7.46 (t, 2H, J=7.5 Hz), 7.78 (d, 1H, J=9.0 Hz), 7.96 (d, 2H, J=9.0 Hz).

Compound Ii-131

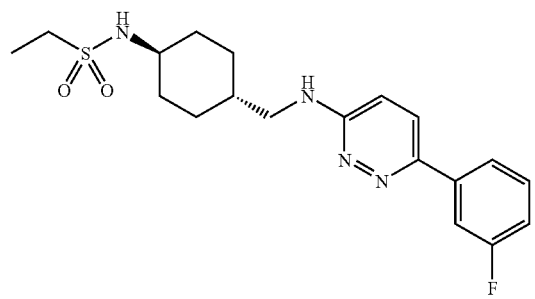

¹H-NMR (DMSO-d₆) δ: 0.96-1.12 (m, 2H), 1.15-1.30 (m, 2H), 1.18 (t, 3H, J=7.2 Hz), 1.48-1.62 (m, 1H), 1.78-1.96 (m, 4H), 2.98 (q, 2H, J=7.2 Hz), 2.94-3.10 (m, 1H), 3.22-3.28 (m, 2H), 6.89 (d, 1H, J=9.0 Hz), 7.02 (d, 1H, J=9.0 Hz), 7.10 (t, 1H, J=5.4 Hz), 7.22 (td, 1H, J=9.0, 3.0 Hz), 7.47-7.56 (m, 1H), 7.77-7.88 (m, 3H).

Compound Ii-132

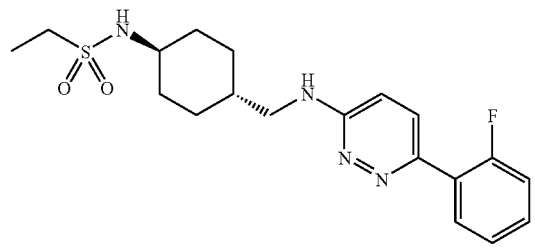

¹H-NMR (DMSO-d₆) δ: 0.96-1.13 (m, 2H), 1.15-1.32 (m, 2H), 1.19 (t, 3H, J=7.5 Hz), 1.48-1.65 (m, 1H), 1.78-1.96 (m, 4H), 2.98 (q, 2H, J=7.2 Hz), 2.94-3.12 (m, 1H), 3.22-3.28 (m, 2H), 6.89 (d, 1H, J=9.0 Hz), 7.01 (d, 1H, J=6.0 Hz), 7.09 (t, 1H, J=5.4 Hz), 7.27-7.35 (m, 2H), 7.42-7.50 (m, 1H), 7.57 (dd, 1H, J=9.0, 3.0 Hz), 7.86 (td, 1H, J=7.5, 3.0 Hz).

Compound Ii-133

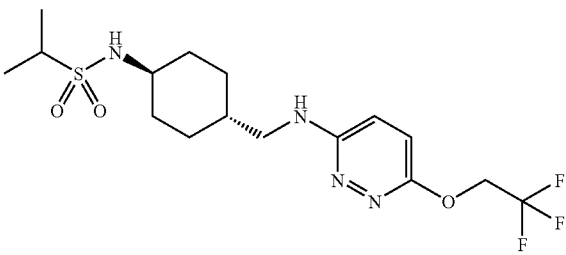

¹H-NMR (DMSO-d₆) δ: 0.92-1.08 (m, 2H), 1.15-1.30 (m, 2H), 1.21 (d, 6H, J=6.6 Hz), 1.42-1.58 (m, 1H), 1.72-1.94 (m, 4H), 2.95-3.20 (m, 4H), 4.89-4.98 (m, 2H), 6.65 (brs, 1H), 6.92 (d, 1H, J=9.0 Hz), 6.91-6.98 (m, 1H), 7.03 (d, 1H, J=9.0 Hz).

Compound Ii-134

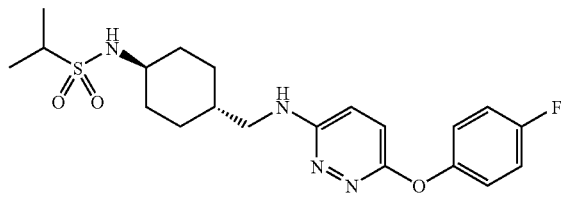

¹H-NMR (DMSO-d₆) δ: 0.90-1.08 (m, 2H), 1.15-1.30 (m, 2H), 1.21 (d, 6H, J=6.6 Hz), 1.42-1.58 (m, 1H), 1.72-1.94 (m, 4H), 2.92-3.20 (m, 4H), 6.74 (t, 1H, J=6.0 Hz), 6.94 (t, 1H, J=6.0 Hz), 6.97 (s, 1H), 7.08-7.24 (m, 5H).

Compound Ii-135

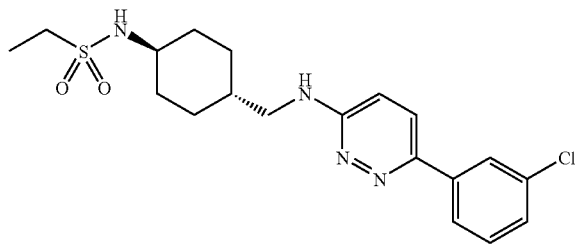

¹H-NMR (DMSO-d₆) δ: 0.95-1.10 (m, 2H), 1.12-1.30 (m, 2H), 1.19 (t, 3H, J=7.2 Hz), 1.48-1.60 (m, 1H), 1.76-1.94 (m, 4H), 2.92-3.10 (m, 1H), 2.97 (q, 2H, J=7.2 Hz), 3.18-3.30 (m, 2H), 6.89 (d, 1H, J=9.6 Hz), 7.02 (brs, 1H), 7.11 (t, 1H, J=5.4 Hz), 7.42-7.56 (m, 2H), 7.85 (d, 1H, J=9.6 Hz), 7.93 (d, 1H, J=7.5 Hz), 8.03 (s, 1H).

Compound Ii-136

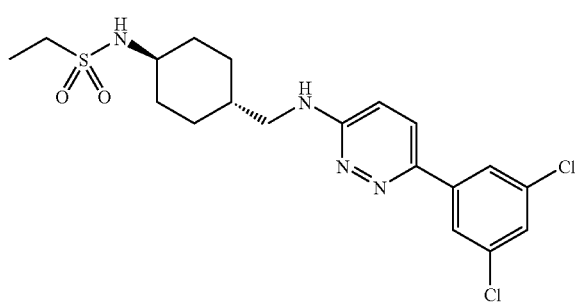

¹H-NMR (DMSO-d₆) δ: 0.98-1.12 (m, 2H), 1.13-1.30 (m, 2H), 1.18 (t, 3H, J=7.2 Hz), 1.48-1.62 (m, 1H), 1.78-1.96 (m, 4H), 2.92-3.12 (m, 1H), 2.97 (q, 2H, J=7.2 Hz), 3.22-3.32 (m, 2H), 6.89 (d, 1H, J=9.0 Hz), 7.01 (d, 1H, J=7.5 Hz), 7.20 (t, 1H, J=6.0 Hz), 7.62 (s, 1H), 7.91 (d, 1H, J=9.0 Hz), 8.02 (s, 2H).

Compound Ii-137

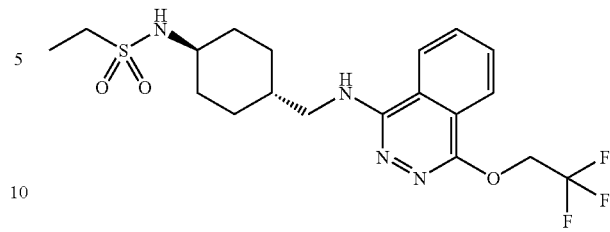

¹H-NMR (DMSO-d₆) δ: 0.95-1.12 (m, 2H), 1.13-1.30 (m, 2H), 1.18 (t, 3H, J=7.2 Hz), 1.65-1.95 (m, 5H), 2.93-3.12 (m, 1H), 2.97 (q, 2H, J=7.2 Hz), 3.25-3.40 (m, 2H), 5.07-5.16 (m, 2H), 7.01 (d, 1H, J=7.5 Hz), 7.25 (t, 1H, J=6.0 Hz), 7.92-8.03 (m, 3H), 8.33 (d, 1H, J=6.0 Hz).

Compound Ii-138

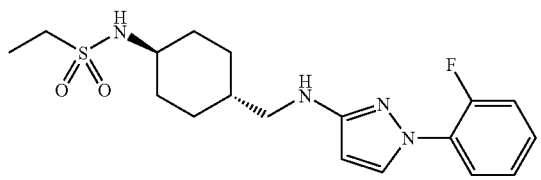

¹H-NMR (DMSO-d₆) δ: 0.91-1.26 (m, 4H), 1.19 (t, 3H, J=7.5 Hz), 1.36-1.43 (m, 1H), 1.78-1.90 (m, 4H), 2.90-3.07 (m, 3H), 2.96 (q, 2H, J=7.5 Hz), 5.69 (t, 1H, J=5.7 Hz), 5.81 (d, 1H, J=2.4 Hz), 7.00 (d, 1H, J=7.8 Hz), 7.16-7.39 (m, 3H), 7.73-7.79 (m, 1H), 7.86-7.88 (m, 1H).

Compound Ii-139

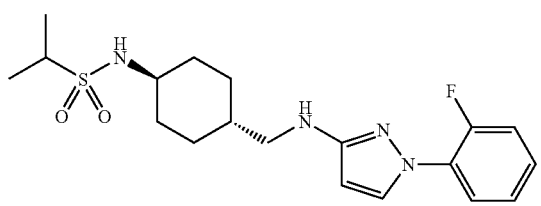

¹H-NMR (DMSO-d₆) δ: 0.90-1.06 (m, 4H), 1.20 (s, 3H), 1.22 (s, 3H), 1.40-1.52 (m, 1H), 1.81 (d, 2H, J=12.4 Hz), 1.88 (d, 2H, J=12.4 Hz), 2.90-2.98 (m, 2H), 2.99-3.13 (m, 2H), 5.68 (t, 1H, J=5.6 Hz), 5.81 (s, 1H), 6.93 (d, 1H, J=8.8 Hz), 7.16-7.40 (m, 3H), 7.76 (t, 1H, J=8.0 Hz), 7.87 (s, 1H).

Compound Ii-140

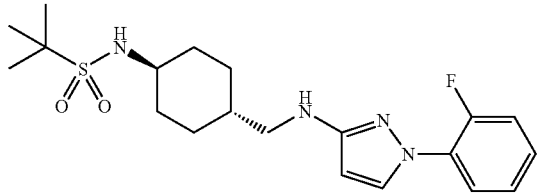

¹H-NMR (DMSO-d₆) δ: 0.90-1.06 (m, 4H), 1.26 (s, 9H), 1.40-1.49 (m, 1H), 1.82 (d, 2H, J=12.4 Hz), 1.91 (d, 2H, J=12.4 Hz), 2.90-2.99 (m, 2H), 3.01-3.06 (m, 1H), 5.67 (t,

1H, J=6.0 Hz), 5.81 (s, 1H), 6.74 (d, 1H, J=8.4 Hz), 7.14-7.40 (m, 3H), 7.76 (t, 1H, J=8.4 Hz), 7.87 (s, 1H).

Compound Ii-141

Compound Ii-144

Compound Ii-142

Compound Ii-145

Compound Ii-143

Compound Ii-146

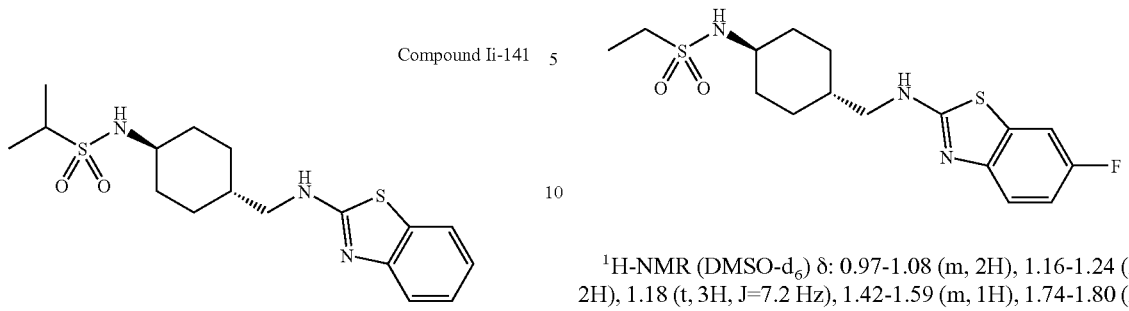

¹H-NMR (DMSO-d₆) δ: 0.97-1.06 (m, 2H), 1.18-1.27 (m, 2H), 1.21 (d, 6H, J=6.9 Hz), 1.45-1.59 (m, 1H), 1.76-1.81 (m, 2H), 1.87-1.91 (m, 2H), 2.97-3.09 (m, 1H), 3.10-3.13 (m, 1H), 3.17-3.22 (m, 2H), 6.94-7.02 (m, 2H), 6.98 (td, 1H, J=7.8, 1.2 Hz), 7.36 (dd, 1H, J=7.8, 0.6 Hz), 7.65 (dd, 1H, J=7.8, 0.6 Hz), 8.00-8.05 (m, 1H).

¹H-NMR (DMSO-d₆) δ: 0.97-1.08 (m, 2H), 1.16-1.24 (m, 2H), 1.18 (t, 3H, J=7.2 Hz), 1.42-1.59 (m, 1H), 1.74-1.80 (m, 2H), 1.85-1.90 (m, 2H), 2.92-3.03 (m, 1H), 2.97 (q, 2H, J=7.5 Hz), 3.18 (t, 2H, J=6.3 Hz), 6.99-7.07 (m, 2H), 7.33 (dd, 1H, J=9.0, 4.8 Hz), 7.58 (dd, 1H, J=8.7, 2.7 Hz), 8.00 (t, 1H, J=5.4 Hz).

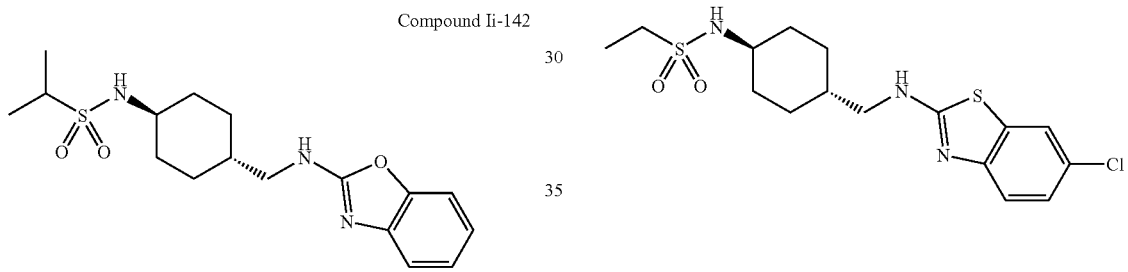

¹H-NMR (DMSO-d₆) δ: 0.96-1.04 (m, 2H), 1.18-1.28 (m, 2H), 1.20 (d, 6H, J=6.9 Hz), 1.43-1.59 (m, 1H), 1.74-1.79 (m, 2H), 1.85-1.90 (m, 2H), 2.92-3.07 (m, 1H), 3.09-3.18 (m, 3H), 6.92-6.99 (m, 2H), 7.10 (td, 1H, J=7.8, 1.2 Hz), 7.21 (dd, 1H, J=7.8, 0.6 Hz), 7.31 (dd, 1H, J=7.8, 0.6 Hz), 7.89-7.97 (m, 1H).

¹H-NMR (DMSO-d₆) δ: 0.97-1.09 (m, 2H), 1.17-1.23 (m, 2H), 1.18 (t, 3H, J=7.2 Hz), 1.43-1.59 (m, 1H), 1.72-1.81 (m, 2H), 1.85-1.92 (m, 2H), 2.95-3.06 (m, 1H), 2.97 (q, 2H, J=7.5 Hz), 3.19 (t, 2H, J=6.0 Hz), 7.01 (d, 1H, J=8.1 Hz), 7.20-7.23 (m, 1H), 7.33 (dd, 1H, J=8.7, 0.6 Hz), 7.58 (dd, 1H, J=2.1, 0.9 Hz), 8.11-8.18 (m, 1H).

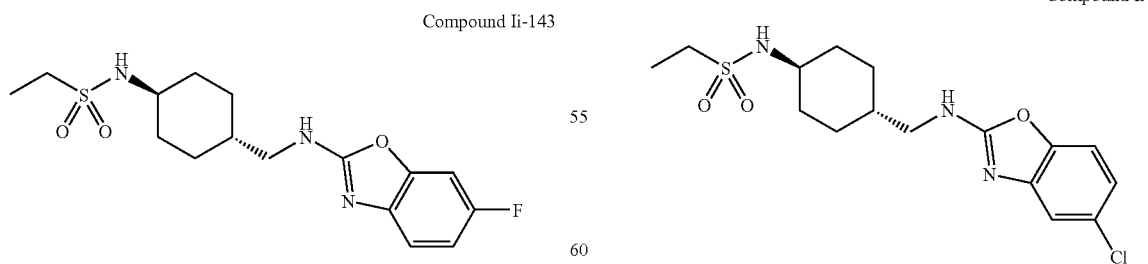

¹H-NMR (DMSO-d₆) δ: 0.97-1.07 (m, 2H), 1.17-1.23 (m, 2H), 1.18 (t, 3H, J=7.2 Hz), 1.42-1.57 (m, 1H), 1.73-1.78 (m, 2H), 1.86-1.90 (m, 2H), 2.93-3.02 (m, 1H), 2.97 (q, 2H, J=7.2 Hz), 3.11 (t, 2H, J=6.3 Hz), 6.91-7.02 (m, 2H), 7.19 (dd, 1H, J=8.4, 4.8 Hz), 7.34 (dd, 1H, J=9.3, 2.4 Hz), 8.00 (t, 1H, J=6.0 Hz).

¹H-NMR (DMSO-d₆) δ: 0.98-1.06 (m, 2H), 1.15-1.21 (m, 2H), 1.18 (t, 3H, J=7.2 Hz), 1.42-1.58 (m, 1H), 1.70-1.81 (m, 2H), 1.82-1.96 (m, 2H), 2.93-3.00 (m, 3H), 3.13-3.19 (m, 2H), 6.98-7.02 (m, 2H), 7.26-7.27 (m, 1H), 7.32-7.35 (m, 1H), 8.18-8.21 (m, 1H).

Compound Ii-147

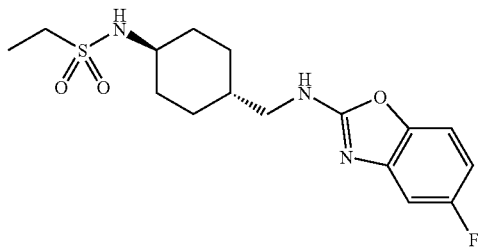

¹H-NMR (DMSO-d₆) δ: 0.98-1.04 (m, 2H), 1.16-1.23 (m, 2H), 1.18 (t, 3H, J=7.2 Hz), 1.43-1.59 (m, 1H), 1.73-1.78 (m, 2H), 1.86-1.89 (m, 2H), 2.93-3.00 (m, 3H), 3.11-3.15 (m, 2H), 6.72-6.79 (m, 1H), 7.00-7.08 (m, 2H), 7.29-7.34 (m, 1H), 8.13-8.16 (m, 1H).

Compound Ii-150

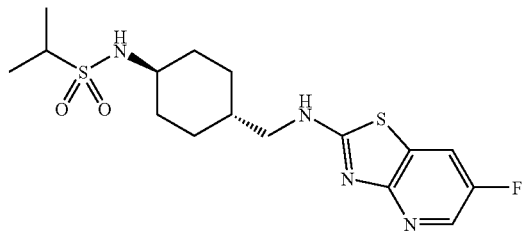

¹H-NMR (DMSO-d₆) δ: 0.98-1.08 (m, 2H), 1.15-1.29 (m, 2H), 1.21 (d, 6H, J=6.9 Hz), 1.44-1.60 (m, 1H), 1.74-1.80 (m, 2H), 1.86-1.91 (m, 2H), 2.95-3.17 (m, 2H), 3.21-3.27 (m, 2H), 6.95-6.98 (m, 1H), 8.10 (dd, 1H, J=8.4, 2.7 Hz), 8.19 (dd, 1H, J=3.0, 1.5 Hz), 8.44-8.47 (m, 1H).

Compound Ii-148

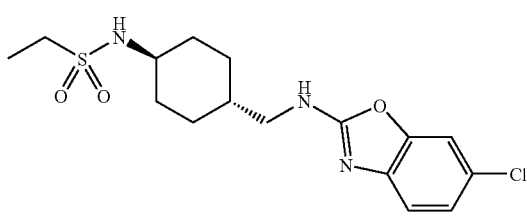

¹H-NMR (DMSO-d₆) δ: 0.94-1.06 (m, 2H), 1.15-1.26 (m, 2H), 1.18 (t, 3H, J=7.2 Hz), 1.45-1.58 (m, 1H), 1.72-1.80 (m, 2H), 1.84-1.92 (m, 2H), 2.96 (q, 2H, J=7.2 Hz), 2.96-3.05 (m, 1H), 3.09-3.16 (m, 2H), 6.99 (d, 1H, J=8.0 Hz), 7.13 (dd, 1H, J=8.0, 2.0 Hz), 7.20 (d, 1H, J=8.4 Hz), 7.49 (d, 1H, J=2.0 Hz), 8.11 (t, 1H, J=6.0 Hz).

Compound Ii-151

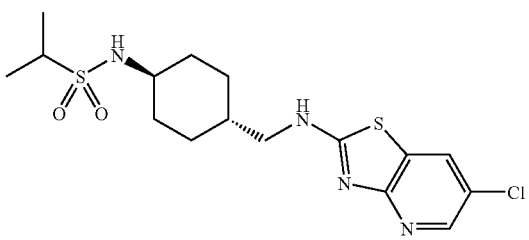

¹H-NMR (DMSO-d₆) δ: 0.99-1.04 (m, 2H), 1.15-1.23 (m, 2H), 1.21 (d, 6H, J=6.3 Hz), 1.43-1.59 (m, 1H), 1.73-1.81 (m, 2H), 1.85-1.91 (m, 2H), 2.97-3.18 (m, 2H), 3.21-3.29 (m, 2H), 6.95-6.98 (m, 1H), 8.20-8.23 (m, 2H), 8.58-8.61 (m, 1H).

Compound Ii-149

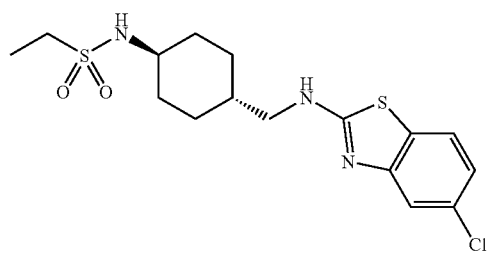

1H-NMR (DMSO-d₆) δ: 0.96-1.08 (m, 2H), 1.12-1.24 (m, 2H), 1.18 (t, 3H, J=7.2 Hz), 1.43-1.59 (m, 1H), 1.74-1.80 (m, 2H), 1.86-1.91 (m, 2H), 2.93-3.01 (m, 3H), 3.17-3.22 (m, 2H), 7.00-7.05 (m, 2H), 7.37-7.39 (m, 1H), 7.65-7.68 (m, 1H), 8.22-8.26 (m, 1H).

Compound Ii-152

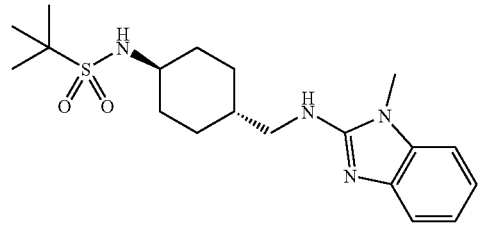

¹H-NMR (DMSO-d₆) δ: 0.96-1.04 (m, 2H), 1.15-1.26 (m, 2H), 1.25 (s, 9H), 1.56-1.62 (m, 1H), 1.78-1.83 (m, 2H), 1.87-1.93 (m, 2H), 2.98-3.08 (m, 1H), 3.17 (t, 2H, J=6.3 Hz), 3.48 (s, 3H), 6.47 (d, 2H, J=8.7 Hz), 6.89-6.96 (m, 2H), 7.11-7.19 (m, 2H).

Compound Ii-153
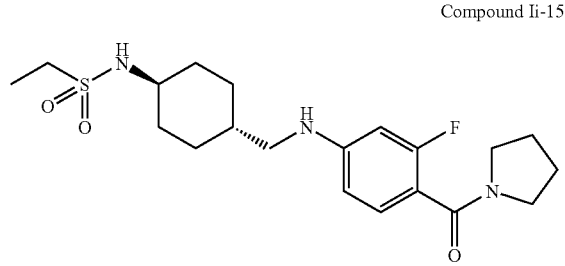
¹H-NMR (DMSO-d₆) δ: 0.95-1.04 (m, 2H), 1.13-1.30 (m, 2H), 1.18 (t, 3H, J=7.5 Hz), 1.41 (m, 1H), 1.71-1.94 (m, 4H), 2.80-2.89 (m, 2H), 2.92-3.10 (m, 2H), 2.97 (q, 2H, J=7.5 Hz), 3.21-3.30 (m, 2H), 6.25-6.35 (m, 2H), 6.39 (dd, 1H, J=8.4, 2.1 Hz), 7.01 (d, 1H, J=7.5 Hz), 7.01 (dd, 1H, J=8.4, 8.4 Hz).
Compound Ii-154
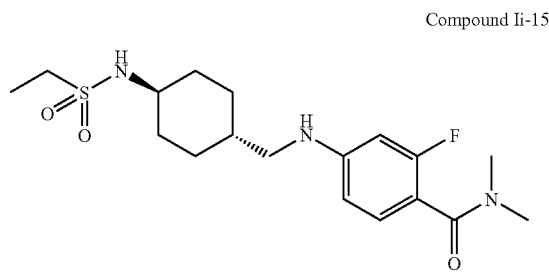
¹H-NMR (DMSO-d₆) δ: 0.91-1.09 (m, 2H), 1.16-1.28 (m, 2H), 1.18 (t, 3H, J=7.5 Hz), 1.42 (m, 1H), 1.74-1.95 (m, 4H), 2.80-3.16 (m, 9H), 2.97 (q, 2H, J=7.5 Hz), 6.24-6.36 (m, 2H), 6.30 (dd, 1H, J=8.4, 2.1 Hz), 7.10 (dd, 1H, J=8.4, 2.1 Hz), 7.05 (d, 1H, J=8.4 Hz).
Compound Ii-155
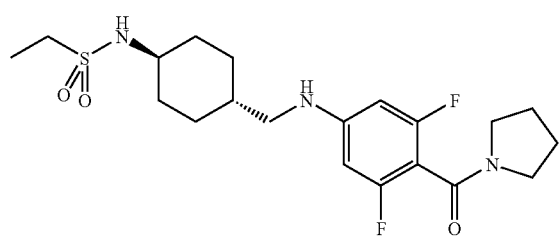
Compound Ii-156
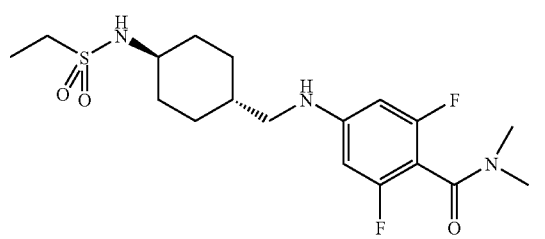
Compound Ii-157
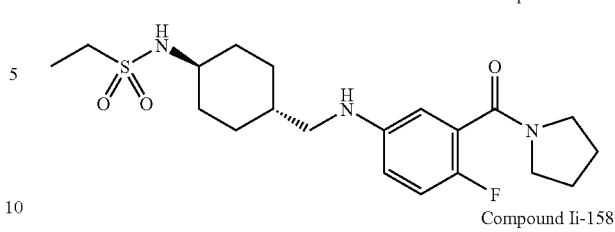
Compound Ii-158
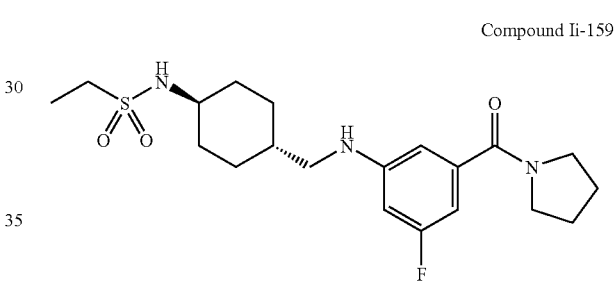
¹H-NMR (DMSO-d₆) δ: 0.91-1.07 (m, 2H), 1.10-1.30 (m, 5H), 1.41 (m, 1H), 1.76-1.94 (m, 4H), 2.74-2.83 (m, 2H), 2.83 (s, 3H), 2.90-3.08 (m, 3H), 2.96 (s, 3H), 5.68 (m, 1H), 6.39 (m, 1H), 6.58 (m, 1H), 6.95 (dd, 1H, J=8.4, 8.4 Hz), 7.00 (d, 1H, J=7.8 Hz).
Compound Ii-159
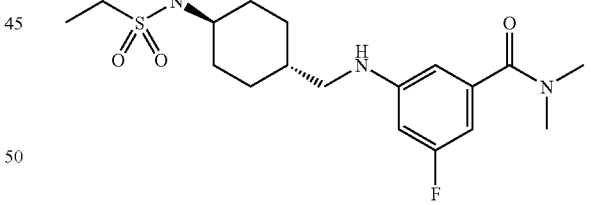
Compound Ii-160
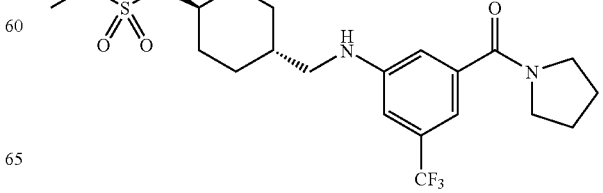
Compound Ii-161

Compound Ii-162
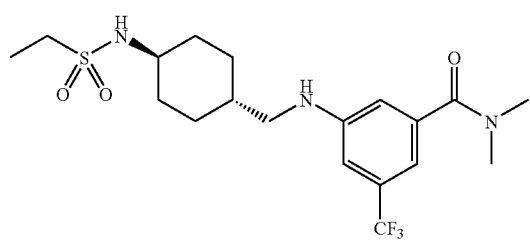
Compound Ii-163
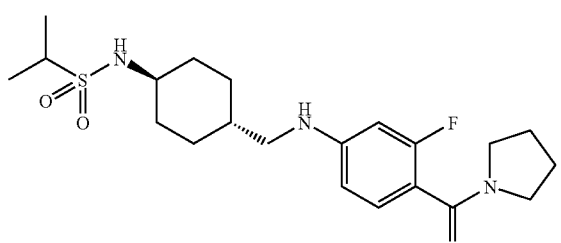
Compound Ii-164
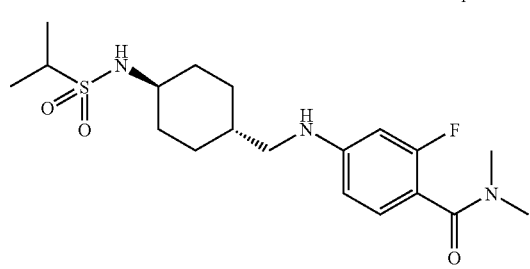
Compound Ii-165
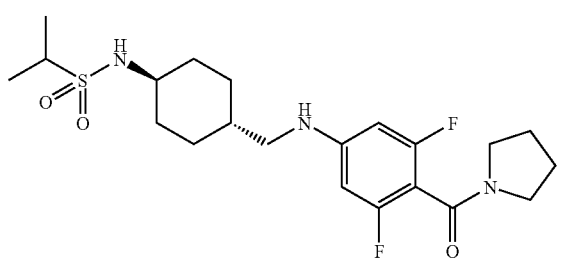
Compound Ii-166
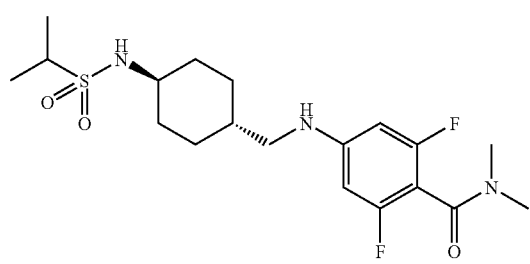
Compound Ii-167
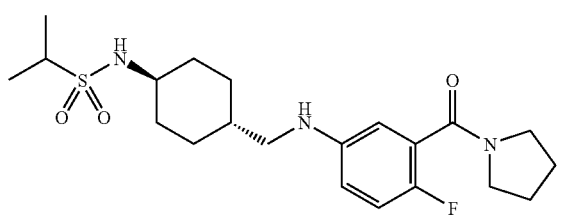
Compound Ii-168
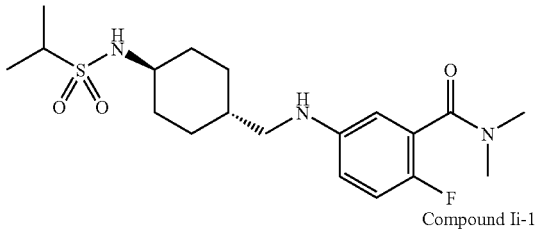
Compound Ii-169
Compound Ii-170
Compound Ii-171
Compound Ii-172
Compound Ii-173
¹H-NMR (DMSO-d₆) δ: 0.95-1.08 (m, 2H), 1.15-1.28 (m, 2H), 1.19 (t, 3H, J=7.2 Hz), 1.43 (m, 1H), 1.76-1.85 (m, 2H), 1.85-1.93 (m, 2H), 2.76-2.82 (m, 2H), 2.88 (t, 2H, J=6.0 Hz), 2.97 (t, 2H, J=7.2 Hz), 3.00 (m, 1H), 3.64-3.70 (m, 4H), 6.33 (m, 1H), 6.37 (d, 1H, J=8.4 Hz), 6.56 (s, 1H), 7.00 (d, 1H, J=7.8 Hz), 7.28 (d, 1H, J=8.4 Hz).
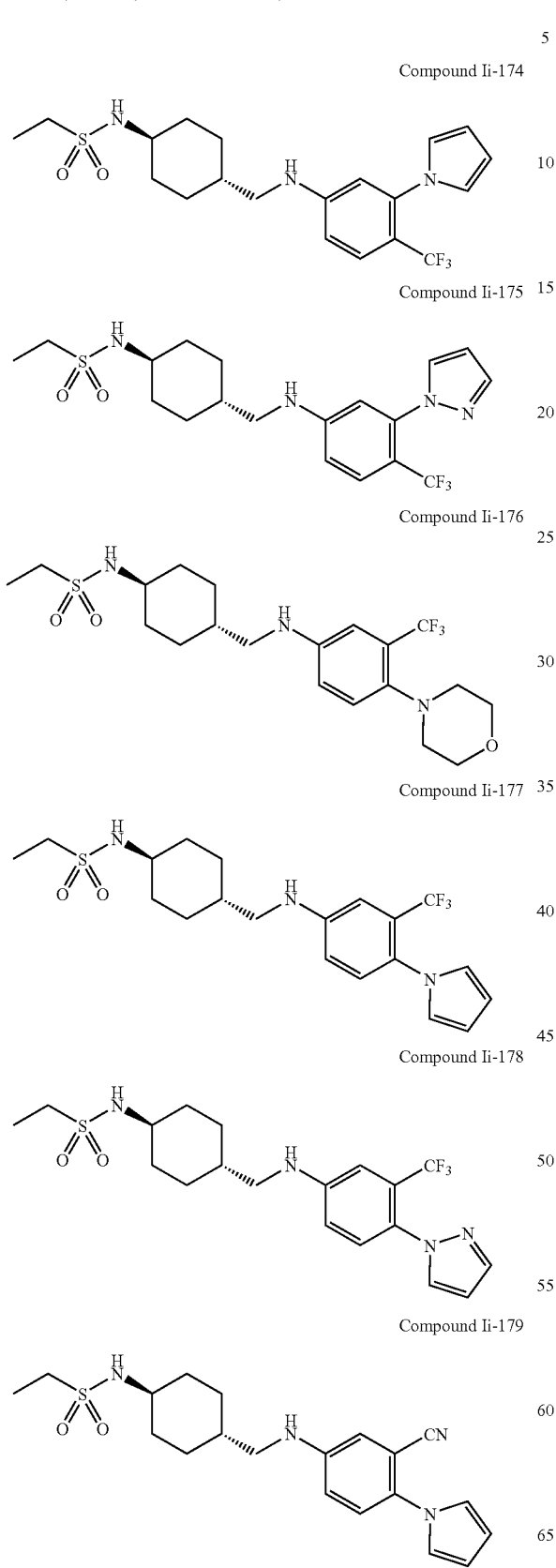
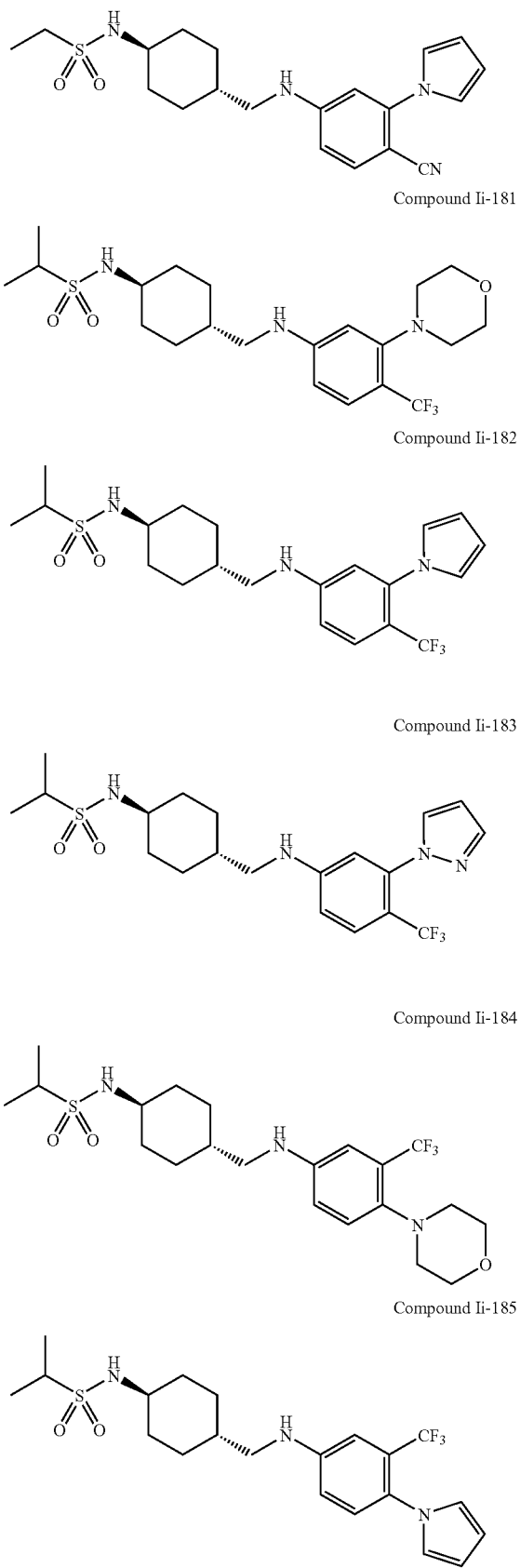

Compound Ii-186
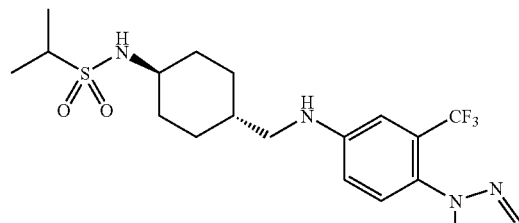
Compound Ii-187
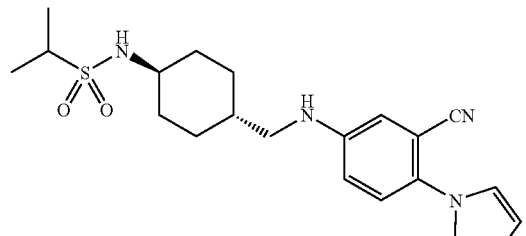
Compound Ii-188
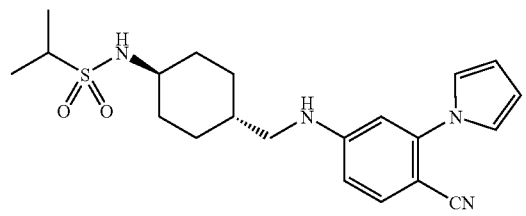
Compound Ii-189
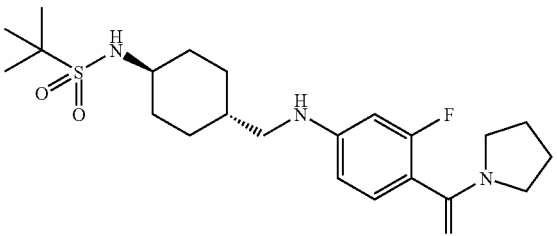
Compound Ii-190
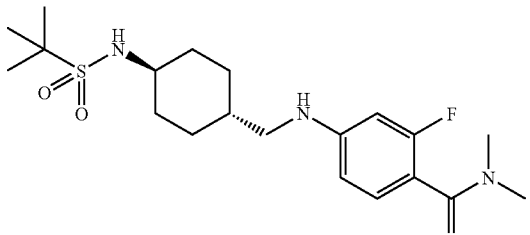
Compound Ii-191
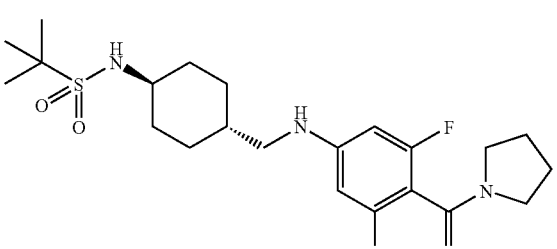
Compound Ii-192
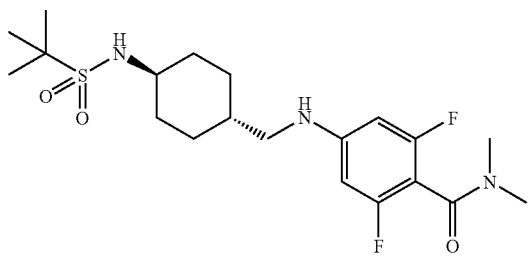
Compound Ii-193
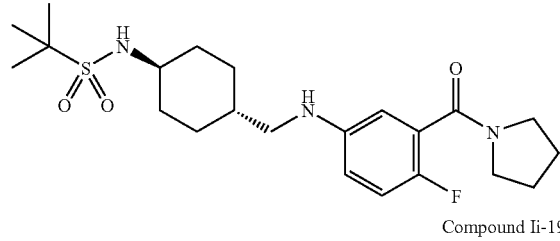
Compound Ii-194
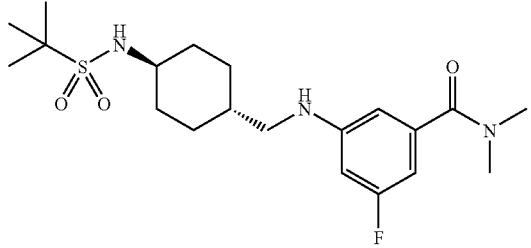
Compound Ii-195
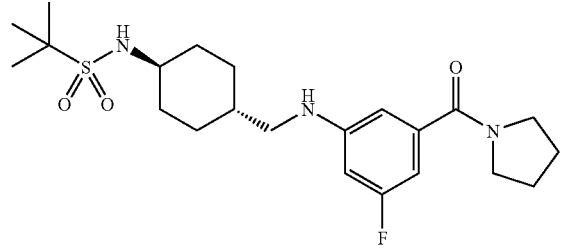
Compound Ii-196
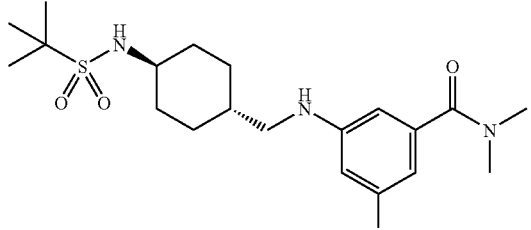
Compound Ii-197
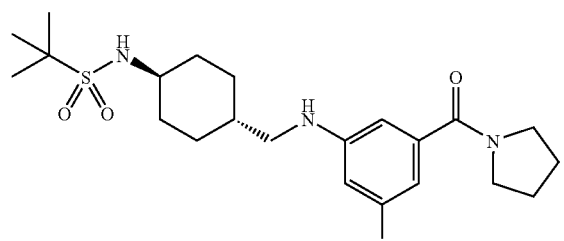

Compound Ii-198
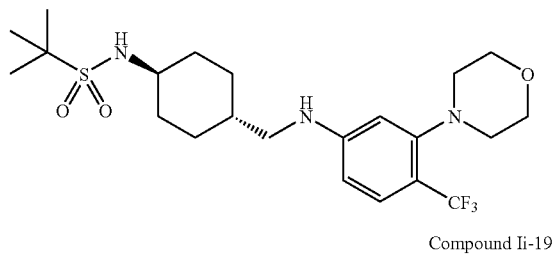
Compound Ii-199
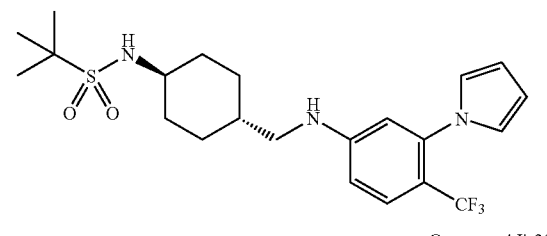
Compound Ii-200
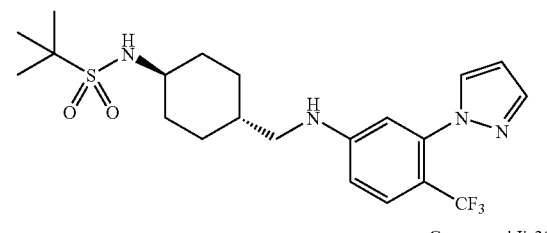
Compound Ii-201
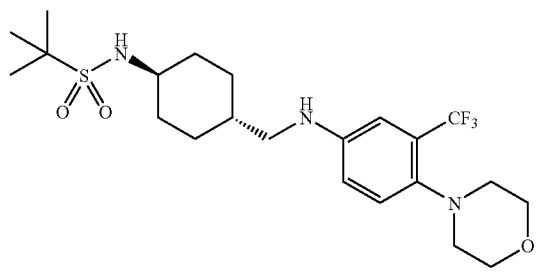
Compound Ii-202
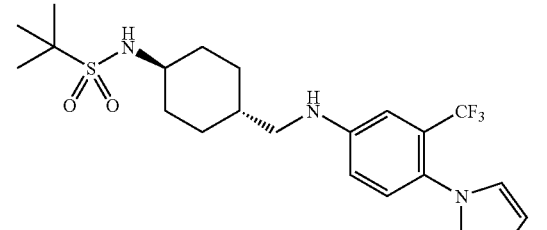
Compound Ii-203
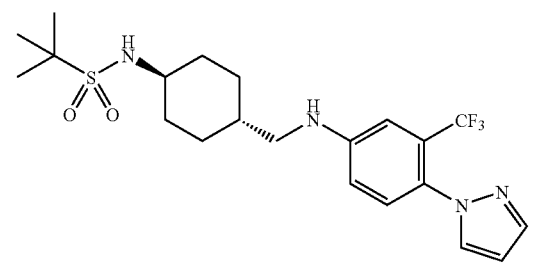
Compound Ii-204
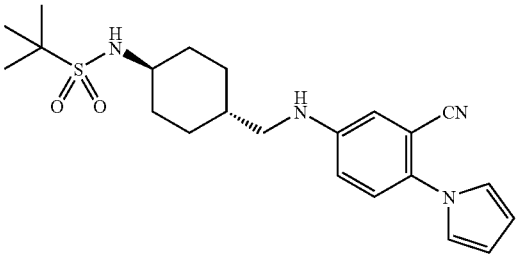
Compound Ii-205
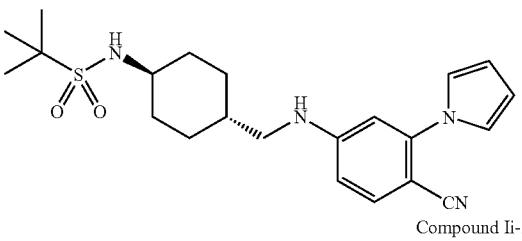
Compound Ii-206
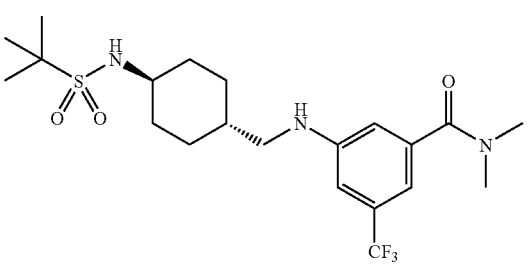
Compound Ij-2
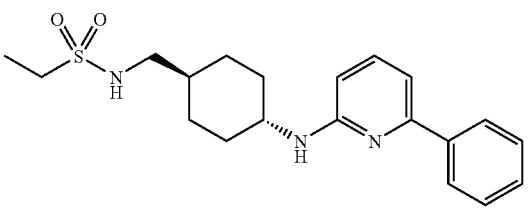
$^1$H-NMR (DMSO-d$_6$) δ: 0.98-1.24 (m, 4H), 1.19 (t, 3H, J=7.5 Hz), 1.40 (m, 1H), 1.78-1.88 (m, 2H), 2.02-2.14 (m, 2H), 2.80 (t, 2H, J=6.0 Hz), 2.86 (q, 2H, J=7.2 Hz), 3.64-3.82 (m, 1H), 6.40 (d, 2H, J=8.1 Hz), 7.01 (d, 2H, J=7.2 Hz), 7.32-7.50 (m, 4H), 7.99 (d, 2H, J=6.9 Hz)
Compound Ij-3
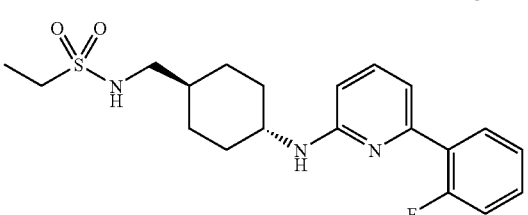
$^1$H-NMR (DMSO-d$_6$) δ: 0.96-1.26 (m, 4H), 1.18 (t, 3H, J=7.5 Hz), 1.40 (m, 1H), 1.78-1.88 (m, 2H), 2.02-2.14 (m, 2H), 2.78 (t, 2H, J=6.0 Hz), 2.98 (q, 2H, J=7.5 Hz), 3.60-3.78 (m, 1H), 6.40-6.50 (m, 2H), 6.85-6.92 (m, 1H), 6.97-7.03 (m, 1H), 7.22-7.35 (m, 2H), 7.36-7.46 (m, 2H), 7.88-7.96 (m, 1H)

Compound Ij-4

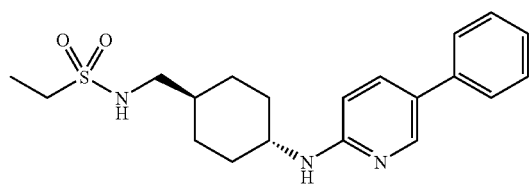

¹H-NMR (DMSO-d₆) δ: 0.92-1.24 (m, 4H), 1.19 (t, 3H, J=7.2 Hz), 1.38 (m, 1H), 1.78-1.88 (m, 2H), 1.96-2.06 (m, 2H), 2.78 (t, 2H, J=6.0 Hz), 2.98 (q, 2H, J=7.5 Hz), 3.60-3.78 (m, 1H), 6.50 (t, 1H, J=3.9 Hz), 6.53 (s, 1H), 7.00 (t, 1H, J=5.7 Hz), 7.25 (t, 1H, J=7.2 Hz), 7.34-7.45 (m, 2H), 7.55 (d, 2H, J=7.2 Hz), 7.67 (dd, 1H, J=8.7, 2.7 Hz), 8.29 (d, 1H, J=2.7 Hz)

Compound Ij-5

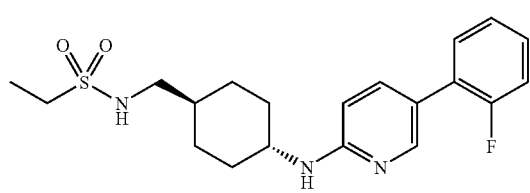

¹H-NMR (DMSO-d₆) δ: 0.92-1.24 (m, 4H), 1.19 (t, 3H, J=7.2 Hz), 1.38 (m, 1H), 1.78-1.88 (m, 2H), 1.96-2.06 (m, 2H), 2.78 (t, 2H, J=6.0 Hz), 2.98 (q, 2H, J=7.5 Hz), 3.60-3.78 (m, 1H), 6.52 (d, 1H, J=8.4 Hz), 6.60 (d, 1H, J=7.8 Hz), 7.01 (t, 1H, J=5.7 Hz), 7.20-7.36 (m, 3H), 7.46 (t, 1H, J=8.1 Hz), 7.55 (d, 1H, J=8.7 Hz), 8.15 (s, 1H)

Compound Ij-6

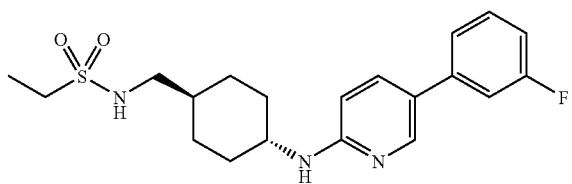

¹H-NMR (DMSO-d₆) δ: 0.92-1.24 (m, 4H), 1.19 (t, 3H, J=7.2 Hz), 1.40 (m, 1H), 1.78-1.88 (m, 2H), 1.96-2.06 (m, 2H), 2.78 (t, 2H, J=6.0 Hz), 2.98 (q, 2H, J=7.5 Hz), 3.60-3.78 (m, 1H), 6.51 (d, 1H, J=8.7 Hz), 6.60 (d, 1H, J=7.5 Hz), 7.01 (t, 1H, J=5.7 Hz), 7.02-7.12 (m, 1H), 7.36-7.48 (m, 3H), 7.71 (dd, 1H, J=8.7, 2.1 Hz), 8.33 (d, 1H, J=2.1 Hz)

Compound Ij-7

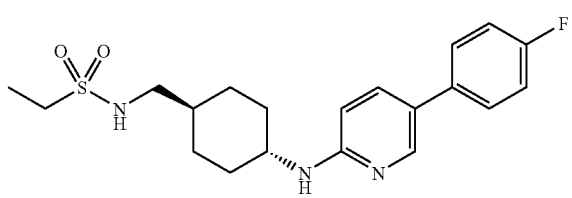

¹H-NMR (DMSO-d₆) δ: 0.92-1.24 (m, 4H), 1.19 (t, 3H, J=7.2 Hz), 1.40 (m, 1H), 1.78-1.88 (m, 2H), 1.96-2.06 (m, 2H), 2.78 (t, 2H, J=6.0 Hz), 2.98 (q, 2H, J=7.5 Hz), 3.60-3.78 (m, 1H), 6.50 (d, 2H, J=8.7 Hz), 6.99 (t, 1H, J=6.0 Hz), 7.16-7.26 (m, 2H), 7.52-7.68 (m, 3H), 8.25 (s, 1H)

Compound Ij-8

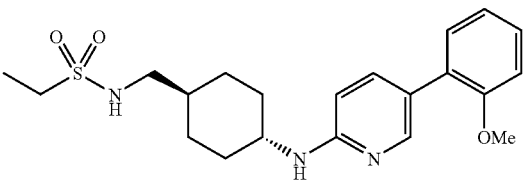

¹H-NMR (CDCl₃) δ: 1.15-1.26 (m, 4H), 1.40 (t, 3H, J=7.5 Hz), 1.55-1.58 (m, 1H), 1.93 (d, 2H, J=9.7 Hz), 2.23 (d, 2H, J=9.7 Hz), 3.01-3.11 (m, 4H), 3.56-3.61 (m, 1H), 3.84 (s, 3H), 4.34 (t, 1H, J=6.1 Hz), 4.83-4.86 (m, 1H), 6.46 (d, 1H, J=8.6 Hz), 6.99 (d, 1H, J=8.5 Hz), 7.05 (d, 1H, J=8.5 Hz), 7.29 (s, 1H), 7.30-7.34 (m, 1H), 7.69 (dd, 1H, J=8.7, 2.4 Hz), 8.25 (s, 1H).

Compound Ij-9

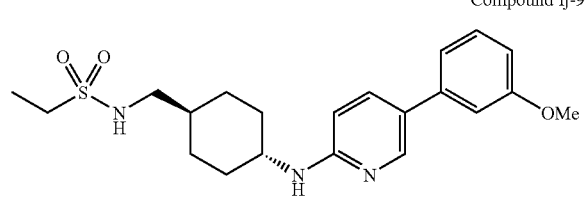

¹H-NMR (CDCl₃) δ: 1.16-1.24 (m, 4H), 1.40 (t, 3H, J=6.2 Hz), 1.55-1.59 (m, 1H), 1.94 (d, 2H, J=11.8 Hz), 2.23 (d, 2H, J=11.8 Hz), 3.03-3.09 (m, 4H), 3.58-3.62 (m, 1H), 3.88 (s, 3H), 4.29 (t, 1H, J=6.4 Hz), 4.85-4.89 (m, 1H), 6.49 (d, 1H, J=8.7 Hz), 6.88 (dd, 1H, J=8.7, 2.2 Hz), 7.04-7.06 (m, 1H), 7.10 (d, 1H, J=8.7 Hz), 7.36 (t, 1H, J=7.9 Hz), 7.70 (dd, 1H, J=8.7, 2.2 Hz), 8.32 (s, 1H).

Compound Ij-10

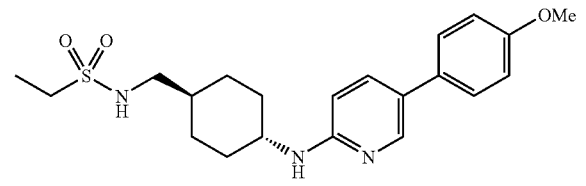

¹H-NMR (CDCl₃) δ: 1.19-1.30 (m, 4H), 1.41 (t, 3H, J=6.3 Hz), 1.56-1.59 (m, 1H), 1.94 (d, 2H, J=11.1 Hz), 2.23 (d, 2H, J=11.1 Hz), 3.01-3.11 (m, 4H), 3.57-3.61 (m, 1H), 3.87 (s, 3H), 4.27 (t, 1H, J=6.4 Hz), 4.98 (s, 1H), 6.50 (dd, 1H, J=8.7, 2.2 Hz), 6.99 (d, 2H, J=8.9 Hz), 7.43 (d, 2H, J=8.7 Hz), 7.68 (dd, 1H, J=8.7, 2.2 Hz), 8.25 (s, 1H).

Compound Ij-11

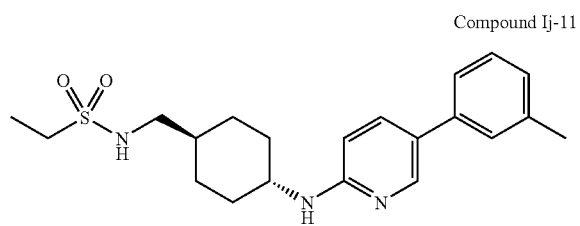

¹H-NMR (DMSO-d₆) δ: 0.93-1.08 (m, 2H), 1.09-1.25 (m, 5H), 1.39 (m, 1H), 1.75-1.86 (m, 2H), 1.95-2.07 (m, 2H), 2.34 (s, 3H), 2.78 (t, 2H, J=6.2 Hz), 2.98 (q, 2H, J=7.3 Hz), 3.65 (m, 1H), 6.45-6.53 (m, 2H), 7.01 (t, 1H, J=5.6 Hz), 7.07 (d, 1H, J=7.1 Hz), 7.23-7.38 (m, 3H), 7.64 (dd, 1H, J1=8.8 Hz, J2=2.5 Hz), 8.26 (d, 1H, J=2.5 Hz).

Compound Ij-12

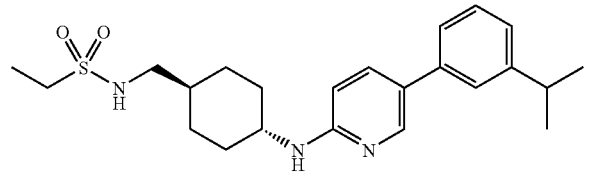

¹H-NMR (DMSO-d₆) δ: 0.93-1.08 (m, 2H), 1.09-1.27 (m, 11H), 1.39 (m, 1H), 1.76-1.87 (m, 2H), 1.96-2.06 (m, 2H), 2.78 (t, 2H, J=6.2 Hz), 2.84-3.03 (m, 3H), 3.66 (m, 1H), 6.45-6.54 (m, 2H), 7.01 (t, 1H, J=5.8 Hz), 7.13 (d, 1H, J=6.9 Hz), 7.27-7.41 (m, 3H), 7.66 (dd, 1H, J1=8.8 Hz, J2=2.5 Hz), 8.27 (d, 1H, J=2.2 Hz).

Compound Ij-13

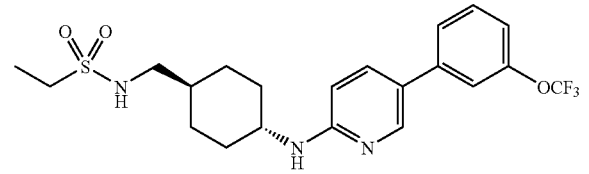

¹H-NMR (DMSO-d₆) δ: 0.92-1.09 (m, 2H), 1.09-1.25 (m, 5H), 1.39 (m, 1H), 1.76-1.85 (m, 2H), 1.95-2.06 (m, 2H), 2.78 (t, 2H, J=6.2 Hz), 2.98 (q, 2H, J=7.3 Hz), 3.68 (m, 1H), 6.52 (d, 1H, J=8.8 Hz), 6.66 (d, 1H, J=8.0 Hz), 7.02 (t, 1H, J=5.5 Hz), 7.23 (d, 1H, J=8.1 Hz), 7.49-7.55 (m, 2H), 7.62 (d, 1H, J1=8.5 Hz), 7.72 (dd, 1H, J1=8.8 Hz, J2=2.5 Hz), 8.35 (d, 1H, J=2.5 Hz).

Compound Ij-14

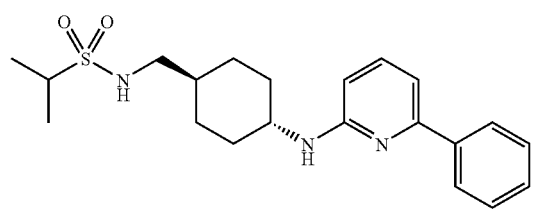

¹H-NMR (DMSO-d₆) δ: 0.92-1.22 (m, 4H), 1.22 (d, 6H, J=6.4 Hz), 1.39 (m, 1H), 1.76-1.86 (m, 2H), 1.95-2.03 (m, 2H), 2.81 (t, 2H, J=6.4 Hz), 3.10-3.20 (m, 1H), 3.60-3.75 (m, 1H), 6.65 (d, 1H, J=4.8 Hz), 6.70 (s, 1H), 6.88-6.98 (m, 2H), 8.16 (d, 1H, J=5.2 Hz).

Compound Ij-15

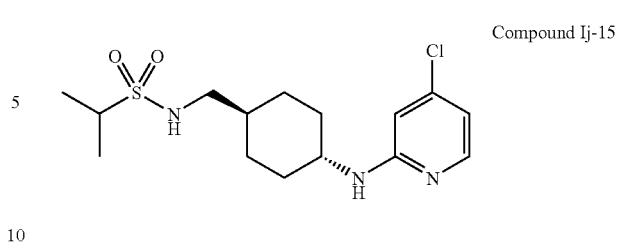

¹H-NMR (CDCl₃) δ: 1.02-1.28 (m, 4H), 1.38 (d, 6H, J=6.9 Hz), 1.52 (m, 1H), 1.85-1.94 (m, 2H), 2.11-2.21 (m, 2H), 3.01 (t, 2H, J=6.6 Hz), 3.10-3.25 (m, 1H), 3.38-3.54 (m, 1H), 4.22 (t, 1H, J=6.3 Hz), 4.58 (d, 1H, J=7.8 Hz), 6.34 (d, 1H, J=1.8 Hz), 6.53 (dd, 1H, J=5.4, 1.8 Hz), 7.93 (d, 1H, J=5.4 Hz).

Compound Ij-16

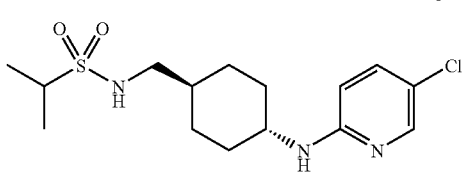

¹H-NMR (CDCl₃) δ: 1.03-1.28 (m, 4H), 1.37 (d, 6H, J=6.9 Hz), 1.52 (m, 1H), 1.84-1.93 (m, 2H), 2.11-2.21 (m, 2H), 3.01 (t, 2H, J=6.6 Hz), 3.09-3.24 (m, 1H), 3.40-3.54 (m, 1H), 4.26 (t, 1H, J=6.6 Hz), 4.44 (d, 1H, J=8.1 Hz), 6.29 (d, 1H, J=8.7 Hz), 7.33 (dd, 1H, J=8.7, 2.7 Hz), 7.99 (d, 1H, J=2.7 Hz).

Compound Ij-17

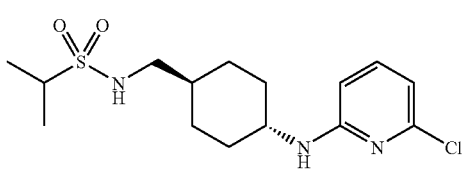

¹H-NMR (DMSO-d₆) δ: 0.92-1.22 (m, 4H), 1.21 (d, 6H, J=6.8 Hz), 1.36 (m, 1H), 1.76-1.84 (m, 2H), 1.92-2.00 (m, 2H), 2.80 (t, 2H, J=6.4 Hz), 3.08-3.18 (m, 1H), 3.45-3.56 (m, 1H), 6.36 (d, 1H, J=8.4 Hz), 6.43 (d, 1H, J=7.2 Hz), 6.75 (d, 1H, J=7.6 Hz), 6.94 (t, 1H, J=6.0 Hz), 7.33 (t, 1H, J=7.6 Hz).

Compound Ij-18

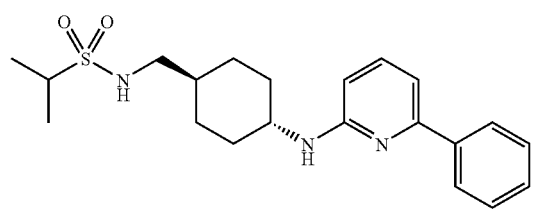

¹H-NMR (DMSO-d₆) δ: 0.98-1.24 (m, 4H), 1.22 (d, 6H, J=6.9 Hz), 1.40 (m, 1H), 1.78-1.88 (m, 2H), 2.04-2.14 (m, 2H), 2.83 (t, 2H, J=6.0 Hz), 3.10-3.22 (m, 1H), 3.64-3.82 (m, 1H), 6.40 (d, 2H, J=8.4 Hz), 6.95-7.05 (m, 2H), 7.35-7.50 (m, 4H), 7.99 (d, 2H, J=7.2 Hz)

Compound Ij-19

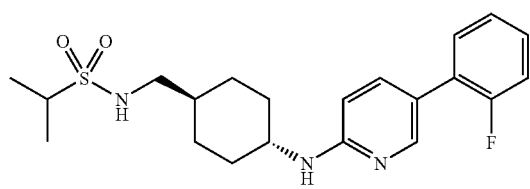

¹H-NMR (CDCl₃) δ: 1.22-1.38 (m, 4H), 1.38 (d, 6H, J=8.0 Hz), 1.54 (m, 1H), 1.86-1.95 (m, 2H), 2.18-2.26 (m, 2H), 3.03 (t, 2H, J=6.0 Hz), 3.12-3.22 (m, 1H), 3.52-3.64 (m, 1H), 4.16 (t, 1H, J=6.4 Hz), 4.82-4.92 (m, 1H), 6.46 (d, 1H, J=8.0 Hz), 7.10-7.20 (m, 2H), 7.23-7.33 (m, 1H), 7.37 (t, 1H, J=8.0 Hz), 7.65 (d, 1H, J=8.7 Hz), 8.24 (s, 1H).

Compound Ij-20

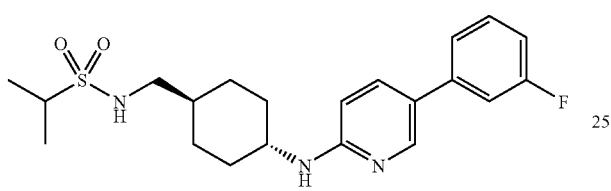

¹H-NMR (CDCl₃) δ: 1.22-1.38 (m, 4H), 1.39 (d, 6H, J=8.0 Hz), 1.54 (m, 1H), 1.86-1.95 (m, 2H), 2.18-2.26 (m, 2H), 3.03 (t, 2H, J=6.0 Hz), 3.12-3.22 (m, 1H), 3.52-3.64 (m, 1H), 4.16 (t, 1H, J=6.4 Hz), 4.78-4.88 (m, 1H), 6.46 (d, 1H, J=8.0 Hz), 6.98 (t, 1H, J=5.7 Hz), 7.18 (d, 1H, J=8.0 Hz), 7.23-7.29 (m, 1H), 7.33-7.40 (m, 1H), 7.65 (d, 1H, J=8.7 Hz), 8.29 (s, 1H).

Compound Ij-21

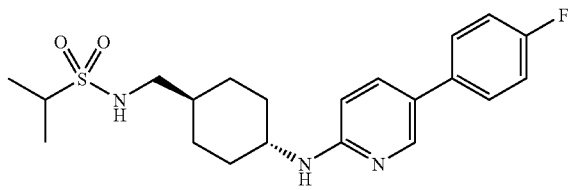

¹H-NMR (CDCl₃) δ: 1.10-1.30 (m, 4H), 1.38 (d, 6H, J=8.0 Hz), 1.54 (m, 1H), 1.86-1.95 (m, 2H), 2.18-2.26 (m, 2H), 3.03 (t, 2H, J=6.0 Hz), 3.13-3.22 (m, 1H), 3.52-3.64 (m, 1H), 4.15 (t, 1H, J=6.4 Hz), 4.78-4.88 (m, 1H), 6.46 (d, 1H, J=8.0 Hz), 7.07-7.14 (m, 2H), 7.40-7.46 (m, 2H), 7.62 (d, 1H, J=8.7 Hz), 8.23 (s, 1H).

Compound Ij-22

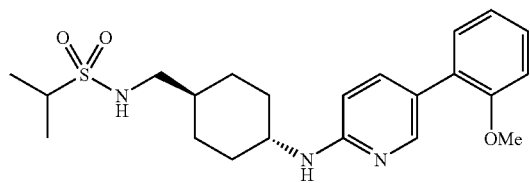

¹H-NMR (DMSO-d₆) δ: 0.95-1.25 (m, 4H), 1.22 (d, 6H, J=6.6 Hz), 1.25-1.50 (br, 1H), 1.81 (d, 2H, J=11.4 Hz), 2.00 (d, 2H, J=10.5 Hz), 2.81 (t, 2H, J=6.6 Hz), 3.05-3.22 (m, 1H), 3.58-3.80 (m, 1H), 3.76 (s, 3H), 6.49 (d, 2H, J=8.7 Hz), 6.50-6.70 (br, 1H), 6.95-7.10 (m, 3H), 7.20-7.32 (m, 2H), 7.51 (d, 1H, J=7.2 Hz), 8.05 (br, 1H). ESI (positive) 418.3 [M+H]+

Compound Ij-23

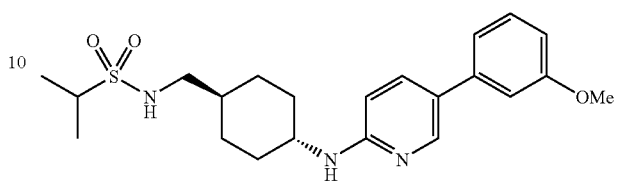

¹H-NMR (DMSO-d₆) δ: 0.95-1.32 (m, 4H), 1.22 (d, 6H, J=6.6 Hz), 1.25-1.55 (br, 1H), 1.82 (d, 2H, J=11.4 Hz), 2.01 (d, 2H, J=10.2 Hz), 2.81 (t, 2H, J=6.6 Hz), 3.05-3.22 (m, 1H), 3.58-3.78 (m, 1H), 3.80 (s, 3H), 6.59 (d, 2H, J=9.6 Hz), 6.85 (dd, 1H, J=8.4 Hz, 2.4 Hz), 6.99 (t, 3H, J=5.7 Hz), 7.05-7.18 (m, 2H), 7.32 (d, 1H, J=7.8 Hz), 7.76 (d, 1H, J=8.4 Hz), 8.27 (d, 1H, J=2.1 Hz). ESI (positive) 418.3 [M+H]+

Compound Ij-24

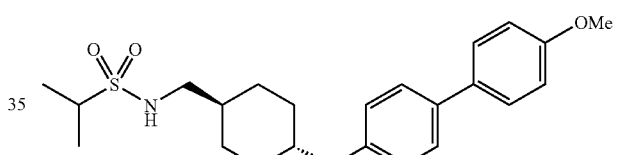

¹H-NMR (DMSO-d₆) δ: 0.92-1.25 (m, 4H), 1.22 (d, 6H, J=6.6 Hz), 1.28-1.48 (m, 1H), 1.81 (d, 2H, J=10.8 Hz), 2.00 (d, 2H, J=9.6 Hz), 2.81 (t, 2H, J=6.6 Hz), 3.08-3.22 (m, 1H), 3.58-3.74 (m, 1H), 3.77 (s, 3H), 6.51 (d, 2H, J=8.7 Hz), 6.97 (d, 2H, J=8.7 Hz), 6.98 (brs, 1H), 7.48 (d, 2H, J=8.7 Hz), 7.63 (dd, 1H, J=11.4 Hz, 2.4 Hz), 8.21 (d, 1H, J=2.4 Hz). ESI (positive) 418.3[M+H]+

Compound Ij-25

¹H-NMR (DMSO-d₆) δ: 0.92-1.22 (m, 4H), 1.27 (s, 9H), 1.38 (m, 1H), 1.78-1.88 (m, 2H), 1.95-2.05 (m, 2H), 2.88 (t, 2H, J=6.0 Hz), 3.60-3.80 (m, 1H), 6.65 (d, 1H, J=5.4 Hz), 6.70 (s, 1H), 6.87 (t, 1H, J=6.0 Hz), 6.94 (d, 1H, J=7.8 Hz), 8.16 (d, 1H, J=5.4 Hz)

Compound Ij-26

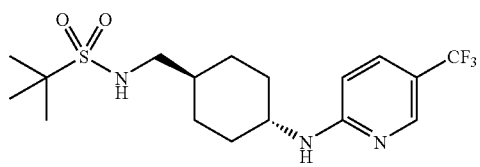

¹H-NMR (DMSO-d₆) δ: 0.92-1.22 (m, 4H), 1.27 (s, 9H), 1.38 (m, 1H), 1.78-1.88 (m, 2H), 1.94-2.04 (m, 2H), 2.88 (t, 2H, J=6.0 Hz), 3.60-3.80 (m, 1H), 6.53 (d, 1H, J=8.7 Hz), 6.87 (t, 1H, J=5.7 Hz), 7.19 (d, 1H, J=7.5 Hz), 7.59 (dd, 1H, J=9.0, 2.4 Hz), 8.26 (d, 1H, J=2.4 Hz)

Compound Ij-27

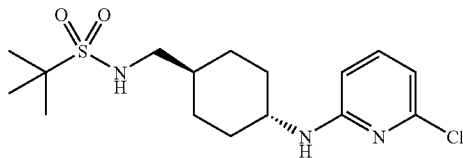

¹H-NMR (DMSO-d₆) δ: 0.92-1.22 (m, 4H), 1.26 (s, 9H), 1.38 (m, 1H), 1.76-1.86 (m, 2H), 1.92-2.02 (m, 2H), 2.88 (t, 2H, J=6.0 Hz), 3.40-3.60 (m, 1H), 6.36 (d, 1H, J=8.1 Hz), 6.43 (d, 1H, J=6.9 Hz), 6.80 (d, 1H, J=7.5 Hz), 6.86 (t, 1H, J=5.4 Hz), 7.34 (t, 1H, J=8.4 Hz)

Compound Ij-28

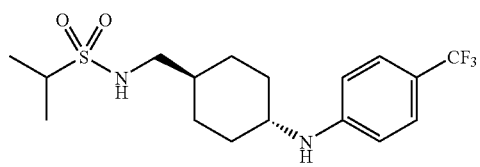

¹H-NMR ((DMSO-d₆) δ: 0.93-1.18 (m, 4H), 1.21 (d, 6H, J=6.9 Hz), 1.39 (m, 1H), 1.75-1.86 (m, 2H), 1.94-2.05 (m, 2H), 2.80 (t, 2H, J=6.0 Hz), 3.09-3.27 (m, 2H), 6.19 (d, 1H, J=8.1 Hz), 6.64 (d, 2H, J=8.7 Hz), 6.98 (t, 1H, J=6.0 Hz), 7.33 (d, 2H, J=8.7 Hz) Mass: 379 [M+H]+

Compound Ij-29

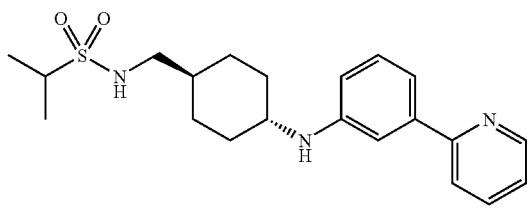

¹H-NMR (DMSO-d₆) δ: 0.93-1.18 (m, 4H), 1.22 (s, 3H), 1.24 (s, 3H), 1.32-1.49 (m, 2H), 1.82 (d, 2H, J=11.2 Hz), 2.04 (d, 2H, J=11.2 Hz), 2.75-2.87 (m, 2H), 3.07-3.28 (m, 2H), 6.64 (s, 1H), 6.96 (s, 1H), 7.10-7.22 (m, 2H), 7.25-7.39 (m, 2H), 7.77-7.90 (m, 2H), 8.63 (s, 1H). Melting point: 161-162° c.

Compound Ij-30

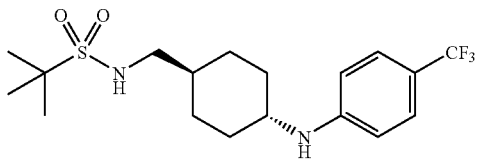

¹H-NMR (DMSO-d₆) δ: 0.92-1.22 (m, 4H), 1.27 (s, 9H), 1.37 (m, 1H), 1.76-1.86 (m, 2H), 1.94-2.05 (m, 2H), 2.88 (t, 2H, J=6.3 Hz), 3.19 (m, 1H), 6.19 (d, 1H, J=7.5 Hz), 6.64 (d, 2H, J=8.7 Hz), 6.88 (d, 1H, J=6.0 Hz), 7.33 (d, 2H, J=8.7 Hz) Mass: 392M+

Compound Ij-31

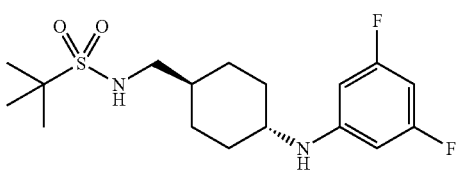

¹H-NMR (DMSO-d₆) δ: 0.92-1.16 (m, 4H), 1.26 (s, 9H), 1.36 (m, 1H), 1.72-1.83 (m, 2H), 1.92-2.02 (m, 2H), 2.87 (t, 2H, J=6.3 Hz), 3.12 (m, 1H), 6.09-6.23 (m, 4H), 6.87 (t, 1H, J=6.0 Hz) Mass: 361[M+H]+

Compound Ij-32

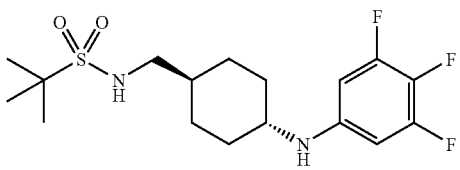

¹H-NMR (CDCl₃) δ: 1.00-1.20 (m, 4H), 1.40 (s, 9H), 1.42-1.64 (m, 2H), 1.84-1.95 (m, 2H), 2.09-2.20 (m, 2H), 3.07 (m, 1H), 3.07 (t, 2H, J=6.3 Hz), 3.90 (m, 1H), 6.10 (dd, 2H, J=9.6, 5.4 Hz).

Compound Ij-33

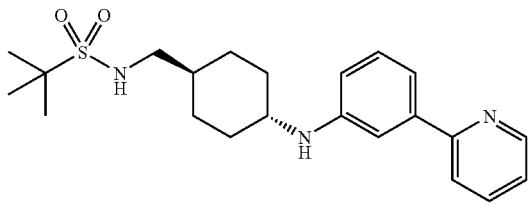

¹H-NMR (DMSO-d₆) δ: 0.93-1.21 (m, 5H), 1.28 (s, 9H), 1.33-1.46 (m, 1H), 1.82 (d, 2H, J=11.6 Hz), 2.04 (d, 2H, J=11.6 Hz), 2.86-2.95 (m, 2H), 3.03-3.29 (m, 1H), 6.59-6.71 (m, 1H), 6.80-6.92 (m, 1H), 7.09-7.21 (m, 2H), 7.27-7.37 (m, 2H), 7.77-7.88 (m, 2H), 8.58-8.67 (s, 1H). Melting point: 172-173° C.

Compound Ij-34

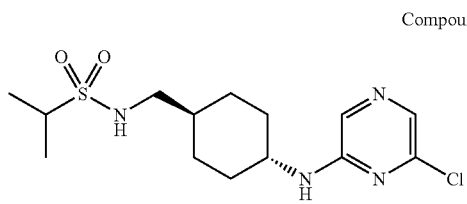

$^1$H-NMR (DMSO-d$_6$) δ: 0.96-1.08 (m, 2H), 1.12-1.24 (m, 2H), 1.21 (d, 6H, J=6.4 Hz), 1.38 (m, 1H), 1.76-1.86 (m, 2H), 1.92-2.00 (m, 2H), 2.80 (t, 2H, J=6.4 Hz), 3.10-3.20 (m, 1H), 3.48-3.60 (m, 1H), 6.95 (t, 1H, J=5.6 Hz), 7.41 (d, 1H, J=7.6 Hz), 7.63 (s, 1H), 7.82 (s, 1H).

Compound Ij-35

$^1$H-NMR (DMSO-d$_6$) δ: 0.96-1.26 (m, 4H), 1.27 (s, 9H), 1.38 (m, 1H), 1.78-1.88 (m, 2H), 1.92-2.02 (m, 2H), 2.88 (t, 2H, J=6.0 Hz), 3.48-3.62 (m, 1H), 6.87 (t, 1H, J=6.0 Hz), 7.45 (d, 1H, J=7.5 Hz), 7.63 (s, 1H), 7.82 (s, 1H)

Compound Ij-36

$^1$H-NMR (DMSO-d$_6$) δ: 0.96-1.06 (m, 2H), 1.12-1.20 (m, 2H), 1.21 (d, 6H, J=6.6 Hz), 1.39 (m, 1H), 1.78-1.84 (m, 2H), 1.95-1.99 (m, 2H), 2.81 (t, 2H, J=6.0 Hz), 3.10-3.20 (m, 1H), 3.74-3.88 (m, 1H), 6.80 (s, 1H), 6.98 (t, 1H, J=6.0 Hz), 7.93 (d, 2H, J=7.2 Hz), 8.53 (s, 1H).

Compound Ij-37

$^1$H-NMR (DMSO-d$_6$) δ: 0.96-1.30 (m, 4H), 1.19 (t, 3H, J=7.2 Hz), 1.42 (m, 1H), 1.78-1.88 (m, 2H), 2.04-2.16 (m, 2H), 2.80 (t, 2H, J=6.0 Hz), 2.99 (q, 2H, J=7.5 Hz), 3.72-3.90 (m, 1H), 6.85 (d, 1H, J=9.6 Hz), 6.93 (d, 1H, J=7.5 Hz), 7.04 (t, 1H, J=5.7 Hz), 7.26-7.38 (m, 2H), 7.40-7.52 (m, 1H), 7.57 (d, 1H, J=9.0 Hz), 7.85 (t, 1H, J=7.8 Hz)

Compound Ij-38

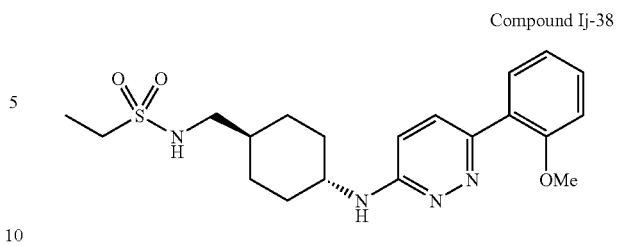

$^1$H-NMR (DMSO-d$_6$) δ: 0.96-1.30 (m, 4H), 1.19 (t, 3H, J=7.2 Hz), 1.42 (m, 1H), 1.78-1.88 (m, 2H), 2.04-2.16 (m, 2H), 2.80 (t, 2H, J=6.0 Hz), 2.99 (q, 2H, J=7.5 Hz), 3.72-3.90 (m, 1H), 3.80 (s, 3H), 6.72 (d, 1H, J=7.8 Hz), 6.77 (d, 1H, J=9.0 Hz), 6.98-7.10 (m, 2H), 7.12 (d, 1H, J=8.4 Hz), 7.38 (t, 1H, J=8.1 Hz), 7.56 (d, 1H, J=9.3 Hz), 7.61 (d, 1H, J=7.8 Hz)

Compound Ij-39

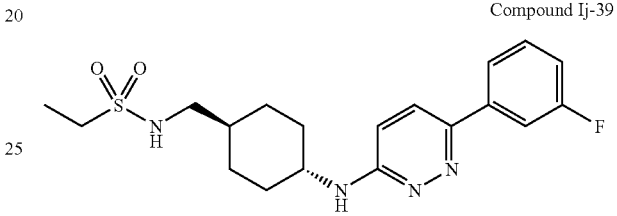

$^1$H-NMR (DMSO-d$_6$) δ: 0.96-1.30 (m, 4H), 1.19 (t, 3H, J=7.2 Hz), 1.42 (m, 1H), 1.78-1.88 (m, 2H), 2.04-2.16 (m, 2H), 2.80 (t, 2H, J=6.3 Hz), 2.99 (q, 2H, J=7.5 Hz), 3.72-3.90 (m, 1H), 6.85 (d, 1H, J=9.6 Hz), 6.92 (d, 1H, J=7.5 Hz), 7.04 (t, 1H, J=5.7 Hz), 7.21 (t, 1H, J=8.7 Hz), 7.46-7.56 (m, 1H), 7.75-7.88 (m, 3H)

Compound Ij-40

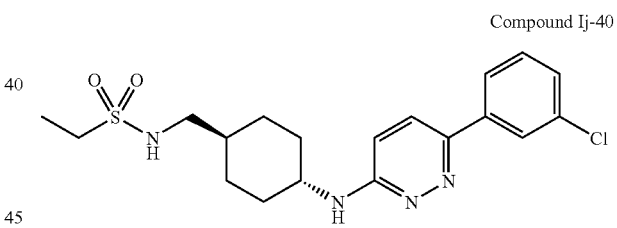

$^1$H-NMR (DMSO-d$_6$) δ: 0.96-1.10 (m, 2H), 1.19 (t, 3H, J=7.2 Hz), 1.15-1.26 (m, 2H), 1.42 (m, 1H), 1.78-1.88 (m, 2H), 2.04-2.14 (m, 2H), 2.80 (t, 2H, J=6.3 Hz), 2.99 (q, 2H, J=7.5 Hz), 3.76-3.87 (m, 1H), 6.85 (d, 1H, J=9.6 Hz), 6.91 (d, 1H, J=7.5 Hz), 7.01 (t, 1H, J=5.7 Hz), 7.42-7.52 (m, 2H), 7.83 (d, 1H, J=8.0 Hz), 7.93 (d, 1H, J=8.0 Hz), 8.02 (s, 1H).

Compound Ij-41

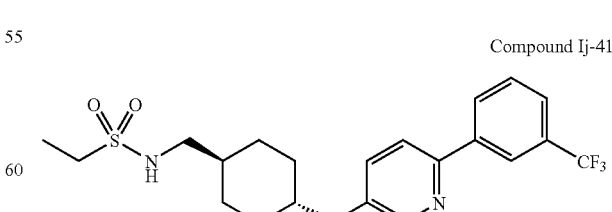

$^1$H-NMR (DMSO-d$_6$) δ: 0.96-1.30 (m, 4H), 1.20 (t, 3H, J=7.5 Hz), 1.42 (m, 1H), 1.78-1.88 (m, 2H), 2.04-2.16 (m, 2H), 2.80 (t, 2H, J=6.3 Hz), 2.99 (q, 2H, J=7.5 Hz), 3.76-3.90

(m, 1H), 6.88 (d, 1H, J=9.3 Hz), 6.97 (d, 1H, J=7.5 Hz), 7.03 (t, 1H, J=5.7 Hz), 7.67-7.77 (m, 2H), 7.92 (d, 1H, J=9.6 Hz), 8.26 (d, 1H, J=6.9 Hz), 8.33 (s, 1H)

2H), 2.83 (t, 2H, J=6.3 Hz), 3.10-3.22 (m, 1H), 3.74-3.92 (m, 1H), 6.85 (d, 1H, J=9.0 Hz), 6.91 (d, 1H, J=7.5 Hz), 6.98 (t, 1H, J=6.0 Hz), 7.25-7.36 (m, 2H), 7.40-7.50 (m, 1H), 7.57 (d, 1H, J=6.9 Hz), 7.85 (t, 1H, J=8.1 Hz)

Compound Ij-42

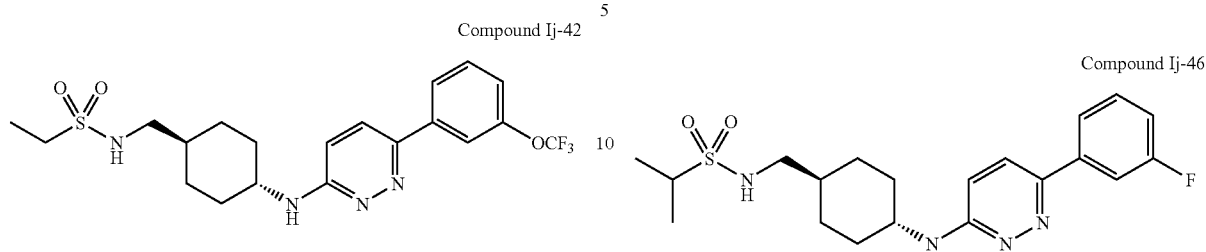

$^1$H-NMR (DMSO-$d_6$) δ: 0.93-1.10 (m, 2H), 1.20 (t, 3H, J=7.2 Hz), 1.22-1.28 (m, 1H), 1.35-1.50 (m, 2H), 1.84 (d, 2H, J=12.0 Hz), 2.08 (d, 2H, J=12.0 Hz), 2.63-2.76 (m, 2H), 2.91-3.03 (m, 2H), 3.75-3.90 (m, 1H), 6.86 (d, 1H, J=9.2 Hz), 6.93 (d, 1H, J=7.2 Hz), 6.98-7.07 (m, 1H), 7.36 (d, 1H, J=7.2 Hz), 7.59 (t, 1H, J=8.0 Hz), 7.85 (d, 1H, J=9.2 Hz), 7.91-8.02 (m, 2H). Melting point: 144-145° C.

Compound Ij-46

$^1$H-NMR (DMSO-$d_6$) δ: 0.96-1.28 (m, 4H), 1.22 (d, 6H, J=6.6 Hz), 1.42 (m, 1H), 1.78-1.88 (m, 2H), 2.04-2.16 (m, 2H), 2.83 (t, 2H, J=6.3 Hz), 3.10-3.22 (m, 1H), 3.74-3.92 (m, 1H), 6.85 (d, 1H, J=9.3 Hz), 6.90 (d, 1H, J=7.5 Hz), 6.98 (t, 1H, J=6.0 Hz), 7.21 (t, 1H, J=7.8 Hz), 7.46-7.56 (m, 1H), 7.75-7.86 (m, 3H)

Compound Ij-43

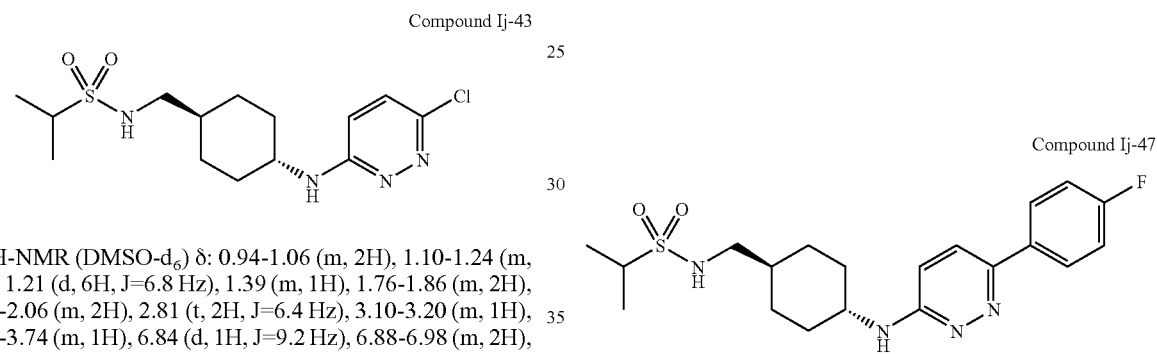

$^1$H-NMR (DMSO-$d_6$) δ: 0.94-1.06 (m, 2H), 1.10-1.24 (m, 2H), 1.21 (d, 6H, J=6.8 Hz), 1.39 (m, 1H), 1.76-1.86 (m, 2H), 1.98-2.06 (m, 2H), 2.81 (t, 2H, J=6.4 Hz), 3.10-3.20 (m, 1H), 3.62-3.74 (m, 1H), 6.84 (d, 1H, J=9.2 Hz), 6.88-6.98 (m, 2H), 7.31 (d, 1H, J=9.6 Hz).

Compound Ij-47

Compound Ij-44

$^1$H-NMR (DMSO-$d_6$) δ: 0.96-1.28 (m, 4H), 1.22 (d, 6H, J=6.9 Hz), 1.42 (m, 1H), 1.78-1.88 (m, 2H), 2.04-2.16 (m, 2H), 2.83 (t, 2H, J=6.0 Hz), 3.10-3.22 (m, 1H), 3.74-3.92 (m, 1H), 6.81 (d, 1H, J=7.5 Hz), 6.84 (d, 1H, J=9.3 Hz), 6.98 (t, 1H, J=6.3 Hz), 7.25-7.35 (m, 2H), 7.77 (d, 1H, J=9.3 Hz), 7.96-8.06 (m, 2H)

$^1$H-NMR (DMSO-$d_6$) δ: 0.94-1.26 (m, 4H), 1.20 (d, 6H, J=6.6 Hz), 1.40 (m, 1H), 1.78-1.88 (m, 2H), 2.04-2.16 (m, 2H), 2.81 (t, 2H, J=6.3 Hz), 3.06-3.20 (m, 1H), 3.72-3.90 (m, 1H), 6.75-6.88 (m, 2H), 6.97 (t, 1H, J=6.0 Hz), 7.30-7.48 (m, 3H), 7.76 (d, 1H, J=9.3 Hz), 7.94 (d, 2H, J=8.4 Hz)

Compound Ij-48

Compound Ij-45

$^1$H-NMR (DMSO-$d_6$) δ: 0.96-1.28 (m, 4H), 1.22 (d, 6H, J=6.9 Hz), 1.42 (m, 1H), 1.78-1.88 (m, 2H), 2.04-2.16 (m, 2H), 2.83 (t, 2H, J=6.3 Hz), 3.10-3.22 (m, 1H), 3.74-3.92 (m, 1H), 3.80 (s, 3H), 6.71 (d, 1H, J=7.8 Hz), 6.76 (d, 1H, J=9.3 Hz), 6.98 (t, 1H, J=5.7 Hz), 7.05 (d, 1H, J=7.2 Hz), 7.12 (d, 1H, J=7.8 Hz), 7.38 (t, 1H, J=8.4 Hz), 7.56 (d, 1H, J=9.3 Hz), 7.62 (d, 1H, J=6.9 Hz)

$^1$H-NMR (DMSO-$d_6$) δ: 0.96-1.28 (m, 4H), 1.22 (d, 6H, J=6.9 Hz), 1.42 (m, 1H), 1.78-1.88 (m, 2H), 2.04-2.16 (m,

Compound Ij-49

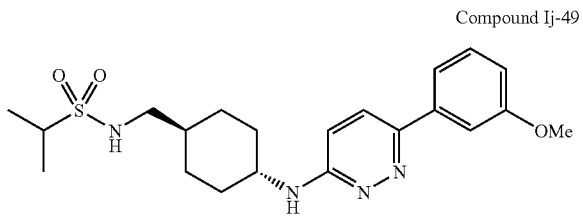

¹H-NMR (DMSO-d₆) δ: 0.96-1.28 (m, 4H), 1.22 (d, 6H, J=6.6 Hz), 1.42 (m, 1H), 1.78-1.88 (m, 2H), 2.04-2.16 (m, 2H), 2.83 (t, 2H, J=6.0 Hz), 3.10-3.22 (m, 1H), 3.74-3.92 (m, 1H), 3.82 (s, 3H), 6.78-6.88 (m, 2H), 6.92-7.04 (m, 2H), 7.37 (t, 1H, J=7.5 Hz), 7.46-7.58 (m, 2H), 7.79 (d, 1H, J=9.3 Hz)

Compound Ij-50

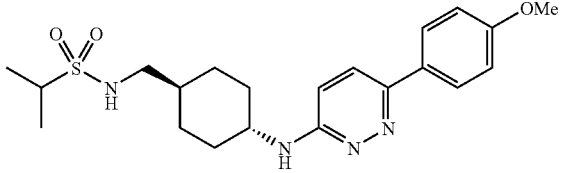

¹H-NMR (DMSO-d₆) δ: 0.96-1.28 (m, 4H), 1.22 (d, 6H, J=6.9 Hz), 1.42 (m, 1H), 1.78-1.88 (m, 2H), 2.04-2.16 (m, 2H), 2.83 (t, 2H, J=6.0 Hz), 3.10-3.22 (m, 1H), 3.74-3.92 (m, 1H), 3.80 (s, 3H), 6.70 (d, 1H, J=7.8 Hz), 6.82 (d, 1H, J=9.3 Hz), 6.95-7.05 (m, 3H), 7.72 (d, 1H, J=9.3 Hz), 7.90 (d, 2H, J=9.0 Hz).

Compound Ij-51

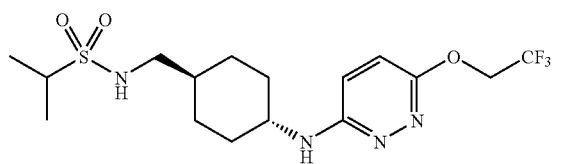

¹H-NMR (DMSO-d₆) δ: 0.92-1.05 (m, 2H), 1.07-1.20 (m, 2H), 1.22 (d, 6H, J=6.9 Hz), 1.39 (m, 1H), 1.76-1.85 (m, 2H), 2.02-2.10 (m, 2H), 2.81 (t, 2H, J=6.3 Hz), 3.09-3.20 (m, 1H), 3.57-3.68 (m, 1H), 4.89-4.98 (m, 2H), 6.47 (d, 1H, J=8.0 Hz), 6.88 (d, 1H, J=7.5 Hz), 6.96 (t, 1H, J=6.0 Hz), 7.02 (d, 1H, J=7.5 Hz).

Compound Ij-52

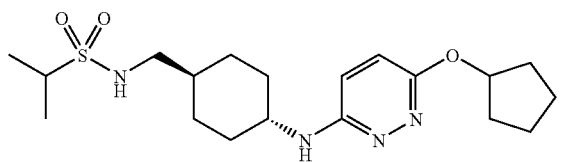

¹H-NMR (DMSO-d₆) δ: 0.92-1.05 (m, 2H), 1.07-1.20 (m, 2H), 1.22 (d, 6H, J=6.9 Hz), 1.39 (m, 1H), 1.52-1.74 (m, 6H), 1.77-1.85 (m, 2H), 1.87-1.97 (m, 2H), 2.02-2.09 (m, 2H), 2.81 (t, 2H, J=6.3 Hz), 3.09-3.20 (m, 1H), 3.55-3.65 (m, 1H), 5.25-5.32 (m, 1H), 6.19 (d, 1H, J=8.0 Hz), 6.77 (s, 2H), 6.95 (t, 1H, J=6.0 Hz).

Compound Ij-53

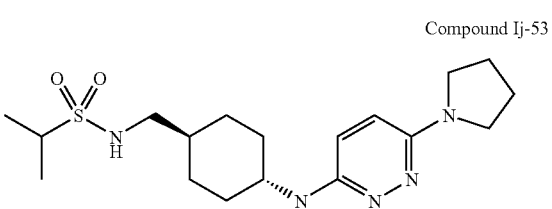

¹H-NMR (DMSO-d₆) δ: 0.92-1.15 (m, 4H), 1.21 (d, 6H, J=6.9 Hz), 1.38 (m, 1H), 1.77-1.85 (m, 2H), 1.88-1.95 (m, 4H), 2.02-2.09 (m, 2H), 2.80 (t, 2H, J=6.3 Hz), 3.09-3.20 (m, 1H), 3.25-3.35 (m, 4H), 3.55-3.65 (m, 1H), 5.80-5.85 (m, 1H), 6.72 (d, 1H, J=8.0 Hz), 6.80 (d, 1H, J=8.0 Hz), 6.96 (t, 1H, J=6.0 Hz).

Compound Ij-54

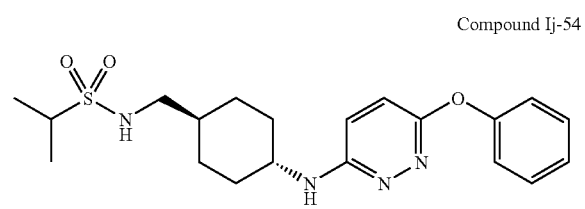

¹H-NMR (DMSO-d₆) δ: 0.92-1.20 (m, 4H), 1.21 (d, 6H, J=6.9 Hz), 1.38 (m, 1H), 1.77-1.85 (m, 2H), 2.02-2.09 (m, 2H), 2.80 (t, 2H, J=6.3 Hz), 3.09-3.20 (m, 1H), 3.58-3.65 (m, 1H), 6.56 (d, 1H, J=8.0 Hz), 6.90-6.98 (m, 2H), 7.03-7.10 (m, 3H), 7.15 (t, 1H, J=8.0 Hz), 6.38 (t, 2H, J=8.0 Hz).

Compound Ij-55

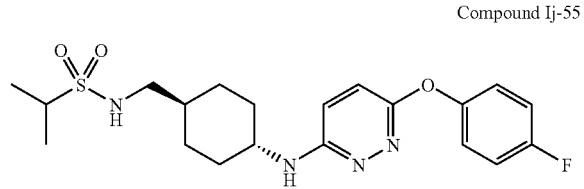

¹H-NMR (DMSO-d₆) δ: 0.92-1.20 (m, 4H), 1.21 (d, 6H, J=6.9 Hz), 1.38 (m, 1H), 1.77-1.85 (m, 2H), 2.02-2.09 (m, 2H), 2.80 (t, 2H, J=6.3 Hz), 3.09-3.20 (m, 1H), 3.58-3.65 (m, 1H), 6.55 (d, 1H, J=8.0 Hz), 6.90-6.98 (m, 2H), 7.05-7.15 (m, 3H), 7.21 (t, 2H, J=8.0 Hz).

Compound Ij-56

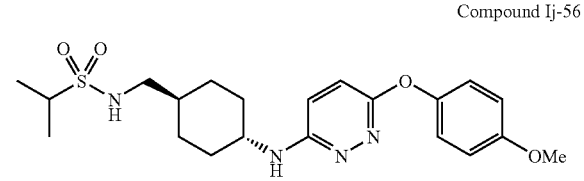

¹H-NMR (DMSO-d₆) δ: 0.92-1.20 (m, 4H), 1.21 (d, 6H, J=6.9 Hz), 1.38 (m, 1H), 1.77-1.85 (m, 2H), 2.02-2.09 (m, 2H), 2.80 (t, 2H, J=6.3 Hz), 3.09-3.20 (m, 1H), 3.58-3.65 (m, 1H), 3.75 (s, 3H), 6.49 (d, 1H, J=8.0 Hz), 6.87-6.98 (m, 4H), 7.00-7.07 (m, 3H).

Compound Ij-57

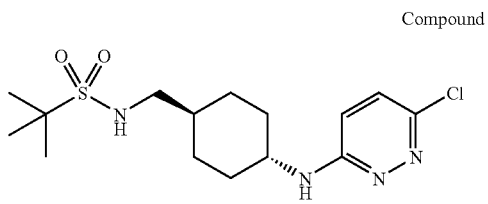

¹H-NMR (DMSO-d₆) δ: 0.96-1.28 (m, 4H), 1.27 (s, 9H), 1.40 (m, 1H), 1.78-1.88 (m, 2H), 2.00-2.10 (m, 2H), 2.88 (t, 2H, J=6.0 Hz), 3.60-3.76 (m, 1H), 6.82-6.92 (m, 2H), 6.96 (d, 1H, J=7.8 Hz), 7.32 (d, 1H, J=9.6 Hz).

Compound Ij-58

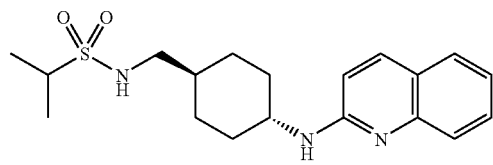

¹H-NMR (DMSO-d₆) δ: 0.99-1.28 (m, 4H), 1.21 (d, 6H, J=6.9 Hz), 1.39 (m, 1H), 1.78-1.86 (m, 2H), 2.04-2.10 (m, 2H), 2.82 (t, 2H, J=6.1 Hz), 3.06-3.20 (m, 1H), 3.80-3.96 (m, 1H), 6.71 (d, 1H, J=9.0 Hz), 6.76-6.86 (m, 1H), 6.90-6.98 (m, 1H), 7.10 (t, 1H, J=8.1 Hz), 7.39-7.50 (m, 2H), 7.56 (d, 1H, J=7.5 Hz), 7.78 (d, 1H, J=7.5 Hz).

Compound Ij-59

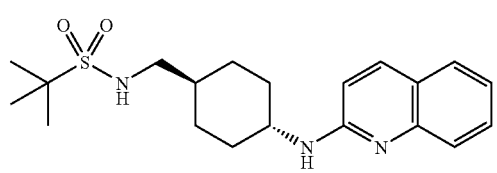

¹H-NMR (DMSO-d₆) δ: 0.99-1.28 (m, 4H), 1.27 (s, 9H), 1.40 (m, 1H), 1.80-1.85 (m, 2H), 2.04-2.09 (m, 2H), 2.91 (t, 2H, J=6.1 Hz), 3.80-3.96 (m, 1H), 6.70 (d, 1H, J=9.0 Hz), 6.81-6.87 (m, 2H), 7.10 (t, 1H, J=8.1 Hz), 7.39-7.44 (m, 2H), 7.56 (d, 1H, J=7.5 Hz), 7.79 (d, 1H, J=7.5 Hz).

Compound Ij-60

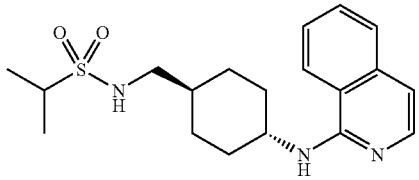

¹H-NMR (DMSO-d₆) δ: 0.97-1.09 (m, 2H), 1.23 (d, 6H, J=6.9 Hz), 1.31-1.50 (m, 2H), 1.82-1.87 (m, 2H), 2.01-2.05 (m, 2H), 2.83 (t, 2H, J=6.0 Hz), 3.11-3.20 (m, 1H), 4.00-4.18 (m, 1H), 6.83 (d, 1H, J=5.7 Hz), 6.90-7.06 (m, 2H), 7.45 (t, 1H, J=6.9 Hz), 7.59 (t, 1H, J=8.1 Hz), 7.67 (d, 1H, J=8.4 Hz), 7.83 (d, 1H, J=5.7 Hz), 8.27 (d, 1H, J=7.5 Hz).

Compound Ij-61

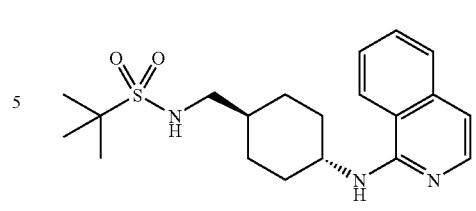

¹H-NMR (DMSO-d₆) δ: 0.96-1.09 (m, 2H), 1.28 (s, 9H), 1.29-1.50 (m, 2H), 1.82-1.87 (m, 2H), 2.01-2.05 (m, 2H), 2.91 (t, 2H, J=7.8 Hz), 4.00-4.18 (m, 1H), 6.82-6.89 (m, 2H), 6.97 (d, 1H, J=7.5 Hz), 7.45 (t, 1H, J=7.2 Hz), 7.59 (t, 1H, J=8.1 Hz), 7.67 (d, 1H, J=7.8 Hz), 7.84 (d, 1H, J=6.0 Hz), 8.27 (d, 1H, J=8.4 Hz).

Compound Ij-62

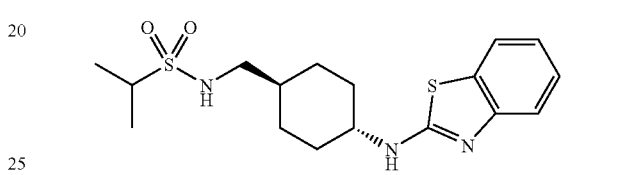

¹H-NMR (DMSO-d₆) δ: 0.96-1.14 (m, 2H), 1.18-1.30 (m, 2H), 1.22 (d, 6H, J=6.6 Hz), 1.40 (m, 1H), 1.78-1.88 (m, 2H), 2.04-2.14 (m, 2H), 2.81 (t, 2H, J=6.3 Hz), 3.10-3.20 (m, 1H), 3.58-3.70 (m, 1H), 6.95-7.03 (m, 2H), 7.20 (t, 1H, J=7.5 Hz), 7.37 (d, 1H, J=8.1 Hz), 7.64 (d, 1H, J=7.5 Hz), 7.92 (d, 1H, J=7.8 Hz).

Compound Ij-63

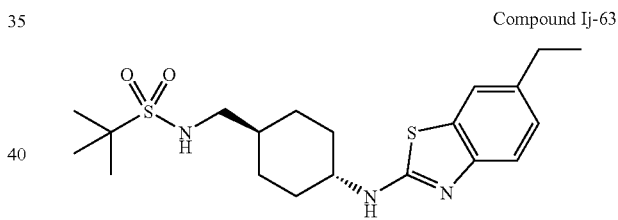

¹H-NMR (DMSO-d₆) δ: 1.00 (dd, 2H, J=24.8, 10.6 Hz), 1.15-1.22 (m, 2H), 1.18 (t, 3H, J=7.6 Hz), 1.27 (s, 9H), 1.34-1.40 (m, 1H), 1.81 (d, 2H, J=11.6 Hz), 2.07 (d, 2H, J=11.6 Hz), 2.60 (q, 2H, J=7.6 Hz), 2.89 (t, 2H, J=6.3 Hz), 3.52-3.63 (m, 1H), 6.87 (t, 1H, J=5.8 Hz), 7.04 (d, 1H, J=7.9 Hz), 7.27 (d, 1H, J=8.2 Hz), 7.47 (s, 1H), 7.80 (d, 1H, J=7.6 Hz).

Compound Ij-64

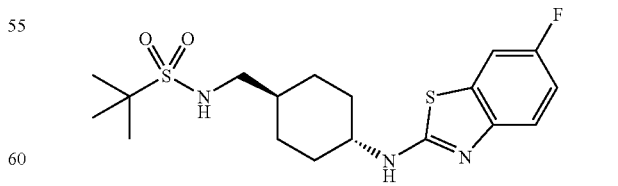

¹H-NMR (DMSO-d₆) δ: 0.92-1.10 (m, 2H), 1.12-1.25 (m, 2H), 1.27 (s, 9H), 1.37 (m, 1H), 1.76-1.84 (m, 2H), 2.02-2.12 (m, 2H), 2.89 (t, 2H, J=6.0 Hz), 3.50-3.66 (m, 1H), 6.87 (t, 1H, J=5.7 Hz), 7.03 (dd, 1H, J=8.7, 2.7 Hz), 7.32-7.37 (m, 1H), 7.58 (dd, 1H, J=8.7, 2.7 Hz), 7.92 (d, 1H, J=7.2 Hz).

Compound Ij-65

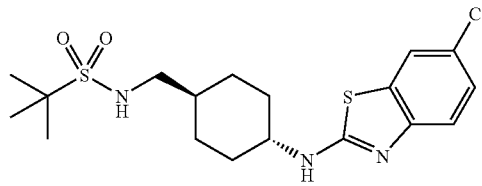

¹H-NMR (DMSO-d₆) δ: 1.01 (dd, 2H, J=24.6, 10.2 Hz), 1.21 (dd, 2H, J=24.6, 10.2 Hz), 1.27 (s, 9H), 1.34-1.40 (m, 1H), 1.82 (d, 2H, J=11.2 Hz), 2.08 (d, 2H, J=11.2 Hz), 2.89 (t, 2H, J=6.2 Hz), 3.59-3.65 (m, 1H), 6.87 (t, 1H, J=5.8 Hz), 7.21 (dd, 1H, J=8.6, 2.4 Hz), 7.34 (d, 1H, J=8.6 Hz), 7.77 (d, 1H, J=1.8 Hz), 8.06 (d, 1H, J=7.6 Hz).

Compound Ij-66

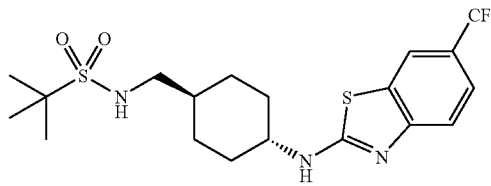

¹H-NMR (CDCl₃) δ: 1.09-1.46 (m, 4H), 1.41 (s, 9H), 1.54 (m, 1H), 1.90-2.00 (m, 2H), 2.24-2.34 (m, 2H), 3.09 (t, 2H, J=6.6 Hz), 3.46-3.60 (m, 1H), 3.99 (t, 1H, J=6.6 Hz), 6.58 (brs, 1H), 7.58 (s, 2H), 7.85 (s, 1H).

Compound Ij-67

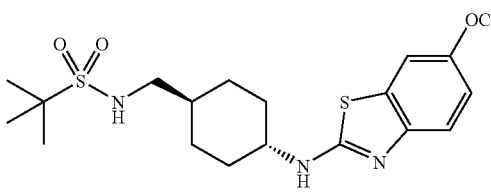

¹H-NMR (DMSO-d₆) δ: 0.90-1.30 (m, 4H), 1.27 (s, 9H), 1.30-1.48 (m, 1H), 1.82 (d, 2H, J=11.1 Hz), 2.08 (d, 2H, J=9.6 Hz), 2.89 (t, 2H, J=6.3 Hz), 3.55-3.70 (m, 1H), 6.87 (t, 1H, J=5.7 Hz), 7.17 (m, 1H), 7.41 (d, 1H, J=8.7 Hz), 7.77 (d, 1H, J=1.5 Hz), 8.10 (d, 1H, J=7.5 Hz). ESI (positive) m/z 466.2 [M+H]+

Compound Ij-68

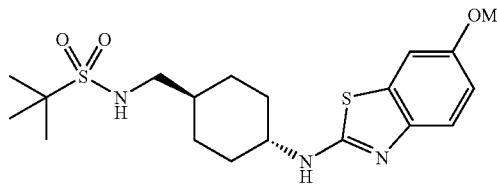

¹H-NMR (DMSO-d₆) δ: 0.90-1.28 (m, 4H), 1.25 (s, 9H), 1.32 (m, 1H), 1.76-1.82 (m, 2H), 2.00-2.10 (m, 2H), 2.87 (t, 2H, J=6.6 Hz), 3.50-3.62 (m, 1H), 3.71 (s, 3H), 6.77 (dd, 1H, J=8.7, 2.7 Hz), 6.84 (t, 1H, J=5.7 Hz), 7.22-7.28 (m, 2H), 7.66 (d, 1H, J=7.2 Hz).

Compound Ij-69

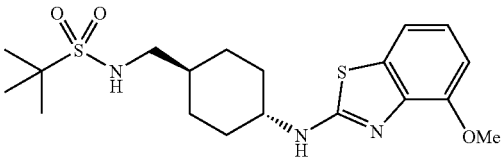

¹H-NMR (DMSO-d₆) δ: 0.94-1.10 (m, 2H), 1.12-1.25 (m, 2H), 1.27 (s, 9H), 1.37 (m, 1H), 1.76-1.84 (m, 2H), 2.02-2.12 (m, 2H), 2.90 (t, 2H, J=6.0 Hz), 3.52-3.68 (m, 1H), 3.84 (s, 3H), 6.82 (d, 1H, J=8.1 Hz), 6.88 (t, 1H, J=5.4 Hz), 6.95 (t, 1H, J=7.8 Hz), 7.23 (d, 1H, J=7.8 Hz), 7.83 (d, 1H, J=7.8 Hz).

Compound Ij-70

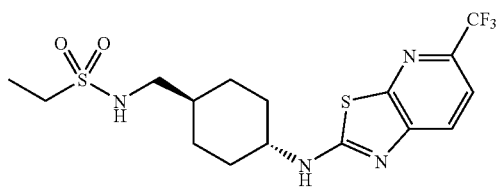

¹H-NMR (DMSO-d₆) δ: 0.98-1.10 (m, 2H), 1.19 (t, 3H, J=7.2 Hz), 1.17-1.32 (m, 2H), 1.40 (m, 1H), 1.76-1.88 (m, 2H), 2.04-2.14 (m, 2H), 2.79 (t, 2H, J=6.0 Hz), 2.98 (q, 2H, J=7.2 Hz), 3.60-3.78 (m, 1H), 7.03 (t, 1H, J=6.3 Hz), 7.45-7.54 (m, 2H), 8.10 (s, 1H), 8.34 (d, 1H, J=7.2 Hz).

Compound Ij-71

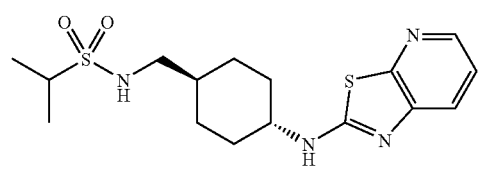

¹H-NMR (DMSO-d₆) δ: 1.01 (dd, 2H, J=26.1, 12.3 Hz), 1.16-1.22 (m, 2H), 1.22 (d, 6H, J=6.6 Hz), 1.35-1.41 (m, 1H), 1.70-1.77 (m, 1H), 1.82 (d, 2H, J=11.6 Hz), 2.08 (d, 2H, J=11.6 Hz), 2.81 (t, 2H, J=6.3 Hz), 3.66-3.72 (m, 1H), 6.99 (t, 1H, J=6.3 Hz), 7.23 (dd, 1H, J=8.1, 4.7 Hz), 7.66 (d, 1H, J=8.1 Hz), 8.07 (d, 1H, J=4.7 Hz), 8.26 (d, 1H, J=6.3 Hz).

Compound Ij-72

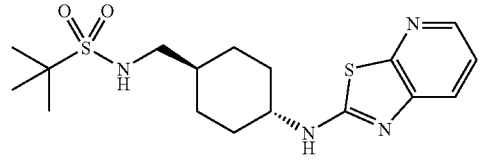

¹H-NMR (DMSO-d₆) δ: 1.01 (dd, 2H, J=24.8, 11.3 Hz), 1.18-1.23 (m, 2H), 1.27 (s, 9H), 1.36-1.39 (m, 1H), 1.82 (d, 2H, J=11.5 Hz), 2.08 (d, 2H, J=11.5 Hz), 2.89 (t, 2H, J=6.1 Hz), 3.65-3.73 (m, 1H), 6.87 (t, 1H, J=5.7 Hz), 7.23 (dd, 1H, J=8.1, 4.8 Hz), 7.66 (d, 1H, J=7.9 Hz), 8.07 (d, 1H, J=4.7 Hz), 8.26 (d, 1H, J=7.6 Hz).

Compound Ij-73

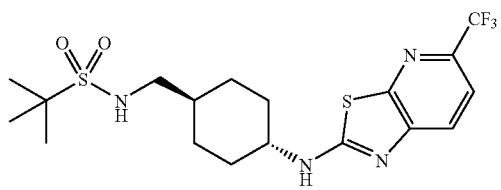

¹H-NMR (CDCl₃)δ: 1.09-1.46 (m, 4H), 1.41 (s, 9H), 1.55 (m, 1H), 1.92-2.02 (m, 2H), 2.24-2.34 (m, 2H), 3.09 (t, 2H, J=6.3 Hz), 3.58-3.72 (m, 1H), 3.98 (t, 1H, J=6.0 Hz), 6.30 (brs, 1H), 7.62 (d, 1H, J=8.1 Hz), 7.77 (d, 1H, J=8.4 Hz).

Compound Ij-74

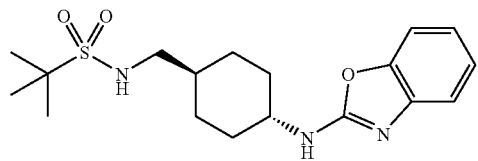

¹H-NMR (DMSO-d₆) δ: 0.90-1.08 (m, 2H), 1.12-1.40 (m, 3H), 1.25 (s, 9H), 1.76-1.86 (m, 2H), 1.98-2.10 (m, 2H), 2.87 (d, 2H, J=6.3 Hz), 3.40-3.56 (m, 1H), 6.85 (brs, 1H), 6.93 (t, 1H, J=7.5 Hz), 7.07 (t, 1H, J=7.5 Hz), 7.20 (d, 1H, J=7.5 Hz), 7.29 (d, 1H, J=7.8 Hz), 7.79 (brs, 1H).

Compound Ij-75

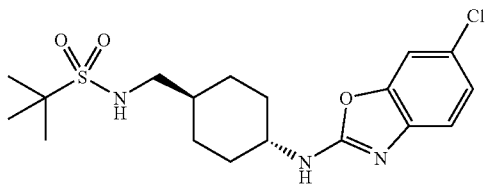

¹H-NMR (CDCl₃) δ: 1.08-1.26 (m, 2H), 1.36-1.60 (m, 3H), 1.40 (s, 9H), 1.92-2.02 (m, 2H), 2.22-2.32 (m, 2H), 3.08 (t, 2H, J=6.6 Hz), 3.68-3.80 (m, 1H), 4.03 (t, 1H, J=6.0 Hz), 7.06 (brs, 1H), 7.20-7.36 (m, 3H).

Compound Ij-76

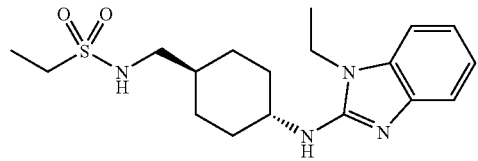

¹H-NMR (DMSO-d₆) δ: 1.02 (dd, 2H, J=25.2, 12.4 Hz), 1.17 (t, 3H, J=7.1 Hz), 1.20 (t, 3H, J=7.3 Hz), 1.26-1.35 (m, 2H), 1.37-1.42 (m, 1H), 1.83 (d, 2H, J=11.6 Hz), 2.05 (d, 2H, J=11.6 Hz), 2.80 (t, 2H, J=6.4 Hz), 2.99 (q, 2H, J=7.3 Hz), 3.65-3.72 (m, 1H), 4.01 (q, 2H, J=7.1 Hz), 6.32 (d, 1H, J=7.9 Hz), 6.86-6.94 (m, 2H), 7.01 (t, 1H, J=6.0 Hz), 7.12 (d, 1H, J=6.9 Hz), 7.17 (d, 1H, J=6.8 Hz).

Compound Ij-77

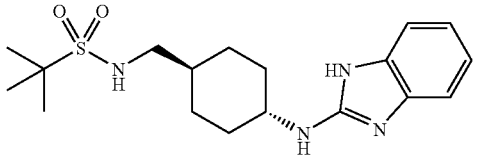

¹H-NMR (DMSO-d₆) δ: 1.02 (dd, 2H, J=24.8, 10.8 Hz), 1.19-1.21 (m, 2H), 1.30 (s, 9H), 1.37-1.41 (m, 1H), 1.84 (d, 2H, J=10.6 Hz), 2.06 (d, 2H, J=10.6 Hz), 2.92 (t, 2H, J=6.3 Hz), 3.50-3.52 (m, 1H), 6.42 (d, 1H, J=8.1 Hz), 6.83 (d, 1H, J=7.9 Hz), 6.88-6.92 (m, 2H), 7.11-7.14 (m, 2H), 10.58 (s, 1H).

Compound Ij-78

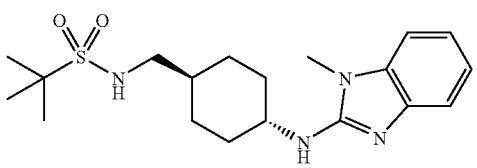

¹H-NMR (DMSO-d₆) δ: 0.97-1.05 (m, 2H), 1.20-1.26 (m, 2H), 1.28 (s, 9H), 1.34-1.38 (m, 1H), 1.84 (d, 2H, J=11.5 Hz), 2.07 (d, 2H, J=11.5 Hz), 2.90 (t, 2H, J=6.1 Hz), 3.47 (s, 3H), 3.63-3.69 (m, 1H), 6.34 (d, 1H, J=7.6 Hz), 6.87-6.93 (m, 3H), 7.11 (d, 1H, J=8.4 Hz), 7.17 (d, 1H, J=8.4 Hz).

Compound Ij-79

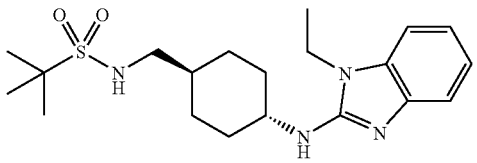

¹H-NMR (DMSO-d₆) δ: 1.03 (dd, 2H, J=23.6, 10.8 Hz), 1.18 (t, 3H, J=7.5 Hz), 1.25-1.34 (m, 2H), 1.29 (s, 9H), 1.37-1.40 (m, 1H), 1.86 (d, 2H, J=11.7 Hz), 2.07 (d, 2H, J=11.7 Hz), 2.92 (t, 2H, J=6.2 Hz), 3.67-3.73 (m, 1H), 4.03 (q, 2H, J=7.1 Hz), 6.34 (d, 1H, J=7.9 Hz), 6.87-6.96 (m, 3H), 7.14 (dd, 1H, J=8.1, 1.2 Hz), 7.19 (dd, 1H, J=8.1, 1.2 Hz).

Compound Ij-80

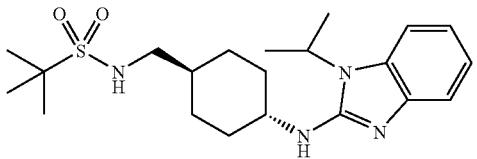

¹H-NMR (DMSO-d₆) δ: 1.00 (dd, 2H, J=23.2, 11.9 Hz), 1.19-1.25 (m, 2H), 1.28 (s, 9H), 1.33-1.38 (m, 1H), 1.45 (s, 3H), 1.47 (s, 3H), 1.83 (d, 2H, J=11.1 Hz), 2.07 (d, 2H, J=11.1 Hz), 2.90 (t, 2H, J=6.1 Hz), 3.62-3.70 (m, 1H), 4.57-4.66 (m, 1H), 6.21 (d, 1H, J=7.9 Hz), 6.82-6.94 (m, 3H), 7.18 (d, 1H, J=7.6 Hz), 7.31 (d, 1H, J=7.6 Hz).

Compound Ij-81

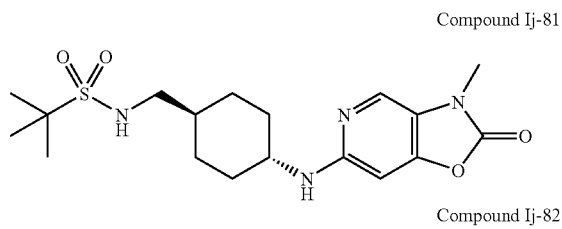

Compound Ij-82

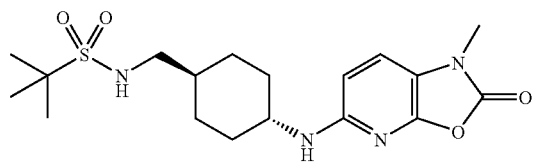

¹H-NMR (DMSO-d₆) δ: 0.90-1.19 (m, 4H), 1.28 (s, 9H), 1.32-1.45 (m, 1H), 1.80 (d, 2H, J=11.2 Hz), 1.98 (d, 2H, J=11.2 Hz), 2.84-2.93 (m, 2H), 3.26 (s, 3H), 3.40-3.53 (m, 1H), 6.29 (d, 1H, J=8.0 Hz), 6.38 (d, 1H, J=7.2 Hz), 6.86 (s, 1H), 7.33 (d, 1H, J=8.4 Hz).

Compound Ij-83

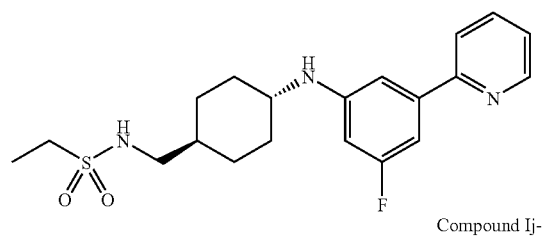

Compound Ij-84

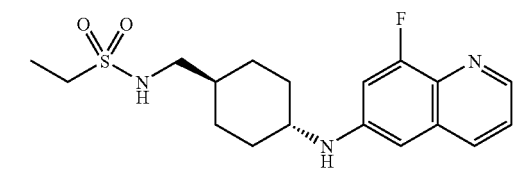

¹H-NMR (DMSO-d₆) δ: 0.92-1.20 (m, 4H), 1.18 (t, 3H, J=7.2 Hz), 1.40 (m, 1H), 1.75-1.85 (m, 2H), 1.96-2.06 (m, 2H), 2.78 (t, 2H, J=6.0 Hz), 2.98 (q, 2H, J=7.2 Hz), 3.60-3.78 (m, 1H), 6.38 (d, 1H, J=8.1 Hz), 6.67 (s, 1H), 6.72 (d, 1H, J=5.4 Hz), 7.00 (t, 1H, J=6.0 Hz), 7.36-7.54 (m, 3H), 7.62 (d, 2H, J=6.9 Hz), 8.00 (d, 1H, J=5.4 Hz)

Compound Ij-85

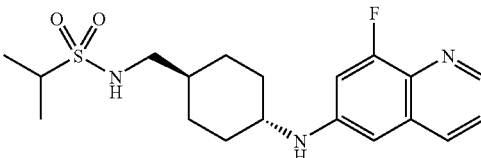

¹H-NMR (DMSO-d₆) δ: 1.00-1.20 (m, 4H), 1.20 (t, 3H, J=7.2 Hz), 1.43 (m, 1H), 1.80-1.88 (m, 2H), 2.03-2.13 (m, 2H), 2.81 (t, 3H, J=6.0 Hz), 3.00 (q, 2H, J=7.2 Hz), 3.26 (m, 1H), 6.17 (d, 1H, J=7.6 Hz), 6.57 (s, 1H), 6.96-7.07 (m, 2H), 7.35 (dd, 1H, J=8.4, 4.0 Hz), 8.02 (d, 1H, J=8.4 Hz), 8.47 (d, 1H, J=4.0 Hz).

Compound Ij-86

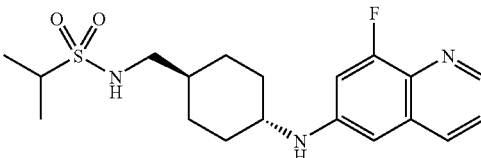

¹H-NMR (DMSO-d₆) δ: 1.00-1.24 (m, 4H), 1.23 (d, 6H, J=6.4 Hz), 1.42 (m, 1H), 1.80-1.88 (m, 2H), 2.03-2.12 (m, 2H), 2.79-2.87 (m, 2H), 3.16 (m, 1H), 3.27 (m, 1H), 6.17 (d, 1H, J=8.0 Hz), 6.57 (s, 1H), 6.99 (d, 1H, J=8.0 Hz), 7.01 (s, 1H), 7.35 (dd, 1H, J=8.0, 4.0 Hz), 8.02 (d, 1H, J=8.0 Hz), 8.47 (d, 1H, J=2.8 Hz).

Compound Ij-87

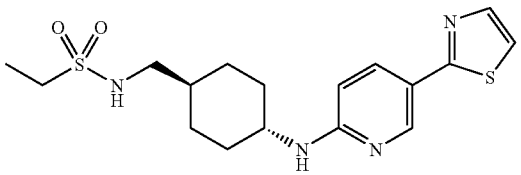

¹H-NMR (DMSO-d₆) δ: 0.95-1.08 (m, 2H), 1.11-1.25 (m, 2H), 1.20 (t, 3H, J=7.2 Hz), 1.40 (m, 1H), 1.76-1.86 (m, 2H), 1.97-2.04 (m, 2H), 2.73-2.82 (m, 2H), 2.99 (q, 2H, J=7.2 Hz), 3.70 (m, 1H), 6.53 (d, 1H, J=8.8 Hz), 6.53 (d, 1H, J=8.8 Hz), 7.01 (t, 1H, J=6.0 Hz), 7.58 (d, 1H, J=3.2 Hz), 7.79 (d, 1H, J=3.2 Hz), 7.86 (d, 1H, J=8.8 Hz), 8.55 (s, 1H).

Compound Ij-88

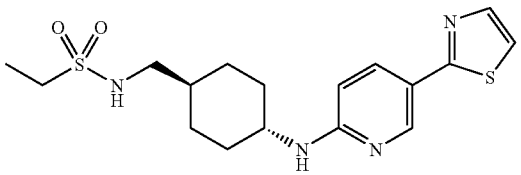

¹H-NMR (DMSO-d₆) δ: 0.92-1.07 (m, 2H), 1.09-1.20 (m, 2H), 1.19 (t, 6H, J=7.2 Hz), 1.39 (m, 1H), 1.75-1.83 (m, 2H), 1.95-2.03 (m, 2H), 2.74-2.81 (m, 2H), 2.98 (q, 2H, J=7.2 Hz), 3.66 (m, 1H), 6.48 (d, 1H, J=8.4 Hz), 6.60 (d, 1H, J=7.6 Hz), 7.00 (t, 1H, J=5.6 Hz), 7.06 (dd, 1H, J=4.8, 2.4 Hz), 7.25 (d, 1H, J=2.4 Hz), 7.37 (d, 1H, J=4.8 Hz), 7.60 (dd, 1H, J=8.4, 2.0 Hz), 8.26 (s, 1H).

Compound Ij-89

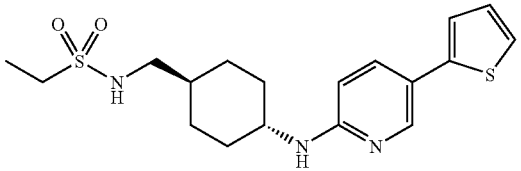

¹H-NMR (DMSO-d₆) δ: 0.93-1.07 (m, 2H), 1.10-1.20 (m, 2H), 1.19 (t, 3H, J=7.2 Hz), 1.39 (m, 1H), 1.76-1.84 (m, 2H), 1.96-2.04 (m, 2H), 2.73-2.81 (m, 2H), 2.98 (q, 2H, J=7.2 Hz), 3.65 (m, 1H), 6.41-6.50 (m, 2H), 7.01 (t, 1H, J=6.0 Hz), 7.44 (d, 1H, J=4.0 Hz), 7.58 (m, 1H), 7.59 (s, 1H), 7.68 (d, 1H, J=8.0 Hz), 8.34 (s, 1H).

(m, 2H), 2.76-2.82 (m, 2H), 3.10-3.19 (m, 1H), 3.20-3.25 (m, 4H), 3.58-3.65 (m, 1H), 3.69-3.74 (m, 4H), 6.04 (d, 1H, J=7.5 Hz), 6.72 (d, 1H, J=9.6 Hz), 6.95-6.99 (m, 1H), 7.10 (d, 1H, J=9.6 Hz).

Compound Ij-90

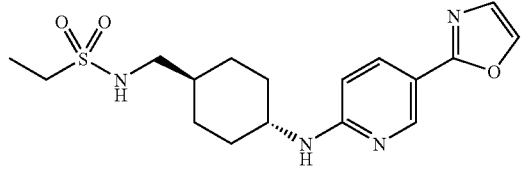

¹H-NMR (DMSO-d₆) δ: 0.95-1.08 (m, 2H), 1.12-1.25 (m, 2H), 1.19 (t, 3H, J=7.2 Hz), 1.39 (m, 1H), 1.76-1.86 (m, 2H), 1.94-2.03 (m, 2H), 2.75-2.82 (m, 2H), 2.98 (q, 2H, J=7.2 Hz), 3.71 (m, 1H), 6.54 (d, 1H, J=8.8 Hz), 6.98-7.07 (m, 2H), 7.25 (s, 1H), 7.85 (dd, 1H, J=8.8, 2.0 Hz), 8.07 (s, 1H), 8.56 (d, 1H, J=2.0 Hz).

Compound Ij-94

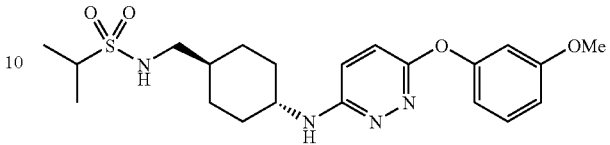

¹H-NMR (DMSO-d₆) δ: 0.96-1.42 (m, 5H), 1.22 (d, 6H, J=6.9 Hz), 1.79-1.83 (m, 2H), 2.03-2.07 (m, 2H), 2.80 (d, 2H, J=6.3 Hz), 3.10-3.19 (m, 1H), 3.54-3.70 (m, 1H), 3.74 (s, 3H), 6.57-6.64 (m, 3H), 6.72-6.75 (m, 1H), 6.90-7.09 (m, 3H), 7.24-7.30 (m, 1H).

Compound Ij-95

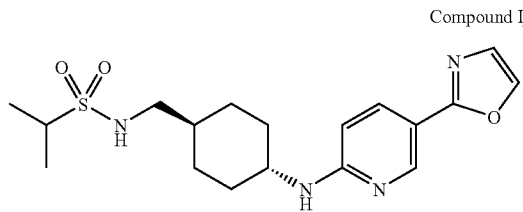

Compound Ij-91

¹H-NMR (DMSO-d₆) δ: 0.93-1.07 (m, 2H), 1.11-1.22 (m, 2H), 1.21 (d, 6H, J=6.8 Hz), 1.38 (m, 1H), 1.77-1.85 (m, 2H), 1.95-2.03 (m, 2H), 2.77-2.83 (m, 2H), 3.14 (m, 1H), 3.72 (m, 1H), 6.53 (d, 1H, J=8.8 Hz), 6.97 (t, 1H, J=6.0 Hz), 7.02 (d, 1H, J=7.6 Hz), 7.25 (s, 1H), 7.84 (dd, 1H, J=8.8, 2.0 Hz), 8.06 (s, 1H), 8.56 (d, 1H, J=2.0 Hz).

¹H-NMR (DMSO-d₆) δ: 0.93-1.04 (m, 2H), 1.10-1.18 (m, 2H), 1.21 (d, 6H, J=6.6 Hz), 1.34-1.44 (m, 1H), 1.78-1.87 (m, 2H), 2.02-2.12 (m, 2H), 2.77-2.84 (m, 2H), 3.10-3.20 (m, 1H), 3.52-3.70 (m, 1H), 6.64 (d, 1H, J=8.0 Hz), 6.88-7.06 (m, 5H), 7.12 (d, 1H, J=8.0 Hz), 7.37-7.46 (m, 1H).

Compound Ij-96

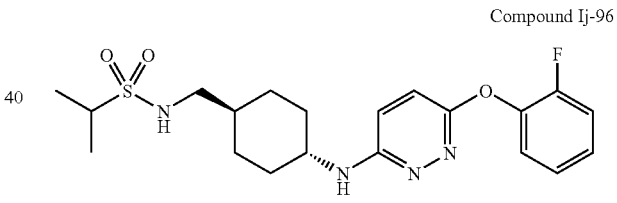

Compound Ij-92

¹H-NMR (DMSO-d₆) δ: 0.90-1.04 (m, 2H), 1.05-1.18 (m, 2H), 1.21 (d, 6H, J=6.6 Hz), 1.33-1.43 (m, 1H), 1.75-1.84 (m, 2H), 1.98-2.08 (m, 2H), 2.76-2.84 (m, 2H), 3.08-3.18 (m, 1H), 3.52-3.64 (m, 1H), 6.55 (d, 1H, J=8.0 Hz), 6.91-7.00 (m, 2H), 7.15-7.38 (m, 5H).

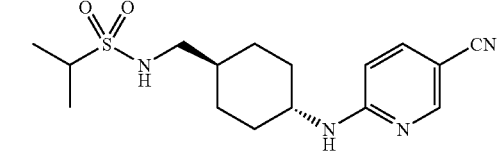

¹H-NMR (DMSO-d₆) δ: 0.92-1.03 (m, 2H), 1.11-1.23 (m, 2H), 1.21 (d, 6H, J=6.8 Hz), 1.37 (m, 1H), 1.75-1.83 (m, 2H), 1.91-1.99 (m, 2H), 2.36-2.42 (m, 2H), 3.12 (m, 1H), 3.70 (m, 1H), 6.49 (d, 1H, J=9.2 Hz), 6.97 (t, 1H, J=6.0 Hz), 7.47 (d, 1H, J=8.0 Hz), 7.62 (d, 1H, J=8.0 Hz), 8.36 (s, 1H).

Compound Ij-97

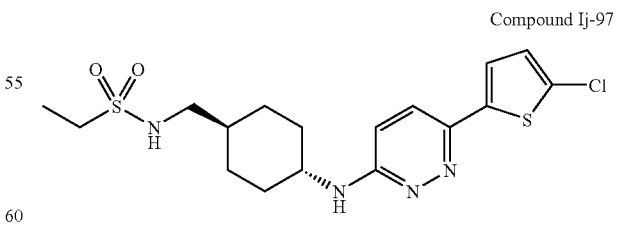

Compound Ij-93

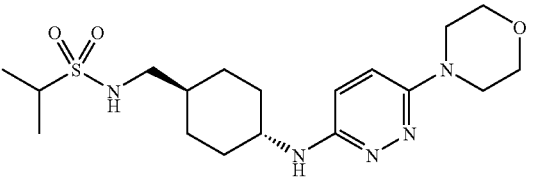

¹H-NMR (DMSO-d₆) δ: 0.95-1.13 (m, 4H), 1.23 (d, 6H, J=6.9 Hz), 1.31-1.44 (m, 1H), 1.78-1.82 (m, 2H), 2.03-2.06

¹H-NMR (DMSO-d₆) δ: 0.96-1.08 (m, 2H), 1.12-1.25 (m, 2H), 1.19 (t, 3H, J=7.2 Hz), 1.35-1.47 (m, 1H), 1.78-1.87 (m, 2H), 2.02-2.10 (m, 2H), 2.78-2.83 (m, 2H), 2.98 (q, 2H, J=7.2 Hz), 3.70-3.82 (m, 1H), 6.82 (d, 1H, J=8.0 Hz), 6.93 (d, 1H, J=8.0 Hz), 7.01 (t, 1H, J=4.5 Hz), 7.13 (d, 1H, J=4.0 Hz), 7.43 (d, 1H, J=4.0 Hz), 7.76 (d, 1H, J=8.0 Hz).

1H), 3.56-3.68 (m, 1H), 6.62 (d, 1H, J=8.0 Hz), 6.93 (d, 1H, J=8.0 Hz), 6.98 (t, 1H, J=4.5 Hz), 7.10-7.15 (m, 3H), 7.43 (d, 2H, J=8.0 Hz).

Compound Ij-98

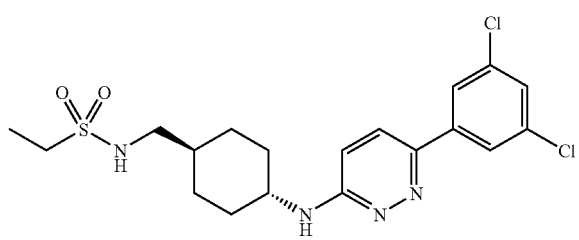

$^1$H-NMR (DMSO-d$_6$) δ: 0.97-1.10 (m, 2H), 1.17-1.28 (m, 2H), 1.19 (t, 3H, J=7.2 Hz), 1.37-1.49 (m, 1H), 1.80-1.88 (m, 2H), 2.04-2.12 (m, 2H), 2.77-2.83 (m, 2H), 2.99 (q, 2H, J=7.2 Hz), 3.76-3.88 (m, 1H), 6.85 (d, 1H, J=8.0 Hz), 6.99-7.05 (m, 2H), 7.61 (s, 1H), 7.90 (d, 1H, J=8.0 Hz), 8.02 (s, 2H).

Compound Ij-99

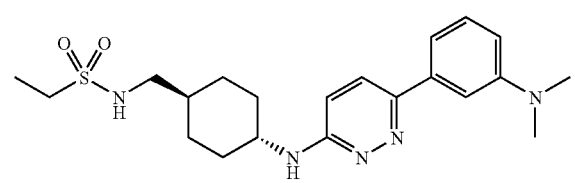

$^1$H-NMR (DMSO-d$_6$) δ: 0.98-1.10 (m, 2H), 1.14-1.26 (m, 2H), 1.19 (t, 3H, J=7.2 Hz), 1.37-1.48 (m, 1H), 1.80-1.88 (m, 2H), 2.04-2.13 (m, 2H), 2.77-2.83 (m, 2H), 2.96 (s, 6H), 2.99 (q, 2H, J=7.2 Hz), 3.76-3.86 (m, 1H), 6.72-6.78 (m, 2H), 6.82 (d, 1H, J=8.0 Hz), 7.02 (t, 1H, J=4.5 Hz), 7.18 (d, 1H, J=8.0 Hz), 7.26 (t, 1H, J=8.0 Hz), 7.34 (s, 1H), 7.74 (d, 1H, J=8.0 Hz).

Compound Ij-100

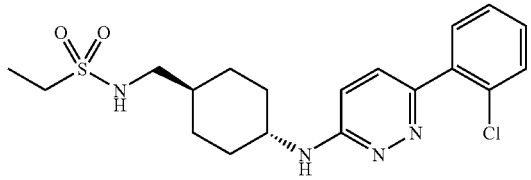

$^1$H-NMR (DMSO-d$_6$) δ: 0.98-1.10 (m, 2H), 1.16-1.27 (m, 2H), 1.19 (t, 3H, J=7.2 Hz), 1.37-1.48 (m, 1H), 1.80-1.88 (m, 2H), 2.04-2.13 (m, 2H), 2.77-2.83 (m, 2H), 2.99 (q, 2H, J=7.2 Hz), 3.76-3.86 (m, 1H), 6.83 (d, 1H, J=8.0 Hz), 6.89 (d, 1H, J=8.0 Hz), 7.02 (t, 1H, J=4.5 Hz), 7.42-7.50 (m, 3H), 7.53-7.59 (m, 2H).

Compound Ij-101

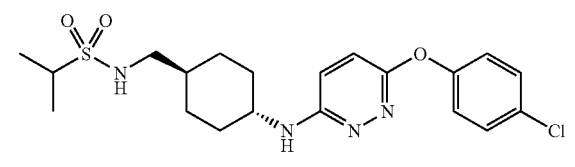

$^1$H-NMR (DMSO-d$_6$) δ: 0.92-1.05 (m, 2H), 1.08-1.20 (m, 2H), 1.21 (d, 6H, J=6.6 Hz), 1.36-1.43 (m, 1H), 1.76-1.84 (m, 2H), 2.02-2.09 (m, 2H), 2.77-2.83 (m, 2H), 3.10-3.20 (m,

Compound Ij-102

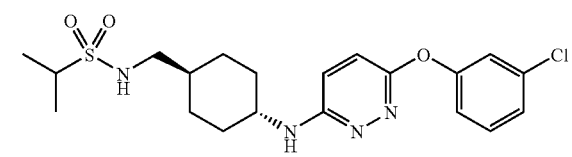

$^1$H-NMR (DMSO-d$_6$) δ: 0.92-1.05 (m, 2H), 1.08-1.20 (m, 2H), 1.21 (d, 6H, J=6.6 Hz), 1.36-1.43 (m, 1H), 1.76-1.84 (m, 2H), 2.02-2.09 (m, 2H), 2.77-2.83 (m, 2H), 3.10-3.20 (m, 1H), 3.57-3.68 (m, 1H), 6.65 (d, 1H, J=8.0 Hz), 6.94 (d, 1H, J=8.0 Hz), 6.97 (t, 1H, J=4.5 Hz), 7.06 (d, 1H, J=8.0 Hz), 7.13 (d, 1H, J=8.0 Hz), 7.18-7.26 (m, 2H), 7.41 (t, 1H, J=8.0 Hz).

Compound Ij-103

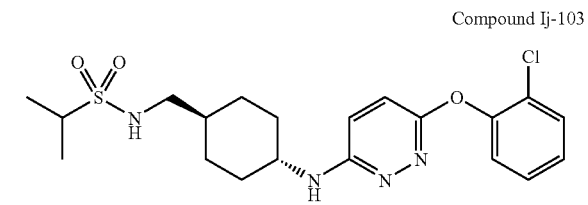

$^1$H-NMR (DMSO-d$_6$) δ: 0.88-1.04 (m, 2H), 1.05-1.20 (m, 2H), 1.21 (d, 6H, J=6.6 Hz), 1.33-1.43 (m, 1H), 1.77-1.82 (m, 2H), 2.00-2.07 (m, 2H), 2.76-2.82 (m, 2H), 3.08-3.20 (m, 1H), 3.52-3.64 (m, 1H), 6.57 (d, 1H, J=8.0 Hz), 6.92-7.00 (m, 2H), 7.17 (d, 1H, J=8.0 Hz), 7.23-7.28 (m, 2H), 7.38 (t, 1H, J=8.0 Hz), 7.56 (d, 1H, J=8.0 Hz).

Compound Ij-104

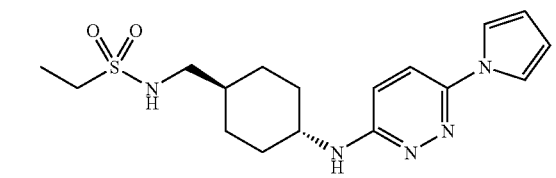

$^1$H-NMR (DMSO-d$_6$) δ: 0.96-1.08 (m, 2H), 1.12-1.24 (m, 2H), 1.19 (t, 3H, J=7.6 Hz), 1.35-1.46 (m, 1H), 1.78-1.86 (m, 2H), 2.04-2.12 (m, 2H), 2.76-2.82 (m, 2H), 2.98 (q, 2H, J=7.6 Hz), 3.67-3.78 (m, 1H), 6.27 (s, 2H), 6.71 (d, 1H, J=8.0 Hz), 6.93 (d, 1H, J=8.0 Hz), 7.02 (brs, 1H), 7.52 (s, 2H), 7.67 (d, 1H, J=8.0 Hz).

Compound Ij-105

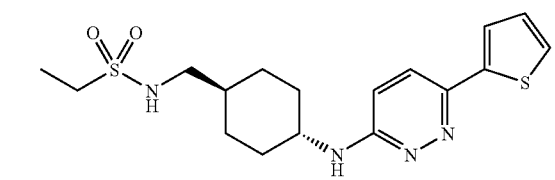

$^1$H-NMR (DMSO-d$_6$) δ: 0.96-1.08 (m, 2H), 1.13-1.25 (m, 2H), 1.19 (t, 3H, J=7.6 Hz), 1.35-1.46 (m, 1H), 1.78-1.87 (m,

2H), 2.04-2.12 (m, 2H), 2.76-2.83 (m, 2H), 2.99 (q, 2H, J=7.6 Hz), 3.72-3.82 (m, 1H), 6.82 (d, 1H, J=8.0 Hz), 6.85 (d, 1H, J=8.0 Hz), 7.03 (t, 1H, J=4.5 Hz), 7.12 (t, 1H, J=4.0 Hz), 7.51 (d, 1H, J=4.0 Hz), 7.56 (d, 1H, J=4.0 Hz), 7.76 (d, 1H, J=8.0 Hz).

2H), 2.00-2.08 (m, 2H), 2.29 (s, 3H), 2.76-2.83 (m, 2H), 3.08-3.18 (m, 1H), 3.56-3.66 (m, 1H), 6.55 (d, 1H, J=8.0 Hz), 6.90 (d, 1H, J=8.0 Hz), 6.93-7.00 (m, 3H), 7.05 (d, 1H, J=8.0 Hz), 7.17 (d, 2H, J=8.0 Hz).

Compound Ij-106

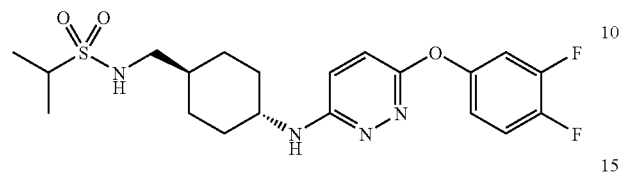

$^1$H-NMR (DMSO-d$_6$) δ: 0.88-1.02 (m, 2H), 1.07-1.20 (m, 2H), 1.21 (d, 6H, J=6.6 Hz), 1.33-1.45 (m, 1H), 1.76-1.85 (m, 2H), 2.02-2.08 (m, 2H), 2.76-2.83 (m, 2H), 3.10-3.20 (m, 1H), 3.57-3.67 (m, 1H), 6.63 (d, 1H, J=8.0 Hz), 6.92-7.00 (m, 3H), 7.13 (d, 1H, J=8.0 Hz), 7.29-7.36 (m, 1H), 7.42-7.50 (m, 1H).

Compound Ij-110

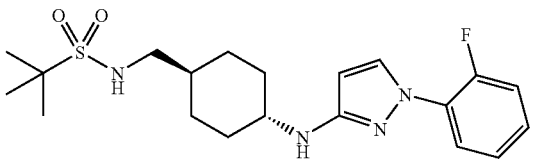

$^1$H-NMR (DMSO-d$_6$) δ: 0.91-1.19 (m, 4H), 1.28 (s, 9H), 1.32-1.43 (m, 1H), 1.80 (d, 2H, J=12.0 Hz), 2.07 (d, 2H, J=12.0 Hz), 2.88 (t, 2H, J=6.4 Hz), 3.16-3.27 (m, 1H), 5.47 (d, 1H, J=7.6 Hz), 5.80 (s, 1H), 6.83 (d, 1H, J=6.0 Hz), 7.15-7.40 (m, 3H), 7.75 (t, 1H, J=8.4 Hz), 7.86 (s, 1H).

Compound Ij-107

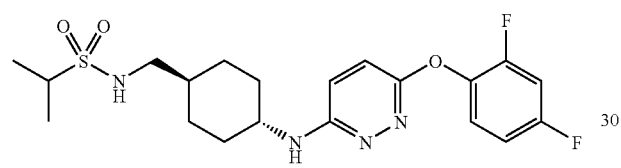

$^1$H-NMR (DMSO-d$_6$) δ: 0.88-1.02 (m, 2H), 1.07-1.20 (m, 2H), 1.21 (d, 6H, J=6.6 Hz), 1.33-1.43 (m, 1H), 1.75-1.83 (m, 2H), 1.98-2.06 (m, 2H), 2.76-2.83 (m, 2H), 3.08-3.18 (m, 1H), 3.52-3.63 (m, 1H), 6.57 (d, 1H, J=8.0 Hz), 6.93 (d, 1H, J=8.0 Hz), 6.97 (t, 1H, J=4.5 Hz), 7.12 (t, 1H, J=4.0 Hz), 7.19 (d, 1H, J=8.0 Hz), 7.33-7.47 (m, 2H).

Compound Ij-111

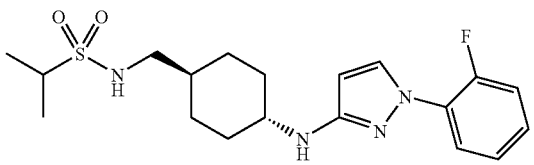

$^1$H-NMR (DMSO-d$_6$) δ: 0.91-1.19 (m, 4H), 1.21 (d, 6H, J=6.9 Hz), 1.32-1.43 (m, 1H), 1.76-1.82 (m, 2H), 2.02-2.12 (m, 2H), 2.77-2.83 (m, 2H), 3.08-3.27 (m, 2H), 5.48 (d, 1H, J=8.1 Hz), 5.80 (d, 1H, J=2.7 Hz), 6.95 (t, 1H, J=6.0 Hz), 7.15-7.39 (m, 3H), 7.75 (td, 1H, J=8.4, 1.8 Hz), 7.86 (t, 1H, J=2.7 Hz).

Compound Ij-108

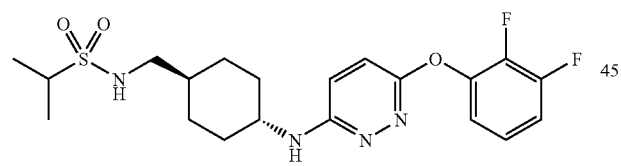

$^1$H-NMR (DMSO-d$_6$) δ: 0.88-1.02 (m, 2H), 1.07-1.20 (m, 2H), 1.21 (d, 6H, J=6.6 Hz), 1.33-1.43 (m, 1H), 1.75-1.83 (m, 2H), 1.98-2.07 (m, 2H), 2.76-2.83 (m, 2H), 3.08-3.18 (m, 1H), 3.54-3.63 (m, 1H), 6.63 (d, 1H, J=8.0 Hz), 6.93-7.00 (m, 2H), 7.14 (t, 1H, J=8.0 Hz), 7.20-7.37 (m, 3H).

Compound Ij-112

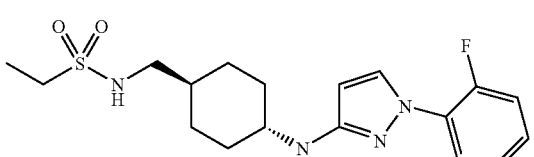

$^1$H-NMR (DMSO-d$_6$) δ: 0.91-1.19 (m, 4H), 1.18 (t, 3H, J=7.2 Hz), 1.30-1.45 (m, 1H), 1.76-1.82 (m, 2H), 2.02-2.12 (m, 2H), 2.77-2.83 (m, 2H), 2.98 (q, 2H, J=7.2 Hz) 3.10-3.30 (m, 1H), 5.48 (d, 1H, J=7.8 Hz), 5.80 (d, 1H, J=2.7 Hz), 6.99 (t, 1H, J=6.0 Hz), 7.15-7.40 (m, 3H), 7.75 (td, 1H, J=8.4, 1.8 Hz), 7.86 (t, 1H, J=2.7 Hz).

Compound Ij-109

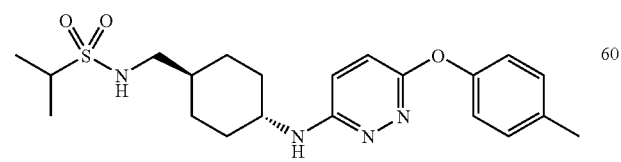

$^1$H-NMR (DMSO-d$_6$) δ: 0.82-1.05 (m, 2H), 1.05-1.20 (m, 2H), 1.21 (d, 6H, J=6.6 Hz), 1.32-1.43 (m, 1H), 1.76-1.83 (m,

Compound Ij-113

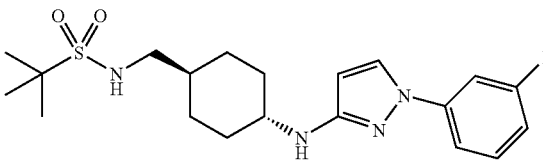

Compound Ij-114

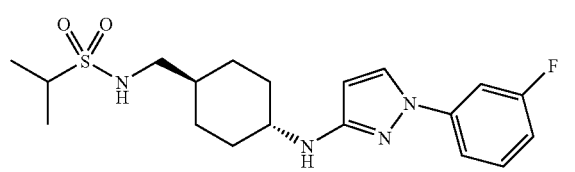

Compound Ij-115

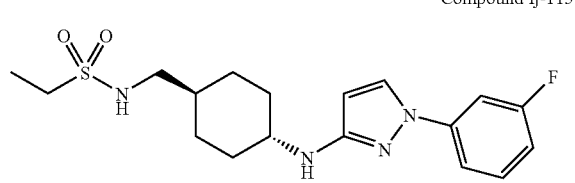

¹H-NMR (DMSO-d₆) δ: 0.92-1.19 (m, 4H), 1.19 (t, 3H, J=7.2 Hz), 1.30-1.45 (m, 1H), 1.76-1.84 (m, 2H), 2.02-2.12 (m, 2H), 2.74-2.82 (m, 2H), 2.98 (q, 2H, J=7.2 Hz) 3.15-3.30 (m, 1H), 5.53 (d, 1H, J=8.1 Hz), 5.80 (d, 1H, J=2.4 Hz), 6.92 (t, 1H, J=8.4 Hz), 7.01 (t, 1H, J=6.0 Hz), 7.37-7.43 (m, 3H), 8.21 (d, 1H, J=2.4 Hz).

Compound Ij-116

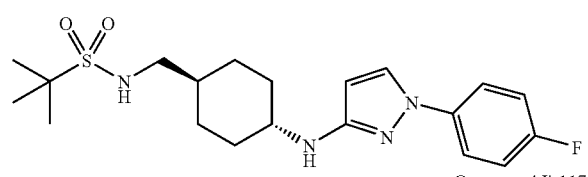

Compound Ij-117

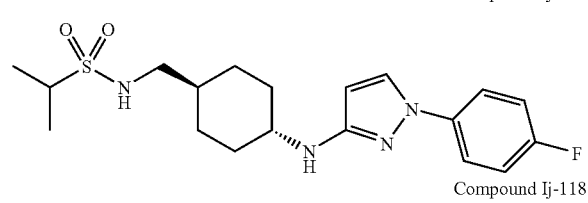

Compound Ij-118

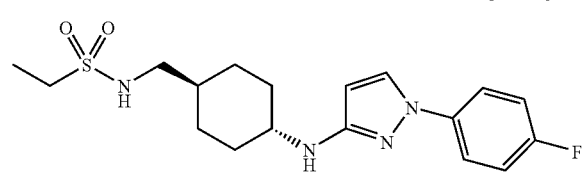

¹H-NMR (DMSO-d₆) δ: 0.92-1.19 (m, 4H), 1.19 (t, 3H, J=7.5 Hz), 1.30-1.45 (m, 1H), 1.75-1.86 (m, 2H), 2.02-2.12 (m, 2H), 2.74-2.83 (m, 2H), 2.97 (q, 2H, J=7.5 Hz) 3.13-3.30 (m, 1H), 5.38 (d, 1H, J=8.4 Hz), 5.75 (d, 1H, J=2.7 Hz), 6.99 (t, 1H, J=6.3 Hz), 7.18-7.28 (m, 2H), 7.63-7.70 (m, 2H), 8.11 (d, 1H, J=2.7 Hz).

Compound Ij-119

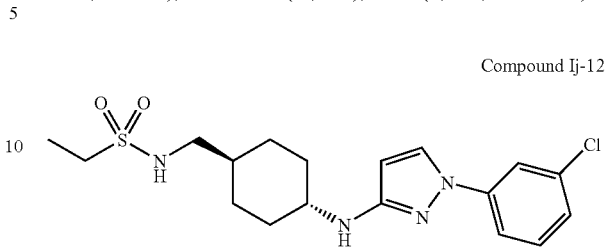

¹H-NMR (DMSO-d₆) δ: 0.88-1.19 (m, 4H), 1.18 (t, 3H, J=7.5 Hz), 1.28-1.45 (m, 1H), 1.73-1.83 (m, 2H), 2.02-2.13 (m, 2H), 2.73-2.81 (m, 2H), 2.95 (q, 2H, J=7.5 Hz) 3.12-3.30 (m, 1H), 5.36 (d, 1H, J=7.5 Hz), 5.76 (d, 1H, J=2.4 Hz), 6.98 (t, 1H, J=6.0 Hz), 7.30 (td, 1H, J=7.5, 1.8 Hz), 7.42 (td, 1H, J=7.8, 1.5 Hz), 7.53-7.60 (m, 2H), 7.84 (d, 1H, J=2.7 Hz).

Compound Ij-120

¹H-NMR (DMSO-d₆) δ: 0.92-1.19 (m, 4H), 1.19 (t, 3H, J=7.5 Hz), 1.30-1.45 (m, 1H), 1.74-1.84 (m, 2H), 2.02-2.10 (m, 2H), 2.75-2.82 (m, 2H), 2.97 (q, 2H, J=7.5 Hz) 3.20-3.30 (m, 1H), 5.52 (d, 1H, J=7.8 Hz), 5.80 (d, 1H, J=2.4 Hz), 6.99 (t, 1H, J=6.0 Hz), 7.13 (d, 1H, J=8.1 Hz), 7.40 (t, 1H, J=8.1 Hz), 7.62 (d, 1H, J=8.4 Hz), 7.72 (s, 1H), 8.22 (d, 1H, J=2.4 Hz).

Compound Ij-121

¹H-NMR (DMSO-d₆) δ: 0.92-1.19 (m, 4H), 1.19 (t, 3H, J=7.5 Hz), 1.30-1.45 (m, 1H), 1.74-1.84 (m, 2H), 2.02-2.12 (m, 2H), 2.75-2.82 (m, 2H), 2.98 (q, 2H, J=7.5 Hz) 3.15-3.30 (m, 1H), 5.47 (d, 1H, J=8.1 Hz), 5.78 (d, 1H, J=2.4 Hz), 7.00 (t, 1H, J=6.0 Hz), 7.43 (d, 2H, J=7.8 Hz), 7.67 (d, 2H, J=9.0 Hz), 8.17 (d, 1H, J=2.4 Hz).

Compound Ij-122

¹H-NMR (DMSO-d₆) δ: 0.94-1.07 (m, 4H), 1.19 (t, 3H, J=7.2 Hz), 1.32-1.50 (m, 1H), 1.81-1.84 (m, 2H), 1.99-2.07 (m, 2H), 2.77-2.81 (m, 2H), 2.98 (q, 2H, J=7.2 Hz) 3.60-3.77 (m, 1H), 7.01-7.05 (m, 1H), 7.22-7.40 (m, 4H), 7.81-7.87 (m, 1H), 8.02 (s, 1H), 8.36 (s, 1H).

Compound Ij-123

¹H-NMR (DMSO-d₆) δ: 0.95-1.12 (m, 4H), 1.18 (t, 3H, J=7.2 Hz), 1.32-1.50 (m, 1H), 1.77-1.81 (m, 2H), 1.96-1.99 (m, 2H), 2.74-2.78 (m, 2H), 2.97 (q, 2H, J=7.2 Hz), 3.54-3.70 (m, 1H), 4.81 (q, 2H, J=9.0 Hz), 6.50-6.53 (m, 1H), 6.99-7.03 (m, 1H), 7.50 (d, 1H, J=0.9 Hz) 7.83 (d, 1H, J=0.9 Hz).

Compound Ij-124

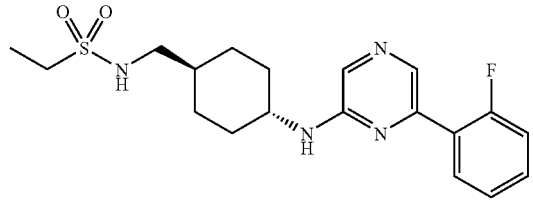

¹H-NMR (DMSO-d₆) δ: 0.95-1.23 (m, 4H), 1.19 (t, 3H, J=7.2 Hz), 1.32-1.50 (m, 1H), 1.77-1.81 (m, 2H), 2.03-2.07 (m, 2H), 2.74-2.80 (m, 2H), 2.97 (q, 2H, J=7.2 Hz), 3.61-3.73 (m, 1H), 7.00-7.04 (m, 1H), 7.09-7.12 (m, 1H), 7.29-7.37 (m, 2H), 7.45-7.52 (m, 1H), 7.88-7.94 (m, 2H), 8.04-8.05 (m, 1H).

Compound Ij-125

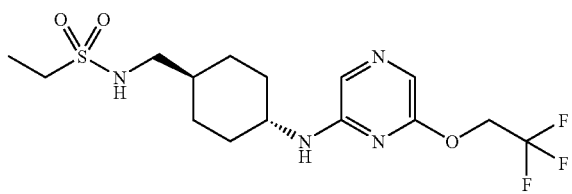

¹H-NMR (DMSO-d₆) δ: 0.94-1.14 (m, 4H), 1.19 (t, 3H, J=7.2 Hz), 1.32-1.50 (m, 1H), 1.79-1.83 (m, 2H), 1.97-2.03 (m, 2H), 2.76-2.81 (m, 2H), 2.98 (q, 2H, J=7.2 Hz), 3.50-3.63 (m, 1H), 4.43 (q, 2H, J=9.0 Hz), 7.00-7.04 (m, 1H), 7.13-7.15 (m, 1H), 7.35 (s, 1H) 7.55 (s, 1H).

Compound Ij-126

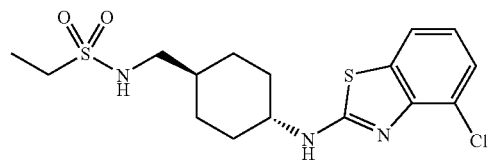

¹H-NMR (DMSO-d₆) δ: 1.02-1.08 (m, 2H), 1.17-1.29 (m, 2H), 1.19 (t, 3H, J=7.5 Hz), 1.36-1.43 (m, 1H), 1.79-1.85 (m, 2H), 2.05-2.11 (m, 2H), 2.79 (t, 2H, J=6.0 Hz), 2.99 (q, 2H, J=7.5 Hz), 3.53-3.62 (m, 1H), 6.98 (t, 1H, J=7.8 Hz), 7.03 (t, 1H, J=6.3 Hz), 7.28 (dd, 1H, J=7.5, 1.2 Hz), 7.63 (dd, 1H, J=7.5, 1.2 Hz), 8.28 (d, 1H, J=7.5 Hz).

Compound Ij-127

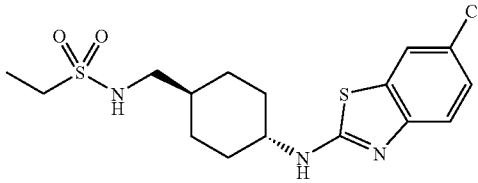

¹H-NMR (DMSO-d₆) δ: 0.97-1.05 (m, 2H), 1.18-1.24 (m, 2H), 1.16 (t, 3H, J=7.5 Hz), 1.34-1.41 (m, 1H), 1.77-1.81 (m, 2H), 2.02-2.08 (m, 2H), 2.76 (t, 2H, J=6.0 Hz), 2.96 (q, 2H, J=7.5 Hz), 3.55-3.64 (m, 1H), 7.00 (t, 1H, J=7.8 Hz), 7.18 (dd, 1H, J=8.4, 1.8 Hz), 7.32 (dd, 1H, J=8.4, 0.6 Hz), 7.74 (d, 1H, J=1.8 Hz), 8.04 (d, 1H, J=7.8 Hz).

Compound Ij-128

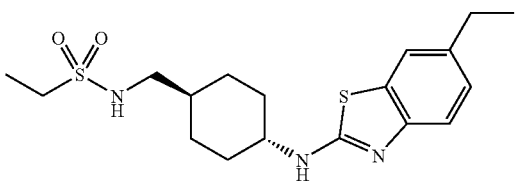

¹H-NMR (DMSO-d₆) δ: 0.98-1.07 (m, 2H), 1.15-1.26 (m, 8H), 1.32-1.43 (m, 1H), 1.78-1.84 (m, 2H), 1.98-2.09 (m, 2H), 2.60 (q, 2H, J=7.5 Hz), 2.78 (t, 2H, J=6.3 Hz), 2.96 (q, 2H, J=7.5 Hz), 3.55-3.64 (m, 1H), 6.98-7.05 (m, 2H), 7.27 (dd, 1H, J=7.8, 1.8 Hz), 7.47 (m, 1H), 7.84 (d, 1H, J=7.5 Hz).

Compound Ij-129

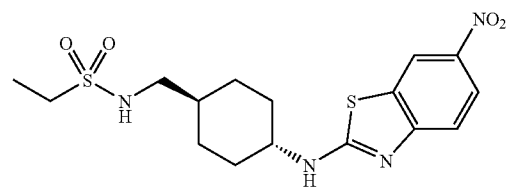

¹H-NMR (DMSO-d₆) δ: 0.92-1.15 (m, 2H), 1.15-1.35 (m, 2H), 1.19 (t, 3H, J=7.2 Hz), 1.33-1.48 (m, 1H), 1.78-1.88 (m, 2H), 2.04-2.16 (m, 2H), 2.78-2.84 (m, 2H), 2.97 (q, 2H, J=7.2 Hz), 3.62-3.80 (m, 1H), 7.02 (t, 1H, J=6.0 Hz), 7.45 (d, 1H, J=9.0 Hz), 8.09 (dd, 1H, J=9.0, 2.4 Hz), 8.68 (d, 1H, J=2.4 Hz), 8.70 (brs, 1H).

Compound Ij-130

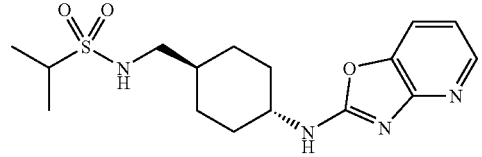

¹H-NMR (DMSO-d₆) δ: 0.88-1.10 (m, 2H), 1.15-1.46 (m, 3H), 1.21 (d, 6H, J=6.6 Hz), 1.78-1.88 (m, 2H), 1.98-2.08 (m, 2H), 2.76-2.86 (m, 2H), 3.10-3.20 (m, 1H), 3.46-3.62 (m, 1H), 6.91-6.96 (m, 1H), 7.01 (brs, 1H), 7.64 (d, 1H, J=7.8 Hz), 8.07 (d, 1H, J=5.1 Hz), 8.35 (d, 1H, J=7.8 Hz).

J=7.5, 0.6 Hz), 7.60 (dd, 1H, J=8.4, 1.5 Hz), 8.17 (d, 1H, J=1.5 Hz), 8.50 (d, 1H, J=7.5 Hz).

Compound Ij-131

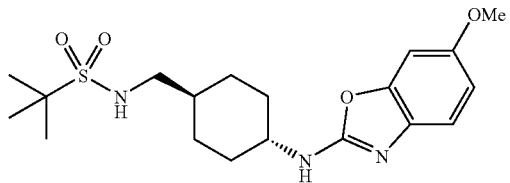

¹H-NMR (DMSO-d₆) δ: 0.92-1.05 (m, 2H), 1.15-1.30 (m, 2H), 1.27 (s, 9H), 1.30-1.43 (m, 1H), 1.77-1.86 (m, 2H), 1.98-2.08 (m, 2H), 2.86-2.92 (m, 2H), 3.35-3.50 (m, 1H), 3.73 (s, 3H), 6.69 (dd, 1H, J=8.4, 2.0 Hz), 6.86 (t, 1H, J=6.0 Hz), 7.01 (d, 1H, J=2.0 Hz), 7.10 (d, 1H, J=8.4 Hz), 7.62 (d, 1H, J=7.6 Hz).

Compound Ij-135

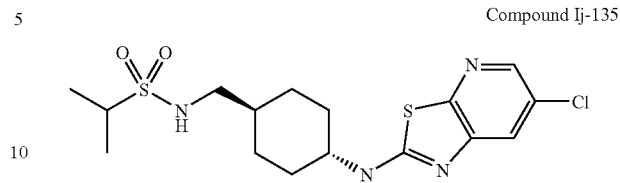

¹H-NMR (DMSO-d₆) δ: 0.98-1.08 (m, 2H), 1.15-1.25 (m, 2H), 1.21 (d, 6H, J=6.6 Hz), 1.35-1.44 (m, 1H), 1.80-1.84 (m, 2H), 2.05-2.08 (m, 2H), 2.81 (t, 2H, J=6.3 Hz), 3.10-3.19 (m, 1H), 3.62-3.78 (m, 1H), 6.98 (t, 1H, J=6.0 Hz), 7.79 (d, 1H, J=2.1 Hz), 8.10 (d, 1H, J=2.1, 1.5 Hz), 8.52 (d, 1H, J=6.9 Hz).

Compound Ij-132

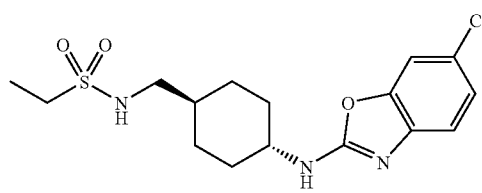

¹H-NMR (DMSO-d₆) δ: 0.92-1.08 (m, 2H), 1.15-1.33 (m, 2H), 1.19 (t, 3H, J=7.2 Hz), 1.33-1.42 (m, 1H), 1.76-1.86 (m, 2H), 1.98-2.08 (m, 2H), 2.76-2.82 (m, 2H), 2.97 (q, 2H, J=7.2 Hz), 3.40-3.58 (m, 1H), 7.01 (t, 1H, J=6.0 Hz), 7.13 (d, 1H, J=8.4 Hz), 7.20 (d, 1H, J=8.4 Hz), 7.49 (s, 1H), 8.01 (d, 1H, J=7.6 Hz).

Compound Ij-136

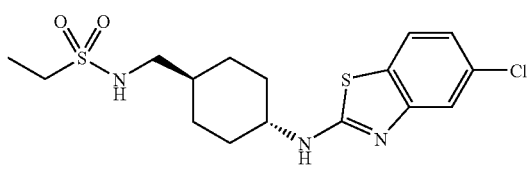

¹H-NMR (DMSO-d₆) δ: 0.97-1.08 (m, 2H), 1.17-1.24 (m, 2H), 1.19 (t, 3H, J=7.5 Hz), 1.33-1.41 (m, 1H), 1.78-1.83 (m, 2H), 2.04-2.08 (m, 2H), 2.78 (t, 2H, J=6.3 Hz), 2.98 (q, 2H, J=7.2 Hz), 3.56-3.67 (m, 1H), 7.00-7.04 (m, 2H), 7.39 (d, 1H, J=2.1 Hz), 7.66 (dd, 1H, J=8.4, 1.8 Hz), 8.14 (d, 1H, J=7.5 Hz).

Compound Ij-133

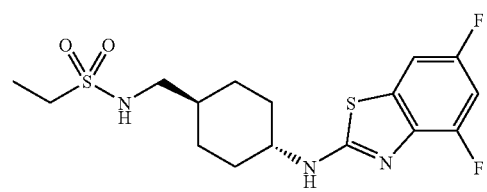

¹H-NMR (DMSO-d₆) δ: 0.96-1.10 (m, 2H), 1.16-1.28 (m, 2H), 1.19 (t, 3H, J=7.2 Hz), 1.33-1.46 (m, 1H), 1.78-1.85 (m, 2H), 2.04-2.12 (m, 2H), 2.76-2.82 (m, 2H), 2.98 (q, 2H, J=7.2 Hz), 3.55-3.70 (m, 1H), 7.01 (t, 1H, J=6.0 Hz), 7.12 (t, 1H, J=9.6 Hz), 7.48 (d, 1H, J=7.6 Hz), 8.13 (d, 1H, J=7.6 Hz).

Compound Ij-137

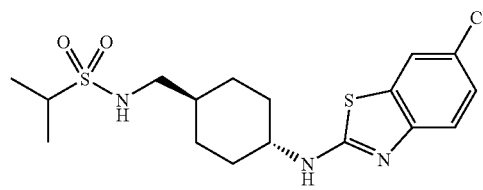

¹H-NMR (DMSO-d₆) δ: 0.96-1.10 (m, 2H), 1.12-1.28 (m, 2H), 1.21 (d, 6H, J=6.9 Hz), 1.31 (t, 3H, J=6.9 Hz), 1.33-1.46 (m, 1H), 1.76-1.85 (m, 2H), 2.02-2.16 (m, 2H), 2.78-2.84 (m, 2H), 3.10-3.22 (m, 1H), 3.50-3.64 (m, 1H), 3.98 (q, 2H, J=6.9 Hz), 6.78 (dd, 1H, J=8.7, 2.7 Hz), 6.98 (t, 1H, J=6.0 Hz), 7.23-7.27 (m, 2H), 7.68 (d, 1H, J=7.2 Hz).

Compound Ij-134

¹H-NMR (DMSO-d₆) δ: 0.98-1.08 (m, 2H), 1.15-1.26 (m, 2H), 1.21 (d, 6H, J=6.9 Hz), 1.33-1.42 (m, 1H), 1.39-1.84 (m, 2H), 2.05-2.09 (m, 2H), 2.81 (t, 2H, J=6.3 Hz), 3.10-3.20 (m, 1H), 3.61-3.75 (m, 1H), 6.98 (t, 1H, J=6.0 Hz), 7.45 (dd, 1H,

Compound Ij-138

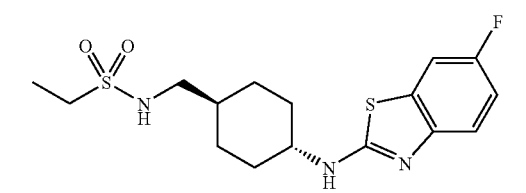

¹H-NMR (DMSO-d₆) δ: 0.94-1.08 (m, 2H), 1.14-1.26 (m, 2H), 1.19 (t, 3H, J=7.2 Hz), 1.33-1.45 (m, 1H), 1.77-1.86 (m,

2H), 2.03-2.12 (m, 2H), 2.76-2.82 (m, 2H), 2.98 (q, 2H, J=7.2 Hz), 3.52-3.68 (m, 1H), 6.97-7.06 (m, 2H), 7.34 (dd, 1H, J=8.4, 4.8 Hz), 7.56 (dd, 1H, J=8.4, 2.4 Hz), 7.91 (d, 1H, J=7.6 Hz).

2H), 2.01-2.05 (m, 2H), 2.77 (t, 2H, J=6.0 Hz), 2.98 (q, 2H, J=7.2 Hz), 3.41-3.58 (m, 1H), 6.97 (dd, 1H, J=8.4, 2.4 Hz), 6.99-7.03 (m, 1H), 7.27 (d, 1H, J=2.4 Hz), 7.34 (dd, 1H, J=8.4, 0.3 Hz), 8.07-8.14 (m, 1H).

Compound Ij-139

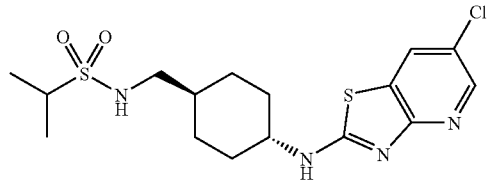

¹H-NMR (DMSO-d₆) δ: 0.96-1.12 (m, 2H), 1.16-1.32 (m, 2H), 1.21 (d, 6H, J=6.6 Hz), 1.32-1.46 (m, 1H), 1.78-1.86 (m, 2H), 2.02-2.16 (m, 2H), 2.78-2.84 (m, 2H), 3.10-3.21 (m, 1H), 3.58-3.76 (m, 1H), 7.00 (t, 1H, J=6.0 Hz), 8.19-8.23 (m, 2H), 8.52 (d, 1H, J=6.9 Hz).

Compound Ij-143

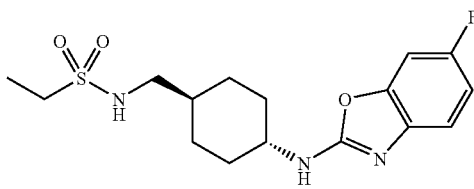

¹H-NMR (DMSO-d₆) δ: 0.94-1.08 (m, 2H), 1.16-1.33 (m, 2H), 1.19 (t, 3H, J=7.2 Hz), 1.33-1.45 (m, 1H), 1.77-1.86 (m, 2H), 2.00-2.08 (m, 2H), 2.74-2.82 (m, 2H), 2.98 (q, 2H, J=7.2 Hz), 3.38-3.54 (m, 1H), 6.90-7.00 (m, 1H), 7.02 (t, 1H, J=4.5 Hz), 7.19 (dd, 1H, J=8.4, 5.1 Hz), 7.33 (dd, 1H, J=8.4, 2.7 Hz), 7.88 (d, 1H, J=7.8 Hz).

Compound Ij-140

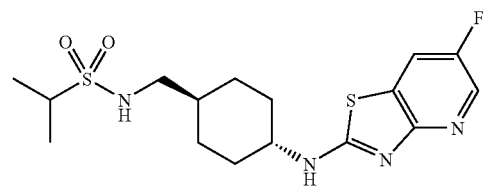

¹H-NMR (DMSO-d₆) δ: 0.96-1.12 (m, 2H), 1.12-1.30 (m, 2H), 1.21 (d, 6H, J=6.6 Hz), 1.32-1.46 (m, 1H), 1.78-1.86 (m, 2H), 2.02-2.16 (m, 2H), 2.78-2.84 (m, 2H), 3.10-3.20 (m, 1H), 3.58-3.78 (m, 1H), 7.01 (t, 1H, J=6.0 Hz), 8.08 (dd, 1H, J=8.4, 2.7 Hz), 8.19 (d, 1H, J=2.7 Hz), 8.38 (d, 1H, J=7.2 Hz).

Compound Ij-144

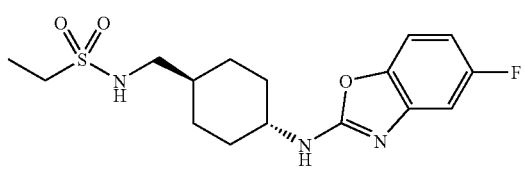

¹H-NMR (DMSO-d₆) δ: 0.94-1.06 (m, 2H), 1.19-1.29 (m, 2H), 1.18 (t, 3H, J=7.2 Hz), 1.31-1.41 (m, 1H), 1.79-1.84 (m, 2H), 2.01-2.05 (m, 2H), 2.77 (t, 2H, J=6.0 Hz), 2.98 (q, 2H, J=6.9 Hz), 3.41-3.57 (m, 1H), 6.71-6.79 (m, 1H), 7.06-7.08 (m, 2H), 7.31 (dd, 1H, J=8.7, 4.8 Hz), 8.03 (d, 1H, J=7.8 Hz).

Compound Ij-141

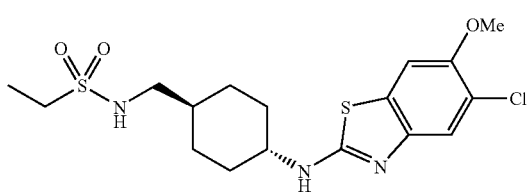

¹H-NMR (DMSO-d₆) δ: 0.97-1.08 (m, 2H), 1.15-1.22 (m, 5H), 1.34-1.42 (m, 1H), 1.78-1.83 (m, 2H), 2.04-2.08 (m, 2H), 2.78 (t, 2H, J=6.0 Hz), 2.98 (q, 2H, J=7.2 Hz), 3.53-3.62 (m, 1H), 3.81 (s, 1H), 7.02 (t, 1H, J=6.3 Hz), 7.41 (s, 1H), 7.53 (s, 1H), 7.88 (d, 1H, J=7.5 Hz).

Compound Ij-145

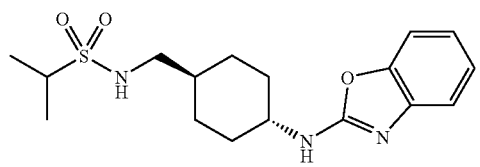

¹H-NMR (DMSO-d₆) δ: 0.95-1.16 (m, 2H), 1.18-1.44 (m, 3H), 1.21 (d, 6H, J=6.6 Hz), 1.78-1.86 (m, 2H), 2.02-2.12 (m, 2H), 2.78-2.84 (m, 2H), 3.10-3.20 (m, 1H), 3.40-3.58 (m, 1H), 6.95 (t, 1H, J=7.8 Hz), 7.01 (brs, 1H), 7.09 (t, 1H, J=6.9 Hz), 7.22 (d, 1H, J=6.6 Hz), 7.31 (d, 1H, J=7.8 Hz), 7.83 (d, 1H, J=7.8 Hz).

Compound Ij-142

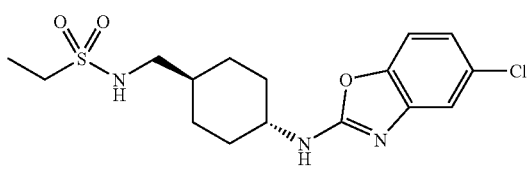

¹H-NMR (DMSO-d₆) δ: 0.94-1.06 (m, 2H), 1.17-1.30 (m, 2H), 1.18 (t, 3H, J=7.5 Hz), 1.32-1.41 (m, 1H), 1.79-1.84 (m,

Compound Ij-146

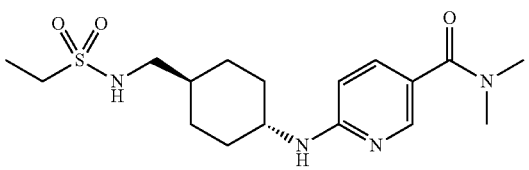

Compound Ij-147

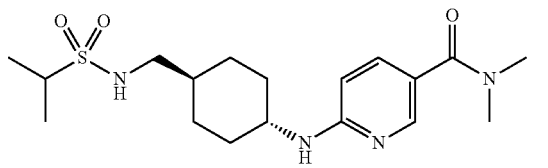

Compound Ij-148

Compound Ij-149

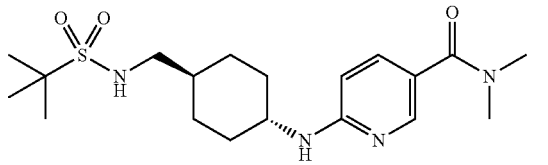

¹H-NMR (DMSO-d₆) δ: 0.93-1.10 (m, 2H), 1.13-1.30 (m, 2H), 1.19 (t, 3H, J=7.5 Hz), 1.39 (m, 1H), 1.76-1.87 (m, 2H), 2.02-2.14 (m, 2H), 2.79 (t, 2H, J=6.3 Hz), 2.98 (q, 2H, J=7.5 Hz), 3.56-3.70 (m, 1H), 6.95-7.05 (m, 2H), 7.20 (t, 1H, J=7.8 Hz), 7.37 (d, 1H, J=7.8 Hz), 7.64 (d, 1H, J=7.5 Hz), 7.92 (d, 1H, J=7.5 Hz). Melting point: 168-169° C. Anal. Calcd for C16H23N3O2S2: C, 54.36; H, 6.56; N, 11.89; S, 18.14. Found: C, 54.33; H, 6.55; N, 11.89; S, 18.05.

Compound Ij-150

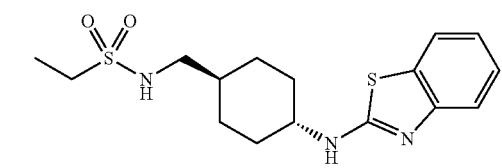

¹H-NMR (DMSO-d₆) δ: 0.93-1.10 (m, 2H), 1.12-1.30 (m, 2H), 1.19 (t, 3H, J=7.2 Hz), 1.39 (m, 1H), 1.77-1.87 (m, 2H), 1.99-2.12 (m, 2H), 2.78 (t, 2H, J=6.6 Hz), 2.98 (q, 2H, J=7.2 Hz), 3.40-3.58 (m, 1H), 6.95 (t, 1H, J=7.8 Hz), 7.02 (t, 1H, J=6.0 Hz), 7.09 (t, 1H, J=7.8 Hz), 7.22 (d, 1H, J=7.5 Hz), 7.31 (d, 1H, J=8.1 Hz), 7.83 (d, 1H, J=7.8 Hz). Melting point: 170-171° C. Anal. Calcd for C16H23N3O3S: C, 56.95; H, 6.87; N, 12.45; S, 9.50. Found: C, 56.91; H, 6.91; N, 12.43; S, 9.51.

Compound Ij-151

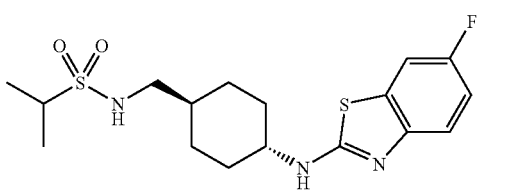

¹H-NMR (DMSO-d₆) δ: 0.92-1.10 (m, 2H), 1.12-1.30 (m, 2H), 1.21 (d, 6H, J=6.9 Hz), 1.38 (m, 1H), 1.76-1.87 (m, 2H), 2.02-2.14 (m, 2H), 2.81 (t, 2H, J=6.0 Hz), 3.08-3.22 (m, 1H), 3.54-3.70 (m, 1H), 6.83 (t, 1H, J=10.5 Hz), 6.99 (t, 1H, J=5.4 Hz), 7.17 (dd, 1H, J=10.5, 2.1 Hz), 7.63 (dd, 1H, J=8.4, 5.7 Hz), 8.10 (d, 1H, J=7.5 Hz). Melting point: 165-166° C. Anal. Calcd for C17H24FN3O2S2: C, 52.96; H, 6.27; F, 4.93; N, 10.90; S, 16.63. Found: C, 52.99; H, 6.31; F, 5.00; N, 10.91; S, 16.84.

Compound Ij-152

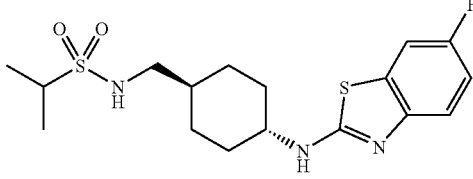

¹H-NMR (DMSO-d₆) δ: 0.92-1.09 (m, 2H), 1.11-1.28 (m, 2H), 1.22 (d, 6H, J=6.9 Hz), 1.38 (m, 1H), 1.75-1.82 (m, 2H), 2.02-2.12 (m, 2H), 2.81 (t, 2H, J=6.3 Hz), 3.10-3.20 (m, 1H), 3.52-3.67 (m, 1H), 6.98 (t, 1H, J=6.0 Hz), 7.03 (td, 1H, J=9.6, 2.7 Hz), 7.34 (dd, 1H, J=9.0, 5.1 Hz), 7.57 (dd, 1H, J=9.0, 2.7 Hz), 7.91 (d, 1H, J=7.2 Hz). Melting point: 151-152° C. Anal. Calcd for C₁₇H₄₂FN₃O₂S₂: C, 52.96; H, 6.27; F, 4.93; N, 10.90; S, 16.63.

Found: C, 52.97; H, 6.28; F, 4.90; N, 10.87; S, 16.71.

Compound Ij-153

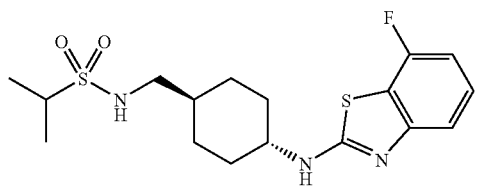

¹H-NMR (DMSO-d₆) δ: 0.94-1.12 (m, 2H), 1.14-1.31 (m, 2H), 1.22 (d, 6H, J=6.6 Hz), 1.39 (m, 1H), 1.76-1.87 (m, 2H), 2.02-2.15 (m, 2H), 2.81 (t, 2H, J=6.3 Hz), 3.10-3.22 (m, 1H), 3.55-3.70 (m, 1H), 6.84-6.94 (m, 1H), 6.99 (t, 1H, J=6.0 Hz), 7.18-7.28 (m, 2H), 8.21 (d, 1H, J=7.2 Hz).

Compound Ij-154

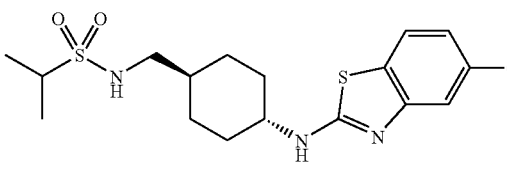

¹H-NMR (DMSO-d₆) δ: 0.93-1.10 (m, 2H), 1.13-1.30 (m, 2H), 1.22 (d, 6H, J=6.9 Hz), 1.38 (m, 1H), 1.76-1.87 (m, 2H), 2.02-2.14 (m, 2H), 2.81 (t, 2H, J=6.0 Hz), 3.08-3.22 (m, 1H), 3.54-3.70 (m, 1H), 6.98 (t, 1H, J=6.0 Hz), 7.02 (dd, 1H, J=8.1, 2.1 Hz), 7.39 (d, 1H, J=2.1 Hz), 7.66 (d, 1H, J=8.1 Hz), 8.15 (d, 1H, J=7.5 Hz). Melting point: 166-167° C. Anal. Calcd for C₁₇H₂₄ClN₃O₂S₂: C, 50.79; H, 6.02; Cl, 8.82; N, 10.45; S, 15.95. Found: C, 50.84; H, 6.04; Cl, 8.80; N, 10.44; S, 16.00.

Compound Ij-155

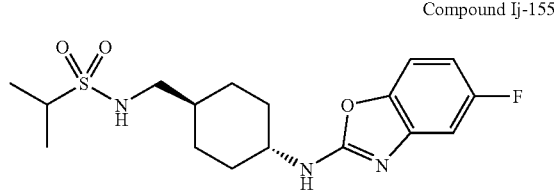

¹H-NMR (DMSO-d₆) δ: 0.92-1.08 (m, 2H), 1.20-1.34 (m, 2H), 1.22 (d, 6H, J=6.8 Hz), 1.38 (m, 1H), 1.78-1.86 (m, 2H), 1.99-2.14 (m, 2H), 2.80 (t, 2H, J=6.4 Hz), 3.10-3.20 (m, 1H), 3.42-3.54 (m, 1H), 6.74 (td, 1H, J=8.8, 2.8 Hz), 6.98 (t, 1H, J=5.6 Hz), 7.06 (dd, 1H, J=9.6, 2.8 Hz), 7.30 (dd, 1H, J=8.0, 4.4 Hz), 8.02 (d, 1H, J=8.0 Hz). Anal. Calcd for C17H24FN3O3S: C, 55.27; H, 6.55; F, 5.14; N, 11.37; S, 8.68. Found: C, 55.16; H, 6.50; F, 5.16; N, 11.30; S, 8.42.

Compound Ij-156

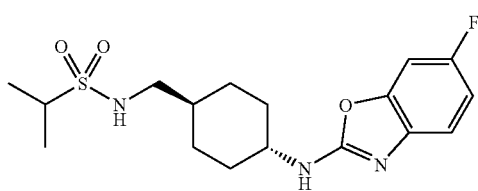

¹H-NMR (DMSO-d₆) δ: 0.92-1.08 (m, 2H), 1.20-1.34 (m, 2H), 1.22 (d, 6H, J=6.9 Hz), 1.38 (m, 1H), 1.78-1.86 (m, 2H), 2.00-2.14 (m, 2H), 2.81 (t, 2H, J=6.3 Hz), 3.10-3.21 (m, 1H), 3.38-3.54 (m, 1H), 6.90-7.00 (m, 2H), 7.19 (dd, 1H, J=8.4, 4.8 Hz), 7.33 (dd, 1H, J=8.4, 2.4 Hz), 7.86 (d, 1H, J=7.8 Hz). Melting point: 170-171° C. Anal. Calcd for C₁₇H₂₄FN₃O₃S: C, 55.27; H, 6.55; F, 5.14; N, 11.37; S, 8.68. Found: C, 55.31; H, 6.59; F, 5.13; N, 11.46; S, 8.59.

Compound Ij-157

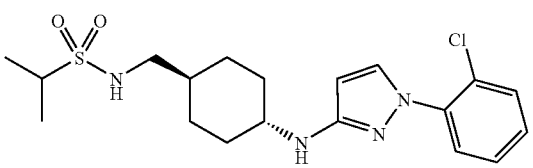

¹H-NMR (DMSO-d₆) δ: 0.88-1.20 (m, 4H), 1.20 (d, 6H, J=6.9 Hz), 1.36 (m, 1H), 1.75-1.83 (m, 2H), 2.02-2.13 (m, 2H), 2.79 (t, 2H, J=6.0 Hz), 3.05-3.25 (m, 2H), 5.36 (d, 1H, J=7.8 Hz), 5.76 (d, 1H, J=2.4 Hz), 6.95 (t, 1H, J=6.9 Hz), 7.30 (td, 1H, J=7.5, 1.8 Hz), 7.42 (td, 1H, J=7.8, 1.5 Hz), 7.53-7.60 (m, 2H), 7.84 (d, 1H, J=2.7 Hz). Melting point: 142-143° C.

Compound Ij-158

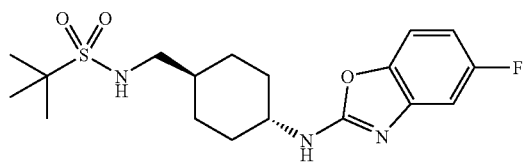

¹H-NMR (DMSO-d₆) δ: 0.92-1.08 (m, 2H), 1.19-1.34 (m, 2H), 1.27 (s, 9H), 1.38 (m, 1H), 1.78-1.86 (m, 2H), 1.99-2.14 (m, 2H), 2.88 (t, 2H, J=6.3 Hz), 3.40-3.56 (m, 1H), 6.75 (td, 1H, J=8.7, 2.7 Hz), 6.87 (t, 1H, J=6.0 Hz), 7.06 (dd, 1H, J=9.3, 2.7 Hz), 7.31 (dd, 1H, J=8.7, 4.5 Hz), 8.02 (d, 1H, J=7.8 Hz). Melting point: 220-221° C. Calcd for C₁₈H₂₆FN₃O₃S: C, 56.38; H, 6.83; F, 4.95; N, 10.96; S, 8.36. Found: C, 56.41; H, 6.90; F, 4.96; N, 11.07; S, 8.36.

Compound Ij-159

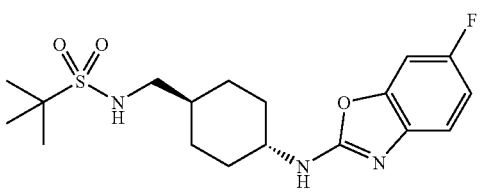

¹H-NMR (DMSO-d₆) δ: 0.91-1.08 (m, 2H), 1.16-1.46 (m, 3H), 1.27 (s, 9H), 1.77-1.87 (m, 2H), 1.98-2.10 (m, 2H), 2.89 (t, 2H, J=6.0 Hz), 3.38-3.54 (m, 1H), 6.88 (t, 1H, J=5.7 Hz), 6.90-7.00 (m, 1H), 7.19 (dd, 1H, J=8.7, 5.1 Hz), 7.34 (dd, 1H, J=8.7, 2.7 Hz), 7.88 (d, 1H, J=7.5 Hz). Anal. Calcd for C₁₈H₂₆FN₃O₃S: C, 56.38; H, 6.83; F, 4.95; N, 10.96; S, 8.36. Found: C, 56.39; H, 6.93; F, 4.98; N, 11.09; S, 8.29.

Compound Ij-160

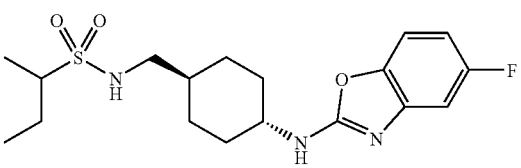

¹H-NMR (DMSO-d₆) δ: 0.95 (t, 3H, J=7.8 Hz), 0.92-1.07 (m, 2H), 1.21 (d, 3H, J=6.9 Hz), 1.20-1.47 (m, 4H), 1.77-1.96 (m, 3H), 1.98-2.08 (m, 2H), 2.79 (t, 2H, J=6.3 Hz), 2.85-2.98 (m, 1H), 3.42-3.57 (m, 1H), 6.71-6.80 (m, 1H), 7.00 (t, 1H, J=5.7 Hz), 7.06 (dd, 1H, J=9.3, 2.7 Hz), 7.31 (dd, 1H, J=8.7, 4.5 Hz), 8.02 (d, 1H, J=7.8 Hz). Melting point: 172-173° C. Anal. Calcd for C18H26FN3O3S: C, 56.38; H, 6.83; F, 4.95; N, 10.96; S, 8.36. Found: C, 56.37; H, 6.84; F, 5.04; N, 11.12; S, 8.14.

Compound Ij-161

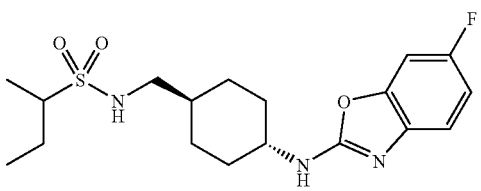

¹H-NMR (DMSO-d₆) δ: 0.95 (t, 3H, J=7.5 Hz), 0.92-1.08 (m, 2H), 1.21 (d, 3H, J=6.9 Hz), 1.20-1.47 (m, 4H), 1.77-1.96 (m, 3H), 1.98-2.08 (m, 2H), 2.79 (t, 2H, J=6.3 Hz), 2.85-2.98 (m, 1H), 3.38-3.56 (m, 1H), 6.90-6.98 (m, 1H), 7.00 (t, 1H, J=6.0 Hz), 7.19 (dd, 1H, J=8.7, 5.1 Hz), 7.33 (dd, 1H, J=8.7, 2.7 Hz), 7.88 (d, 1H, J=7.8 Hz). Melting point: 173-174° C. Anal. Calcd for C₁₈H₂₆FN₃O₃S: C, 56.38; H, 6.83; F, 4.95; N, 10.96; S, 8.36. Found: C, 56.45; H, 6.80; F, 4.93; N, 11.02; S, 8.54.

Experiment 1 Transportability Through the Blood-Brain Barrier and Potential for Drug-Drug Interactions Through P-gp Transportability of the compounds of this invention through the blood-brain barrier (blood-brain partition coefficient; Kp) in mice (Jcl; C57BL/6J mice, ♂, 7 weeks) was defined from the difference in concentration of the compounds between in plasma and in brain after intravenous administration of the compounds (0.5 mg/2 mL/kg). The brain Kp value of Compound (1-72) ($Kp_{cont.}$) was 1.29 showing high transportability through the blood-brain barrier.

To examine the potential for drug-drug interactions through P-gp in vivo, the Kp values of compounds of this invention with ($Kp_{CSA}$) or without ($Kp_{Cont.}$) cyclosporin A (20 mg/kg), a P-gp inhibitor, were calculated. The $Kp_{CSA}$ value of Compound (I-72) was 1.14, and the calculated $Kp_{CSA}$ $Kp_{Cont.}$ ratio was 0.9. The result indicate that Compound (I-72) has no significant potential for drug-drug interactions through P-gp in mice.

On the other hand the potential for drug-drug interactions through P-pg of amide compound B which has similar structure of Compound (1-72) was also examined in mice. The $Kp_{Cont.}$ and $Kp_{CSA}$ were 0.04 and 0.84, respectively. The $Kp_{CSA}/Kp_{Cont}$ ratio was 20.5, indicating that the compound is effectively excreted through P-gp from the brain to vessels, and that significant drug-drug interactions through P-gp could be induced in mice.

Compound B

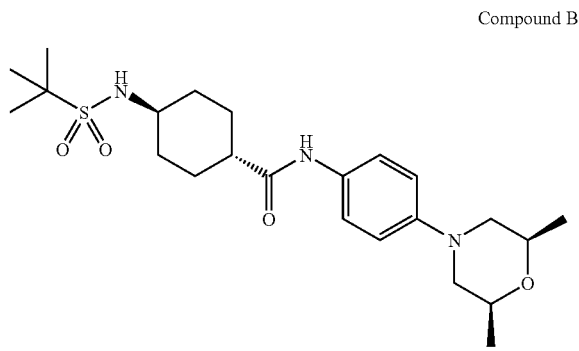

Experiment 2-1 Affinity for Mouse NPY Y5 Receptor cDNA sequence encoding a mouse NPY Y5 receptor (Biochim. Biophys. Acta 1328:83-89, 1997) was cloned in a vector (pME18S, Takebe et al. Mol. Cell. Biol. 8, 466-472). The obtained expression vector was transfected into CHO cells as a host by using Lipofect AMINE reagent (Trademark, Gico BRL Co., Ltd.) according to the instruction manual. The cells that stably express mouse NPY Y5 receptor were obtained.

The membranes prepared from the CHO cells expressing mouse NPY Y5 receptor, the compound of this invention and 30,000 cpm [$^{125}$I] peptide YY (60 pM of final concentration: Amersham) were incubated in the assay buffer (20 mM HEPES-Hanks buffer containing 0.1% bovine serum albumin, pH 7.4) at 25° C. for 2 hours, and then the membrane was filtered from the mixture through a glassfilter (GF/C) presoaked with 1% polyethyleneimine. After washing with 50 mM Tris-HCl buffer (pH 7.4), radioactivity retained on the filters was quantified with a gamma counter.

Nonspecific binding was defined as the amount of radioactivity bound to the membranes after incubation in the presence of 200 nM of peptide YY. The 50% inhibitory concentration of the test compound against the specific peptide YY binding ($IC_{50}$ value) was calculated (Inui, A. et al. Endocrinology 131, 2090-2096 (1992)). The results are shown in Table 1.

The compounds of this invention inhibited the binding of peptide YY (NPY homologue) to mouse NPY Y5 receptor, indicating that the compounds of this invention have an affinity for the mouse NPY Y5 receptor.

TABLE 1

| Compound No. | Binding $IC_{50}$ (nM) |
|---|---|
| Ii-1 | 0.10 |
| Ii-16 | 1.2 |
| Ii-34 | 11 |
| Ii-44 | 3.4 |
| Ij-1 | 0.70 |
| Ij-52 | 0.99 |
| Ij-59 | 2.5 |
| Ij-66 | 0.39 |
| Ij-149 | 0.92 |
| Ij-150 | 4.66 |
| Ij-151 | 0.12 |
| Ij-152 | 0.35 |
| Ij-153 | 0.12 |
| Ij-154 | 0.17 |
| Ij-155 | 0.88 |
| Ij-156 | 0.68 |
| Ij-157 | 0.16 |
| Ij-158 | 0.85 |
| Ij-159 | 0.60 |
| Ij-160 | 0.55 |
| Ij-161 | 0.69 |

Experiment 2-2 Affinity for Human NPY Y5 Receptor cDNA sequence encoding a human NPY Y5 receptor (WO9616542) was cloned in a vector (pME18S, Takebe et al. Mol. Cell. Biol. 8, 466-472). The obtained expression vector was transfected into CHO cells as a host by using Lipofect AMINE reagent (Trademark, Gico BRL Co., Ltd.) according to the instruction manual. The cells that stably express human NPY Y5 receptor were obtained.

The membranes prepared from the CHO cells expressing human NPY Y5 receptor, the compound of this invention and 30,000 cpm [$^{125}$I] peptide YY (60 pM of final concentration: Amersham) were incubated in the assay buffer (20 mM HEPES-Hanks buffer containing 0.1% bovine serum albumin, pH 7.4) at 25° C. for 2 hours, and then the membrane was filtered from the mixture through a glassfilter (GF/C) presoaked with 1% polyethyleneimine. After washing with 50 mM Tris-HCl buffer (pH 7.4), radioactivity retained on the filters was quantified with a gamma counter.

Nonspecific binding was defined as the amount of radioactivity bound to the membranes after incubation in the presence of 200 nM of peptide YY. The 50% inhibitory concentration of the test compound against the specific peptide YY binding ($IC_{50}$ value) was calculated (Inui, A. et al. Endocrinology 131, 2090-2096 (1992)).

The compounds of this invention inhibited the binding of peptide YY (NPY homologue) to human NPY Y5 receptor, indicating that the compounds of this invention have an affinity for the human NPY Y5 receptor.

Experiment 3 Inhibitory Effect on cAMP Production in CHO Cells

CHO cells expressing human NPY Y5 receptor were incubated in the presence of 0.1 mM isobutylmethylxanthine (SIGMA) and 0.2 mM RO-201724 (Calbiochem) at 37° C. for 20 min. After the incubation the compound of this invention was added, and then the mixture was incubated for 10 min. Next, 50 nM NPY and 10 μM forskolin (SIGMA) were added, and the mixture was incubated for 30 min. After termination of the reaction by adding 1N HCl, the amount of cAMP in the supernatant was determined with a EIA kit (Amersham LIFE SCIENCE). The inhibitory activity of NPY against forskolin stimulated cAMP production was expressed as 100% and the 50% inhibitory concentration (IC50 value) of the compound of this invention against the NPY activity was calculated.

Experiment 4

Using the membranes prepared from Y1-expression cells (human neuroblastoma, SK-N-MC) and the membranes prepared from Y2-expression cells (human neuroblastoma, SMS-KAN), the experiment was carried out in a similar way as Experiment 2-2 to determine the affinity of the compounds for NPY Y1 and NPY Y2 receptor. The results showed that the compounds of this invention had no significant affinity for their receptors, indicating high selectivity for NPY Y5 receptor.

Experiment 5

Under diethylether anesthesia the skull of male C57BL/6J mice (12-14 week old, 25-30 g) was exposed by making an incision about 1-cm long from external occipital crest to nasal dorsum, and then drilled in the 1-mm lateral position to the left following 1-mm posterior from bregma. After recovery from anesthesia mice were dosed with either 0.5% hydroxypropylmethyl cellulose solution (vehicle, Shin-Etsu Chemical Co., Ltd) or the compounds of this invention suspended in the 0.5% hydroxypropylmethyl cellulose solution. At one hour after the treatment, each animal received saline or a NPY Y5 receptor specific agonist, [cPP$^{1-7}$, NPY$^{19-23}$, Ala$^{31}$, Aib$^{32}$, Gln$^{34}$]-hPancreatic Polypeptide (0.1 nmol/1.5 μL saline/mouse) through the skull opening using a canula. Residual food was measured at 2 and 4 hours after the treatment. The inhibition ratio of Y5 agonist-induced food intake by the compounds was calculated as follows; inhibition ratio (%)= [1−(food intake (g) by the compound treated and Y5 agonist received mice−food intake (g) by the vehicle treated and saline received mice)/(food intake (g) by the vehicle treated and Y5 agonist received mice−food intake (g) by the vehicle treated and saline received mice)]×100. As shown in Table 2, the compounds at 1.5 mg/kg, 6 mg/kg or 12.5 mg/kg caused a significant inhibition in Y5 agonist induced-food intake compared to the 0.5% hydroxypropylmethyl cellulose solution. The inhibition ratios 4 hours after dosing are shown in Table 2.

TABLE 2

| Compound No. | Inhibition ratio |
|---|---|
| Ii-45 | 76.2% |
| Ii-55 | 64.3% |
| Ij-4 | 88.2% |
| Ij-110 | 90.3% |
| Ij-149 | 62.6% |
| Ij-150 | 25.3% |
| Ij-151 | 78.4%* |
| Ij-152 | 62.6%* |
| Ij-153 | 73.0% |
| Ij-154 | 81.3% |
| Ij-155 | 56.1%* |
| Ij-156 | 90.4%** |
| Ij-158 | 70.5% |
| Ij-159 | 83.2% |
| Ij-160 | 36.6%* |
| Ij-161 | 15.8%* |

*Dose: 1.5 mg/kg
**Dose: 12.5 mg/kg

Experiment 6

Prior to administration of the compounds of this invention, male C57BL/6J mice were given a high-fat diet to induce obese. The high-fat diet-induced obese mice (13-14 week old, body weight 28-33 g) were dosed with 0.5% hydroxypropylmethyl cellulose solution (vehicle, Shin-Etsu Chemical Co., Ltd) or the compounds of this invention suspended in the 0.5% hydroxypropylmethyl cellulose solution twice a day (b.i.d.) for 3 weeks with the same diet. The changes in body weight were monitored daily. As shown in FIGS. 1 and 2, the compounds of this invention at 6 mg/kg b.i.d. resulted in a significant suppression of body weight gain compared to the 0.5% hydroxypropylmethyl cellulose solution (vehicle).

Formulation Example

The following Formulation Examples are only exemplified and not intended to limit the scope of this invention.

| Formulation Example 1 | Tablets |
|---|---|
| Compound (I-1) | 15 mg |
| Starch | 15 mg |
| Lactose | 15 mg |
| Crystalline cellulose | 19 mg |
| Polyvinyl alcohol | 3 mg |
| Distilled water | 30 ml |
| Calcium stearate | 3 mg |

All of the above ingredients except for calcium stearate are uniformly mixed. Then the mixture was crushed, granulated and dried to obtain a suitable size of granules. Next, calcium stearate was added to the granules. Finally, tableting was performed under a compression force.

| Formulation Example 2 | Capsules |
|---|---|
| Compound (I-2) | 10 mg |
| Magnesium stearate | 10 mg |
| Lactose | 80 mg |

The above ingredients were mixed uniformly to obtain powders or fine granules, and then the obtained mixture was filled in capsules.

| Formulation Example 3 | Granules |
|---|---|
| Compound (I-3) | 30 g |
| Lactose | 265 g |
| Magnesium Stearate | 5 g |

After the above ingredients are mixed uniformly, the mixture was compressed. The compressed matters were crushed, granulated and sieved to obtain suitable size of granules.

INDUSTRIAL APPLICABILITY

As shown in the above Experiments, the compounds for this invention have NPY Y5 receptor antagonistic activity. Therefore, this invention are very useful as an anorectic or anti-obesity composition.

The invention claimed is:
1. A compound of:

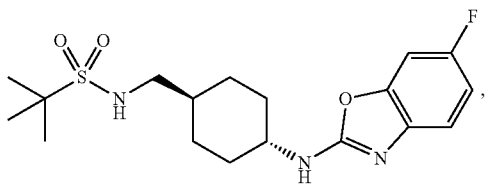

or a pharmaceutically acceptable salt thereof.

2. A pharmaceutical composition, comprising a compound of:

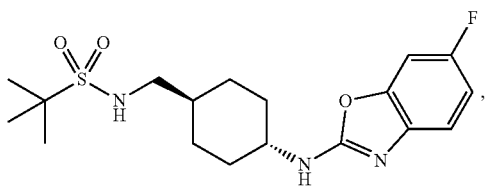

or a pharmaceutically acceptable salt thereof.

3. A pharmaceutical composition according to claim 2, exhibiting NPY Y5 receptor antagonistic activity.

4. An anorectic or anti-obesity composition comprising a compound or pharmaceutically acceptable salt thereof according to claim 1.

5. A method for suppressing appetite, comprising administering an effective amount of a compound or pharmaceutically acceptable salt thereof according to claim 1 to a subject in need thereof.

6. A method for treating obesity, comprising administering an effective amount of a compound or pharmaceutically acceptable salt thereof according to claim 1 to a subject in need thereof.

7. A method for treating an obesity-related disorder, comprising administering an effective amount of a compound or pharmaceutically acceptable salt thereof according to claim 1 to a subject in need thereof, wherein said obesity-related disorder is overeating, hypertension, impaired glucose tolerance, diabetes, metabolic syndrome, abnormal lipid metabolism, dyslipidemia, arteriosclerosis, hyperuricemia, gout, fatty liver, endometrial, breast, prostate and colon cancer, osteoarthritis, lumbago, obstructive sleep apnea syndrome, coronary artery disease, cerebral infarction, menstrual disorder, Prader-Willi Syndrome, Frohlich's syndrome, or pickwickian syndrome.

8. A method for weight management for obesity, comprising administering an effective amount of a compound or pharmaceutically acceptable salt thereof according to claim 1 to a subject in need thereof.

9. A method for inducing weight loss, comprising administering an effective amount of a compound or pharmaceutically acceptable salt thereof according to claim 1 to a subject in need thereof.

10. A method for accelerating weight loss, comprising administering an effective amount of a compound or pharmaceutically acceptable salt thereof according to claim 1 to a subject in need thereof.

11. A method for maintaining body weight, comprising administering an effective amount of a compound or pharmaceutically acceptable salt thereof according to claim 1 to a subject in need thereof.

12. A method for managing body weight, comprising administering an effective amount of a compound or pharmaceutically acceptable salt thereof according to claim 1 to a subject in need thereof.

* * * * *